United States Patent
Lee et al.

(10) Patent No.: US 9,878,986 B2
(45) Date of Patent: Jan. 30, 2018

(54) COMPOUNDS FOR SELECTIVE HISTONE DEACETYLASE INHIBITORS, AND PHARMACEUTICAL COMPOSITION COMPRISING THE SAME

(71) Applicant: CHONG KUN DANG PHARMACEUTICAL CORP., Seoul (KR)

(72) Inventors: Changsik Lee, Gyeonggi-do (KR); Hyun-Mo Yang, Gyeonggi-do (KR); Hojin Choi, Gyeonggi-do (KR); Dohoon Kim, Gyeonggi-do (KR); Soyoung Kim, Gyeonggi-do (KR); Nina Ha, Gyeonggi-do (KR); Hyojin Lim, Gyeonggi-do (KR); Eunhee Ko, Gyeonggi-do (KR); Seongae Yoon, Gyeonggi-do (KR); Daekwon Bae, Gyeonggi-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 14/785,812

(22) PCT Filed: Apr. 29, 2014

(86) PCT No.: PCT/KR2014/003776
§ 371 (c)(1),
(2) Date: Oct. 20, 2015

(87) PCT Pub. No.: WO2014/178606
PCT Pub. Date: Nov. 6, 2014

(65) Prior Publication Data
US 2016/0083354 A1    Mar. 24, 2016
US 2017/0152230 A9    Jun. 1, 2017

(30) Foreign Application Priority Data
Apr. 29, 2013   (KR) .................. 10-2013-0047212

(51) Int. Cl.
| | |
|---|---|
| C07D 231/56 | (2006.01) |
| C07D 209/14 | (2006.01) |
| C07D 213/40 | (2006.01) |
| C07D 401/12 | (2006.01) |
| C07D 403/12 | (2006.01) |
| C07D 413/12 | (2006.01) |
| C07D 239/26 | (2006.01) |
| C07D 215/12 | (2006.01) |
| C07D 213/75 | (2006.01) |
| C07D 295/215 | (2006.01) |

(Continued)

(52) U.S. Cl.
CPC ......... *C07D 231/56* (2013.01); *C07D 207/08* (2013.01); *C07D 207/10* (2013.01); *C07D 209/08* (2013.01); *C07D 209/14* (2013.01); *C07D 211/26* (2013.01); *C07D 211/46* (2013.01); *C07D 211/52* (2013.01); *C07D 213/40* (2013.01); *C07D 213/74* (2013.01); *C07D 213/75* (2013.01); *C07D 215/12* (2013.01); *C07D 239/26* (2013.01); *C07D 239/42* (2013.01); *C07D 265/30* (2013.01); *C07D 295/215* (2013.01); *C07D 309/08* (2013.01); *C07D 309/10* (2013.01); *C07D 317/58* (2013.01); *C07D 319/18* (2013.01); *C07D 401/12* (2013.01); *C07D 403/12* (2013.01); *C07D 405/12* (2013.01); *C07D 407/12* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | | |
|---|---|---|---|
| 5,369,108 A | 11/1994 | Breslow et al. | 514/266 |
| 6,174,905 B1 | 1/2001 | Suzuki et al. | 514/346 |

(Continued)

FOREIGN PATENT DOCUMENTS

| | | |
|---|---|---|
| CN | 101230049 A | 7/2008 |
| EP | 0 847 992 | 6/1998 |

(Continued)

OTHER PUBLICATIONS

Cancer Drug Design and Discovery, Neidle, Stephen ed. (Elsevier/Academic Press), pp. 427-431 (2008).*

(Continued)

*Primary Examiner* — Emily Bernhardt
(74) *Attorney, Agent, or Firm* — Dentons US LLP; Stephanie Seidman

(57) ABSTRACT

Provided are urea derivatives of Formula I:

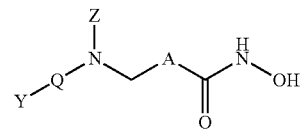

with histone deacetylase (HDAC) inhibitory activity, optical isomers thereof, pharmaceutically acceptable salts thereof and pharmaceutical compositions comprising the same. The provided urea derivatives of Formula I are selective histone deacetylase (HDAC) inhibitors and are effective for the treatment of histone deacetylase-mediated diseases such as malignant tumors, inflammatory diseases, rheumatoid arthritis, and neurodegeneration.

7 Claims, 4 Drawing Sheets

(51) Int. Cl.

| | |
|---|---|
| *C07D 239/42* | (2006.01) |
| *C07D 213/74* | (2006.01) |
| *C07D 309/08* | (2006.01) |
| *C07D 309/10* | (2006.01) |
| *C07D 317/58* | (2006.01) |
| *C07D 405/12* | (2006.01) |
| *C07D 407/12* | (2006.01) |
| *C07D 417/12* | (2006.01) |
| *C07D 265/30* | (2006.01) |
| *C07D 319/18* | (2006.01) |
| *C07D 207/08* | (2006.01) |
| *C07D 207/10* | (2006.01) |
| *C07D 209/08* | (2006.01) |
| *C07D 211/26* | (2006.01) |
| *C07D 211/46* | (2006.01) |
| *C07D 211/52* | (2006.01) |

(56) References Cited

U.S. PATENT DOCUMENTS

| | | | |
|---|---|---|---|
| 8,466,161 B2 | 6/2013 | Lee et al. | 514/256 |
| 2004/0053960 A1 | 3/2004 | Georges et al. | 514/307 |
| 2004/0142953 A1 | 7/2004 | Delorme et al. | 514/275 |
| 2005/0085515 A1 | 4/2005 | Watkins et al. | 514/352 |
| 2006/0189674 A1 | 8/2006 | Remiszewski et al. | 514/419 |
| 2008/0255149 A1 | 10/2008 | Dobler et al. | 514/255.01 |
| 2010/0152188 A1 | 6/2010 | Srinivas et al. | 514/236.8 |
| 2010/0261710 A1 | 10/2010 | Ashwell et al. | 514/220 |
| 2011/0212969 A1 | 9/2011 | Blackburn et al. | 514/249 |
| 2012/0028963 A1 | 2/2012 | Lee et al. | 514/218 |
| 2012/0196885 A1 | 8/2012 | Cossio Mora et al. | 514/275 |
| 2014/0128408 A1 | 5/2014 | Kozikowski et al. | 514/254.09 |
| 2014/0315889 A1 | 10/2014 | Kim et al. | 514/210.21 |

FOREIGN PATENT DOCUMENTS

| | | |
|---|---|---|
| EP | 2 305 643 | 4/2011 |
| KR | 10-2010-0108220 | 10/2010 |
| WO | WO 2002/022577 | 3/2002 |
| WO | WO 2002/030879 | 4/2002 |
| WO | WO 2002/051842 | 7/2002 |
| WO | WO 2003/070691 | 8/2003 |
| WO | WO 2004/069823 | 8/2004 |
| WO | WO 2005/092899 | 10/2005 |
| WO | WO 2007/017728 | 2/2007 |
| WO | WO 2007/038459 | 4/2007 |
| WO | WO 2009/026446 | 2/2009 |
| WO | WO 2011/106632 | 9/2011 |
| WO | WO 2012/106343 | 8/2012 |
| WO | WO 2015/102426 | 7/2015 |

OTHER PUBLICATIONS

Carey et al. Current Opinion in Pharmacology, vol. 6, p. 369-375 (2006).*
Lane et al. J.Clin.Oncol. 27, pp. 5459-5468 (2009).*
Elaut et al. Current Pharmaceutical Design, vol. 13, pp. 2584-2620 (2007).*
Dallavalle et al. Biochemical Pharmacology 84 (2012) 756-765.*
Chuang et al. Trends in Neurosciences vol. 32 No. 11, pp. 591-601 (2009).*
Partial Machine Translation for WO 03/070691 (Aug. 28, 2003).*
Letter/Written Disclosure of the Information Disclosure Statement for the above-referenced application, mailed on Jan. 21, 2016, 2 pages.
Dokmanovic et al., "Histone deacetylase inhibitors: overview and perspectives." Mol Cancer Res., 5:981-987 (2007).
Emanuele et al., "Histone deacetylase inhibitors: apoptotic effects and clinical implications," International Journal of Onocology 33:637-646 (2008).
English language abstract of Chinese Patent Publication No. CN101230049A, published Jul. 30, 2008, Espacenet, 1 page.
Johnstone, R.W., "Histone-deacetylase inhibitors: novel drugs for the treatment of cancer." Nat. Rev. Drug Discov. 1:287-299 (2002).
Kattar et al., "Parallel medicinal chemistry approaches to selective HDAC1/HDAC2 inhibitor (SHI-1:2) optimization." Bioorg Med Chem Lett. 19(4):1168-1172 (2009).
Maiso et al., "The histone deacetylase inhibitor LBH589 is a potent antimyeloma agent that overcomes drug resistance." Cancer Res. 66:5781-5789 (2006).
Marks et al., "Histone deacetylase inhibitors as new cancer drugs." Curr Opin Oncol., 13:477-483 (2001).
Marks et al., "Histone deacetylases and cancer: causes and therapies." Nature Cancer Rev 1:194-202 (2001).
Strahl, B.D. & Allis, C. D. "The language of covalent histone modifications." Nature 403:41-45 (2000).
Woods et al., "IL-4 adenoviral gene therapy reduces inflammation, proinflammatory cytokines, vascularization, and bony destruction in rat adjuvant-induced arthritis," J. Immunology 166(2):1214-1222 (2001).
International Search Report and Written Opinion, dated Aug. 29, 2014, in connection with International Patent Application No. PCT/KR2014/003776, 9 pages.
International Preliminary Report on Patentability, dated Nov. 3, 2015, in connection with International Patent Application No. PCT/KR2014/003776, 6 pages.
Letter/Written Disclosure of the Information Disclosure Statement for the above-referenced application, filed herewith on Aug. 31, 2016, 2 pages.
Examination Report, dated Apr. 26, 2016, in connection with Australian Patent Application No. 2014260605, 2 pages.
Response, filed Jun. 17, 2016, to Examination Report, dated Apr. 26, 2016, in connection with Australian Patent Application No. 2014260605, 4 pages.
Notice of Acceptance, dated Jul. 1, 2016, in connection with Australian Patent Application No. 2014260605, 3 pages.
Extended European Search Report, dated Aug. 16, 2016, in connection with European Patent Application No. 14792173.8, 7 pages.
Letter/Written Disclosure of the Supplemental Information Disclosure Statement for the above-referenced application, filed herewith on May 12, 2017, 2 pages.
Examiner's Report, dated Aug. 15, 2016, in connection with corresponding Canadian Patent Application No. 2,908,542, 7 pages.
Response, submitted Feb. 9, 2017, to Examiner's Report, dated Aug. 15, 2016, in connection with corresponding Canadian Patent Application No. 2,908,542, 534 pages.
Response, submitted Feb. 28, 2017, to Extended European Search Report, dated Aug. 16, 2016, in connection with corresponding European Patent Application No. 14792173.8, 52 pages.
Letter/Written Disclosure of the Supplemental Information Disclosure Statement for the above-referenced application, filed herewith on Apr. 5, 2017, 2 pages.
Official Action, dated Mar. 15, 2017, in connection with corresponding Russian Patent Application No. 2015150946 [English translation and original document in Russian], 14 pages.
Letter/Written Disclosure of the Supplemental Information Disclosure Statement for the above-referenced application, filed herewith on Aug. 31, 2017, 2 pages.
Communication Pursuant to Article 94(3) EPC (Examination Report), dated Jun. 28, 2017, in connection with corresponding European Patent Application No. 14 792 173.8, 5 pages.

* cited by examiner

[Fig. 1]
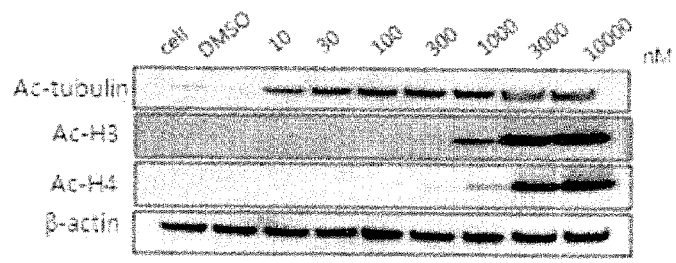
[Fig. 2]
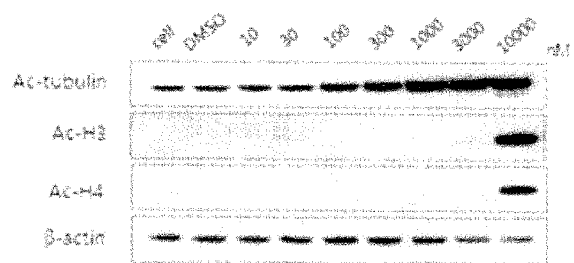
[Fig. 3]
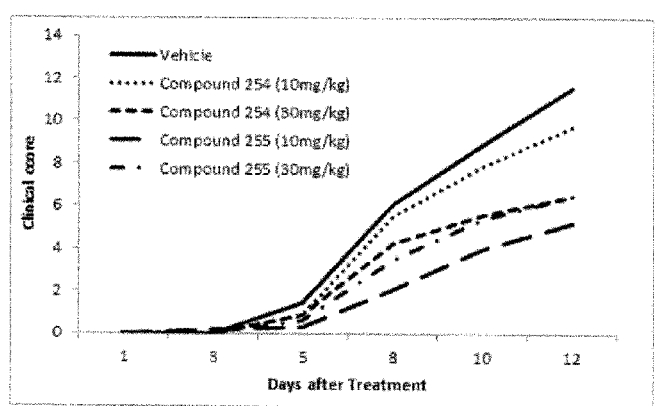
[Fig. 4]
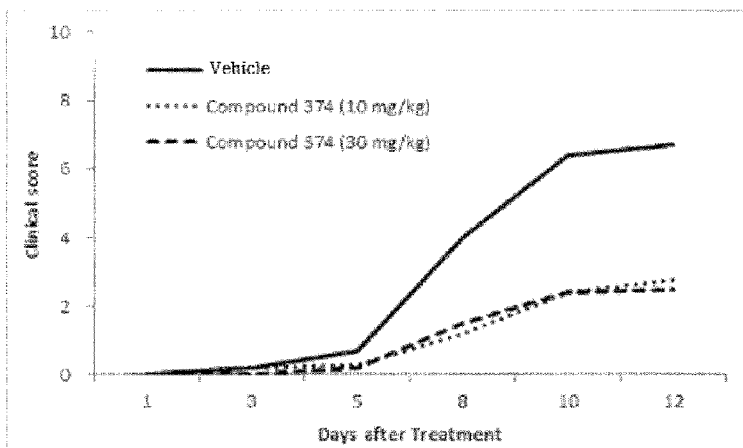

[Fig. 6]
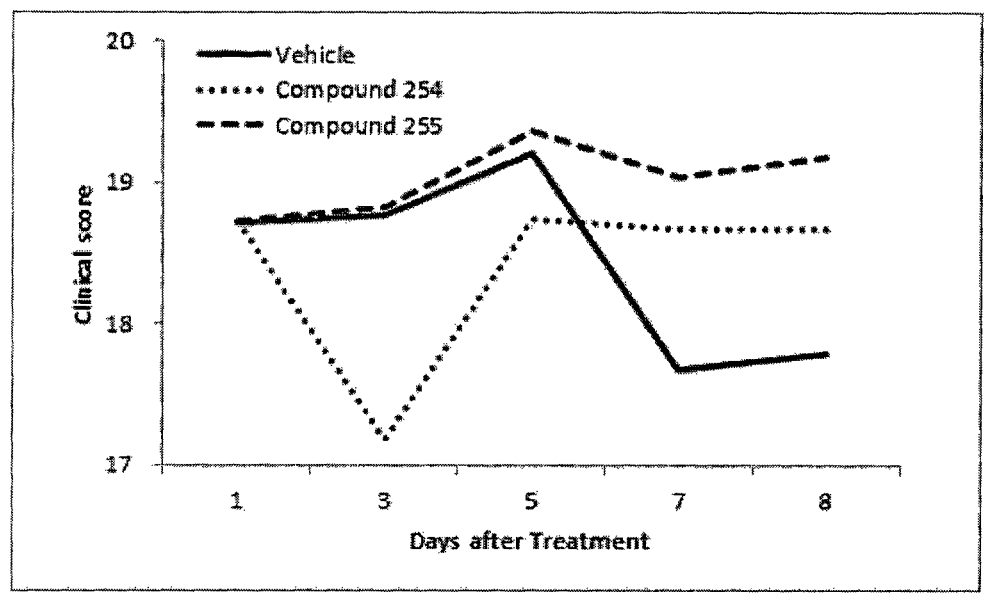

[Fig. 7]
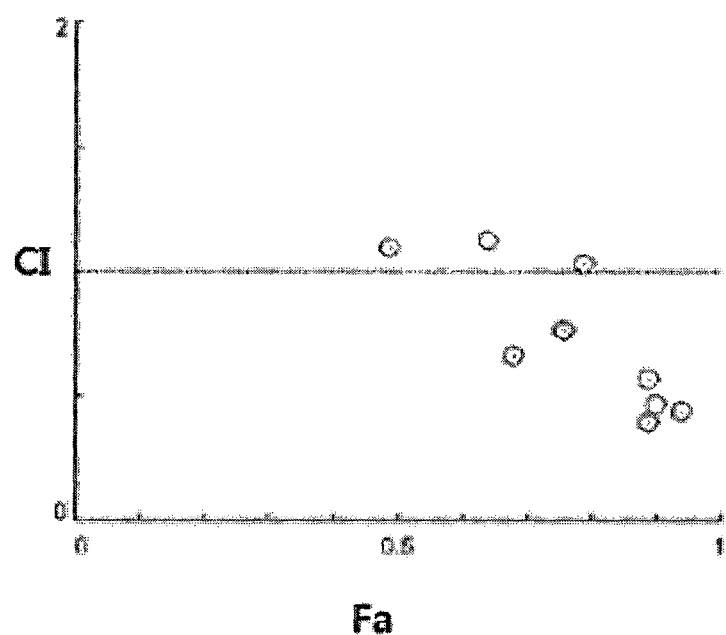

COMPOUNDS FOR SELECTIVE HISTONE DEACETYLASE INHIBITORS, AND PHARMACEUTICAL COMPOSITION COMPRISING THE SAME

RELATED APPLICATIONS

This application is the U.S. National Stage of International Application. No. PCT/KR2014/003776, filed 29 Apr. 2014, which claims benefit of priority to Korean Patent Application KR 10-2013-0047212, filed 29 Apr. 2013, the specification of which is incorporated by reference herein.

TECHNICAL FIELD

The present invention relates to novel compounds having histone deacetylase (HDAC) inhibitory activity, optical isomers thereof, pharmaceutically acceptable salts thereof, their use for the preparation of medicaments for the treatment of HDAC-mediated diseases, a pharmaceutical composition comprising the same, a treatment method using the composition, and a preparation method thereof.

BACKGROUND ART

The cellular transcriptional regulation is a complex biological process. One of the basic principles is the post-translation modification of histone proteins H2A/B, H3 and H4 that form the octameric histone core complex. The complex N-terminal modifications at lysine residues by acetylation or methylation and at serine residues by phosphorylation constitute part of the so-called "histone code" (Stahl & Ellis, Nature 403, 41-45, 2000).

In a simple model, acetylation of positively charged lysine residues decreases affinity to negatively charged DNA, thus transcription factors may be easily entered.

Histone acetylation and deacetylation is catalysed by histone acetyltransferases (HATs) and histone deacetylases (HDACs), respectively. The HDAC is associated with transcriptional repressor complexes, switching chromatin to a transcriptionally inactive, silent structure (Marks et al. Nature Cancer Rev 1, 189-202, 2001). The opposite holds true for certain HATs which are associated with transcriptional activator complexes. Three different classes of HDACs, located in the nucleus, have been described so far, namely, class I (HDAC 1-3, 8; Mr=42-55 kDa) sensitive towards inhibition Trichostatin A (TSA), class II (HDAC 4-7, 9, 10; Mr=120-130 kDa) sensitive to TSA, and class III (Sir2) which are quite distinct by their NAD+ dependency and TSA insensitivity.

Inhibitors of histone deacetylases (HDACs) constitute a new class of anticancer drugs with differentiation and apoptosis activity. By targeting histone deacetylases (HDACs), the HDAC inhibitors affect histone (protein) acetylation and chromatin structure, inducing a complex transcriptional reprogramming, exemplified by reactivation of tumor suppressor genes and repression of oncogenes. In addition to generating acetylation of N-terminal lysine residue in core histone protein, there are non-histone targets important for cancer cell biology, including heat-shock-protein (HSP90), tubulin or p53 tumor suppressor protein. Therefore, the HDAC inhibitors can be used for the treatment of cancers as well as inherited metabolic diseases, autoimmune diseases, etc., since the efficacy in animal models for inflammatory diseases, rheumatoid arthritis, and neurodegeneration has been shown.

Examples of histone deacetylase-mediated diseases include cell proliferative diseases including malignant tumors such as cancers, etc., autosomal dominant diseases such as Huntington's diseases, etc., inherited metabolic diseases such as cystic fibrosis, hepatic fibrosis, kidney fibrosis, pulmonary fibrosis, skin fibrosis, etc, autoimmune diseases such as rheumatoid arthritis, etc., acute and chronic neurological diseases such as diabetes, stroke, etc., hypertrophy such as cardiac hypertrophy, etc., hemorrhagic heart failure, amyotrophic lateral sclerosis, glaucoma, ocular diseases (associated with angiogenesis), Alzheimer's disease, etc.

HDAC inhibitors known up to now can be classified into four categories according to their structures: 1) short chain fatty acids (butyric acid, valproic acid); 2) hydroxamic acids (trichostatin A, SAHA, LBH-589); 3) cyclic peptides (desipeptide); and 4)benzamide (MS-275, MGCD-0103) (International Journal of Oncology 33, 637-646, 2008). These many HDAC inhibitors (SAHA, LBH-589, MS-275, etc.) effectively induce growth inhibition, differentiation, and apoptosis of various transformed cells in culture medium as well as in animal models (Marks, P. A et. al., Curr Opin Oncol. 2001. 13. 477-483), and some HDAC inhibitors such as SAHA, LBH-589, MS-275, etc. are clinically evaluated for the treatment of various cancers (Johnstone, R. W Nat. Rev. Drug Discov. 2002 1. 287-299). Typical examples of HDAC inhibitor compounds that are currently known include hydroxamate compounds, such as SAHA (U.S. Pat. No. 771,760, Zolinza, Vorinostat), PXD101 (WO 02/30879, Belinostat), LBH-589 (WO 02/22577, Panobinostat), and benzamide compounds such as MS-275 (EP8799) and MGCD0103 (WO 04/69823). Among these compounds, SAHA was approved on October 2006 and has been used for the treatment of CTCL (cutaneous T-cell lymphoma). Diseases for which medicine is efficacious have been additionally expanded, but it is known that there are drawbacks in terms of effectiveness and side effects (Cancer Res 2006, 66, 5781-5789).

That is, although many HDAC inhibitors have been reported to date, most of the HDAC inhibitors have drawbacks in terms of efficacy and side effects. Therefore, in order to overcome these drawbacks, there is a continuous need to develop an effective HDAC inhibitor with high selectivity and less side effects (Mol Cancer Res, 5, 981, 2007).

DISCLOSURE OF INVENTION

Technical Problem

An object of the present invention is to provide novel compounds, optical isomers thereof, or pharmaceutical salts thereof.

Another object of the present invention is to provide a pharmaceutical composition comprising novel compounds with highly selective histone deacetylase (HDAC) inhibitory activity, optical isomers thereof, or pharmaceutical salts thereof.

Still another object of the present invention is to provide a preparation method thereof.

Yet another object of the present invention is to provide a pharmaceutical composition comprising the above compounds for the treatment of diseases associated with HDAC activity, including cancers, inflammatory diseases, autoimmune diseases, neurological or neurodegenerative diseases, etc.

Still yet another object of the present invention is to provide their use for the preparation of medicaments for the treatment of HDAC-mediated diseases such as cancers, inflammatory diseases, autoimmune diseases, neurological or neurodegenerative diseases, etc.

A further object of the present invention is to provide a method for the treatment of HDAC-mediated diseases such as cancers, inflammatory diseases, autoimmune diseases, neurological or neurodegenerative diseases, etc., the method comprising administering a therapeutically effective amount of the pharmaceutical composition comprising the above compounds.

Solution to Problem

The present inventors have found novel compounds with histone deacetylase (HDAC) inhibitory activity and used the same for the treatment of histone deacetylase-mediated diseases, thus completing the present invention.

According to the above objects, the present invention provides a compound of the following Formula I, an optical isomer thereof, or a pharmaceutically acceptable salt thereof:

[Formula I]

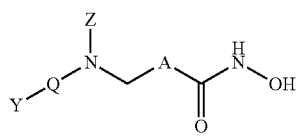

wherein A is

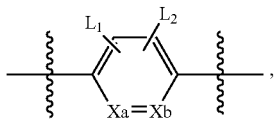

Xa and Xb are each independently C or N,
$L_1$ and $L_2$ are each independently hydrogen, —F, —Cl, —Br, —I, —CF$_3$, or —C$_{1-3}$ straight or branched chain alkyl,
Q is C(=O), S((=O)$_2$), S(=O), or C(=NH),
Y is selected from the group consisting of:

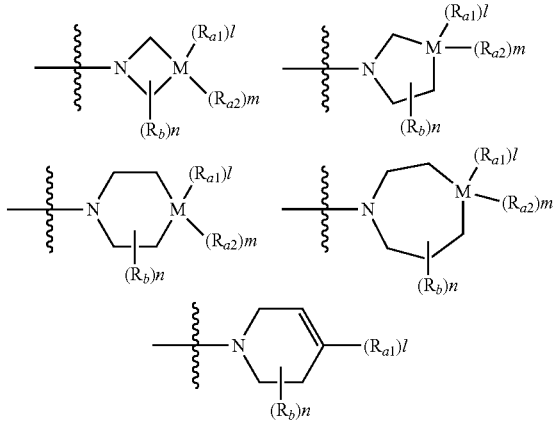

M is C, O, N, S(=O)$_2$, or S,
l and m are each independently an integer of 0 or 1,
$R_{a1}$ and $R_{a2}$ are each independently hydrogen; hydroxy; —C$_{1-4}$ straight or branched chain alkyl, unsubstituted or substituted with one or more F, Cl, Br or I; —C$_{1-4}$ straight or branched chain alcohol; benzhydryl; —C$_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I); a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I); phenyl, unsubstituted or substituted with one or more F, Cl, Br, I, C$_{1-4}$ alkoxy, C$_{1-2}$ alkyl, or hydroxy; benzyl, unsubstituted or substituted with one or more F, Cl, Br, I, C$_{1-4}$ alkoxy, C$_{1-2}$ alkyl, or hydroxy; —S((=O)$_2$)CH$_3$; —F; —Cl; —Br; —I; —C$_{1-6}$ straight or branched chain alkoxy; —C$_{2-6}$ alkyl alkoxy; —C(=O)Rx, wherein Rx is straight or branched C$_{1-3}$ alkyl or C$_{3-10}$ cycloalkyl;

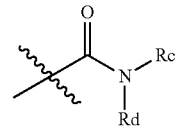

wherein $R_c$ and $R_d$ are each independently hydrogen, C$_{1-3}$ straight or branched chain alkyl;

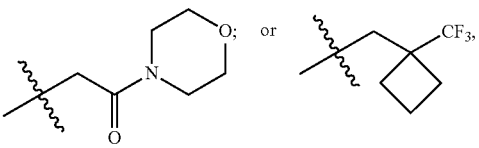 [SMILES: *CC(=O)N1CCOCC1 ; *CC1(C(F)(F)F)CCC1]

(wherein the structure of heterocyclic compound in $R_{a1}$ and $R_{a2}$ mentioned as alkyl substituted with heterocyclic compound or heterocyclic compound is preferably pyridine, morpholine or tetrahydropyran)
n is an integer of 0, 1, or 2,
$R_b$ is hydrogen; hydroxy; —C$_{1-6}$ straight or branched chain alkyl, unsubstituted or substituted with one or more F, Cl, Br, or I; —C(=O)CH$_3$; —C$_{1-4}$ straight or branched chain alcohol; —C$_{1-6}$ straight or branched chain alkoxy; —C$_{2-6}$ straight or branched chain alkyl alkoxy; —CF$_3$; —F; —Cl; —Br; —I; or

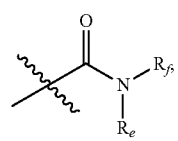

Wherein $R_e$ and $R_f$ are each independently hydrogen or —C$_{1-3}$ straight or branched chain alkyl, and
Z is phenyl; or a saturated or unsaturated 5- to 7-membered heterocycle comprising 1 to 3 heteroatoms selected from N, O, and S as a ring member, wherein the phenyl or heterocycle of Z may be unsubstituted or substituted with at least one hydroxy; —$C_{1-4}$ straight or branched chain alkyl, unsubstituted or having one or more substituents; —$CF_3$, unsubstituted or having one or more substituents; —CN, unsubstituted or having one or more substituents; —$C_{1-6}$ straight or branched chain alkoxy, unsubstituted or having one or more substituents; —$C_{2-6}$ straight or branched chain alkyl alkoxy, unsubstituted or having one or more substituents; —$C_{1-3}$ alcohol, unsubstituted or having one or more substituents; phenyl, unsubstituted or having one or more substituents; heterocycle, unsubstituted or having one or more substituents; or halogen unsubstituted or having one or more substituents.

Preferably, Z may be selected from the group consisting of the following compounds:

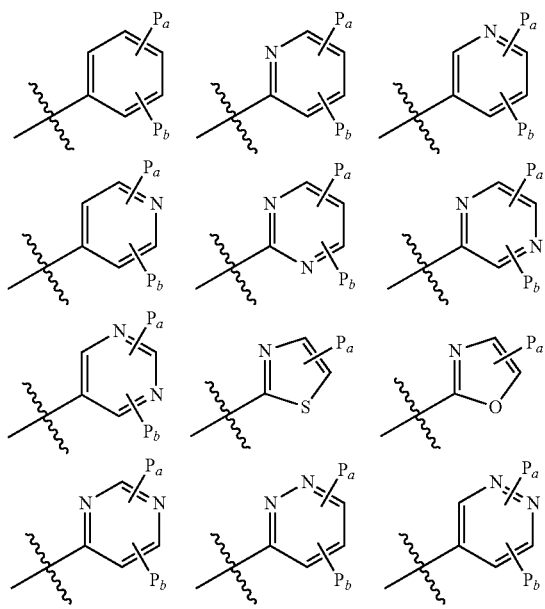

wherein $P_a$ and $P_b$ are each independently

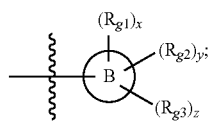

hydrogen; hydroxy; —$C_{1-4}$ straight or branched chain alkyl, unsubstituted or substituted with one or more F, Cl, Br or I; —F; —Cl; —Br; —I; —$CF_3$; —$OCF_3$; —CN; —$C_{1-6}$ straight or branched alkoxy; —$C_{2-6}$ straight or branched alkyl alkoxy; —$CH_2F$; or —$C_{1-3}$ alcohol, wherein

B is selected from phenyl, pyridine, pyrimidine, thiazole, indole, indazole, piperazine, quinoline, furan, tetrahydropyridine, piperidine, or the following group:

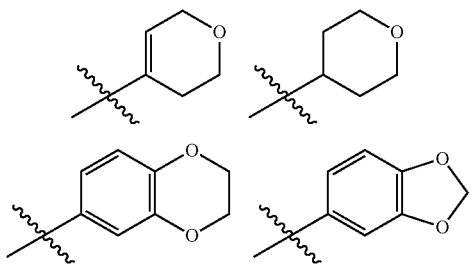

x, y and z are each independently an integer of 0 or 1, and $R_{g1}$, $R_{g2}$ and $R_{g3}$ are each independently selected from hydrogen; hydroxy; —$C_{1-3}$ alkyl; —$CF_3$; —$C_{1-6}$ straight or branched chain alkoxy; —$C_{2-6}$ straight or branched chain alkyl alkoxy; —$C(=O)CH_3$; —$C_{1-4}$ straight or branched chain alcohol; —$N(CH_3)_2$; —F; —Cl; —Br; —I; phenyl; —$S((=O)_2)CH_3$; or the following group:

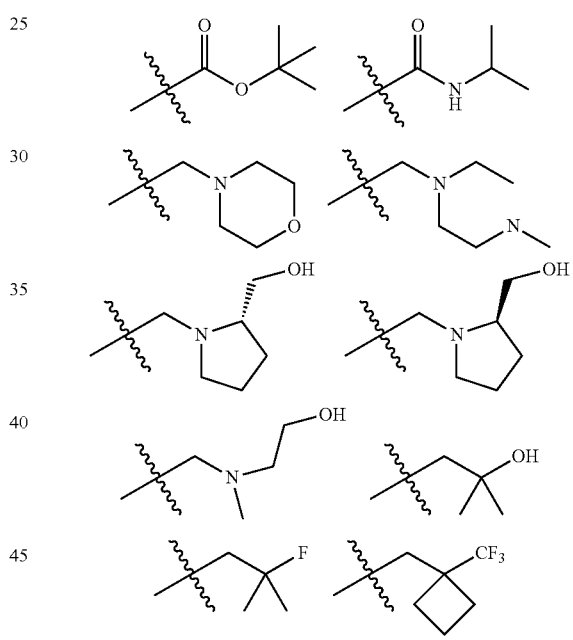

Preferably, the compound represented by the above Formula I may be a compound represented by the following Formula II:

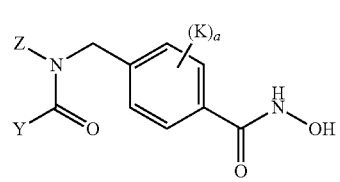

[Formula II]

wherein
a is an integer of 0, 1 or 2,
K is independently hydrogen, —F, —Cl, —Br or —I, Y is selected from the group consisting of:

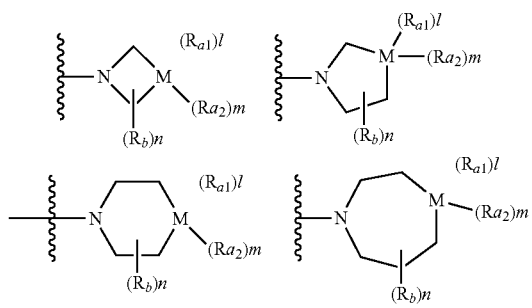

M is C, O or N,
l and m are each independently an integer of 0 or 1,
$R_{a1}$ and $R_{a2}$ are each independently hydrogen; hydroxy; —$C_{1-4}$ straight or branched chain alkyl, unsubstituted or substituted with one or more F, Cl, Br or I; —$C_{1-4}$ straight or branched chain alcohol; benzhydryl; —$C_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I); a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I); phenyl, unsubstituted or substituted with one or more F, Cl, Br, I, $C_{1-4}$ alkoxy, $C_{1-2}$ alkyl, or hydroxy; benzyl, unsubstituted or substituted with one or more F, Cl, Br, I, $C_{1-4}$ alkoxy, $C_{1-2}$ alkyl, or hydroxy; —S((=O)$_2$)CH$_3$; —F; —Cl; —Br; —I; —$C_{1-6}$ straight or branched chain alkoxy; —$C_{2-6}$ alkyl alkoxy; —C(=O)R$_x$, wherein R$_x$ is straight or branched $C_{1-3}$ alkyl or $C_{3-10}$ cycloalkyl;

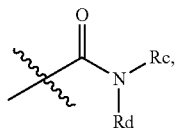

wherein $R_c$ and $R_d$ are each independently hydrogen, $C_{1-3}$ straight or branched chain alkyl;

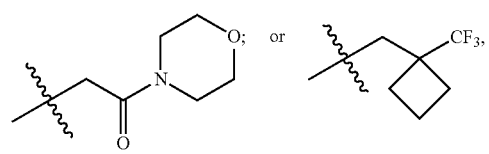 [SMILES: *CC(=O)N1CCOCC1 ; *CC1(C(F)(F)F)CCC1]

n is an integer of 0, 1, or 2,
$R_b$ is hydrogen; hydroxy; —$C_{1-6}$ straight or branched chain alkyl, unsubstituted or substituted with one or more F, Cl, Br, or I; —C(=O)CH$_3$; —$C_{1-4}$ straight or branched chain alcohol; —$C_{1-6}$ straight or branched chain alkoxy; —$C_{2-6}$ straight or branched alkyl alkoxy; —CF$_3$; —F; —Cl; —Br; —I; or

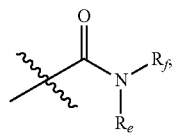

wherein $R_e$ and $R_f$ are each independently hydrogen or —$C_{1-3}$ straight or branched chain alkyl, and
Z is selected from the group consisting of the following compounds:

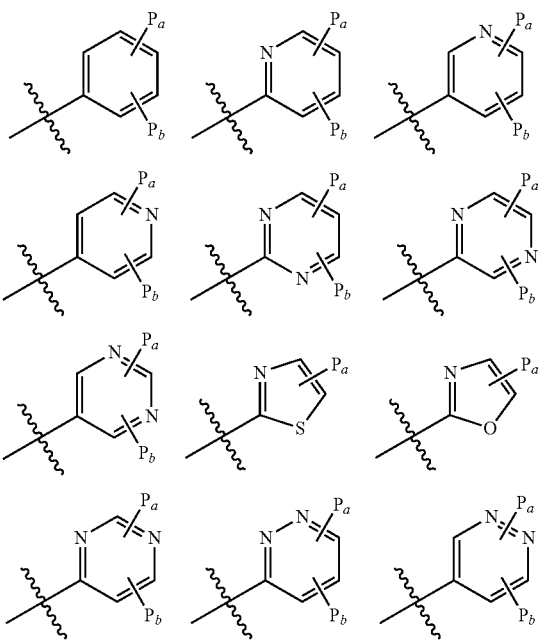

wherein $P_a$ and $P_b$ are each independently

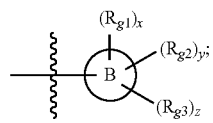

hydrogen; hydroxy; —$C_{1-4}$ straight or branched chain alkyl, unsubstituted or substituted with one or more F, Cl, Br or I; —F; —Cl; —Br; —I; —CF$_3$; —OCF$_3$; —CN; —$C_{1-6}$ straight or branched alkoxy; —$C_{2-6}$ straight or branched alkyl alkoxy; —CH$_2$F; or —$C_{1-3}$ alcohol,
wherein

is selected from phenyl, pyridine, pyrimidine, thiazole, indole, indazole, piperazine, quinoline, furan, tetrahydropyridine, piperidine, or the following group:

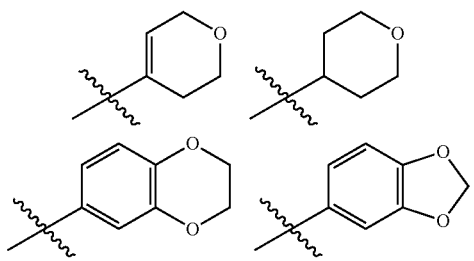

the indazole of

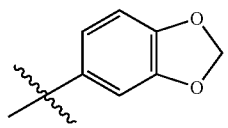 [SMILES: *c1ccc2c(c1)OCO2]

may be indazol-5-yl or indazol-6-yl,
the pyridine of

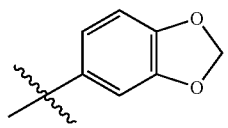 [SMILES: *c1ccc2c(c1)OCO2]

may be pyridine-3-yl,
the indole of

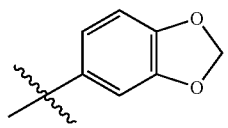 [SMILES: *c1ccc2c(c1)OCO2]

may be indol-4-yl, indol-5-yl or indol-6-yl,
the pyrimidine of

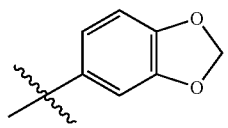 [SMILES: *c1ccc2c(c1)OCO2]

may be pyrimidin-5-yl,
the quinoline of

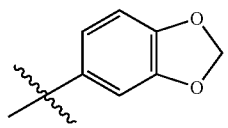 [SMILES: *c1ccc2c(c1)OCO2]

may be quinolin-7yl,
the furan of

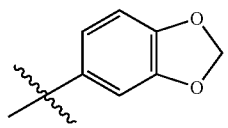 [SMILES: *c1ccc2c(c1)OCO2]

may be furan-3-yl,
the tetrahydropyridine of

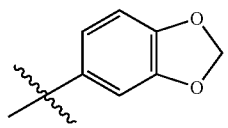 [SMILES: *c1ccc2c(c1)OCO2]

may be 1,2,3,6-tetrahydropyridin-4-yl, the piperidine of

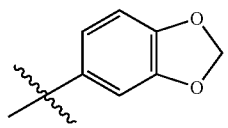 [SMILES: *c1ccc2c(c1)OCO2]

may be piperidin-4-yl,
the

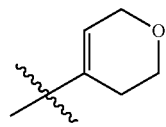

of

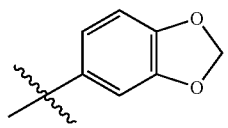 [SMILES: *c1ccc2c(c1)OCO2]

may be benzo[d][1,3]dioxol-5-yl,
the

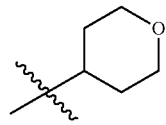

of

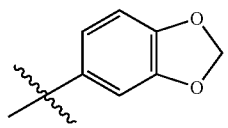 [SMILES: *c1ccc2c(c1)OCO2]

may be 3,6-dihydro-2H-pyran-4yl,
the

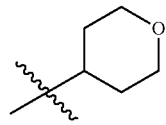

of

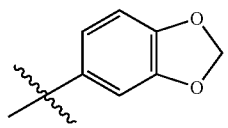 [SMILES: *c1ccc2c(c1)OCO2]

may be tetrahydro-2H-pyran-4-yl,
the

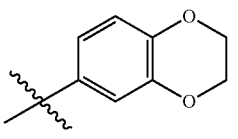 [SMILES: *c1ccc2c(c1)OCCO2]

of

may be 2,3-dihydrobenzo[b][1,4]dioxin-6-yl, x, y and z are each independently an integer of 0 or 1, and $R_{g1}$, $R_{g2}$ and $R_{g3}$ are each independently selected from hydrogen; hydroxy; —$C_{1-3}$ alkyl; —$CF_3$; —$C_{1-6}$ straight or branched chain alkoxy; —$C_{2-6}$ straight or branched chain alkyl alkoxy; —C(=O)$CH_3$; —$C_{1-4}$ straight or branched chain alcohol; —N($CH_3$)$_2$; —F; —Cl; —Br; —I; phenyl; —S((=O)$_2$)$CH_3$; or the following group:

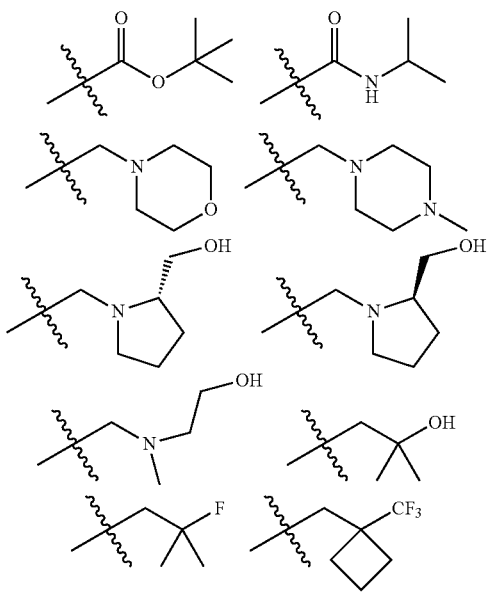

In according to embodiments of the present invention, The compound represented by the above Formula II may preferably include following structure:
wherein
a is an integer of 0, 1 or 2,
K is independently hydrogen, —F, —Cl, —Br or —I,
Y is

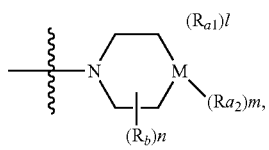

M is C, O or N,
l and m are each independently an integer of 0 or 1,
$R_{a1}$ and $R_{a2}$ are each independently hydrogen; hydroxy; —$C_{1-4}$ straight or branched chain alkyl, unsubstituted or substituted with one or more F, Cl, Br or I; —$C_{1-4}$ straight or branched chain alcohol; benzhydryl; —$C_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, O$CH_3$, $CH_3$, $CH_2CH_3$, F, Cl, Br, or I); a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, O$CH_3$, $CH_3$, $CH_2CH_3$, F, Cl, Br, or I); phenyl, unsubstituted or substituted with one or more F, Cl, Br, I, $C_{1-4}$ alkoxy, $C_{1-2}$ alkyl, or hydroxy; benzyl, unsubstituted or substituted with one or more F, Cl, Br, I, $C_{1-4}$ alkoxy, $C_{1-2}$ alkyl, or hydroxy; —S((=O)$_2$)$CH_3$; —F; —Cl; —Br; —I; —$C_{1-6}$ straight or branched chain alkoxy; —$C_{2-6}$ alkyl alkoxy; —C(=O)$R_x$, wherein $R_x$ is straight or branched $C_{1-3}$ alkyl or $C_{3-10}$ cycloalkyl; or,

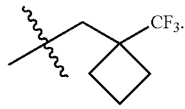 [SMILES: *CC1(C(F)(F)F)CCC1]

n is an integer of 0, 1, or 2,
$R_b$ is hydrogen; —$C_{1-6}$ straight or branched chain alkyl, unsubstituted or substituted with one or more F, Cl, Br, or I; and
Z is selected from the group consisting of the following compounds:

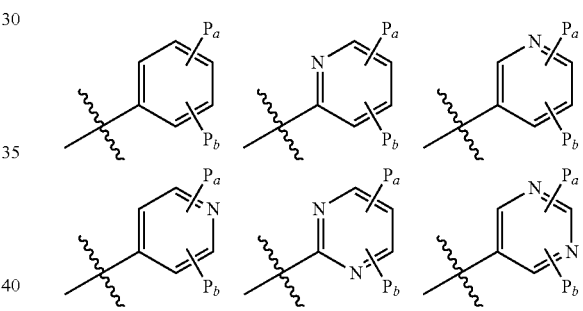

wherein $P_a$ and $P_b$ are each independently hydrogen; hydroxy; —$C_{1-4}$ straight or branched chain alkyl, unsubstituted or substituted with one or more F, Cl, Br or I; —F; —Cl; —Br; —I; —$CF_3$; —O$CF_3$; —CN; —$C_{1-6}$ straight or branched alkoxy; —$C_{2-6}$ straight or branched alkyl alkoxy; —$CH_2F$; —$C_{1-3}$ alcohol;

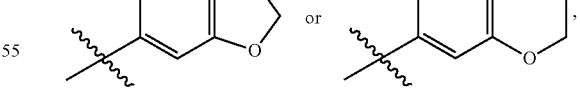

the

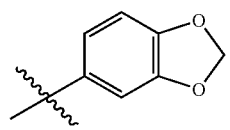 [SMILES: *c1ccc2c(c1)OCO2]

may be benzo[d][1,3]dioxol-5-yl,

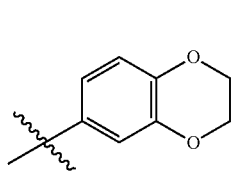 [SMILES: *c1ccc2c(c1)OCCO2]

may be 2,3-dihydrobenzo[b][1,4]dioxin-6-yl.

More preferably, the compound represented by the above Formula II may be a compound represented by the following Formula III:

[Formula III]

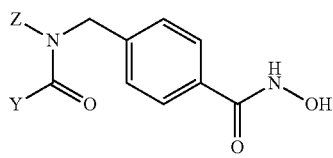

Wherein
Y is

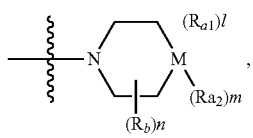

M is C, O or N, l and m are each independently an integer of 0 or 1, $R_{a1}$ and $R_{a2}$ are each independently hydrogen; —$C_{1-4}$ straight or branched chain alkyl, unsubstituted or substituted with one or more F, Cl, Br or I; —$C_{1-4}$ straight or branched chain alkyl substituted with a phenyl, pyridine or pyrimidine (wherein the phenyl, pyridine or pyrimidine may be unsubstituted or at least one hydrogen may be optionally substituted with OH, $OCH_3$, $CH_3$, $CH_2CH_3$, F, Cl, Br, or I);

n is an integer of 0, 1, or 2, $R_b$ is hydrogen; —$C_{1-6}$ straight or branched chain alkyl, unsubstituted or substituted with one or more F, Cl, Br, or I; and Z is selected from the group consisting of the following compounds:

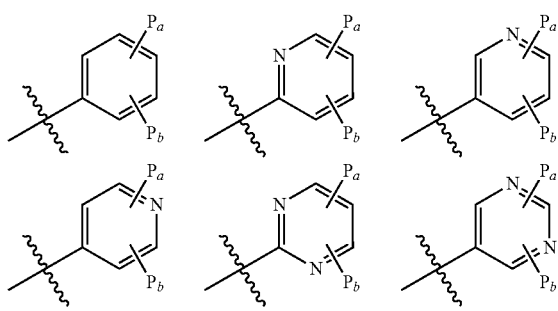

wherein $P_a$ and $P_b$ are each independently hydrogen; —F; —Cl; —Br; —$CF_3$; —$OCF_3$; —$CH_2F$;

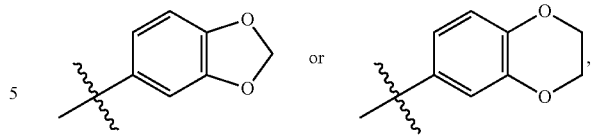

the

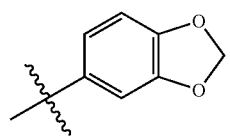 [SMILES: *c1ccc2c(c1)OCO2]

may be benzo[d][1,3]dioxol-5-yl,
the

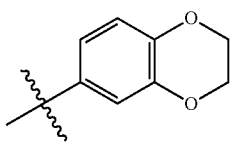 [SMILES: *c1ccc2c(c1)OCCO2]

may be 2,3-dihydrobenzo[b][1,4]dioxin-6-yl.

The compound represented by the above Formula I may be a compound represented by the following Formula I-1:

[Formula I-1]

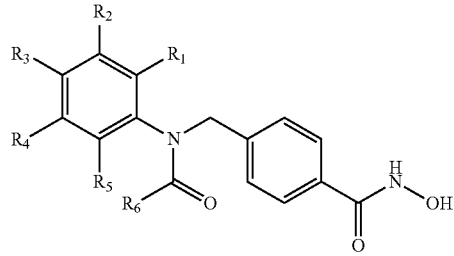

wherein $R_1$ to $R_5$ are each independently hydrogen, —F, —Cl, —Br, —I, —$CF_3$, —$CH_3$, —$CH_2CH_3$, —$OCH_3$, or —$OCF_3$ and $R_6$ is piperidine; piperidine substituted with one or more $C_{1-3}$ alkyl; morpholine; morpholine substituted with one or more $C_{1-3}$ alkyl; piperazine; piperazine substituted with one or more $C_{1-3}$ alkyl, —C(=O)$CH_3$, benzhydryl, phenyl, benzyl, pyridine, —$C_{1-2}$ alkyl morpholine, or morpholine ethanone (wherein phenyl or benzyl may be unsubstituted or at least one hydrogen may be optionally substituted with —$OCH_3$, —$CH_3$, —$CH_2CH_3$, —F, —Cl, —Br, or —I); (piperazinyl)ethanone; (R)-3-fluoropyrrolidine; (S)-3-fluoropyrrolidine; (R)-pyrrolidin-2-yl-methanol; (S)-2-(trifluoromethyl)pyrrolidine; azetidine; difluoroazetidine; phenylpiperidinol; or oxazepane.

Preferably, the compound represented by the above Formula I-1 may be Compound 255, 256, 279, 374, 385, 386, 389, 390, 391, 392, 393, 394, 413, 414, 415, 416, 438, 439, 440, 441, 453, 454, 455, 456, 457, 458, 459, 460, 461, 477, 478, 479, 480, 481, 482, 484, 485, 486, 494, 495, 496, 497, 498, 520, 521, 522, 529, 530, 543, 544, 545, 580, 683, 684, 717, 718, 771, 772, 773, 774, 776, 791, 800 or 801 described in the present invention.

The compound represented by the above Formula I may be a compound represented by the following Formula I-2:

[Formula I-2]

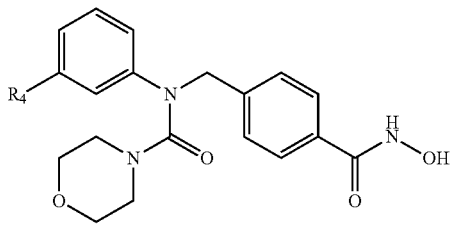

wherein R₄ is indole, pyridine, difluorophenyl, (dimethylamino)pyridine, pyrimidine, bis(trifluorophenyl)phenyl, 2,3-dihydrobenzo[b][1,4]dioxin, trimethoxyphenyl, dimethylphenyl, furan, 3,6-dihydro-2H-pyran, 1-methyl-1,2,3,6-tetrahydropyridine, 1-Boc-1,2,3,6-tetrahydropyridine, benzo[d][1,3]dioxole, or tetrahydro-2H-pyran.

Preferably, the compound represented by the above Formula I-2 may be Compound 261, 262, 263, 395, 396, 397, 398, 399, 400, 401, 402, 403, 404, 405, 418 or 483 described in the present invention.

The compound represented by the above Formula I may be a compound represented by the following Formula I-3:

[Formula I-3]

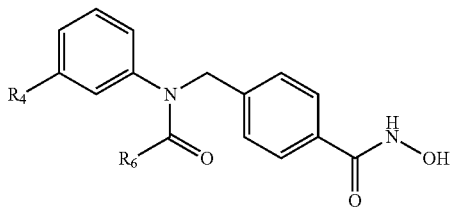

wherein R₄ is 1-C$_{1-3}$ alkyl-1H-indazole and R₆ is morpholine, piperidine, or piperazine, wherein the piperazine is unsubstituted or substituted with —C$_{1-3}$ alkyl.

Preferably, the compound represented by the above Formula I-3 may be Compound 252, 253, 254 or 260 described in the present invention.

The compound represented by the above Formula I may be a compound represented by the following Formula I-4:

[Formula I-4]

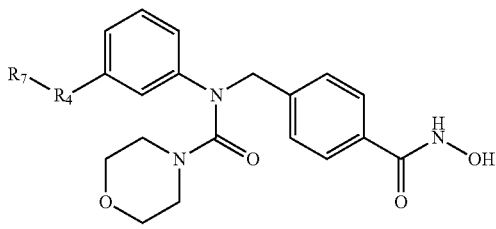

wherein R₄ is tetrahydropyridine or piperidine and R₇ is nothing, acetyl, methylsulfonyl, N-isopropylcarbamoyl, 2-hydroxy-2-methylpropyl, 2-fluoro-2-methylpropyl, t-butylcarboxylate.

Preferably, the compound represented by the above Formula I-4 may be Compound 419, 420, 489, 490, 491, 492, 493, 517 or 518 described in the present invention.

The compound represented by the above Formula I may be a compound represented by the following Formula I-5:

[Formula I-5]

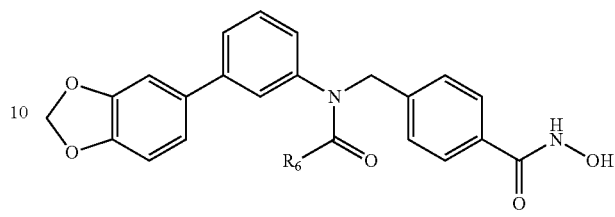

wherein R₆ is piperidine, piperidinol, dimethylmorpholine, phenylpiperidinol, methylpiperazine, 2-(piperazin-1-yl)ethanol, pyrrolidine, (S)-pyrrolidin-2-ylmethanol, cyclopropyl(piperazin-1-yl)methanol, or azetidine.

Preferably, the compound represented by the above Formula I-5 may be Compound 462, 463, 464, 465, 466, 467, 468, 469, 470 or 471 described in the present invention.

The compound represented by the above Formula I may be a compound represented by the following Formula I-6:

[Formula I-6]

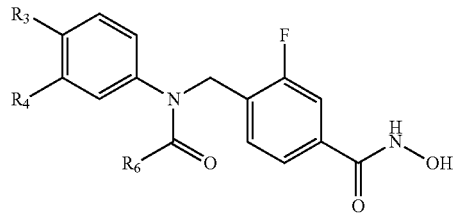

wherein R₃ and R₄ are each independently hydrogen, —F, —Cl, —Br, —I, —CF₃, benzo[d][1,3]dioxole or dihydro-2H-pyran, and R₆ is morpholine, hydroxypiperidine or difluoroazetidine.

Preferably, the compound represented by the above Formula I-6 may be Compound 487, 488, 511, 512, 513, 514, 532, 577 or 578 described in the present invention.

The compound represented by the above Formula I may be a compound represented by the following Formula I-7:

[Formula I-7]

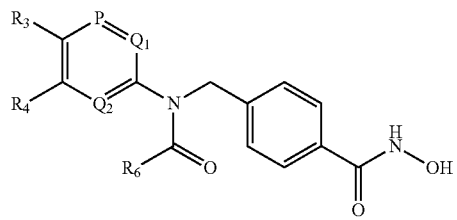

wherein P, Q₁ and Q₂ are each independently C or N, R₃ and R₄ are each independently hydrogen, —F, —Cl, —Br, —I, or —CF₃, and R₆ is piperidine, piperidine substituted with one or more C$_{1-3}$ alkyl, morpholine, morpholine substituted with one or more C$_{1-3}$ alkyl, phenyltetrahydropyridine, piperazine substituted with one or more C$_{1-3}$ alkyl, benzylpiperazine, phenylpiperidinol, (methoxyphenyl)piperazine, (fluorophenyl)piperazine, pyrrolidine, diazepane substituted with one or more $C_{1-3}$ alkyl, azetidine, (dimethylphenyl)piperazine, (1,4-diazepan-1-yl)ethanone, cyclopropyl(piperazin-1-yl)methanone, or fluoropyrrolidine.

Preferably, the compound represented by the above Formula I-7 may be Compound 280, 281, 309, 311, 312, 313, 341, 342, 343, 352, 353, 354, 355, 356, 357, 358, 376, 377, 379, 450, 451, 533, 778, 826, 827, 828 or 829 described in the present invention.

The compound represented by the above Formula I may be a compound represented by the following Formula I-8:

[Formula I-8]

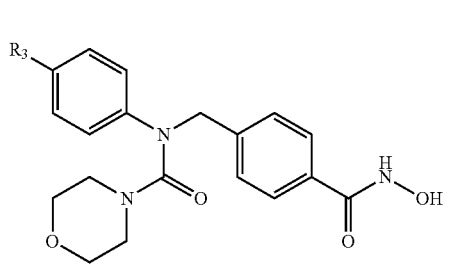

wherein $R_3$ is 1-methyl-1H-indazole, phenyl, difluorophenyl, pyridine, pyrimidine, quinoline, biphenyl, indole, trimethoxyphenyl, bis(trifluoromethyl)phenyl, —F, —Cl, —Br, or —I.

Preferably, the compound represented by the above Formula I-8 may be Compound 329, 330, 331, 332, 333, 334, 335, 336, 337, 338, 339, 340 or 372 described in the present invention.

The compound represented by the above Formula I may be a compound represented by the following Formula I-9:

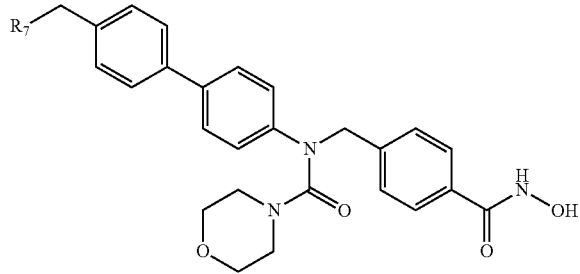

wherein $R_7$ is morpholine, piperazine substituted with one or more $C_{1-3}$ alkyl, (S)-pyrrolidin-2-ylmethanol, or (methylamino)ethanol.

Preferably, the compound represented by the above Formula I-9 may be Compound 380, 381, 382 or 383 described in the present invention.

The compound represented by the above Formula I may be a compound represented by the following Formula I-10:

[Formula I-10]

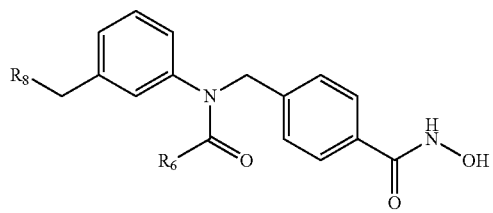

wherein $R_8$ is hydroxy, —F, —Cl, —Br, or —I and $R_6$ is morpholine, ethylpiperazine, or piperazinyl-2-fluoro-2-methylpropyl.

Preferably, the compound represented by the above Formula I-10 may be Compound 499, 500, 765 or 766 described in the present invention.

The compound represented by the above Formula I may be a compound represented by the following Formula I-11:

[Formula I-11]

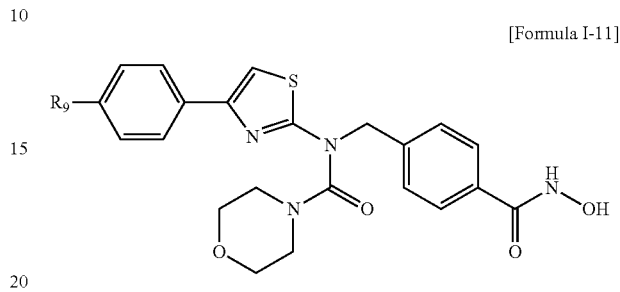

wherein $R_9$ is hydrogen, hydroxy, —F, —Cl, —Br, or —I.

Preferably, the compound represented by the above Formula I-11 may be Compound 370 or 371 described in the present invention.

The compound represented by the above Formula I may be a compound represented by the following Formula I-12:

[Formula I-12]

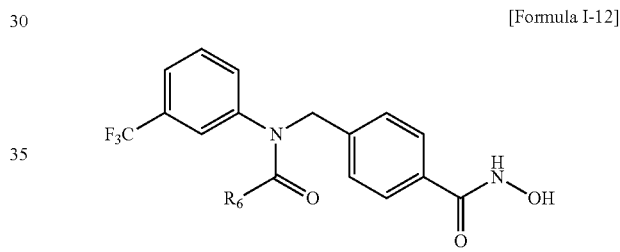

wherein $R_6$ may be selected from the following group:

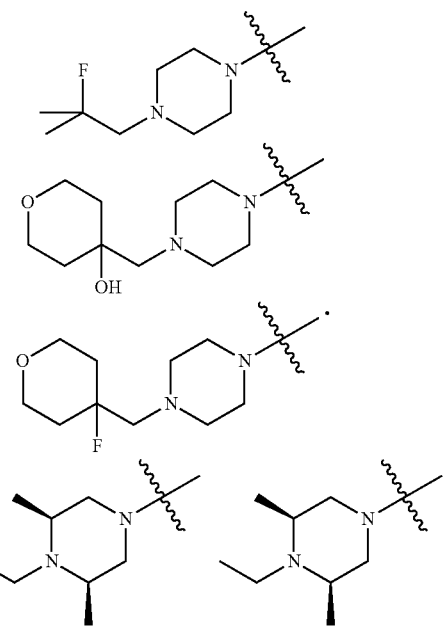

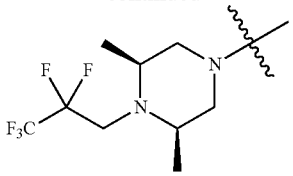

Preferably, the compound represented by the above Formula I-12 may be Compound 531, 651, 716, 797, 802 or 803 described in the present invention.

The compounds represented by Formulas I and I-1 to I-12 are as follows:

| | |
|---|---|
| 252 | N-(4-(hydroxycarbamoyl)benzyl)-N-(3-(1-methyl-1H-indazol-5-yl)phenyl)morpholine-4-carboxamide |
| 253 | N-(4-(hydroxycarbamoyl)benzyl)-4-methyl-N-(3-(1-methyl-1H-indazol-5-yl)phenyl)piperazine-1-carboxamide |
| 254 | N-(4-(hydroxycarbamoyl)benzyl)-N-(3-(1-methyl-1H-indazol-6-yl)phenyl)morpholine-4-carboxamide |
| 255 | N-(3-bromophenyl)-N-(4-(hydroxycarbamoyl)benzyl)morpholine-4-carboxamide |
| 256 | N-(3-bromophenyl)-N-(4-(hydroxycarbamoyl)benzyl)-4-methylpiperazine-1-carboxamide |
| 260 | N-(4-(hydroxycarbamoyl)benzyl)-N-(3-(1-methyl-1H-indazol-5-yl)phenyl)piperidine-1-carboxamide |
| 261 | N-(3-(1H-indol-6-yl)phenyl)-N-(4-(hydroxycarbamoyl)benzyl)morpholine-4-carboxamide |
| 262 | N-(4-(hydroxycarbamoyl)benzyl)-N-(3-(pyridin-3-yl)phenyl)morpholine-4-carboxamide |
| 263 | N-(3-(1H-indol-5-yl)phenyl)-N-(4-(hydroxycarbamoyl)benzyl)morpholine-4-carboxamide |
| 279 | N-(4-(hydroxycarbamoyl)benzyl)-N-phenylmorpholine-4-carboxamide |
| 280 | N-(4-(hydroxycarbamoyl)benzyl)-N-(pyridin-2-yl)morpholine-4-carboxamide |
| 281 | N-(4-(hydroxycarbamoyl)benzyl)-N-(pyridin-3-yl)morpholine-4-carboxamide |
| 309 | 4-benzyl-N-(4-(hydroxycarbamoyl)benzyl)-N-(pyrimidin-2-yl)piperazine-1-carboxamide |
| 311 | 4-hydroxy-N-(4-(hydroxycarbamoyl)benzyl)-4-phenyl-N-(pyrimidin-2-yl)piperidine-1-carboxamide |
| 312 | N-(4-(hydroxycarbamoyl)benzyl)-N-(pyrimidin-2-yl)morpholine-4-carboxamide |
| 313 | N-(4-(hydroxycarbamoyl)benzyl)-2,6-dimethyl-N-(pyrimidin-2-yl)morpholine-4-carboxamide |
| 329 | N-(4-(hydroxycarbamoyl)benzyl)-N-(4-(1-methyl-1H-indazol-6-yl)phenyl)morpholine-4-carboxamide |
| 330 | N-(biphenyl-4-yl)-N-(4-(hydroxycarbamoyl)benzyl)morpholine-4-carboxamide |
| 331 | N-(3',5'-difluorobiphenyl-4-yl)-N-(4-(hydroxycarbamoyl)benzyl)morpholine-4-carboxamide |
| 332 | N-(4-(hydroxycarbamoyl)benzyl)-N-(4-(pyridin-3-yl)phenyl)morpholine-4-carboxamide |
| 333 | N-(4-(hydroxycarbamoyl)benzyl)-N-(4-(pyrimidin-5-yl)phenyl)morpholine-4-carboxamide |
| 334 | N-(4-(hydroxycarbamoyl)benzyl)-N-(4-(quinolin-7-yl)phenyl)morpholine-4-carboxamide |
| 335 | N-(4-(hydroxycarbamoyl)benzyl)-N-(4-(biphenyl-3-yl)phenyl)morpholine-4-carboxamide |
| 336 | N-(4-(1H-indol-5-yl)phenyl)-N-(4-(hydroxycarbamoyl)benzyl)morpholine-4-carboxamide |
| 337 | N-(4-(1H-indol-6-yl)phenyl)-N-(4-(hydroxycarbamoyl)benzyl)morpholine-4-carboxamide |
| 338 | N-(4-(hydroxycarbamoyl)benzyl)-N-(3',4',5'-trimethoxybiphenyl-4-yl)morpholine-4-carboxamide |
| 339 | N-(3',5'-bis(trifluoromethyl)biphenyl-4-yl)-N-(4-(hydroxycarbamoyl)benzyl)morpholine-4-carboxamide |
| 340 | N-(4-(1H-indol-4-yl)phenyl)-N-(4-(hydroxycarbamoyl)benzyl)morpholine-4-carboxamide |
| 341 | N-(4-(hydroxycarbamoyl)benzyl)-N-(pyridin-2-yl)piperidine-1-carboxamide |
| 342 | N-(4-(hydroxycarbamoyl)benzyl)-4-methyl-N-(pyridin-2-yl)piperidine-1-carboxamide |
| 343 | N-(4-(hydroxycarbamoyl)benzyl)-2,6-dimethyl-N-(pyridin-2-yl)morpholine-4-carboxamide |
| 352 | N-(4-(hydroxycarbamoyl)benzyl)-4-phenyl-N-(pyridin-2-yl)-5,6-dihydropyridine-1(2H)-carboxamide |
| 353 | N-(4-(hydroxycarbamoyl)benzyl)-4-methyl-N-(pyridin-2-yl)piperazine-1-carboxamide |
| 354 | 4-ethyl-N-(4-(hydroxycarbamoyl)benzyl)-N-(pyridin-2-yl)piperazine-1-carboxamide |
| 355 | 4-benzyl-N-(4-(hydroxycarbamoyl)benzyl)-N-(pyridin-2-yl)piperazine-1-carboxamide |
| 356 | N-(4-(hydroxycarbamoyl)benzyl)-4-(2-methoxyphenyl)-N-(pyridin-2-yl)piperazine-1-carboxamide |
| 357 | 4-(4-fluorophenyl)-N-(4-(hydroxycarbamoyl)benzyl)-N-(pyridin-2-yl)piperazine-1-carboxamide |
| 358 | N-(4-(hydroxycarbamoyl)benzyl)-N-(pyridin-2-yl)pyrrolidine-1-carboxamide |
| 370 | N-(4-(hydroxycarbamoyl)benzyl)-N-(4-phenylthiazol-2-yl)morpholine-4-carboxamide |
| 371 | N-(4-(4-chlorophenyl)thiazol-2-yl)-N-(4-(hydroxycarbamoyl)benzyl)morpholine-4-carboxamide |
| 372 | N-(4-bromophenyl)-N-(4-(hydroxycarbamoyl)benzyl)morpholine-4-carboxamide |
| 374 | N-(4-(hydroxycarbamoyl)benzyl)-N-(3-(trifluoromethyl)phenyl)morpholine-4-carboxamide |
| 376 | N-(4-(hydroxycarbamoyl)benzyl)-4-methyl-N-(pyridin-2-yl)-1,4-diazepane-1-carboxamide |
| 377 | N-(4-(hydroxycarbamoyl)benzyl)-N-(pyridin-2-yl)azetidine-1-carboxamide |
| 379 | 4-(3,4-dimethylphenyl)-N-(4-(hydroxycarbamoyl)benzyl)-N-(pyridin-2-yl)piperazine-1-carboxamide |
| 380 | N-(4-(hydroxycarbamoyl)benzyl)-N-(4'-(morpholinomethyl)biphenyl-4-yl)morpholine-4-carboxamide |
| 381 | N-(4-(hydroxycarbamoyl)benzyl)-N-(4'-((4-methylpiperazin-1-yl)methyl)biphenyl-4-yl)morpholine-4-carboxamide |
| 382 | (S)-N-(4-(hydroxycarbamoyl)benzyl)-N-(4'-((2-(hydroxymethyl)pyrrolidin-1-yl)methyl)biphenyl-4-yl)morpholine-4-carboxamide |
| 383 | N-(4-(hydroxycarbamoyl)benzyl)-N-(4'-(((2-hydroxyethyl)(methyl)amino)methyl)biphenyl-4-yl)morpholine-4-carboxamide |
| 385 | N-(4-(hydroxycarbamoyl)benzyl)-N-(4-(trifluoromethyl)phenyl)morpholine-4-carboxamide |
| 386 | N-(4-(hydroxycarbamoyl)benzyl)-2,6-dimethyl-N-(3-(trifluoromethyl)phenyl)morpholine-4-carboxamide |
| 389 | N-(4-chloro-3-(trifluoromethyl)phenyl)-N-(4-(hydroxycarbamoyl)benzyl)piperidine-1-carboxamide |
| 390 | N-(4-chloro-3-(trifluoromethyl)phenyl)-N-(4-(hydroxycarbamoyl)benzyl)-4-methylpiperidine-1-carboxaraide |
| 391 | N-(4-chloro-3-(trifluoromethyl)phenyl)-N-(4-(hydroxycarbamoyl)benzyl)morpholine-4-carboxamide |
| 392 | N-(4-chloro-3-(trifluoromethyl)phenyl)-N-(4-(hydroxycarbamoyl)benzyl)-2,6-dimethylmorpholine-4-carboxamide |
| 393 | N-(4-chloro-3-(trifluoromethyl)phenyl)-N-(4-(hydroxycarbamoyl)benzyl)-4-methylpiperazine-1-carboxamide |
| 394 | N-(4-chloro-3-(trifluoromethyl)phenyl)-4-ethyl-N-(4-(hydroxycarbamoyl)benzyl)piperazine-1-carboxamide |
| 395 | N-(3',5'-difluorobiphenyl-3-yl)-N-(4-(hydroxycarbamoyl)benzyl)morpholine-4-carboxamide |
| 396 | N-(3-(6-(dimethylamino)pyridin-3-yl)phenyl)-N-(4-(hydroxycarbamoyl)benzyl)morpholine-4-carboxamide |
| 397 | N-(4-(hydroxycarbamoyl)benzyl)-N-(3-(pyrimidin-5-yl)phenyl)morpholine-4-carboxamide |
| 398 | N-(3',5'-bis(trifluoromethyl)biphenyl-3-yl)-N-(4-(hydroxycarbamoyl)benzyl)morpholine-4-carboxamide |
| 399 | N-(3-(2,3-dihydrobenzo[b][1,4]dioxin-6-yl)phenyl)-N-(4-(hydroxycarbamoyl)benzyl)morpholine-4-carboxamide |
| 400 | N-(4-(hydroxycarbamoyl)benzyl)-N-(3',4',5'-trimethoxybiphenyl-3-yl)morpholine-4-carboxamide |
| 401 | N-(2',6'-dimethylbiphenyl-3-yl)-N-(4-(hydroxycarbamoyl)benzyl)morpholine-4-carboxamide |
| 402 | N-(3-(furan-3-yl)phenyl)-N-(4-(hydroxycarbamoyl)benzyl)morpholine-4-carboxamide |
| 403 | N-(3-(3,6-dihydro-2H-pyran-4-yl)phenyl)-N-(4-(hydroxycarbamoyl)benzyl)morpholine-4-carboxamide |
| 404 | N-(4-(hydroxycarbamoyl)benzyl)-N-(3-(1-methyl-1,2,3,6-tetrahydropyridin-4-yl)phenyl)morpholine-4-carboxamide |

| | |
|---|---|
| 405 | tert-butyl-4-(3-(N-(4-(hydroxycarbamoyl)benzyl)morpholine-4-carboxamido)phenyl)-5,6-dihydropyridine-1(2H)-carboxylate |
| 413 | N-(2,4-difluorophenyl)-N-(4-(hydroxycarbamoyl)benzyl)morpholine-4-carboxamide |
| 414 | N-(2,4-difluorophenyl)-N-(4-(hydroxycarbamoyl)benzyl)piperidine-1-carboxamide |
| 415 | N-(2,4-difluorophenyl)-N-(4-(hydroxycarbamoyl)benzyl)-2,6-dimethylmorpholine-4-carboxamide |
| 416 | N-(2,4-difluorophenyl)-N-(4-(hydroxycarbamoyl)benzyl)-4-methylpiperazine-1-carboxamide |
| 418 | N-(3-(benzo[d][1,3]dioxol-5-yl)phenyl)-N-(4-(hydroxycarbamoyl)benzyl)morpholine-4-carboxamide |
| 419 | N-(3-(1-acetyl-1,2,3,6-tetrahydropyridin-4-yl)phenyl)-N-(4-(hydroxycarbamoyl)benzyl)morpholine-4-carboxamide |
| 420 | N-(4-(hydroxycarbamoyl)benzyl)-N-(3-(1-(methylsulfonyl)-1,2,3,6-tetrahydropyridin-4-yl)phenyl)morpholine-4-carboxamide |
| 438 | N-(2-fluoro-4-methylphenyl)-N-(4-(hydroxycarbamoyl)benzyl)piperidine-1-carboxamide |
| 439 | N-(2-fluoro-4-methylphenyl)-N-(4-(hydroxycarbamoyl)benzyl)morpholine-4-carboxamide |
| 440 | N-(2-fluoro-4-methylphenyl)-N-(4-(hydroxycarbamoyl)benzyl)-2,6-dimethylmorpholine-4-carboxamide |
| 441 | N-(2-fluoro-4-methylphenyl)-N-(4-(hydroxycarbamoyl)benzyl)-4-methylpiperazine-1-carboxamide |
| 450 | 4-acetyl-N-(4-(hydroxycarbamoyl)benzyl)-N-(pyridin-2-yl)-1,4-diazepane-1-carboxamide |
| 451 | 4-(cyclopropanecarbonyl)-N-(4-(hydroxycarbamoyl)benzyl)-N-(pyridin-2-yl)piperazine-1-carboxamide |
| 453 | 4-ethyl-N-(2-fluoro-4-methylphenyl)-N-(4-(hydroxycarbamoyl)benzyl)piperazine-1-carboxamide |
| 454 | N-(2-fluoro-4-methylphenyl)-N-(4-(hydroxycarbamoyl)benzyl)-4-(2-methoxyphenyl)piperazine-1-carboxamide |
| 455 | N-(2-fluoro-4-methylphenyl)-4-(4-fluorophenyl)-N-(4-(hydroxycarbamoyl)benzyl)piperazine-1-carboxamide |
| 456 | N-(3-chloro-4-fluorophenyl)-N-(4-(hydroxycarbamoyl)benzyl)piperidine-1-carboxamide |
| 457 | N-(3-chloro-4-fluorophenyl)-N-(4-(hydroxycarbamoyl)benzyl)-4-methylpiperidine-1-carboxamide |
| 458 | N-(3-chloro-4-fluorophenyl)-N-(4-(hydroxycarbamoyl)benzyl)morpholine-4-carboxamide |
| 459 | N-(4-(hydroxycarbamoyl)benzyl)-4-methyl-N-(3-(trifluoromethyl)phenyl)piperidine-1-carboxamide |
| 460 | N-(4-(hydroxycarbamoyl)benzyl)-N-(3-(trifluoromethyl)phenyl)piperidine-1-carboxamide |
| 461 | 4-ethyl-N-(4-(hydroxycarbamoyl)benzyl)-N-(3-(trifluoromethyl)phenyl)piperazine-1-carboxamide |
| 462 | N-(3-(benzo[d][1,3]dioxol-5-yl)phenyl)-N-(4-(hydroxycarbamoyl)benzyl)piperidine-1-carboxamide |
| 463 | N-(3-(benzo[d][1,3]dioxol-5-yl)phenyl)-4-hydroxy-N-(4-(hydroxycarbamoyl)benzyl)piperidine-1-carboxamide |
| 464 | N-(3-(benzo[d][1,3]dioxol-5-yl)phenyl)-N-(4-(hydroxycarbamoyl)benzyl)-2,6-dimethylmorpholine-4-carboxamide |
| 465 | N-(3-(benzo[d][1,3]dioxol-5-yl)phenyl)-4-hydroxy-N-(4-(hydroxycarbamoyl)benzyl)-4-phenylpiperidine-1-carboxamide |
| 466 | N-(3-(benzo[d][1,3]dioxol-5-yl)phenyl)-N-(4-(hydroxycarbamoyl)benzyl)-4-methylpiperazine-1-carboxamide |
| 467 | N-(3-(benzo[d][1,3]dioxol-5-yl)phenyl)-N-(4-(hydroxycarbamoyl)benzyl)-4-(2-hydroxyethyl)piperazine-1-carboxamide |
| 468 | N-(3-(benzo[d][1,3]dioxol-5-yl)phenyl)-N-(4-(hydroxycarbamoyl)benzyl)pyrrolidine-1-carboxamide |
| 469 | (S)-N-(3-(benzo[d][1,3]dioxol-5-yl)phenyl)-N-(4-(hydroxycarbamoyl)benzyl)-2-(hydroxymethyl)pyrrolidine-1-carboxamide |
| 470 | N-(3-(benzo[d][1,3]dioxol-5-yl)phenyl)-4-(cyclopropanecarbonyl)-N-(4-(hydroxycarbamoyl)benzyl)piperazine-1-carboxamide |
| 471 | N-(3-(benzo[d][1,3]dioxol-5-yl)phenyl)-N-(4-(hydroxycarbamoyl)benzyl)azetidine-1-carboxamide |
| 477 | N-(3-chloro-4-fluorophenyl)-N-(4-(hydroxycarbamoyl)benzyl)-2,6-dimethylmorpholine-4-carboxamide |
| 478 | N-(3-chloro-4-fluorophenyl)-N-(4-(hydroxycarbamoyl)benzyl)-4-methylpiperazine-1-carboxamide |
| 479 | N-(3-chloro-4-fluorophenyl)-4-ethyl-N-(4-(hydroxycarbamoyl)benzyl)piperazine-1-carboxamide |
| 480 | 4-benzyl-N-(3-chloro-4-fluorophenyl)-N-(4-(hydroxycarbamoyl)benzyl)piperazine-1-carboxamide |
| 481 | N-(3-chloro-4-fluorophenyl)-N-(4-(hydroxycarbamoyl)benzyl)-4-(2-methoxyphenyl)piperazine-1-carboxamide |
| 482 | N-(3-chloro-4-fluorophenyl)-4-(4-fluorophenyl)-N-(4-(hydroxycarbamoyl)benzyl)piperazine-1-carboxamide |
| 483 | N-(4-(hydroxycarbamoyl)benzyl)-N-(3-(tetrahydro-2H-pyran-4-yl)phenyl)morpholine-4-carboxamide |
| 484 | N-(4-(hydroxycarbamoyl)benzyl)-N-(3-methoxyphenyl)morpholine-4-carboxamide |
| 485 | 3,3-difluoro-N-(4-(hydroxycarbamoyl)benzyl)-N-(4-(trifluoromethyl)phenyl)azetidine-1-carboxamide |
| 486 | 4-hydroxy-N-(4-(hydroxycarbamoyl)benzyl)-4-phenyl-N-(4-(trifluoromethyl)phenyl)piperidine-1-carboxamide |
| 487 | N-(3-bromophenyl)-N-(2-fluoro-4-(hydroxycarbamoyl)benzyl)morpholine-4-carboxamide |
| 488 | N-(3-bromophenyl)-N-(2-fluoro-4-(hydroxycarbamoyl)benzyl)-4-hydroxypiperidine-1-carboxamide |
| 489 | tert-butyl-4-(3-(N-(4-(hydroxycarbamoyl)benzyl)morpholine-4-carboxamido)phenyl)piperidine-1-carboxylate |
| 490 | N-(3-(1-acetylpiperidin-4-yl)phenyl)-N-(4-(hydroxycarbamoyl)benzyl)morpholine-4-carboxamide |
| 491 | N-(4-(hydroxycarbamoyl)benzyl)-N-(3-(1-(methylsulfonyl)piperidin-4-yl)phenyl)morpholine-4-carboxamide |
| 492 | N-(4-(hydroxycarbamoyl)benzyl)-N-(3-(1-(isopropylcarbamoyl)piperidin-4-yl)phenyl)morpholine-4-carboxamide |
| 493 | N-(4-(hydroxycarbamoyl)benzyl)-N-(3-(piperidin-4-yl)phenyl)morpholine-4-carboxamide hydrochloride |
| 494 | 4-acetyl-N-(4-(hydroxycarbamoyl)benzyl)-N-(3-(trifluoromethyl)phenyl)piperazine-1-carboxamide |
| 495 | (R)-3-fluoro-N-(4-(hydroxycarbamoyl)benzyl)-N-(3-(trifluoromethyl)phenyl)pyrrolidine-1-carboxamide |
| 496 | (S)-3-fluoro-N-(4-(hydroxycarbamoyl)benzyl)-N-(3-(trifluoromethyl)phenyl)pyrrolidine-1-carboxamide |
| 497 | (R)-N-(4-(hydroxycarbamoyl)benzyl)-2-(hydroxymethyl)-N-(3-(trifluoromethyl)phenyl)pyrrolidine-1-carboxamide |
| 498 | (S)-N-(4-(hydroxycarbamoyl)benzyl)-2-(trifluoromethyl)-N-(3-(trifluoromethyl)phenyl)pyrrolidine-1-carboxamide |
| 499 | N-(4-(hydroxycarbamoyl)benzyl)-N-(3-(hydroxymethyl)phenyl)morpholine-4-carboxamide |
| 500 | N-(3-(fluoromethyl)phenyl)-N-(4-(hydroxycarbamoyl)benzyl)morpholine-4-carboxamide |
| 511 | N-(3-(benzo[d][1,3]dioxol-5-yl)phenyl)-N-(2-fluoro-4-(hydroxycarbamoyl)benzyl)morpholine-4-carboxamide |
| 512 | N-(3-(3,6-dihydro-2H-pyran-4-yl)phenyl)-N-(2-fluoro-4-(hydroxycarbamoyl)benzyl)morpholine-4-carboxamide |
| 513 | N-(3-(benzo[d][1,3]dioxol-5-yl)phenyl)-N-(2-fluoro-4-(hydroxycarbamoyl)benzyl)-4-hydroxypiperidine-1-carboxamide |
| 514 | N-(3-(3,6-dihydro-2H-pyran-4-yl)phenyl)-N-(2-fluoro-4-(hydroxycarbamoyl)benzyl)-4-hydroxypiperidine-1-carboxamide |
| 517 | N-(3-(1-(2-hydroxy-2-methylpropyl)piperidin-4-yl)phenyl)-N-(4-(hydroxycarbamoyl)benzyl)morpholine-4-carboxamide |
| 518 | N-(3-(1-(2-fluoro-2-methylpropyl)piperidin-4-yl)phenyl)-N-(4-(hydroxycarbamoyl)benzyl)morpholine-4-carboxamide |
| 520 | (R)-3-fluoro-N-(4-(hydroxycarbamoyl)benzyl)-N-(4-(trifluoromethyl)phenyl)pyrrolidine-1-carboxamide |
| 521 | (S)-3-fluoro-N-(4-(hydroxycarbamoyl)benzyl)-N-(4-(trifluoromethyl)phenyl)pyrrolidine-1-carboxamide |
| 522 | (R)-N-(4-(hydroxycarbamoyl)benzyl)-2-(hydroxymethyl)-N-(4-(trifluoromethyl)phenyl)pyrrolidine-1-carboxamide |
| 529 | 4-acetyl-N-(3-fluorophenyl)-N-(4-(hydroxycarbamoyl)benzyl)piperazine-1-carboxamide |
| 530 | N-(3-fluorophenyl)-N-(4-(hydroxycarbamoyl)benzyl)morpholine-4-carboxamide |

| | |
|---|---|
| 531 | 4-(2-fluoro-2-methylpropyl)-N-(4-(hydroxycarbamoyl)benzyl)-N-(3-(trifluoromethyl)phenyl)piperazine-1-carboxamide |
| 532 | N-(2-fluoro-4-(hydroxycarbamoyl)benzyl)-N-(3-(trifluoromethyl)phenyl)morpholine-4-carboxamide |
| 533 | N-(5-chloropyridin-2-yl)-N-(4-(hydroxycarbamoyl)benzyl)morpholine-4-carboxamide |
| 543 | N-(4-(hydroxycarbamoyl)benzyl)-4-(2-morpholinoethyl)-N-(4-(trifluoromethyl)phenyl)piperazine-1-carboxamide |
| 544 | N-(4-(hydroxycarbamoyl)benzyl)-4-(pyridin-4-yl)-N-(4-(trifluoromethyl)phenyl)piperazine-1-carboxamide |
| 545 | N-(4-(hydroxycarbamoyl)benzyl)-4-(2-morpholino-2-oxoethyl)-N-(4-(trifluoromethyl)phenyl)piperazine-1-carboxamide |
| 577 | N-(2-fluoro-4-(hydroxycarbamoyl)benzyl)-N-(4-(trifluoromethyl)phenyl)morpholine-4-carboxamide |
| 578 | 3,3-difluoro-N-(2-fluoro-4-(hydroxycarbamoyl)benzyl)-N-(4-(trifluoromethyl)phenyl)azetidine-1-carboxamide |
| 580 | N-(4-(hydroxycarbamoyl)benzyl)-N-(4-(trifluoromethyl)phenyl)-1,4-oxazepane-4-carboxamide |
| 651 | N-(4-(hydroxycarbamoyl)benzyl)-4-((4-hydroxytetrahydro-2H-pyran-4-yl)methyl)-N-(3-(trifluoromethyl)phenyl)piperazine-1-carboxamide |
| 683 | 4-benzyl-N-(4-(hydroxycarbamoyl)benzyl)-N-(3-(trifluoromethyl)phenyl)piperazine-1-carboxamide |
| 684 | N-(4-(hydroxycarbamoyl)benzyl)-4-(3-methoxyphenyl)-N-(3-(trifluoromethyl)phenyl)piperazine-1-carboxamide |
| 716 | 4-((4-fluorotetrahydro-2H-pyran-4-yl)methyl)-N-(4-(hydroxycarbamoyl)benzyl)-N-(3-(trifluoromethyl)phenyl)piperazine-1-carboxamide |
| 717 | N-(4-(hydroxycarbamoyl)benzyl)-4-phenyl-N-(3-(trifluoromethyl)phenyl)piperazine-1-carboxamide |
| 718 | 4-benzhydryl-N-(4-(hydroxycarbamoyl)benzyl)-N-(3-(trifluoromethyl)phenyl)piperazine-1-carboxamide |
| 765 | 4-ethyl-N-(3-(fluoromethyl)phenyl)-N-(4-(hydroxycarbamoyl)benzyl)piperazine-1-carboxamide |
| 766 | 4-(2-fluoro-2-methylpropyl)-N-(3-(fluoromethyl)phenyl)-N-(4-(hydroxycarbamoyl)benzyl)piperazine-1-carboxamide |
| 771 | N-(4-(hydroxycarbamoyl)benzyl)-N-(2-(trifluoromethoxy)phenyl)morpholine-4-carboxamide |
| 772 | N-(4-(hydroxycarbamoyl)benzyl)-N-(4-(trifluoromethoxy)phenyl)morpholine-4-carboxamide |
| 773 | N-(4-(hydroxycarbamoyl)benzyl)-N-(3-(trifluoromethoxy)phenyl)morpholine-4-carboxamide |
| 774 | N-(4-(hydroxycarbamoyl)benzyl)-N-(2-methoxy-5-(trifluoromethyl)phenyl)morpholine-4-carboxamide |
| 776 | N-(2-chloro-5-(trifluoromethyl)phenyl)-N-(4-(hydroxycarbamoyl)benzyl)morpholine-4-carboxamide |
| 778 | N-(4-(hydroxycarbamoyl)benzyl)-N-(6-(trifluoromethyl)pyridin-2-yl)morpholine-4-carboxamide |
| 791 | N-(2,3-difluorophenyl)-N-(4-(hydroxycarbamoyl)benzyl)morpholine-4-carboxamide |
| 797 | (3S,5R)-4-ethyl-N-(4-(hydroxycarbamoyl)benzyl)-3,5-dimethyl-N-(3-(trifluoromethyl)phenyl)piperazine-1-carboxamide |
| 800 | N-(4-(hydroxycarbamoyl)benzyl)-2,6-dimethyl-N-(3-(trifluoromethoxy)phenyl)morpholine-4-carboxamide |
| 801 | N-(4-(hydroxycarbamoyl)benzyl)-2,6-dimethyl-N-(2-(trifluoromethoxy)phenyl)morpholine-4-carboxamide |
| 802 | (3S,5R)-4-benzyl-N-(4-(hydroxycarbamoyl)benzyl)-3,5-dimethyl-N-(3-(trifluoromethyl)phenyl)piperazine-1-carboxamide |
| 803 | (3S,5R)-N-(4-(hydroxycarbamoyl)benzyl)-3,5-dimethyl-4-(2,2,3,3,3-pentafluoropropyl)-N-(3-(trifluoromethyl)phenyl)piperazine-1-carboxamide |
| 826 | 4-ethyl-N-(4-(hydroxycarbamoyl)benzyl)-N-(6-(trifluoromethyl)pyridin-2-yl)piperazine-1-carboxamide |
| 827 | N-(4-(hydroxycarbamoyl)benzyl)-2,6-dimethyl-N-(6-(trifluoromethyl)pyridin-2-yl)morpholine-4-carboxamide |
| 828 | N-(4-(hydroxycarbamoyl)benzyl)-N-(6-(trifluoromethyl)pyridin-2-yl)piperidine-1-carboxamide |
| 829 | (S)-3-fluoro-N-(4-(hydroxycarbamoyl)benzyl)-N-(6-(trifluoromethyl)pyridin-2-yl)pyrrolidine-1-carboxamide |

In the present invention, the pharmaceutically acceptable salt refers to salts commonly used in the pharmaceutical industry, such as inorganic ion salts formed with calcium, potassium, sodium, magnesium, etc., inorganic acid salts formed with hydrochloric acid, nitric acid, phosphoric acid, bromic acid, iodic acid, perchloric acid, tartaric acid, sulfuric acid, etc., organic acid salts formed with acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc, sulfonic acid salts formed with methanesulfonic acid, ethanesulfonic acid, benzenesulfonic acid, p-toluenesulfonic acid, naphthalenesulfonic acid, etc., amino acid salts formed with glycine, arginine, lysine, etc., and amine salts formed with trimethylamine, triethylamine, ammonia, pyridine, picoline, but the types of salts used in the present invention are not limited to the above-mentioned salts.

In the present invention, a preferred salt is a hydrochloric acid salt, and preferred examples of this compound include Compounds 461 and 493 described in the present specification.

A specific preparation method of a novel compound of Formula I, an optical isomer thereof, or a pharmaceutically acceptable salt thereof is shown in the following reaction schemes 1 to 12.

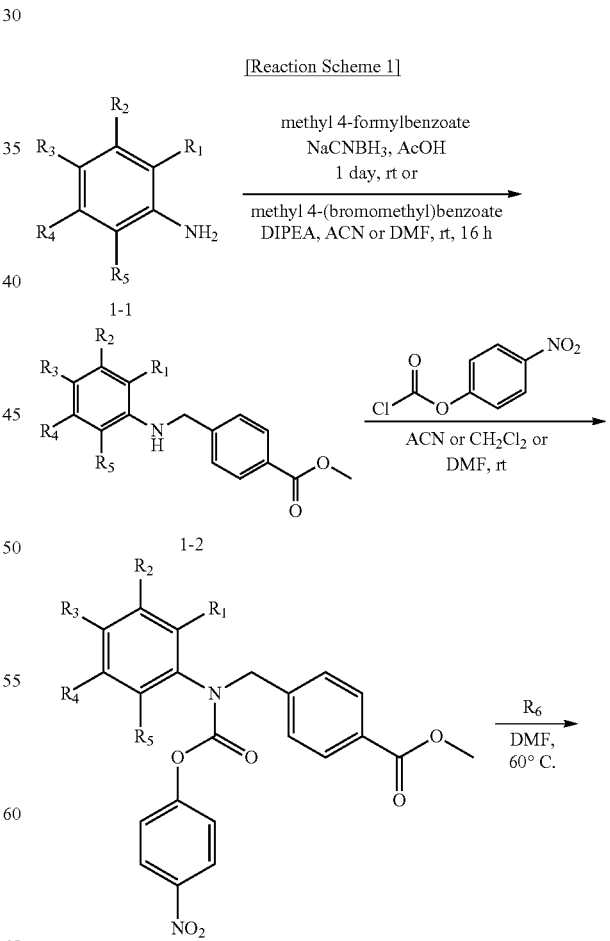

[Reaction Scheme 1]

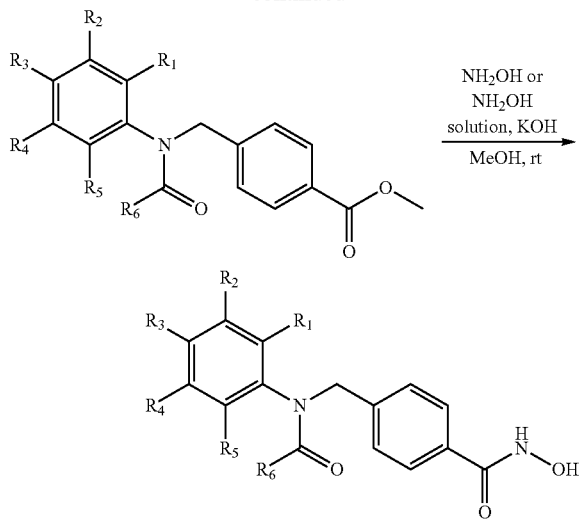

$R_{1,2,3,4,5} = H$
Compound 279: $R_5$ = morpholine $R_{1,4,5} = H$, $R_2 = CF_3$, $R_3 = Cl$
Compound 389: $R_6$ = piperidine
Compound 390: $R_6$ = 4-methylpiperidine
Compound 391: $R_6$ = morpholine
Compound 392: $R_6$ = 2,6-dimethylmorpholine
Compound 393: $R_6$ = 1-methylpiperazine
Compound 394: $R_6$ = 1-ethylpiperazine $R_{2,4,5} = H$, $R_1 = F$, $R_3 = F$
Compound 413: $R_6$ = morpholine
Compound 414: $R_6$ = piperidine
Compound 415: $R_6$ = 2,6-dimethylmorpholine
Compound 416: $R_6$ = 1-methylpiperazine $R_{1,2,3,5} = H$
Compound 255: $R_4$ = Br, $R_6$ = morpholine
Compound 256: $R_4$ = Br, $R_6$ = 1-methylpiperazine
Compound 484: $R_4$ = methoxy, $R_6$ = morpholine
Compound 529: $R_4$ = F, $R_6$ = 1-(piperazin-1-yl)ethanone
Compound 530: $R_4$ = F, $R_6$ = morpholine
Compound 683: $R_4$ = $CF_3$, $R_6$ = 1-benzylpiperazine
Compound 684: $R_4$ = $CF_3$, $R_6$ = 1-(3-methoxybenzyl)piperazine
Compound 717: $R_4$ = $CF_3$, $R_6$ = 1-phenylpiperazine
Compound 718: $R_4$ = $CF_3$, $R_6$ = 1-benzhydrylpiperazine
Compound 773: $R_4$ = $OCF_3$, $R_6$ = morpholine
Compound 800: $R_4$ = $OCF_3$, $R_6$ = 2,6-dimethylmorpholine $R_{2,4,5} = H$, $R_1 = F$, $R_3 = CH_3$
Compound 438: $R_6$ = piperidine
Compound 439: $R_6$ = morpholine
Compound 440: $R_6$ = 2,6-dimethylmorpholine
Compound 441: $R_6$ = 1-methylpiperazine
Compound 453: $R_6$ = 1-ethylpiperazine
Compound 454: $R_6$ = 1-(2-methoxyphenyl)piperazine
Compound 455: $R_6$ = 1-(4-fluorophenyl)piperazine $R_{1,4,5} = H$, $R_2 = Cl$, $R_3 = F$
Compound 456: $R_6$ = piperidine
Compound 457: $R_6$ = 4-methylpiperidine
Compound 458: $R_6$ = morpholine
Compound 477: $R_6$ = 2,6-dimethylmorpholine
Compound 478: $R_6$ = 1-methylpiperazine
Compound 479: $R_6$ = 1-ethylpiperazine
Compound 480: $R_6$ = 1-benzylpiperazine
Compound 481: $R_6$ = 1-(2-methoxyphenyl)piperazine
Compound 482: $R_6$ = 1-(4-fluorophenyl)piperazine $R_{2,3,4,5} = H$, $R_1 = OCF_3$
Compound 771: $R_6$ = morpholine
Compound 801: $R_6$ = 2,6-dimethylmorpholine $R_{2,3,5} = H$, $R_4 = CF_3$
Compound 774: $R_1 = OCH_3$, $R_6$ = morpholine
Compound 776: $R_1 = Cl$, $R_6$ = morpholine $R_{3,4,5} = H$, $R_{1,2} = F$
Compound 791: $R_6$ = morpholine $R_{1,2,3,5} = H$, $R_4 = CF_3$
Compound 374: $R_6$ = morpholine
Compound 459: $R_6$ = 4-methylpiperidine
Compound 460: $R_6$ = piperidine
Compound 386: $R_6$ = 2,6-dimethylmorpholine
Compound 461: $R_6$ = 4-ethylpiperazine
Compound 494: $R_6$ = 1-(piperazin-1-yl)ethanone
Compound 495: $R_6$ = (R)-3-fluoropyrrolidine
Compound 496: $R_6$ = (S)-3-fluoropyrrolidine
Compound 497: $R_6$ = (R)-pyrrolidin-2-ylmethanol
Compound 498: $R_6$ = (S)-2-(trifluoromethyl)pyrrolidine $R_{1,2,4,5} = H$, $R_3 = CF_3$
Compound 385: $R_6$ = morpholine
Compound 485: $R_6$ = 3,3-difluoroazetidine
Compound 486: $R_6$ = 4-phenylpiperidin-4-o
Compound 520: $R_6$ = (S)-3-fluoropyrrolidine
Compound 521: $R_6$ = (R)-3-fluoropyrrolidine
Compound 522: $R_6$ = (S)-pyrrolidin-2-ylmethanol
Compound 543: $R_6$ = 4-(2-(piperazin-1-yl)ethyl)morpholine
Compound 544: $R_6$ = 1-(pyridin-4-yl)piperazine
Compound 545: $R_6$ = 1-morpholino-2-(piperazin-1-yl)ethanone
Compound 580: $R_6$ = 1,4-oxazepane $R_{1,2,4,5} = H$, $R_3 = OCF_3$
Compound 772: $R_6$ = morpholine In reaction scheme 1, the compound of Formula I-2 was synthesized by the reductive amination of the compound of Formula I-1 with methyl 4-formylbenzoate at room temperature for 12 to 24 hours or with methyl 4-(bromomethyl)benzoate at room temperature for 16 hours, and the compound of Formula I-3 was synthesized by the reaction of the compound of Formula I-2 with 4-nitrophenyl carbonochloridate at room temperature for 12 to 24 hours.

Then, the compound of Formula I-4 was synthesized by the reaction of the compound of Formula I-3 with amine derivative ($R_6$) in the presence of dimethylformamide solvent at room temperature or at 60° C. for 1 to 2 days. Finally, the target compound 255, 256, 279, 374, 385, 386, 389, 390, 391, 392, 393, 394, 413, 414, 415, 416, 438, 439, 440, 441, 453, 454, 455, 456, 457, 458, 459, 460, 461, 477, 478, 479, 480, 481, 482, 484, 485, 486, 494, 495, 496, 497, 498, 520, 521, 522, 529, 530, 543, 544, 545, 580, 683, 684, 717, 718, 771, 772, 773, 774, 776, 791, 800 or 801 was synthesized by the reaction of the compound of Formula I-4 with potassium hydroxide (KOH), methanol and hydroxylamine hydrochloride ($HONH_2HCl$) at room temperature or with hydroxylamine ($NH_2OH$) aqueous solution and potassium hydroxide (KOH), which were sequentially added dropwise, at room temperature.

[Reaction Scheme 2]

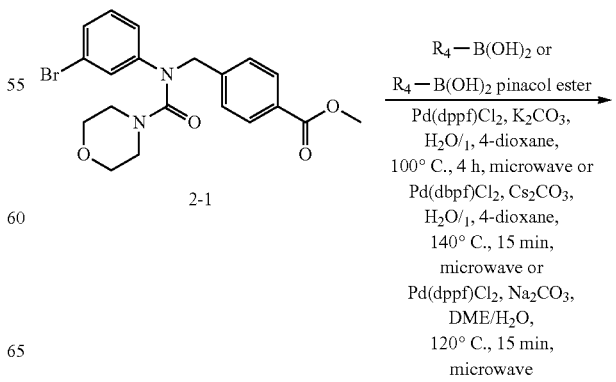

-continued

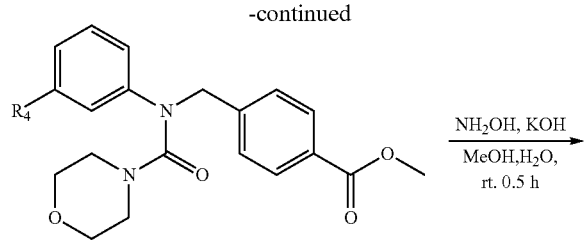

2-2

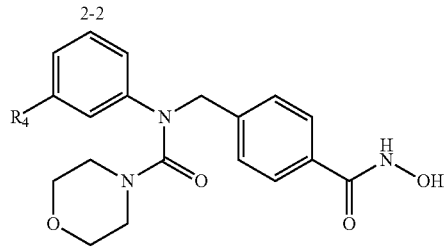

Compound 261: R₄ = 6-indole, R₆ = morpholine
Compound 262: R₄ = 3-pyridine, R₆ = morpholine
Compound 263: R₄ = 5-indole, R₆ = morpholine
Compound 395: R₄ = 3,5-difluorophenyl
Compound 396: R₄ = 6-(dimethylamino)pyridin-3-yl
Compound 397: R₄ = pyrimidin-5-yl
Compound 398: R₄ = 3,5-bis(trifluoromethyl)phenyl
Compound 399: R₄ = 2,3-dihydrobenzo[b][1,4]dioxin-6-yl
Compound 400: R₄ = 3,4,5-trimethoxyphenyl
Compound 401: R₄ = 2,6-dimethylphenyl
Compound 402: R₄ = furan-3-yl
Compound 403: R₄ = 3,6-dihydro-2H-pyran-4-y
Compound 404: R₄ = 1-methyl-1,2,3,6-tetrahydropyridin-4-yl
Compound 405: R₄ = 1-Boc-1,2,3,6-tetrahydropyridin-4-yl
Compound 418: R₄ = benzo[d][1,3]dioxol-5-yl

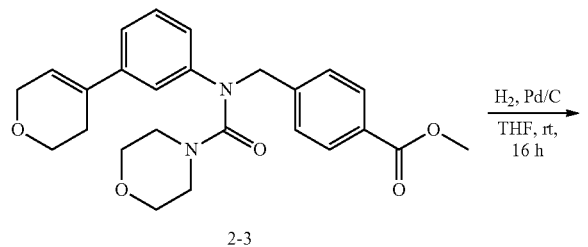

2-3

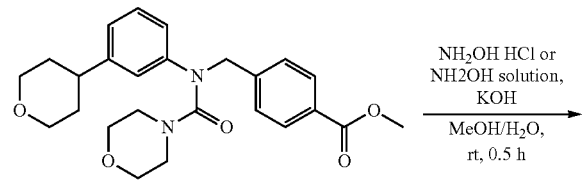

2-4

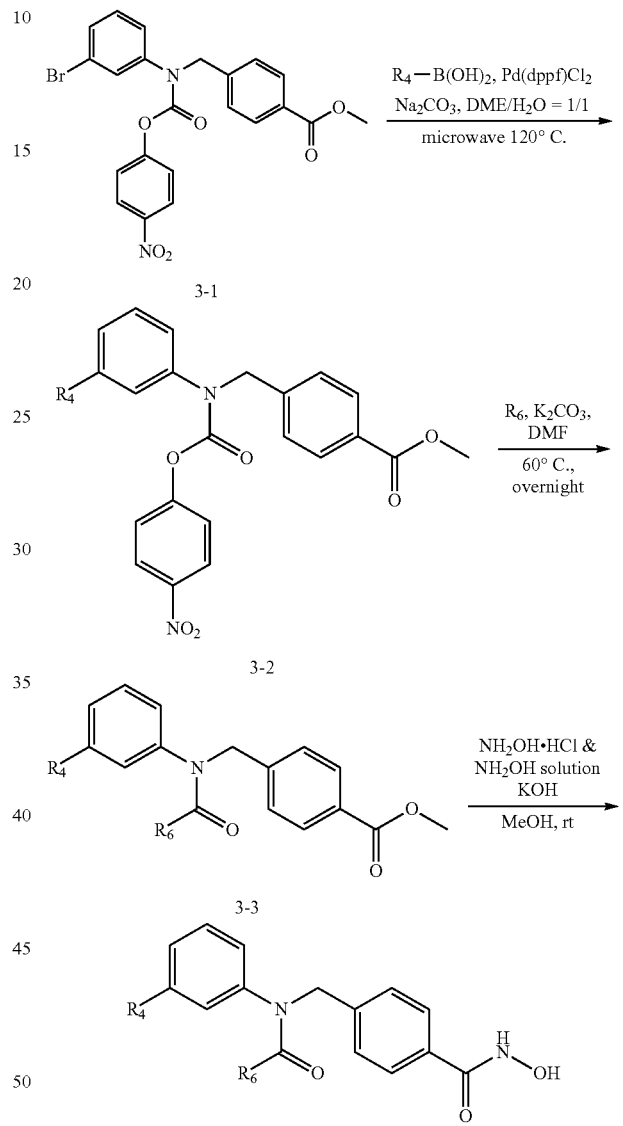

Compound 483

In reaction scheme 2, the compound of Formula 2-2 was synthesized by the Suzuki reaction of the compound of Formula 2-1 with boronic acid, and then the compound of Formula 2-4 was synthesized by the reduction of the compound of Formula 2-3 with hydrogen and palladium. Finally, the target compound 261, 262, 263, 395, 396, 397, 398, 399, 400, 401, 402, 403, 404, 405, 418 or 483 was synthesized by dissolving the compound of Formula 2-2 or 2-4 in methanol, followed by the reaction with hydroxylamine hydrochloride (HONH₂HCl) and potassium hydroxide (KOH) at room temperature or with hydroxylamine (NH₂OH) aqueous solution and potassium hydroxide (KOH), which were sequentially added dropwise, at room temperature.

[Reaction Scheme 3]

Compound 252: R₄ = 1-methyl-1H-indazol-5-yl, R₆ = morpholine
Compound 253: R₄ = 1-methyl-1H-indazol-5-yl, R₆ = 1-methylpiperazine
Compound 254: R₄ = 1-methyl-1H-indazol-6-yl, R₆ = morpholine
Compound 260: R₄ = 1-methyl-1H-indazol-5-yl, R₆ = piperidine In reaction scheme 3, the compound of Formula 3-2 was synthesized by the Suzuki reaction of the compound of Formula 3-1 with boronic acid, and then the compound of Formula 3-3 was synthesized by the reaction of the compound of Formula 3-2 with amine derivative (R₆) at 50 to 60° C. Finally, the target compound 252, 253, 254 or 260 was synthesized by dissolving the compound of Formula 3-3 in methanol, followed by the reaction with hydroxylamine hydrochloride, potassium hydroxide (KOH), and hydroxylamine aqueous solution (50 wt %), which were added dropwise, at room temperature.

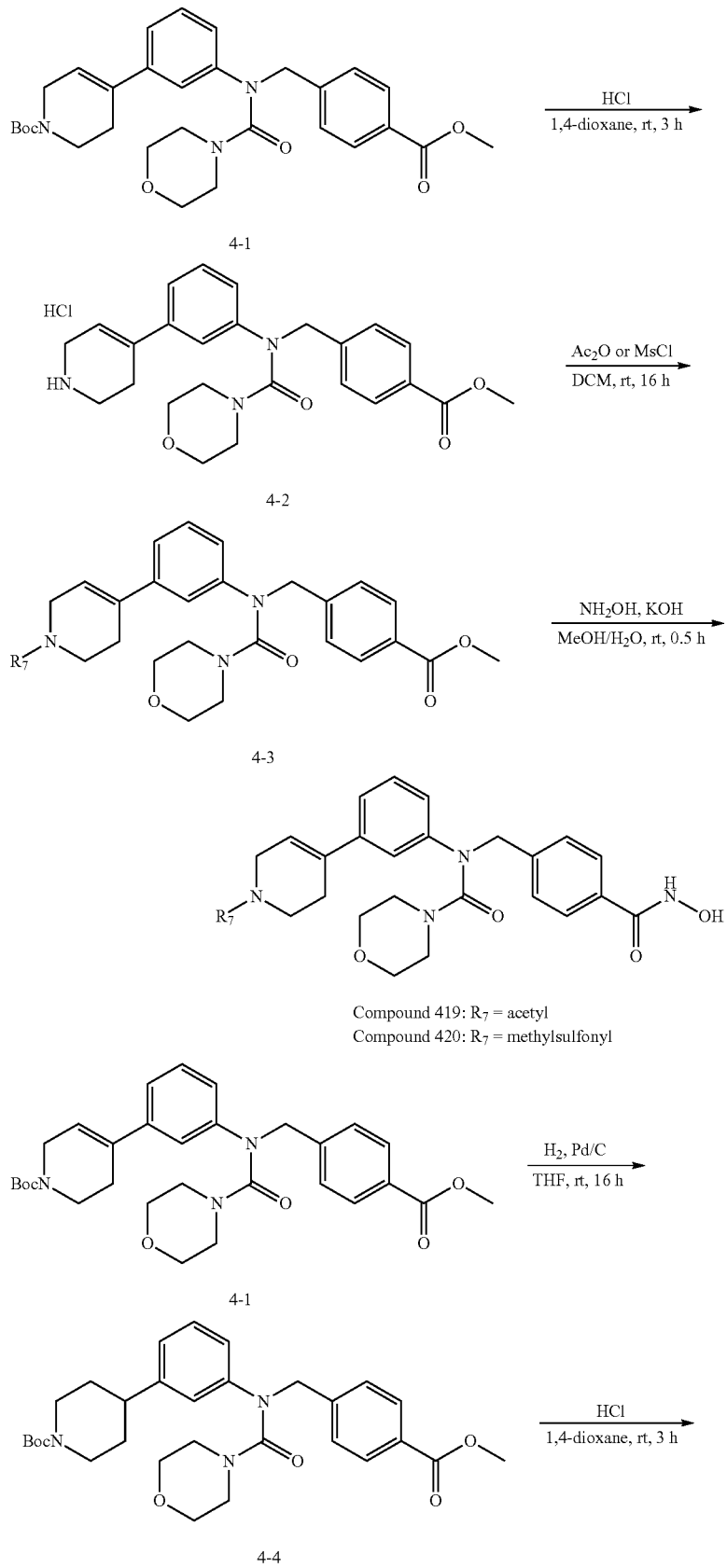
[Reaction Scheme 4]
Compound 419: R<sub>7</sub> = acetyl
Compound 420: R<sub>7</sub> = methylsulfonyl -continued
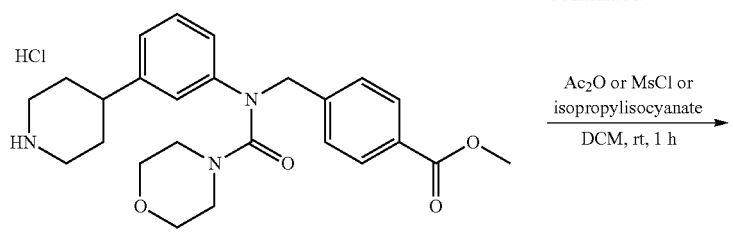
4-5
Ac₂O or MsCl or
isopropylisocyanate
———————————→
DCM, rt, 1 h
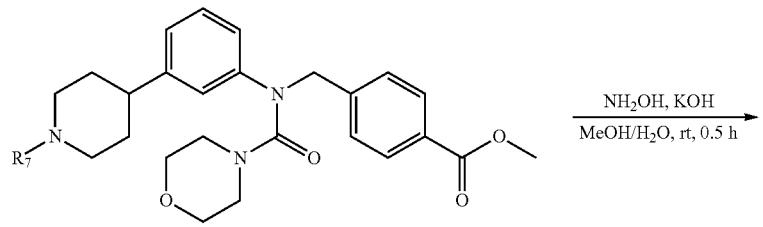
4-6
NH₂OH, KOH
———————————→
MeOH/H₂O, rt, 0.5 h
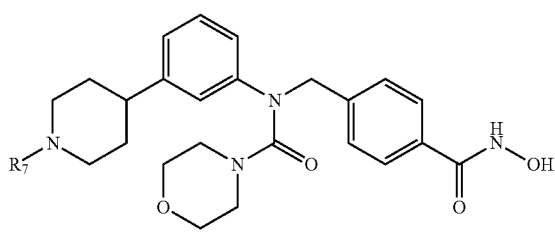
Compound 490: R₇ = acetyl
Compound 491: R₇ = methylsulfonyl
Compound 492: R₇ = N-isopropylcarbamoyl
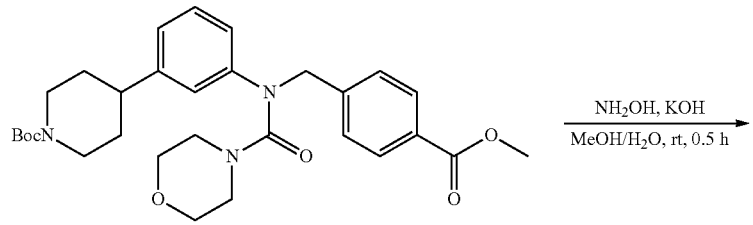
4-4
NH₂OH, KOH
———————————→
MeOH/H₂O, rt, 0.5 h
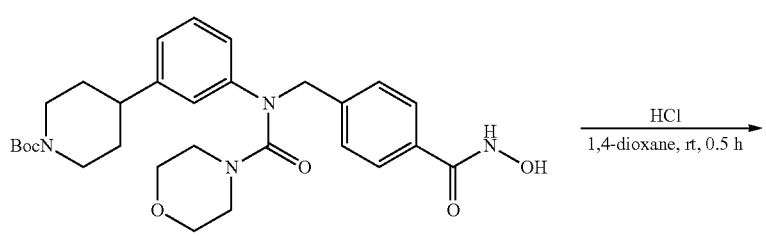
Compound 489
HCl
———————————→
1,4-dioxane, rt, 0.5 h
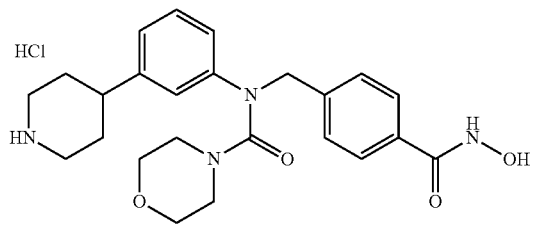
Compound 493

-continued

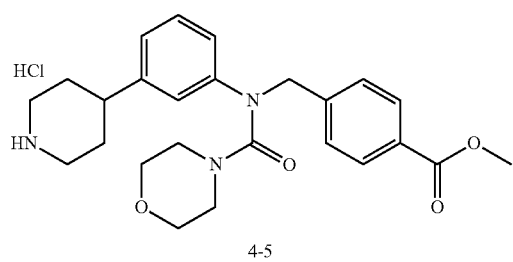
4-5

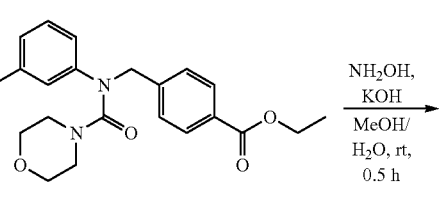

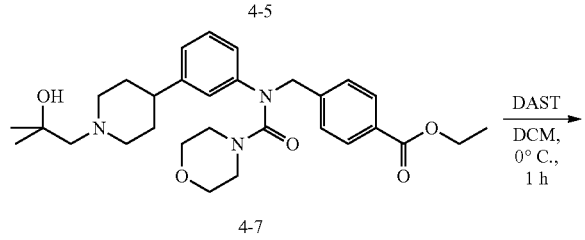
4-7

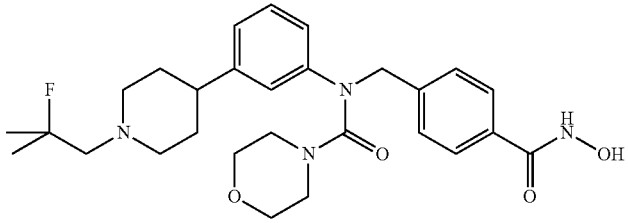
4-8

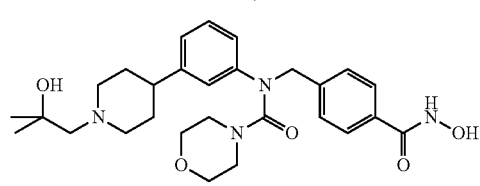
Compound 517

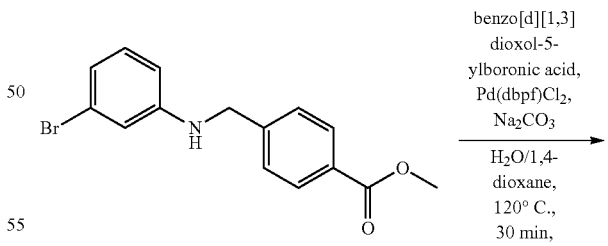
Compound 518

In reaction scheme 4, the compound of Formula 4-2 was synthesized by the reaction of the compound of Formula 4-1 with hydrogen chloride, and then the compound of Formula 4-3 was synthesized using acetic acid anhydride or methane sulfonyl chloride. Next, the compound of Formula 4-4 was synthesized by the reduction of the compound of Formula 4-1 with hydrogen and palladium, and the compound of Formula 4-6 was synthesized by the same method. Subsequently, the compound of Formula 4-7 was synthesized by the reaction of the compound of Formula 4-5 with 2,2-dimethyloxirane in a microwave reactor at 120° C., and then the compound of Formula 4-8 was synthesized using diethylaminosulfur trifluoride (DAST). Finally, the target compound 419, 420, 489, 490, 491, 492, 493, 517 or 518 was synthesized by dissolving compound formula 4-3, 4-6, 4-4, 4-7 or 4-8 in methanol, followed by the reaction with hydroxylamine ($NH_2OH$) aqueous solution and potassium hydroxide (KOH), which were sequentially added dropwise, at room temperature.

[Reaction Scheme 5]

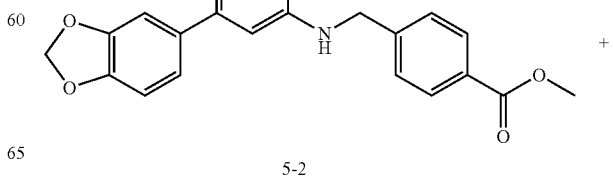

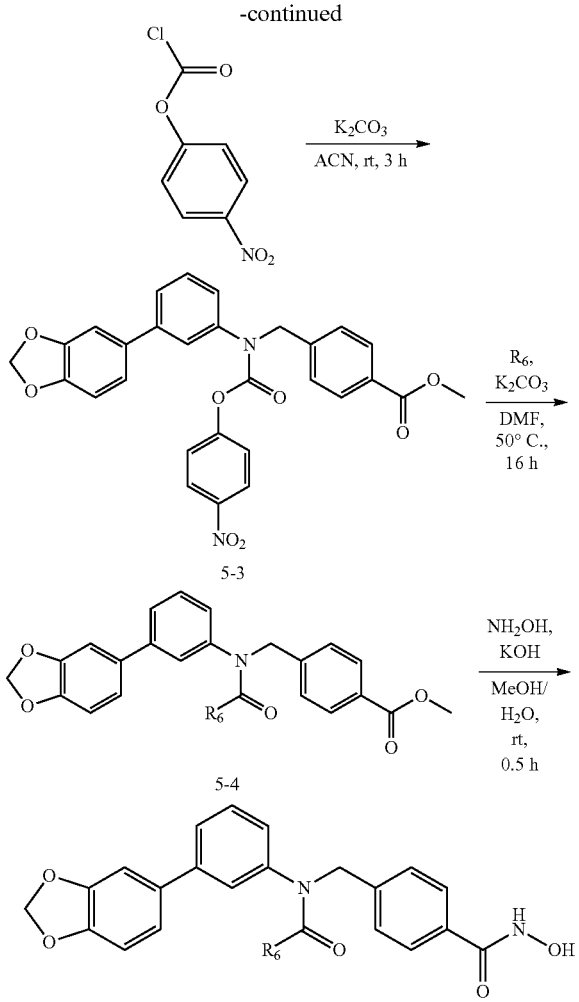

Compound 462: R$_6$ = piperidine
Compound 463: R$_6$ = piperidin-4-ol
Compound 464: R$_6$ = 2,6-dimethylmorpholine
Compound 465: R$_6$ = 4-phenylpiperidin-4-ol
Compound 466: R$_6$ = 1-methylpiperazine
Compound 467: R$_6$ = 2-(piperazin-1-yl)ethanol
Compound 468: R$_6$ = pyrrolidine
Compound 469: R$_6$ = (S)-pyrrolidin-2-ylmethanol
Compound 470: R$_6$ = cyclopropyl(piperazin-1-yl)methanone
Compound 471: R$_6$ = azetidine In reaction scheme 5, the compound of Formula 5-2 was synthesized by the Suzuki reaction of the compound of Formula 5-1 with boronic acid, and then the compound of Formula 5-3 was synthesized by the reaction of the compound of Formula 5-2 with 4-nitrophenyl chloroformate at room temperature. Next, the compound of Formula 5-4 was synthesized by the reaction of the compound of Formula 5-3 with amine derivative (R$_6$) at 50° C. Finally, the target compound 462, 463, 464, 465, 466, 467, 468, 469, 470 or 471 was synthesized by dissolving the compound of Formula 5-4 in methanol, followed by the reaction with hydroxylamine (NH$_2$OH) aqueous solution and potassium hydroxide (KOH), which were sequentially added dropwise, at room temperature.

[Reaction Scheme 6]

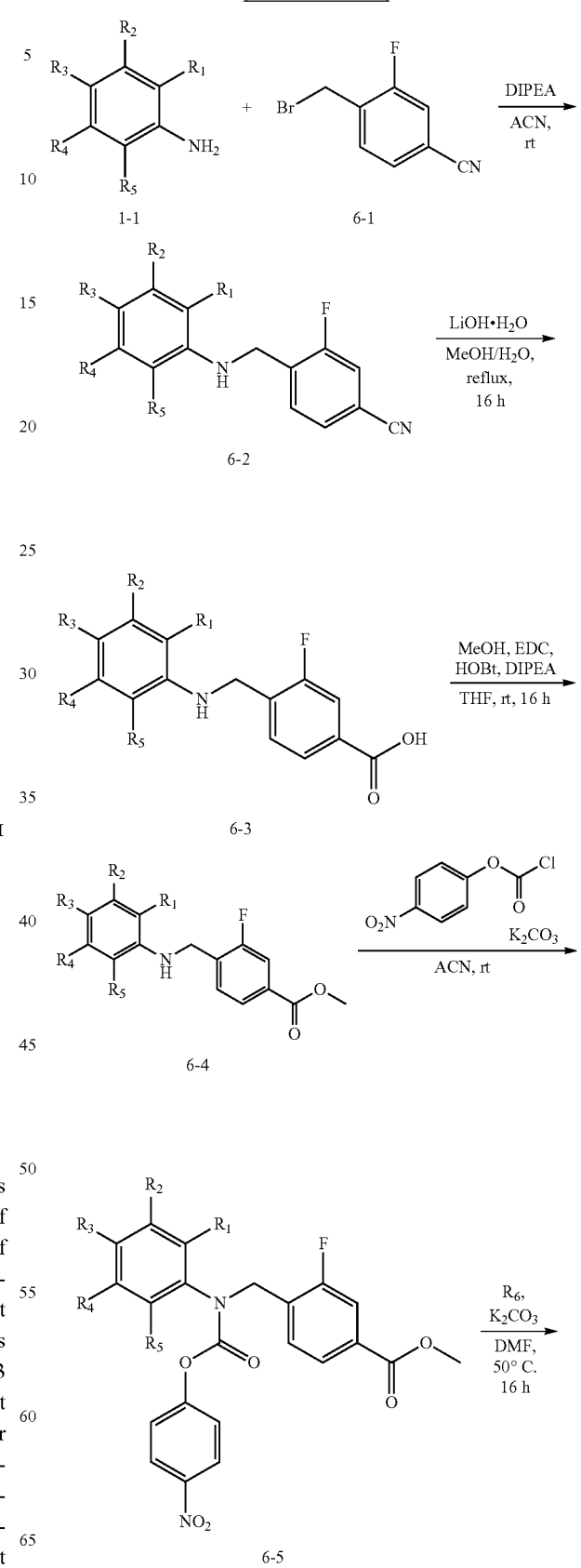

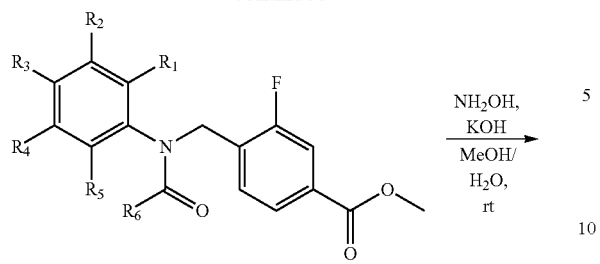

6-6

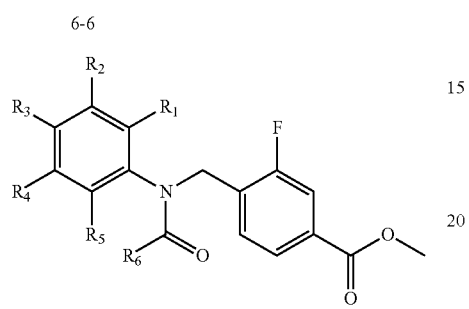

Compound 487: R$_{1,2,3,5}$ = H, R$_4$ = Br,
R$_6$ = morpholine
Compound 488: R$_{1,2,3,5}$ = H, R$_4$ = Br,
R$_6$ = 4-hydroxypiperidine
Compound 532: R$_{1,2,3,5}$ = H, R$_4$ = CF$_3$, R$_6$ = morpholine
Compound 577: R$_{1,2,4,5}$ = H, R$_4$ = CF$_3$, R$_6$ = morpholine
Compound 578: R$_{1,2,4,5}$ = H, R$_3$ = CF$_3$,
R$_6$ = 3,3-difluoroazetidine

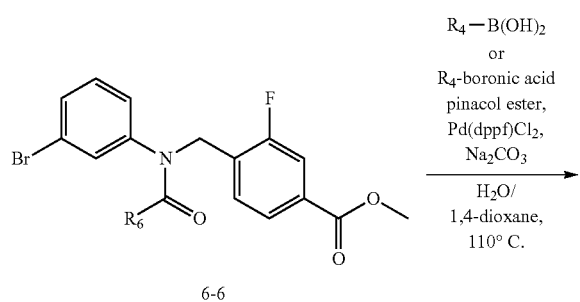

6-6

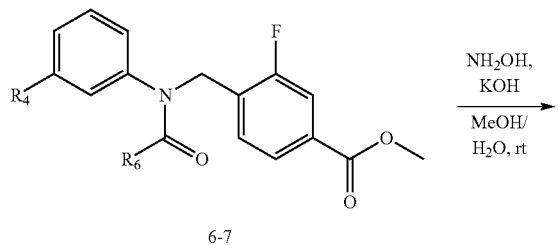

6-7

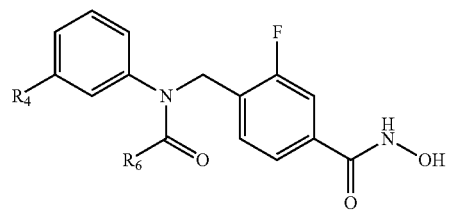

Compound 511: R$_4$ = benzo[d][1,3]dioxol-5-yl,
R$_6$ = morpholine
Compound 512: R$_4$ = 3,6-dihydro-2H-pyran-4-yl,
R$_6$ = morpholine
Compound 513: R$_4$ = benzo[d][1,3]dioxol-5-yl,
R$_6$ = hydroxypiperidine
Compound 514: R$_4$ = 3,6-dihydro-2H-pyran-4-yl,
R$_6$ = hydroxypiperidine In reaction scheme 6, the compound of Formula 6-2 was synthesized by the substitution of the compound of Formula I-1 with the compound of Formula 6-1, and then the compound of Formula 6-3 was synthesized by the hydrolysis of the compound of Formula 6-2 with lithium hydroxide (LiOH). Next, the compound of Formula 6-4 was synthesized by the reaction of the compound of Formula 6-3 with methanol, 1-ethyl-3-[3-dimethylaminopropyl]carbodiimide hydrochloride (EDC) and 1-hydroxybenzotriazole hydrate (HOBt), and then the compound of Formula 6-5 was synthesized by the reaction of the compound of Formula 6-4 with 4-nitrophenyl chloroformate at room temperature. Subsequently, the compound of Formula 6-6 was synthesized by the reaction of the compound of Formula 6-5 with amine derivative (R$_6$) at 50° C., and then the compound of Formula 6-7 was synthesized by the Suzuki reaction of the compound of Formula 6-6 with boronic acid, if necessary. Finally, the target compound 487, 488, 511, 512, 513, 514, 532, 577 or 578 was synthesized by dissolving the compound of Formula 6-6 or 6-7 in methanol, followed by the reaction with hydroxylamine (NH$_2$OH) aqueous solution and potassium hydroxide (KOH), which were sequentially added dropwise, at room temperature.

[Reaction Reaction scheme 7]

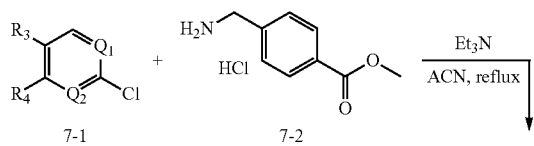

7-1    7-2

-continued

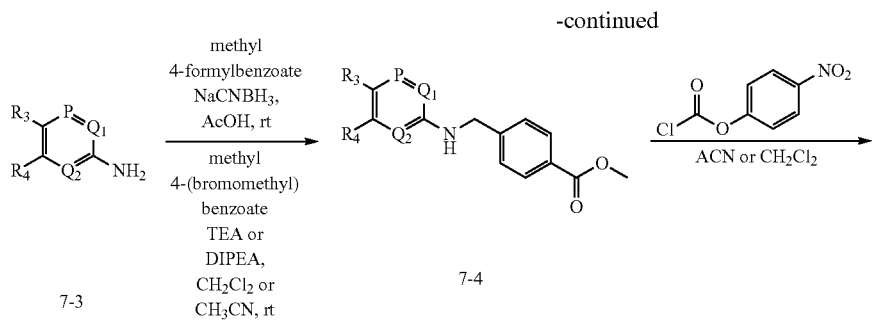

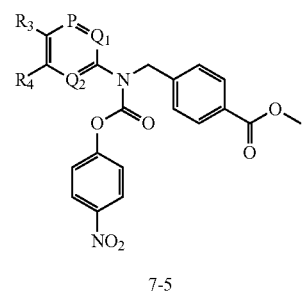

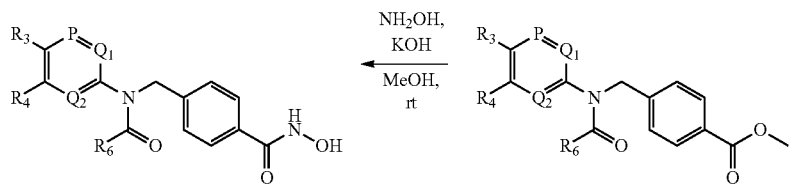

$Q_1 = C$, $P = C$, $Q_2 = N$, $R_{3,4} = H$
Compound 341: $R_6$ = piperidine
Compound 342: $R_6$ = 4-methylpiperidine
Compound 343: $R_6$ = 2,6-dimethylmorpholine
Compound 352: $R_6$ = 4-phenyl-1,2,3,6-tetrahydropyridine
Compound 353: $R_6$ = 1-methylpiperazine
Compound 354: $R_6$ = 1-ethylpiperazine
Compound 355: $R_6$ = 1-benzylpiperazine
$Q_1 = N$, $P = C$, $Q_2 = N$, $R_{3,4} = H$
Compound 309: $R_6$ = 1-benzylpiperazine
Compound 311: $R_6$ = 4-phenylpiperidin-4-ol
Compound 312: $R_6$ = morpholine
Compound 313: $R_6$ = 2,6-dimethylmorpholine
$Q_1 = C$, $P = C$, $Q_2 = N$, $R_{3,4} = H$
Compound 356: $R_6$ = 1-(2-methoxyphenyl)piperazine
Compound 357: $R_6$ = 1-(4-fluorophenyl)piperazine
Compound 358: $R_6$ = pyrrolidine
Compound 376: $R_6$ = 1-methyl-1,4-diazepane
Compound 377: $R_6$ = azetidine
Compound 379: $R_6$ = 1-(3,4-dimethylphenyl)piperazine
Compound 450: $R_6$ = 1-(1,4-diazepan-1-yl)ethanone
Compound 451: $R_6$ = cyclopropyl(piperazin-1-yl)methanone
Compound 280: $P = C$, $Q_1 = N$, $Q_2 = C$, $R_{3,4} = H$, $R_6$ = morpholine
Compound 281: $P = N$, $Q_1 = C$, $Q_2 = C$, $R_{3,4} = H$, $R_6$ = morpholine
Compound 533: $Q_1 = C$, $P = C$, $Q_2 = N$, $R_3 = Cl$, $R_4 = H$, $R_6$ = morpholine
Compound 778: $Q_1 = C$, $P = C$, $Q_2 = N$, $R_3 = H$, $R_4 = CF_3$, $R_6$ = morpholine
Compound 826: $Q_1 = C$, $P = C$, $Q_2 = N$, $R_3 = H$, $R_4 = CF_3$, $R_6$ = 1-ethylpiperazine
Compound 827: $Q_1 = C$, $P = C$, $Q_2 = N$, $R_3 = H$, $R_4 = CF_3$, $R_6$ = 2,6-dimethylmorpholine
Compound 828: $Q_1 = C$, $P = C$, $Q_2 = N$, $R_3 = H$, $R_4 = CF_3$, $R_6$ = piperidine
Compound 829: $Q_1 = C$, $P = C$, $Q_2 = N$, $R_3 = H$, $R_4 = CF_3$, $R_6$ = (S)-3-fluoropyrrolidine In reaction scheme 7, the compound of Formula 7-4 was synthesized by the reductive amination of the compound of Formula 7-3 or by the substitution of the compound of Formula 7-1 with the compound of Formula 7-2. Then, the compound of Formula 7-5 was synthesized by the reaction of the compound of Formula 7-4 with 4-nitrophenyl chloroformate at room temperature or at 60° C. Subsequently, the compound of Formula 7-6 was synthesized by the reaction of the compound of Formula 7-5 with amine derivative ($R_6$) at 60° C. or by adding acyl chloride to the compound of Formula 7-4. Finally, the target compound 280, 281, 309, 311, 312, 313, 341, 342, 343, 352, 353, 354, 355, 356, 357, 358, 376, 377, 379, 450, 451, 533, 778, 826, 827, 828 or 829 was synthesized by dissolving the compound of Formula 7-6 in methanol, followed by the reaction with hydroxylamine ($NH_2OH$) aqueous solution and potassium hydroxide (KOH), which were sequentially added dropwise, at room temperature.

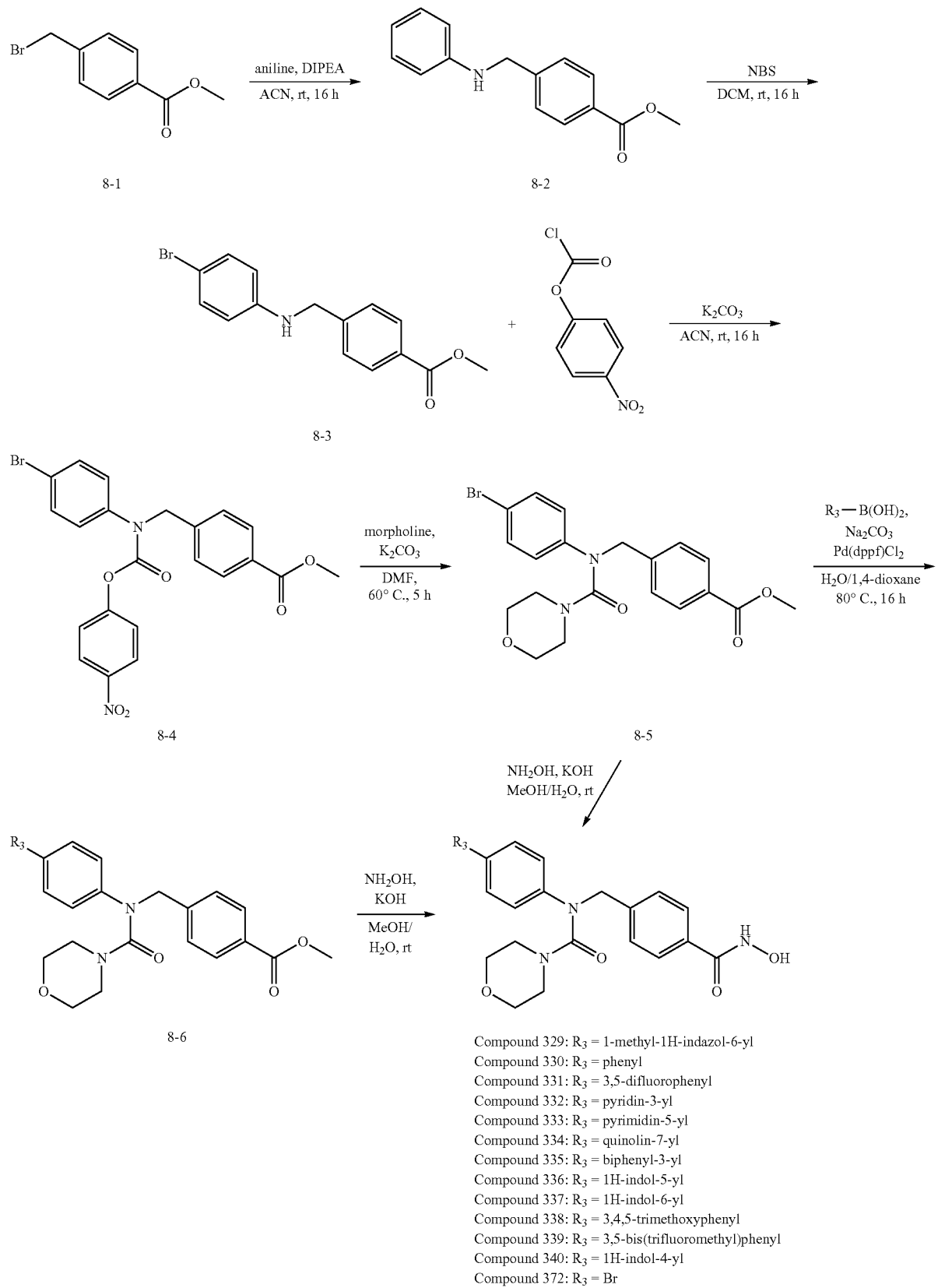

In reaction scheme 8, the compound of Formula 8-2 was synthesized by the substitution of the compound of Formula 8-1 with aniline, and then the compound of Formula 8-3 was synthesized by the reaction of the compound of Formula 8-2 with N-bromosuccinimide at room temperature. Next, the compound of Formula 8-4 was synthesized by the reaction of the compound of Formula 8-3 with 4-nitrophenyl chloroformate at room temperature, and then the compound of Formula 8-5 was synthesized by the substitution of the compound of Formula 8-4 with morpholine at 60° C. Subsequently, the compound of Formula 8-6 was synthesized by the Suzuki reaction of the compound of Formula 8-5 with boronic acid. Finally, the target compound 329, 330, 331, 332, 333, 334, 335, 336, 337, 338, 339, 340 or 372 was synthesized by dissolving the compound of Formula 8-5 or 8-6 in methanol, followed by the reaction with hydroxylamine (NH$_2$OH) aqueous solution and potassium hydroxide (KOH), which were sequentially added dropwise, at room temperature.

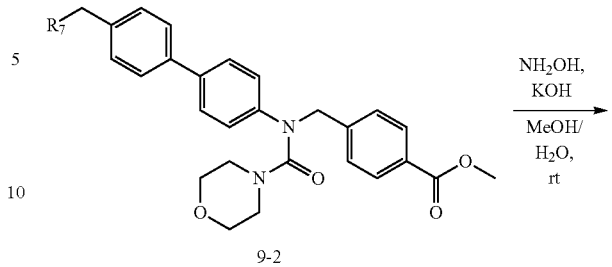

9-2

[Reaction Scheme 9]

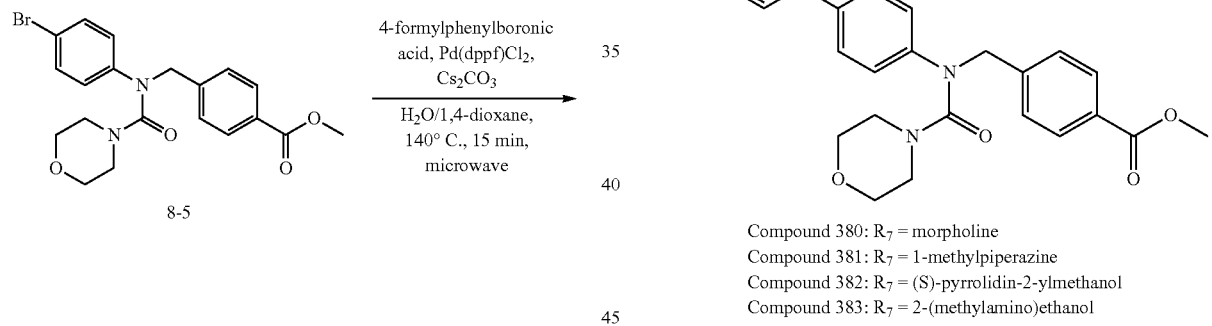

Compound 380: R$_7$ = morpholine
Compound 381: R$_7$ = 1-methylpiperazine
Compound 382: R$_7$ = (S)-pyrrolidin-2-ylmethanol
Compound 383: R$_7$ = 2-(methylamino)ethanol

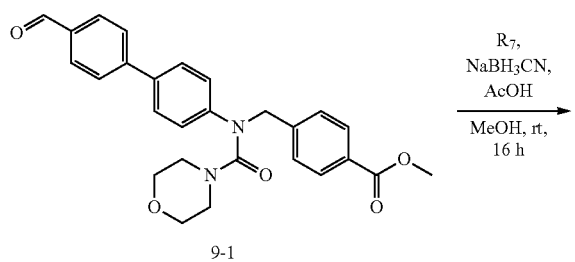

9-1

In reaction scheme 9, the compound of Formula 9-1 was synthesized by the Suzuki reaction of the compound of Formula 8-5 with 4-formylphenylboronic acid, and then the compound of Formula 9-2 was synthesized by the reductive amination of the compound of Formula 9-1 with amine derivative (R$_7$). Finally, the target compound 380, 381, 382 or 383 was synthesized by dissolving the compound of Formula 9-2 in methanol, followed by the reaction with hydroxylamine (NH$_2$OH) aqueous solution and potassium hydroxide (KOH), which were sequentially added dropwise, at room temperature.

[Reaction Scheme 10]
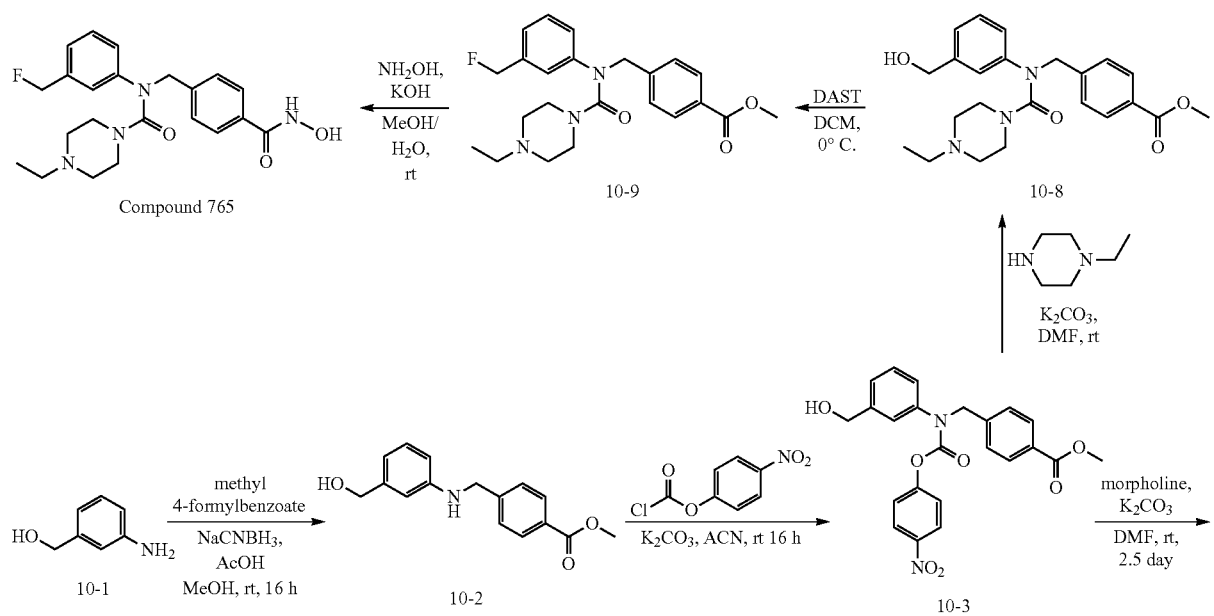
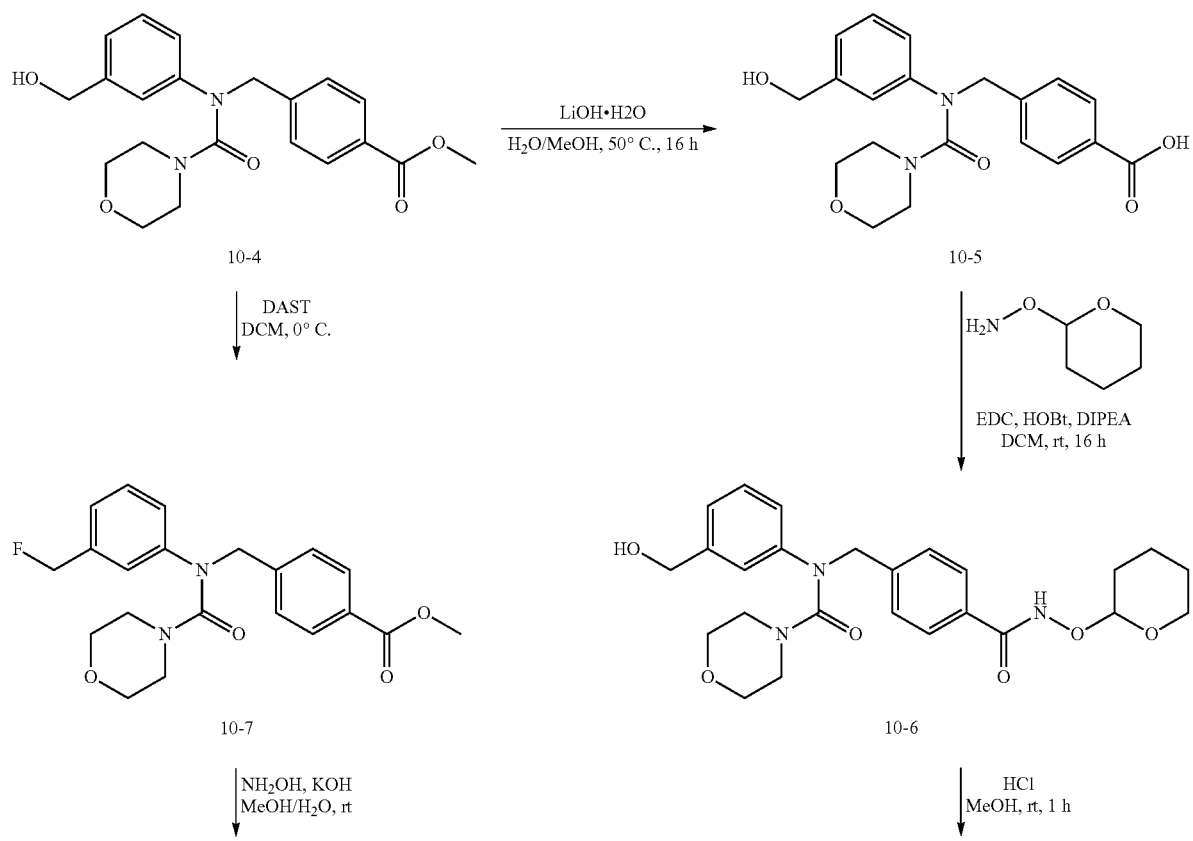

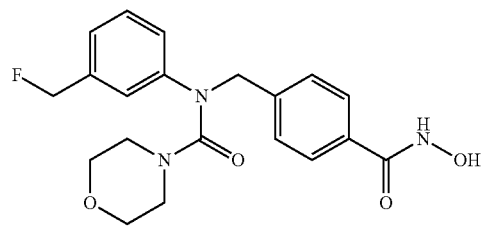

Compound 500

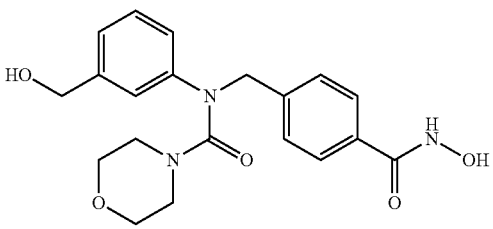

Compound 499

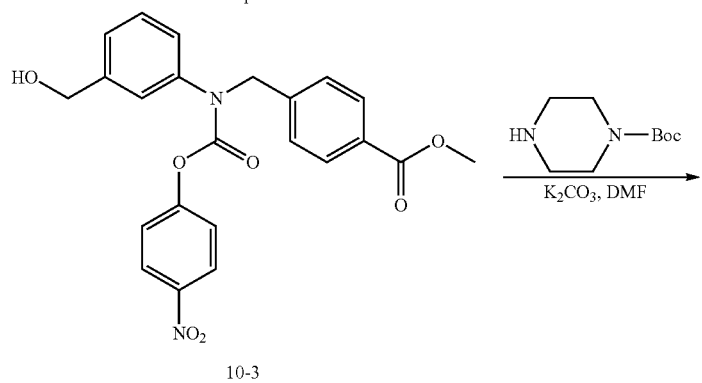

10-3

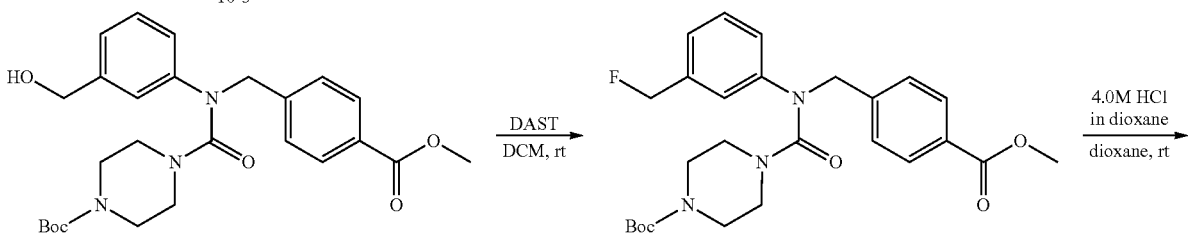

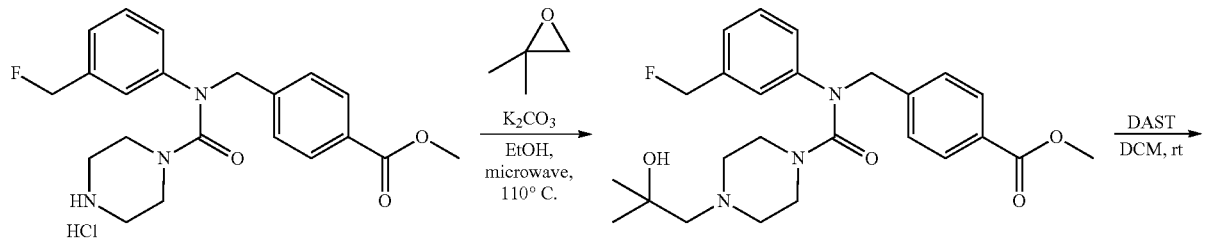

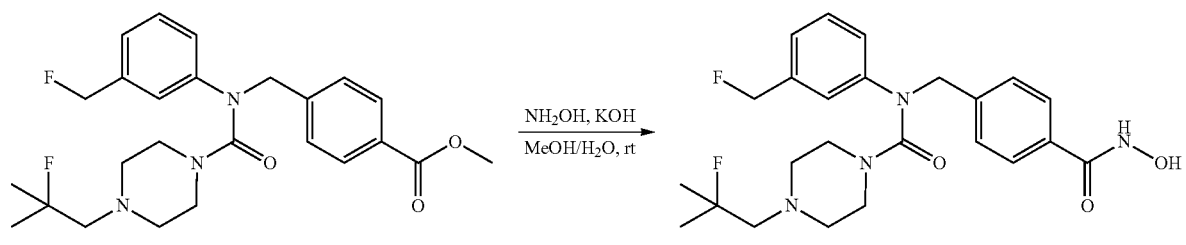

In reaction scheme 10, the compound of Formula 10-2 was synthesized by the reductive amination of the compound of Formula 10-1 with methyl 4-formylbenzoate, and the compound of Formula 10-3 was synthesized by the reaction of the compound of Formula 10-2 with 4-nitrophenyl chloroformate at room temperature. Next, the compound of Formula 10-4 was synthesized by the substitution of the compound of Formula 10-3 with morpholine at room temperature, and then the compound of Formula 10-5 was synthesized by the hydrolysis of the compound of Formula 10-4 with lithium hydroxide (LiOH). Subsequently, the compound of Formula 10-6 was synthesized by the reaction of the compound of Formula 10-5 with (tetrahydropyran-2-yl)hydroxylamine, 1-ethyl-3-[3-dimethylaminopropyl]carbodiimide hydrochloride (EDC) and 1-hydroxybenzotriazole hydrate (HOBt) at room temperature. Then, the target Compound 499 was synthesized by dissolving the compound of Formula 10-6 in methanol and adding hydrogen chloride at room temperature.

The compound of Formula 10-7 was synthesized by the reaction of the compound of Formula 10-4 with diethylaminosulfur trifluoride (DAST), and then the target Compound 500 was synthesized by dissolving the compound of Formula 10-7 in methanol, followed by the reaction with hydroxylamine (NH₂OH) aqueous solution and potassium hydroxide (KOH), which were sequentially added dropwise, at room temperature.

The compound of Formula 10-8 was synthesized by the substitution of the compound of Formula 10-3 with ethylpiperazine, and then the compound of Formula 10-9 was synthesized using diethylaminosulfur trifluoride (DAST). Next, the target Compound 765 was synthesized by dissolving the compound of Formula 10-9 in methanol, followed by the reaction with hydroxylamine (NH₂OH) aqueous solution and potassium hydroxide (KOH), which were sequentially added dropwise, at room temperature.

The compound of Formula 10-11 was synthesized by the introduction of Boc-piperazine into the compound of Formula 10-3, followed by the reaction with diethylaminosulfur trifluoride (DAST). And then, the compound of Formula 10-12 was synthesized by Boc-deprotection under acidic conditions. Next, the compound of Formula 10-13 was synthesized by the reaction of the compound of Formula 10-12 with 2,2-dimethyloxirane under microwave irradiation, and then the compound of Formula 10-14 was synthesized using diethylaminosulfur trifluoride (DAST). Finally, the target Compound 766 was synthesized by dissolving the compound of Formula 10-14 in methanol, followed by the reaction with hydroxylamine (NH₂OH) aqueous solution and potassium hydroxide (KOH), which were sequentially added dropwise, at room temperature.

[Reaction Scheme 11]

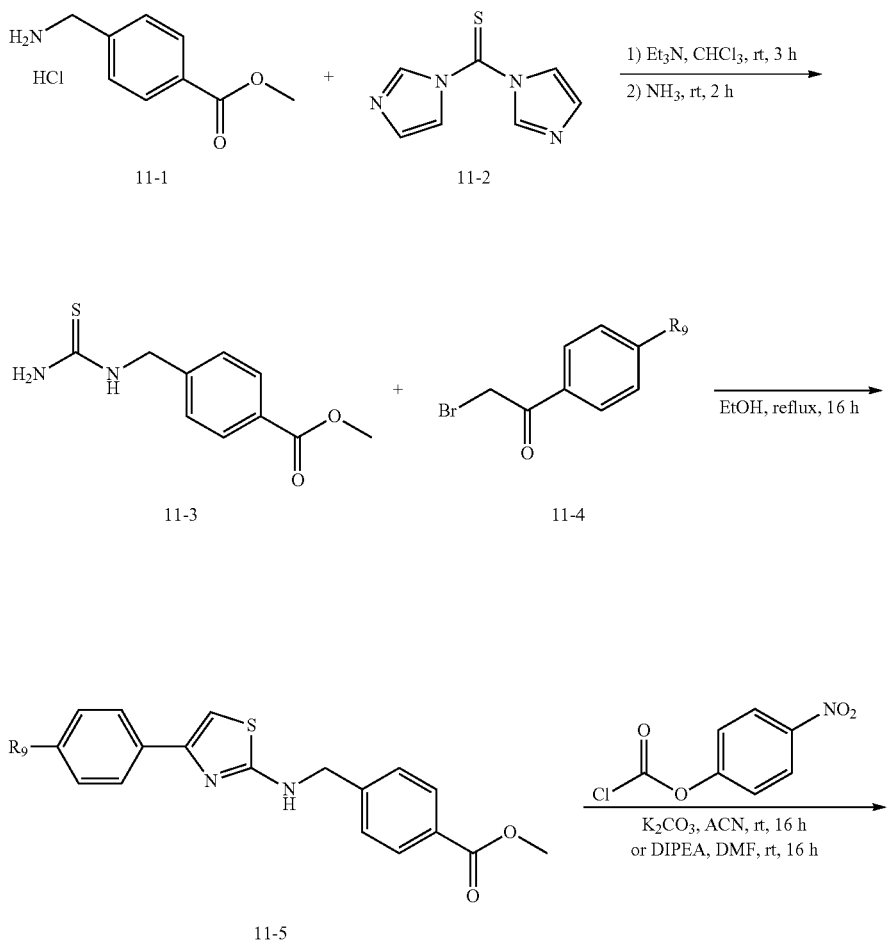

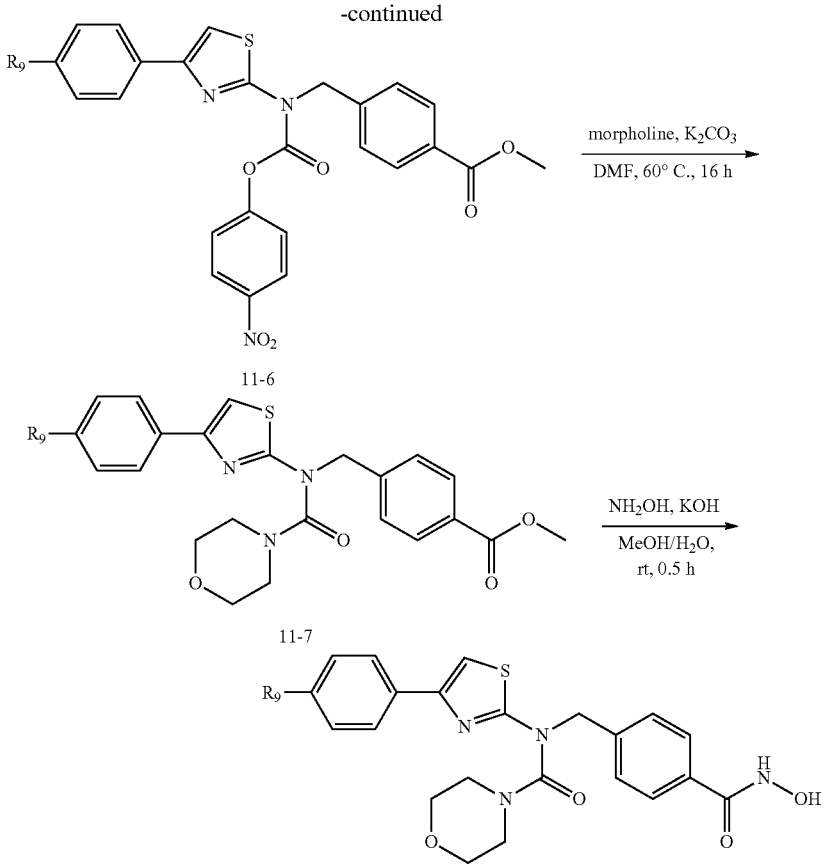

Compound 370: R₈ = H
Compound 371: R₈ = Cl

In reaction scheme 11, the compound of Formula 11-3 was synthesized by the substitution of the compound of Formula 11-2 with the compound of Formula 11-1 twice, and then the compound of Formula 11-5 was synthesized by the cyclization of the compound of Formula 11-3 with the compound of Formula 11-4 by stirring under reflux in the presence of ethanol solvent. Next, the compound of Formula 11-6 was synthesized by the reaction of the compound of Formula 11-5 with 4-nitrophenyl chloroformate at room temperature, and then the compound of Formula 11-7 was synthesized by the substitution of the compound of Formula 11-6 with morpholine at 60° C. Finally, the target Compounds 370 or 731 were synthesized by dissolving the compound of Formula 11-7 in methanol, followed by the reaction with hydroxylamine (NH₂OH) aqueous solution and potassium hydroxide (KOH), which were sequentially added dropwise, at room temperature.

[Reaction Scheme 12]

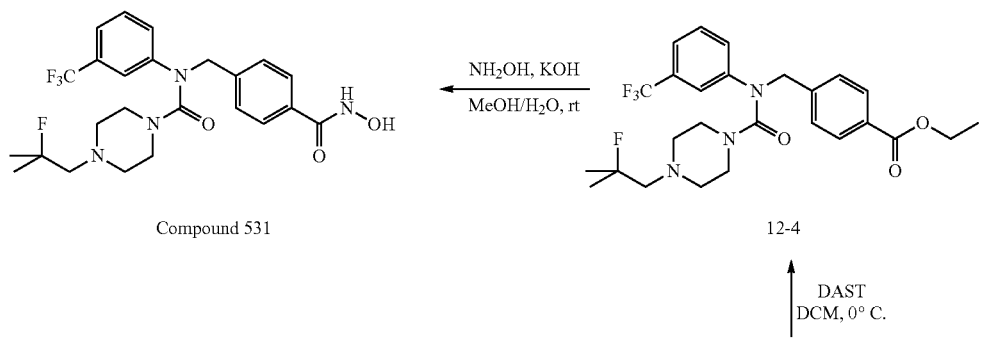

Compound 531

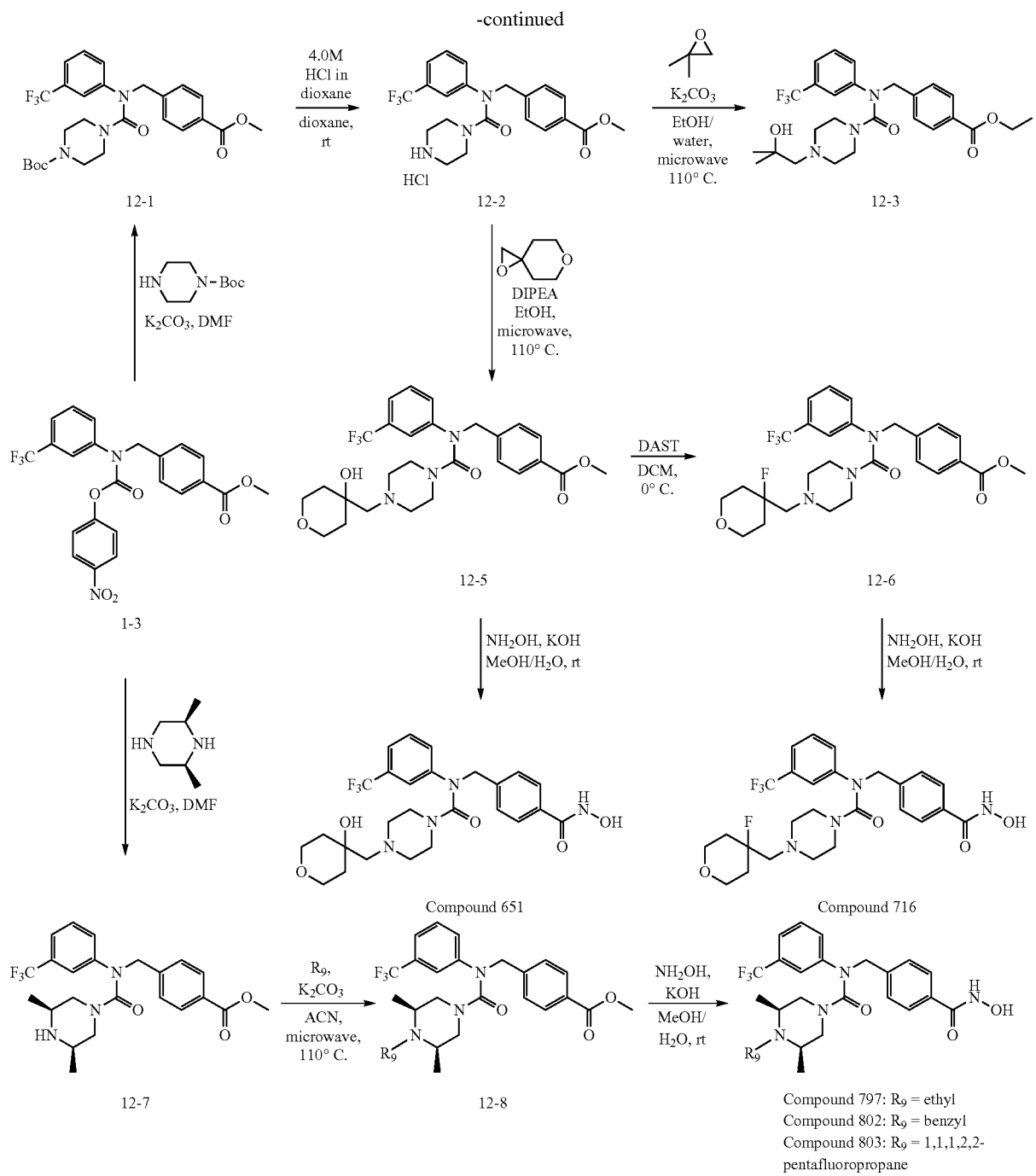

In reaction scheme 12, the compound of Formula 12-1 was synthesized by the reaction of the compound of Formula I-3 with N-boc-piperazine, and then the compound of Formula 12-2 was synthesized by Boc-deprotection under acidic conditions. Next, the compound of Formula 12-3 was synthesized by the reaction of the compound of Formula 12-2 with 2,2-dimethyloxirane under microwave irradiation, and then the compound of Formula 12-4 was synthesized using diethylaminosulfur trifluoride (DAST). Then, the Compound 531 was synthesized by dissolving the compound of Formula 12-4 in methanol, followed by the reaction with hydroxylamine (NH$_2$OH) aqueous solution and potassium hydroxide (KOH), which were sequentially added dropwise, at room, temperature.

The compound of Formula 12-5 was synthesized by the reaction of the compound of Formula 12-2 with 1,6-dioxaspiro[2,5]octane under microwave irradiation, and then the Compound 651 was synthesized by dissolving the compound of Formula 12-5 in methanol, followed by the reaction with hydroxylamine (NH$_2$OH) aqueous solution and potassium hydroxide (KOH), which were sequentially added dropwise, at room temperature.

The compound of Formula 12-6 was synthesized by the reaction of the compound of Formula 12-5 with DAST, and then the Compound 716 was synthesized by dissolving the compound of Formula 12-6 in methanol, followed by the reaction with hydroxylamine (NH$_2$OH) aqueous solution and potassium hydroxide (KOH), which were sequentially added dropwise, at room temperature.

The compound of Formula 12-8 was synthesized by the introduction of amine derivative (R$_6$) into the compound of Formula I-3, followed by the substitution, and then the target compound 797, 802 or 803 was synthesized by dissolving the compound of Formula 12-8 in methanol, followed by the reaction with hydroxylamine (NH$_2$OH) aqueous solution and potassium hydroxide (KOH), which were sequentially added dropwise, at room temperature.

The present invention provides a pharmaceutical composition for the prevention or treatment of histone deacetylase-mediated diseases, comprising a compound represented by the following Formula I, an optical isomer thereof, or a pharmaceutically acceptable salt thereof as an active ingredient.

[Formula I]

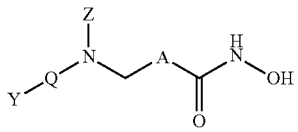

wherein Y, Q, Z and A are the same as defined above.

Examples of histone deacetylase-mediated diseases may include cell proliferative diseases including malignant tumors such as cancers, etc., inflammatory diseases, autosomal dominant diseases such as Huntington's diseases, etc., inherited metabolic diseases such as cystic fibrosis, hepatic fibrosis, kidney fibrosis, pulmonary fibrosis, skin fibrosis, etc, autoimmune diseases such as rheumatoid arthritis, etc., acute and chronic neurological diseases such as diabetes, stroke, etc., hypertrophy such as cardiac hypertrophy, etc., hemorrhagic heart failure, amyotrophic lateral sclerosis, glaucoma, ocular diseases (associated with angiogenesis), neurodegenerative diseases, etc., and further include symptoms and diseases associated with abnormal function of histone deacetylase.

The compound represented by Formula I of the present invention may be one of the compounds represented by the above Formula I-1 to I-12, Formula II or Formula III.

The pharmaceutically acceptable salt is the same as those described with respect to the compound represented by the above Formula I.

For administration, the pharmaceutical composition of the present invention may further comprise one or more pharmaceutically acceptable carriers in addition to the compound represented by the above Formula I, an optical isomer thereof or a pharmaceutically acceptable salt thereof. Examples of the pharmaceutically acceptable carrier include saline, sterile water, Ringer's solution, buffered saline, dextrose solution, maltodextrin solution, glycerol, ethanol and combinations thereof. If necessary, other general additives, such as antioxidant, buffer solution, anti-bacterial agent, etc., may be added to the composition. Moreover, the pharmaceutical composition of the present invention may be formulated into injections such as aqueous solution, suspension, emulsion, etc., pills, capsules, granule, or tablets by adding diluent, dispersant, surfactant, binder, and lubricant. Accordingly, the composition of the present invention can be presented as patches, liquids, pills, capsules, granules, tablets, suppositories, etc. These formulations may be formulated by suitable methods in the art or methods described in Remington's Pharmaceutical Science (latest edition), Mack Publishing Company, Easton Pa., depending on the disease and/or ingredients.

The composition of the present invention may be administered orally or parenterally (e.g., intravenously, subcutaneously, intraperitoneally, or topically) at a dose depending on various factors including the patient's weight, age, gender, state of health, diet, administration time, administration route, excretion rate, severity of disease, etc. The daily dose of the composition of the present invention may be about 1 to 500 mg/kg, preferably 5 to 100 mg/kg, and the composition of the present invention may be administered once or several times a day.

The pharmaceutical composition of the present invention may further comprise one or more active ingredients having the same or similar efficacy in addition to the compound represented by the above Formula I, an optical isomer thereof or a pharmaceutically acceptable salt thereof.

The present invention provides a method for the prevention or treatment of histone deacetylase-mediated diseases, comprising administering a therapeutically effective amount of a compound represented by the above Formula I, an optical isomer thereof or a pharmaceutically acceptable salt thereof.

As used herein, the term "therapeutically effective amount" refers to the amount of a compound represented by the above Formula I, which is effective for the prevention or treatment of histone deacetylase-mediated diseases.

Moreover, the present invention provides a method for inhibiting histone deacetylase (HDAC), comprising administering an effective amount of a compound represented by the above Formula I, an optical isomer thereof or a pharmaceutically acceptable salt thereof to a mammal including a human.

The method for the prevention or treatment of histone deacetylase-mediated diseases according to the present invention further includes managing the disease itself before the onset of symptoms as well as inhibiting or avoiding the symptoms by administering the compound represented by the above Formula I. In the management of the disease, the preventive or therapeutic dose of a specific active ingredient may vary depending on the nature and severity of the disease or condition and the administration route of the active ingredient. The dose and the frequency of the dose may vary depending on the individual patient's age, weight, and response. The suitable dose and use may be easily selected by those having ordinary skill in the art based on these factors. Moreover, the method for the prevention or treatment of histone deacetylase-mediated diseases according to the present invention may further comprise administering a therapeutically effective amount of an additional active ingredient that improve the treatment of disease together with the compound represented by the above Formula I. The additional active ingredient may exhibit a synergistic or additive effect together with the compound represented by the above Formula I.

The present invention further provides the use of a compound represented by the above Formula I, an optical isomer thereof or a pharmaceutically acceptable salt thereof in the preparation of medicaments for the treatment of HDAC-mediated diseases. The compound represented by the above Formula I for the preparation of medicaments may comprise a pharmaceutically acceptable adjuvant, diluent, carrier, etc. and may be prepared into combined formulations together with other active ingredients to have synergistic activities.

The matters mentioned in the use, the composition, and the treatment method of the present invention are applied equally unless they are contradictory to each other.

Advantageous Effects of Invention

The compound represented by the above Formula I, an optical isomer thereof or a pharmaceutically acceptable salt thereof according to the present invention can selectively inhibit HDAC and thus have excellent effects on the prevention and treatment of histone deacetylase-mediated diseases.

BRIEF DESCRIPTION OF DRAWINGS

FIG. 1 shows the acetylation levels of Tubulin, Histone H3 and Histone H4 after the treatment with Compound 255.

FIG. 2 shows the acetylation levels of Tubulin, Histone H3 and Histone H4 after the treatment with Compound 374.

FIG. 3 shows the improvement of arthritis after the treatment with Compound 254 or Compound 255 to collagen-induced arthritis models.

FIG. 4 shows the improvement of arthritis after the treatment with Compound 374 to collagen-induced arthritis models.

FIG. 6 shows the recovery of weight after the treatment with Compound 254 or 255 to colitis models.

FIG. 7 shows the combination index after the combination treatment of Compound 255 and Velcade.

MODE FOR THE INVENTION

Figure 5A:
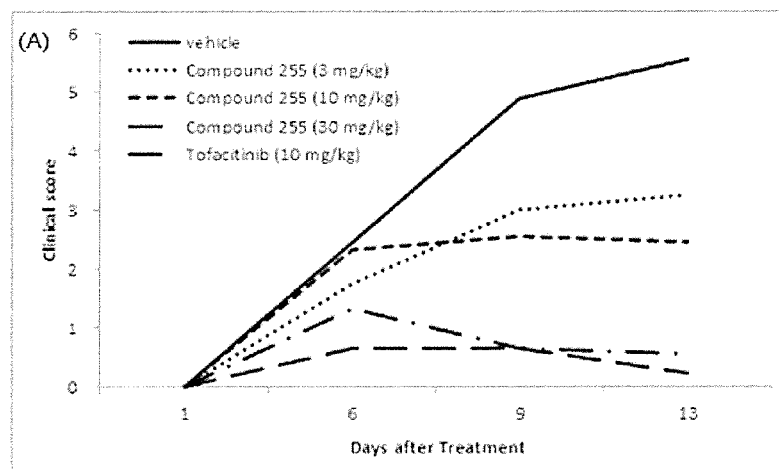
FIGS. 5A-5C show the improvement of arthritis after the treatment with Compound 255 (FIG. 5A), 374 (FIG. 5B) or 461 (FIG. 5C) to adjuvant-induced arthritis models.

Hereinafter, the present invention will be described in further detail with reference to examples, preparation examples and test examples. It is to be understood, however, that these examples are for illustrative purposes only and are not intended to limit the scope of the present invention.

Unless otherwise stated, reagents and solvents mentioned below were those available from Sigma-Aldrich and TCI, HPLC was Waters e2695, silica gel for column chromatography was Merck (230~400 mesh), $^1$H NMR data was measured using Bruker 400 MHz and Mass spectrum was agilent 1100 series.

Preparation of Novel Urea Compounds

Preparing methods of compound of formula 1 are described with reaction formula.

Example 1: Synthesis of Compound 252

Formula 1-2: methyl 4-((3-bromophenylamino)methyl)benzoate

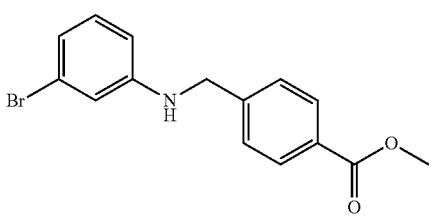 [SMILES: COC(=O)c1ccc(CNc2cccc(Br)c2)cc1]

Compound of Formula 1-1 (3-bromobenzenamine; 5 g, 29 mmol) was dissolved in dichloromethane (200 mL), and then methyl 4-formylbenzoate (5.7 g, 35 mmol) and acetic acid (1.74 mL, 29 mmol) were added and stirred for 1 hour. Then, sodium cyanoborohydride (2.2 g, 35 mmol) was slowly added dropwise and stirred for 1 day. Water was poured into the reaction mixture, and the organic layer was extracted. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-2 (7.8 g, 84%) in the form of a white solid.

Formula 3-1: methyl 4-(((3-bromophenyl)((4-nitrophenoxy)carbonyl)amino)methyl)benzoate

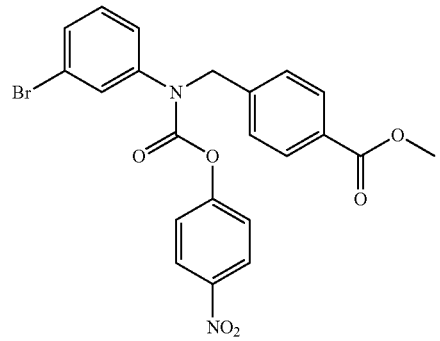 [SMILES: COC(=O)c1ccc(CN(C(=O)Oc2ccc([N+](=O)[O-])cc2)c2cccc(Br)c2)cc1]

Compound of Formula 1-2 (methyl 4-((3-bromophenylamino)methyl)benzoate; 5.90 g, 18.4 mmol) was dissolved in acetonitrile (200 mL), and then potassium carbonate (5.09 g, 36.9 mmol) and 4-nitrophenyl chloroformate (4.09 g, 20.3 mmol) were added. Then, the mixture was heated and stirred at 50° C. for 1 day. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=1%) to give the desired compound of Formula 3-1 (7.3 g, 82%) in the form of a white solid.

Formula 3-2: methyl 4-(((3-(1-methyl-1H-indazol-5-yl)phenyl)((4-nitrophenoxy)carbonyl)amino) methyl)benzoate

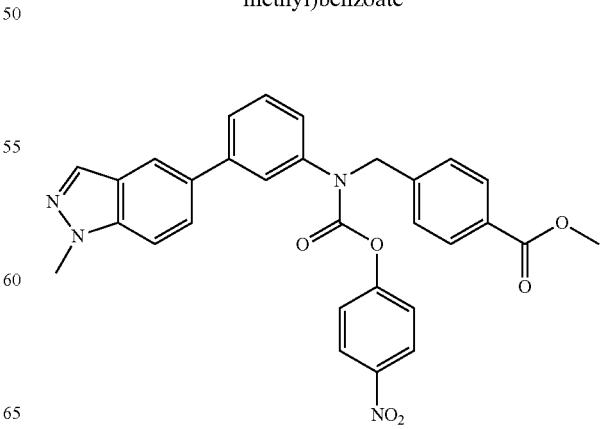

Compound of Formula 3-1 (methyl 4-(((3-bromophenyl)((4-nitrophenoxy)carbonyl)amino)methyl)benzoate; 1.00 g, 2.06 mmol), 1-methyl-1H-indazol-5-ylboronic acid (0.435 g, 2.473 mmol), Pd(dppf)Cl₂ (0.168 g, 0.206 mmol), and sodium carbonate (0.693 g, 4.53 mmol) were mixed with dimethoxyethane (5 mL)/H₂O (5 mL), heated at 120° C. for 15 minutes under microwave irradiation, and then the temperature was lowered to room temperature. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 3-2 (0.620 g, 56%) in the form of a white solid.

Formula 3-3: methyl 4-((N-(3-(1-methyl-1H-indazol-5-yl)phenyl)morpholine-4-carboxamido)methyl) benzoate

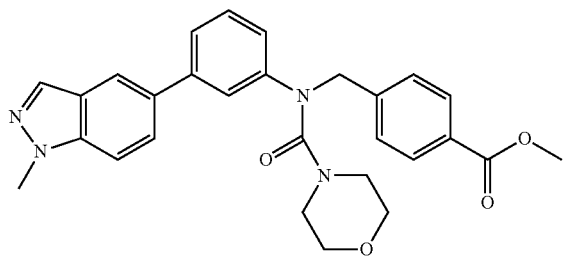 [SMILES: COC(=O)c1ccc(CN(C(=O)N2CCOCC2)c2cccc(-c3ccc4c(cnn4C)c3)c2)cc1]

Compound of Formula 3-2 (methyl 4-(((3-(1-methyl-1H-indazol-5-yl)phenyl)((4-nitrophenoxy)carbonyl)amino)methyl)benzoate; 0.05 g, 0.093 mmol) was dissolved in dimethylformamide (10 mL), and then morpholine (0.012 mL, 0.14 mmol) and potassium carbonate (0.039 g, 0.28 mmol) were added. Then, the mixture was heated and stirred at 60° C. for 12 hours. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 3-3 (0.035 g, 77%) in the form of a colorless liquid.

Compound 252: N-(4-(hydroxycarbamoyl)benzyl)-N-(3-(1-methyl-1H-indazol-5-yl)phenyl)morpholine-4-carboxamide

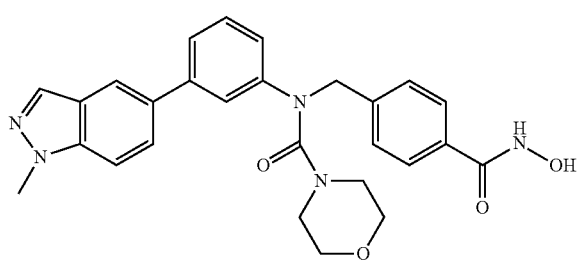 [SMILES: Cn1ncc2cc(-c3cccc(N(Cc4ccc(C(=O)NO)cc4)C(=O)N4CCOCC4)c3)ccc21]

Compound of Formula 3-3 (methyl 4-((N-(3-(1-methyl-1H-indazol-5-yl)phenyl)morpholine-4-carboxamido)methyl)benzoate; 0.035 g, 0.072 mmol) was dissolved in methanol (10 mL), and then hydroxylamine hydrochloride (0.025 g, 0.361 mmol), potassium hydroxide (0.041 g, 0.722 mmol), and hydroxylamine (50 wt % aqueous solution; 0.186 mL, 1.445 mmol) were added dropwise and stirred at room temperature for 6 hours. After completion of the reaction, the methanol was removed under reduced pressured, and then 2 N hydrogen chloride was added to precipitate a solid. Then, the resulting solid was filtered and dried to give the desired Compound 252 (0.016 g, 46%) in the form of a white solid.

¹H NMR (400 MHz, DMSO-d₆) δ 8.08 (s, 1H), 7.97 (s, 1H), 7.69-7.64 (m, 4H), 7.43-7.35 (m, 5H), 7.08 (d, 1H, J=7.0 Hz), 4.93 (s, 2H), 4.05 (s, 3H), 3.40-3.37 (m, 4H), 3.19-3.16 (m, 4H); MS (ESI) m/z 486.1 (M⁺+H).

Example 2: Synthesis of Compound 253

Formula 3-3: methyl 4-((4-methyl-N-(3-(1-methyl-1H-indazol-5-yl)phenyl)piperazine-1-carboxamido)methyl)benzoate

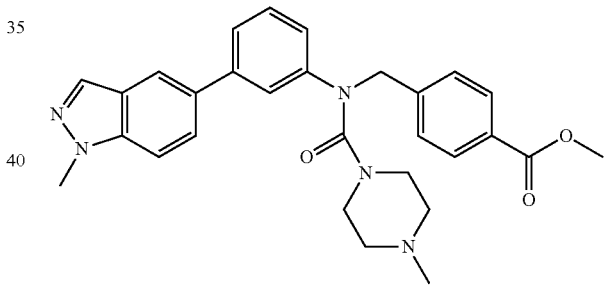

Compound of Formula 3-2 (methyl 4-(((3-(1-methyl-1H-indazol-5-yl)phenyl)((4-nitrophenoxy)carbonyl)amino)methyl)benzoate; 0.05 g, 0.093 mmol) was dissolved in dimethylformamide (10 mL), and then n-methylpiperazine (0.016 mL, 0.14 mmol) and potassium carbonate (0.039 g, 0.28 mmol) were added. Then, the mixture was heated and stirred at 55° C. for 12 hours. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 3-3 (0.044 g, 95%) in the form of a colorless liquid.

Compound 253: N-(4-(hydroxycarbamoyl)benzyl)-4-methyl-N-(3-(1-methyl-1H-indazol-5-yl)phenyl)piperazine-1-carboxamide

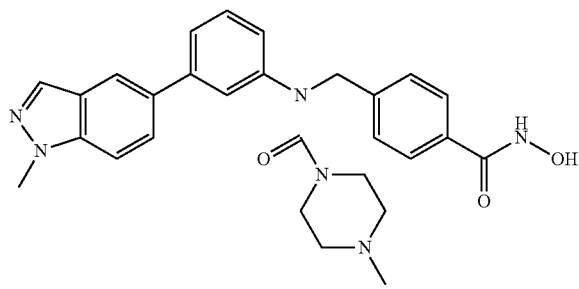

Compound of Formula 3-3 (methyl 4-((4-methyl-N-(3-(1-methyl-1H-indazol-5-yl)phenyl)piperazine-1-carboxamido)meth yl)benzoate; 0.044 g, 0.088 mmol) was dissolved in methanol (5 mL), and then hydroxylamine hydrochloride (0.031 g, 0.442 mmol), potassium hydroxide (0.049 g, 0.884 mmol), and hydroxylamine (50 wt % aqueous solution; 0.228 mL, 1.77 mmol) were added dropwise and stirred at room temperature for 6 hours. After completion of the reaction, the methanol was removed under reduced pressured, and then 2 N hydrogen chloride was added to precipitate a white solid. Then, the resulting solid was filtered and dried to give the desired Compound 253 (0.02 g, 45%) in the form of a white solid.

$^1$H NMR (400 MHz, DMSO-d$_6$) δ 8.08 (s, 1H), 7.97 (s, 1H), 7.69-7.64 (m, 4H), 7.41-7.37 (m, 5H), 7.07-7.06 (m, 1H), 4.92 (s, 2H), 4.06 (s, 3H), 3.20-3.19 (m, 4H), 2.13-2.11 (m, 4H), 2.06 (s, 3H); MS (ESI) m/z 499.2 (M$^+$+H).

Example 3: Synthesis of Compound 254

Formula 3-2: methyl 4-(((3-(1-methyl-1H-indazol-6-yl)phenyl)((4-nitrophenoxy)carbonyl)amino)methyl)benzoate

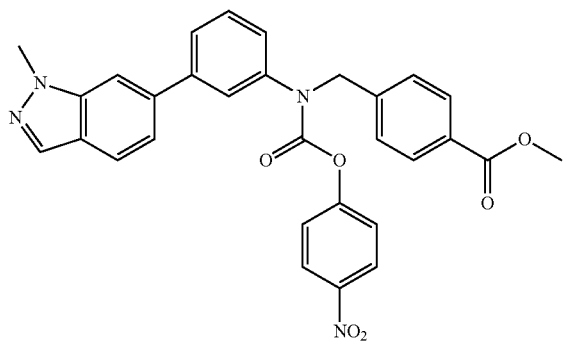 [SMILES: COC(=O)c1ccc(CN(C(=O)Oc2ccc([N+](=O)[O-])cc2)c2cccc(-c3ccc4cnn(C)c4c3)c2)cc1]

Compound of Formula 3-1 (methyl 4-(((3-bromophenyl)((4-nitrophenoxy)carbonyl)amino)methyl)benzoate; 1.00 g, 2.06 mmol), 1-methyl-1H-indazol-6-ylboronic acid (0.435 g, 2.47 mmol), Pd(dppf)Cl$_2$ (0.168 g, 0.206 mmol), and sodium carbonate (0.693 g, 4.53 mmol) were mixed with dimethoxyethane (5 mL)/H$_2$O (5 mL), heated at 120° C. for 15 minutes under microwave irradiation, and then the temperature was lowered to room temperature. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 3-2 (1.03 g, 93%) in the form of a white solid.

Formula 3-3: methyl 4-((N-(3-(1-methyl-1H-indazol-6-yl)phenyl)morpholine-4-carboxamido)methyl)benzoate

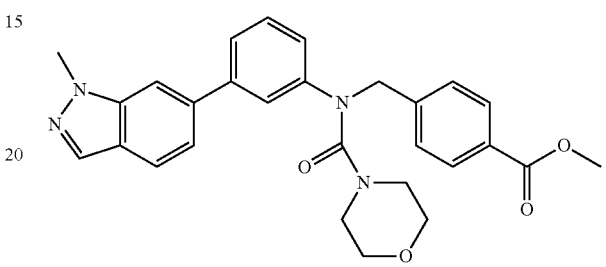

Compound of Formula 3-2 (methyl 4-(((3-(1-methyl-1H-indazol-6-yl)phenyl)((4-nitrophenoxy)carbonyl)amino)methyl)benzoate; 0.05 g, 0.093 mmol) was dissolved in dimethylformamide (10 mL), and then morpholine (0.011 mL, 0.14 mmol) and potassium carbonate (0.0386 g, 0.28 mmol) were added. Then, the mixture was heated and stirred at 60° C. for 12 hours. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 3-3 (0.035 g, 78%) in the form of a white solid.

Compound 254: N-(4-(hydroxycarbamoyl)benzyl)-N-(3-(1-methyl-1H-indazol-6-yl)phenyl)morpholine-4-carboxamide

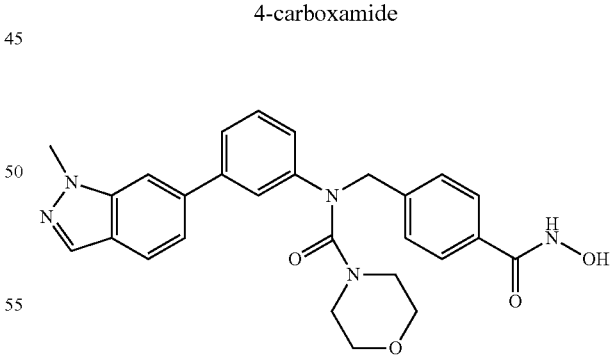

Compound of Formula 3-3 (methyl 4-((N-(3-(1-methyl-1H-indazol-6-yl)phenyl)morpholine-4-carboxamido)methyl)benzoate; 0.035 g, 0.072 mmol) was dissolved in methanol (5 mL), and then hydroxylamine hydrochloride (0.025 g, 0.361 mmol), potassium hydroxide (0.041 g, 0.722 mmol), and hydroxylamine (50 wt % aqueous solution; 0.186 mL, 1.45 mmol) were added dropwise and stirred at room temperature for 6 hours. After completion of the reaction, the methanol was removed under reduced pressured, and then 2 N hydrogen chloride was added to precipitate a solid. Then, the resulting solid was filtered and dried to give the desired Compound 254 (0.024 g, 68%) in the form of a white solid.

$^1$H NMR (400 MHz, DMSO-$d_6$) δ 8.04 (s, 1H), 7.83 (s, 1H), 7.80 (d, 1H, J=8.4 Hz), 7.65 (d, 2H, J=8.2 Hz), 7.52 (s, 1H), 7.48 (d, 1H, J=7.9 Hz), 7.43-7.38 (m, 4H), 7.14 (d, 1H, J=7.9 Hz), 4.95 (s, 2H), 4.09 (s, 2H), 3.41-3.40 (m, 4H), 3.19-3.18 (m, 4H); MS (ESI) m/z 486.1 (M$^+$+H).

Example 4: Synthesis of Compound 255

Formula 1-4: methyl 4-((N-(3-bromophenyl)morpholine-4-carboxamido)methyl)benzoate

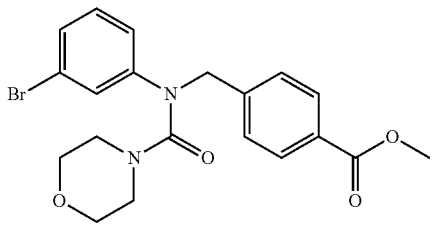 [SMILES: COC(=O)c1ccc(CN(C(=O)N2CCOCC2)c2cccc(Br)c2)cc1]

Compound of Formula 1-3 (methyl 4-(((3-bromophenyl)((4-nitrophenoxy)carbonyl)amino)methyl)benzoate; 1.5 g, 3.09 mmol) was dissolved in acetonitrile (50 ml), and potassium carbonate (1.28 g, 9.3 mmol) and morpholine (0.40 mL, 4.64 mmol) were slowly added. Then, the temperature was slowly raised and the mixture was stirred at 80° C. for 3 hours. The temperature was lowered to room temperature, and dimethylformamide (50 ml) was further added and stirred at 80° C. for 5 hours. Then, the reaction was completed, and the organic layer was washed three times with saturated ammonium chloride aqueous solution, dehydrated with sodium sulfate, and filtered. Then, the filtrate was then concentrated under reduced pressure, and the concentrate was purified by column chromatography (silica; ethyl acetate/hexane=0-50%) to give the desired compound of Formula 1-4 (0.45 g, 33.6%) in the form of a transparent oil.

Compound 255: N-(3-bromophenyl)-N-(4-(hydroxycarbamoyl)benzyl)morpholine-4-carboxamide

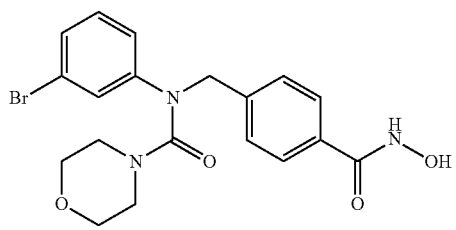 [SMILES: O=C(NO)c1ccc(CN(C(=O)N2CCOCC2)c2cccc(Br)c2)cc1]

Compound of Formula 1-4 (methyl 4-((N-(3-bromophenyl)morpholine-4-carboxamido)methyl)benzoate; 0.05 g, 0.12 mmol) was dissolved in methanol (2 ml), and hydroxylamine hydrochloride (0.040 g, 0.58 mmol) was slowly added. Then, potassium hydroxide (0.065 g, 1.15 mmol) was added and stirred at room temperature for 10 minutes, and hydroxylamine (50.0 wt % aqueous solution; 0.14 mL, 2.31 mmol) was added. The mixture was stirred at room temperature for 1 day, and the organic solvent was then concentrated under reduced pressure and then neutralized by adding 2 N hydrochloric acid. Then, organic layer was washed three times with saturated sodium chloride aqueous solution, dehydrated with anhydrous sodium sulfate, and filtered, and the filtrate was then concentrated under reduced pressure. The concentrate was purified by column chromatography (silica; ethyl acetate/hexane=0-80%) to give the desired Compound 255 (0.036 g, 72%) in the form of a white solid.

$^1$H NMR (400 MHz, CDCl$_3$-$d_6$) δ 7.63 (d, 2H, J=7.8 Hz), 7.27-7.20 (m, 4H), 7.13 (t, 1H, J=7.8 Hz), 6.96 (d, 1H, J=7.1 Hz), 4.83 (s, 2H), 3.49 (brs, 4H), 3.23 (brs, 4H); MS (ESI) m/z 436 (M$^+$+H).

Example 5: Synthesis of Compound 256

Formula 1-4: methyl 4-((N-(3-bromophenyl)-4-methylpiperazine-1-carboxamido)methyl)benzoate

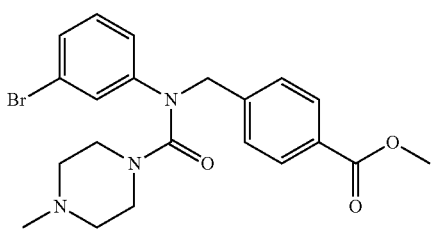 [SMILES: COC(=O)c1ccc(CN(C(=O)N2CCN(C)CC2)c2cccc(Br)c2)cc1]

Compound of Formula 1-3 (methyl 4-(((3-bromophenyl)((4-nitrophenoxy)carbonyl)amino)methyl)benzoate; 1.5 g, 3.09 mmol) was dissolved in acetonitrile (50 ml), and potassium carbonate (1.28 g, 9.3 mmol) and 1-methylpiperazine (0.52 mL, 4.64 mmol) were slowly added. Then, the temperature was slowly raised and the mixture was stirred at 80° C. for 3 hours. The temperature was lowered to room temperature, and dimethylformamide (50 ml) was further added and stirred at 80° C. for 5 hours. Then, the reaction was completed, and the organic layer was washed three times with saturated ammonium chloride aqueous solution, dehydrated with sodium sulfate, and filtered. Then, the filtrate was then concentrated under reduced pressure, and the concentrate was purified by column chromatography (silica; ethyl acetate/hexane=0-50%) to give the desired compound of Formula 1-4 (0.9 g, 65%) in the form of a transparent oil.

Compound 256: N-(3-bromophenyl)-N-(4-(hydroxycarbamoyl)benzyl)methylpiperazine-1-carboxamide

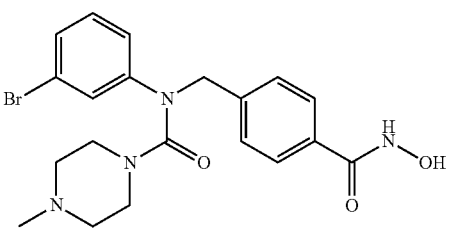

Compound of Formula 1-4 (methyl 4-((N-(3-bromophenyl)-4-methylpiperazine-1-carboxamido)methyl)benzoate; 0.05 g, 0.12 mmol) was dissolved in methanol (2 ml), and hydroxylamine hydrochloride (0.039 g, 0.56 mmol) was slowly added. Then, potassium hydroxide (0.063 g, 1.12 mmol) was added and stirred at room temperature for 10 minutes, and hydroxylamine (50.0 wt % aqueous solution; 0.14 mL, 2.24 mmol) was added. The mixture was stirred at room temperature for 1 day, and the organic solvent was then concentrated under reduced pressure and then neutralized by adding 2 N hydrochloric acid. Then, organic layer was washed three times with saturated sodium chloride aqueous solution, dehydrated with anhydrous sodium sulfate, and filtered to give the desired Compound 256 (0.05 g, 99%) in the form of a yellow solid.

$^1$H NMR (400 MHz, MeOD-$d_3$) δ 7.65 (d, 2H, J=8.2 Hz), 7.39 (d, 2H, J=8.0 Hz), 7.30-7.09 (m, 4H), 4.91 (brs, 2H), 3.26 (m, 4H), 2.26 (m, 4H), 2.22 (s, 3H); MS (ESI) m/z 449 (M$^+$+H).

Example 6: Synthesis of Compound 260

Formula 3-3: methyl 4-((N-(3-(1-methyl-1H-indazol-5-yl)phenyl)piperidine-1-carboxamido)methyl)benzoate

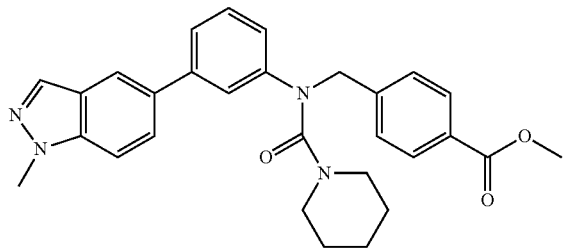 [SMILES: COC(=O)c1ccc(CN(C(=O)N2CCCCC2)c2cccc(-c3ccc4c(cnn4C)c3)c2)cc1]

Compound of Formula 3-2 (methyl 4-(((3-(1-methyl-1H-indazol-5-yl)phenyl)((4-nitrophenoxy)carbonyl)amino)methyl)benzoate; 0.05 g, 0.093 mmol) was dissolved in dimethylformamide (3 mL), and then piperidine (0.012 mL, 0.14 mmol) and potassium carbonate (0.039 g, 0.28 mmol) were added. Then, the mixture was heated and stirred at 60° C. for 12 hours. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20-30%) to give the desired compound of Formula 3-3 (0.042 g, 93.4%) in the form of a colorless liquid.

Compound 260: N-(4-(hydroxycarbamoyl)benzyl)-N-(3-(1-methyl-1H-indazol-5-yl)phenyl)piperidine-1-carboxamide

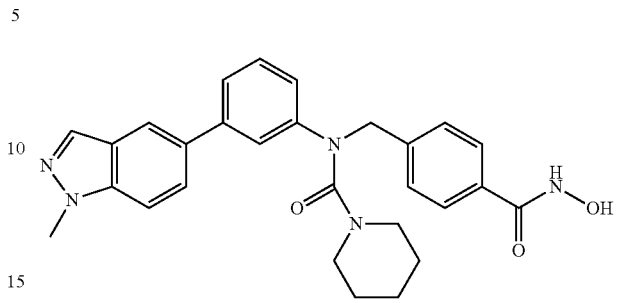

Compound of Formula 3-3 (methyl 4-((N-(3-(1-methyl-1H-indazol-5-yl)phenyl)piperidine-1-carboxamido)methyl)benzoate; 0.042 g, 0.087 mmol) was dissolved in methanol (5 mL), and then hydroxylamine hydrochloride (0.030 g, 0.435 mmol), potassium hydroxide (0.049 g, 0.87 mmol), and hydroxylamine (50 wt % aqueous solution; 0.224 mL, 1.74 mmol) were added dropwise and stirred at room temperature for 6 hours. After completion of the reaction, the methanol was removed under reduced pressured, and then 2 N hydrogen chloride was added to precipitate a solid. Then, the resulting solid was filtered and dried to give the desired Compound 260 (0.036 g, 85.5%) in the form of a white solid.

$^1$H NMR (400 MHz, DMSO-$d_6$) δ 8.08 (s, 1H), 7.95 (s, 1H), 7.71-7.64 (m, 4H), 7.37-7.36 (m, 5H), 7.04-7.03 (m, 1H), 4.90 (s, 2H), 4.05 (s, 3H), 3.18-3.17 (m, 4H), 1.42-1.41 (m, 2H), 1.29-1.28 (m, 4H); MS (ESI) m/z 483.56 (M$^+$+H).

Example 7: Synthesis of Compound 261

Formula 2-2: methyl 4-((N-(3-(1H-indol-6-yl)phenyl)morpholine-4-carboxamido)methyl)benzoate

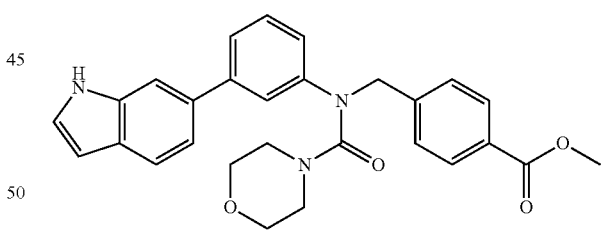

Compound of Formula 2-1 (methyl 4-((N-(3-bromophenyl)morpholine-4-carboxamido)methyl)benzoate; 0.12 g, 0.28 mmol) was placed in a microwave reactor, and then dimethoxyethane (5 mL) was added. Then, indole-6-boronic acid (0.054 g, 0.33 mmol) and Pd(dppf)Cl$_2$ (0.023 g, 0.028 mmol) were slowly added, and saturated sodium carbonate aqueous solution (0.093 g, 0.61 mmol) was then added. The mixture was stirred at 120° C. for 15 minutes under microwave irradiation, and then the reaction was completed. After washing three times with saturated sodium chloride aqueous solution, the organic layer was dehydrated with sodium sulfate, filtered, and concentrated. Then, the filtrate was concentrated under reduced pressure. The concentrate was purified by column chromatography (silica; ethyl acetate/ hexane=0-80%) to give the desired compound of Formula 2-2 (0.091 g, 70%) in the form of a whit solid.

Compound 261: N-(3-(1H-indol-6-yl)phenyl)-N-(4-(hydroxycarbamoyl)benzyl)morpholine-4-carboxamide

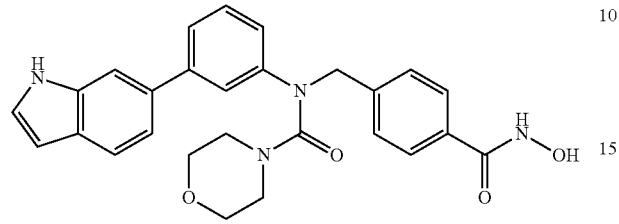

Compound of Formula 2-2 (methyl 4-((N-(3-(1H-indol-6-yl)phenyl)morpholine-4-carboxamido)methyl)benzoate; 0.09 g, 0.19 mmol) was dissolved in methanol (10 mL), and then hydroxylamine hydrochloride (0.067 g, 0.96 mmol) was slowly added. Then, potassium hydroxide (0.11 g, 1.92 mmol) was added and stirred at room temperature for 10 minutes, and then hydroxylamine (50.0 wt % aqueous solution; 0.23 mL, 3.83 mmol) was added and stirred at room temperature for 1 day. The organic solvent was concentrated under reduced pressure and then neutralized by adding 2 N hydrochloric acid. Then, the produced solid was filtered and dried to give the desired Compound 261 (0.05 g, 55%) in the form of a yellow solid.

$^1$H NMR (400 MHz, CDCl$_3$-d$_6$) δ 7.65 (d, 2H, J=8.2 Hz), 7.60-7.57 (m, 2H), 7.40-7.36 (m, 6H, J=7.8 Hz), 7.24 (d, 1H, J=8.2 Hz), 7.09-7.07 (m, 1H), 6.43 (s, 1H), 4.93 (s, 2H), 3.50 (m, 4H), 4.93 (m, 4H), 2.49 (s, 3H); MS (ESI) m/z 471 (M$^+$+H).

Example 8: Synthesis of Compound 262

Formula 2-2: methyl 4-((N-(3-(pyridin-3-yl)phenyl)morpholine-4-carboxamido)methyl)benzoate

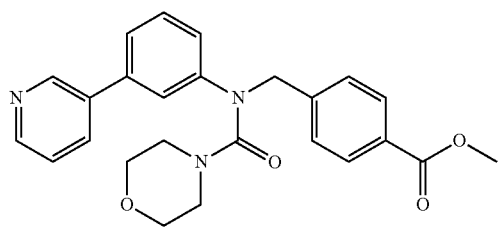 [SMILES: COC(=O)c1ccc(CN(C(=O)N2CCOCC2)c2cccc(-c3cccnc3)c2)cc1]

Compound of Formula 2-1 (methyl 4-((N-(3-bromophenyl)morpholine-4-carboxamido)methyl)benzoate; 0.11 g, 0.25 mmol) was placed in a microwave reactor, and then dimethoxyethane (5 mL) was added. Then, pyridine-3-boronic acid (0.037 g, 0.31 mmol) and Pd(dppf)Cl$_2$ (0.021 g, 0.025 mmol) were slowly added, and saturated sodium carbonate aqueous solution (0.085 g, 0.56 mmol) was then added. The mixture was stirred at 120° C. for 15 minutes under microwave irradiation, and then the reaction was completed. After washing three times with saturated sodium chloride aqueous solution, the organic layer was dehydrated with sodium sulfate, filtered, and concentrated. Then, the filtrate was concentrated under reduced pressure. The concentrate was purified by column chromatography (silica; ethyl acetate/hexane=0-80%) to give the desired compound of Formula 2-2 (0.064 g, 58%) in the form of a whit solid.

Compound 262: N-(4-(hydroxycarbamoyl)benzyl)-N-(3-(pyridin-3-yl)phenyl)morpholine-4-carboxamide

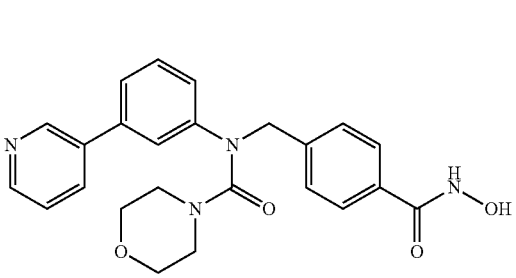 [SMILES: O=C(NO)c1ccc(CN(C(=O)N2CCOCC2)c2cccc(-c3cccnc3)c2)cc1]

Compound of Formula 2-2 (methyl 4-((N-(3-(pyridin-3-yl)phenyl)morpholine-4-carboxamido)methyl)benzoate; 0.06 g, 0.14 mmol) was dissolved in methanol (10 mL), and then hydroxylamine hydrochloride (0.048 g, 0.70 mmol) was slowly added. Then, potassium hydroxide (0.078 g, 1.40 mmol) was added and stirred at room temperature for 10 minutes, and then hydroxylamine (50.0 wt % aqueous solution; 0.17 mL, 2.78 mmol) was added and stirred at room temperature for 1 day. The organic solvent was concentrated under reduced pressure and then neutralized by adding 2 N hydrochloric acid. The organic layer was washed with ether and three times with saturated sodium chloride aqueous solution, dehydrated with anhydrous sodium sulfate, and then filtered to give the desired Compound 262 (0.045 g, 75%) in the form of a white solid.

$^1$H NMR (400 MHz, MeOD-d$_3$) δ 8.86 (s, 1H), 8.64 (d, 1H, J=4.0 Hz), 8.29 (d, 1H, J=8.1 Hz), 7.24-7.26 (m, 9H), 5.02 (m, 4H), 3.30 (m, 4H); MS (ESI) m/z 433 (M$^+$+H).

Example 9: Synthesis of Compound 263

Formula 2-2: methyl 4-((N-(3-(1H-indole-5-yl)phenyl)morpholine-4-carboxamido)methyl)benzoate

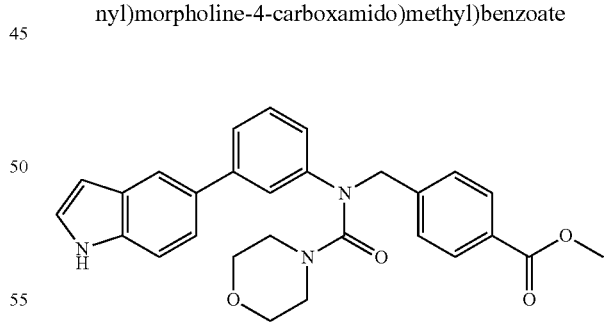

Compound of Formula 2-1 (methyl 4-((N-(3-bromophenyl)morpholine-4-carboxamido)methyl)benzoate; 0.05 g, 0.12 mmol) was placed in a microwave reactor, and then dimethoxyethane (5 mL) was added. Then, indole-5-boronic acid (0.023 g, 0.14 mmol) and Pd(dppf)Cl$_2$ (0.009 g, 0.012 mmol) were slowly added, and saturated sodium carbonate aqueous solution (0.039 g, 0.25 mmol) was then added. The mixture was stirred at 120° C. for 15 minutes under microwave irradiation, and then the reaction was completed. After washing three times with saturated sodium chloride aqueous solution, the organic layer was dehydrated with sodium sulfate, filtered, and concentrated. Then, the filtrate was concentrated under reduced pressure. The concentrate was purified by column chromatography (silica; ethyl acetate/hexane=0-80%) to give the desired compound of Formula 2-2 (0.040 g, 74%) in the form of a white solid.

Compound 263: N-(3-(1H-indol-5-yl)phenyl)-N-(4-(hydroxycarbamoyl)benzyl)morpholine-4-carboxamide

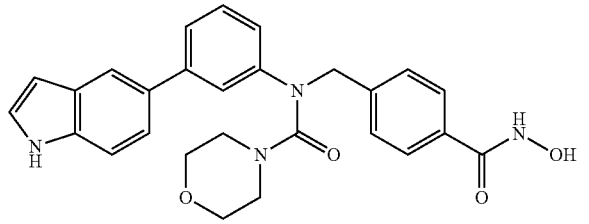 [SMILES: O=C(NO)c1ccc(CN(C(=O)N2CCOCC2)c2cccc(-c3ccc4[nH]ccc4c3)c2)cc1]

Compound of Formula 2-2 (methyl 4-((N-(3-(1H-indole-5-yl)phenyl)morpholine-4-carboxamido)methyl)benzoate; 0.040 g, 0.085 mmol) was dissolved in methanol (2 mL), and then hydroxylamine hydrochloride (0.030 g, 0.43 mmol) was slowly added. Then, potassium hydroxide (0.48 g, 0.85 mmol) was added and stirred at room temperature for 10 minutes, and then hydroxylamine (50.0 wt % aqueous solution; 0.11 mL, 1.70 mmol) was added and stirred at room temperature for 1 day. The organic solvent was concentrated under reduced pressure and then neutralized by adding 2 N hydrochloric acid. Then, the produced solid was filtered and dried to give the desired Compound 263 (0.03 g, 82%) in the form of a yellow solid.

$^1$H NMR (400 MHz, CDCl$_3$) δ 8.99 (brs, 1H), 7.75 (s, 1H), 7.64 (d, 1H, J=7.8 Hz), 7.44-7.05 (m, 9H), 6.46 (s, 1H), 4.93 (s, 2H), 3.39 (m, 4H), 3.17 (m, 4H); MS (ESI) m/z 471 (M$^+$+H).

Example 10: Synthesis of Compound 279

Formula 1-2: methyl 4-((phenylamino)methyl)benzoate

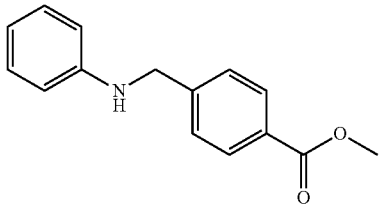 [SMILES: COC(=O)c1ccc(CNc2ccccc2)cc1]

Compound of Formula 1-1 (aniline; 0.20 g, 2.15 mmol) was dissolved in dichloroethane (10 mL), and then triethylamine (0.45 mL, 3.22 mmol) was slowly added. Then, methyl 4-(bromomethyl)benzoate (0.74 g, 3.22 mmol) was added, the temperature was slowly raised to 60° C., and the mixture was stirred for 1 hour. The reaction was completed, and the organic layer was washed three times with saturated sodium chloride aqueous solution, dehydrated with anhydrous sodium sulfate, and then filtered. The filtrate was concentrated under reduced pressure, and then the concentrate was purified by column chromatography (silica; ethyl acetate/hexane=0-50%) to give the desired compound of Formula 1-2 (0.15 g, 29%) in the form of a yellow oil.

Formula 1-3: methyl 4-((((4-nitrophenoxy)carbonyl)(phenyl)amino)methyl)benzoate

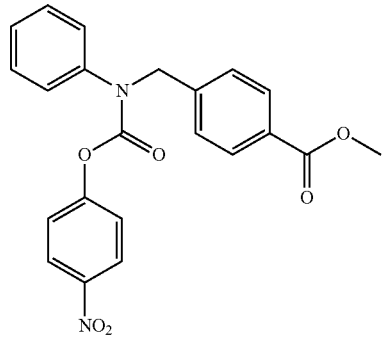 [SMILES: COC(=O)c1ccc(CN(C(=O)Oc2ccc([N+](=O)[O-])cc2)c2ccccc2)cc1]

Compound of Formula 1-2 (methyl 4-((phenylamino)methyl)benzoate; 0.15 g, 0.62 mmol) was dissolved in acetonitrile (3 mL), and then potassium carbonate (0.17 g, 1.24 mmol) was slowly added and stirred at room temperature for 10 minutes. Then, 4-nitrophenyl chloroformate (0.14 g, 0.68 mmol) was added, the temperature was slowly raised to 50° C., and the mixture was stirred for 12 hours. After completion of the reaction, the solvent was evaporated under reduced pressure, and the ethyl acetate layer was washed three times with saturated sodium chloride aqueous solution, and then the organic layer was dehydrated with sodium sulfate, and then filtered. The filtrate was concentrated under reduced pressure, and then the concentrate was purified by column chromatography (silica; ethyl acetate/hexane=0-20%) to give the desired compound of Formula 1-3 (0.18 g, 71%) in the form of a transparent oil.

Formula 1-3: methyl 4-((N-(phenylmorpholine-4-carboxamido)methyl)benzoate

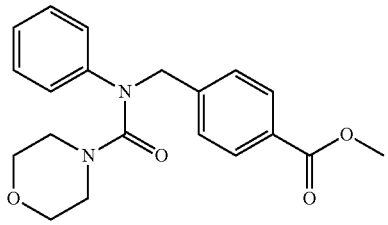

Compound of Formula 1-4 (methyl 4-((((4-nitrophenoxy)carbonyl)(phenyl)amino)methyl)benzoate; 0.18 g, 0.44 mmol) was dissolved in dimethylformamide (5 mL), and then potassium carbonate (0.18 g, 1.33 mmol) and morpholine (0.060 g, 0.67 mmol) were slowly added. The temperature was lowered to room temperature, and dimethylformamide (50 ml) was further added. Then, the temperature was slowly raised to 80° C., and the mixture was stirred for 3 hours. Then, the temperature was raised again to 80° C., and the mixture was stirred for 5 hours. The reaction was completed, and the organic layer was washed three times with saturated ammonium chloride aqueous solution, dehydrated with sodium sulfate, and then filtered. The filtrate was concentrated under reduced pressure, and the concentrate was purified by column chromatography (silica; ethyl acetate/hexane=0-50%) to give the desired compound of Formula 1-4 (0.10 g, 64%) in the form of a pale yellow solid.

Compound 279: N-(4-(hydroxycarbamoyl)benzyl)-N-phenylmorpholine-4-carboxamide

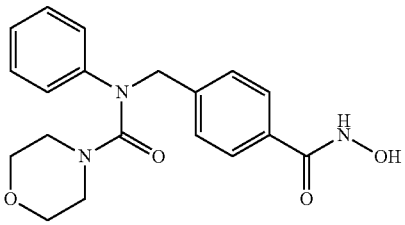 [SMILES: O=C(NO)c1ccc(CN(C(=O)N2CCOCC2)c2ccccc2)cc1]

Compound of Formula 1-4 (methyl 4-((N-phenylmorpholine-4-carboxamido)methyl)benzoate; 0.15 g, 0.42 mmol) was dissolved in methanol (5 ml), and then hydroxylamine hydrochloride (0.15 g, 2.12 mmol) was slowly added. Then, potassium hydroxide (0.24 g, 4.23 mmol) was added and stirred at room temperature for about 10 minutes, and then hydroxylamine (50.0 wt % aqueous solution; 0.56 mL, 8.46 mmol) was added and stirred at room temperature for 1 day. The organic solvent was concentrated under reduced pressure, washed twice with ether after adding water, neutralized by adding 2 N hydrochloric acid, and then further extracted with ethyl acetate. Then, the organic layer was washed twice with saturated sodium chloride aqueous solution, dehydrated with anhydrous sodium sulfate, and then filtered to give the desired Compound 279 (0.080 g, 53%) in the form of a white solid.

$^1$H NMR (400 MHz, MeOD-$d_3$) δ 7.66 (d, 2H, J=8.1 Hz), 7.41 (d, 2H, J=8.1 Hz), 7.34 (t, 2H, J=7.8 Hz), 7.15 (d, 2H, J=8.4 Hz), 4.92 (s, 2H), 3.46 (t, 4H, J=4.7 Hz), 3.22 (t, 4H, J=4.7 Hz); MS (ESI) m/z 356 (M$^+$+H).

Example 11: Synthesis of Compound 280

Formula 7-4: methyl 4-((pyridin-2-ylamino)methyl)benzoate

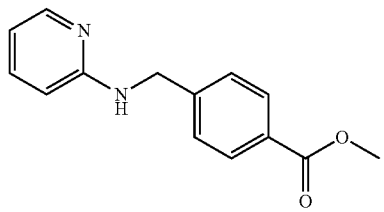 [SMILES: COC(=O)c1ccc(CNc2ccccn2)cc1]

Compound of Formula 7-3 (pyridin-2-amine, 0.2 g, 2.13 mmol) was dissolved in methanol (10 mL), and then methyl 4-formylbenzoate (0.35 g, 2.13 mmol) was added and stirred at room temperature for 20 minutes. Then, sodium cyanoborohydride (0.13 g, 2.13 mmol) and acetic acid (0.12 mL, 2.13 mmol) were slowly added and stirred at room temperature for 5 hours. The organic layer was washed three times with saturated sodium chloride aqueous solution, dehydrated with sodium sulfate, and then filtered. The filtrate was concentrated under reduced pressure, and the concentrate was purified by column chromatography (silica; ethyl acetate/hexane=0-30%) to give the desired compound of Formula 7-4 (0.10 g, 19%) in the form of a transparent oil.

$^1$H NMR (400 MHz, CDCl$_3$) δ 8.17 (d, 1H, J=5.8 Hz), 8.06 (d, 2H, J=8.4 Hz), 7.66 (t, 1H, J=7.8 Hz), 7.44 (d, 2H, J=8.0 Hz), 6.76 (t, 1H, J=6.7 Hz), 6.58 (d, 1H, J=8.6 Hz), 4.67 (d, 2H, J=6.0 Hz), 3.92 (s, 3H)

Formula 7-5: methyl 4-((((4-nitrophenoxy)carbonyl)(pyridin-2-yl)amino)methyl)benzoate

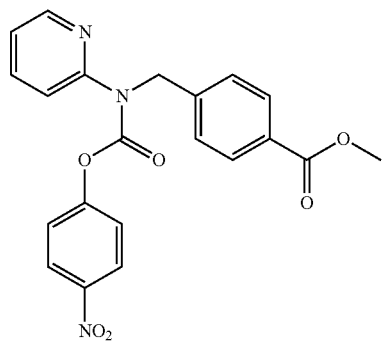

Formula 7-4 (methyl 4-((pyridin-2-ylamino)methyl)benzoate; 0.040 g, 0.16 mmol) was dissolved in dimethylformamide (3 mL), and then potassium carbonate (0.046 g, 0.33 mmol) was slowly added. Then, 4-nitrophenyl chloroformate (0.037 g, 0.18 mmol) was added, the temperature was slowly raised to 50° C., and the mixture was stirred for 2 days hours. After completion of the reaction, the ethyl acetate layer was washed three times with saturated ammonium chloride aqueous solution, and then the organic layer was dehydrated with sodium sulfate, and then filtered. The filtrate was concentrated under reduced pressure, and then the concentrate was purified by column chromatography (silica; ethyl acetate/hexane=0-50%) to give the desired compound of Formula 7-5 (0.048 g, 71%) in the form of a yellow oil.

$^1$H NMR (400 MHz, CDCl$_3$) δ 8.49-8.48 (m, 1H), 8.24 (dd, 2H, J=7.0, 2.2 Hz), 8.17 (dd, 2H, J=7.2, 2.0 Hz), 8.00 (d, 2H, J=8.4 Hz), 7.78 (t, 1H, J=3.8 Hz), 7.44 (d, 2H, J=8.0 Hz), 6.91 (dd, 2H, J=7.3, 2.1 Hz), 5.39 (brs, 2H), 3.92 (s, 3H); MS (ESI) m/z 408 (M$^+$+H)

Formula 7-6: methyl 4-((N-(pyridin-2-yl)morpholine-4-carboxamido)methyl)benzoate

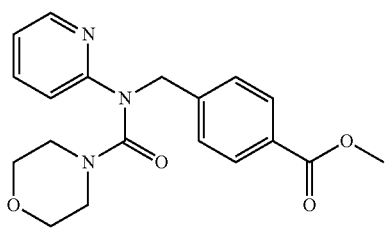 [SMILES: COC(=O)c1ccc(CN(C(=O)N2CCOCC2)c2ccccn2)cc1]

Compound of Formula 7-5 (methyl 4-((((4-nitrophenoxy)carbonyl)(pyridin-2-yl)amino)methyl)benzoate; 0.040 g, 0.098 mmol) was dissolved in dimethylformamide (5 ml), and then potassium carbonate (0.040 g, 0.30 mmol) and morpholine (0.013 mL, 0.15 mmol) were slowly added. Then, the temperature was slowly raised to 80° C., and the mixture was stirred for 3 hours. The reaction was completed, and the organic layer was washed three times with saturated ammonium chloride, dehydrated with sodium sulfate, and then filtered. The filtrate was concentrated under reduced pressure, and then the concentrate was purified by column chromatography (silica; ethyl acetate/hexane=0-50%) to give the desired compound of Formula 7-6 (0.022 g, 63%) in the form of a pale yellow solid.

$^1$H NMR (400 MHz, CDCl$_3$) δ 8.37-8.35 (m, 1H), 7.95 (d, 2H, J=8.4 Hz), 7.60-7.58 (m, 1H), 7.47 (d, 2H, J=8.4 Hz), 6.94-6.89 (m, 2H), 5.13 (s, 2H), 3.89 (s, 3H), 3.53-3.51 (m, 4H), 3.31-3.29 (m, 4H)

Compound 280: N-(4-(hydroxycarbamoyl)benzyl)-N-(pyridin-2-yl)morpholine-4-carboxamide

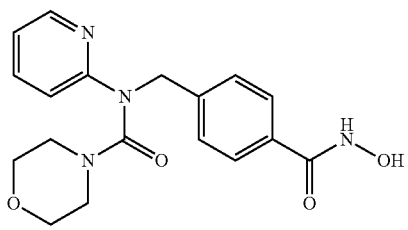 [SMILES: O=C(NO)c1ccc(CN(C(=O)N2CCOCC2)c2ccccn2)cc1]

Compound of Formula 7-6 (methyl 4-((N-(pyridin-2-yl)morpholine-4-carboxamido)methyl)benzoate; 0.022 g, 0.062 mmol) was dissolved in methanol (2 mL), and then hydroxylamine hydrochloride (0.022 g, 0.31 mmol) was slowly added. Then, potassium hydroxide (0.035 g, 0.62 mmol) was added and stirred at room temperature for about 10 minutes, and then hydroxylamine (50.0 wt % aqueous solution; 0.082 mL, 1.24 mmol) was added and stirred at room temperature for 1 day. Then, the organic solvent was concentrated under reduced pressure and then neutralized by adding 2 N hydrochloric acid. Then, the organic layer was washed three times with saturated sodium chloride aqueous solution, dehydrated with anhydrous sodium sulfate, and then filtered to give the desired Compound 280 (0.007 g, 32%) in the form of a white solid.

$^1$H NMR (400 MHz, MeOD-d$_3$) δ 8.32 (d, 1H, J=3.6 Hz), 7.72 (t, 1H, J=6.6 Hz), 7.67 (d, 2H, J=8.2 Hz), 7.48 (d, 2H, J=8.2 Hz), 7.08-7.01 (m, 2H), 5.08 (s, 2H), 3.52 (t, 4H, J=4.8 Hz), 3.29 (t, 4H, J=4.8 Hz); MS (ESI) m/z 357 (M$^+$+H).

Example 12: Synthesis of Compound 281

Formula 7-4: methyl 4-((pyridin-3-ylamino)methyl)benzoate

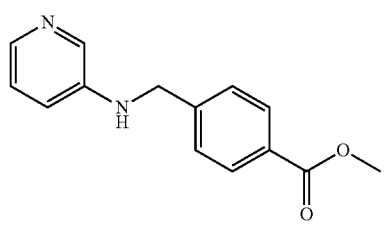 [SMILES: COC(=O)c1ccc(CNc2cccnc2)cc1]

Compound of Formula 7-3 (pyridin-3-amine, 0.5 g, 5.31 mmol) was dissolved in methanol (10 mL), and then methyl 4-formylbenzoate (1.03 g, 5.31 mmol) was added and stirred at room temperature for 20 minutes. Then, sodium cyanoborohydride (0.33 g, 5.31 mmol) and acetic acid (0.32 mL, 5.31 mmol) were slowly added and stirred at room temperature for 5 hours. The organic layer was washed three times with saturated sodium chloride aqueous solution, dehydrated with sodium sulfate, and then filtered. The filtrate was concentrated under reduced pressure, and the concentrate was purified by column chromatography (silica; ethyl acetate/hexane=0-30%) to give the desired compound of Formula 7-4 (0.85 g, 66%) in the form of a white solid.

Formula 7-5: methyl 4-((((4-nitrophenoxy)carbonyl)(pyridin-3-yl)amino)methyl)benzoate

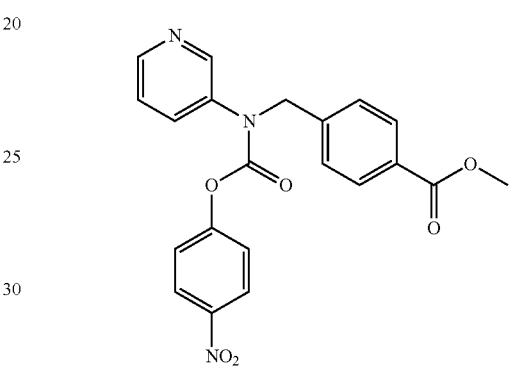

Compound of Formula 7-4 (methyl 4-((pyridin-3-ylamino)methyl)benzoate; 0.20 g, 0.83 mmol) was dissolved in dimethylformamide (3 mL), and then 4-nitrophenyl chloroformate (0.18 g, 0.90 mmol) and potassium carbonate (0.23 g, 1.65 mmol) were added. Then, the temperature was slowly raised to 90° C., and the mixture was stirred for 1 day. After completion of the reaction, the ethyl acetate layer was washed three times with saturated ammonium chloride aqueous solution, and then the organic layer was dehydrated with sodium sulfate, and then filtered. The filtrate was concentrated under reduced pressure, and then the concentrate was purified by column chromatography (silica; ethyl acetate/hexane=0-100%) to give the desired compound of Formula 7-5 (0.030 g, 8%) in the form of a white solid.

Formula 7-6: methyl 4-((N-(pyridin-3-yl)morpholine-4-carboxamido)methyl)benzoate

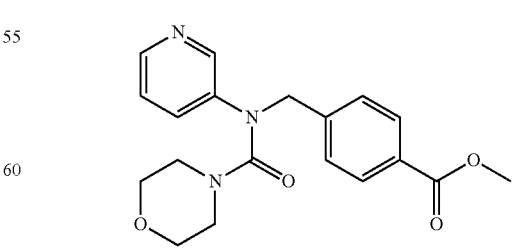

Compound of Formula 7-5 (methyl 4-((((4-nitrophenoxy)carbonyl)(pyridin-3-yl)amino)methyl)benzoate; 0.025 g, 0.061 mmol) was dissolved in dimethylformamide (1 mL), and then potassium carbonate (0.025 g, 0.184 mmol) and morpholine (0.008 g, 0.092 mmol) were added. Then, the temperature was slowly raised to 60° C., and the mixture was stirred for 3 hours. After completion of the reaction, the ethyl acetate layer was washed three times with saturated ammonium chloride aqueous solution, and then the organic layer was dehydrated with sodium sulfate, and then filtered. The filtrate was concentrated under reduced pressure, and then the concentrate was purified by column chromatography (silica; methanol/dichloromethane=0-10%) to give the desired compound of Formula 7-6 (0.018 g, 83%) in the form of a pale yellow solid.

Compound 281: N-(4-(hydroxycarbamoyl)benzyl)-N-(pyridin-3-yl)morpholine-4-carboxamide

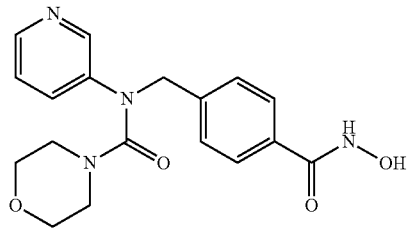 [SMILES: O=C(NO)c1ccc(CN(C(=O)N2CCOCC2)c2cccnc2)cc1]

Compound of Formula 7-6 (methyl 4-((N-(pyridin-3-yl)morpholine-4-carboxamido)methyl)benzoate; 0.018 g, 0.051 mmol) was dissolved in methanol (5 mL), and then hydroxylamine hydrochloride (0.018 g, 0.25 mmol) was slowly added. Then, potassium hydroxide (0.028 g, 0.51 mmol) was added and stirred at room temperature for about 10 minutes, and then hydroxylamine (50.0 wt % aqueous solution; 0.067 mL, 1.0 mmol) was added and stirred at room temperature for 1 day. Then, the organic layer was concentrated under reduced pressure and then neutralized by adding 2 N hydrochloric acid. Then, the organic layer was washed three times with saturated sodium chloride aqueous solution, dehydrated with anhydrous sodium sulfate, and then filtered to give the desired Compound 281 (0.010 g, 55%) in the form of a white solid.

$^1$H NMR (400 MHz, MeOD-d$_3$) δ 8.11 (s, 1H), 8.06 (d, 1H, J=4.1 Hz), 8.03 (d, 2H, J=8.3 Hz), 7.42 (d, 2H, J=2.8 Hz), 7.27-7.21 (m, 2H), 4.93 (s, 2H), 3.51 (t, 4H, J=4.7 Hz), 3.25 (t, 4H, J=4.8 Hz); MS (ESI) m/z 357 (M$^+$+H).

Example 13: Synthesis of Compound 309

Formula 7-4: methyl 4-((pyrimidin-2-ylamino)methyl)benzoate

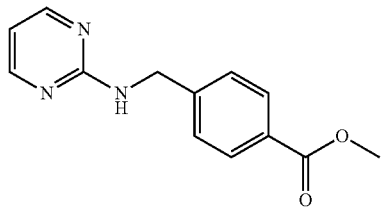 [SMILES: COC(=O)c1ccc(CNc2ncccn2)cc1]

Compound of Formula 7-1 (2-chloropyrimidine; 6.25 g, 54.6 mmol) and compound of Formula 7-2 (methyl 4-(aminomethyl)benzoate hydrochloride; 10.0 g, 49.6 mmol) were dissolved in ethanol (150 mL), and the triethylamine (17.0 mL, 124 mmol) was added and stirred under reflux for 3 days. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 7-4 (8.06 g, 67%) in the form of a white solid.

Formula 7-5: methyl 4-((((4-nitrophenoxy)carbonyl)(pyrimidin-2-yl)amino)methyl)benzoate

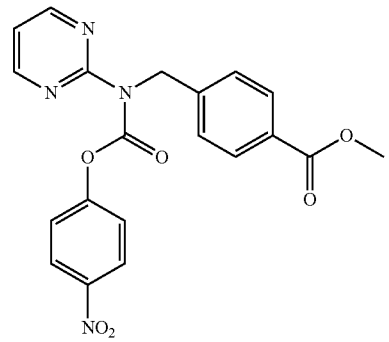 [SMILES: COC(=O)c1ccc(CN(C(=O)Oc2ccc([N+](=O)[O-])cc2)c2ncccn2)cc1]

Compound of Formula 7-4 (methyl 4-((pyrimidin-2-ylamino)methyl)benzoate; 8.06 g, 33.1 mmol) and 4-nitrophenyl chloroformate (7.01 g, 34.8 mmol) were dissolved in acetonitrile (150 mL), and then potassium carbonate (6.87 g, 49.7 mmol) was added and stirred at room temperature for 16 hours. Then, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 7-5 (1.50 g, 11%) in the form of a light yellow liquid.

Formula 7-6: methyl 4-((4-benzyl-N-(pyrimidin-2-yl)piperazine-1-carboxamido)methyl)benzoate

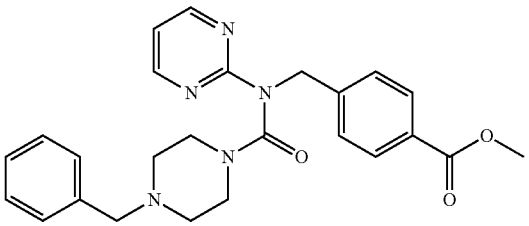 [SMILES: COC(=O)c1ccc(CN(C(=O)N2CCN(Cc3ccccc3)CC2)c2ncccn2)cc1]

Compound of Formula 7-5 (methyl 4-((((4-nitrophenoxy)carbonyl)(pyrimidin-2-yl)amino)methyl)benzoate; 0.150 g, 0.367 mmol) was dissolved in dimethylformamide (1 mL), and then 1-benzylpiperazine (0.130 g, 0.735 mmol) and potassium carbonate (0.152 g, 1.10 mmol) were added and stirred at 60° C. for 16 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 7-6 (0.132 g, 81%) in the form of a yellow liquid.

Compound 309: 4-benzyl-N-(4-(hydroxycarbamoyl)benzyl)-N-(pyrimidin-2-yl)piperazine-1-carboxamide

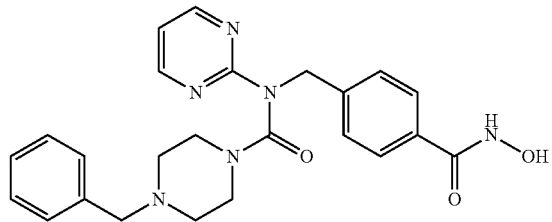 [SMILES: O=C(NO)c1ccc(CN(C(=O)N2CCN(Cc3ccccc3)CC2)c2ncccn2)cc1]

Compound of Formula 7-6 (methyl 4-((4-benzyl-N-(pyrimidin-2-yl)piperazine-1-carboxamido)methyl)benzoate; 0.132 g, 0.296 mmol) was dissolved in methanol (5 mL), and then hydroxylamine (50.0 wt % aqueous solution; 0.906 mL, 14.8 mmol) and potassium hydroxide (0.166 g, 2.96 mmol) were added sequentially and then stirred at room temperature for 30 minutes. After completion of the reaction, the reaction solution was concentrated under reduced pressure until its volume became about 2 mL, and saturated sodium hydrogen carbonate aqueous solution (1-2 mL) was added and stirred. Then, the solid product was filtered, washed with water, and then vacuum dried to give the desired Compound 309 (0.079 g, 60%) in the form of a light yellow solid.

$^1$H NMR (400 MHz, DMSO-$d_6$) δ 11.18 (s, 1H), 9.03 (s, 1H), 8.50 (d, 2H, J=4.8 Hz), 7.68 (d, 2H, J=8.4 Hz), 7.39 (d, 2H, J=8.4 Hz), 7.32-7.21 (m, 5H) 6.93 (t, 1H, J=4.8 Hz), 4.97 (s, 2H), 3.40 (s, 2H), 3.29 (m, 4H), 2.19 (m, 4H). MS (ESI) m/z 447 (M$^+$+H).

Example 14: Synthesis of Compound 311

Formula 7-6: methyl 4-((4-hydroxy-4-phenyl-N-(pyrimidin-2-yl)piperidine-1-carboxamido)methyl)benzoate

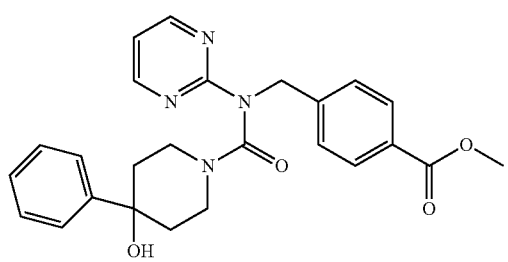 [SMILES: COC(=O)c1ccc(CN(C(=O)N2CCC(O)(c3ccccc3)CC2)c2ncccn2)cc1]

Compound of Formula 7-5 (methyl 4-((((4-nitrophenoxy)carbonyl)(pyrimidin-2-yl)amino)methyl)benzoate; 0.150 g, 0.367 mmol) was dissolved in dimethylformamide (1 mL), and then 4-phenylpiperidine-4-ol (0.130 g, 0.735 mmol) and potassium carbonate (0.152 g, 1.10 mmol) were added and stirred at 60° C. for 16 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=30%) to give the desired compound of Formula 7-6 (0.104 g, 63%) in the form of a light yellow liquid.

Compound 311: 4-hydroxy-N-(4-(hydroxycarbamoyl)benzyl)-4-phenyl-N-(pyrimidin-2-yl)piperidine-1-carboxamide

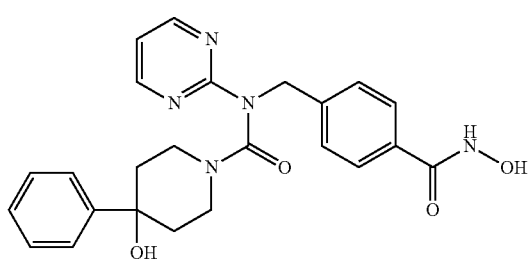 [SMILES: O=C(NO)c1ccc(CN(C(=O)N2CCC(O)(c3ccccc3)CC2)c2ncccn2)cc1]

Compound of Formula 7-6 (methyl 4-((4-hydroxy-4-phenyl-N-(pyrimidin-2-yl)piperidine-1-carboxamido)methyl)benzoate; 0.104 g, 0.233 mmol) was dissolved in methanol (5 mL), and then hydroxylamine (50.0 wt % aqueous solution; 1.43 mL, 23.3 mmol) and potassium hydroxide (0.131 g, 2.33 mmol) were added sequentially and then stirred at room temperature for 30 minutes. After completion of the reaction, the reaction solution was concentrated under reduced pressure until its volume became about 2 mL, and saturated sodium hydrogen carbonate aqueous solution (1-2 mL) was added and stirred. Then, the solid product was filtered, washed with water, and then vacuum dried to give the desired Compound 311 (0.072 g, 69%) in the form of a white solid.

$^1$H NMR (400 MHz, DMSO-$d_6$) δ 11.19 (s, 1H), 9.04 (s, 1H), 8.54 (d, 2H, J=4.8 Hz), 7.73 (d, 2H, J=8.3 Hz), 7.45 (d, 2H, J=8.3 Hz), 7.30-7.26 (m, 4H), 7.19 (m, 1H), 6.93 (t, 1H, J=4.8 Hz), 5.08 (s, 1H), 5.01 (brs, 2H), 3.73 (brs, 2H), 3.18-3.11 (m, 2H), 1.56-1.47 (m, 4H). MS (ESI) m/z 448 (M$^+$+H).

Example 15: Synthesis of Compound 312

Formula 7-6: methyl 4-((N-(pyrimidin-2-yl)morpholine-4-carboxamido)methyl)benzoate

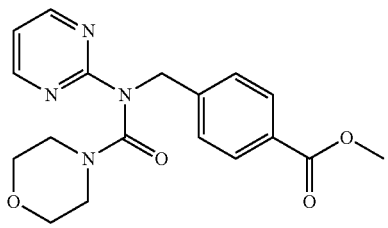 [SMILES: COC(=O)c1ccc(CN(C(=O)N2CCOCC2)c2ncccn2)cc1]

Compound of Formula 7-4 (methyl 4-((pyrimidin-2-ylamino)methyl)benzoate; 0.200 g, 0.822 mmol) was dissolved in acetonitrile (2 mL), and then morpholine-4-carbonyl chloride (0.185 g, 1.23 mmol) and N,N- diisopropylethylamine (0.291 mL, 1.64 mmol) were added and stirred at 60° C. for 16 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=30%) to give the desired compound of Formula 7-6 (0.179 g, 61%) in the form of a light yellow solid.

Compound 312: N-(4-(hydroxycarbamoyl)benzyl)-N-(pyrimidin-2-yl)morpholine-4-carboxamide

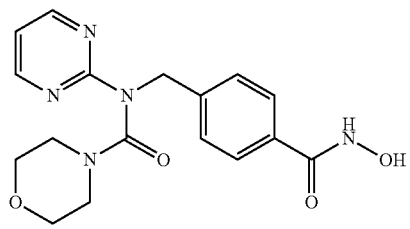 [SMILES: O=C(NO)c1ccc(CN(C(=O)N2CCOCC2)c2ncccn2)cc1]

Compound of Formula 7-6 (methyl 4-((N-(pyrimidin-2-yl)morpholine-4-carboxamido)methyl)benzoate; 0.179 g, 0.502 mmol) was dissolved in methanol (5 mL), and then hydroxylamine (50.0 wt % aqueous solution; 2.15 mL, 35.2 mmol) and potassium hydroxide (0.282 g, 5.02 mmol) were added sequentially and then stirred at room temperature for 30 minutes. After completion of the reaction, the reaction solution was concentrated under reduced pressure until its volume became about 2 mL, and the organic layer was extracted with ethyl acetate and saturated sodium hydrogen carbonate aqueous solution. The organic layer was washed three times with water, dehydrated with anhydrous magnesium sulfate, filtered, and then concentrated under reduced pressure. The residue was recrystallized with diethylether and hexane to give the desired Compound 312 (0.036 g, 20%) in the form of a white solid.

$^1$H NMR (400 MHz, DMSO-$d_6$) δ 11.18 (s, 1H), 8.53 (d, 2H, J=4.8 Hz), 7.68 (d, 2H, J=7.6 Hz), 7.40 (d, 2H, J=8.1 Hz), 6.96 (t, 1H, J=4.8 Hz), 4.98 (s, 2H), 3.40 (m, 4H), 3.28 (m, 4H). MS (ESI) m/z 358 (M$^+$+H).

Example 16: Synthesis of Compound 313

Formula 7-6: methyl 4-((2,6-dimethyl-N-(pyrimidin-2-yl)morpholine-4-carboxamido)methyl)benzoate

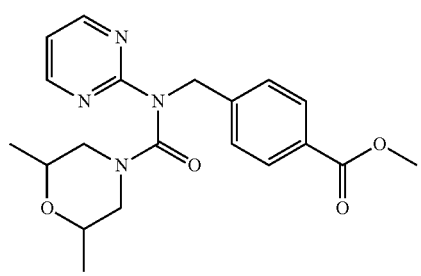

Compound of Formula 7-5 (methyl 4-((((4-nitrophenoxy)carbonyl)(pyrimidin-2-yl)amino)methyl)benzoate; 0.150 g, 0.367 mmol) was dissolved in dimethylformamide (1 mL), and then 2,6-dimethylmorpholine (0.085 g, 0.735 mmol) and potassium carbonate (0.152 g, 1.10 mmol) were added and stirred at 60° C. for 16 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 7-6 (0.062 g, 44%) in the form of a yellow liquid.

Compound 313: N-(4-(hydroxycarbamoyl)benzyl)-2,6-dimethyl-N-(pyrimidin-2-yl)morpholine-4-carboxamide

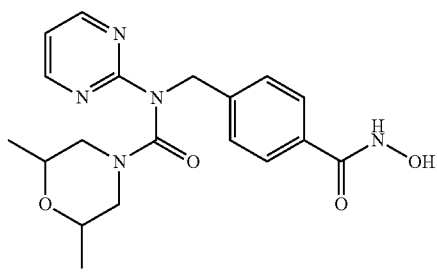 [SMILES: CC1CN(C(=O)N(Cc2ccc(C(=O)NO)cc2)c2ncccn2)CC(C)O1]

Compound of Formula 7-6 (methyl 4-((2,6-dimethyl-N-(pyrimidin-2-yl)morpholine-4-carboxamido)methyl)benzoate; 0.062 g, 0.161 mmol) was dissolved in methanol (5 mL), and then hydroxylamine (50.0 wt % aqueous solution; 0.986 mL, 16.1 mmol) and potassium hydroxide (0.091 g, 1.61 mmol) were added sequentially and then stirred at room temperature for 30 minutes. After completion of the reaction, the reaction solution was concentrated under reduced pressure until its volume became about 2 mL, and the organic layer was extracted with ethyl acetate and saturated sodium hydrogen carbonate aqueous solution. The organic layer was washed three times with water, dehydrated with anhydrous magnesium sulfate, filtered, and then concentrated under reduced pressure. The residue was recrystallized with diethylether and hexane to give the desired Compound 313 (0.037 g, 60%) in the form of a white solid.

$^1$H NMR (400 MHz, DMSO-$d_6$) δ 11.18 (s, 1H), 9.02 (s, 1H), 8.52 (d, 2H, J=4.4 Hz), 7.68 (d, 2H, J=7.8 Hz), 7.40 (d, 2H, J=7.8 Hz), 6.95 (t, 1H, J=4.6 Hz), 4.98 (s, 2H), 3.68 (brs, 2H), 3.21 (brs, 2H), 2.44-2.41 (m, 2H), 0.97 (s, 3H), 0.96 (s, 3H). MS (ESI) m/z 386 (M$^+$+H).

Example 17: Synthesis of Compound 329

Formula 8-2: methyl 4-((phenylamino)methyl)benzoate

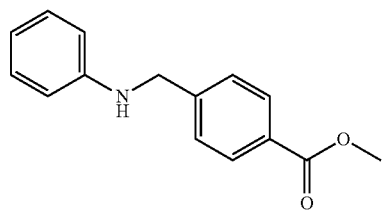 [SMILES: COC(=O)c1ccc(CNc2ccccc2)cc1]

Compound of Formula 8-1 (methyl 4-(bromomethyl)benzoate; 12.5 g, 54.8 mmol) and aniline (5.00 mL, 54.8 mmol) were dissolved in acetonitrile (70 mL), and then N,N-diisopropylethylamine (11.6 mL, 65.7 mmol) were added and stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=15%) to give the desired compound of Formula 8-2 (9.13 g, 69%) in the form of a yellow liquid.

Formula 8-3: methyl 4-((4-bromophenylamino)methyl)benzoate

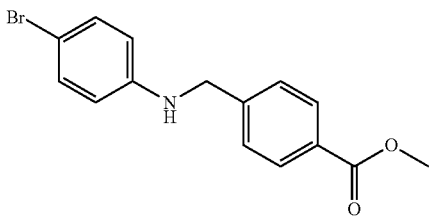

Compound of Formula 8-2 (methyl 4-((phenylamino)methyl)benzoate; 9.13 g, 37.8 mmol) was dissolved in dichloromethane (70 mL), and the N-bromosuccinimide (7.07 g, 39.7 mmol) was added and stirred at room temperature for 16 hours. After completion of the reaction, the organic layer was concentrated under reduced pressure, and then the residue was purified and concentrated by column chromatography (silica; ethyl acetate/hexane=15%) to give the desired compound of Formula 8-3 (9.57 g, 79%) in the form of a white solid.

Formula 8-4: methyl 4-(((4-bromophenyl)((4-nitrophenoxy)carbonyl)amino)methyl)benzoate

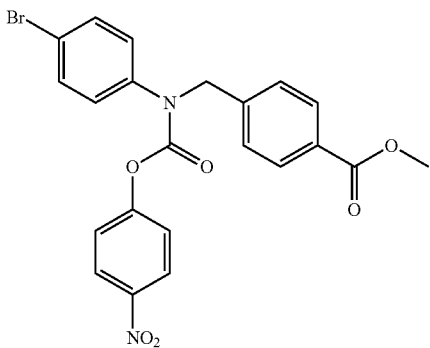 [SMILES: COC(=O)c1ccc(CN(C(=O)Oc2ccc([N+](=O)[O-])cc2)c2ccc(Br)cc2)cc1]

Compound of Formula 8-3 (methyl 4-((4-bromophenylamino)methyl)benzoate; 7.67 g, 24.0 mmol) and 4-nitrophenyl chloroformate (5.31 g, 26.4 mmol) were dissolved in acetonitrile (70 mL), and then potassium carbonate (4.97 g, 35.9 mmol) was added and stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=20%) to give the desired compound of Formula 8-4 (11.2 g, 96%) in the form of a yellow liquid.

Formula 8-5: methyl 4-((N-(4-bromophenyl)morpholine-4-carboxamido)methyl)benzoate

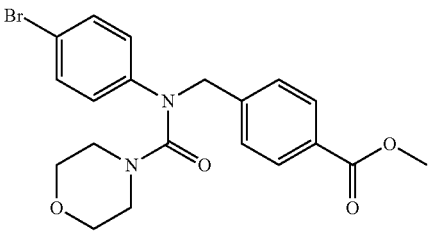 [SMILES: COC(=O)c1ccc(CN(C(=O)N2CCOCC2)c2ccc(Br)cc2)cc1]

Compound of Formula 8-4 (methyl 4-(((4-bromophenyl)((4-nitrophenoxy)-carbonyl)amino)methyl)benzoate; 5.00 g, 10.3 mmol) was dissolved in dimethylformamide (20 mL), and then morpholine (1.35 g, 15.5 mmol) and potassium carbonate (2.85 g, 20.6 mmol) were added and stirred at 60° C. for 5 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 8-5 (3.86 g, 87%) in the form of a yellow solid.

Formula 8-6: methyl 4-((N-(4-(1-methyl-1H-indazol-6-yl)phenyl)morpholine-4-carboxamido)methyl)benzoate

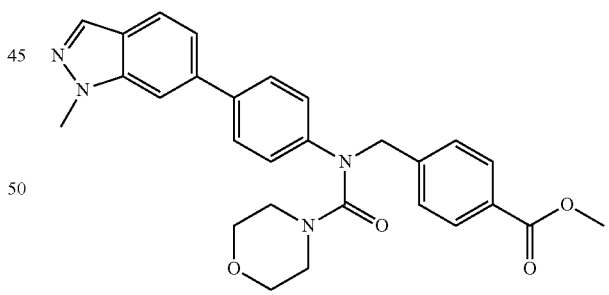

Compound of Formula 8-5 (methyl 4-((N-(4-bromophenyl)morpholine-4-carboxamido)methyl)benzoate; 0.185 g, 0.427 mmol), 1-methyl-indazol-6-ylboronic acid (0.090 g, 0.512 mmol), and Pd(dppf)Cl$_2$ (0.035 g, 0.043 mmol) were dissolved in 1,4-dioxane (3 mL), and then sodium carbonate (0.181 g, 1.71 mmol) dissolved in water (1 mL) was added to the reaction solution and stirred at 80° C. for 16 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/ hexane=30%) to give the desired compound of Formula 8-6 (0.112 g, 71%) in the form of a white solid.

Compound 329: N-(4-(hydroxycarbamoyl)benzyl)-N-(4-(1-methyl-1H-indazol-6-yl)phenyl)morpholine-4-carboxamide

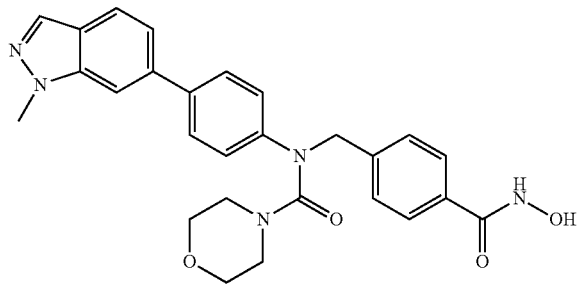 [SMILES: Cn1ncc2ccc(-c3ccc(N(Cc4ccc(C(=O)NO)cc4)C(=O)N4CCOCC4)cc3)cc21]

Compound of Formula 8-6 (methyl 4-((N-(4-(1-methyl-1H-indazol-6-yl)phenyl)morpholine-4-carboxamido)methyl)benzoate; 0.112 g, 0.231 mmol) was dissolved in methanol (5 mL), and then hydroxylamine (50.0 wt % aqueous solution; 1.41 mL, 23.1 mmol) and potassium hydroxide (0.130 g, 2.31 mmol) added sequentially and then stirred at room temperature for 30 minutes. After completion of the reaction, the reaction solution was concentrated under reduced pressure until its volume became about 2 mL, and saturated ammonium chloride aqueous solution (1-2 mL) was added and stirred. Then, the solid product was filtered, washed with water, and then vacuum dried to give the desired Compound 329 (0.096 g, 86%) in the form of a light brown solid.

$^1$H NMR (400 MHz, DMSO-$d_6$) δ 8.02 (s, 1H), 7.88 (s, 1H), 7.77 (d, 1H, J=8.4 Hz), 7.73 (d, 2H, J=8.6 Hz), 7.66 (d, 2H, J=8.2 Hz), 7.42-7.39 (m, 3H), 7.26 (d, 2H, J=8.5 Hz), 4.93 (s, 2H), 4.07 (s, 3H), 3.47-3.43 (m, 4H), 3.22-3.17 (m, 4H). MS (ESI) m/z 486 (M$^+$+H).

Example 18: Synthesis of Compound 330

Formula 8-6: methyl 4-((N-(biphenyl-4-yl)morpholine-4-carboxamido)methyl)benzoate

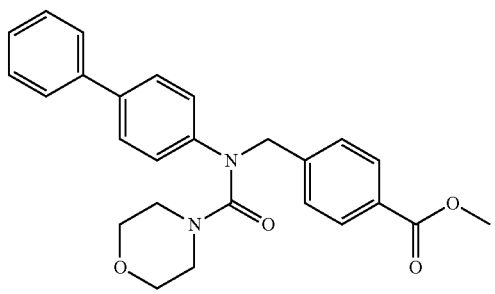 [SMILES: COC(=O)c1ccc(CN(C(=O)N2CCOCC2)c2ccc(-c3ccccc3)cc2)cc1]

Compound of Formula 8-5 (methyl 4-((N-(4-bromophenyl)morpholine-4-carboxamido)methyl)benzoate; 0.200 g, 0.462 mmol), phenylboronic acid (0.068 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=60%) to give the desired compound of Formula 8-6 (0.160 g, 81%) in the form of a white solid.

Compound 330: N-(biphenyl-4-yl)-N-(4-(hydroxycarbamoyl)benzyl)morpholine-4-carboxamide

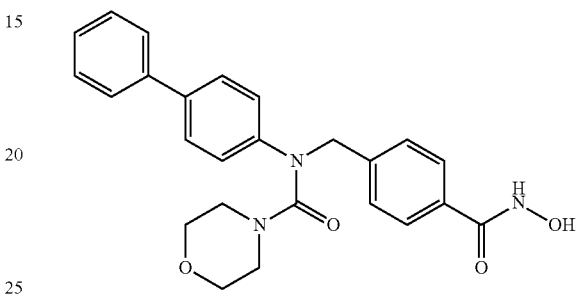

Compound of Formula 8-6 (methyl 4-((N-(biphenyl-4-yl)morpholine-4-carboxamido)methyl)benzoate; 0.160 g, 0.372 mmol) was dissolved in methanol (10 mL), and then hydroxylamine (50.0 wt % aqueous solution; 2.27 mL, 37.2 mmol) and potassium hydroxide (0.209 g, 3.72 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 330 (0.120 g, 75%) in the form of a light brown solid.

MS (ESI) m/z 432 (M$^+$+H).

Example 19: Synthesis of Compound 331

Formula 8-6: methyl 4-((N-(3',5'-difluorobiphenyl-4-yl)morpholine-4-carboxamido)methyl)benzoate

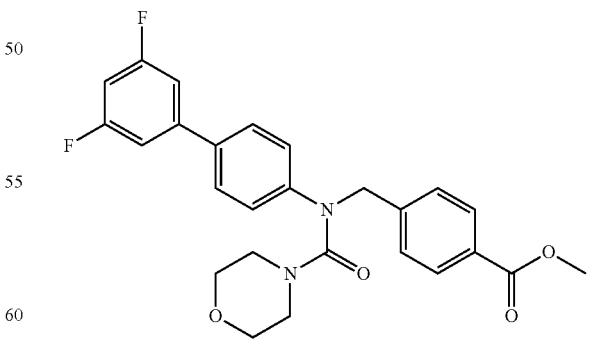

Compound of Formula 8-5 (methyl 4-((N-(4-bromophenyl)morpholine-4-carboxamido)methyl)benzoate; 0.200 g, 0.462 mmol), 3'5'-difluorophenylboronic acid (0.088 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=60%) to give the desired compound of Formula 8-6 (0.169 g, 79%) in the form of a white solid.

Compound 331: N-(3',5'-difluorobiphenyl-4-yl)-N-(4-(hydroxycarbamoyl)benzyl)morpholine-4-carboxamide

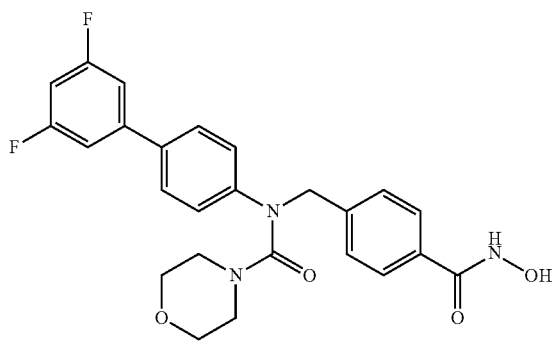 [SMILES: O=C(NO)c1ccc(CN(C(=O)N2CCOCC2)c2ccc(-c3cc(F)cc(F)c3)cc2)cc1]

Compound of Formula 8-6 (methyl 4-((N-(3',5'-difluorobiphenyl-4-yl)morpholine-4-carboxamido)methyl)benzoate; 0.169 g, 0.362 mmol) was dissolved in methanol (10 mL), and then hydroxylamine (50.0 wt % aqueous solution; 2.22 mL, 36.2 mmol) and potassium hydroxide (0.203 g, 3.62 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 331 (0.102 g, 60%) in the form of a light brown solid.

$^1$H NMR (400 MHz, DMSO-$d_6$) δ 7.70 (d, 2H, J=8.8 Hz), 7.65 (d, 2H, J=8.3 Hz), 7.43-7.37 (m, 4H), 7.22 (d, 2H, J=8.8 Hz), 7.17 (m, 1H), 4.92 (s, 2H), 3.44 (t, 4H, J=4.6 Hz), 3.18 (t, 4H, J=4.6 Hz). MS (ESI) m/z 468 (M$^+$+H).

Example 20: Synthesis of Compound 332

Formula 8-6: methyl 4-((N-(4-(pyridine-3-yl)phenyl)morpholine-4-carboxamido)methyl)benzoate

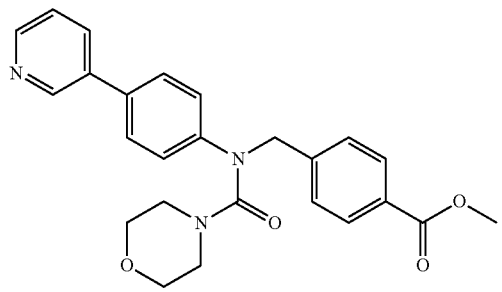 [SMILES: COC(=O)c1ccc(CN(C(=O)N2CCOCC2)c2ccc(-c3cccnc3)cc2)cc1]

Compound of Formula 8-5 (methyl 4-((N-(4-bromophenyl)morpholine-4-carboxamido)methyl)benzoate; 0.200 g, 0.462 mmol), pyridine-3-ylboronic acid (0.068 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=75%) to give the desired compound of Formula 8-6 (0.132 g, 66%) in the form of a white solid.

Compound 332: N-(4-(hydroxycarbamoyl)benzyl)-N-(4-(pyridin-3-yl)phenyl)morpholine-4-carboxamide

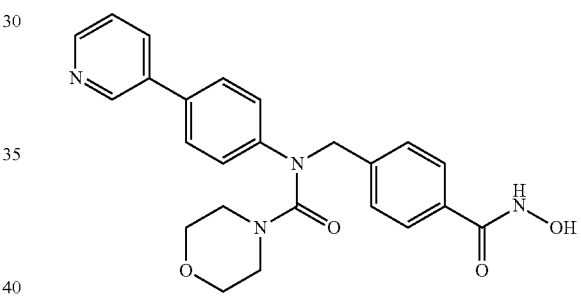

Compound of Formula 8-6 (methyl 4-((N-(4-(pyridine-3-yl)phenyl)morpholine-4-carboxamido)methyl)benzoate; 0.132 g, 0.306 mmol) was dissolved in methanol (10 mL), and then hydroxylamine (50.0 wt % aqueous solution; 1.87 mL, 30.6 mmol) and potassium hydroxide (0.172 g, 3.06 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 332 (0.051 g, 39%) in the form of a brown solid.

$^1$H NMR (400 MHz, DMSO-$d_6$) δ 11.15 (s, 1H), 9.00 (s, 1H), 8.86 (s, 1H), 8.52 (s, 1H), 8.04 (d, 1H, J=5.2 Hz), 7.71-7.65 (m, 4H), 7.43-7.38 (m, 3H), 7.26 (d, 2H, J=6.8 Hz), 4.93 (s, 2H), 3.44 (m, 4H), 3.19 (m, 4H). MS (ESI) m/z 433 (M$^+$+H).

Example 21: Synthesis of Compound 333

Formula 8-6: methyl 4-((N-(4-(pyrimidin-5-yl)phenyl)morpholine-4-carboxamido)methyl)benzoate

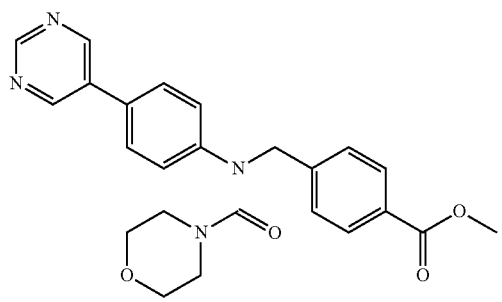

Compound of Formula 8-5 (methyl 4-((N-(4-bromophenyl)morpholine-4-carboxamido)methyl)benzoate; 0.200 g, 0.462 mmol), pyrimidin-5-ylboronic acid (0.069 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=75%) to give the desired compound of Formula 8-6 (0.148 g, 74%) in the form of a white solid.

Compound 333: N-(4-(hydroxycarbamoyl)benzyl)-N-(4-(pyrimidin-5-yl)phenyl)morpholine-4-carboxamide

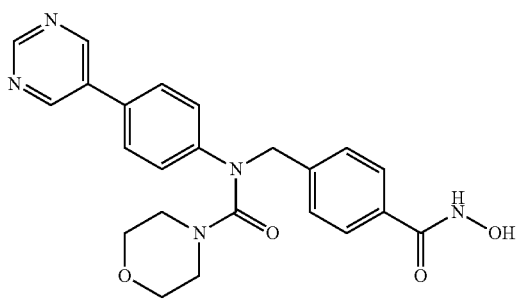 [SMILES: O=C(NO)c1ccc(CN(C(=O)N2CCOCC2)c2ccc(-c3cncnc3)cc2)cc1]

Compound of Formula 8-6 (methyl 4-((N-(4-(pyrimidin-5-yl)phenyl)morpholine-4-carboxamido)methyl)benzoate; 0.148 g, 0.342 mmol) was dissolved in methanol (10 mL), and then hydroxylamine (50.0 wt % aqueous solution; 2.09 mL, 34.2 mmol) and potassium hydroxide (0.192 g, 3.42 mmol) were added sequentially and then stirred at room temperature for 30 minutes. After completion of the reaction, the reaction solution was concentrated under reduced pressure until its volume became about 3 mL, and the organic layer was extracted with ethyl acetate and saturated sodium hydrogen carbonate aqueous solution. The organic layer was dehydrated with anhydrous magnesium sulfate, filtered, and then concentrated under reduced pressure. The residue was recrystallized with dichloromethane and hexane to give the desired Compound 333 (0.060 g, 40%) in the form of a white solid.
$^1$H NMR (400 MHz, DMSO-d$_6$) δ 9.13 (s, 1H), 9.10 (s, 2H), 7.77 (d, 2H, J=8.7 Hz), 7.65 (d, 2H, J=8.3 Hz), 7.39 (d, 2H, J=8.2 Hz), 7.29 (d, 2H, J=8.7 Hz), 4.94 (s, 2H), 3.45 (t, 4H, J=4.6 Hz), 3.19 (t, 4H, J=4.6 Hz). MS(ESI) m/z 434 (M$^+$+H).

Example 22: Synthesis of Compound 334

Formula 8-6: methyl 4-((N-(4-(quinolin-7-yl)phenyl)morpholine-4-carboxamido)methyl)benzoate

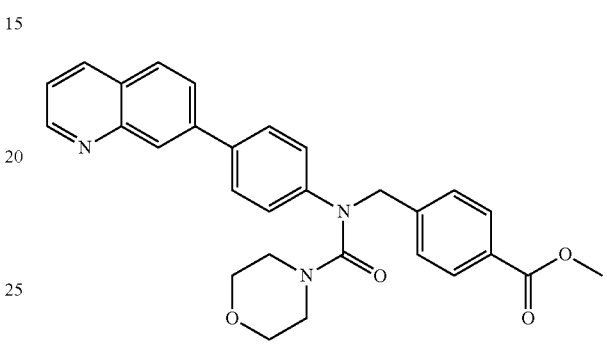

Compound of Formula 8-5 (methyl 4-((N-(4-bromophenyl)morpholine-4-carboxamido)methyl)benzoate; 0.200 g, 0.462 mmol), quinolin-7-ylboronic acid (0.096 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.192 g, 86%) in the form of a light brown solid.

Compound 334: N-(4-(hydroxycarbamoyl)benzyl)-N-(4-(quinolin-7-yl)phenyl)morpholine-4-carboxamide

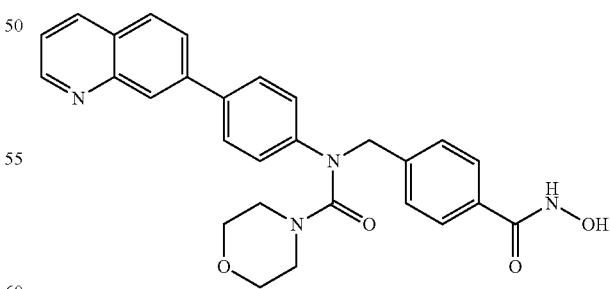

Compound of Formula 8-6 (methyl 4-((N-(4-(quinolin-7-yl)phenyl)morpholine-4-carboxamido)methyl)benzoate; 0.192 g, 0.399 mmol) was dissolved in methanol (10 mL), and then hydroxylamine (50.0 wt % aqueous solution; 2.44 mL, 39.9 mmol) and potassium hydroxide (0.224 g, 3.99 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 334 (0.173 g, 90%) in the form of a light brown solid.

$^1$H NMR (400 MHz, DMSO-$d_6$) δ 8.89 (m, 1H), 8.41 (dd, 1H, J=8.3, 1.7 Hz), 7.96 (m, 1H), 7.74 (m, 1H), 7.71-7.63 (m, 5H), 7.55 (dd, 1H, J=8.2, 4.1 Hz), 7.43 (d, 2H, J=8.2 Hz), 7.25 (d, 2H, J=8.6 Hz), 4.95 (s, 2H), 3.48-3.45 (m, 4H), 3.24-3.20 (m, 4H). MS(ESI) m/z 483 (M$^+$+H).

Example 23: Synthesis of Compound 335

Formula 8-6: methyl 4-((N-(4-(biphenyl-3-yl)phenyl)morpholine-4-carboxamido)methyl)benzoate

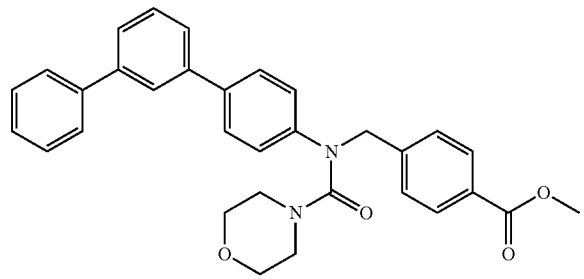 [SMILES: COC(=O)c1ccc(CN(C(=O)N2CCOCC2)c2ccc(-c3cccc(-c4ccccc4)c3)cc2)cc1]

Compound of Formula 8-5 (methyl 4-((N-(4-bromophenyl)morpholine-4-carboxamido)methyl)benzoate; 0.200 g, 0.462 mmol), biphenyl-3-ylboronic acid (0.110 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.230 g, 98%) in the form of a white solid.

Compound 335: N-(4-(hydroxycarbamoyl)benzyl)-N-(4-(biphenyl-3-yl)phenyl)morpholine-4-carboxamide

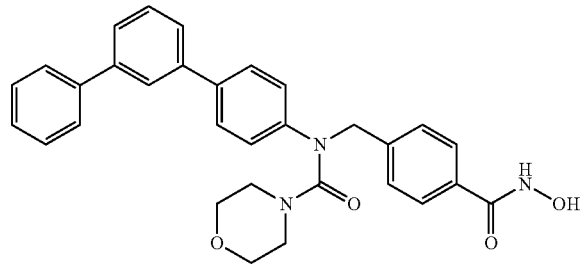 [SMILES: O=C(NO)c1ccc(CN(C(=O)N2CCOCC2)c2ccc(-c3cccc(-c4ccccc4)c3)cc2)cc1]

Compound of Formula 8-6 (methyl 4-((N-(4-(biphenyl-3-yl)phenyl)morpholine-4-carboxamido)methyl)benzoate; 0.230 g, 0.454 mmol) was dissolved in methanol (10 mL), and then hydroxylamine (50.0 wt % aqueous solution; 2.78 mL, 45.4 mmol) and potassium hydroxide (0.255 g, 4.54 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 335 (0.220 g, 96%) in the form of a light brown solid.

$^1$H NMR (400 MHz, DMSO-$d_6$) δ 7.86 (s, 1H), 7.75-7.70 (m, 4H), 7.67 (d, 2H, J=8.3 Hz), 7.63-7.60 (m, 2H), 7.53-7.45 (m, 3H), 7.41-7.39 (m, 3H), 7.24 (d, 2H, J=8.6 Hz), 4.92 (s, 2H), 3.44-3.42 (m, 4H), 3.19-3.17 (m, 4H). MS (ESI) m/z 508 (M$^+$+H).

Example 24: Synthesis of Compound 336

Formula 8-6: methyl 4-((N-(4-(1H-indol-5-yl)phenyl)morpholine-4-carboxamido)methyl)benzoate

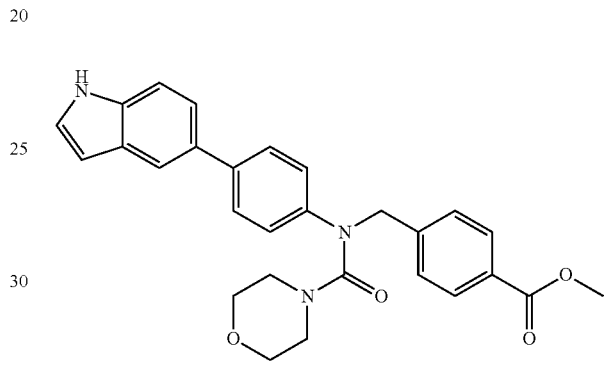

Compound of Formula 8-5 (methyl 4-((N-(4-bromophenyl)morpholine-4-carboxamido)methyl)benzoate; 0.200 g, 0.462 mmol), indol-5-ylboronic acid (0.089 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.191 g, 88%) in the form of a light brown solid.

Compound 336: N-(4-(1H-indol-5-yl)phenyl)-N-(4-(hydroxycarbamoyl)benzyl)morpholine-4-carboxamide

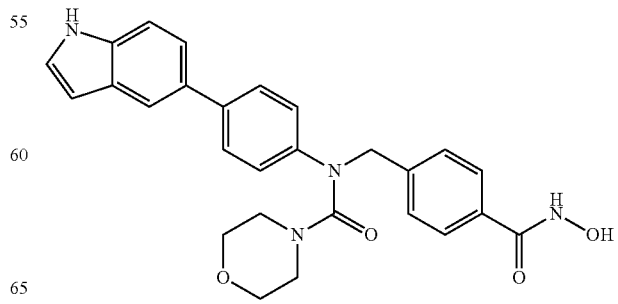

Compound of Formula 8-6 (methyl 4-((N-(4-(1H-indol-5-yl)phenyl)morpholine-4-carboxamido)methyl)benzoate; 0.191 g, 0.407 mmol) was dissolved in methanol (10 mL), and then hydroxylamine (50.0 wt % aqueous solution; 2.49 mL, 40.7 mmol) and potassium hydroxide (0.228 g, 4.07 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 336 (0.185 g, 97%) in the form of a white solid.

$^1$H NMR (400 MHz, DMSO-d$_6$) δ 11.14 (s, 1H), 7.77 (s, 1H), 7.66 (d, 2H, J=8.2 Hz), 7.61 (d, 2H, J=8.6 Hz), 7.44-7.38 (m, 3H), 7.36-7.33 (m, 2H), 7.19 (d, 2H, J=8.6 Hz), 6.44 (s, 1H), 4.90 (s, 2H), 3.45-3.41 (m, 4H), 3.21-3.17 (m, 4H). MS (ESI) m/z 471 (M$^+$+H).

Example 25: Synthesis of Compound 337

Formula 8-6: methyl 4-((N-(4-(1H-indol-6-yl)phenyl)morpholine-4-carboxamido)methyl)benzoate

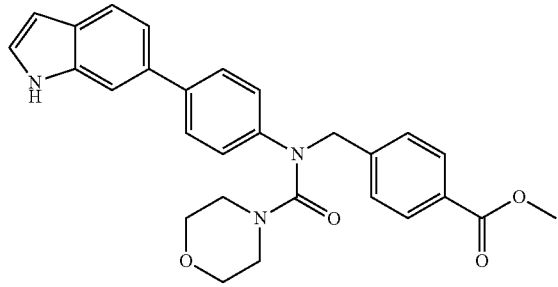 [SMILES: COC(=O)c1ccc(CN(C(=O)N2CCOCC2)c2ccc(-c3ccc4cc[nH]c4c3)cc2)cc1]

Compound of Formula 8-5 (methyl 4-((N-(4-bromophenyl)morpholine-4-carboxamido)methyl)benzoate; 0.200 g, 0.462 mmol), indol-6-ylboronic acid (0.089 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.201 g, 93%) in the form of a light brown solid.

Compound 337: N-(4-(1H-indol-6-yl)phenyl)-N-(4-(hydroxycarbamoyl)benzyl)morpholine-4-carboxamide

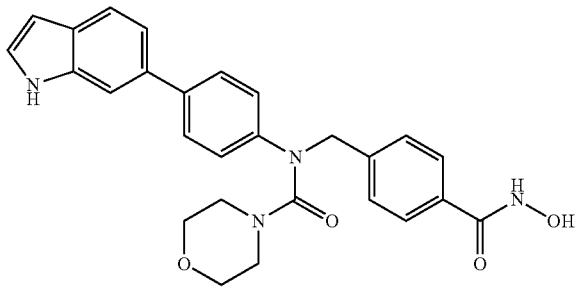 [SMILES: O=C(NO)c1ccc(CN(C(=O)N2CCOCC2)c2ccc(-c3ccc4cc[nH]c4c3)cc2)cc1]

Compound of Formula 8-6 (methyl 4-((N-(4-(1H-indol-6-yl)phenyl)morpholine-4-carboxamido)methyl)benzoate; 0.201 g, 0.428 mmol) was dissolved in methanol (10 mL), and then hydroxylamine (50.0 wt % aqueous solution; 2.62 mL, 42.8 mmol) and potassium hydroxide (0.240 g, 4.28 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 337 (0.195 g, 97%) in the form of a light brown solid.

$^1$H NMR (400 MHz, DMSO-d$_6$) δ 11.15 (s, 1H), 7.67 (d, 2H, J=8.2 Hz), 7.63-7.56 (m, 4H), 7.39 (d, 2H, J=8.2 Hz), 7.36 (m, 1H), 7.26 (m, 1H), 7.21 (d, 2H, J=8.6 Hz), 6.42 (s, 1H), 4.91 (s, 2H), 3.44-3.42 (m, 4H), 3.19-3.17 (m, 4H). MS (ESI) m/z 471 (M$^+$+H).

Example 26: Synthesis of Compound 338

Formula 8-6: methyl 4-((N-(3',4',5'-trimethoxybiphenyl-4-yl)phenyl)morpholine-4-carboxamido)methyl)benzoate

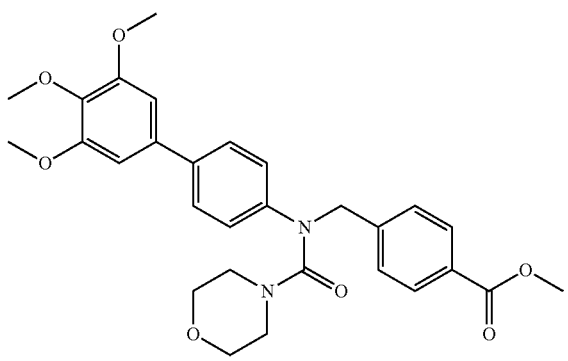

Compound of Formula 8-5 (methyl 4-((N-(4-bromophenyl)morpholine-4-carboxamido)methyl)benzoate; 0.200 g, 0.462 mmol), 3,4,5-trimethoxyphenylboronic acid (0.117 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours.

After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.121 g, 50%) in the form of a white solid.

Compound 338: N-(4-(hydroxycarbamoyl)benzyl)-N-(3',4',5'-trimethoxybiphenyl-4-yl)morpholine-4-carboxamide

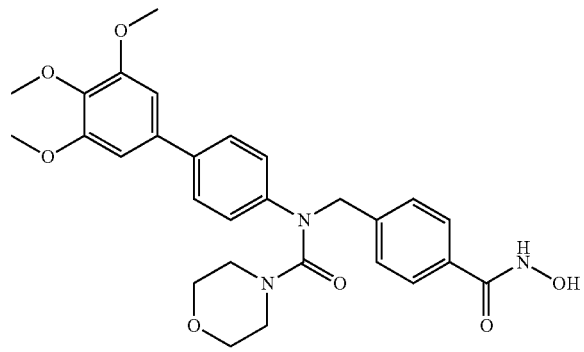 [SMILES: COc1cc(-c2ccc(N(Cc3ccc(C(=O)NO)cc3)C(=O)N3CCOCC3)cc2)cc(OC)c1OC]

Compound of Formula 8-6 (methyl 4-((N-(3',4',5'-trimethoxybiphenyl-4-yl)phenyl)morpholine-4-carboxamido)methyl)benzoate; 0.121 g, 0.232 mmol) was dissolved in methanol (10 mL), and then hydroxylamine (50.0 wt % aqueous solution; 1.42 mL, 23.2 mmol) and potassium hydroxide (0.130 g, 2.32 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 338 (0.038 g, 31%) in the form of a white solid.

$^1$H NMR (400 MHz, DMSO-$d_6$) δ 7.66-7.61 (m, 4H), 7.38 (d, 2H, J=8.2 Hz), 7.20 (d, 2H, J=8.6 Hz), 6.86 (s, 2H), 4.91 (s, 2H), 3.83 (s, 6H), 3.66 (s, 3H), 3.44 (t, 4H, J=4.3 Hz), 3.17 (t, 4H, J=4.4 Hz). MS (ESI) m/z 522 (M$^+$+H).

Example 27: Synthesis of Compound 339

Formula 8-6: methyl 4-((N-(3',5'-bis(trifluoromethyl)biphenyl-4-yl))morpholine-4-carboxamido)methyl)benzoate

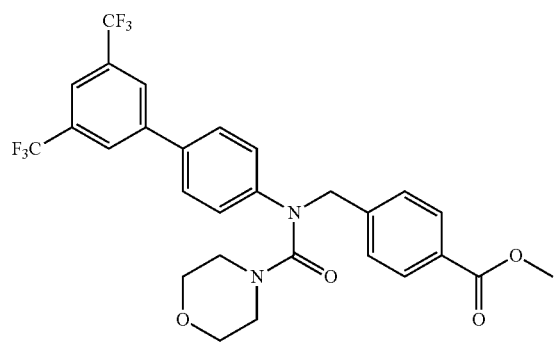 [SMILES: COC(=O)c1ccc(CN(C(=O)N2CCOCC2)c2ccc(-c3cc(C(F)(F)F)cc(C(F)(F)F)c3)cc2)cc1]

Compound of Formula 8-5 (methyl 4-((N-(4-bromophenyl)morpholine-4-carboxamido)methyl)benzoate; 0.200 g, 0.462 mmol), 3,5-bis(trifluoromethyl)phenylboronic acid (0.143 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 8-6 (0.203 g, 78%) in the form of a white solid.

Compound 339: N-(3',5'-bis(trifluoromethyl)biphenyl-4-yl)-N-(4-(hydroxycarbamoyl)benzyl)morpholine-4-carboxamide

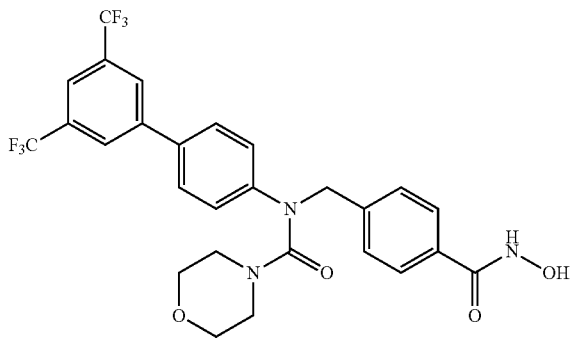 [SMILES: O=C(NO)c1ccc(CN(C(=O)N2CCOCC2)c2ccc(-c3cc(C(F)(F)F)cc(C(F)(F)F)c3)cc2)cc1]

Compound of Formula 8-6 (methyl 4-((N-(3',5'-bis(trifluoromethyl)biphenyl-4-yl))morpholine-4-carboxamido)methyl)benzoate; 0.203 g, 0.358 mmol) was dissolved in methanol (10 mL), and then hydroxylamine (50.0 wt % aqueous solution; 2.19 mL, 35.8 mmol) and potassium hydroxide (0.201 g, 3.58 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 339 (0.197 g, 97%) in the form of a light brown solid.

$^1$H NMR (400 MHz, DMSO-$d_6$) δ 8.29 (s, 2H), 8.03 (s, 1H), 7.82 (d, 2H, J=8.6 Hz), 7.66 (d, 2H, J=8.2 Hz), 7.40 (d, 2H, J=8.2 Hz), 7.28 (d, 2H, J=8.6 Hz), 4.94 (s, 2H), 3.47-3.43 (m, 4H), 3.21-3.15 (m, 4H). MS (ESI) m/z 568 (M$^+$+H).

Example 28: Synthesis of Compound 340

Formula 8-6: methyl 4-((N-(4-(1H-indol-4-yl)phenyl)morpholine-4-carboxamido)methyl)benzoate

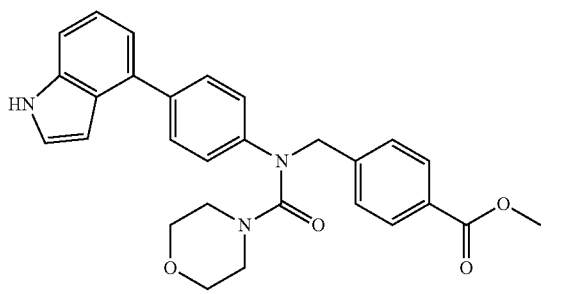 [SMILES: COC(=O)c1ccc(CN(C(=O)N2CCOCC2)c2ccc(-c3cccc4[nH]ccc34)cc2)cc1]

Compound of Formula 8-5 (methyl 4-((N-(4-bromophenyl)morpholine-4-carboxamido)methyl)benzoate; 0.200 g, 0.462 mmol), indol-4-ylboronic acid (0.089 g, 0.554 mmol), and Pd(dppf)Cl$_2$ (0.038 g, 0.046 mmol) were dissolved in 1,4-dioxane (3 mL), and then sodium carbonate (0.196 g, 1.85 mmol) dissolved in water (1 mL) was added to the reaction solution and stirred at 100° C. for 6 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=70%) to give the desired compound of Formula 8-6 (0.142 g, 66%) in the form of a light yellow solid.

Compound 340: N-(4-(1H-indol-4-yl)phenyl)-N-(4-(hydroxycarbamoyl)benzyl)morpholine-4-carboxamide

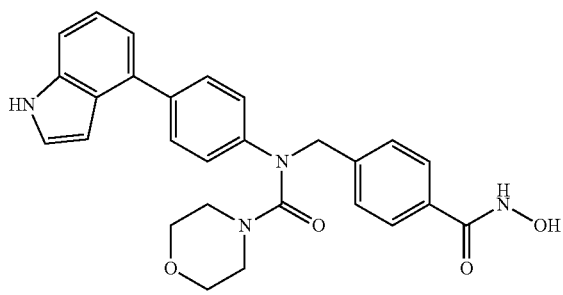 [SMILES: O=C(NO)c1ccc(CN(C(=O)N2CCOCC2)c2ccc(-c3cccc4[nH]ccc34)cc2)cc1]

Compound of Formula 8-6 (methyl 4-((N-(4-(1H-indol-4-yl)phenyl)morpholine-4-carboxamido)methyl)benzoate; 0.142 g, 0.302 mmol) was dissolved in methanol (10 mL), and then hydroxylamine (50.0 wt % aqueous solution; 1.85 mL, 30.2 mmol) and potassium hydroxide (0.170 g, 3.02 mmol) added sequentially and then stirred at room temperature for 30 minutes. After completion of the reaction, the reaction solution was concentrated under reduced pressure until its volume became about 3 mL, and saturated ammonium chloride aqueous solution (1-2 mL) was added and stirred. Then, the solid product was filtered, washed with water, and then vacuum dried to give the desired Compound 340 (0.105 g, 74%) in the form of a white solid.

$^1$H NMR (400 MHz, DMSO-d$_6$) δ 11.25 (s, 1H), 7.68 (d, 2H, J=8.3 Hz), 7.61 (d, 2H, J=8.6 Hz), 7.41-7.36 (m, 4H), 7.25 (d, 2H, J=8.6 Hz), 7.14 (t, 1H, J=7.7 Hz), 7.04 (d, 1H, J=7.3 Hz), 6.51 (s, 1H), 4.92 (s, 2H), 3.45-3.43 (m, 4H), 3.22-3.20 (m, 4H). MS (ESI) m/z 471 (M$^+$+H).

Example 29: Synthesis of Compound 341

Formula 7-4: methyl 4-((pyridin-2-ylamino)methyl)benzoate

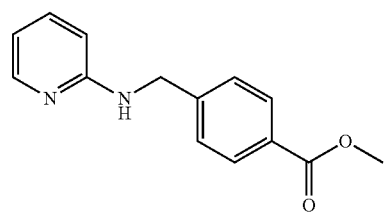

Compound of Formula 7-3 (pyridin-2-amine; 10.0 g, 106 mmol) was dissolved in methanol (100 mL), and then methyl 4-formylbenzoate (17.4 g, 106 mmol) and acetic acid (6.08 mL, 106 mmol) were added and stirred for 1 day. Then, sodium cyanoborohydride (22.5 g, 106 mmol) was added and stirred for 1 day. After completion of the reaction, the produced solid was filtered, and the organic layer was washed with saturated sodium chloride aqueous solution, dehydrated with anhydrous magnesium sulfate, and then concentrated under reduced pressure. The residue was purified and concentrated by column chromatography (silica; dichloromethane/ethyl acetate=5%) to give the desired compound of Formula 7-4 (8.0 g, 31%) in the form of a white solid.

Formula 7-5: methyl 4-((((4-nitrophenoxy)carbonyl)(pyridin-2-yl)amino)methyl)benzoate

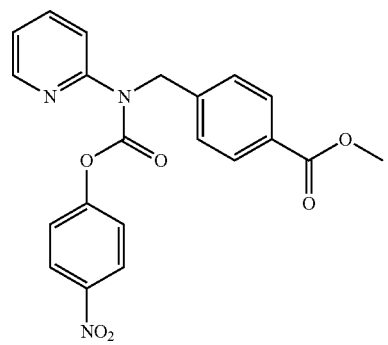

Compound of Formula 7-4 (methyl 4-((pyridin-2-ylamino)methyl)benzoate; 1.80 g, 7.43 mmol) was dissolved in acetonitrile (50 mL), and then potassium carbonate (3.08 g, 22.3 mmol) and 4-nitrophenyl chloroformate (2.24 g, 11.1 mmol) were added. Then, the mixture was heated and stirred at about 50° C. for 1 day. Water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; hexane/ethyl acetate=30%) to give the desired compound of Formula 7-5 (0.98 g, 32%) in the form of a white solid.

Formula 7-6: methyl 4-((N-(pyridin-2-yl)piperidine-1-carboxamido)methyl)benzoate

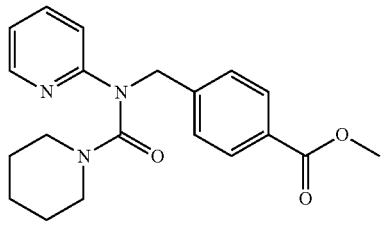 [SMILES: COC(=O)c1ccc(CN(C(=O)N2CCCCC2)c2ccccn2)cc1]

Compound of Formula 7-5 (methyl 4-((((4-nitrophenoxy)carbonyl)(pyridin-2-yl)amino)methyl)benzoate; 0.30 g, 0.736 mmol) was dissolved in dimethylformamide (4 mL), and then piperidine (0.06 mL, 0.736 mmol) and potassium carbonate (0.122 g, 0.884 mmol) were added, and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.27 g, 104%) in the form of a yellow oil.

Compound 341: N-(4-(hydroxycarbamoyl)benzyl)-N-(pyridin-2-yl)piperidine-1-carboxamide

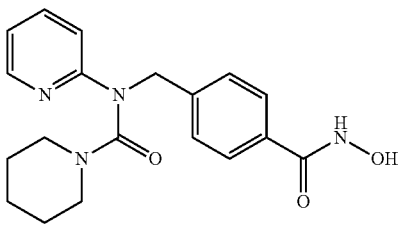 [SMILES: O=C(NO)c1ccc(CN(C(=O)N2CCCCC2)c2ccccn2)cc1]

Compound of Formula 7-6 (methyl 4-((N-(pyridin-2-yl)piperidine-1-carboxamido)methyl)benzoate; 0.13 g, 0.38 mmol) was dissolved in methanol (10 mL), and then hydroxylamine (0.13 g, 1.89 mmol) and potassium hydroxide (0.21 g, 3.79 mmol) were added and stirred for 5 minutes. Then, hydroxylamine (50 wt % aqueous solution; 0.98 mL, 7.58 mmol) was added dropwise and stirred at room temperature for 12 hours. After completion of the reaction, 2 N hydrogen chloride was added, and the organic layer was extracted with ethyl acetate, washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 341 (0.09 g, 70%) in the form of a white solid.

$^1$H NMR (400 MHz, MeOD-d$_3$) δ 8.31-8.29 (m, 1H), 7.72-7.66 (m, 3H), 7.49 (d, 2H, J=8.3 Hz), 7.01-6.98 (m, 2H), 5.07 (s, 2H), 3.27 (t, 4H, J=5.5 Hz), 1.57-1.53 (m, 2H), 1.45-1.41 (m, 4H); MS (ESI) m/z 355.2 (M$^+$+H).

Example 30: Synthesis of Compound 342

Formula 7-6: methyl 4-((4-methyl-N-(pyridin-2-yl)piperidine-1-carboxamido)methyl)benzoate

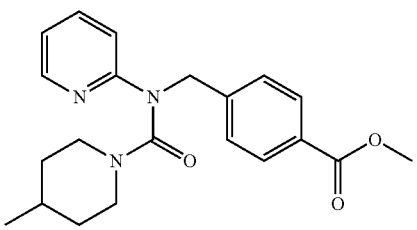

Compound of Formula 7-5 (methyl 4-((((4-nitrophenoxy)carbonyl)(pyridin-2-yl)amino)methyl)benzoate; 0.300 g, 0.736 mmol) was dissolved in dimethylformamide (4 mL), and then 4-methylpiperidine (0.07 g, 0.736 mmol) and potassium carbonate (0.122 g, 0.884 mmol) were added, and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.27 g, 100%) in the form of a yellow oil.

Compound 342: N-(4-(hydroxycarbamoyl)benzyl)-4-methyl-N-(pyridin-2-yl)piperidine-1-carboxamide

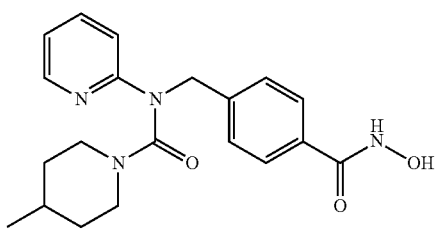 [SMILES: CC1CCN(C(=O)N(Cc2ccc(C(=O)NO)cc2)c2ccccn2)CC1]

Compound of Formula 7-6 (methyl 4-((4-methyl-N-(pyridin-2-yl)piperidine-1-carboxamido)methyl)benzoate; 0.15 g, 0.40 mmol) was dissolved in methanol (10 mL), and then hydroxylamine (0.14 g, 2.00 mmol) and potassium hydroxide (0.22 g, 4.00 mmol) were added and stirred for 5 minutes. Then, hydroxylamine (50 wt % aqueous solution; 1.03 mL, 8.00 mmol) was added dropwise and stirred at room temperature for 12 hours. After completion of the reaction, 2 N hydrogen chloride was added, and the organic layer was extracted with ethyl acetate, washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 342 (0.09 g, 64%) in the form of a colorless oil.

$^1$H NMR (400 MHz, MeOD-d$_3$) δ 8.31-8.29 (m, 1H), 7.71-7.67 (m, 3H), 7.48 (d, 2H, J=8.3 Hz), 7.01-6.98 (m, 2H), 5.07 (s, 2H), 3.83 (d, 2H, J=13.2 Hz), 2.72 (td, 2H, J=12.6, 2.0 Hz), 1.55-1.50 (m, 3H), 0.97-0.93 (m, 2H), 0.95 (m, 3H); MS (ESI) m/z 369.1 (M$^+$+H).

Example 31: Synthesis of Compound 343

Formula 7-6: methyl 4-((2,6-dimethyl-N-(pyridin-2-yl)morpholine-4-carboxamido)methyl)benzoate

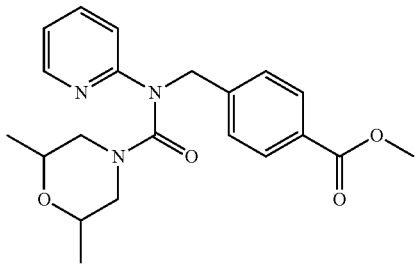

Compound of Formula 7-5 (methyl 4-((((4-nitrophenoxy)carbonyl)(pyridin-2-yl)amino)methyl)benzoate; 0.300 g, 0.736 mmol) was dissolved in dimethylformamide (4 mL), and then 2,6-dimethylmorpholine (0.085 g, 0.736 mmol) and potassium carbonate (0.122 g, 0.884 mmol) were added, and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.17 g, 60%) in the form of a white oil.

Compound 343: N-(4-(hydroxycarbamoyl)benzyl)-2,6-dimethyl-N-(pyridin-2-yl)morpholine-4-carboxamide

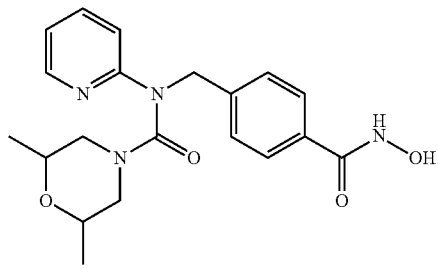 [SMILES: CC1CN(C(=O)N(Cc2ccc(C(=O)NO)cc2)c2ccccn2)CC(C)O1]

Compound of Formula 7-6 (methyl 4-((2,6-dimethyl-N-(pyridin-2-yl)morpholine-4-carboxamido)methyl)benzoate; 0.116 g, 0.303 mmol) was dissolved in methanol (10 mL), and then hydroxylamine (0.105 g, 1.51 mmol) and potassium hydroxide (0.169 g, 3.02 mmol) were added and stirred for 5 minutes. Then, hydroxylamine (50 wt % aqueous solution; 0.778 mL, 6.05 mmol) was added dropwise and stirred at room temperature for 12 hours. After completion of the reaction, 2 N hydrogen chloride was added, and the organic layer was extracted with ethyl acetate, washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 343 (0.107 g, 92%) in the form of a colorless oil.

$^1$H NMR (400 MHz, MeOD-d$_3$) δ 8.32 (dd, 1H, J=4.9, 1.1 Hz), 7.74-7.69 (m, 1H), 7.67 (d, 2H, J=8.2 Hz), 7.48 (d, 2H, J=8.2 Hz), 7.05-7.02 (m, 2H), 5.08 (s, 2H), 3.65 (d, 2H, J=12.9 Hz), 3.43-3.37 (m, 2H), 2.46-2.40 (m, 2H), 1.03 (d, 6H, J=6.2 Hz); MS (ESI) m/z 385.1 (M$^+$+H).

Example 32: Synthesis of Compound 352

Formula 7-6: methyl 4-((4-phenyl-N-(pyridin-2-yl)-1,2,3,6-tetrahydropyridine-1-carboxamido)methyl)benzoate

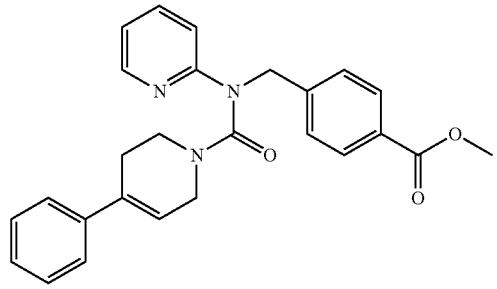 [SMILES: COC(=O)c1ccc(CN(C(=O)N2CC=C(c3ccccc3)CC2)c2ccccn2)cc1]

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (3 mL), and then 4-phenyl-1,2,3,6-tetrahydropyridine (0.264 g, 1.35 mmol) and potassium carbonate (0.339 g, 2.46 mmol) were added, and the mixture was heated and stirred at 55° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=25%) to give the desired compound of Formula 7-6 (0.57 g, 108%) in the form of a yellow oil.

Compound 352: N-(4-(hydroxycarbamoyl)benzyl)-4-phenyl-N-(pyridin-2-yl)-5,6-dihydropyridine-1(2H)-carboxamide

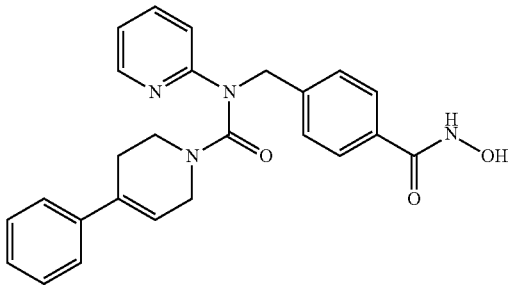 [SMILES: O=C(NO)c1ccc(CN(C(=O)N2CC=C(c3ccccc3)CC2)c2ccccn2)cc1]

Compound of Formula 7-6 (methyl 4-((4-phenyl-N-(pyridin-2-yl)-1,2,3,6-tetrahydropyridine-1-carboxamido)methyl)benzoate; 0.386 g, 0.903 mmol) was dissolved in methanol (20 mL), and then hydroxylamine (0.313 g, 4.51 mmol) and potassium hydroxide (0.507 g, 9.03 mmol) were added and stirred for 5 minutes. Then, hydroxylamine (50 wt % aqueous solution; 2.33 mL, 18.1 mmol) was added dropwise and stirred at room temperature for 12 hours. After completion of the reaction, the methanol was evaporated under reduced pressure, and the solid was precipitated by adding 2 N hydrogen chloride. The solid was filtered and dried to give the desired Compound 352 (0.22 g, 57%) in the form of a white solid.

$^1$H NMR (400 MHz, MeOD-$d_3$) δ 8.33 (dd, 1H, J=5.0, 1.2 Hz), 7.74-7.70 (m, 1H), 7.65 (d, 2H, J=8.3 Hz), 7.49 (d, 2H, J=8.3 Hz), 7.36-7.23 (m, 5H), 7.09-7.02 (m, 2H), 5.97 (t, 1H, J=3.2 Hz), 5.12 (s, 2H), 3.90 (d, 2H, J=3.0 Hz), 3.59 (t, 2H, J=5.7 Hz), 2.43 (d, 2H, J=5.7 Hz); MS (ESI) m/z 429.1 (M$^+$+H).

Example 33: Synthesis of Compound 353

Formula 7-6: methyl 4-((4-methyl-N-(pyridin-2-yl)-piperazine-1-carboxamido)methyl)benzoate

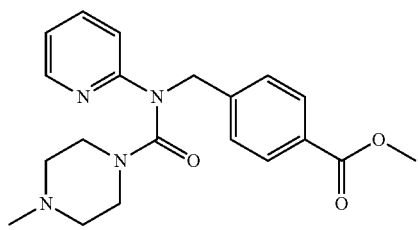

Compound of Formula 7-5 (methyl 4-((((4-nitrophenoxy)carbonyl)(pyridin-2-yl)amino)methyl)benzoate; 0.5 g, 1.23 mmol) was dissolved in dimethylformamide (3 mL), and then 1-methylpiperazine (0.15 ml, 1.35 mmol) and potassium carbonate (0.339 g, 2.46 mmol) were added, and the mixture was heated and stirred at 55° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 7-6 (0.33 g, 73%) in the form of a yellow oil.

Compound 353: N-(4-(hydroxycarbamoyl)benzyl)-4-methyl-N-(pyridin-2-yl)piperazine-1-carboxamide

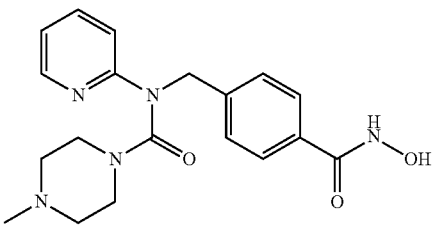 [SMILES: CN1CCN(C(=O)N(Cc2ccc(C(=O)NO)cc2)c2ccccn2)CC1]

Compound of Formula 7-6 (methyl 4-((4-methyl-N-(pyridin-2-yl)-piperazine-1-carboxamido)methyl)benzoate; 0.23 g, 0.624 mmol) was dissolved in methanol (20 mL), and then hydroxylamine (0.217 g, 3.12 mmol) and potassium hydroxide (0.35 g, 6.24 mmol) were added and stirred for 5 minutes. Then, hydroxylamine (50 wt % aqueous solution; 1.61 mL, 12.49 mmol) was added dropwise and stirred at room temperature for 12 hours. After completion of the reaction, the methanol was evaporated under reduced pressure, 2 N hydrogen chloride was added, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=10%) to give the desired Compound 353 (0.04 g, 17%) in the form of a colorless oil.

$^1$H NMR (400 MHz, MeOD-$d_3$) δ 8.33 (dd, 1H, J=4.9, 1.6 Hz), 7.75-7.71 (m, 1H), 7.68 (d, 2H, J=8.2 Hz), 7.48 (d, 2H, J=8.1 Hz), 7.09 (d, 1H, J=8.2 Hz), 7.06-7.03 (m, 1H), 5.08 (s, 2H), 3.41-3.38 (m, 4H), 2.59-2.57 (m, 4H), 2.44 (s, 3H); MS (ESI) m/z 370.1 (M$^+$+H).

Example 34: Synthesis of Compound 354

Formula 7-6: methyl 4-((4-ethyl-N-(pyridin-2-yl)-piperazine-1-carboxamido)methyl)benzoate

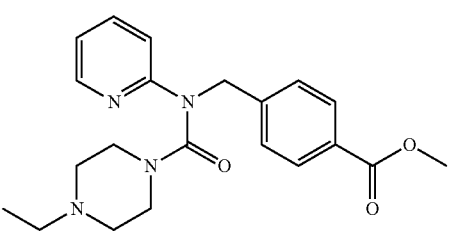 [SMILES: CCN1CCN(C(=O)N(Cc2ccc(C(=O)OC)cc2)c2ccccn2)CC1]

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (3 mL), and then 1-ethylpiperazine (0.154 g, 1.35 mmol) and potassium carbonate (0.339 g, 2.45 mmol) were added, and the mixture was heated and stirred at 55° C. for 12 hours. Then, the dimethylformamide was removed under reduced pressure, water was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=30%) to give the desired compound of Formula 7-6 (0.3 g, 64%) in the form of a yellow oil.

Compound 354: 4-ethyl-N-(4-(hydroxycarbamoyl)benzyl)-N-(pyridin-2-yl)piperazine-1-carboxamide

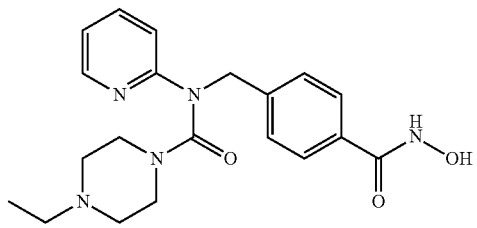 [SMILES: CCN1CCN(C(=O)N(Cc2ccc(C(=O)NO)cc2)c2ccccn2)CC1]

Compound of Formula 7-6 (methyl 4-((4-ethyl-N-(pyridin-2-yl)-piperazine-1-carboxamido)methyl)benzoate; 0.23 g, 0.60 mmol) was dissolved in methanol (20 mL), and then hydroxylamine (0.209 g, 3.01 mmol) and potassium hydroxide (0.337 g, 6.01 mmol) were added and stirred for 5 minutes. Then, hydroxylamine (50 wt % aqueous solution; 1.55 mL, 12.02 mmol) was added dropwise and stirred at room temperature for 12 hours. After completion of the reaction, 2 N hydrogen chloride was added and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=10%) to give the desired Compound 354 (0.038 g, 17%) in the form of a colorless oil.

$^1$H NMR (400 MHz, MeOD-d$_3$) δ 8.31 (dd, 1H, J=4.8, 1.2 Hz), 7.73-7.66 (m, 3H), 7.48 (d, 2H, J=8.2 Hz), 7.06-7.01 (m, 2H), 5.08 (s, 2H), 3.36-3.31 (m, 4H), 2.46-2.37 (m, 6H), 1.07 (t, 3H, J=7.2 Hz); MS (ESI) m/z 384.1 (M$^+$+H).

Example 35: Synthesis of Compound 355

Formula 7-6: methyl 4-((4-benzyl-N-(pyridin-2-yl)-piperazine-1-carboxamido)methyl)benzoate

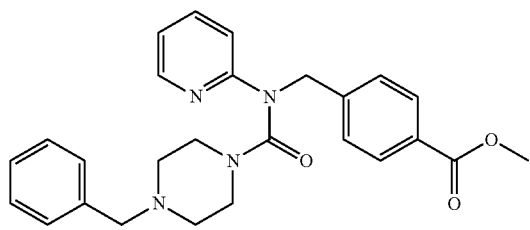

Compound of Formula 7-5 (methyl 4-(((((4-nitrophenoxy)carbonyl)(pyridin-2-yl)amino)methyl)benzoate; 0.50 g, 1.23 mmol) was dissolved in dimethylformamide (3 mL), and then 1-benzylpiperazine (0.231 ml, 1.35 mmol) and potassium carbonate (0.339 g, 2.46 mmol) were added, and the mixture was heated and stirred at 55° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=25%) to give the desired compound of Formula 7-6 (0.185 g, 34%) in the form of a yellow oil.

Compound 355: 4-benzyl-N-(4-(hydroxycarbamoyl)benzyl)-N-(pyridin-2-yl)piperazine-1-carboxamide

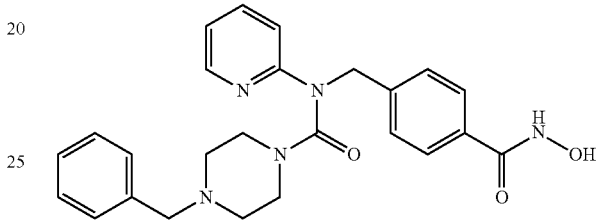

Compound of Formula 7-6 (methyl 4-((4-benzyl-N-(pyridin-2-yl)-piperazine-1-carboxamido)methyl)benzoate; 0.136 g, 0.31 mmol) was dissolved in methanol (20 mL), and then hydroxylamine (0.106 g, 1.53 mmol) and potassium hydroxide (0.172 g, 3.06 mmol) were added and stirred for 5 minutes. Then, hydroxylamine (50 wt % aqueous solution; 0.788 mL, 6.12 mmol) was added dropwise and stirred at room temperature for 12 hours. After completion of the reaction, the methanol was evaporated under reduced pressure, and the solid was precipitated by adding 2 N hydrogen chloride. The solid was filtered to give the desired Compound 355 (0.077 g, 57%) in the form of a white solid.

$^1$H NMR (400 MHz, MeOD-d$_3$) δ 8.31 (dd, 1H, J=4.8, 0.9 Hz), 7.72-7.65 (m, 3H), 7.47 (d, 2H, J=8.2 Hz), 7.32-7.24 (m, 5H), 7.03-7.00 (m, 2H), 5.07 (s, 2H), 3.48 (s, 2H), 3.31-3.30 (m, 4H), 2.32-2.29 (m, 4H); MS (ESI) m/z 446.1 (M$^+$+H).

Example 36: Synthesis of Compound 356

Formula 7-6: methyl 4-((4-(2-methoxyphenyl)-N-(pyridin-2-yl)piperazine-1-carboxamido)methyl)benzoate

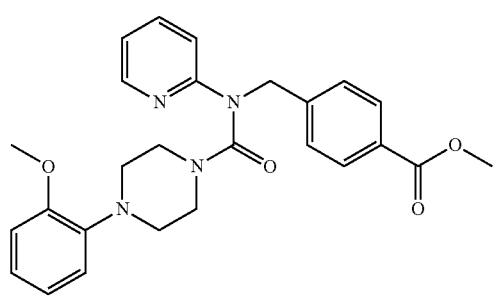 [SMILES: COC(=O)c1ccc(CN(C(=O)N2CCN(c3ccccc3OC)CC2)c2ccccn2)cc1]

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (3 mL), and then 1-(2-methoxyphenyl)piperazine (0.236 mL, 1.35 mmol) and potassium carbonate (0.339 g, 2.46 mmol) were added, and the mixture was heated and stirred at 55° C. for 12 hours. Then, the dimethylformamide was removed under reduced pressure, water was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.565 g, 100%) in the form of a yellow oil.

Compound 356: N-(4-(hydroxycarbamoyl)benzyl)-4-(2-methoxyphenyl)-N-(pyridin-2-yl)piperazine-1-carboxamide

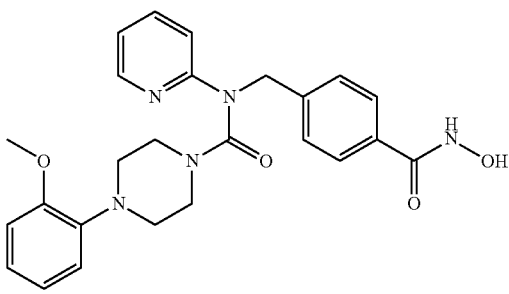 [SMILES: COc1ccccc1N1CCN(C(=O)N(Cc2ccc(C(=O)NO)cc2)c2ccccn2)CC1]

Compound of Formula 7-6 (methyl 4-((4-(2-methoxyphenyl)-N-(pyridin-2-yl)piperazine-1-carboxamido)methyl)benzoate; 0.395 g, 0.858 mmol) was dissolved in methanol (20 mL), and then hydroxylamine (0.298 g, 4.29 mmol) and potassium hydroxide (0.481 g, 8.58 mmol) were added and stirred for 5 minutes. Then, hydroxylamine (50 wt % aqueous solution; 2.21 mL, 17.15 mmol) was added dropwise and stirred at room temperature for 12 hours. After completion of the reaction, 2 N hydrogen chloride was added, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=10%) to give the desired Compound 356 (0.28 g, 70%) in the form of a colorless oil.

$^1$H NMR (400 MHz, MeOD-$d_3$) δ 8.33 (dd, 1H, J=4.9, 1.2 Hz), 7.74-7.71 (m, 1H), 7.68 (d, 2H, J=8.2 Hz), 7.51 (d, 2H, J=8.2 Hz), 7.09-6.87 (m, 6H), 5.11 (s, 2H), 3.82 (s, 3H), 3.47-3.44 (m, 4H), 2.87-2.85 (m, 4H); MS (ESI) m/z 446.1 (M$^+$+H).

Example 37: Synthesis of Compound 357

Formula 7-6: methyl 4-((4-(4-fluorophenyl)-N-(pyridin-2-yl)piperazine-1-carboxamido)methyl)benzoate

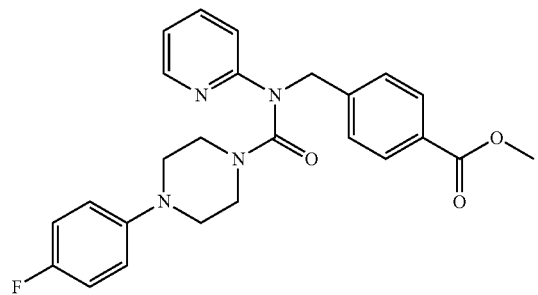 [SMILES: COC(=O)c1ccc(CN(C(=O)N2CCN(c3ccc(F)cc3)CC2)c2ccccn2)cc1]

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (3 mL), and then 1-(4-fluorophenyl)piperazine (0.243 mL, 1.35 mmol) and potassium carbonate (0.339 g, 2.46 mmol) were added, and the mixture was heated and stirred at 55° C. for 12 hours. Then, the dimethylformamide was removed under reduced pressure, water was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=25%) to give the desired compound of Formula 7-6 (0.54 g, 98%) in the form of a yellow oil.

Compound 357: 4-(4-fluorophenyl)-N-(4-(hydroxycarbamoyl)benzyl)-N-(pyridin-2-yl)piperazine-1-carboxamide

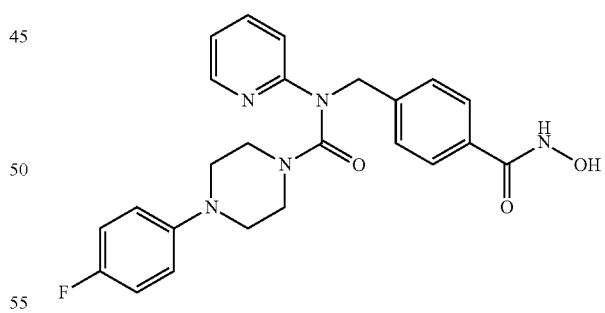

Compound of Formula 7-6 (methyl 4-((4-(4-fluorophenyl)-N-(pyridin-2-yl)piperazine-1-carboxamido)methyl)benzoate; 0.31 g, 0.691 mmol) was dissolved in methanol (20 mL), and then hydroxylamine (0.24 g, 3.46 mmol) and potassium hydroxide (0.3881 g, 6.91 mmol) were added and stirred for 5 minutes. Then, hydroxylamine (50 wt % aqueous solution; 1.78 mL, 13.8 mmol) was added dropwise and stirred at room temperature for 12 hours. After completion of the reaction, 2 N hydrogen chloride was added, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=10%) to give the desired Compound 357 (0.27 g, 87%) in the form of a colorless oil.

$^1$H NMR (400 MHz, MeOD-d$_3$) δ 8.34-8.33 (m, 1H), 7.75-7.71 (m, 1H), 7.67 (d, 2H, J=8.2 Hz), 7.51 (d, 2H, J=8.2 Hz), 7.09 (d, 1H, J=8.3 Hz), 7.05-6.89 (m, 5H), 5.11 (s, 2H), 3.46-3.44 (m, 4H), 2.96-2.93 (m, 4H); MS (ESI) m/z 450.1 (M$^+$+H).

Example 38: Synthesis of Compound 358

Formula 7-6: methyl 4-((N-(pyridin-2-yl)pyrrolidine-1-carboxamido)methyl)benzoate

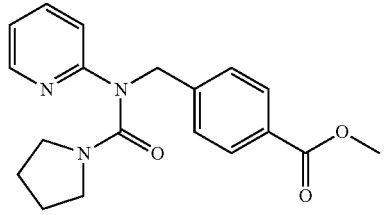 [SMILES: COC(=O)c1ccc(CN(C(=O)N2CCCC2)c2ccccn2)cc1]

Compound of Formula 7-5 (methyl 4-((((4-nitrophenoxy)carbonyl)(pyridin-2-yl)amino)methyl)benzoate; 0.20 g, 0.491 mmol) was dissolved in dimethylformamide (4 mL), and then pyrrolidine (0.035 mL, 0.491 mmol) and potassium carbonate (0.081 g, 0.589 mmol) were added, and the mixture was heated and stirred at 55° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.031 g, 19%) in the form of a colorless oil.

Compound 358: N-(4-(hydroxycarbamoyl)benzyl)-N-(pyridin-2-yl)pyrrolidine-1-carboxamide

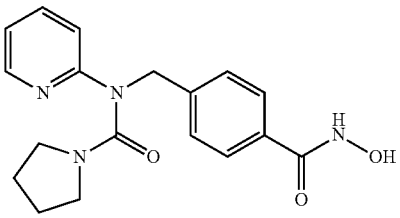 [SMILES: O=C(NO)c1ccc(CN(C(=O)N2CCCC2)c2ccccn2)cc1]

Compound of Formula 7-6 (methyl 4-((N-(pyridin-2-yl)pyrrolidine-1-carboxamido)methyl)benzoate; 0.031 g, 0.091 mmol) was dissolved in methanol (4 mL), and then hydroxylamine (0.032 g, 0.457 mmol) and potassium hydroxide (0.051 g, 0.913 mmol) were added and stirred for 5 minutes. Then, hydroxylamine (50 wt % aqueous solution; 0.135 mL, 1.83 mmol) was added dropwise and stirred at room temperature for 12 hours. After completion of the reaction, the methanol was evaporated under reduced pressure, 2 N hydrogen chloride was added, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=10%) to give the desired Compound 358 (0.012 g, 39%) in the form of a colorless oil.

$^1$H NMR (400 MHz, MeOD-d$_3$) δ 8.31 (dd, 1H, J=4.9, 1.3 Hz), 7.73-7.69 (m, 1H), 7.65 (d, 2H, J=8.2 Hz), 7.47 (d, 2H, J=8.2 Hz), 7.07-7.02 (m, 2H), 5.08 (s, 2H), 3.19-3.18 (m, 4H), 1.80-1.77 (m, 4H); MS (ESI) m/z 341.2 (M$^+$+H).

Example 39: Synthesis of Compound 370

Formula 11-3: methyl 4-(thioureidomethyl)benzoate

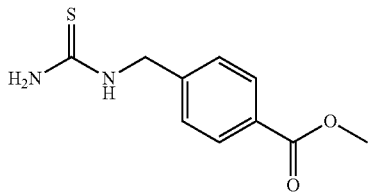

Compound of Formula 11-2 (1,1'-thiocarbonyldiimidazole; 8.26 g, 46.4 mmol) was dissolved in hydrogen chloride (40 mL), and then triethylamine (6.34 mL, 46.4 mmol) and compound of Formula 11-1 (4-(aminomethyl)benzoate hydrochloride; 8.50 g, 42.2 mmol) were slowly added sequentially and then stirred at room temperature for 3 hours. Then, ammonia (28.0 wt % aqueous solution; 30 mL) and methanol (10 mL) were added to the mixture and stirred at room temperature for 2 hours, and then hexane (85 mL) and water (45 mL) were further added and stirred at the same temperature for 1 hour. The solid product was filtered, washed with hexane and then with water, and then vacuum dried to give the desired compound of Formula 11-3 (9.40 g, 99%) in the form of a light brown solid.

Formula 11-5: methyl 4-((4-phenylthiazol-2-ylamino)methyl)benzoate

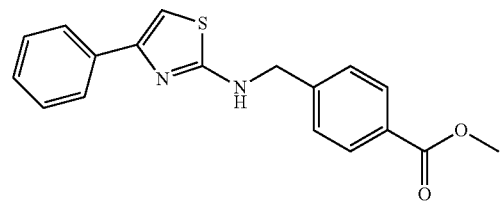 [SMILES: COC(=O)c1ccc(CNc2nc(-c3ccccc3)cs2)cc1]

Compound of Formula 11-3 (methyl 4-(thioureidomethyl)benzoate; 0.180 g, 0.803 mmol) and compound of Formula 11-4 (2-bromoacetophenone; 0.084 g, 0.843 mmol) were dissolved in ethanol (5 mL) and then stirred under reflux for 16 hours. After completion of the reaction, the temperature reaction solution was cooled to room temperature, and then ethyl acetate and hexane were added and stirred. Then, the solid product was filtered and vacuum dried to give the desired compound of Formula 11-5 (0.175 g, 67%) in the form of a light brown solid.

Formula 11-6: methyl 4-((((4-nitrophenoxy)carbonyl)(4-phenylthiazol-2-yl)amino)methyl)benzoate

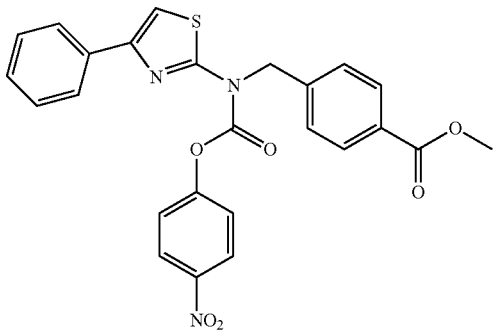 [SMILES: COC(=O)c1ccc(CN(C(=O)Oc2ccc([N+](=O)[O-])cc2)c2nc(-c3ccccc3)cs2)cc1]

Compound of Formula 11-5 (methyl 4-((4-phenylthiazol-2-ylamino)methyl)benzoate; 0.175 g, 0.539 mmol) and 4-nitrophenyl chloroformate (0.141 g, 0.701 mmol) were dissolved in acetonitrile (10 mL), and then potassium carbonate (0.112 g, 0.809 mmol) was added and stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=20%) to give the desired compound of Formula 11-6 (0.160 g, 61%) in the form of a yellow solid.

Formula 11-7: methyl 4-((N-(4-phenylthiazol-2-yl)morpholine-4-carboxamido)methyl)benzoate

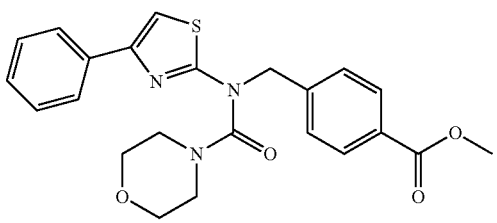 [SMILES: COC(=O)c1ccc(CN(C(=O)N2CCOCC2)c2nc(-c3ccccc3)cs2)cc1]

Compound of Formula 11-6 (methyl 4-((((4-nitrophenoxy)carbonyl)(4-phenylthiazol-2-yl)amino)methyl)benzoate; 0.160 g, 0.327 mmol) was dissolved in dimethylformamide (5 mL), and then morpholine (0.057 g, 0.654 mmol) and potassium carbonate (0.136 g, 0.981 mmol) were added and stirred at 60° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 11-7 (0.085 g, 59%) in the form of a light yellow solid.

Compound 370: N-(4-(hydroxycarbamoyl)benzyl)-N-(4-phenylthiazol-2-yl)morpholine-4-carboxamide

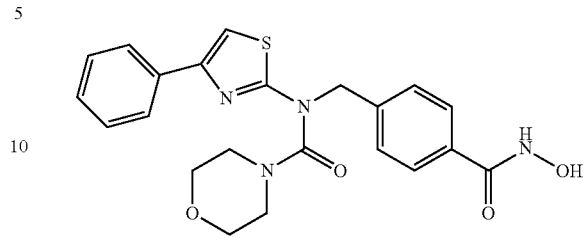

Compound of Formula 11-7 (methyl 4-((N-(4-phenylthiazol-2-yl)morpholine-4-carboxamido)methyl)benzoate; 0.085 g, 0.194 mmol) was dissolved in methanol (5 mL), and then hydroxylamine (50.0 wt % aqueous solution; 1.19 mL, 19.4 mmol) and potassium hydroxide (0.109 g, 1.94 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 370 (0.059 g, 69%) in the form of a white solid.

$^1$H NMR (400 MHz, DMSO-d$_6$) δ 7.82 (d, 2H, J=8.5 Hz), 7.67 (d, 2H, J=8.3 Hz), 7.55 (s, 1H), 7.41-7.35 (m, 4H), 7.29 (m, 1H), 5.13 (s, 2H), 3.59-3.57 (m, 4H), 3.39-3.36 (m, 4H). MS (ESI) m/z 439 (M$^+$+H).

Example 40: Synthesis of Compound 371

Formula 11-5: methyl 4-((4-(4-chlorophenyl)thiazol-2-ylamino)methyl)benzoate

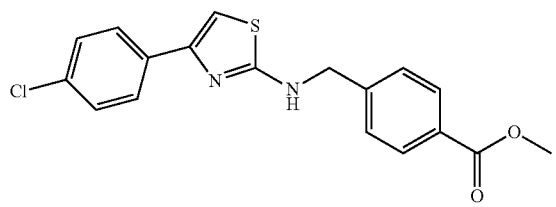 [SMILES: COC(=O)c1ccc(CNc2nc(-c3ccc(Cl)cc3)cs2)cc1]

Compound of Formula 11-3 (methyl 4-(thioureidomethyl)benzoate; 0.500 g, 2.23 mmol) and 2-bromo-4-chloroacetophenone (0.573 g, 2.45 mmol) were dissolved in ethanol (20 mL) and then stirred under reflux for 16 hours. After completion of the reaction, the temperature reaction solution was cooled to room temperature, and then ethyl acetate and hexane were added and stirred. Then, the solid product was filtered and vacuum dried to give the desired compound of Formula 11-5 (0.700 g, 88%) in the form of a white solid.

Formula 11-6: methyl 4-(((4-(4-chlorophenyl)thi-azol-2-yl)((4-nitrophenoxy)carbonyl)amino)methyl)benzoate

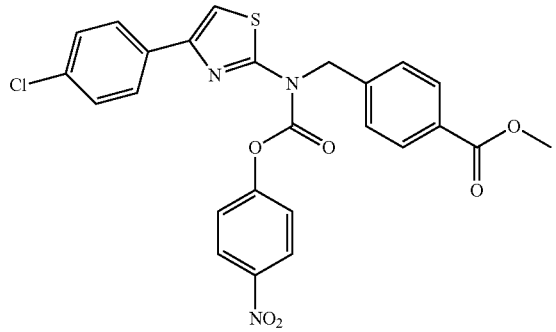 [SMILES: COC(=O)c1ccc(CN(C(=O)Oc2ccc([N+](=O)[O-])cc2)c2nc(-c3ccc(Cl)cc3)cs2)cc1]

Compound of Formula 11-5 (methyl 4-((4-(4-chlorophenyl)thiazol-2-ylamino)methyl)benzoate; 0.500 g, 1.39 mmol) and 4-nitrophenyl chloroformate (0.337 g, 1.67 mmol) were dissolved in dimethylformamide (10 mL), and then N,N-diisopropylethylamine (0.370 ml, 2.09 mmol) was added and stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=15%) to give the desired compound of Formula 11-6 (0.520 g, 71%) in the form of a yellow solid.

Formula 11-7: methyl 4-((N-(4-(4-chlorophenyl)thiazol-2-yl)morpholine-4-carboxamido)methyl)benzoate

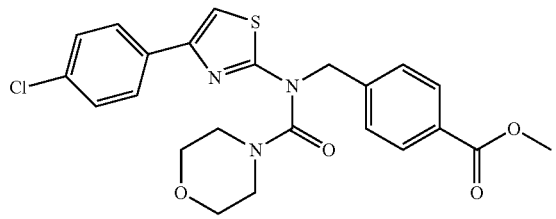 [SMILES: COC(=O)c1ccc(CN(C(=O)N2CCOCC2)c2nc(-c3ccc(Cl)cc3)cs2)cc1]

Compound of Formula 11-6 (methyl 4-(((4-(4-chlorophenyl)thiazol-2-yl)((4-nitrophenoxy)carbonyl)amino)methyl)benzoate; 0.520 g, 0.992 mmol) was dissolved in dimethylformamide (5 mL), and then morpholine (0.173 g, 1.99 mmol) and potassium carbonate (0.412 g, 2.98 mmol) were added and stirred at 60° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=50%) to give the desired compound of Formula 11-7 (0.460 g, 98%) in the form of a white solid.

Compound 371: N-(4-(4-chlorophenyl)thiazol-2-yl)-N-(4-(hydroxycarbamoyl)benzyl)morpholine-4-carboxamide

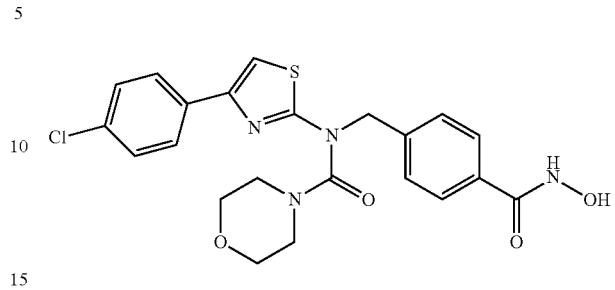

Compound of Formula 11-7 (methyl 4-((N-(4-(4-chlorophenyl)thiazol-2-yl)morpholine-4-carboxamido)methyl)benzoate; 0.460 g, 0.975 mmol) was dissolved in methanol (10 mL), and then hydroxylamine (50.0 wt % aqueous solution; 2.98 mL, 48.7 mmol) and potassium hydroxide (0.547 g, 9.75 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 371 (0.435 g, 94%) in the form of a white solid.

$^1$H NMR (400 MHz, DMSO-$d_6$) δ 11.14 (s, 1H), 9.00 (s, 1H), 7.83 (d, 2H, J=8.5 Hz), 7.67 (d, 2H, J=8.2 Hz), 7.62 (s, 1H), 7.45 (d, 2H, J=8.6 Hz), 7.39 (d, 2H, J=8.0 Hz), 5.14 (s, 2H), 3.60-3.57 (m, 4H), 3.41-3.38 (m, 4H). MS (ESI) m/z 473 (M$^+$+H).

Example 41: Synthesis of Compound 372

Compound 372: N-(4-bromophenyl)-N-(4-(hydroxycarbamoyl)benzyl)morpholine-4-carboxamide

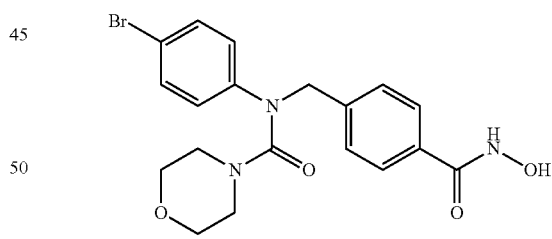

Compound of Formula 8-5 (methyl 4-((N-(4-bromophenyl)morpholine-4-carboxamido)methyl)benzoate; 0.085 g, 0.196 mmol) was dissolved in methanol (5 mL), and then hydroxylamine (50.0 wt % aqueous solution; 1.20 mL, 19.6 mmol) and potassium hydroxide (0.110 g, 1.96 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 372 (0.049 g, 58%) in the form of a light yellow solid.

¹H NMR (400 MHz, DMSO-d₆) δ 7.64 (d, 2H, J=8.4 Hz), 7.45 (dd, 2H, J=6.8, 2.1 Hz), 7.33 (d, 2H, J=8.2 Hz), 7.09 (dd, 2H, J=6.8, 2.1 Hz), 4.85 (s, 2H), 3.41 (t, 4H, J=4.7 Hz), 3.13 (t, 4H, J=4.6 Hz). MS (ESI) m/z 434, 436 (M⁺+H).

Example 42: Synthesis of Compound 374

Formula 1-2: methyl 4-((3-(trifluoromethyl)phenylamino)methyl)benzoate

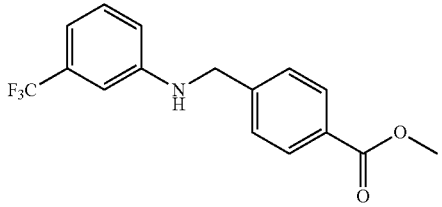 [SMILES: COC(=O)c1ccc(CNc2cccc(C(F)(F)F)c2)cc1]

Compound Formula 1-1 (3-(trifluoromethyl)benzenamine; 0.30 g, 1.84 mmol) and potassium carbonate (0.76 g, 5.53 mmol) were dissolved in dimethylformamide (DMF, 5 mL), and methyl 4-(bromomethyl)benzoate (0.42 g, 1.84 mmol) was then added. The mixture was reacted at room temperature for 1 day and then diluted with ethyl acetate. The reaction mixture was washed with saturated sodium chloride aqueous solution, dehydrated with anhydrous magnesium sulfate, filtered, and then concentrated under reduced pressure. The residue was purified by column chromatography (silica; ethyl acetate/hexane=20%) to give the desired compound of Formula 1-2 (0.37 g, 65%).

¹H NMR (400 MHz, DMSO-d₆) δ 7.93 (d, 2H, J=8.3 Hz), 7.49 (d, 2H, J=8.3 Hz), 7.24 (t, 1H, J=7.9 Hz), 6.88-6.78 (m, 4H), 4.42 (d, 2H, J=6.1 Hz), 3.83 (s, 3H), MS (ESI) m/z 310 (M⁺+H).

Formula 1-3: methyl 4-((((4-nitrophenoxy)carbonyl) (3-(trifluoromethyl)phenyl)amino)methyl)benzoate

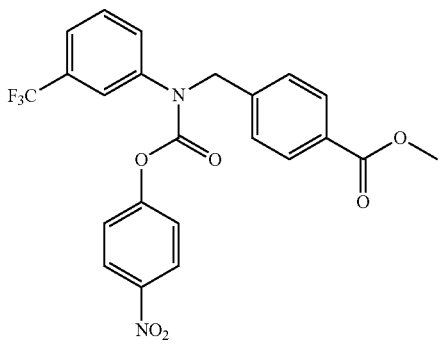 [SMILES: COC(=O)c1ccc(CN(C(=O)Oc2ccc([N+](=O)[O-])cc2)c2cccc(C(F)(F)F)c2)cc1]

Compound of Formula 1-2 (methyl 4-((3-(trifluoromethyl)phenylamino)methyl)benzoate; 0.26 g, 0.82 mmol) and 4-nitrophenyl carbonochloridate (0.33 g, 1.65 mmol) were dissolved in acetonitrile (10 mL), and potassium carbonate (0.34 g, 2.47 mmol) was then added. The mixture was reacted at room temperature for 1 day and then diluted with ethyl acetate. The reaction mixture was washed with saturated sodium chloride aqueous solution, dehydrated with anhydrous sodium sulfate, filtered, and then concentrated under reduced pressure. The residue was purified by column chromatography (silica; ethyl acetate/hexane=20%) to give the desired compound of Formula 1-3 (0.35 g, 89%) in the form of a colorless oil.

¹H NMR (400 MHz, CDCl₃) δ 8.20 (d, 2H, J=10.2 Hz), 8.01 (d, 2H, J=7.8 Hz), 7.56-7.46 (m, 3H), 7.35 (d, 3H, J=8.0 Hz), 7.26 (d, 2H, J=8.1 Hz), 5.01 (bs, 2H), 3.90 (s, 3H).

Formula 1-4: methyl 4-((N-(3-(trifluoromethyl)phenyl)morpholine-4-carboxamido)methyl)benzoate

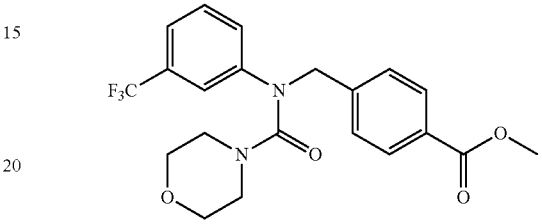

Compound of Formula 1-3 (methyl 4-((((4-nitrophenoxy) carbonyl)(3-(trifluoromethyl)phenyl)amino)methyl)benzoate; 0.29 g, 0.60 mmol) was dissolved in dimethylformamide (10 mL), and potassium carbonate (0.25 g, 1.81 mmol) and morpholine (0.05 mL, 0.60 mmol) were then added. The mixture was reacted at 60° C. for 2 days and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=50%) to give the desired compound of Formula 1-4 (0.15 g, 60%).

¹H NMR (400 MHz, DMSO-d₆) δ 7.97 (d, 2H, J=8.2 Hz), 7.43-7.32 (m, 5H), 7.20 (d, 1H, J=8.0 Hz), 4.94 (s, 2H), 3.90 (s, 3H), 3.50 (t, 4H, J=4.8 Hz), 3.25 (t, 4H, J=4.8 Hz), MS (ESI) m/z 423 (M⁺+H).

Compound 374: N-(4-(hydroxycarbamoyl)benzyl)-N-(3-(trifluoromethyl)phenyl)morpholine-4-carboxamide

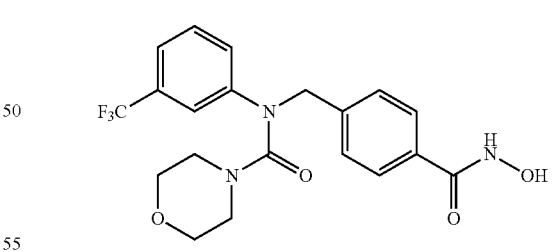

Compound of Formula 1-4 (methyl 4-((N-(3-(trifluoromethyl)phenyl)morpholine-4-carboxamido)methyl)benzoate; 0.15 g, 0.36 mmol) was dissolved in methanol (5 mL), and hydroxylamine aqueous solution (50 wt %, 1 mL) and potassium hydroxide (0.10 g, 1.81 mmol) were then added and stirred overnight. After completion of the reaction, the methanol was removed by distillation under reduced pressure, and the organic layer was extracted with ethyl acetate and water, dehydrated with anhydrous sodium sulfate, filtered, and then concentrated under reduced pressure. The residue was stirred in diethyl ether to give a solid product, and the resulting solid was filter and dried to give the desired Compound 374 (0.082 g, 54%) in the form of a white solid.

$^1$H NMR (400 MHz, MeOD-d$_3$) δ 11.14 (brs, 1H), 8.99 (brs, 1H), 7.85 (d, 2H, J=8.0 Hz), 7.66-7.27 (m, 6H), 4.94 (s, 2H), 3.41 (s, 2H), 3.15 (s, 2H). MS (ESI) m/z 424 (M$^+$+H).

Example 43: Synthesis of Compound 376

Formula 7-6: methyl 4-((4-methyl-N-(pyridin-2-yl)-1,4-diazepane-1-carboxamido)methyl)benzoate

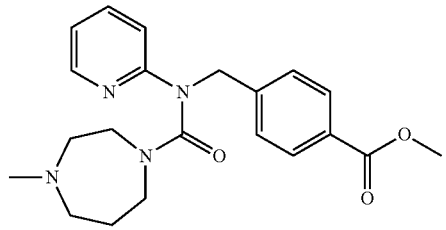

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (4 mL), and then 1-methyl-1,4-diazepane (0.183 mL, 1.47 mmol) and potassium carbonate (0.339 g, 2.45 mmol) were added, and the mixture was heated and stirred at 55° C. for 12 hours. Then, the dimethylformamide was removed under reduced pressure, saturated ammonium chloride aqueous solution was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50%) to give the desired compound of Formula 7-6 (0.32 g, 68%) in the form of a pale yellow oil.

Compound 376: N-(4-(hydroxycarbamoyl)benzyl)-4-methyl-N-(pyridin-2-yl)-1,4-diazepane-1-carboxamide

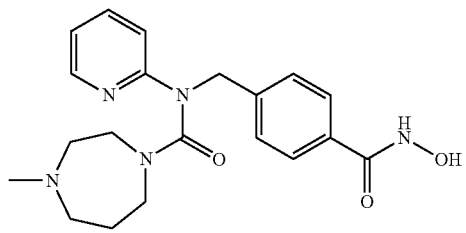 [SMILES: CN1CCCN(C(=O)N(Cc2ccc(C(=O)NO)cc2)c2ccccn2)CC1]

Compound of Formula 7-6 (methyl 4-((4-methyl-N-(pyridin-2-yl)-1,4-diazepane-1-carboxamido)methyl)benzoate; 0.15 g, 0.39 mmol) was dissolved in methanol (20 mL), and then hydroxylamine (0.136 g, 1.96 mmol) and potassium hydroxide (0.22 g, 3.92 mmol) were added and stirred for 5 minutes. Then, hydroxylamine (50 wt % aqueous solution; 1.01 mL, 7.84 mmol) was added dropwise and stirred at room temperature for 6 hours. After completion of the reaction, the methanol was evaporated by reduced pressure, 1 N hydrogen chloride was added, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 376 (0.009 g, 6%) in the form of a white solid.

$^1$H NMR (400 MHz, MeOD-d$_3$) δ 8.33-8.31 (m, 1H), 7.74-7.72 (m, 1H), 7.67 (d, 2H, J=8.3 Hz), 7.50 (d, 2H, J=8.2 Hz), 7.10-7.04 (m, 2H), 5.09 (d, 2H, J=2.4 Hz), 3.96-3.93 (m, 2H), 3.56-2.95 (m, 6H), 2.88 (s, 3H), 2.06-2.02 (m, 2H); MS (ESI) m/z 384.1 (M$^+$+H).

Example 44: Synthesis of Compound 377

Formula 7-6: methyl 4-((N-(pyridin-2-yl)azetidine-1-carboxamido)methyl)benzoate

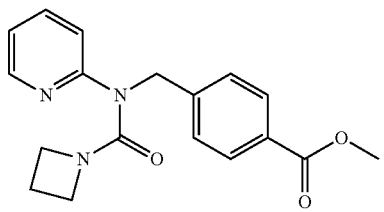 [SMILES: COC(=O)c1ccc(CN(C(=O)N2CCC2)c2ccccn2)cc1]

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (4 mL), and then azetidine (0.183 g, 1.47 mmol) and potassium carbonate (0.339 g, 2.45 mmol) were added, and the mixture was heated and stirred at 55° C. for 1 day. Then, the dimethylformamide was removed under reduced pressure, water was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.03 g, 8%) in the form of a white solid.

Compound 377: N-(4-(hydroxycarbamoyl)benzyl)-N-(pyridin-2-yl)azetidine-1-carboxamide

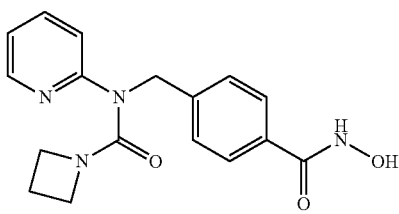 [SMILES: O=C(NO)c1ccc(CN(C(=O)N2CCC2)c2ccccn2)cc1]

Compound of Formula 7-6 (methyl 4-((N-(pyridin-2-yl)azetidine-1-carboxamido)methyl)benzoate; 0.03 g, 0.09 mmol) was dissolved in methanol (20 mL), and then hydroxylamine (0.032 g, 0.092 mmol) and potassium hydroxide (0.052 g, 0.922 mmol) were added and stirred for 5 minutes. Then, hydroxylamine (50 wt % aqueous solution; 0.238 mL, 1.84 mmol) was added dropwise and stirred at room temperature for 6 hours. After completion of the reaction, 1 N hydrogen chloride was added and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 377 (0.013 g, 43%) in the form of a white solid.

$^1$H NMR (400 MHz, MeOD-d$_3$) δ 8.38-8.36 (m, 1H), 7.78-7.74 (m, 1H), 7.64 (d, 2H, J=8.3 Hz), 7.40 (d, 2H, J=8.3 Hz), 7.24 (d, 1H, J=8.2 Hz), 7.15-7.11 (m, 1H), 5.09 (s, 2H), 3.73 (t, 4H, J=7.7 Hz), 2.12 (tt, 2H, J=7.7 Hz); MS (ESI) m/z 327.2 (M$^+$+H).

Example 45: Synthesis of Compound 379

Formula 7-6: methyl 4-((4-(3,4-dimethylphenyl-N-(pyridin-2-yl)piperazine-1-carboxamido)methyl)benzoate

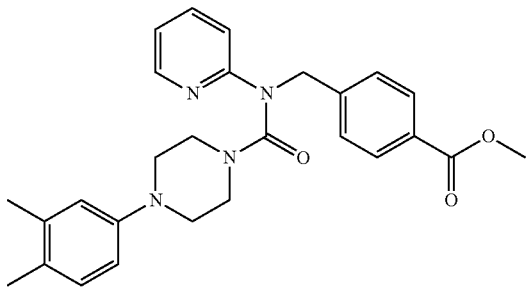

Compound of Formula 7-5 (methyl 4-((((4-nitrophenoxy)carbonyl)(pyridin-2-yl)amino)methyl)benzoate; 0.50 g, 1.23 mmol) was dissolved in dimethylformamide (4 mL), and then 1-(3,4-dimethylphenyl)piperazine (0.28 g, 1.47 mmol) and potassium carbonate (0.339 g, 2.46 mmol) were added, and the mixture was heated and stirred at 55° C. for 1 day. Then, the dimethylformamide was removed under reduced pressure, water was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 7-6 (0.4 g, 71%) in the form of a yellow oil.

Compound 379: 4-(3,4-dimethylphenyl)-N-(4-(hydroxycarbamoyl)benzyl)-N-(pyridin-2-yl)piperazine-1-carboxamide

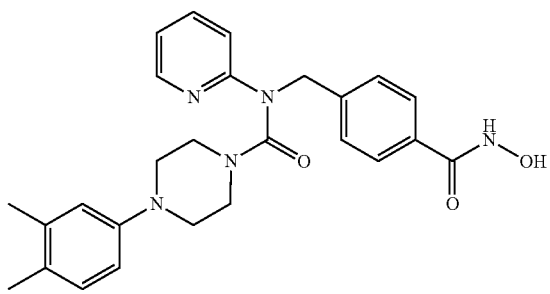 [SMILES: Cc1ccc(N2CCN(C(=O)N(Cc3ccc(C(=O)NO)cc3)c3ccccn3)CC2)cc1C]

Compound of Formula 7-6 (methyl 4-((4-(3,4-dimethylphenyl-N-(pyridin-2-yl)piperazine-1-carboxamido)methyl)benzoate; 0.1 g, 0.218 mmol) was dissolved in methanol (20 mL), and then hydroxylamine (0.076 g, 1.09 mmol) and potassium hydroxide (0.122 g, 2.18 mmol) were added and stirred for 5 minutes. Then, hydroxylamine (50 wt % aqueous solution; 0.56 mL, 4.36 mmol) was added dropwise and stirred at room temperature for 6 hours. After completion of the reaction, 2 N hydrogen chloride was added and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired Compound 379 (0.05 g, 52%) in the form of a white solid.

$^1$H NMR (400 MHz, MeOD-d$_3$) δ 8.33 (dd, 1H, J=4.9, 1.2 Hz), 7.74-7.70 (m, 1H), 7.67 (d, 2H, J=8.3 Hz), 7.50 (d, 2H, J=8.3 Hz), 7.08 (d, 1H, J=8.3 Hz), 7.05-7.02 (m, 1H), 6.97 (d, 1H, J=8.3 Hz), 6.72 (d, 1H, J=2.2 Hz), 6.63 (dd, 1H, J=8.2, 2.4 Hz), 5.10 (s, 2H), 3.45-3.43 (m, 4H), 2.95-2.93 (m, 4H), 2.20 (s, 3H), 2.15 (s, 3H); MS (ESI) m/z 460.2 (M$^+$+H).

Example 46: Synthesis of Compound 380

Formula 9-1: methyl 4-((N-(4'-formylbiphenyl-4-yl)morpholine-4-carboxamido)methyl)benzoate

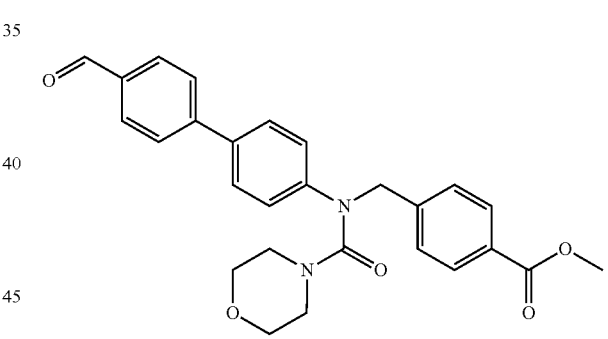

Compound of Formula 8-5 (methyl 4-((N-(4-bromophenyl)morpholine-4-carboxamido)methyl)benzoate; 1.00 g, 2.31 mmol), 4-formylphenylboronic acid (0.415 g, 2.77 mmol), and Pd(dppf)Cl$_2$ (0.094 g, 0.115 mmol) were dissolved in 1,4-dioxane (12 mL), and then cesium carbonate (2.24 g, 6.92 mmol) dissolved in water (3 mL) was added to the reaction solution and then stirred at 140° C. for 15 minutes in a microwave reactor. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=50%) to give the desired compound of Formula 9-1 (0.750 g, 71%) in the form of a light yellow solid.

Formula 9-2: methyl 4-((N-(4'-(morpholinomethyl)biphenyl-4-yl)morpholine-4-carboxamido)methyl)benzoate

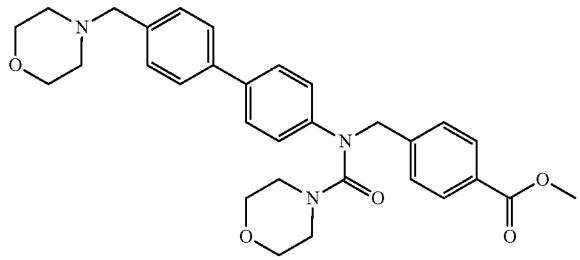 [SMILES: COC(=O)c1ccc(CN(C(=O)N2CCOCC2)c2ccc(-c3ccc(CN4CCOCC4)cc3)cc2)cc1]

Compound of Formula 9-1 (methyl 4-((N-(4'-formylbiphenyl-4-yl)morpholine-4-carboxamido)methyl)benzoate; 0.150 g, 0.327 mmol) was dissolved in methanol (5 mL), and then morpholine (0.086 g, 0.981 mmol) and acetic acid (0.094 mL, 1.64 mmol) were added and stirred at room temperature for 1 hour. Then, sodium cyanoborohydride (0.041 g, 0.654 mmol) was added and stirred at the same temperature for 16 hours. After completion of the reaction, the organic layer was extracted with ethyl acetate and saturated sodium hydrogen carbonate aqueous solution and concentrated under reduced pressure. Then, the organic layer was dehydrated with anhydrous magnesium sulfate and filtered, and then the filtrate was concentrated under reduced pressure. Then, the residue was purified and concentrated by column chromatography (silica; ethyl acetate/hexane=25%) to give the desired compound of Formula 9-2 (0.136 g, 79%) in the form of a white solid.

Compound 380: N-(4-(hydroxycarbamoyl)benzyl)-N-(4'-(morpholinomethyl)biphenyl-4-yl)morpholine-4-carboxamide

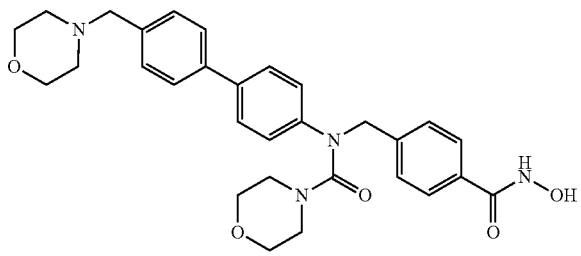 [SMILES: O=C(NO)c1ccc(CN(C(=O)N2CCOCC2)c2ccc(-c3ccc(CN4CCOCC4)cc3)cc2)cc1]

Compound of Formula 9-2 (methyl 4-((N-(4'-(morpholinomethyl)biphenyl-4-yl)morpholine-4-carboxamido)methyl)benzoate; 0.130 g, 0.245 mmol) was dissolved in methanol (10 mL), and hydroxylamine (50.0 wt % aqueous solution; 1.50 mL, 24.5 mmol) and potassium hydroxide (0.138 g, 2.46 mmol) were added and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was dehydrated with anhydrous magnesium sulfate, filtered, and then concentrated under reduced pressure. The residue was recrystallized with dichloromethane and hexane to give the desired Compound 380 (0.073 g, 56%) in the form of a white solid.

$^1$H NMR (400 MHz, DMSO-$d_6$) δ 11.14 (brs, H), 9.14 (brs, 1H), 7.65 (d, 2H, J=8.1 Hz), 7.62-7.56 (m, 4H), 7.39-7.33 (m, 4H), 7.21 (d, 2H, J=8.5 Hz), 4.90 (s, 2H), 3.58-3.55 (m, 4H), 3.46 (s, 2H), 3.42-3.37 (m, 8H), 3.17 (m, 4H). MS (ESI) m/z 529 (M$^+$+H).

Example 47: Synthesis of Compound 381

Formula 9-2: methyl 4-((N-(4'-((4-methylpiperazin-1-yl)methyl)biphenyl-4-yl)morpholine-4-carboxamido)methyl)benzoate

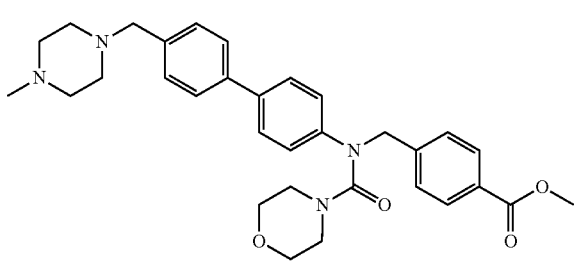

Compound of Formula 9-1 (methyl 4-((N-(4'-formylbiphenyl-4-yl)morpholine-4-carboxamido)methyl)benzoate; 0.150 g, 0.327 mmol) was dissolved in methanol (5 mL), and then 1-methylpiperazine (0.098 g, 0.981 mmol) and acetic acid (0.094 mL, 1.64 mmol) were added and stirred at room temperature for 1 hour. Then, sodium cyanoborohydride (0.041 g, 0.654 mmol) was added and stirred at the same temperature for 16 hours. After completion of the reaction, the organic layer was extracted with ethyl acetate and saturated sodium hydrogen carbonate aqueous solution and concentrated under reduced pressure. Then, the organic layer was dehydrated with anhydrous magnesium sulfate and filtered, and then the filtrate was concentrated under reduced pressure. Then, the residue was purified and concentrated by column chromatography (silica; methanol/dichloromethane=10%) to give the desired compound of Formula 9-2 (0.140 g, 79%) in the form of a white solid.

Compound 381: N-(4-(hydroxycarbamoyl)benzyl)-N-(4'-((4-methylpiperazin-1-yl)methyl)biphenyl-4-yl) morpholine-4-carboxamide

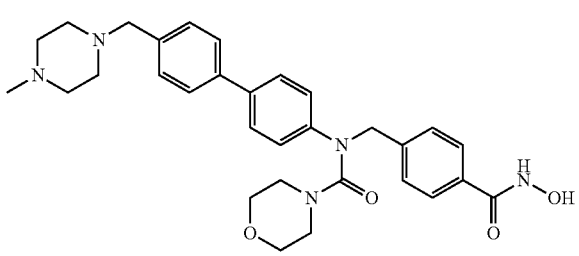 [SMILES: CN1CCN(Cc2ccc(-c3ccc(N(Cc4ccc(C(=O)NO)cc4)C(=O)N4CCOCC4)cc3)cc2)CC1]

Compound of Formula 9-2 (methyl 4-((N-(4'-((4-methylpiperazin-1-yl)methyl)biphenyl-4-yl)morpholine-4-carboxamido)methyl)benzoate; 0.140 g, 0.258 mmol) was dissolved in methanol (10 mL), and hydroxylamine (50.0 wt % aqueous solution; 1.58 mL, 25.8 mmol) and potassium hydroxide (0.145 g, 2.58 mmol) were added and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was dehydrated with anhydrous magnesium sulfate, filtered, and then concentrated under reduced pressure. The residue was recrystallized with dichloromethane and hexane to give the desired Compound 381 (0.093 g, 66%) in the form of a white solid.

$^1$H NMR (400 MHz, DMSO-d$_6$) δ 7.65 (d, 2H, J=7.8 Hz), 7.61-7.56 (m, 4H), 7.38 (d, 2H, J=8.0 Hz), 7.32 (d, 2H, J=7.6 Hz), 7.21 (d, 2H, J=8.5 Hz), 4.90 (s, 2H), 3.59-3.39 (m, 10H), 3.17 (m, 4H), 2.40-2.23 (m, 4H), 2.18 (s, 3H). MS (ESI) m/z 544 (M$^+$+H).

Example 48: Synthesis of Compound 382

Formula 9-2: (S)-methyl 4-((N-(4'-((2-(hydroxymethyl)pyrrolidin-1-yl)methyl)biphenyl-4-yl)morpholine-4-carboxamido)methyl)benzoate

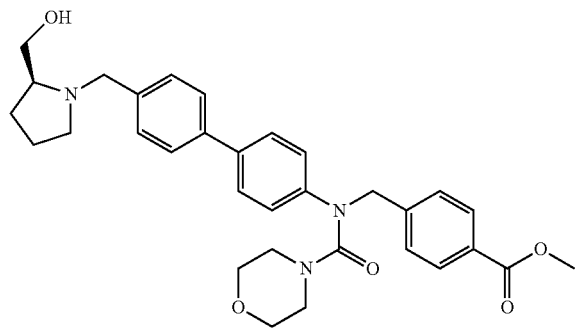 [SMILES: COC(=O)c1ccc(CN(C(=O)N2CCOCC2)c2ccc(-c3ccc(CN4CCC[C@H]4CO)cc3)cc2)cc1]

Compound of Formula 9-1 (methyl 4-((N-(4'-formylbiphenyl-4-yl)morpholine-4-carboxamido)methyl)benzoate; 0.150 g, 0.327 mmol) was dissolved in methanol (5 mL), and then (S)-pyrrolidin-2yl-methanol (0.099 g, 0.981 mmol) and acetic acid (0.094 mL, 1.64 mmol) were added and stirred at room temperature for 1 hour. Then, sodium cyanoborohydride (0.041 g, 0.654 mmol) was added and stirred at the same temperature for 16 hours. After completion of the reaction, the organic layer was extracted with ethyl acetate and saturated sodium hydrogen carbonate aqueous solution and concentrated under reduced pressure. Then, the organic layer was dehydrated with anhydrous magnesiumسulfate and filtered, and then the filtrate was concentrated under reduced pressure. Then, the residue was purified and concentrated by column chromatography (silica; methanol/dichloromethane=10%) to give the desired compound of Formula 9-2 (0.123 g, 69%) in the form of a white solid.

Compound 382: (S)—N-(4-(hydroxycarbamoyl)benzyl)-N-(4'-((2-(hydroxymethyl)pyrrolidin-1-yl)methy 1)biphenyl-4-yl)morpholine-4-carboxamide

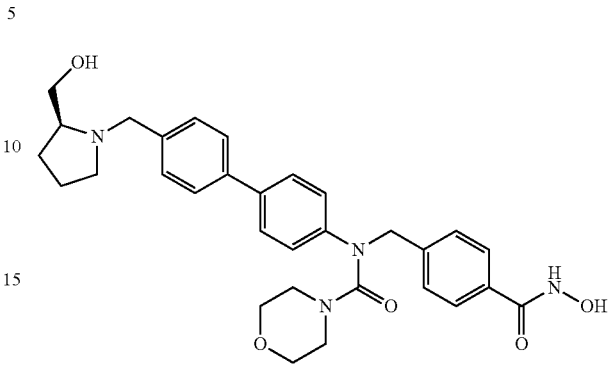

Compound of Formula 9-2 ((S)-methyl 4-((N-(4'-((2-(hydroxymethyl)pyrrolidin-1-yl)methyl)biphenyl-4-yl)morpholine-4-carboxamido)methyl)benzoate; 0.120 g, 0.221 mmol) was dissolved in methanol (10 mL), and hydroxylamine (50.0 wt % aqueous solution; 1.35 mL, 22.1 mmol) and potassium hydroxide (0.124 g, 2.21 mmol) were added and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was dehydrated with anhydrous magnesium sulfate, filtered, and then concentrated under reduced pressure to give the desired Compound 382 (0.036 g, 30%) in the form of a colorless liquid.

$^1$H NMR (400 MHz, DMSO-d$_6$) δ 7.65 (d, 2H, J=7.8 Hz), 7.61-7.55 (m, 4H), 7.39-7.34 (m, 4H), 7.21 (d, 2H, J=8.3 Hz), 4.90 (s, 2H), 4.06 (m, 1H), 3.47-3.39 (m, 6H), 3.37-3.35 (m, 2H), 3.17 (m, 4H), 2.24-2.20 (m, 2H), 1.64-1.52 (m, 5H). MS (ESI) m/z 545 (M$^+$+H).

Example 49: Synthesis of Compound 383

Formula 9-2: methyl 4-((N-(4'-(((2-(hydroxyethyl)(methyl)amino)methyl)biphenyl-4-yl)morpholine-4-carboxamido)methyl)benzoate

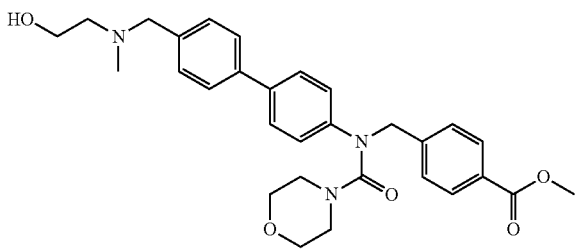 [SMILES: COC(=O)c1ccc(CN(C(=O)N2CCOCC2)c2ccc(-c3ccc(CN(C)CCO)cc3)cc2)cc1]

Compound of Formula 9-1 (methyl 4-((N-(4'-formylbiphenyl-4-yl)morpholine-4-carboxamido)methyl)benzoate; 0.150 g, 0.327 mmol) was dissolved in methanol (5 mL), and then 2-(methylamino)ethanol (0.074 g, 0.981 mmol) and acetic acid (0.094 mL, 1.64 mmol) were added and stirred at room temperature for 1 hour. Then, sodium cyanoborohydride (0.041 g, 0.654 mmol) was added and stirred at the same temperature for 16 hours. After completion of the reaction, the organic layer was extracted with ethyl acetate and saturated sodium hydrogen carbonate aqueous solution and concentrated under reduced pressure. Then, the organic layer was dehydrated with anhydrous magnesium sulfate and filtered, and then the filtrate was concentrated under reduced pressure. Then, the residue was purified and concentrated by column chromatography (silica; methanol/dichloromethane=7%) to give the desired compound of Formula 9-2 (0.152 g, 90%) in the form of a white solid.

Compound 383: N-(4-(hydroxycarbamoyl)benzyl)-N-(4'-(((2-hydroxyethyl)(methyl)amino)methyl)biphenyl-4-yl)morpholine-4-carboxamide

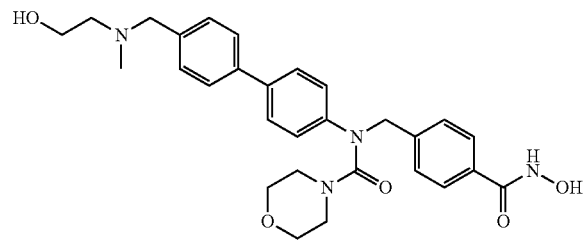 [SMILES: CN(CCO)Cc1ccc(-c2ccc(N(Cc3ccc(C(=O)NO)cc3)C(=O)N3CCOCC3)cc2)cc1]

Compound of Formula 9-2 (methyl 4-((N-(4'-(((2-(hydroxyethyl)(methyl)amino)methyl)biphenyl-4-yl)morpholine-4-carboxamido)methyl)benzoate; 0.150 g, 0.290 mmol) was dissolved in methanol (10 mL), and hydroxylamine (50.0 wt % aqueous solution; 1.77 mL, 29.0 mmol) and potassium hydroxide (0.163 g, 2.90 mmol) were added and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was dehydrated with anhydrous magnesium sulfate, filtered, and then concentrated under reduced pressure to give the desired Compound 383 (0.023 g, 15%) in the form of a colorless liquid.

$^1$H NMR (400 MHz, DMSO-d$_6$) δ 7.66-7.56 (m, 6H), 7.39-7.34 (m, 4H), 7.21 (d, 2H, J=8.6 Hz), 4.90 (s, 2H), 3.51-3.48 (m, 4H), 3.42-3.37 (m, 4H), 3.17 (m, 4H), 2.45-2.43 (m, 2H), 2.22 (m, 1H), 2.15 (s, 3H). MS (ESI) m/z 519 (M$^+$+H).

Example 50: Synthesis of Compound 385

Formula 1-2: methyl 4-((4-(trifluoromethyl)phenylamino)methyl)benzoate

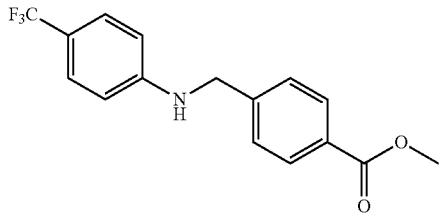 [SMILES: COC(=O)c1ccc(CNc2ccc(C(F)(F)F)cc2)cc1]

Compound of Formula 1-1 (4-(trifluoromethyl)benzenamine; 0.30 g, 1.84 mmol) and potassium carbonate (0.76 g, 5.53 mmol) were dissolved in dimethylformamide (10 mL), and methyl 4-(bromomethyl)benzoate (0.84 g, 3.67 mmol) was then added. The mixture was reacted at room temperature for 1 day and then diluted with ethyl acetate. The reaction mixture was washed with water and saturated sodium chloride aqueous solution, dehydrated with anhydrous sodium sulfate, filtered, and then concentrated under reduced pressure. The residue was purified by column chromatography (silica; ethyl acetate/hexane=20%) to give the desired compound of Formula 1-2 (0.27 g, 47%).

Formula 1-3: methyl 4-((((4-nitrophenoxy)carbonyl)(4-(trifluoromethyl)phenyl)amino)methyl)benzoate

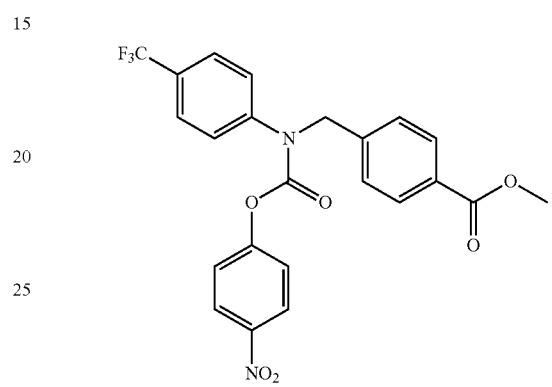

Compound of Formula 1-2 (methyl 4-((4-(trifluoromethyl)phenylamino)methyl)benzoate; 0.27 g, 0.87 mmol) and 4-nitrophenyl carbonochloridate (0.35 g, 1.74 mmol) were dissolved in acetonitrile (10 mL), and potassium carbonate (0.36 g, 2.61 mmol) was then added. The mixture was reacted at room temperature for 1 day and then diluted with ethyl acetate. The reaction mixture was washed with water and saturated sodium chloride aqueous solution, dehydrated with anhydrous sodium sulfate, filtered, and then concentrated under reduced pressure. The residue was purified by column chromatography (silica; ethyl acetate/hexane=20%) to give the desired compound of Formula 1-3 (0.40 g, 97%).

Formula 1-4: methyl 4-((N-(4-(trifluoromethyl)phenyl)morpholine-4-carboxamido)methyl)benzoate

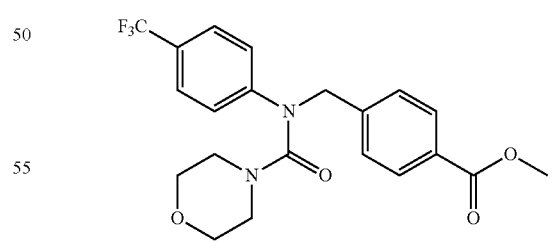

Compound of Formula 1-3 (methyl 4-((((4-nitrophenoxy)carbonyl)(4-(trifluoromethyl)phenyl)amino)methyl)benzoate; 0.39 g, 0.84 mmol) was dissolved in dimethylformamide, and potassium carbonate (0.25 g, 1.81 mmol) and morpholine (10 mL) were then added. The mixture was reacted at 60° C. for 2 days and diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=50%) to give the desired compound of Formula 1-4 (0.20 g, 60%).

Compound 385, N-(4-(hydroxycarbamoyl)benzyl)-N-(4-(trifluoromethyl)phenyl)morpholine-4-carboxamide

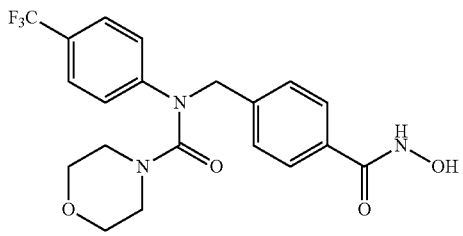 [SMILES: O=C(NO)c1ccc(CN(C(=O)N2CCOCC2)c2ccc(C(F)(F)F)cc2)cc1]

Compound of Formula 1-4 (methyl 4-((N-(4-(trifluoromethyl)phenyl)morpholine-4-carboxamido)methyl)benzoate; 0.20 g, 0.48 mmol) was dissolved in methanol, and hydroxylamine (50 wt % aqueous solution; 0.29 mL) and potassium hydroxide (0.13 g, 2.39 mmol) were then added and stirred overnight. After completion of the reaction, the methanol was removed by distillation under reduced pressure, and the organic layer was extracted with ethyl acetate and water, dehydrated with anhydrous sodium sulfate, filtered, and then concentrated under reduced pressure. The residue was stirred in diethyl ether to give a white solid, and the resulting solid was filter and dried to give the desired Compound 385 (0.10 g, 50%) in the form of a white solid.

$^1$H NMR (400 MHz, DMSO-$d_6$) δ 11.14 (brs, 1H), 8.99 (brs, 1H), 7.67-7.62 (m, 4H), 7.38 (d, 2H, J=8.2 Hz), 7.29 (d, 2H, J=8.5 Hz), 4.94 (s, 2H), 3.47-3.44 (m, 4H), 3.21-3.18 (m, 4H). MS (ESI) m/z 424 (M$^+$+H).

Example 51: Synthesis of Compound 386

Formula 1-2: methyl 4-((3-(trifluoromethyl)phenylamino)methyl)benzoate

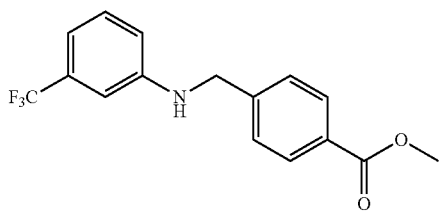 [SMILES: COC(=O)c1ccc(CNc2cccc(C(F)(F)F)c2)cc1]

Compound of Formula 1-1 (3-(trifluoromethyl)benzenamine; 1.00 g, 6.21 mmol) and methyl 4-formylbenzoate (1.02 g, 6.21 mmol) were dissolved in methanol (10 ml), and sodium cyanoborohydride (NaCNBH3) (0.41 g, 6.21 mmol) and acetic acid (0.71 mL, 2.00 mmol) was added. The mixture was reacted at room temperature for 2 day and then the methanol was evaporated by reduced pressure. The reaction was completed by adding saturated sodium hydrogen carbonate solution. The reaction mixture was extracted with ethyl acetate, dehydrated with anhydrous sodium sulfate, filtered, and then concentrated under reduced pressure. The residue was purified by column chromatography (silica; ethyl acetate/hexane=20%) to give the desired compound of Formula 1-2 (1.43 g, 74.5%).

Formula 1-3: methyl 4-((((4-nitrophenoxy)carbonyl)(3-(trifluoromethyl)phenyl)amino)methyl)benzoate

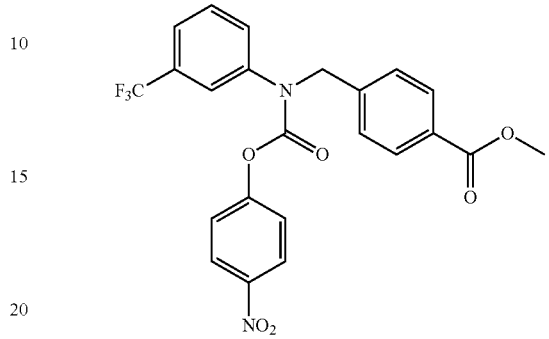

Compound of Formula 1-2 (methyl 4-((3-(trifluoromethyl)phenylamino)methyl)benzoate; 1.04 g, 3.36 mmol) and 4-nitrophenyl carbonochloridate (1.36 g, 6.73 mmol) were dissolved in acetonitrile (30 mL), and potassium carbonate (1.39 g, 10.1 mmol) was then added. The mixture was reacted at room temperature for 1 day and then diluted with ethyl acetate. The reaction mixture was washed with water and saturated sodium chloride aqueous solution and water, dehydrated with anhydrous sodium sulfate, filtered, and then concentrated under reduced pressure. The residue was purified by column chromatography (silica; ethyl acetate/hexane=20%) to give the desired compound of Formula 1-3 (1.51 g, 95%).

Formula 1-4: methyl 4-((2,6-dimethyl-N-(3-(trifluoromethyl)phenyl)morpholine-4-carboxamido)methyl)benzoate

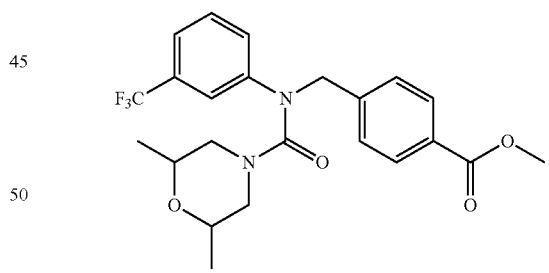

Compound of Formula 1-3 (methyl 4-((((4-nitrophenoxy)carbonyl)(3-(trifluoro-methyl)phenyl)amino)methyl)benzoate; 0.38 g, 0.80 mmol) was dissolved in dimethylformamide (10 ml), and potassium carbonate (0.33 g, 2.38 mmol) and 2,6-dimethylmorpholine (0.09, 0.80 mmol) were then added. The mixture was reacted at 60° C. for 2 days and then it was diluted with ethyl acetate and washed with saturated ammonium chloride solution. The organic layer was dehydrated with anhydrous magnesium sulfate, filtered, and then concentrated under reduced pressure. The residue was purified by column chromatography (silica; ethyl acetate/hexane=50%) to give the desired compound of Formula 1-4 (0.21 g, 59%).

Compound 386, N-(4-(hydroxycarbamoyl)benzyl)-2,6-dimethyl-N-(3-(trifluoromethyl)phenyl)morpholine-4-carboxamide

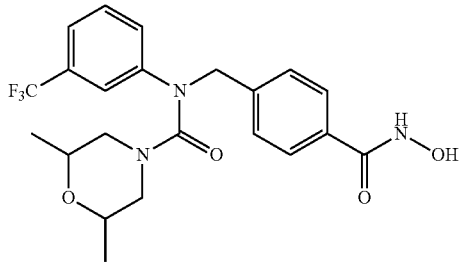 [SMILES: CC1CN(C(=O)N(Cc2ccc(C(=O)NO)cc2)c2cccc(C(F)(F)F)c2)CC(C)O1]

Compound of Formula 1-4 (methyl 4-((2,6-dimethyl-N-(3-(trifluoromethyl)-phenyl)morpholine-4-carboxamido)methyl)benzoate; 0.21 g, 0.47 mmol) was dissolved in methanol (50 mL), and hydroxylamine aqueous solution (50 wt %, 0.29 mL) and potassium hydroxide (0.13 g, 2.35 mmol) were then added and stirred overnight. After completion of the reaction, the methanol was removed by distillation under reduced pressure, and the organic layer was extracted with ethyl acetate and water, dehydrated with anhydrous magnesium sulfate, filtered, and then concentrated under reduced pressure. The residue was stirred in diethyl ether to give a white solid, and the resulting solid was filter and dried to give the desired Compound 386 (0.10 g, 48%) in the form of a white solid.

$^1$H NMR (400 MHz, DMSO-d$_6$) δ 11.13 (brs, 1H), 8.98 (brs, 1H), 7.65 (d, 2H, J=8.3 Hz), 7.54-7.50 (m, 1H), 7.43-7.36 (m, 5H), 3.55 (d, 2H, J=12.4 Hz), 2.36-2.31 (m, 2H), 0.94 (s, 3H), 0.93 (s, 3H). MS (ESI) m/z 452 (M$^+$+H).

Example 52: Synthesis of Compound 389

Formula 1-2: methyl 4-((4-chloro-3-(trifluoromethyl)phenylamino)methyl)benzoate

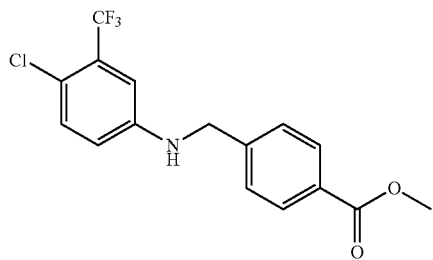 [SMILES: COC(=O)c1ccc(CNc2ccc(Cl)c(C(F)(F)F)c2)cc1]

Compound of Formula 1-1 (4-chloro-3-(trifluoromethyl)benzenamine; 5 g, 25.6 mmol) and methyl 4-formylbenzoate (4.19 g, 25.6 mmol) were dissolved in methanol (100 mL) and stirred for 1 hour. Then, acetic acid (1.58 mL, 25.6 mmol) and sodium cyanoborohydride (1.61 g, 25.6 mmol) were added and stirred for 1 day. The methanol was partially removed by air-drying to precipitate a solid, and the resulting solid was filtered and dried to give the desired compound of Formula 1-2 (3.4 g, 39%) in the form of a white solid.

Formula 1-3: methyl 4-(((4-chloro-3-(trifluoromethyl)phenyl)((4-nitrophenoxy)carbonyl)amino)methyl)benzoate

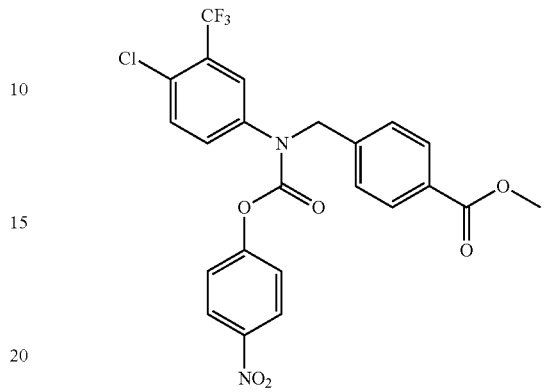

Compound of Formula 1-2 (methyl 4-((4-chloro-3-(trifluoromethyl)phenylamino)methyl)benzoate; 2 g, 5.82 mmol) and 4-nitrophenyl chloroformate (1.17 g, 5.82 mmol) were dissolved in dichloromethane (50 mL) and stirred at room temperature for 2 days to precipitate a solid, and the resulting solid was filter and dried to give the desired compound of Formula 1-3 (3.14 g, 106%) in the form of a yellow solid.

Formula 1-4: methyl 4-((N-(4-chloro-3-(trifluoromethyl)phenyl)piperidine-1-carboxamido)methyl)benzoate

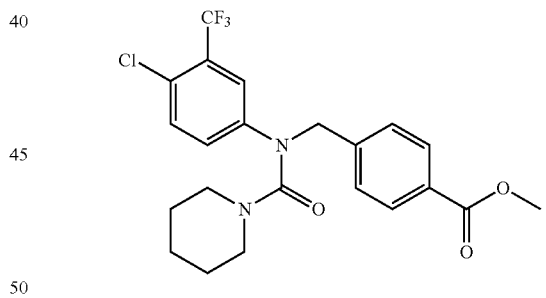

Compound of Formula 1-3 (methyl 4-(((4-chloro-3-(trifluoromethyl)phenyl)((4-nitrophenoxy)carbonyl)amino)methyl)benzoate; 0.50 g, 0.983 mmol) and piperidine (0.097 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.425 g, 95%) in the form of a colorless oil.

Compound 389: N-(4-chloro-3-(trifluoromethyl)phenyl)-N-(4-(hydroxycarbamoyl)benzyl)piperidine-1-carboxamide

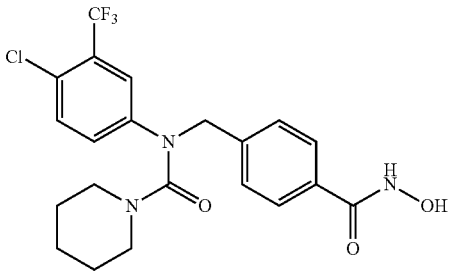

Compound of Formula 1-4 (methyl 4-((N-(4-chloro-3-(trifluoromethyl)phenyl)piperidine-1-carboxamido)methyl)benzoate; 0.263 g, 0.578 mmol) was dissolved in methanol (20 mL), and hydroxylamine hydrochloride (0.201 g, 2.89 mmol) and potassium hydroxide (0.324 g, 5.78 mmol) were added and stirred. Then, hydroxylamine (50 wt % aqueous solution; 1.49 mL, 11.56 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 389 (0.18 g, 68%) in the form of an apricot solid.

$^1$H NMR (400 MHz, DMSO-$d_6$) δ 7.64 (d, 2H, J=8.1 Hz), 7.58 (d, 1H, J=8.7 Hz), 7.43 (d, 1H, J=2.6 Hz), 7.35 (dd, 1H, J=8.8, 2.6 Hz), 7.28 (d, 2H, J=8.1 Hz), 4.87 (s, 2H), 3.71-3.68 (m, 2H), 2.69-2.63 (m, 2H), 1.50-1.44 (m, 2H), 0.87-0.81 (m, 4H); MS (ESI) m/z 456.1 (M$^+$+H).

Example 53: Synthesis of Compound 390

Formula 1-4: methyl 4-((N-(4-chloro-3-(trifluoromethyl)phenyl)-4-methylpiperidine-1-carboxamido)methyl)benzoate

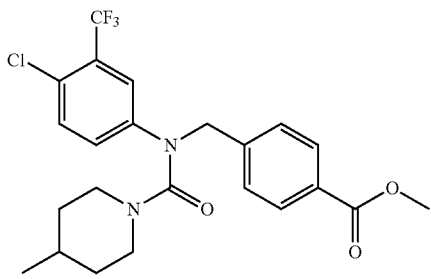 [SMILES: COC(=O)c1ccc(CN(C(=O)N2CCC(C)CC2)c2ccc(Cl)c(C(F)(F)F)c2)cc1]

Compound of Formula 1-3 (methyl 4-(((4-chloro-3-(trifluoromethyl)phenyl)((4-nitrophenoxy)carbonyl)amino)methyl)benzoate; 0.50 g, 0.983 mmol) and 4-methylpiperidine (0.116 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.369 g, 80%) in the form of a white oil.

Compound 390: N-(4-chloro-3-(trifluoromethyl)phenyl)-N-(4-(hydroxycarbamoyl)benzyl)-4-methylpiperidine-1-carboxamide

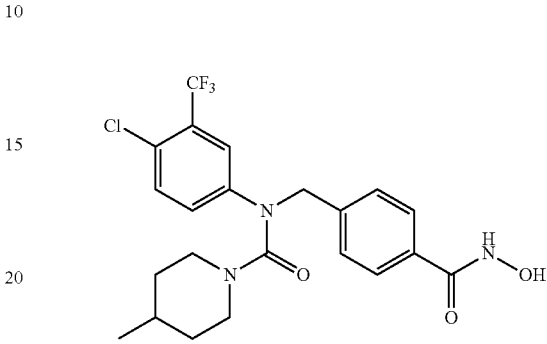

Compound of Formula 1-4 (methyl 4-((N-(4-chloro-3-(trifluoromethyl)phenyl)-4-methylpiperidine-1-carboxamido)methyl)benzoate, 0.239 g, 0.51 mmol) was dissolved in methanol (20 mL), and hydroxylamine hydrochloride (0.177 g, 2.55 mmol) and potassium hydroxide (0.286 g, 5.09 mmol) were added and stirred. Then, hydroxylamine (50 wt % aqueous solution; 1.31 mL, 10.19 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 390 (0.175 g, 73%) in the form of an apricot solid.

$^1$H NMR (400 MHz, DMSO-$d_6$) δ 7.64 (d, 2H, J=8.2 Hz), 7.58 (d, 1H, J=8.8 Hz), 7.44 (d, 1H, J=2.6 Hz), 7.34 (dd, 1H, J=8.8, 2.6 Hz), 7.29 (d, 2H, J=8.2 Hz), 4.88 (s, 2H), 3.18-3.15 (m, 4H), 1.46-1.45 (m, 3H), 1.33-1.32 (m, 5H); MS (ESI) m/z 470.1 (M$^+$+H).

Example 54: Synthesis of Compound 391

Formula 1-4: methyl 4-((N-(4-chloro-3-(trifluoromethyl)phenyl)morpholine-4-carboxamido)methyl)benzoate

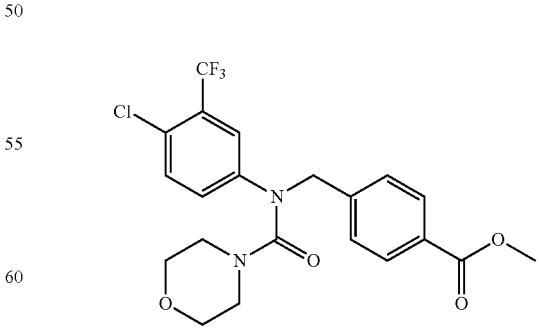

Compound of Formula 1-3 (methyl 4-(((4-chloro-3-(trifluoromethyl)phenyl)((4-nitrophenoxy)carbonyl)amino)methyl)benzoate; 0.50 g, 0.983 mmol) and morpholine (0.086 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.229 g, 51%) in the form of a white oil.

Compound 391: N-(4-chloro-3-(trifluoromethyl) phenyl)-N-(4-(hydroxycarbamoyl)benzyl)morpholine-4-carboxamide

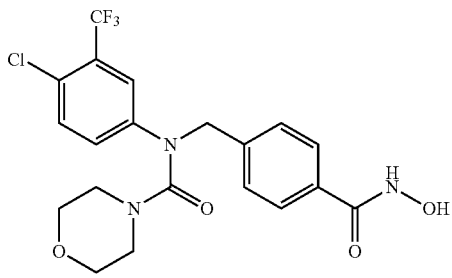 [SMILES: O=C(NO)c1ccc(CN(C(=O)N2CCOCC2)c2ccc(Cl)c(C(F)(F)F)c2)cc1]

Compound of Formula 1-4 (methyl 4-((N-(4-chloro-3-(trifluoromethyl)phenyl)morpholine-4-carboxamido) methyl)benzoate, 0.138 g, 0.302 mmol) was dissolved in methanol (20 mL), and hydroxylamine hydrochloride (0.105 g, 1.51 mmol) and potassium hydroxide (0.169 g, 3.02 mmol) were added and stirred. Then, hydroxylamine (50 wt % aqueous solution; 0.778 mL, 6.04 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 391 (0.089 g, 64%) in the form of an white solid.

$^1$H NMR (400 MHz, DMSO-$d_6$) δ 11.13 (s, 1H), 8.99 (s, 1H), 7.65 (d, 2H, J=8.3 Hz), 7.60 (d, 1H, J=8.7 Hz), 7.54 (d, 1H, J=2.6 Hz), 7.43-7.40 (m, 1H), 7.36 (d, 2H, J=8.2 Hz), 4.94 (s, 2H), 3.44-3.42 (m, 4H), 3.18-3.16 (m, 4H); MS (ESI) m/z 458.1 (M$^+$+H).

Example 55: Synthesis of Compound 392

Formula 1-4: methyl 4-((N-(4-chloro-3-(trifluoromethyl)phenyl)-2,6-dimethylmorpholine-4-carboxamido)methyl)benzoate

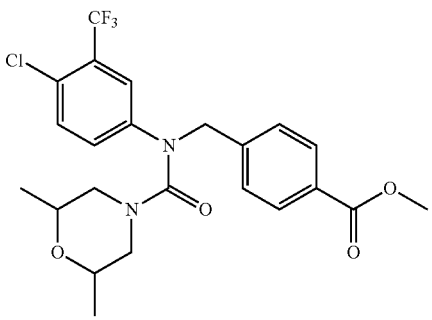 [SMILES: COC(=O)c1ccc(CN(C(=O)N2CC(C)OC(C)C2)c2ccc(Cl)c(C(F)(F)F)c2)cc1]

Compound of Formula 1-3 (methyl 4-(((4-chloro-3-(trifluoromethyl)phenyl)((4-nitrophenoxy)carbonyl)amino) methyl)benzoate; 0.50 g, 0.983 mmol) and 2,6-dimethylmorpholine (0.12 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.2 g, 42%) in the form of a white oil.

Compound 392: N-(4-chloro-3-(trifluoromethyl) phenyl)-N-(4-(hydroxycarbamoyl)benzyl)-2,6-dimethylmorpholine-4-carboxamide

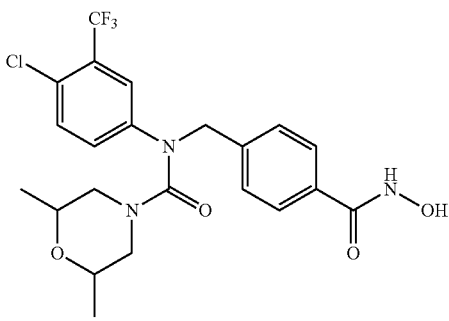 [SMILES: CC1CN(C(=O)N(Cc2ccc(C(=O)NO)cc2)c2ccc(Cl)c(C(F)(F)F)c2)CC(C)O1]

Compound of Formula 1-4 (methyl 4-((N-(4-chloro-3-(trifluoromethyl)phenyl)-2,6-dimethylmorpholine-4-carboxamido)methyl)benzoate, 0.121 g, 0.250 mmol) was dissolved in methanol (20 mL), and hydroxylamine hydrochloride (0.087 g, 1.25 mmol) and potassium hydroxide (0.14 g, 2.49 mmol) were added and stirred. Then, hydroxylamine (50 wt % aqueous solution; 0.643 mL, 4.99 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 392 (0.056 g, 46%) in the form of an white solid.

$^1$H NMR (400 MHz, DMSO-d$_6$) δ 7.64 (d, 2H, J=8.3 Hz), 7.59 (d, 1H, J=8.8 Hz), 7.49 (d, 1H, J=2.6 Hz), 7.39-7.36 (m 1H), 7.30 (d, 2H, J=8.2 Hz), 4.89 (s, 2H), 3.58-3.55 (m, 2H), 2.40-2.32 (m, 4H), 0.96 (d, 6H, J=6.2 Hz); MS (ESI) m/z 486.1 (M$^+$+H).

Example 56: Synthesis of Compound 393

Formula 1-4: methyl 4-((N-(4-chloro-3-(trifluoromethyl)phenyl)-4-methylpiperazine-1-carboxamido)methyl)benzoate

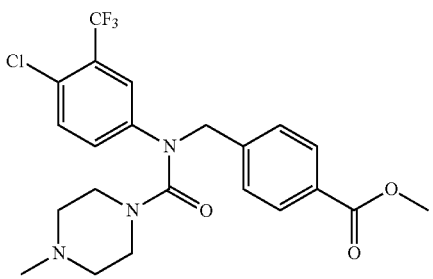 [SMILES: COC(=O)c1ccc(CN(C(=O)N2CCN(C)CC2)c2ccc(Cl)c(C(F)(F)F)c2)cc1]

Compound of Formula 1-3 (methyl 4-(((4-chloro-3-(trifluoromethyl)phenyl)((4-nitrophenoxy)carbonyl)amino)methyl)benzoate; 0.50 g, 0.983 mmol) and 1-methylpiperazine (0.109 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.420 g, 91%) in the form of a yellow oil.

Compound 393: N-(4-chloro-3-(trifluoromethyl)phenyl)-N-(4-(hydroxycarbamoyl)benzyl)-4-methylpiperazine-1-carboxamide

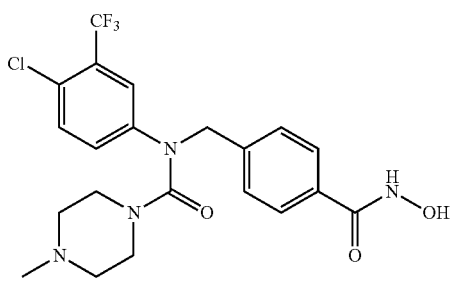

Compound of Formula 1-4 (methyl 4-((N-(4-chloro-3-(trifluoromethyl)phenyl)-4-methylpiperazine-1-carboxamido)methyl)benzoate, 0.251 g, 0.534 mmol) was dissolved in methanol (20 mL), and hydroxylamine hydrochloride (0.185 g, 2.67 mmol) and potassium hydroxide (0.299 g, 5.34 mmol) were added and stirred. Then, hydroxylamine (50 wt % aqueous solution; 1.38 mL, 10.7 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 393 (0.19 g, 75%) in the form of an white solid.

$^1$H NMR (400 MHz, DMSO-d$_6$) δ 11.13 (s, 1H), 8.99 (s, 1H), 7.65 (d, 2H, J=8.1 Hz), 7.60 (d, 1H, J=8.7 Hz), 7.49 (d, 1H, J=2.4 Hz), 7.40-7.35 (m, 3H), 5.75 (s, 1H), 4.92 (s, 2H), 3.17 (m, 4H), 2.14 (m, 4H), 2.10 (s, 3H); MS (ESI) m/z 471.1 (M$^+$+H).

Example 57: Synthesis of Compound 394

Formula 1-4: methyl 4-((N-(4-chloro-3-(trifluoromethyl)phenyl)-4-ethylpiperazine-1-carboxamido)methyl)benzoate

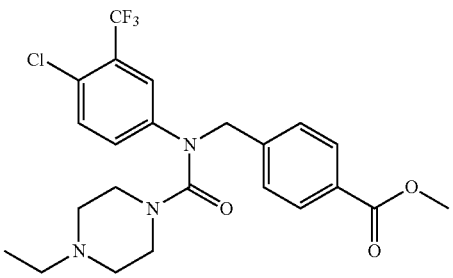 [SMILES: CCN1CCN(C(=O)N(Cc2ccc(C(=O)OC)cc2)c2ccc(Cl)c(C(F)(F)F)c2)CC1]

Compound of Formula 1-3 (methyl 4-(((4-chloro-3-(trifluoromethyl)phenyl)((4-nitrophenoxy)carbonyl)amino)methyl)benzoate; 0.5 g, 0.983 mmol) and 1-ethylpiperazine (0.125 mL, 0.983 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.411 g, 86%) in the form of a yellow oil.

Compound 394: N-(4-chloro-3-(trifluoromethyl)phenyl)-4-ethyl-N-(4-(hydroxycarbamoyl)benzyl)piperazine-1-carboxamide

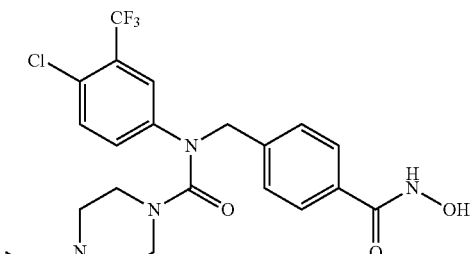

Compound of Formula 1-4 (methyl 4-((N-(4-chloro-3-(trifluoromethyl)phenyl)-4-ethylpiperazine-1-carboxamido)methyl)benzoate, 0.261 g, 0.539 mmol) was dissolved in methanol (20 mL), and hydroxylamine hydrochloride (0.187 g, 2.69 mmol) and potassium hydroxide (0.303 g, 5.39 mmol) were added and stirred. Then, hydroxylamine (50 wt % aqueous solution; 1.39 mL, 10.79 mmol) was added dropwise and stirred at room temperature for 6 hours. After completion of the reaction, the methanol was removed under reduced pressure, saturated sodium hydrogen carbonate aqueous solution was added to precipitate a solid, and the resulting solid was filter and dried to give the desired Compound 394 (0.25 g, 95%) in the form of an pale yellow solid.

$^1$H NMR (400 MHz, DMSO-$d_6$) δ 11.13 (s, 1H), 9.00 (s, 1H), 7.65 (d, 2H, J=8.2 Hz), 7.60 (d, 1H, J=8.8 Hz), 7.49 (d, 1H, J=2.4 Hz), 7.40-7.35 (m, 3H), 5.75 (s, 2H), 4.92 (s, 2H), 3.18 (m, 4H), 2.24 (q, 2H, J=7.2 Hz), 2.19 (m, 4H), 0.93 (t, 3H, J=7.1 Hz); MS (ESI) m/z 485.1 (M$^+$+H).

Example 58: Synthesis of Compound 395

Formula 2-2: methyl 4-((N-(3',5'-difluorobiphenyl-3-yl)morpholine-4-carboxamido)methyl)benzoate

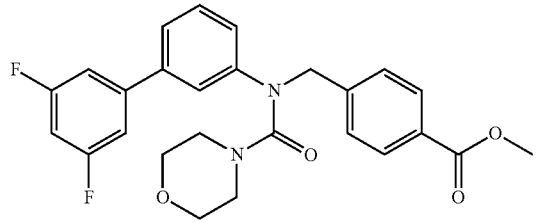 [SMILES: COC(=O)c1ccc(CN(C(=O)N2CCOCC2)c2cccc(-c3cc(F)cc(F)c3)c2)cc1]

Compound of Formula 2-1 (methyl 4-((N-(3-bromophenyl)morpholine-4-carboxamido)methyl)benzoate; 0.200 g, 0.462 mmol), 3,5-difluorophenylboronic acid (0.088 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.180 g, 84%) in the form of a light brown solid.

Compound 395: N-(3',5'-difluorobiphenyl-3-yl)-N-(4-(hydroxycarbamoyl)benzyl)morpholine-4-carboxamide

Compound of Formula 2-2 (methyl 4-((N-(3',5'-difluorobiphenyl-3-yl)morpholine-4-carboxamido)methyl)benzoate; 0.180 g, 0.386 mmol) was dissolved in methanol (10 mL), and hydroxylamine (50.0 wt % aqueous solution; 2.36 mL, 38.6 mmol) and potassium hydroxide (0.217 g, 3.86 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 395 (0.159 g, 88%) in the form of a light brown solid.

$^1$H NMR (400 MHz, DMSO-$d_6$) δ 7.64 (d, 2H, J=8.2 Hz), 7.57 (s, 1H), 7.46-7.36 (m, 6H), 7.23 (m, 1H), 7.15 (m, 1H), 4.96 (s, 2H), 3.40-3.37 (m, 4H), 3.17-3.14 (m, 4H). MS (ESI) m/z 468 (M$^+$+H).

Example 59: Synthesis of Compound 396

Formula 2-2: methyl 4-((N-(3-(6-(dimethylamino)pyridin-3-yl)phenyl)morpholine-4-carboxamido)methyl)benzoate

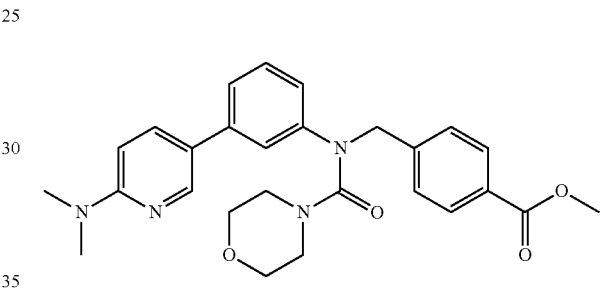

Compound of Formula 2-1 (methyl 4-((N-(3-bromophenyl)morpholine-4-carboxamido)methyl)benzoate; 0.200 g, 0.462 mmol), 6-dimethylaminopyridin-3-ylboronic acid (0.092 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.136 g, 62%) in the form of a light brown solid.

Compound 396: N-(3-(6-(dimethylamino)pyridin-3-yl)phenyl)-N-(4-(hydroxycarbamoyl)benzyl)morpholine-4-carboxamide

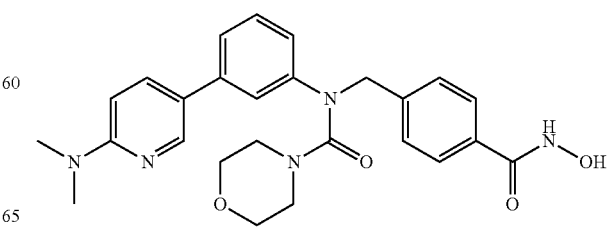

Compound of Formula 2-2 (methyl 4-((N-(3-(6-(dimethylamino)pyridin-3-yl)phenyl)morpholine-4-carboxamido)methyl)benzoate; 0.136 g, 0.287 mmol) was dissolved in methanol (10 mL), and hydroxylamine (50.0 wt % aqueous solution; 1.75 mL, 28.7 mmol) and potassium hydroxide (0.161 g, 2.87 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 396 (0.118 g, 87%) in the form of a light brown solid.

$^1$H NMR (400 MHz, DMSO-$d_6$) δ 8.38 (d, 1H, J=2.5 Hz), 7.78 (m, 1H), 7.64 (d, 2H, J=8.3 Hz), 7.39-7.35 (m, 3H), 7.32-7.29 (m, 2H), 7.05 (m, 1H), 6.69 (d, 1H, J=8.9 Hz), 4.93 (s, 2H), 3.41-3.38 (m, 4H), 3.18-3.15 (m, 4H), 3.05 (s, 6H). MS (ESI) m/z 476 (M$^+$+H).

Example 60: Synthesis of Compound 397

Formula 2-2: methyl 4-((N-(3-(pyrimidin-5-yl)phenyl)morpholine-4-carboxamido)methyl)benzoate

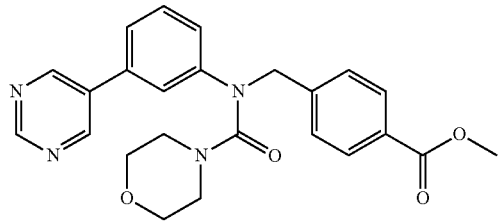

Compound of Formula 2-1 (methyl 4-((N-(3-bromophenyl)morpholine-4-carboxamido)methyl)benzoate; 0.200 g, 0.462 mmol), pyrimidin-5-ylboronic acid (0.069 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=25%) to give the desired compound of Formula 2-2 (0.120 g, 60%) in the form of a yellow solid.

Compound 397: N-(4-(hydroxycarbamoyl)benzyl)-N-(3-(pyrimidin-5-yl)phenyl)morpholine-4-carboxamide

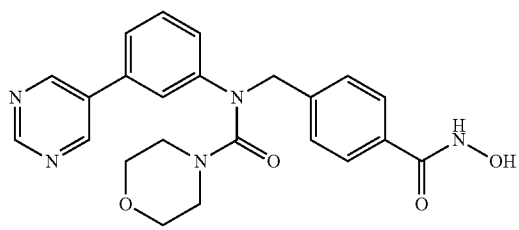

Compound of Formula 2-2 (methyl 4-((N-(3-(pyrimidin-5-yl)phenyl)morpholine-4-carboxamido)methyl)benzoate; 0.120 g, 0.277 mmol) was dissolved in methanol (10 mL), and hydroxylamine (50.0 wt % aqueous solution; 1.70 mL, 27.7 mmol) and potassium hydroxide (0.156 g, 2.78 mmol) were added sequentially and then stirred at room temperature for 30 minutes. After completion of the reaction, the reaction solution was concentrated under reduced pressure until its volume became about 2 mL, and then extracted by ethyl acetate and saturated ammonium chloride aqueous solution. Then, the organic layer was dehydrated with anhydrous magnesium sulfate, and filtered, and the filtrate was then concentrated under reduced pressure to give the desired Compound 397 (0.056 g, 47%) in the form of a brown solid.

$^1$H NMR (400 MHz, DMSO-$d_6$) δ 11.21 (brs, 1H), 9.18 (brs, 1H), 9.13 (s, 2H), 8.97 (s, 1H), 7.66-7.63 (m, 3H), 7.51-7.41 (m, 4H), 7.20 (m, 1H), 4.97 (s, 2H), 3.41-3.37 (m, 4H), 3.19-3.16 (m, 4H). MS (ESI) m/z 434 (M$^+$+H).

Example 61: Synthesis of Compound 398

Formula 2-2: methyl 4-((N-(3',5'-bis(trifluoromethyl)biphenyl-3-yl)morpholine-4-carboxamido)methyl)benzoate

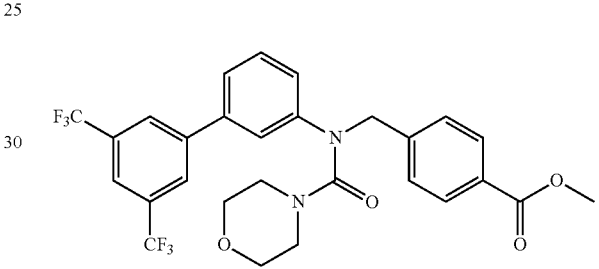

Compound of Formula 2-1 (methyl 4-((N-(3-bromophenyl)morpholine-4-carboxamido)methyl)benzoate; 0.200 g, 0.462 mmol), 3,5-bis(trifluoromethyl)phenylboronic acid (0.143 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=30%) to give the desired compound of Formula 2-2 (0.185 g, 71%) in the form of a white solid.

Compound 398: N-(3',5'-bis(trifluoromethyl)biphenyl-3-yl)-N-(4-(hydroxycarbamoyl)benzyl)morpholine-4-carboxamide

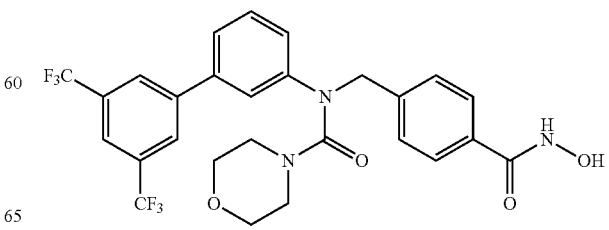

Compound of Formula 2-2 (methyl 4-((N-(3',5'-bis(trifluoromethyl)biphenyl-3-yl)morpholine-4-carboxamido)methyl)benzoate; 0.185 g, 0.327 mmol) was dissolved in methanol (10 mL), and hydroxylamine (50.0 wt % aqueous solution; 2.00 mL, 32.7 mmol) and potassium hydroxide (0.183 g, 3.27 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 398 (0.160 g, 86%) in the form of a white solid.

$^1$H NMR (400 MHz, DMSO-d$_6$) δ 8.31 (s, 2H), 8.09 (s, 1H), 7.74 (s, 1H), 7.64 (d, 2H, J=8.4 Hz), 7.57 (m, 1H), 7.43-7.40 (m, 3H), 7.22 (m, 1H), 4.98 (s, 2H), 3.41-3.38 (m, 4H), 3.19-3.16 (m, 4H). MS (ESI) m/z 568 (M$^+$+H).

Example 62: Synthesis of Compound 399

Formula 2-2: methyl 4-((N-(3-(2,3-dihydrobenzo[b][1,4]dioxin-6-yl)phenyl)morpholine-4-carboxamido)methyl)benzoate

Compound of Formula 2-1 (methyl 4-((N-(3-bromophenyl)morpholine-4-carboxamido)methyl)benzoate; 0.200 g, 0.462 mmol), 2,3-dihydrobenzo[b][1,4]dioxin-6-ylboronic acid (0.100 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.182 g, 81%) in the form of a yellow liquid.

Compound 399: N-(3-(2,3-dihydrobenzo[b][1,4]dioxin-6-yl)phenyl)-N-(4-(hydroxycarbamoyl)benzyl)morpholine-4-carboxamide

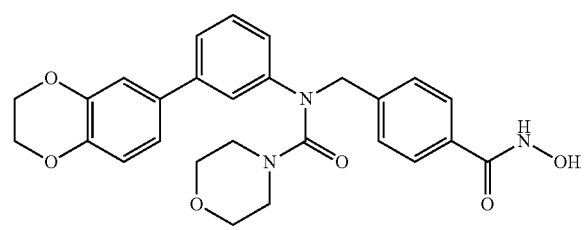 [SMILES: O=C(NO)c1ccc(CN(C(=O)N2CCOCC2)c2cccc(-c3ccc4c(c3)OCCO4)c2)cc1]

Compound of Formula 2-2 (methyl 4-((N-(3-(2,3-dihydrobenzo[b][1,4]dioxin-6-yl)phenyl)morpholine-4-carboxamido)methyl)benzoate; 0.182 g, 0.373 mmol) was dissolved in methanol (10 mL), and hydroxylamine (50.0 wt % aqueous solution; 2.28 mL, 37.3 mmol) and potassium hydroxide (0.209 g, 3.73 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 399 (0.165 g, 91%) in the form of a light brown solid.

$^1$H NMR (400 MHz, DMSO-d$_6$) δ 7.64 (d, 2H, J=8.2 Hz), 7.38 (d, 2H, J=8.2 Hz), 7.34-7.27 (m, 3H), 7.12-7.04 (m, 3H), 6.91 (d, 1H, J=8.3 Hz), 4.92 (s, 2H), 4.26 (s, 4H), 3.40-3.37 (m, 4H), 3.17-3.15 (m, 4H). MS (ESI) m/z 490 (M$^+$+H).

Example 63: Synthesis of Compound 400

Formula 2-2: methyl 4-((N-(3',4',5'-trimethoxybiphenyl-3-yl)morpholine-4-carboxamido)methyl)benzoate

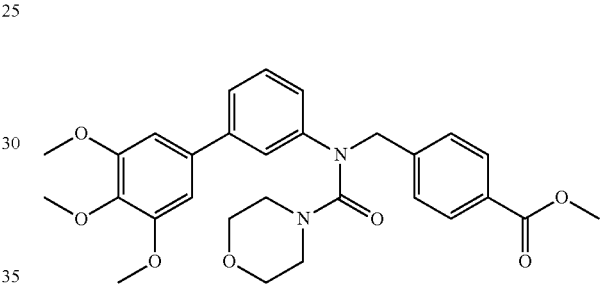

Compound of Formula 2-1 (methyl 4-((N-(3-bromophenyl)morpholine-4-carboxamido)methyl)benzoate; 0.200 g, 0.462 mmol), 3,4,5-trimethoxyphenylboronic acid (0.117 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.146 g, 61%) in the form of a white solid.

Compound 400: N-(4-(hydroxycarbamoyl)benzyl)-N-(3',4',5'-trimethoxybiphenyl-3-yl)morpholine-4-carboxamide

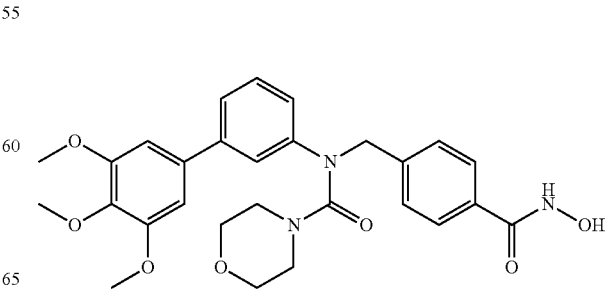

Compound of Formula 2-2 (methyl 4-((N-(3',4',5'-trimethoxybiphenyl-3-yl)morpholine-4-carboxamido)methyl)benzoate; 0.146 g, 0.280 mmol) was dissolved in methanol (10 mL), and hydroxylamine (50.0 wt % aqueous solution; 1.72 mL, 28.1 mmol) and potassium hydroxide (0.157 g, 2.81 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 400 (0.125 g, 86%) in the form of a light brown solid.

$^1$H NMR (400 MHz, DMSO-d$_6$) δ 7.65 (d, 2H, J=8.2 Hz), 7.41-7.39 (m, 3H), 7.37-7.35 (m, 2H), 7.12 (m, 1H), 6.81 (s, 2H), 4.95 (s, 2H), 3.83 (s, 6H), 3.67 (s, 3H), 3.43-3.40 (m, 4H), 3.19-3.16 (m, 4H). MS (ESI) m/z 522 (M$^+$+H).

Example 64: Synthesis of Compound 401

Formula 2-2: methyl 4-((N-(2',6'-dimethylbiphenyl-3-yl)morpholine-4-carboxamido)methyl)benzoate

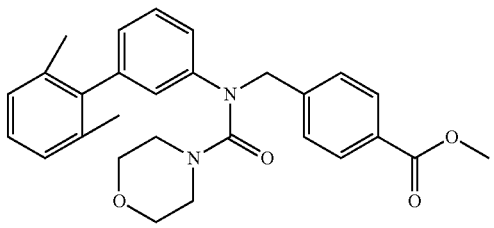 [SMILES: COC(=O)c1ccc(CN(C(=O)N2CCOCC2)c2cccc(-c3c(C)cccc3C)c2)cc1]

Compound of Formula 2-1 (methyl 4-((N-(3-bromophenyl)morpholine-4-carboxamido)methyl)benzoate; 0.200 g, 0.462 mmol), 2,6-dimethylphenylboronic acid (0.083 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.205 g, 97%) in the form of a white solid.

Compound 401

N-(2',6'-dimethylbiphenyl-3-yl)-N-(4-(hydroxycarbamoyl)benzyl)morpholine-4-carboxamide

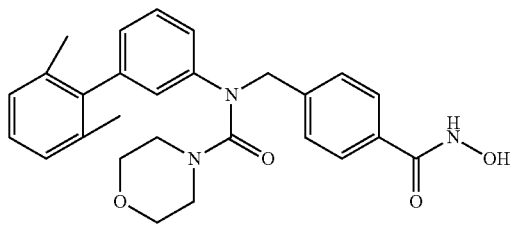 [SMILES: Cc1cccc(C)c1-c1cccc(N(Cc2ccc(C(=O)NO)cc2)C(=O)N2CCOCC2)c1]

Compound of Formula 2-2 (methyl 4-((N-(2',6'-dimethylbiphenyl-3-yl)morpholine-4-carboxamido)methyl)benzoate; 0.205 g, 0.447 mmol) was dissolved in methanol (10 mL), and hydroxylamine (50.0 wt % aqueous solution; 2.74 mL, 44.7 mmol) and potassium hydroxide (0.251 g, 4.47 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 401 (0.195 g, 95%) in the form of a white solid.

$^1$H NMR (400 MHz, DMSO-d$_6$) δ 7.61 (d, 2H, J=8.2 Hz), 7.38 (t, 1H, J=7.8 Hz), 7.33 (d, 2H, J=8.3 Hz), 7.16-7.11 (m, 2H), 7.06 (d, 2H, J=7.4 Hz), 6.81 (d, 1H, J=7.6 Hz), 6.77 (m, 1H), 4.86 (s, 2H), 3.40-3.37 (m, 4H), 3.17-3.14 (m, 4H), 1.83 (s, 6H). MS (ESI) m/z 460 (M$^+$+H).

Example 65: Synthesis of Compound 402

Formula 2-2: methyl 4-((N-(3-(furan-3-yl)phenyl)morpholine-4-carboxamido)methyl)benzoate

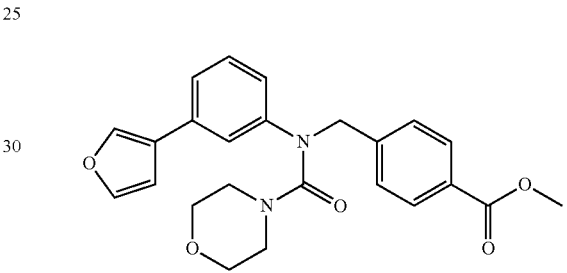

Compound of Formula 2-1 (methyl 4-((N-(3-bromophenyl)morpholine-4-carboxamido)methyl)benzoate; 0.200 g, 0.462 mmol), furan-3-ylboronic acid (0.062 g, 0.554 mmol), and Pd(dppf)Cl$_2$ (0.038 g, 0.046 mmol) were dissolved in 1,4-dioxane (3 mL), and potassium carbonate (0.128 g, 0.923 mmol) dissolved in water (1 mL) was added to the reaction solution and stirred at 100° C. for 4 hours. After completion of the reaction, the organic layer was extracted with ethyl acetate and saturated sodium hydrogen carbonate aqueous solution and concentrated under reduced pressure, and then the residue was purified and concentrated by column chromatography (silica; ethyl acetate/hexane=50%) to give the desired compound of Formula 2-2 (0.113 g, 58%) in the form of a brown solid.

Compound 402: N-(3-(furan-3-yl)phenyl)-N-(4-(hydroxycarbamoyl)benzyl)morpholine-4-carboxamide

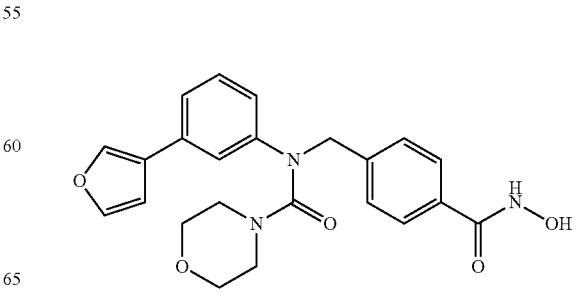

Compound of Formula 2-2 (methyl 4-((N-(3-(furan-3-yl) phenyl)morpholine-4-carboxamido)methyl)benzoate; 0.113 g, 0.269 mmol) was dissolved in methanol (10 mL), and hydroxylamine (50.0 wt % aqueous solution; 1.64 mL, 26.9 mmol) and potassium hydroxide (0.151 g, 2.69 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 402 (0.060 g, 53%) in the form of a brown solid.

$^1$H NMR (400 MHz, DMSO-d$_6$) δ 8.20 (s, 1H), 7.73 (s, 1H), 7.63 (d, 2H, J=8.1 Hz), 7.43 (s, 1H), 7.38 (d, 2H, J=8.1 Hz), 7.30-7.28 (m, 2H), 7.00 (m, 1H), 6.95 (m, 1H), 4.91 (s, 2H), 3.39-3.36 (m, 4H), 3.16-3.13 (m, 4H). MS (ESI) m/z 422 (M$^+$+H).

Example 66: Synthesis of Compound 403

Formula 2-2: methyl 4-((N-(3-(3,6-dihydro-2H-pyran-4-yl)phenyl)morpholine-4-carboxamido) methyl)benzoate

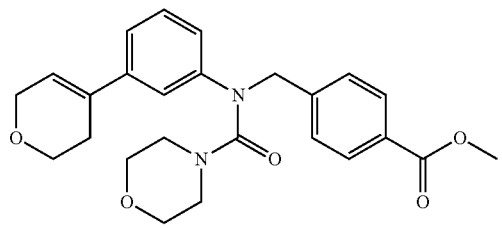 [SMILES: COC(=O)c1ccc(CN(C(=O)N2CCOCC2)c2cccc(C3=CCOCC3)c2)cc1]

Compound of Formula 2-1 (methyl 4-((N-(3-bromophenyl)morpholine-4-carboxamido)methyl)benzoate; 0.400 g, 0.923 mmol), 1,2,3,6-tetrahydropyran-4-boronic acid pinacol ester (0.233 g, 1.11 mmol), and Pd(dppf)Cl$_2$ (0.030 g, 0.046 mmol) were dissolved in 1,4-dioxane (4 mL), and cesium carbonate (0.897 g, 2.77 mmol) dissolved in water (1 mL) was added to the reaction solution and stirred at 140° C. for 15 minutes by using microwave reactor. After completion of the reaction, the organic layer was extracted with ethyl acetate and saturated sodium hydrogen carbonate aqueous solution. Then, the organic layer dehydrated with anhydrous magnesium sulfate and filtered. It was concentrated under reduced pressure, and then the residue was purified and concentrated by column chromatography (silica; ethyl acetate/hexane=50%) to give the desired compound of Formula 2-2 (0.132 g, 33%) in the form of a brown solid.

Compound 403: N-(3-(3,6-dihydro-2H-pyran-4-yl) phenyl)-N-(4-(hydroxycarbamoyl)benzyl)morpholine-4-carboxamide

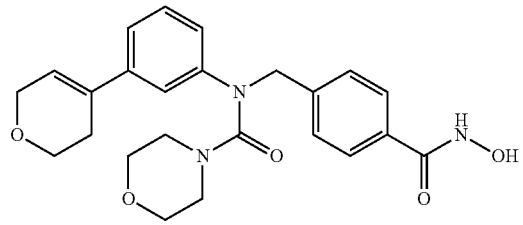 [SMILES: O=C(NO)c1ccc(CN(C(=O)N2CCOCC2)c2cccc(C3=CCOCC3)c2)cc1]

Compound of Formula 2-2 (methyl 4-((N-(3-(3,6-dihydro-2H-pyran-4-yl)phenyl)morpholine-4-carboxamido) methyl)benzoate; 0.050 g, 0.115 mmol) was dissolved in methanol (5 mL), and hydroxylamine (50.0 wt % aqueous solution; 1.40 mL, 22.9 mmol) and potassium hydroxide (0.064 g, 1.15 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 403 (0.030 g, 60%) in the form of a white solid.

$^1$H NMR (400 MHz, DMSO-d$_6$) δ 11.12 (s, 1H), 8.97 (s, 1H), 7.63 (d, 2H, J=8.3 Hz), 7.36 (d, 2H, J=8.3 Hz), 7.27 (t, 1H, J=7.9 Hz), 7.18 (s, 1H), 7.14 (d, 1H, J=7.6 Hz), 7.03 (d, 1H, J=7.8 Hz), 6.23 (m, 1H), 4.88 (s, 2H), 4.19 (d, 2H, J=2.6 Hz), 3.78 (t, 2H, J=5.5 Hz), 3.39-3.36 (m, 4H), 3.14-3.11 (m, 4H), 2.38-2.36 (m, 2H). MS (ESI) m/z 438 (M$^+$+H).

Example 67: Synthesis of Compound 404

Formula 2-2: methyl 4-((N-(3-(1-methyl-1,2,3,6-tetrahydropyridin-4-yl)phenyl)morpholine-4-carboxamido)methyl)benzoate

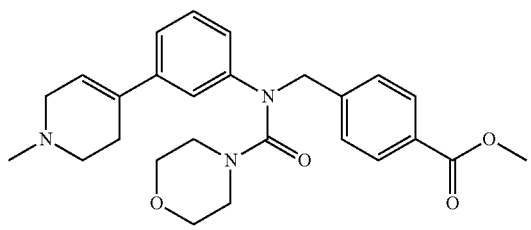

Compound of Formula 2-1 (methyl 4-((N-(3-bromophenyl)morpholine-4-carboxamido)methyl)benzoate; 0.400 g, 0.923 mmol), 1-methyl-1,2,3,6-tetrahydropyridine-4-boronic acid pinacol ester (0.247 g, 1.11 mmol), and Pd(dppf) Cl$_2$ (0.030 g, 0.046 mmol) were dissolved in 1,4-dioxane (4 mL), and cesium carbonate (0.897 g, 2.77 mmol) dissolved in water (1 mL) was added to the reaction solution and stirred at 140° C. for 15 minutes by using microwave reactor. After completion of the reaction, the organic layer was extracted with ethyl acetate and saturated sodium hydrogen carbonate aqueous solution. Then, the organic layer dehydrated with anhydrous magnesium sulfate and filtered. It was concentrated under reduced pressure, and then the residue was purified and concentrated by column chromatography (silica; methanol/dichloromethane=10%) to give the desired compound of Formula 2-2 (0.193 g, 47%) in the form of a brown solid.

Compound 404

N-(4-(hydroxycarbamoyl)benzyl)-N-(3-(1-methyl-1,2,3,6-tetrahydropyridin-4-yl)phenyl) morpholine-4-carboxamide

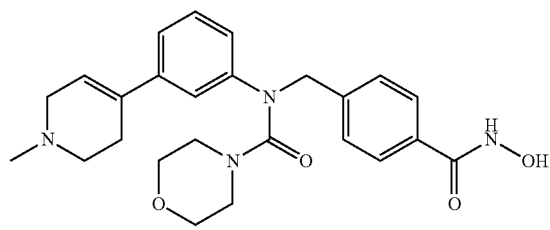 [SMILES: CN1CC=C(c2cccc(N(Cc3ccc(C(=O)NO)cc3)C(=O)N3CCOCC3)c2)CC1]

Compound of Formula 2-2 (methyl 4-((N-(3-(1-methyl-1,2,3,6-tetrahydropyridin-4-yl)phenyl)morpholine-4-carboxamido)methyl)benzoate; 0.050 g, 0.111 mmol) was dissolved in methanol (5 mL), and hydroxylamine (50.0 wt % aqueous solution; 1.36 mL, 22.2 mmol) and potassium hydroxide (0.062 g, 1.11 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 404 (0.015 g, 30%) in the form of a brown solid.

MS (ESI) m/z 451 (M$^+$+H).

Example 68: Synthesis of Compound 405

Formula 2-2: tert-butyl 4-(3-(N-(4-(methoxycarbonyl)benzyl)morpholine-4-carboxamido)phenyl)-5,6-dihydro pyridin-1(2H)-carboxylate

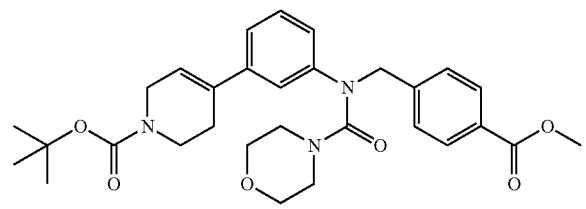 [SMILES: COC(=O)c1ccc(CN(C(=O)N2CCOCC2)c2cccc(C3=CCN(C(=O)OC(C)(C)C)CC3)c2)cc1]

Compound of Formula 2-1 (methyl 4-((N-(3-bromophenyl)morpholine-4-carboxamido)methyl)benzoate; 0.800 g, 1.85 mmol), N-Boc-1,2,3,6-tetrahydropyridin-4-boronic acid pinacol ester (0.685 g, 2.22 mmol), and Pd(dppf)Cl$_2$ (0.060 g, 0.092 mmol) were dissolved in 1,4-dioxane (8 mL), and cesium carbonate (1.79 g, 5.54 mmol) dissolved in water (2 mL) was added to the reaction solution and stirred at 140° C. for 15 minutes by using microwave reactor. After completion of the reaction, the organic layer was extracted with ethyl acetate and saturated sodium hydrogen carbonate aqueous solution. Then, the organic layer dehydrated with anhydrous magnesium sulfate and filtered. It was concentrated under reduced pressure, and then the residue was purified and concentrated by column chromatography (silica; ethyl acetate/hexane=50%) to give the desired compound of Formula 2-2 (0.832 g, 84%) in the form of a brown solid.

Compound 405: tert-butyl 4-(3-(N-(4-(hydroxycarbamoyl)benzyl)morpholine-4-carboxamido)phenyl)-5,6-dihydropyridine-1(2H)-carboxylate

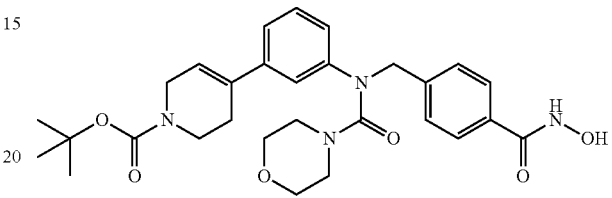

Compound of Formula 2-2 (tert-butyl 4-(3-(N-(4-(methoxycarbonyl)benzyl)morpholine-4-carboxamido)phenyl)-5,6-dihydro pyridin-1(2H)-carboxylate; 0.050 g, 0.093 mmol) was dissolved in methanol (5 mL), and hydroxylamine (50.0 wt % aqueous solution; 1.14 mL, 18.7 mmol) and potassium hydroxide (0.052 g, 0.933 mmol) were added sequentially and then stirred at room temperature for 30 minutes. After completion of the reaction, the reaction solution was concentrated under reduced pressure until its volume became about 1 mL, and then saturated ammonium chloride aqueous solution (1-2 mL) was added and stirred. Then, the solid product was filtered, washed with water, and then vacuum dried to give the desired Compound 405 (0.030 g, 60%) in the form of a white solid.

$^1$H NMR (400 MHz, DMSO-d$_6$) δ 7.63 (d, 2H, J=8.3 Hz), 7.35 (d, 2H, J=8.2 Hz), 7.26 (t, 1H, J=7.9 Hz), 7.18 (s, 1H), 7.12 (d, 1H, J=8.2 Hz), 7.02 (d, 1H, J=8.0 Hz), 6.17 (m, 1H), 4.87 (s, 2H), 3.97 (brs, 2H), 3.50 (t, 2H, J=5.7 Hz), 3.38 (t, 4H, J=4.6 Hz), 3.12 (t, 4H, J=4.5 Hz), 2.40 (brs, 2H), 1.41 (s, 9H). MS (ESI) m/z 537.

Example 69: Synthesis of Compound 413

Formula 1-2: methyl 4-((2,4-difluorophenylamino)methyl)benzoate

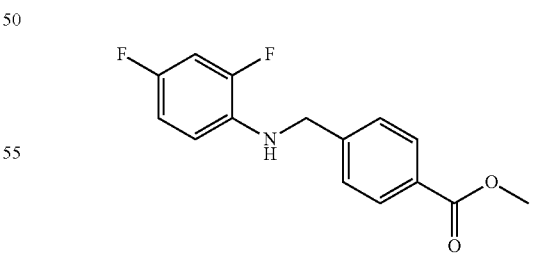

Compound of Formula 1-1 (2,4-difluorobenzenamine; 3.0 g, 23.2 mmol) and methyl 4-formylbenzoate (3.81 g, 23.2 mmol) were dissolved in methanol (500 mL) and stirred at room temperature for 2 hours. Then, acetic acid (1.33 mL, 23.2 mmol) and sodium cyanoborohydride (1.46 g, 23.2 mmol) were added and stirred for 1 day. The methanol was partially removed by air-drying to precipitate a solid, and the resulting solid was filtered and dried to give the desired compound of Formula 1-2 (2.9 g, 45%) in the form of a white solid.

Formula 1-3: methyl 4-(((2,4-difluorophenyl)((4-nitrophenoxy)carbonyl)amino)methyl)benzoate

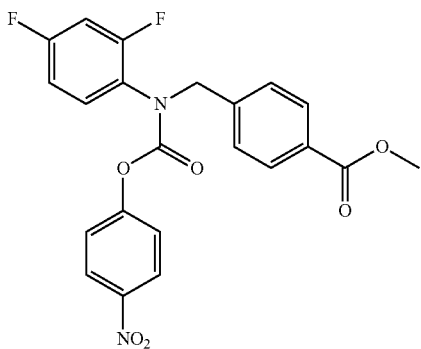 [SMILES: COC(=O)c1ccc(CN(C(=O)Oc2ccc([N+](=O)[O-])cc2)c2ccc(F)cc2F)cc1]

Compound of Formula 1-2 (methyl 4-((2,4-difluorophenylamido)methyl)benzoate; 2 g, 7.21 mmol) and 4-nitrophenyl chloroformate (1.45 g, 7.21 mmol) were dissolved in dichloromethane (50 mL) and stirred at room temperature for 3 days. Then, water was added to extract the organic layer. The organic layer was washed with saturated sodium chloride aqueous solution, dehydrated with anhydrous magnesium sulfate, and then concentrated under reduced pressure. The residue was dried to give the desired compound of Formula 1-3 (2.5 g, 78%) in the form of a yellow oil.

Formula 1-4: methyl 4-((N-(2,4-difluorophenyl)morpholine-4-carboxamido)methyl)benzoate

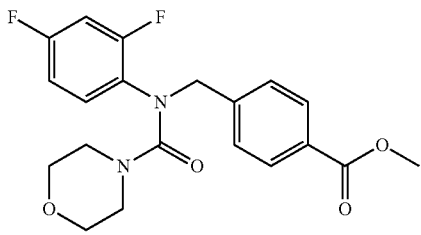 [SMILES: COC(=O)c1ccc(CN(C(=O)N2CCOCC2)c2ccc(F)cc2F)cc1]

Compound of Formula 1-3 (methyl 4-(((2,4-difluorophenyl)((4-nitrophenoxy)carbonyl)amino)methyl)benzoate; 0.50 g, 1.13 mmol) and morpholine (0.098 mL, 1.13 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 1-4 (0.44 g, 98%) in the form of a colorless oil.

Compound 413: N-(2,4-difluorophenyl)-N-(4-(hydroxycarbamoyl)benzyl)morpholine-4-carboxamide

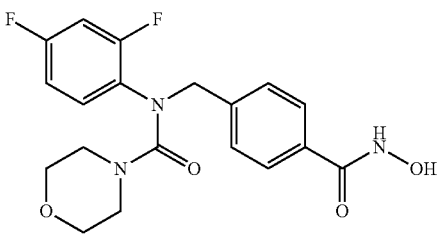

Compound of Formula 1-4 (methyl 4-((N-(2,4-difluorophenyl)morpholine-4-carboxamido)methyl)benzoate; 0.10 g, 0.256 mmol) was dissolved in methanol (20 mL), and hydroxylamine hydrochloride (0.089 g, 1.28 mmol) and potassium hydroxide (0.144 g, 2.56 mmol) were added and stirred. Then, hydroxylamine (50 wt % aqueous solution; 0.329 mL, 5.12 mmol) was added dropwise and stirred at room temperature for 3 hours. After completion of the reaction, the methanol was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. Then, the residue was dissolved in dichloromethane and hexane was added to precipitate a solid, and the resulting solid was filtered and dried to give the desired Compound 413 (0.076 g, 76%) in the form of a pale yellow solid.

$^1$H NMR (400 MHz, MeOD-$d_3$) δ 7.65 (d, 2H, J=8.3 Hz), 7.41 (d, 2H, J=8.2 Hz), 7.27-7.25 (m, 1H), 7.04-6.96 (m, 2H), 4.80 (s, 2H), 3.46-3.43 (m, 4H), 3.22-3.19 (m, 4H); MS (ESI) m/z 392.1 (M$^+$+H).

Example 70: Synthesis of Compound 414

Formula 1-4: methyl 4-((N-(2,4-difluorophenyl)piperidine-1-carboxamido)methyl)benzoate

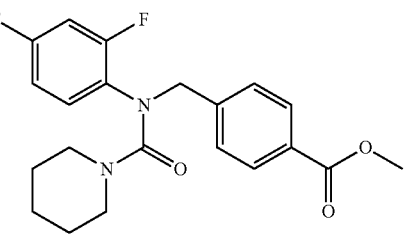

Compound of Formula 1-3 (methyl 4-(((2,4-difluorophenyl)((4-nitrophenoxy)carbonyl)amino)methyl)benzoate; 0.50 g, 1.13 mmol) and piperidine (0.112 mL, 1.13 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10%) to give the desired compound of Formula 1-4 (0.46 g, 104.8%) in the form of a colorless oil.

Compound 414: N-(2,4-difluorophenyl)-N-(4-(hydroxycarbamoyl)benzyl)piperidine-1-carboxamide

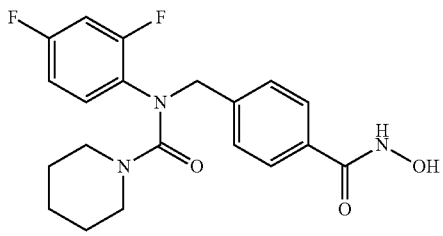

Compound of Formula 1-4 (methyl 4-((N-(2,4-difluorophenyl)piperidine-1-carboxamido)methyl)benzoate; 0.15 g, 0.386 mmol) was dissolved in methanol (20 mL), and hydroxylamine hydrochloride (0.134 g, 1.93 mmol) and potassium hydroxide (0.217 g, 3.86 mmol) were added and stirred. Then, hydroxylamine (50 wt % aqueous solution; 0.496 mL, 7.72 mmol) was added dropwise and stirred at room temperature for 3 hours. After completion of the reaction, the methanol was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. Then, the residue was dissolved in dichloromethane and hexane was added to precipitate a solid, and the resulting solid was filtered and dried to give the desired Compound 414 (0.118 g, 79%) in the form of a pale yellow solid.

$^1$H NMR (400 MHz, MeOD-d$_3$) δ 7.65 (d, 2H, J=8.2 Hz), 7.41 (d, 2H, J=8.1 Hz), 7.23-7.20 (m, 1H), 7.05-6.94 (m, 2H), 4.77 (s, 2H), 3.21-3.18 (m, 4H), 1.51-1.49 (m, 2H), 1.32-1.31 (m, 4H); MS (ESI) m/z 390.1 (M$^+$+H).

Example 71: Synthesis of Compound 415

Formula 1-4: methyl 4-((N-(2,4-difluorophenyl)2,6-dimethylmorpholine-4-carboxamido)methyl)benzoate

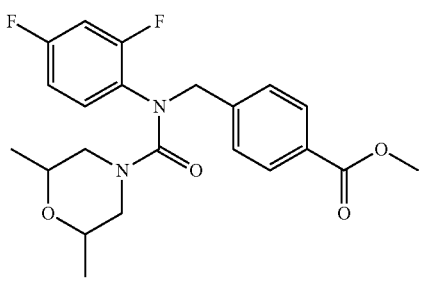 [SMILES: COC(=O)c1ccc(CN(C(=O)N2CC(C)OC(C)C2)c2ccc(F)cc2F)cc1]

Compound of Formula 1-3 (methyl 4-(((2,4-difluorophenyl)((4-nitrophenoxy)carbonyl)amino)methyl)benzoate; 0.50 g, 1.13 mmol) and 2,6-dimethylmorpholine (0.138 mL, 1.13 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 1-4 (0.40 g, 85%) in the form of a colorless oil.

Compound 415: N-(2,4-difluorophenyl)-N-(4-(hydroxycarbamoyl)benzyl)-2,6-dimethylmorpholine-4-carboxamide

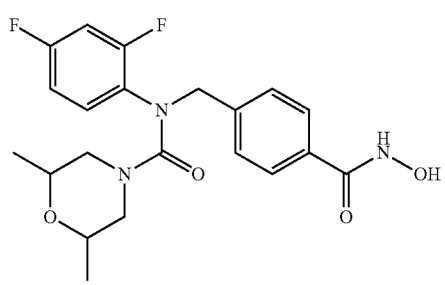 [SMILES: CC1CN(C(=O)N(Cc2ccc(C(=O)NO)cc2)c2ccc(F)cc2F)CC(C)O1]

Compound of Formula 1-4 (methyl 4-((N-(2,4-difluorophenyl)2,6-dimethylmorpholine-4-carboxamido)methyl) benzoate; 0.20 g, 0.478 mmol) was dissolved in methanol (20 mL), and hydroxylamine hydrochloride (0.166 g, 2.39 mmol) and potassium hydroxide (0.268 g, 4.78 mmol) were added and stirred. Then, hydroxylamine (50 wt % aqueous solution; 0.614 mL, 9.56 mmol) was added dropwise and stirred at room temperature for 3 hours. After completion of the reaction, the methanol was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. Then, the residue was dissolved in dichloromethane and hexane was added to precipitate a solid, and the resulting solid was filtered and dried to give the desired Compound 415 (0.086 g, 43%) in the form of a pale yellow solid.

$^1$H NMR (400 MHz, MeOD-d$_3$) δ 7.65 (d, 2H, J=8.0 Hz), 7.41 (d, 2H, J=8.0 Hz), 7.27-7.26 (m, 1H), 7.04-6.94 (m, 2H), 4.79 (s, 2H), 3.58 (d, 2H, J=12.9 Hz), 2.38-2.32 (m, 2H), 1.01 (d, 6H, J=6.2 Hz); MS (ESI) m/z 420.1 (M$^+$+H).

Example 72: Synthesis of Compound 416

Formula 1-4: methyl 4-((N-(2,4-difluorophenyl)-4-methylpiperazine-1-carboxamido)methyl)benzoate

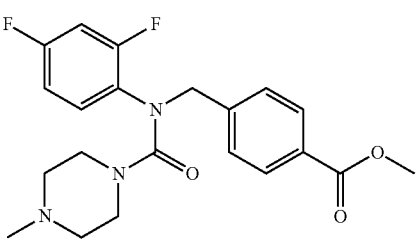 [SMILES: COC(=O)c1ccc(CN(C(=O)N2CCN(C)CC2)c2ccc(F)cc2F)cc1]

Compound of Formula 1-3 (methyl 4-(((2,4-difluorophenyl)((4-nitrophenoxy)carbonyl)amino)methyl)benzoate; 0.50 g, 1.13 mmol) and 1-methylpiperazine (0.126 mL, 1.13 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.46 g, 101%) in the form of a yellow oil.

Compound 416: N-(2,4-difluorophenyl)-N-(4-(hydroxycarbamoyl)benzyl)-4-methylpiperazine-1-carboxamide

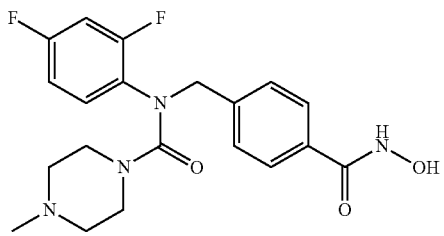 [SMILES: CN1CCN(C(=O)N(Cc2ccc(C(=O)NO)cc2)c2ccc(F)cc2F)CC1]

Compound of Formula 1-4 (methyl 4-((N-(2,4-difluorophenyl)-4-methylpiperazine-1-carboxamido)methyl)benzoate; 0.22 g, 0.545 mmol) was dissolved in methanol (20 mL), and hydroxylamine hydrochloride (0.189 g, 2.73 mmol) and potassium hydroxide (0.306 g, 5.45 mmol) were added and stirred. Then, hydroxylamine (50 wt % aqueous solution; 0.701 mL, 10.9 mmol) was added dropwise and stirred at room temperature for 3 hours. After completion of the reaction, the methanol was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. Then, the residue was dissolved in dichloromethane and hexane was added to precipitate a solid, and the resulting solid was filtered and dried to give the desired Compound 416 (0.154 g, 70%) in the form of a yellow solid.

$^1$H NMR (400 MHz, MeOD-d$_3$) δ 7.65 (d, 2H, J=8.2 Hz), 7.40 (d, 2H, J=8.2 Hz), 7.26-7.25 (m, 1H), 7.04-6.96 (m, 2H), 4.79 (s, 2H), 3.25-3.23 (m, 4H), 2.24-2.21 (m, 7H); MS (ESI) m/z 405.1 (M$^+$+H).

Example 73: Synthesis of Compound 418

Formula 2-2: methyl 4-((N-(3-(benzo[d][1,3]dioxol-5-yl)phenyl)morpholine-4-carboxamido)methyl)benzoate

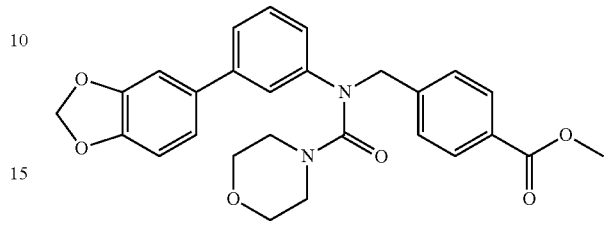

Compound of Formula 2-1 (methyl 4-((N-(3-bromophenyl)morpholine-4-carboxamido)methyl)benzoate; 0.200 g, 0.462 mmol), benzo[d][1,3]dioxol-5-ylboronic acid (0.092 g, 0.554 mmol), and Pd(dppf)Cl$_2$ (0.015 g, 0.023 mmol) were dissolved in 1,4-dioxane (4 mL), and cesium carbonate (0.448 g, 1.39 mmol) dissolved in water (1 mL) was added to the reaction solution and stirred at 140° C. for 15 minutes by using microwave reactor. After completion of the reaction, the organic layer was extracted with ethyl acetate and saturated sodium hydrogen carbonate aqueous solution. Then, the organic layer dehydrated with anhydrous magnesium sulfate and filtered. It was concentrated under reduced pressure, and then the residue was purified and concentrated by column chromatography (silica; ethyl acetate/hexane=30%) to give the desired compound of Formula 2-2 (0.146 g, 67%) in the form of a light brown solid.

Compound 418: N-(3-(benzo[d][1,3]dioxol-5-yl)phenyl)-N-(4-(hydroxycarbamoyl)benzyl)morpholine-4-carboxamide

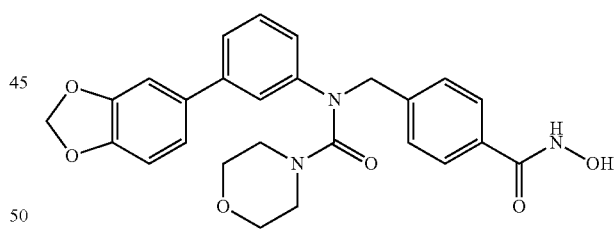

Compound of Formula 2-2 (methyl 4-((N-(3-(benzo[d][1,3]dioxol-5-yl)phenyl)morpholine-4-carboxamido)methyl)benzoate; 0.146 g, 0.308 mmol) was dissolved in methanol (10 mL), and hydroxylamine (50.0 wt % aqueous solution; 1.88 mL, 30.8 mmol) and potassium hydroxide (0.173 g, 3.08 mmol) were added sequentially and then stirred at room temperature for 30 minutes. After completion of the reaction, the reaction solution was concentrated under reduced pressure until its volume became about 2 mL, and then extracted with ethyl acetate and saturated ammonium chloride aqueous solution. Then, the organic layer was washed with water and dehydrated with anhydrous magnesium sulfate. It was filtered and concentrated under reduced pressure to give the desired Compound 418 (0.121 g, 83%) in the form of a light brown solid.

$^1$H NMR (400 MHz, DMSO-d$_6$) δ 7.63 (d, 2H, J=8.2 Hz), 7.34-7.27 (m, 5H), 7.21 (d, 1H, J=1.7 Hz), 7.09 (dd, 1H, J=8.1, 1.8 Hz), 7.05 (d, 1H, J=7.7 Hz), 6.97 (d, 1H, J=8.1 Hz), 6.05 (s, 2H), 4.90 (s, 2H), 3.39 (t, 4H, J=4.5 Hz), 3.16 (t, 4H, J=4.4 Hz). MS (ESI) m/z 476 (M$^+$+H).

Example 74: Synthesis of Compound 419

Formula 4-2: methyl 4-((N-(3-(1,2,3,6-tetrahydro-pyridin-4-yl)phenyl)morpholine-4-carboxamido)methyl)benzoate hydrochloride

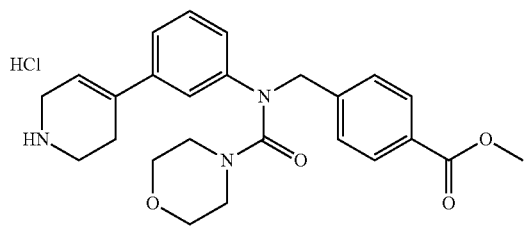 [SMILES: Cl ; COC(=O)c1ccc(CN(C(=O)N2CCOCC2)c2cccc(C3=CCNCC3)c2)cc1]

Compound of Formula 4-1 (tert-butyl 4-(3-(N-(4-(methoxycarbonyl)benzyl)morpholine-4-carboxamido)phenyl)-5,6-dihydro pyridine-1(2H)-carboxylate; 0.510 g, 0.952 mmol) was dissolved in 1,4-dioxane (5 mL), and then hydrogen chloride (4.0 M 1,4-dioxane solution; 4.76 mL, 19.0 mmol) was added and stirred at room temperature for 3 hours. After completion of the reaction, the organic layer was concentrated under reduced pressure, and the residue was recrystallized with dichloromethane and hexane to give the desired compound of Formula 4-2 (0.440 g, 98%) in the form of a brown solid.

Formula 4-3: methyl 4-((N-(3-(1-acetyl-1,2,3,6-tetrahydropyridin-4-yl)phenyl)morpholine-4-carboxamido)methyl)benzoate

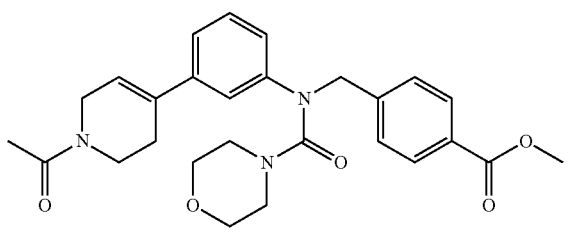 [SMILES: COC(=O)c1ccc(CN(C(=O)N2CCOCC2)c2cccc(C3=CCN(C(C)=O)CC3)c2)cc1]

Compound of Formula 4-2 (methyl 4-((N-(3-(1,2,3,6-tetrahydropyridin-4-yl)phenyl)morpholine-4-carboxamido)methyl)benzoate hydrochloride; 0.140 g, 0.297 mmol) was suspended in dichloromethane (5 mL), and then N,N-diisopropylethylamine (0.158 mL, 0.890 mmol) and acetic acid anhydride (0.036 g, 0.356 mmol) were added sequentially and then stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=25%) to give the desired compound of Formula 4-3 (0.103 g, 73%) in the form of a white solid.

Compound 419: N-(3-(1-acetyl-1,2,3,6-tetrahydro-pyridin-4-yl)phenyl)-N-(4-(hydroxycarbamoyl)benzyl) morpholine-4-carboxamide

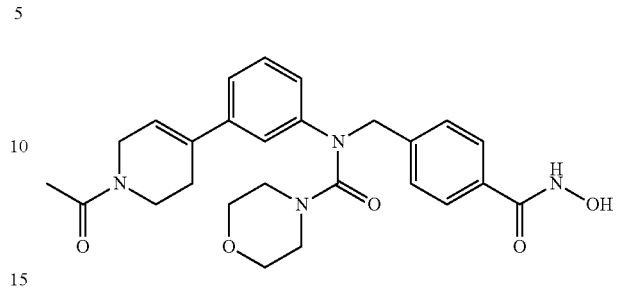

Compound of Formula 4-3 (methyl 4-((N-(3-(1-acetyl-1,2,3,6-tetrahydropyridin-4-yl)phenyl)morpholine-4-carboxamido)methyl)benzoate; 0.103 g, 0.216 mmol) was dissolved in methanol (10 mL), and then hydroxylamine (50.0 wt % aqueous solution; 1.32 mL, 21.6 mmol) and potassium hydroxide (0.121 g, 2.16 mmol) were added sequentially and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was washed with water, dehydrated with anhydrous magnesium sulfate, filtered, and then concentrated under reduced pressure to give the desired Compound 419 (0.043 g, 42%) in the form of a white solid.

$^1$H NMR (400 MHz, DMSO-d$_6$) δ 11.13 (s, 1H), 8.98 (s, 1H), 7.63 (d, 2H, J=8.2 Hz), 7.36 (d, 2H, J=8.2 Hz), 7.27 (t, 1H, J=7.9 Hz), 7.18-7.12 (m, 2H), 7.03 (d, 1H, J=8.4 Hz), 6.16 (m, 1H), 4.87 (s, 2H), 4.12-4.06 (m, 2H), 3.63-3.58 (m, 2H), 3.39 (t, 4H, J=4.5 Hz), 3.12 (t, 4H, J=4.4 Hz), 2.38 (brs, 2H), 2.07 (d, 3H, J=9.0 Hz). MS (ESI) m/z 479 (M$^+$+H).

Example 75: Synthesis of Compound 420

Formula 4-3: methyl 4-((N-(3-(1-(methylsulfonyl)-1,2,3,6-tetrahydropyridin-4-yl)phenyl)morpholine-4-carboxamido)methyl)benzoate

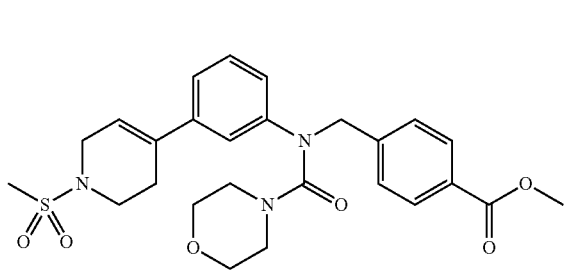

Compound of Formula 4-2 (methyl 4-((N-(3-(1-(methylsulfonyl)-1,2,3,6-tetrahydropyridin-4-yl)phenyl)morpholine-4-carboxamido)methyl)benzoate hydrochloride; 0.140 g, 0.297 mmol) was suspended in dichloromethane (5 mL), and then N,N-diisopropylethylamine (0.158 mL, 0.890 mmol) and methylsulfonyl chloride (0.040 g, 0.356 mmol) were added sequentially and then stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=70%) to give the desired compound of Formula 4-3 (0.114 g, 75%) in the form of a white solid.

Compound 420: N-(4-(hydroxycarbamoyl)benzyl)-N-(3-(1-(methylsulfonyl)-1,2,3,6-tetrahydropyridin-4-yl)phenyl)morpholine-4-carboxamide

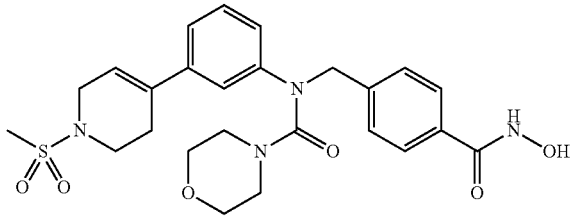 [SMILES: CS(=O)(=O)N1CC=C(c2cccc(N(Cc3ccc(C(=O)NO)cc3)C(=O)N3CCOCC3)c2)CC1]

Compound of Formula 4-3 (methyl 4-((N-(3-(1-(methylsulfonyl)-1,2,36-tetrahydropyridin-4-yl)phenyl)morpholine-4-carboxamido)methyl)benzoate; 0.114 g, 0.222 mmol) was dissolved in methanol (10 mL), and then hydroxylamine (50.0 wt % aqueous solution; 1.36 mL, 22.2 mmol) and potassium hydroxide (0.125 g, 2.22 mmol) were added sequentially and then stirred at room temperature for 30 minutes. After completion of the reaction, the reaction solution was concentrated under reduced pressure until its volume became about 2 mL, and the organic layer was extracted with ethyl acetate and saturated ammonium chloride aqueous solution. The organic layer was washed with water, dehydrated with anhydrous magnesium sulfate, filtered, and then concentrated under reduced pressure to give the desired Compound 420 (0.038 g, 33%) in the form of a light brown solid.

$^1$H NMR (400 MHz, DMSO-d$_6$) δ 7.63 (d, 2H, J=8.0 Hz), 7.34 (d, 2H, J=7.9 Hz), 7.27 (t, 1H, J=7.8 Hz), 7.20 (s, 1H), 7.14 (d, 1H, J=8.3 Hz), 7.04 (d, 1H, J=7.0 Hz), 6.19 (s, 1H), 4.85 (s, 2H), 3.83 (d, 2H, J=2.2 Hz), 3.39-3.35 (m, 6H), 3.14-3.11 (m, 4H), 2.92 (s, 3H), 2.54 (m, 2H). MS (ESI) m/z 515 (M$^+$+H).

Example 76: Synthesis of Compound 438

Formula 1-2: methyl 4-((2-fluoro-4-methylphenylamino)methyl)benzoate

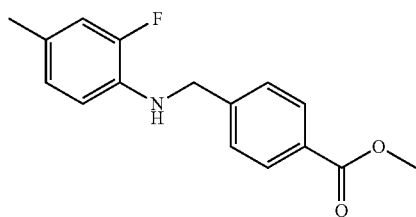

Compound of Formula 1-1 (2-fluoro-4-methylbenzenamine; 3.0 g, 23.9 mmol) and methyl 4-formylbenzoate (3.94 g, 23.9 mmol) were dissolved in methanol (500 mL) and stirred at room temperature for 2 hours. Then, acetic acid (1.44 mL, 23.9 mmol) and sodium cyanoborohydride (1.51 g, 23.9 mmol) were added and stirred for 1 day. The methanol was partially removed by air-drying to precipitate a solid, and the resulting solid was filtered and dried to give the desired compound of Formula 1-2 (4.2 g, 64%) in the form of a white solid.

Formula 1-3: methyl 4-(((2-fluoro-4-methylphenyl)((4-nitrophenoxy)carbonyl)amino)methyl)benzoate

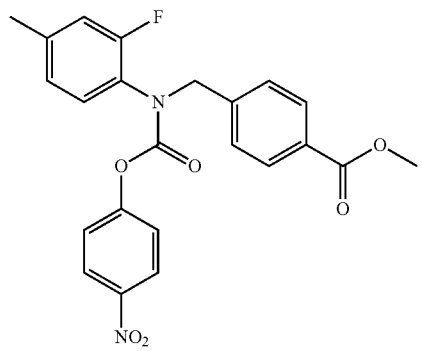

Compound of Formula 1-2 (methyl 4-((2-fluoro-4-methylphenylamino)methyl)benzoate; 2 g, 7.32 mmol) and 4-nitrophenyl chloroformate (1.48 g, 7.32 mmol) were dissolved in dichloromethane (50 mL) and stirred at room temperature for 3 days, and then the organic layer was extracted with water. The organic layer was washed with saturated sodium chloride aqueous solution, dehydrated with anhydrous magnesium sulfate, and then concentrated under reduced pressure. The residue was dried to give the desired compound of Formula 1-3 (2.5 g, 78%) in the form of a yellow solid.

Formula 1-4: methyl 4-((N-(2-fluoro-4-methylphenyl)piperidine-1-carboxamido)methyl)benzoate

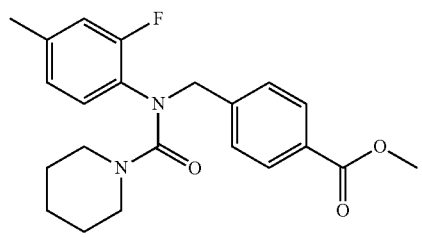

Compound of Formula 1-3 (methyl 4-(((2-fluoro-4-methylphenyl)((4-nitrophenoxy)carbonyl)amino)methyl)benzoate; 0.50 g, 1.14 mmol) and piperidine (0.113 mL, 1.14 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10%) to give the desired compound of Formula 1-4 (0.56 g, 127%) in the form of a white oil.

Compound 438: N-(2-fluoro-4-methylphenyl)-N-(4-(hydroxycarbamoyl)benzyl)piperidine-1-carboxamide

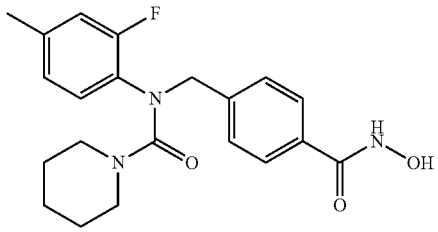 [SMILES: Cc1ccc(N(Cc2ccc(C(=O)NO)cc2)C(=O)N2CCCCC2)c(F)c1]

Compound of Formula 1-4 (methyl 4-((N-(2-fluoro-4-methylphenyl)piperidine-1-carboxamido)methyl)benzoate; 0.281 g, 0.731 mmol) was dissolved in methanol (20 mL), and hydroxylamine hydrochloride (0.254 g, 3.66 mmol) and potassium hydroxide (0.41 g, 7.31 mmol) were added and stirred. Then, hydroxylamine (50 wt % aqueous solution; 0.94 mL, 14.6 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 438 (0.23 g, 82%) in the form of a yellow solid.

$^1$H NMR (400 MHz, DMSO-$d_6$) δ 7.61 (d, 2H, J=8.2 Hz), 7.34 (d, 2H, J=8.2 Hz), 7.13-7.08 (m, 1H), 7.03 (d, 1H, J=11.6 Hz), 6.94 (d, 1H, J=8.2 Hz), 4.68 (s, 2H), 3.09-3.06 (m, 4H), 2.24 (s, 3H), 1.39 (m, 2H), 1.19 (m, 4H); MS (ESI) m/z 386.1 (M$^+$+H).

Example 77: Synthesis of Compound 439

Formula 1-4: methyl 4-((N-(2-fluoro-4-methylphenyl)morpholine-4-carboxamido)methyl)benzoate

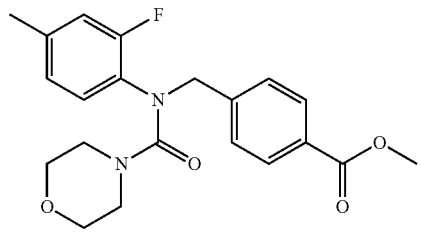

Compound of Formula 1-3 (methyl 4-(((2-fluoro-4-methylphenyl)((4-nitrophenoxy)carbonyl)amino)methyl)benzoate; 0.50 g, 1.14 mmol) and morpholine (0.099 mL, 1.14 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.50 g, 114%) in the form of a white oil.

Compound 439: N-(2-fluoro-4-methylphenyl)-N-(4-(hydroxycarbamoyl)benzyl)morpholine-4-carboxamide

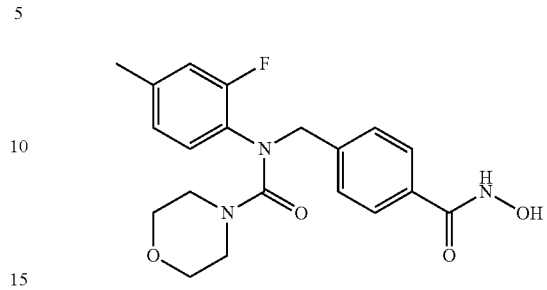

Compound of Formula 1-4 (methyl 4-((N-(2-fluoro-4-methylphenyl)morpholine-4-carboxamido)methyl)benzoate; 0.213 g, 0.551 mmol) was dissolved in methanol (20 mL), and hydroxylamine hydrochloride (0.191 g, 2.76 mmol) and potassium hydroxide (0.309 g, 5.51 mmol) were added and stirred. Then, hydroxylamine (50 wt % aqueous solution; 0.709 mL, 11.0 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 439 (0.175 g, 82%) in the form of a white solid.

$^1$H NMR (400 MHz, DMSO-$d_6$) δ 11.14 (s, 1H), 9.01 (s, 1H), 7.62 (d, 2H, J=8.2 Hz), 7.33 (d, 2H, J=8.2 Hz), 7.17-7.13 (m, 1H), 7.05 (d, 1H, J=11.6 Hz), 6.96 (d, 1H, J=8.2 Hz), 4.72 (s, 2H), 3.33-3.29 (m, 4H), 3.09-3.06 (m, 4H), 3.42 (s, 3H); MS (ESI) m/z 388.2 (M$^+$+H).

Example 78: Synthesis of Compound 440

Formula 1-4: methyl 4-((N-(2-fluoro-4-methylphenyl)2,6-dimethylmorpholine-4-carboxamido)methyl)benzoate

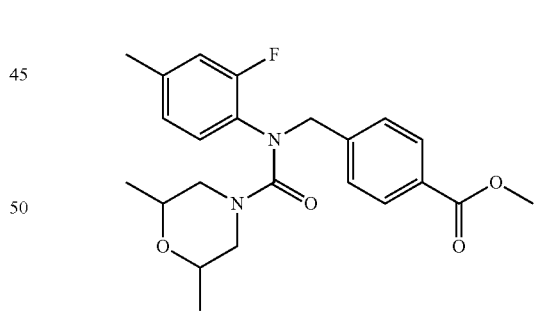

Compound of Formula 1-3 (methyl 4-(((2-fluoro-4-methylphenyl)((4-nitrophenoxy)carbonyl)amino)methyl)benzoate; 0.50 g, 1.14 mmol) and 2,6-dimethylmorpholine (0.14 mL, 1.14 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.27 g, 57%) in the form of a white oil.

Compound 440: N-(2-fluoro-4-methylphenyl)-N-(4-(hydroxycarbamoyl)benzyl)-2,6-dimethylmorpholine-4-carboxamide

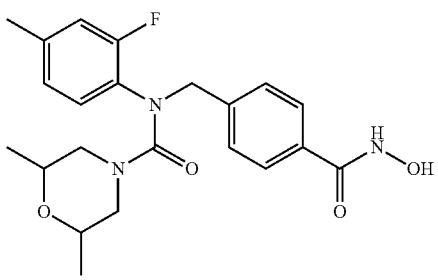 [SMILES: Cc1ccc(N(Cc2ccc(C(=O)NO)cc2)C(=O)N2CC(C)OC(C)C2)c(F)c1]

Compound of Formula 1-4 (methyl 4-((N-(2-fluoro-4-methylphenyl)-2,6-dimethylmorpholine-4-carboxamido) methyl)benzoate; 0.104 g, 0.251 mmol) was dissolved in methanol (20 mL), and hydroxylamine hydrochloride (0.087 g, 1.26 mmol) and potassium hydroxide (0.141 g, 2.51 mmol) were added and stirred. Then, hydroxylamine (50 wt % aqueous solution; 0.323 mL, 5.02 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 440 (0.086 g, 83%) in the form of a white solid.

$^1$H NMR (400 MHz, DMSO-$d_6$) δ 7.60 (d, 2H, J=7.8 Hz), 7.27 (d, 2H, J=6.7 Hz), 7.14-7.12 (m, 1H), 7.03 (d, 1H, J=11.8 Hz), 6.94 (d, 1H, J=8.0 Hz), 4.68 (s, 2H), 3.49 (d, 2H, J=12.7 Hz), 3.19-3.17 (m, 2H), 2.27-2.21 (m, 2H), 0.90 (d, 6H, J=6.1 Hz); MS (ESI) m/z 416.2 (M$^+$+H).

Example 79: Synthesis of Compound 441

Formula 1-4: methyl 4-((N-(2-fluoro-4-methylphenyl)4-methylpiperazine-1-carboxamido)methyl)benzoate

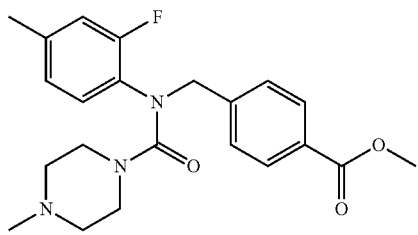

Compound of Formula 1-3 (methyl 4-(((2-fluoro-4-methylphenyl)((4-nitrophenoxy)carbonyl)amino)methyl)benzoate; 0.50 g, 1.14 mmol) and 1-methylpiperazine (0.127 mL, 1.14 mmol) were dissolved in dimethylformamide (10 mL), and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=5%) to give the desired compound of Formula 1-4 (0.43 g, 94%) in the form of a yellow oil.

Compound 441: N-(2-fluoro-4-methylphenyl)-N-(4-(hydroxycarbamoyl)benzyl)-4-methylpiperazine-1-carboxamide

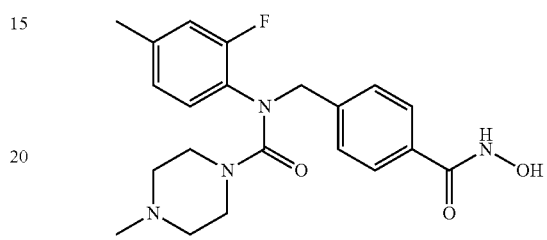

Compound of Formula 1-4 (methyl 4-((N-(2-fluoro-4-methylphenyl)4-methylpiperazine-1-carboxamido)methyl) benzoate; 0.095 g, 0.238 mmol) was dissolved in methanol (20 mL), and hydroxylamine hydrochloride (0.083 g, 1.19 mmol) and potassium hydroxide (0.133 g, 2.38 mmol) were added and stirred. Then, hydroxylamine (50 wt % aqueous solution; 0.306 mL, 4.76 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 441 (0.008 g, 8%) in the form of a white solid.

$^1$H NMR (400 MHz, DMSO-$d_6$) δ 11.14 (s, 1H), 9.01 (s, 1H), 7.61 (d, 2H, J=8.3 Hz), 7.32 (d, 2H, J=8.2 Hz), 7.14-7.10 (m, 1H), 7.05-7.02 (m, 1H), 6.95 (d, 1H, J=8.2 Hz), 4.70 (s, 2H), 3.09-3.07 (m, 4H), 2.24 (s, 3H), 2.05-2.02 (m, 4H); MS (ESI) m/z 401.2 (M$^+$+H).

Example 80: Synthesis of Compound 450

Formula 7-6: methyl 4-((4-acetyl-N-(pyridin-2-yl)-1,4-diazepane-1-carboxamido)methyl)benzoate

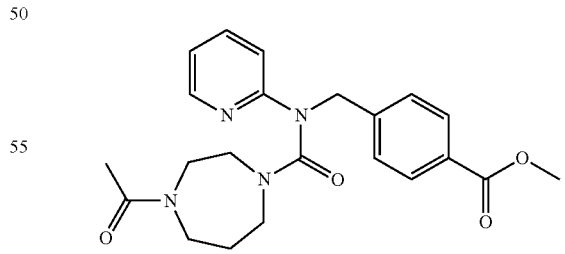

Compound of Formula 7-5 (methyl 4-((((4-nitrophenoxy) carbonyl)(pyridin-2-yl)amino)methyl)benzoate; 0.40 g, 0.74 mmol) was dissolved in dimethylformamide (10 mL), and then 1-(1,4-diazepan-1-yl)ethanone (0.102 mL, 1.08 mmol) was added, and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 7-6 (0.378 g, 94%) in the form of a white oil.

Compound 450: 4-acetyl-N-(4-(hydroxycarbamoyl)benzyl)-N-(pyridin-2-yl)-1,4-diazepane-1-carboxamide

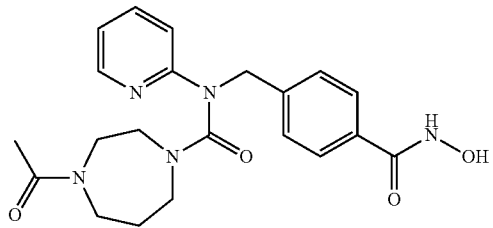 [SMILES: CC(=O)N1CCCN(C(=O)N(Cc2ccc(C(=O)NO)cc2)c2ccccn2)CC1]

Compound of Formula 7-6 (methyl 4-((4-acetyl-N-(pyridin-2-yl)-1,4-diazepane-1-carboxamido)methyl)benzoate; 0.20 g, 0.487 mmol) was dissolved in methanol (20 mL), hydroxylamine (0.169 g, 2.44 mmol) and potassium hydroxide (0.273 g, 4.87 mmol) were added. Then, hydroxylamine (50 wt % aqueous solution; 0.626 mL, 9.75 mmol) was added dropwise and stirred at room temperature for 3 hours. After completion of the reaction, the methanol was removed under reduced pressure, saturated sodium hydrogen carbonate aqueous solution was added to precipitate a solid, and the resulting solid was filter and dried to give the desired Compound 450 (0.07 g, 35%) in the form of a yellow oil.

$^1$H NMR (400 MHz, MeOD-d$_3$) δ 8.33-8.30 (m, 1H), 7.74-7.63 (m, 3H), 7.51-7.46 (m, 2H), 7.06-6.99 (m, 2H), 4.89 (s, 2H), 3.58-3.27 (m, 8H, 1.99-1.96 (m, 3H), 1.76-1.57 (m, 2H); MS (ESI) m/z 412.2 (M$^+$+H).

Example 81: Synthesis of Compound 451

Formula 7-6: methyl 4-((4-(cyclopropanecarbonyl)-N-(pyridin-2-yl)piperazine-1-carboxamido)methyl)benzoate

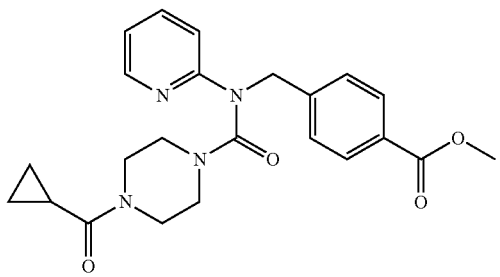 [SMILES: COC(=O)c1ccc(CN(C(=O)N2CCN(C(=O)C3CC3)CC2)c2ccccn2)cc1]

Compound of Formula 7-5 (methyl 4-(((((4-nitrophenoxy)carbonyl)(pyridin-2-yl)amino)methyl)benzoate; 0.40 g, 0.982 mmol) was dissolved in dimethylformamide (10 mL), and then cyclopropyl(piperazin-1-yl)methanone (0.167 mL, 1.17 mmol) was added, and the mixture was heated and stirred at 60° C. for 2 days. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 7-6 (0.4 g, 96%) in the form of a white oil.

Compound 451: 4-(cyclopropanecarbonyl)-N-(4-(hydroxycarbamoyl)benzyl)-N-(pyridin-2-yl)piperazine-1-carboxamide

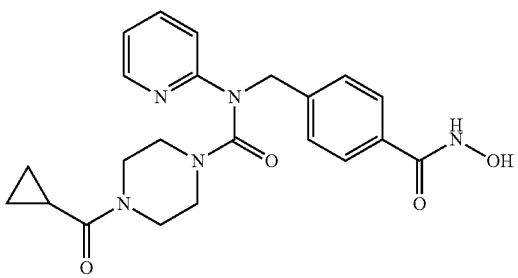 [SMILES: O=C(NO)c1ccc(CN(C(=O)N2CCN(C(=O)C3CC3)CC2)c2ccccn2)cc1]

Compound of Formula 7-6 (methyl 4-((4-(cyclopropanecarbonyl)-N-(pyridin-2-yl)piperazine-1-carboxamido)methyl)benzoate; 0.20 g, 0.473 mmol) was dissolved in methanol (20 mL), hydroxylamine (0.164 g, 2.38 mmol) and potassium hydroxide (0.265 g, 4.73 mmol) were added and stirred. Then, hydroxylamine (50 wt % aqueous solution; 0.61 mL, 9.47 mmol) was added dropwise and stirred at room temperature for 3 hours. After completion of the reaction, saturated sodium hydrogen carbonate aqueous solution was added to precipitate a solid, and the resulting solid was filter and dried to give the desired Compound 451 (0.05 g, 25%) in the form of a yellow oil.

$^1$H NMR (400 MHz, MeOD-d$_3$) δ 8.33 (d, 1H, J=3.7 Hz), 7.75-7.71 (m, 1H), 7.67 (d, 2H, J=8.2 Hz), 7.49 (d, 2H, J=8.2 Hz), 7.10 (d, 1H, J=8.3 Hz), 7.06-7.03 (m, 1H), 5.05 (s, 2H), 3.67 (m, 4H), 3.31 (m, 4H), 1.89-1.86 (m, 1H), 0.89-0.88 (m, 4H); MS (ESI) m/z 424.2 (M$^+$+H).

Example 82: Synthesis of Compound 453

Formula 1-4: methyl 4-((4-ethyl-N-(2-fluoro-4-methylphenyl)piperazine-1-carboxamido)methyl)benzoate

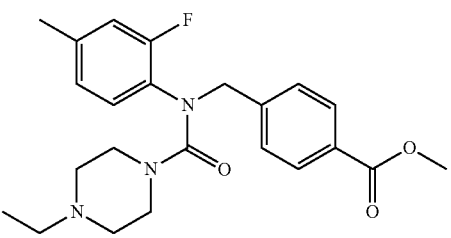 [SMILES: CCN1CCN(C(=O)N(Cc2ccc(C(=O)OC)cc2)c2ccc(C)cc2F)CC1]

Compound of Formula 1-3 (methyl 4-(((2-fluoro-4-methylphenyl)((4-nitrophenoxy)carbonyl)amino)methyl)benzoate; 0.20 g, 0.456 mmol) and 1-ethylpiperazine (0.116 mL, 0.912 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.14 g, 74%) in the form of a yellow oil.

Compound 453: 4-ethyl-N-(2-fluoro-4-methylphenyl)-N-(4-(hydroxycarbamoyl)benzyl)piperazine-1-carboxamide

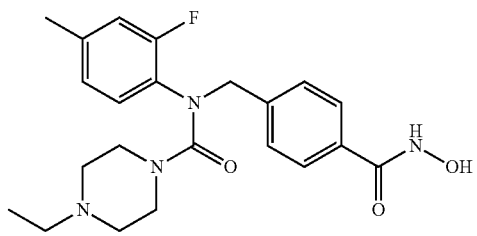 [SMILES: CCN1CCN(C(=O)N(Cc2ccc(C(=O)NO)cc2)c2ccc(C)cc2F)CC1]

Compound of Formula 1-4 (methyl 4-((4-ethyl-N-(2-fluoro-4-methylphenyl)piperazine-1-carboxamido)methyl)benzoate; 0.14 g, 0.339 mmol) was dissolved in methanol (5 mL), and hydroxylamine hydrochloride (0.118 g, 1.69 mmol) and potassium hydroxide (0.19 g, 3.39 mmol) were added and stirred. Then, hydroxylamine (50 wt % aqueous solution; 0.435 mL, 6.77 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 453 (0.12 g, 86%) in the form of a yellow oil.

$^1$H NMR (400 MHz, MeOD-$d_3$) δ 7.64 (d, 2H, J=8.2 Hz), 7.33 (d, 2H, J=8.2 Hz), 7.06-6.93 (m, 3H), 4.77 (s, 2H), 3.26-3.24 (m, 4H), 2.34 (q, 2H, J=7.2 Hz), 2.29 (s, 3H), 2.26-2.23 (m, 4H), 1.03 (t, 3H, J=7.2 Hz); MS (ESI) m/z 415.2 (M$^+$+H).

Example 83: Synthesis of Compound 454

Formula 1-4: methyl 4-((N-(2-fluoro-4-methylphenyl)-4-(2-methoxyphenyl)piperazine-1-carboxamido)methyl)benzoate

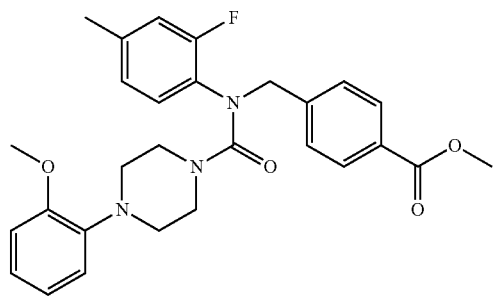 [SMILES: COC(=O)c1ccc(CN(C(=O)N2CCN(c3ccccc3OC)CC2)c2ccc(C)cc2F)cc1]

Compound of Formula 1-3 (methyl 4-(((2-fluoro-4-methylphenyl)((4-nitrophenoxy)carbonyl)amino)methyl)benzoate; 0.20 g, 0.456 mmol) and 4-(2-methoxyphenyl)piperazine (0.175 mL, 0.912 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30%) to give the desired compound of Formula 1-4 (0.15 g, 67%) in the form of a yellow oil.

Compound 454: N-(2-fluoro-4-methylphenyl)-N-(4-(hydroxycarbamoyl)benzyl)-4-(2-methoxyphenyl)piperazine-1-carboxamide

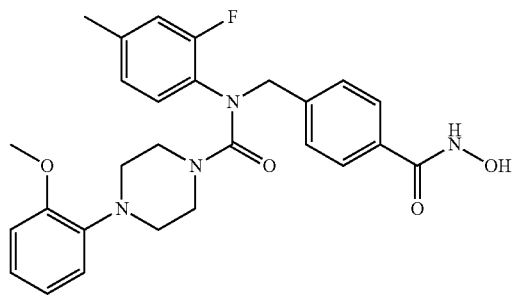 [SMILES: COc1ccccc1N1CCN(C(=O)N(Cc2ccc(C(=O)NO)cc2)c2ccc(C)cc2F)CC1]

Compound of Formula 1-4 (methyl 4-((N-(2-fluoro-4-methylphenyl)-4-(2-methoxyphenyl)piperazine-1-carboxamido)methyl)benzoate; 0.15 g, 0.305 mmol) was dissolved in methanol (5 mL), and hydroxylamine hydrochloride (0.106 g, 1.53 mmol) and potassium hydroxide (0.171 g, 3.05 mmol) were added and stirred. Then, hydroxylamine (50 wt % aqueous solution; 0.392 mL, 6.10 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 454 (0.06 g, 43%) in the form of a yellow solid.

$^1$H NMR (400 MHz, MeOD-$d_3$) δ 7.67 (d, 2H, J=8.0 Hz), 7.44 (d, 2H, J=8.0 Hz), 7.14-7.10 (m, 1H), 7.03-6.84 (m, 6H), 4.83 (s, 2H), 3.82 (s, 3H), 3.38 (m, 4H), 2.80 (m, 4H), 2.33 (s, 3H); MS (ESI) m/z 493.2 (M$^+$+H).

Example 84: Synthesis of Compound 455

Formula 1-4: methyl 4-((N-(2-fluoro-4-methylphenyl)-4-(4-fluorophenyl)piperazine-1-carboxamido)methyl)benzoate

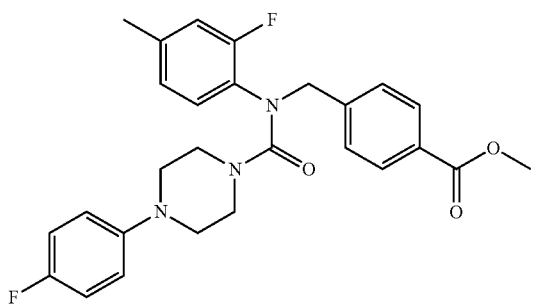 [SMILES: COC(=O)c1ccc(CN(C(=O)N2CCN(c3ccc(F)cc3)CC2)c2ccc(C)cc2F)cc1]

Compound of Formula 1-3 (methyl 4-(((2-fluoro-4-methylphenyl)((4-nitrophenoxy)carbonyl)amino)methyl)benzoate; 0.20 g, 0.456 mmol) and 1-(4-fluorophenyl)piperazine (0.164 mL, 0.912 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.12 g, 55%) in the form of a yellow oil.

Compound 455: N-(2-fluoro-4-methylphenyl)-4-(4-fluorophenyl)-N-(4-(hydroxycarbamoyl)benzyl)piperazine-1-carboxamide

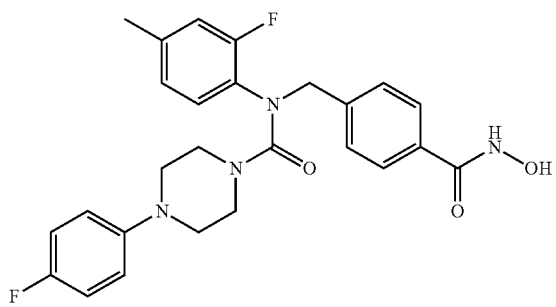 [SMILES: Cc1ccc(N(Cc2ccc(C(=O)NO)cc2)C(=O)N2CCN(c3ccc(F)cc3)CC2)c(F)c1]

Compound of Formula 1-4 (methyl 4-((N-(2-fluoro-4-methylphenyl)-4-(4-fluorophenyl)piperazine-1-carboxamido)methyl)benzoate; 0.12 g, 0.25 mmol) was dissolved in methanol (5 mL), and hydroxylamine hydrochloride (0.087 g, 1.25 mmol) and potassium hydroxide (0.14 g, 2.50 mmol) were added and stirred. Then, hydroxylamine (50 wt % aqueous solution; 0.322 mL, 5.01 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 455 (0.051 g, 42%) in the form of a yellow solid.

$^1$H NMR (400 MHz, MeOD-d$_3$) δ 7.65 (d, 2H, J=8.1 Hz), 7.38 (d, 2H, J=8.1 Hz), 7.10-7.06 (m, 1H), 6.99-6.86 (m, 6H), 4.80 (s, 2H), 3.38-3.35 (m, 4H), 2.87-2.84 (m, 4H), 2.30 (s, 3H); MS (ESI) m/z 481.2 (M$^+$+H).

Example 85: Synthesis of Compound 456

Formula 1-2: methyl 4-((3-chloro-4-fluorophenylamino)methyl)benzoate

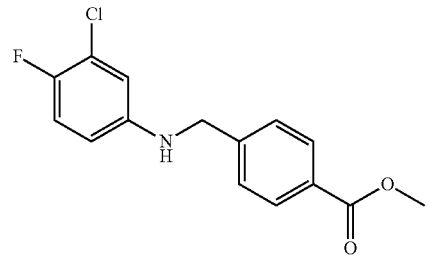 [SMILES: COC(=O)c1ccc(CNc2ccc(F)c(Cl)c2)cc1]

Compound of Formula 1-1 (3-chloro-4-fluorobenzenamine; 2.0 g, 13.7 mmol) and methyl 4-formylbenzoate (2.26 g, 13.7 mmol) were dissolved in methanol (500 mL) and stirred at room temperature for 3 hours. Then, acetic acid (0.786 mL, 13.7 mmol) and sodium cyanoborohydride (0.86 g, 13.7 mmol) were added and stirred for 1 day. The methanol was partially removed by air-drying to precipitate a solid, and the resulting solid was filtered and dried to give the desired compound of Formula 1-2 (2.9 g, 72%) in the form of a gray solid.

Formula 1-3: methyl 4-(((3-chloro-4-fluorophenyl)((4-nitrophenoxy)carbonyl)amino)methyl)benzoate

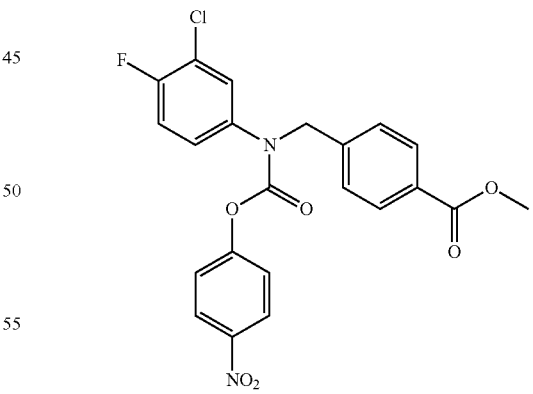

Compound of Formula 1-2 (methyl 4-((3-chloro-4-fluorophenylamido)methyl)benzoate; 2.5 g, 8.51 mmol) and 4-nitrophenyl chloroformate (2.06 g, 10.2 mmol) were dissolved in dichloromethane (50 mL) and stirred at room temperature for 3 days, and then the organic layer was extracted with water. The organic layer was washed with saturated sodium chloride aqueous solution, dehydrated with anhydrous magnesium sulfate, and then concentrated under reduced pressure. The residue was dried to give the desired compound of Formula 1-3 (2.5 g, 64%) in the form of a purple oil.

Formula 1-4: methyl 4-((N-(3-chloro-4-fluorophenyl)piperidine-1-carboxamido)methyl)benzoate

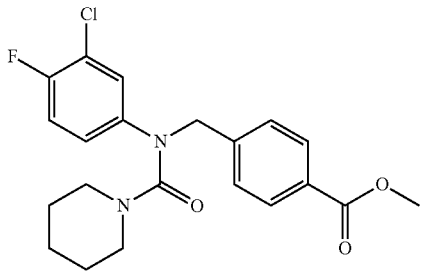

Compound of Formula 1-3 (methyl 4-(((3-chloro-4-fluorophenyl)((4-nitrophenoxy)carbonyl)amino)methyl)benzoate; 0.20 g, 0.436 mmol) and piperidine (0.043 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.15 g, 85%) in the form of a white solid.

Compound 456: N-(3-chloro-4-fluorophenyl)-N-(4-(hydroxycarbamoyl)benzyl)piperidine-1-carboxamide

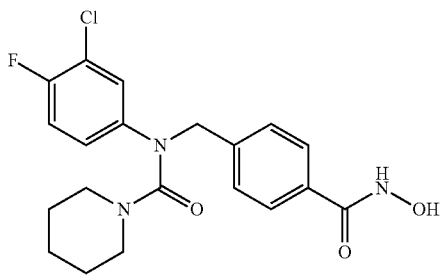

Compound of Formula 1-4 (methyl 4-((N-(3-chloro-4-fluorophenyl)piperidine-1-carboxamido)methyl)benzoate; 0.10 g, 0.247 mmol) was dissolved in methanol (5 mL), and hydroxylamine hydrochloride (0.086 g, 1.23 mmol) and potassium hydroxide (0.139 g, 2.47 mmol) were added and stirred. Then, hydroxylamine (50 wt % aqueous solution; 0.318 mL, 4.94 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 456 (0.066 g, 66%) in the form of a white solid.

$^1$H NMR (400 MHz, DMSO-$d_6$) δ 7.64 (d, 2H, J=8.2 Hz), 7.35-7.29 (m, 4H), 7.10-7.06 (m, 1H), 4.82 (s, 2H), 3.14-3.12 (m, 4H), 1.44-1.43 (m, 2H), 1.30 (m, 4H); MS (ESI) m/z 406.1 (M$^+$+H).

Example 86: Synthesis of Compound 457

Formula 1-4: methyl 4-((N-(3-chloro-4-fluorophenyl)4-methylpiperidine-1-carboxamido)methyl)benzoate

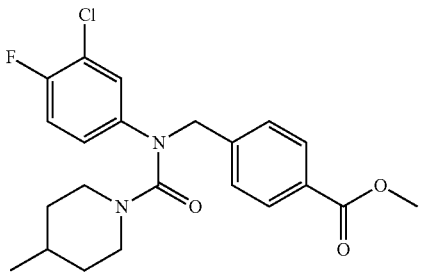

Compound of Formula 1-3 (methyl 4-(((3-chloro-4-fluorophenyl)((4-nitrophenoxy)carbonyl)amino)methyl)benzoate; 0.20 g, 0.436 mmol) and 4-methylpiperidine (0.051 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.17 g, 93%) in the form of a yellow oil.

Compound 457: N-(3-chloro-4-fluorophenyl)-N-(4-(hydroxycarbamoyl)benzyl)-4-methylpiperidine-1-carboxamide

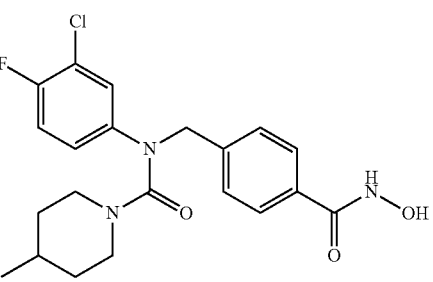

Compound of Formula 1-4 (methyl 4-((N-(3-chloro-4-fluorophenyl)4-methylpiperidine-1-carboxamido)methyl)benzoate; 0.10 g, 0.239 mmol) was dissolved in methanol (5 mL), and hydroxylamine hydrochloride (0.083 g, 1.19 mmol) and potassium hydroxide (0.134 g, 2.39 mmol) were added and stirred. Then, hydroxylamine (50 wt % aqueous solution; 0.307 mL, 4.78 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 457 (0.04 g, 40%) in the form of a white solid.

$^1$H NMR (400 MHz, DMSO-$d_6$) δ 7.64 (d, 2H, J=8.2 Hz), 7.35-7.31 (m, 4H), 7.06-7.04 (m, 1H), 4.82 (s, 2H), 3.69-3.66 (m, 2H), 2.59 (m, 2H), 1.46-1.44 (m, 3H), 0.82-0.81 (m, 5H); MS (ESI) m/z 420.2 (M$^+$+H).

Example 87: Synthesis of Compound 458

Formula 1-4: methyl 4-((N-(3-chloro-4-fluorophenyl)morpholine-4-carboxamido)methyl)benzoate

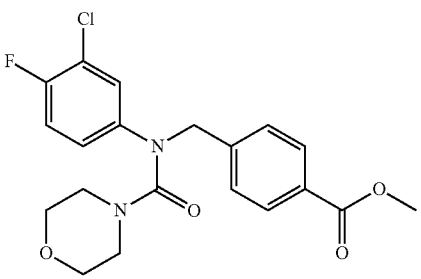 [SMILES: COC(=O)c1ccc(CN(C(=O)N2CCOCC2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and morpholine (0.038 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.022 g, 12%) in the form of a colorless oil.

Compound 458: N-(3-chloro-4-fluorophenyl)-N-(4-(hydroxycarbamoyl)benzyl)morpholine-4-carboxamide

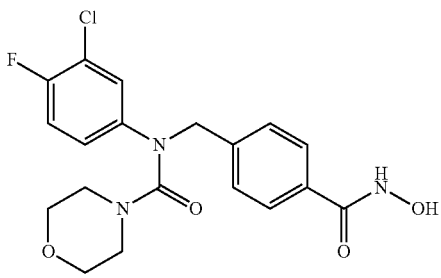

Compound of Formula 1-4 (methyl 4-((N-(3-chloro-4-fluorophenyl)morpholine-4-carboxamido)methyl)benzoate; 0.050 g, 0.123 mmol) was dissolved in methanol (5 mL), and hydroxylamine hydrochloride (0.043 g, 0.614 mmol) and potassium hydroxide (0.069 g, 1.23 mmol) were added and stirred. Then, hydroxylamine (50 wt % aqueous solution; 0.158 mL, 2.46 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 458 (0.017 g, 34%) in the form of a white solid.

$^1$H NMR (400 MHz, DMSO-$d_6$) δ 7.63 (d, 2H, J=8.2 Hz), 7.44-7.42 (m, 1H), 7.33-7.29 (m, 3H), 7.15-7.11 (m, 1H), 4.84 (s, 2H), 3.41-3.40 (m, 4H), 3.14-3.12 (m, 4H); MS (ESI) m/z 408.1 (M$^+$+H).

Example 88: Synthesis of Compound 459

Formula 1-4: methyl 4-((4-methyl-N-(3-(trifluoromethyl)phenyl)piperidine-1-carboxamido)methyl)benzoate

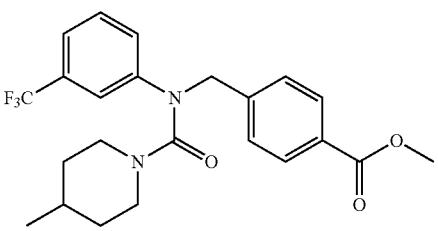

Compound of Formula 1-3 (methyl 4-((((4-nitrophenoxy)carbonyl)(3-(trifluoromethyl)phenyl)amino)methyl)benzoate; 0.38 g, 0.80 mmol) was dissolved in dimethylformamide (10 mL), and potassium carbonate (0.33 g, 2.38 mmol) and 4-methylpiperidine (0.10 mL, 0.80 mmol) were then added. The mixture was reacted at 60° C. for 2 days and then diluted with ethyl acetate and washed with saturated ammonium chloride solution. The organic layer was dehydrated with anhydrous sodium sulfate, filtered, and then concentrated under reduced pressure. The residue was purified by column chromatography (silica; ethyl acetate/hexane=50%) to give the desired compound of Formula 1-4 (0.26 g, 75%).

Compound 459: N-(4-(hydroxycarbamoyl)benzyl)-4-methyl-N-(3-(trifluoromethyl)phenyl)piperidine-1-carboxamide

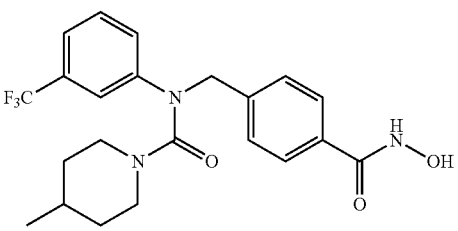 [SMILES: CC1CCN(C(=O)N(Cc2ccc(C(=O)NO)cc2)c2cccc(C(F)(F)F)c2)CC1]

Compound of Formula 1-4 (methyl 4-((4-methyl-N-(3-(trifluoromethyl)phenyl)piperidine-1-carboxamido)methyl)benzoate; 0.26 g, 0.60 mmol) was dissolved in methanol (5 mL), and hydroxylamine (50 wt % aqueous solution; 0.37 mL) and potassium hydroxide (0.17 g, 2.98 mmol) were then added and stirred overnight. After completion of the reaction, the methanol was removed by distillation under reduced pressure, and the organic layer was extracted with ethyl acetate and water, dehydrated with anhydrous magnesium sulfate, filtered, and then concentrated under reduced pressure. The residue was stirred in diethyl ether to give a white solid product, and the resulting solid was filter and dried to give the desired Compound 459 (0.07 g, 26%) in the form of a white solid.

$^1$H NMR (400 MHz, DMSO-$d_6$) δ 11.13 (brs, 1H), 8.98 (brs, 1H), 7.65 (d, 2H, J=8.3 Hz), 7.54-7.50 (m, 1H), 7.43-7.36 (m, 5H), 4.92 (s, 2H), 3.41-3.36 (m, 4H), 2.36-2.26 (m, 3H), 0.94 (s, 3H).

Example 89: Synthesis of Compound 460

Formula 1-4: methyl 4-((N-(3-(trifluoromethyl)phenyl)piperidine-1-carboxamido)methyl)benzoate

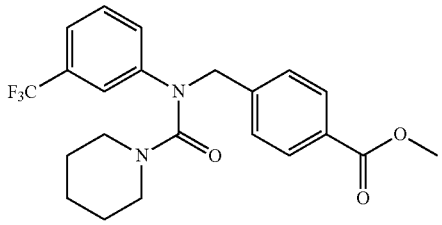 [SMILES: COC(=O)c1ccc(CN(C(=O)N2CCCCC2)c2cccc(C(F)(F)F)c2)cc1]

Compound of Formula 1-3 (methyl 4-((((4-nitrophenoxy)carbonyl)(3-(trifluoromethyl)phenyl)amino)methyl)benzoate; 0.44 g, 0.94 mmol) was dissolved in dimethylformamide (10 mL), and potassium carbonate (0.39 g, 2.81 mmol) and piperidine (0.09 mL, 0.94 mmol) were then added. The mixture was reacted at 60° C. for 1 day and then diluted with ethyl acetate and washed with saturated ammonium chloride solution. The organic layer was dehydrated with anhydrous magnesium sulfate, filtered, and then concentrated under reduced pressure. The residue was purified by column chromatography (silica; ethyl acetate hexane=20%) to give the desired compound of Formula 1-4 (0.16 g, 41%).

Compound 460: N-(4-(hydroxycarbamoyl)benzyl)-N-(3-(trifluoromethyl)phenyl)piperidine-1-carboxamide

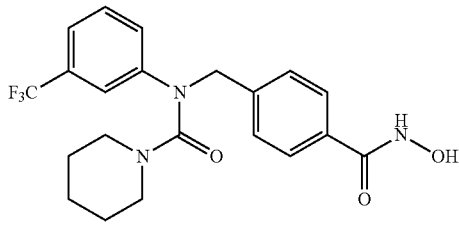 [SMILES: O=C(NO)c1ccc(CN(C(=O)N2CCCCC2)c2cccc(C(F)(F)F)c2)cc1]

Compound of Formula 1-4 (methyl 4-((N-(3-(trifluoromethyl)phenyl)piperidine-1-carboxamido)methyl)benzoate; 0.27 g, 0.65 mmol) was dissolved in methanol (5 mL), and hydroxylamine (50 wt % aqueous solution; 0.40 mL) and potassium hydroxide (0.18 g, 3.27 mmol) were then added and stirred overnight. After completion of the reaction, the methanol was removed by distillation under reduced pressure, and the organic layer was extracted with ethyl acetate and water, dehydrated with anhydrous magnesium sulfate, filtered, and then concentrated under reduced pressure. The residue was stirred in diethyl ether to give a solid product, and the resulting solid was filtered and dried to give the desired Compound 460 (0.07 g, 24%) in the form of a yellow solid.

$^1$H NMR (400 MHz, DMSO-$d_6$) δ 7.65 (d, 2H, J=8.2 Hz), 7.53-7.49 (m, 1H), 7.38-7.32 (m, 5H), 7.15-7.11 (m, 1H), 4.91 (s, 2H), 3.17-3.14 (m, 4H), 1.45-1.46 (m, 2H), 1.30 (brs, 4H); MS (ESI) m/z 422.1 (M$^+$+H).

Example 90: Synthesis of Compound 461

Formula 1-4: methyl 4-((4-ethyl-N-(3-(trifluoromethyl)phenyl)piperazine-1-carboxamido)methyl)benzoate

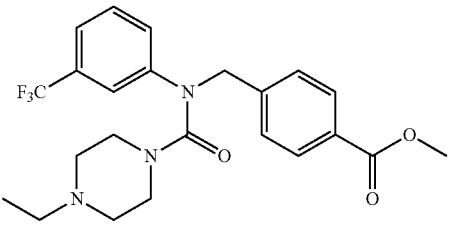 [SMILES: CCN1CCN(C(=O)N(Cc2ccc(C(=O)OC)cc2)c2cccc(C(F)(F)F)c2)CC1]

Compound of Formula 1-3 (methyl 4-((((4-nitrophenoxy)carbonyl)(3-(trifluoromethyl)phenyl)amino)methyl)benzoate; 0.346 g, 0.73 mmol) was dissolved in dimethylformamide (10 mL), and potassium carbonate (0.30 g, 2.19 mmol) and 1-ethylpiperazine (0.09 mL, 0.73 mmol) were then added. The mixture was reacted at 60° C. for 1 day and then diluted with ethyl acetate and washed with saturated ammonium chloride solution. The organic layer was dehydrated with anhydrous magnesium sulfate, filtered, and then concentrated under reduced pressure. The residue was purified by column chromatography (silica; ethyl acetate hexane=50%) to give the desired compound of Formula 1-4 (0.15 g, 46%).

Compound 461: 4-ethyl-N-(4-(hydroxycarbamoyl)benzyl)-N-(3-(trifluoromethyl)phenyl)piperazine-1-carboxamide

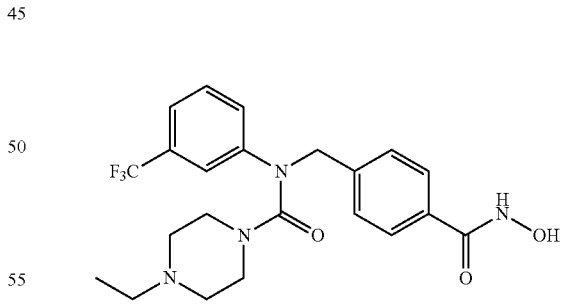

Compound of Formula 1-4 (methyl 4-((4-ethyl-N-(3-(trifluoromethyl)phenyl)piperazine-1-carboxamido)methyl)benzoate; 0.15 g, 0.33 mmol) was dissolved in methanol (10 mL), and hydroxylamine (50 wt % aqueous solution; 0.20 mL) and potassium hydroxide (0.09 g, 1.67 mmol) were then added and stirred overnight. After completion of the reaction, the methanol was removed by distillation under reduced pressure, and the organic layer was extracted with ethyl acetate and water, dehydrated with anhydrous magnesium sulfate, filtered, and then concentrated under reduced pressure. The residue was stirred in diethyl ether to give a solid product, and the resulting solid was filtered and dried to give the desired Compound 461 (0.09 g, 61%) in the form of a yellow solid.

$^1$H NMR (400 MHz, DMSO-d$_6$) δ 11.1 (brs, 1H), 7.65 (d, 2H, J=8.2 Hz), 7.51 (t, 1H, J=7.9 Hz), 7.41-7.36 (m, 5H), 4.92 (s, 2H), 3.17-3.14 (m, 4H), 2.25, 2.22 (ABq, 2H, J=12.4, 7.2 Hz), 2.18-2.15 (m, 4H), 0.92 (t, 3H, J=7.2 Hz); MS (ESI) m/z 451.1 (M$^+$+H).

Example 91: Synthesis of Compound 462

Formula 5-2: methyl 4-((3-(benzo[d][1,3]dioxol-5-yl)phenylamino)methyl)benzoate

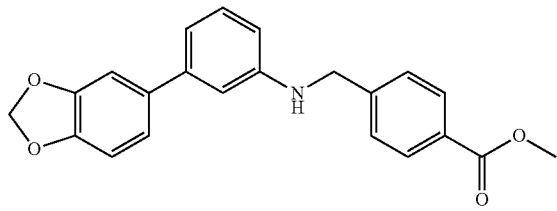 [SMILES: COC(=O)c1ccc(CNc2cccc(-c3ccc4c(c3)OCO4)c2)cc1]

Compound of Formula 5-1 (methyl 4-((3-bromophenylamino)methyl)benzoate; 3.00 g, 9.37 mmol), benzo[d][1,3]dioxol-5-ylboronic acid (1.87 g, 11.2 mmol), and Pd(dbpf)Cl$_2$ (0.305 g, 0.468 mmol) were dissolved in 1,4-dioxane (24 mL), and sodium carbonate (1.99 g, 18.7 mmol) dissolved in water (6 mL) was added to the reaction solution and stirred in a microwave reactor at 120° C. for 30 minutes. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=10%) to give the desired compound of Formula 5-2 (1.52 g, 45%) in the form of a brown solid.

Formula 5-3: methyl 4-(((3-(benzo[d][1,3]dioxol-5-yl)phenyl)((4-nitrophenoxy)carbonyl)amino)methyl)benzoate

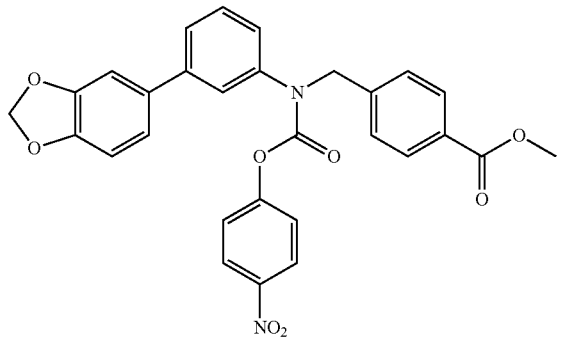 [SMILES: COC(=O)c1ccc(CN(C(=O)Oc2ccc([N+](=O)[O-])cc2)c2cccc(-c3ccc4c(c3)OCO4)c2)cc1]

Compound of Formula 5-2 (methyl 4-((3-(benzo[d][1,3]dioxol-5-yl)phenylamino)methyl)benzoate; 1.52 g, 4.21 mmol) and 4-nitrophenyl chloroformate (0.933 g, 4.63 mmol) were dissolved in acetonitrile (20 mL), and then potassium carbonate (0.872 g, 6.31 mmol) was added and stirred at room temperature for 3 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=20%) to give the desired compound of Formula 5-3 (1.87 g, 84%) in the form of a light yellow solid.

Formula 5-4: methyl 4-((N-(3-(benzo[d][1,3]dioxol-5-yl)phenyl)piperidine-1-carboxamido)methyl)benzoate

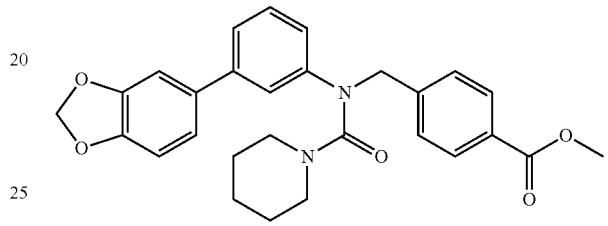

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then piperidine (0.087 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.155 g, 96%) in the form of a light yellow liquid.

Compound 462: N-(3-(benzo[d][1,3]dioxol-5-yl)phenyl)-N-(4-(hydroxycarbamoyl)benzyl)piperidine-1-carboxamide

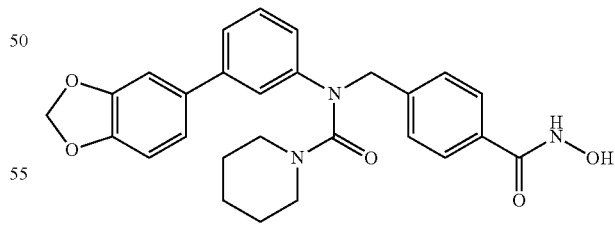

Compound of Formula 5-4 (methyl 4-((N-(3-(benzo[d][1,3]dioxol-5-yl)phenyl)piperidine-1-carboxamido)methyl)benzoate; 0.155 g, 0.328 mmol) was dissolved in methanol (10 mL), and then hydroxylamine (50.0 wt % aqueous solution; 1.00 mL, 16.4 mmol) and potassium hydroxide (0.184 g, 3.28 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 462 (0.153 g, 99%) in the form of a white solid.

$^1$H NMR (400 MHz, DMSO-$d_6$) δ 7.64 (d, 2H, J=8.3 Hz), 7.39 (d, 2H, J=8.2 Hz), 7.36-7.25 (m, 3H), 7.19 (d, 1H, J=1.8 Hz), 7.08 (dd, 1H, J=8.1, 1.8 Hz), 7.02-6.95 (m, 2H), 6.05 (s, 2H), 4.90 (s, 2H), 3.17-3.14 (m, 4H), 1.43 (m, 2H), 1.28 (m, 4H). MS (ESI) m/z 474 (M$^+$+H).

Example 92: Synthesis of Compound 463

Formula 5-4: methyl 4-((N-(3-(benzo[d][1,3]dioxol-5-yl)phenyl)-4-hydroxypiperidine-1-carboxamido)methyl)benzoate

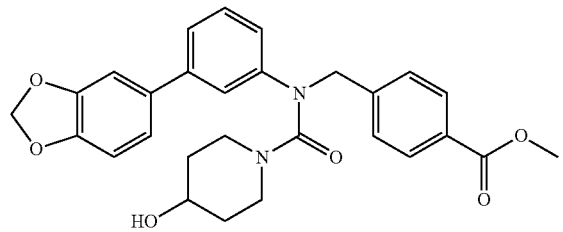

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then 4-hydroxypiperidine (0.104 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=25%) to give the desired compound of Formula 5-4 (0.128 g, 77%) in the form of a light yellow liquid.

Compound 463: N-(3-(benzo[d][1,3]dioxol-5-yl)phenyl)-4-hydroxy-N-(4-(hydroxycarbamoyl)benzyl)piperidine-1-carboxamide

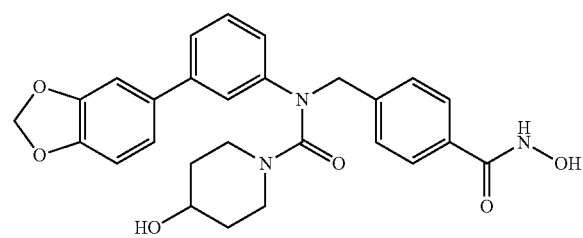 [SMILES: O=C(NO)c1ccc(CN(C(=O)N2CCC(O)CC2)c2cccc(-c3ccc4c(c3)OCO4)c2)cc1]

Compound of Formula 5-4 (methyl 4-((N-(3-(benzo[d][1,3]dioxol-5-yl)phenyl)-4-hydroxypiperidine-1-carboxamido)methyl)benzoate; 0.128 g, 0.262 mmol) was dissolved in methanol (10 mL), and then hydroxylamine (50.0 wt % aqueous solution; 0.801 mL, 13.1 mmol) and potassium hydroxide (0.147 g, 2.62 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 463 (0.085 g, 66%) in the form of a light brown solid.

$^1$H NMR (400 MHz, DMSO-$d_6$) δ 7.64 (d, 2H, J=8.3 Hz), 7.39 (d, 2H, J=8.3 Hz), 7.33-7.27 (m, 3H), 7.20 (d, 1H, J=1.8 Hz), 7.08 (dd, 1H, J=8.1, 1.8 Hz), 7.02-7.00 (m, 1H), 6.97 (d, 1H, J=8.1 Hz), 6.05 (s, 2H), 4.90 (s, 2H), 4.65 (brs, 1H), 3.54-3.51 (m, 3H), 2.87-2.81 (m, 2H), 1.56-1.53 (m, 2H), 1.14-1.09 (m, 2H). MS (ESI) m/z 490 (M$^+$+H).

Example 93: Synthesis of Compound 464

Formula 5-4: methyl 4-((N-(3-(benzo[d][1,3]dioxol-5-yl)phenyl)-2,6-dimethylmorpholine-4-carboxamido)methyl)benzoate

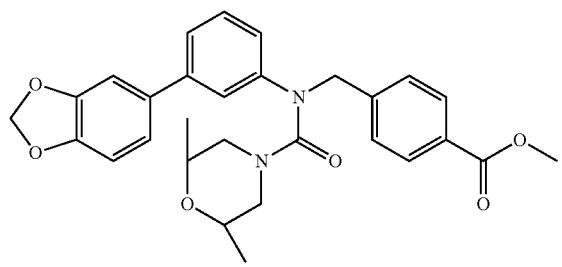 [SMILES: COC(=O)c1ccc(CN(C(=O)N2CC(C)OC(C)C2)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then 2,6-dimethylmorpholine (0.118 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=25%) to give the desired compound of Formula 5-4 (0.116 g, 68%) in the form of a colorless liquid.

Compound 464: N-(3-(benzo[d][1,3]dioxol-5-yl)phenyl)-N-(4-(hydroxycarbamoyl)benzyl)-2,6-dimethylmorpholine-4-carboxamide

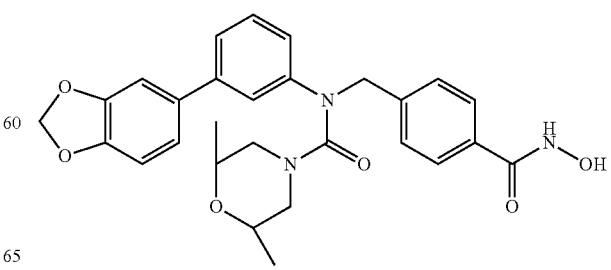

Compound of Formula 5-4 (methyl 4-((N-(3-(benzo[d][1,3]dioxol-5-yl)phenyl)-2,6-dimethylmorpholine-4-carboxamido)methyl)benzoate; 0.116 g, 0.231 mmol) was dissolved in methanol (10 mL), and then hydroxylamine (50.0 wt % aqueous solution; 0.706 mL, 11.5 mmol) and potassium hydroxide (0.130 g, 2.31 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 464 (0.085 g, 73%) in the form of a white solid.

$^1$H NMR (400 MHz, DMSO-$d_6$) δ 7.63 (d, 2H, J=8.3 Hz), 7.40 (d, 2H, J=8.2 Hz), 7.37-7.27 (m, 3H), 7.21 (d, 1H, J=1.8 Hz), 7.09 (dd, 1H, J=8.1, 1.8 Hz), 7.04 (m, 1H), 6.98 (d, 1H, J=8.1 Hz), 6.05 (s, 2H), 4.90 (s, 2H), 3.61-3.58 (m, 2H), 3.29-3.27 (m, 2H), 2.30-2.27 (m, 2H), 0.92 (s, 3H), 0.90 (s, 3H). MS (ESI) m/z 504 (M$^+$+H).

Example 94: Synthesis of Compound 465

Formula 5-4: methyl 4-((N-(3-(benzo[d][1,3]dioxol-5-yl)phenyl)-4-hydroxy-4-phenylpiperidine-1-carboxamido)methyl)benzoate

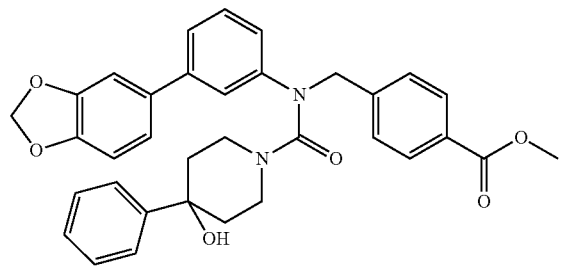 [SMILES: COC(=O)c1ccc(CN(C(=O)N2CCC(O)(c3ccccc3)CC2)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then 4-phenylpiperidin-4-ol (0.182 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.137 g, 71%) in the form of a light yellow liquid.

Compound 465: N-(3-(benzo[d][1,3]dioxol-5-yl)phenyl)-4-hydroxy-N-(4-(hydroxycarbamoyl)benzyl)-4-phenylpiperidine-1-carboxamide

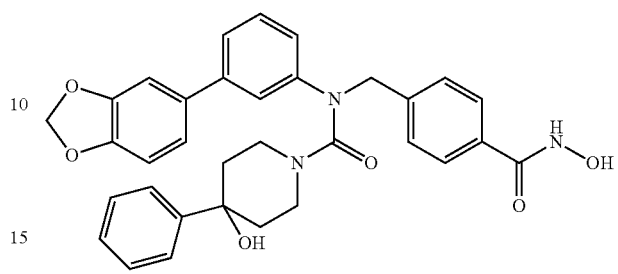

Compound of Formula 5-4 (methyl 4-((N-(3-(benzo[d][1,3]dioxol-5-yl)phenyl)-4-hydroxy-4-phenylpiperidine-1-carboxamido)methyl)benzoate; 0.137 g, 0.243 mmol) was dissolved in methanol (10 mL), and then hydroxylamine (50.0 wt % aqueous solution; 0.742 mL, 12.1 mmol) and potassium hydroxide (0.136 g, 2.43 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 465 (0.118 g, 86%) in the form of a white solid.

$^1$H NMR (400 MHz, DMSO-$d_6$) δ 7.66 (d, 2H, J=8.2 Hz), 7.41 (d, 2H, J=7.9 Hz), 7.38-7.33 (m, 2H), 7.29-7.20 (m, 6H), 7.17-7.06 (m, 3H), 6.99 (d, 1H, J=8.2 Hz), 6.06 (s, 2H), 4.98 (s, 1H), 4.92 (s, 2H), 3.69 (d, 2H, J=11.8 Hz), 3.04 (t, 2H, J=12.2 Hz), 1.63-1.58 (m, 2H), 1.40-1.36 (m, 2H). MS (ESI) m/z 566 (M$^+$+H).

Example 95: Synthesis of Compound 466

Formula 5-4: methyl 4-((N-(3-(benzo[d][1,3]dioxol-5-yl)phenyl)-4-methylpiperazine-1-carboxamido)methyl)benzoate

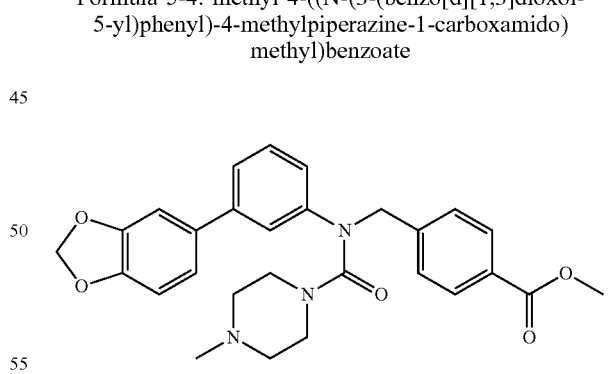

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then 1-methylpiperazine (0.103 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; methanol/dichloromethane=10%) to give the desired compound of Formula 5-4 (0.099 g, 59%) in the form of a yellow liquid.

Compound 466: N-(3-(benzo[d][1,3]dioxol-5-yl)phenyl)-N-(4-(hydroxycarbamoyl)benzyl)-4-methylpiperazine-1-carboxamide

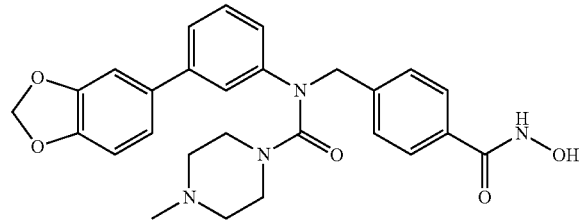 [SMILES: CN1CCN(C(=O)N(Cc2ccc(C(=O)NO)cc2)c2cccc(-c3ccc4c(c3)OCO4)c2)CC1]

Compound of Formula 5-4 (methyl 4-((N-(3-(benzo[d][1,3]dioxol-5-yl)phenyl)-4-methylpiperazine-1-carboxamido)methyl)benzoate; 0.099 g, 0.203 mmol) was dissolved in methanol (10 mL), and then hydroxylamine (50.0 wt % aqueous solution; 0.621 mL, 10.2 mmol) and potassium hydroxide (0.114 g, 2.03 mmol) were added sequentially and then stirred at room temperature for 30 minutes. After completion of the reaction, the reaction solution was concentrated under reduced pressure until its volume became about 1 mL, and saturated sodium hydrogen carbonate aqueous solution (1-2 mL) was added and stirred. Then, the solid product was filtered, washed with water, and then vacuum dried to give the desired Compound 466 (0.036 g, 36%) in the form of a light yellow solid.

$^1$H NMR (400 MHz, DMSO-$d_6$) δ 7.63 (d, 2H, J=8.1 Hz), 7.35 (d, 2H, J=8.2 Hz), 7.32-7.26 (m, 3H), 7.21 (d, 1H, J=1.8 Hz), 7.09 (dd, 1H, J=8.2, 1.7 Hz), 7.02 (m, 1H), 6.98 (d, 1H, J=8.1 Hz), 6.05 (s, 2H), 4.90 (s, 2H), 3.17 (m, 4H), 2.10 (m, 4H), 2.06 (s, 3H). MS (ESI) m/z 489 (M$^+$+H).

Example 96: Synthesis of Compound 467

Formula 5-4: methyl 4-((N-(3-(benzo[d][1,3]dioxol-5-yl)phenyl)-4-(2-hydroxyethyl)piperazine-1-carboxamido)methyl)benzoate

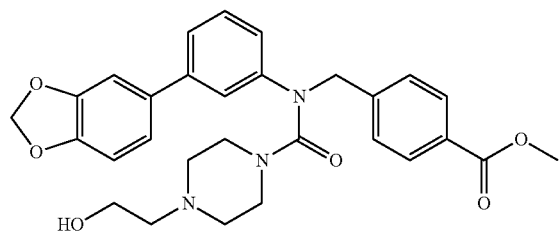 [SMILES: COC(=O)c1ccc(CN(C(=O)N2CCN(CCO)CC2)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then 2-(piperazin-1-yl)ethanol (0.134 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; methanol/dichloromethane=10%) to give the desired compound of Formula 5-4 (0.101 g, 57%) in the form of a yellow liquid.

Compound 467: N-(3-(benzo[d][1,3]dioxol-5-yl)phenyl)-N-(4-(hydroxycarbamoyl)benzyl)-4-(2-hydroxyethyl)piperazine-1-carboxamide

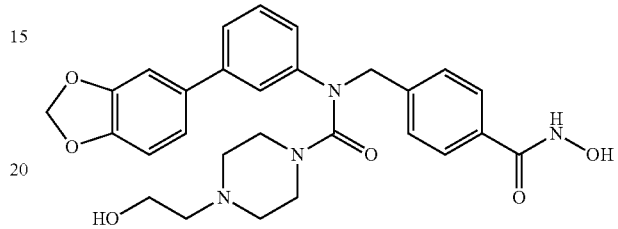

Compound of Formula 5-4 (methyl 4-((N-(3-(benzo[d][1,3]dioxol-5-yl)phenyl)-4-(2-hydroxyethyl)piperazine-1-carboxamido)methyl)benzoate; 0.101 g, 0.195 mmol) was dissolved in methanol (10 mL), and then hydroxylamine (50.0 wt % aqueous solution; 0.597 mL, 9.76 mmol) and potassium hydroxide (0.110 g, 1.95 mmol) were added sequentially and then stirred at room temperature for 30 minutes. After completion of the reaction, the reaction solution was concentrated under reduced pressure until its volume became about 1 mL and extracted with ethyl acetate and saturated sodium hydrogen carbonate aqueous solution. The organic layer was washed with water and dehydrated with anhydrous magnesium sulfate, filtered and then concentrated under reduced pressure to give the desired Compound 467 (0.054 g, 53%) in the form of a light yellow solid.

$^1$H NMR (400 MHz, DMSO-$d_6$) δ 11.12 (s, 1H), 9.00 (s, 1H), 7.64 (d, 2H, J=8.2 Hz), 7.38 (d, 2H, J=8.2 Hz), 7.34-7.26 (m, 3H), 7.21 (d, 1H, J=1.7 Hz), 7.09 (dd, 1H, J=8.2, 1.8 Hz), 7.02 (d, 1H, J=7.9 Hz), 6.98 (d, 1H, J=8.1 Hz), 6.05 (s, 2H), 4.91 (s, 2H), 4.36 (t, 1H, J=5.3 Hz), 3.41 (q, 2H, J=5.9 Hz), 3.16 (m, 4H), 2.27 (t, 2H, J=6.2 Hz), 2.22 (m, 4H). MS (ESI) m/z 519 (M$^+$+H).

Example 97: Synthesis of Compound 468

Formula 5-4: methyl 4-((N-(3-(benzo[d][1,3]dioxol-5-yl)phenyl)pyrrolidine-1-carboxamido)methyl)benzoate

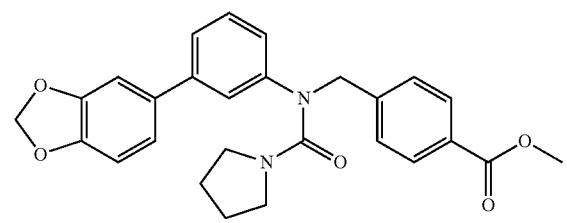 [SMILES: COC(=O)c1ccc(CN(C(=O)N2CCCC2)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then pyrrolidine (0.073 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.148 g, 94%) in the form of a colorless liquid.

Compound 468: N-(3-(benzo[d][1,3]dioxol-5-yl)phenyl)-N-(4-(hydroxycarbamoyl)benzyl)pyrrolidine-1-carboxamide

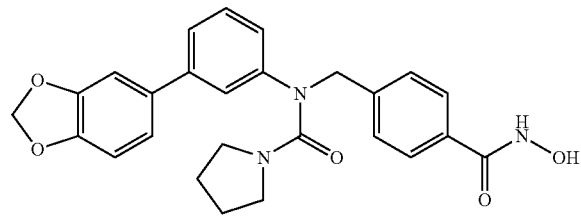 [SMILES: O=C(NO)c1ccc(CN(C(=O)N2CCCC2)c2cccc(-c3ccc4c(c3)OCO4)c2)cc1]

Compound of Formula 5-4 (methyl 4-((N-(3-(benzo[d][1,3]dioxol-5-yl)phenyl)pyrrolidine-1-carboxamido)methyl)benzoate; 0.148 g, 0.323 mmol) was dissolved in methanol (10 mL), and then hydroxylamine (50.0 wt % aqueous solution; 0.987 mL, 16.1 mmol) and potassium hydroxide (0.181 g, 3.23 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 468 (0.137 g, 92%) in the form of a white solid.

$^1$H NMR (400 MHz, DMSO-$d_6$) δ 7.63 (d, 2H, J=8.1 Hz), 7.38 (d, 2H, J=8.2 Hz), 7.31-7.28 (m, 3H), 7.18 (d, 1H, J=1.7 Hz), 7.05 (dd, 1H, J=8.1, 1.9 Hz), 7.00-6.95 (m, 2H), 6.04 (s, 2H), 4.91 (s, 2H), 3.04 (m, 4H), 1.64 (m, 4H). MS (ESI) m/z 460 (M$^+$+H).

Example 98: Synthesis of Compound 469

Formula 5-4: (S)-methyl 4-((N-(3-(benzo[d][1,3]dioxol-5-yl)phenyl)-2(hydroxymethyl)pyrrolidine-1-carboxamido)methyl)benzoate

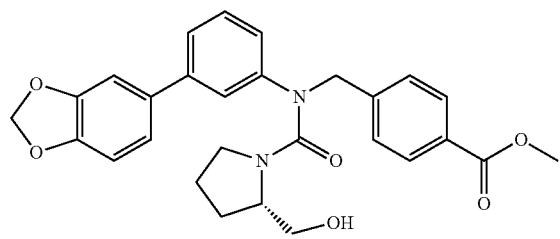 [SMILES: COC(=O)c1ccc(CN(C(=O)N2CCC[C@H]2CO)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then (S)-pyrrolidin-2-yl-methanol (0.104 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.142 g, 85%) in the form of a colorless liquid.

Compound 469: (S)—N-(3-(benzo[d][1,3]dioxol-5-yl)phenyl)-N-(4-(hydroxycarbamoyl)benzyl)-2-(hydroxymethyl)pyrrolidine-1-carboxamide

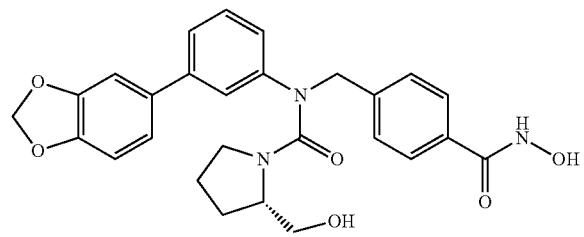 [SMILES: O=C(NO)c1ccc(CN(C(=O)N2CCC[C@H]2CO)c2cccc(-c3ccc4c(c3)OCO4)c2)cc1]

Compound of Formula 5-4 ((S)-methyl 4-((N-(3-(benzo[d][1,3]dioxol-5-yl)phenyl)-2(hydroxymethyl)pyrrolidine-1-carboxamido)methyl)benzoate; 0.142 g, 0.291 mmol) was dissolved in methanol (10 mL), and then hydroxylamine (50.0 wt % aqueous solution; 0.889 mL, 14.5 mmol) and potassium hydroxide (0.163 g, 2.91 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 469 (0.112 g, 79%) in the form of a light yellow solid.

$^1$H NMR (400 MHz, DMSO-$d_6$) δ 7.63 (d, 2H, J=8.2 Hz), 7.39-7.36 (m, 3H), 7.31-7.25 (m, 2H), 7.20 (d, 1H, J=1.8 Hz), 7.11-7.07 (m, 2H), 6.95 (d, 1H, J=8.1 Hz), 6.04 (s, 2H), 5.01 (d, 1H, J=16.1 Hz), 4.85-4.81 (m, 2H), 3.93 (m, 1H), 3.54 (m, 2H), 3.10 (m, 1H), 2.55 (m, 1H), 1.82 (m, 1H), 1.65 (m, 2H), 1.56 (m, 1H). MS (ESI) m/z 490 (M$^+$+H).

Example 99: Synthesis of Compound 470

Formula 5-4: methyl 4-((N-(3-(benzo[d][1,3]dioxol-5-yl)phenyl)-4-(cyclopropanecarbonyl)piperazine-1-carboxamido)methyl)benzoate

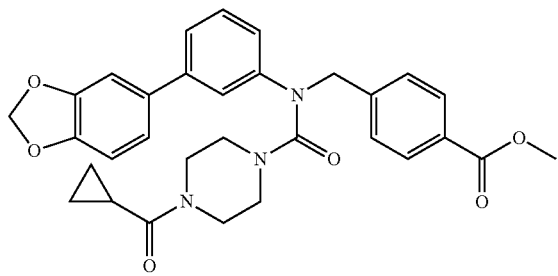 [SMILES: COC(=O)c1ccc(CN(C(=O)N2CCN(C(=O)C3CC3)CC2)c2cccc(-c3ccc4c(c3)OCO4)c2)cc1]

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then cyclopropyl(piperazin-1-yl)methanone (0.158 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.096 g, 52%) in the form of a yellow liquid.

Compound 470: N-(3-(benzo[d][1,3]dioxol-5-yl)phenyl)-4-(cyclopropanecarbonyl)-N-(4-(hydroxycarbamoyl)benzyl)piperazine-1-carboxamide

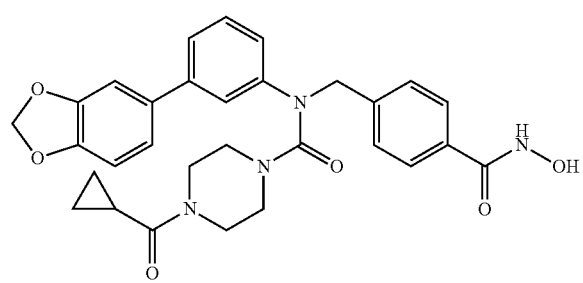 [SMILES: O=C(NO)c1ccc(CN(C(=O)N2CCN(C(=O)C3CC3)CC2)c2cccc(-c3ccc4c(c3)OCO4)c2)cc1]

Compound of Formula 5-4 (methyl 4-((N-(3-(benzo[d][1,3]dioxol-5-yl)phenyl)-4-(cyclopropanecarbonyl)piperazine-1-carboxamido)methyl)benzoate; 0.096 g, 0.177 mmol) was dissolved in methanol (10 mL), and then hydroxylamine (50.0 wt % aqueous solution; 0.542 mL, 8.86 mmol) and potassium hydroxide (0.100 g, 1.77 mmol) were added sequentially and then stirred at room temperature for 30 minutes. After completion of the reaction, the reaction solution was concentrated under reduced pressure until its volume became about 1 mL, and saturated ammonium chloride aqueous solution (1-2 mL) was added and stirred. Then, the solid product was filtered, washed with water, and then vacuum dried to give the desired Compound 470 (0.048 g, 50%) in the form of a light yellow solid.

$^1$H NMR (400 MHz, DMSO-d$_6$) δ 7.63 (d, 2H, J=8.1 Hz), 7.40-7.38 (m, 3H), 7.33-7.31 (m, 2H), 7.23 (d, 1H, J=1.6 Hz), 7.10 (dd, 1H, J=8.1, 1.6 Hz), 7.06 (m, 1H), 6.97 (d, 1H, J=8.2 Hz), 6.05 (s, 2H), 4.93 (s, 2H), 3.50 (m, 4H), 3.21-3.17 (m, 4H), 1.88 (m, 1H), 0.68-0.63 (m, 4H). MS (ESI) m/z 543 (M$^+$+H).

Example 100: Synthesis of Compound 471

Formula 5-4: methyl 4-((N-(3-(benzo[d][1,3]dioxol-5-yl)phenyl)azetidine-1-carboxamido)methyl)benzoate

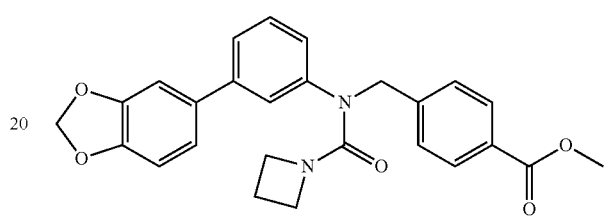

Compound of Formula 5-3 (methyl 4-(((3-(benzo[d][1,3]dioxol-5-yl)phenyl)((4-nitrophenoxy)carbonyl)amino)methyl)benzoate; 0.180 g, 0.342 mmol) was dissolved in dimethylformamide (2 mL), and then azetidine hydrochloride (0.096 g, 1.03 mmol) and potassium carbonate (0.142 g, 1.03 mmol) were added and stirred at 50° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 5-4 (0.150 g, 99%) in the form of a white solid.

Compound 471: N-(3-(benzo[d][1,3]dioxol-5-yl)phenyl)-N-(4-(hydroxycarbamoyl)benzyl)azetidine-1-carboxamide

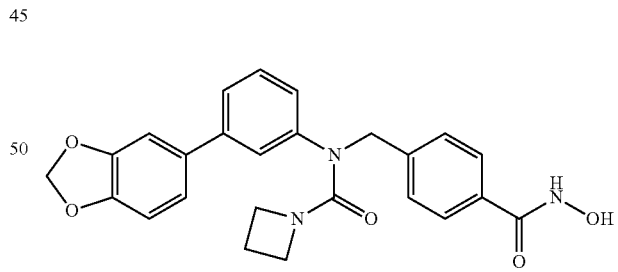

Compound of Formula 5-4 (methyl 4-((N-(3-(benzo[d][1,3]dioxol-5-yl)phenyl)azetidine-1-carboxamido)methyl)benzoate; 0.150 g, 0.337 mmol) was dissolved in methanol (10 mL), and then hydroxylamine (50.0 wt % aqueous solution; 1.03 mL, 16.9 mmol) and potassium hydroxide (0.189 g, 3.38 mmol) were added sequentially and then stirred at room temperature for 30 minutes. After completion of the reaction, the reaction solution was concentrated under reduced pressure until its volume became about 1 mL, and saturated sodium hydrogen carbonate aqueous solution (1-2 mL) was added and stirred. Then, the solid product was filtered, washed with water, and then vacuum dried to give the desired Compound 471 (0.150 g, 99%) in the form of a white solid.

$^1$H NMR (400 MHz, DMSO-$d_6$) δ 7.63 (d, 2H, J=8.2 Hz), 7.40-7.37 (m, 2H), 7.34-7.30 (m, 3H), 7.19 (d, 1H, J=1.8 Hz), 7.08-7.05 (m, 2H), 6.97 (d, 1H, J=8.1 Hz), 6.04 (s, 2H), 4.90 (s, 2H), 3.52-3.48 (m, 4H), 1.94-1.92 (m, 2H). MS (ESI) m/z 446 (M$^+$+H).

Example 101: Synthesis of Compound 477

Formula 1-4: methyl 4-((N-(3-chloro-4-fluorophenyl)-2,6-dimethylmorpholine-4-carboxamido)methyl)benzoate

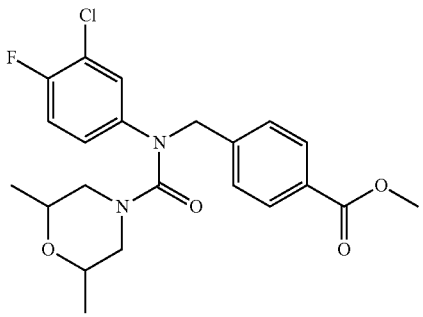 [SMILES: COC(=O)c1ccc(CN(C(=O)N2CC(C)OC(C)C2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and 2,6-dimethylmorpholine (0.053 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.048 g, 25%) in the form of a yellow oil.

Compound 477: N-(3-chloro-4-fluorophenyl)-N-(4-(hydroxycarbamoyl)benzyl)-2,6-dimethylmorpholine-4-carboxamide

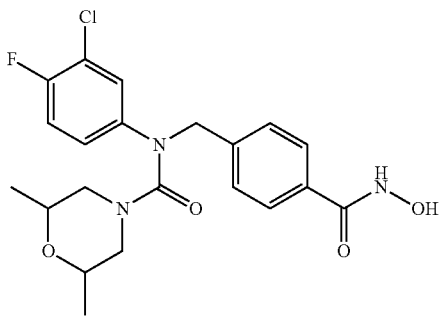 [SMILES: CC1CN(C(=O)N(Cc2ccc(C(=O)NO)cc2)c2ccc(F)c(Cl)c2)CC(C)O1]

Compound of Formula 1-4 (methyl 4-((N-(3-chloro-4-fluorophenyl)-2,6-dimethylmorpholine-4-carboxamido)methyl)benzoate; 0.048 g, 0.11 mmol) was dissolved in methanol (5 mL), and hydroxylamine hydrochloride (0.038 g, 0.552 mmol) and potassium hydroxide (0.062 g, 1.10 mmol) were added and stirred. Then, hydroxylamine (50 wt % aqueous solution; 0.142 mL, 2.21 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 477 (0.022 g, 46%) in the form of a yellow solid.

$^1$H NMR (400 MHz, MeOD-$d_3$) δ 7.67 (d, 2H, J=7.7 Hz), 7.40 (d, 2H, J=7.6 Hz), 7.31-7.30 (m, 1H), 7.22-7.18 (m, 1H), 7.11-7.09 (m, 1H), 3.66-3.62 (m, 2H), 3.43-3.39 (m, 2H), 2.40-2.34 (m, 2H), 1.03 (d, 6H, J=6.1 Hz); MS (ESI) m/z 436.1 (M$^+$+H).

Example 102: Synthesis of Compound 478

Formula 1-4: methyl 4-((N-(3-chloro-4-fluorophenyl)-4-methylpiperazine-1-carboxamido)methyl)benzoate

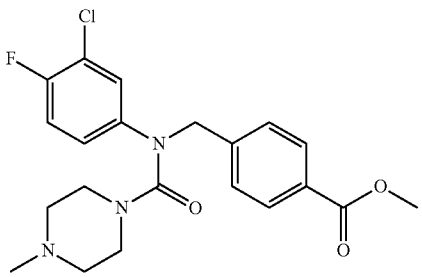 [SMILES: COC(=O)c1ccc(CN(C(=O)N2CCN(C)CC2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and 1-methylpiperazine (0.049 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.13 g, 72%) in the form of a yellow oil.

Compound 478: N-(3-chloro-4-fluorophenyl)-N-(4-(hydroxycarbamoyl)benzyl)-4-methylpiperazine-1-carboxamide

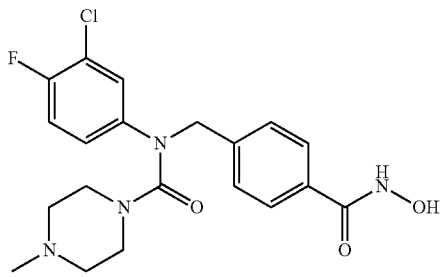 [SMILES: CN1CCN(C(=O)N(Cc2ccc(C(=O)NO)cc2)c2ccc(F)c(Cl)c2)CC1]

Compound of Formula 1-4 (methyl 4-((N-(3-chloro-4-fluorophenyl)-4-methylpiperazine-1-carboxamido)methyl) benzoate; 0.10 g, 0.238 mmol) was dissolved in methanol (5 mL), and hydroxylamine hydrochloride (0.083 g, 1.19 mmol) and potassium hydroxide (0.134 g, 2.38 mmol) were added and stirred. Then, hydroxylamine (50 wt % aqueous solution; 0.307 mL, 4.76 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 478 (0.077 g, 77%) in the form of a yellow oil.

$^1$H NMR (400 MHz, MeOD-$d_3$) δ 7.67 (d, 2H, J=8.1 Hz), 7.38 (d, 2H, J=8.1 Hz), 7.30-7.28 (m, 1H), 7.22-7.17 (m, 1H), 7.10-7.07 (m, 1H), 4.89 (s, 2H), 3.29-3.27 (m, 4H), 2.30-2.27 (m, 4H), 2.23 (s, 3H); MS (ESI) m/z 421.1 (M$^+$+H).

Example 103: Synthesis of Compound 479

Formula 1-4: methyl 4-((N-(3-chloro-4-fluorophenyl)-4-ethylpiperazine-1-carboxamido)methyl)benzoate

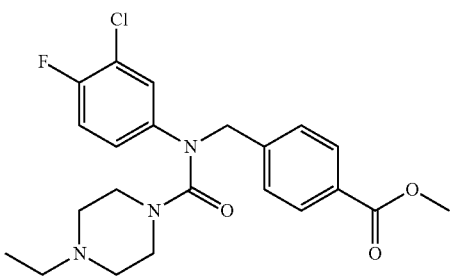 [SMILES: CCN1CCN(C(=O)N(Cc2ccc(C(=O)OC)cc2)c2ccc(F)c(Cl)c2)CC1]

Compound of Formula 1-3 (methyl 4-(((3-chloro-4-fluorophenyl)((4-nitrophenoxy)carbonyl)amino)methyl)benzoate; 0.20 g, 0.436 mmol) and 1-ethylpiperazine (0.055 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=5%) to give the desired compound of Formula 1-4 (0.165 g, 87%) in the form of a yellow oil.

Compound 479: N-(3-chloro-4-fluorophenyl)-4-ethyl-N-(4-(hydroxycarbamoyl)benzyl)piperazine-1-carboxamide

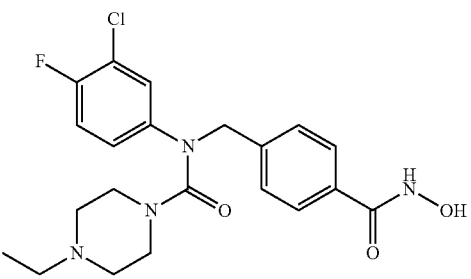 [SMILES: CCN1CCN(C(=O)N(Cc2ccc(C(=O)NO)cc2)c2ccc(F)c(Cl)c2)CC1]

Compound of Formula 1-4 (methyl 4-((N-(3-chloro-4-fluorophenyl)-4-ethylpiperazine-1-carboxamido)methyl) benzoate; 0.10 g, 0.23 mmol) was dissolved in methanol (5 mL), and hydroxylamine hydrochloride (0.08 g, 1.15 mmol) and potassium hydroxide (0.129 g, 2.31 mmol) were added and stirred. Then, hydroxylamine (50 wt % aqueous solution; 0.297 mL, 4.61 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 479 (0.092 g, 92%) in the form of a yellow solid.

$^1$H NMR (400 MHz, MeOD-$d_3$) δ 7.67 (d, 2H, J=8.2 Hz), 7.39 (d, 2H, J=8.2 Hz), 7.30-7.28 (m, 1H), 7.22-7.17 (m, 1H), 7.10 (m, 1H), 4.90 (s, 2H), 3.31-3.28 (m, 4H), 2.41-2.36 (m, 2H), 2.33-2.31 (m, 4H), 1.06 (t, 3H, J=7.2 Hz); MS (ESI) m/z 435.1 (M$^+$+H).

Example 104: Synthesis of Compound 480

Formula 1-4: methyl 4-((4-benzyl-N-(3-chloro-4-fluorophenyl)piperazine-1-carboxamido)methyl) benzoate

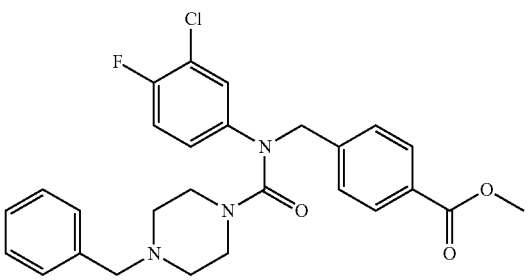 [SMILES: COC(=O)c1ccc(CN(C(=O)N2CCN(Cc3ccccc3)CC2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and 1-benzylpiperazine (0.075 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.151 g, 70%) in the form of a yellow oil.

Compound 480: 4-benzyl-N-(3-chloro-4-fluorophenyl)-N-(4-(hydroxycarbamoyl)benzyl)piperazine-1-carboxamide

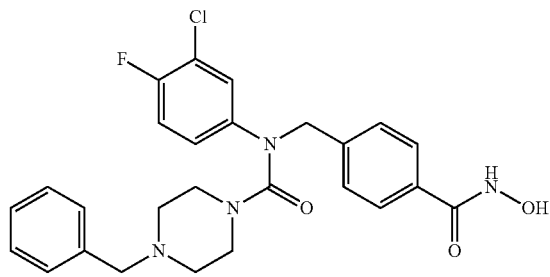 [SMILES: O=C(NO)c1ccc(CN(C(=O)N2CCN(Cc3ccccc3)CC2)c2ccc(F)c(Cl)c2)cc1]

Compound of Formula 1-4 (methyl 4-((4-benzyl-N-(3-chloro-4-fluorophenyl)piperazine-1-carboxamido)methyl)benzoate; 0.10 g, 0.202 mmol) was dissolved in methanol (5 mL), and hydroxylamine hydrochloride (0.07 g, 1.01 mmol) and potassium hydroxide (0.113 g, 2.02 mmol) were added and stirred. Then, hydroxylamine (50 wt % aqueous solution; 0.26 mL, 4.03 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 480 (0.057 g, 57%) in the form of a yellow solid.

$^1$H NMR (400 MHz, MeOD-d$_3$) δ 7.67 (d, 2H, J=8.2 Hz), 7.39 (d, 2H, J=8.2 Hz), 7.32-7.15 (m, 6H), 7.09-7.05 (m, 1H), 4.88 (s, 2H), 3.48 (s, 2H), 3.27 (m, 4H), 2.30 (m, 4H); MS (ESI) m/z 497.2 (M$^+$+H).

Example 105: Synthesis of Compound 481

Formula 1-4: methyl 4-((N-(3-chloro-4-fluorophenyl)-4-(2-methoxyphenyl)piperazine-1-carboxamido)methyl)benzoate

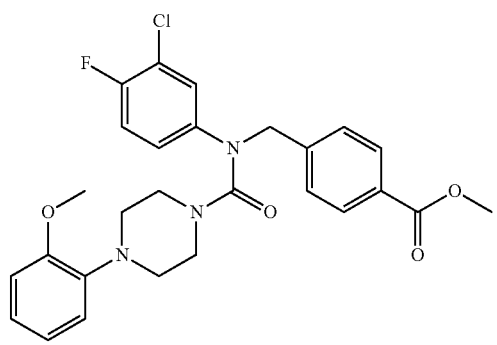 [SMILES: COC(=O)c1ccc(CN(C(=O)N2CCN(c3ccccc3OC)CC2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and 4-(2-methoxyphenyl)piperazine (0.076 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.157 g, 70%) in the form of a yellow oil.

Compound 481: N-(3-chloro-4-fluorophenyl)-N-(4-(hydroxycarbamoyl)benzyl)-4-(2-methoxyphenyl)piperazine-1-carboxamide

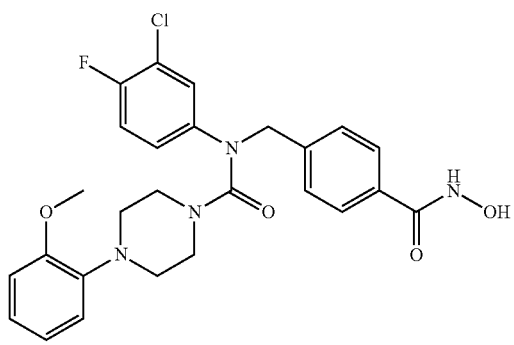 [SMILES: COc1ccccc1N1CCN(C(=O)N(Cc2ccc(C(=O)NO)cc2)c2ccc(F)c(Cl)c2)CC1]

Compound of Formula 1-4 (methyl 4-((N-(3-chloro-4-fluorophenyl)-4-(2-methoxyphenyl)piperazine-1-carboxamido)methyl)benzoate; 0.10 g, 0.195 mmol) was dissolved in methanol (5 mL), and hydroxylamine hydrochloride (0.068 g, 0.977 mmol) and potassium hydroxide (0.109 g, 1.95 mmol) were added and stirred. Then, hydroxylamine (50 wt % aqueous solution; 0.252 mL, 3.91 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 481 (0.037 g, 37%) in the form of a white solid.

$^1$H NMR (400 MHz, MeOD-d$_3$) δ 7.75 (d, 2H, J=8.1 Hz), 7.44 (d, 2H, J=8.1 Hz), 7.41-7.39 (m, 1H), 7.31-7.19 (m, 2H), 7.05-6.93 (m, 4H), 4.96 (s, 2H), 3.86 (s, 3H), 3.44 (m, 4H), 2.92-2.91 (m, 4H); MS (ESI) m/z 513.1 (M$^+$+H).

Example 106: Synthesis of Compound 482

Formula 1-4: methyl 4-((N-(3-chloro-4-fluorophenyl)-4-(4-fluorophenyl)piperazine-1-carboxamido)methyl)benzoate

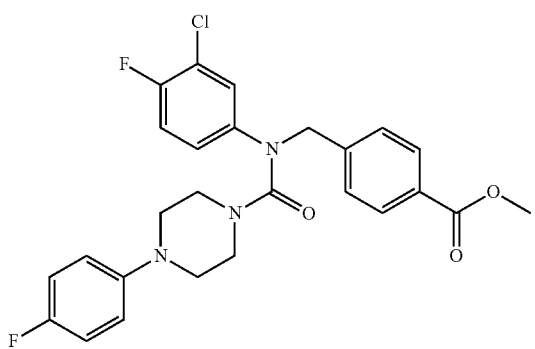 [SMILES: COC(=O)c1ccc(CN(C(=O)N2CCN(c3ccc(F)cc3)CC2)c2ccc(F)c(Cl)c2)cc1]

Compound of Formula 1-3 (methyl 4-(((3-chloro-4-fluorophenyl)((4-nitrophenoxy)carbonyl)amino)methyl)benzoate; 0.20 g, 0.436 mmol) and 1-(4-fluorophenyl)piperazine (0.079 mL, 0.436 mmol) were dissolved in dimethylformamide (10 mL), and the mixture was heated and stirred at 60° C. for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 1-4 (0.184 g, 84%) in the form of a yellow oil.

Compound 482: N-(3-chloro-4-fluorophenyl)-4-(4-fluorophenyl)-N-(4-(hydroxycarbamoyl)benzyl)piperazine-1-carboxamide

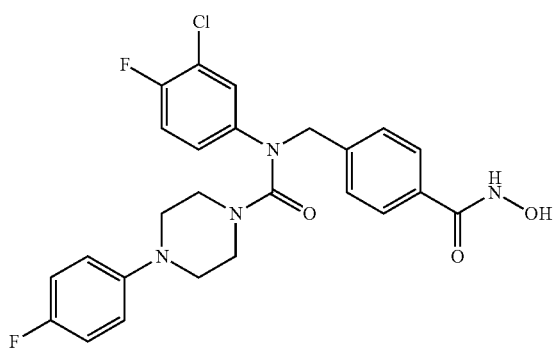 [SMILES: O=C(NO)c1ccc(CN(C(=O)N2CCN(c3ccc(F)cc3)CC2)c2ccc(F)c(Cl)c2)cc1]

Compound of Formula 1-4 (methyl 4-((N-(3-chloro-4-fluorophenyl)-4-(4-fluorophenyl)piperazine-1-carboxamido)methyl)benzoate; 0.10 g, 0.20 mmol) was dissolved in methanol (5 mL), and hydroxylamine hydrochloride (0.069 g, 1.00 mmol) and potassium hydroxide (0.112 g, 2.00 mmol) were added and stirred. Then, hydroxylamine (50 wt % aqueous solution; 0.258 mL, 4.00 mmol) was added dropwise and stirred at room temperature for 3 hours. After completion of the reaction, the methanol was removed under reduced pressure, and saturated sodium hydrogen carbonate aqueous solution was added to precipitate a solid, and the resulting solid was filtered and dried to give the desired Compound 482 (0.029 g, 29%) in the form of a white solid.

$^1$H NMR (400 MHz, MeOD-$d_3$) δ 7.75 (d, 2H, J=6.8 Hz), 7.48-7.43 (m, 3H), 7.34-7.30 (m, 1H), 7.22 (m, 1H), 7.08-6.99 (m, 4H), 4.98 (s, 2H), 3.45 (m, 4H), 3.01 (m, 4H); MS (ESI) m/z 501.1 (M$^+$+H).

Example 107: Synthesis of Compound 483

Formula 2-4: methyl 4-((N-(3-(tetrahydro-2H-pyran-4-yl)phenyl)morpholine-4-carboxamido)methyl)benzoate

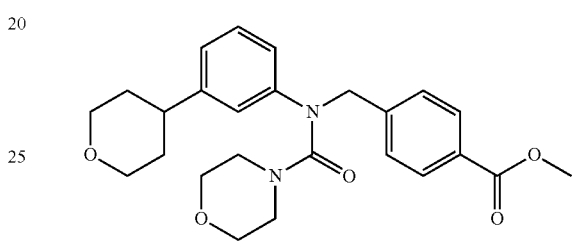

Compound of Formula 2-3 (methyl 4-((N-(3-(3,6-dihydro-2H-pyran-4-yl)phenyl)morpholine-4-carboxamido)methyl)benzoate; 0.260 g, 0.596 mmol) was dissolved in tetrahydrofuran (10 mL) at room temperature, Pd/C (10.0%, 0.032 g, 0.030 mmol) was slowly added, a hydrogen balloon was attached, and then the mixture was stirred at the same temperature for 16 hours. The reaction mixture was filtered through celite pad, and the filtrate was concentrated under reduced pressure. Then, the residue was purified and concentrated by column chromatography (silica; ethyl acetate/hexane=20-50%) to give the desired compound of Formula 2-4 (0.217 g, 83%) in the form of a white solid.

Compound 483: N-(4-(hydroxycarbamoyl)benzyl)-N-(3-(tetrahydro-2H-pyran-4-yl)phenyl)morpholine-4-carboxamide

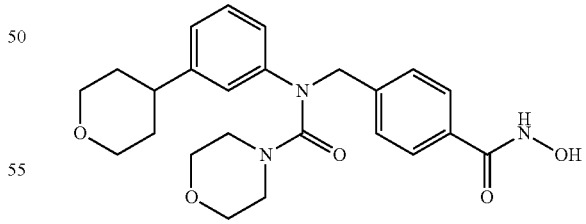

Compound of Formula 2-4 (methyl 4-((N-(3-(tetrahydro-2H-pyran-4-yl)phenyl)morpholine-4-carboxamido)methyl)benzoate; 0.217 g, 0.495 mmol) was dissolved in methanol (10 mL), hydroxylamine (50.0 wt % aqueous solution; 1.51 mL, 24.7 mmol) was added at room temperature, and then potassium hydroxide (0.278 g, 4.95 mmol) was added and stirred at the same temperature for 30 minutes. Then, the reaction mixture was concentrated under reduced pressure until its volume became about 1 mL, and saturated sodium hydrogen carbonate aqueous solution (1-2 mL) was added and stirred. Then, the precipitated solid was filtered and dried to give the desired Compound 483 (0.120 g, 55%) in the form of a white solid.

$^1$H NMR (400 MHz, DMSO-d$_6$) δ 11.12 (brs, 1H), 8.97 (brs, 1H), 7.64 (d, 2H, J=8.2 Hz), 7.34 (d, 2H, J=8.3 Hz), 7.23 (t, 1H, J=7.7 Hz), 6.98-6.94 (m, 3H), 4.84 (s, 2H), 3.93-3.90 (m, 2H), 3.42-3.37 (m, 6H), 3.12-3.10 (m, 4H), 2.69 (m, 1H), 1.62-1.54 (m, 4H). MS (ESI) m/z 440 (M$^+$+H).

Example 108: Synthesis of Compound 484

Formula 1-2: methyl 4-(((3-methoxyphenyl)amino)methyl)benzoate

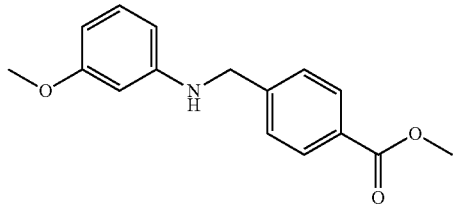

Compound of Formula 1-1 (m-anisidine; 3.23 g, 26.2 mmol) and methyl 4-(bromomethyl)benzoate (5.00 g, 21.8 mmol) were dissolved in acetonitrile (50 mL), and N,N-diisopropylethylamine (5.80 mL, 32.7 mmol) was added and stirred at room temperature for 16 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=5%) to give the desired compound of Formula 1-2 (5.14 g, 87%) in the form of a light yellow liquid.

Formula 1-3: methyl 4-(((3-methoxyphenyl)((4-nitrophenoxy)carbonyl)amino)methyl)benzoate

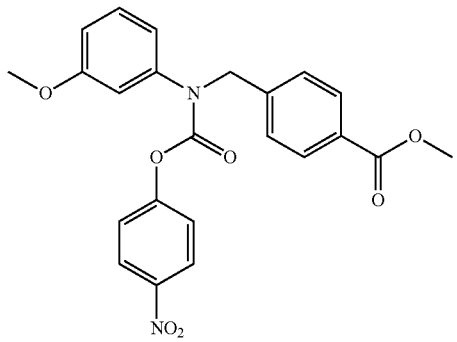

Compound of Formula 1-2 (methyl 4-(((3-methoxyphenyl)amino)methyl)benzoate; 5.14 g, 18.9 mmol) and 4-nitrophenyl chloroformate (4.20 g, 20.8 mmol) were dissolved in acetonitrile (100 mL), and potassium carbonate (3.93 g, 28.4 mmol) was added and stirred at room temperature for 3 hours. After completion of the reaction, the organic layer was extracted with ethyl acetate and saturated sodium hydrogen carbonate aqueous solution, dehydrated with anhydrous magnesium sulfate, and then filtered. The filtrate was concentrated under reduced pressure, and then the residue was purified and concentrated by column chromatography (silica; ethyl acetate/hexane=20%) to give the desired compound of Formula 1-3 (5.88 g, 71%) in the form of a yellow liquid.

Formula 1-4: methyl 4-((N-(3-methoxyphenyl)morpholine-4-carboxamido)methyl)benzoate

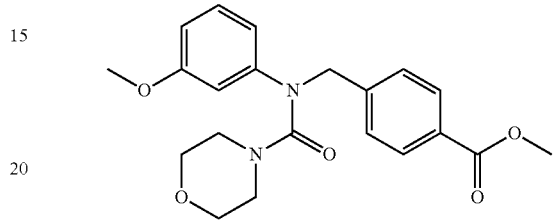

Compound of Formula 1-3 (methyl 4-(((3-methoxyphenyl)((4-nitrophenoxy)carbonyl)amino)methyl)benzoate; 5.88 g, 13.5 mmol) was dissolved in dimethylformamide (50 mL), and morpholine (2.35 g, 27.0 mmol) and potassium carbonate (5.60 g, 40.5 mmol) were added and stirred at 60° C. for 16 hours. After completion of the reaction, the organic layer was extracted with ethyl acetate and saturated ammonium chloride aqueous solution, dehydrated with anhydrous magnesium sulfate, and then filtered. The filtrate was concentrated under reduced pressure, and then the residue was purified and concentrated by column chromatography (silica; ethyl acetate/hexane=30%) to give the desired compound of Formula 1-4 (3.69 g, 71%) in the form of a yellow solid.

Compound 484: N-(4-(hydroxycarbamoyl)benzyl)-N-(3-methyoxyphenyl)morpholine-4-carboxamide

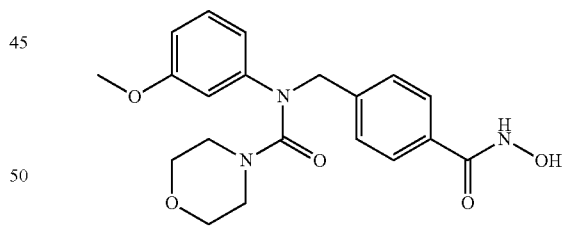

Compound of Formula 1-4 (methyl 4-((N-(3-methoxyphenyl)morpholine-4-carboxamino)methyl)benzoate; 0.180 g, 0.468 mmol) was dissolved in methanol (10 mL), hydroxylamine (50.0 wt % aqueous solution; 1.43 mL, 23.4 mmol) was added at room temperature, and then potassium hydroxide (0.263 g, 4.68 mmol) was added and stirred at the same temperature for 30 minutes. Then, the concentrate was obtained by removing the solvent from the reaction mixture under reduced pressure. Saturated ammonium chloride aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The residue was crystallized with dichloromethane (2 mL) and hexane (10 mL) to give the desired Compound 484 (0.140 g, 78%) in the form of a white solid.

$^1$H NMR (400 MHz, DMSO-$d_6$) δ 7.63 (d, 2H, J=8.1 Hz), 7.32 (m, 2H), 7.19 (t, 1H, J=8.4 Hz), 6.69-6.67 (m, 2H), 6.62 (m, 1H), 4.84 (s, 2H), 3.69 (s, 3H), 3.39-3.36 (m, 4H), 3.15-3.12 (m, 4H). MS (ESI) m/z 386 (M$^+$+H).

Example 109: Synthesis of Compound 485

Formula 1-4: methyl 4-((3,3-difluoro-N-(4-(trifluoromethyl)phenyl)azetidine-1-carboxamido)methyl)benzoate

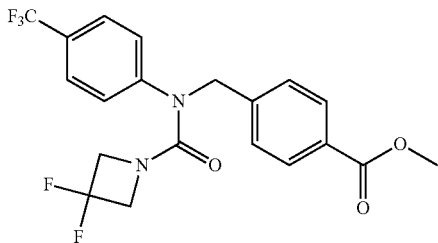 [SMILES: COC(=O)c1ccc(CN(C(=O)N2CC(F)(F)C2)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.22 g, 0.46 mmol) was dissolved in dimethylformamide (5 ml), and potassium carbonate (0.19 g, 1.37 mmol) and 3,3-difluoroazetidine (0.19 g, 0.92 mmol) were then added. The mixture was reacted at 60° C. for 2 days, diluted with ethyl acetate and washed with saturated sodium ammonium chloride solution. The organic layer was dehydrated with anhydrous sodium sulfate, filtered, and then concentrated under reduced pressure. The residue was purified by column chromatography (silica; ethyl acetate/hexane=50%) to give the desired compound of Formula 1-4 (0.20 g, 101%).

Compound 485, 3,3-difluoro-N-(4-(hydroxycarbamoyl)benzyl)-N-(4-(trifluoromethyl)phenyl)azetidine-1-carboxamide

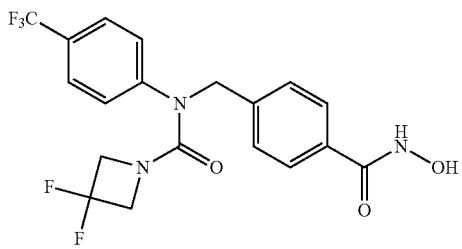 [SMILES: O=C(NO)c1ccc(CN(C(=O)N2CC(F)(F)C2)c2ccc(C(F)(F)F)cc2)cc1]

Compound of Formula 1-4 (methyl 4-((3,3-difluoro-N-(4-(trifluoromethyl)phenyl)azetidine-1-carboxamido)methyl)benzoate; 0.20 g, 0.47 mmol) was dissolved in methanol (10 ml), and hydroxylamine (50 wt % aqueous solution; 0.29 mL) and potassium hydroxide (0.13 g, 2.33 mmol) were then added and stirred overnight. After completion of the reaction, the methanol was removed by distillation under reduced pressure, and the organic layer was extracted with ethyl acetate and water, dehydrated with anhydrous sodium sulfate, filtered, and then concentrated under reduced pressure. The residue was purified by column chromatography (silica; methanol/dichloromethane=10%) to give the desired Compound 485 (0.07 g, 36%) in the form of a white solid.

$^1$H NMR (400 MHz, DMSO-$d_6$) δ 11.13 (brs, 1H), 8.98 (brs, 1H), 7.84-7.81 (m, 2H), 7.43-7.34 (m, 6H), 4.42 (s, 2H), 4.18-4.14 (m, 4H). MS (ESI) m/z 430 (M$^+$+H).

Example 110: Synthesis of Compound 486

Formula 1-4: methyl 4-((4-hydroxy-4-phenyl-N-(4-(trifluoromethyl)phenyl)piperidine-1-carboxamido)methyl)benzoate

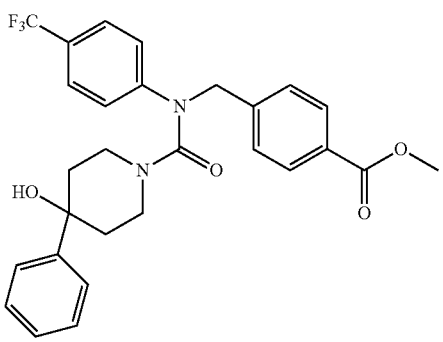 [SMILES: COC(=O)c1ccc(CN(C(=O)N2CCC(O)(c3ccccc3)CC2)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.25 g, 0.53 mmol) was dissolved in dimethylformamide (5 ml), and potassium carbonate (0.22 g, 1.61 mmol) and 4-phenylpiperidin-4-ol (0.19 g, 1.07 mmol) were then added. The mixture was reacted at 60° C. for 2 days, diluted with ethyl acetate and washed with saturated sodium ammonium chloride solution. The organic layer was dehydrated with anhydrous sodium sulfate, filtered, and then concentrated under reduced pressure. The residue was purified by column chromatography (silica; ethyl acetate/hexane=50%) to give the desired compound of Formula 1-4 (0.17 g, 60%).

Compound 486, 4-hydroxy-N-(4-(hydroxycarbamoyl)benzyl)-4-phenyl-N-(4-(trifluoromethyl)phenyl)piperidine-1-carboxamide

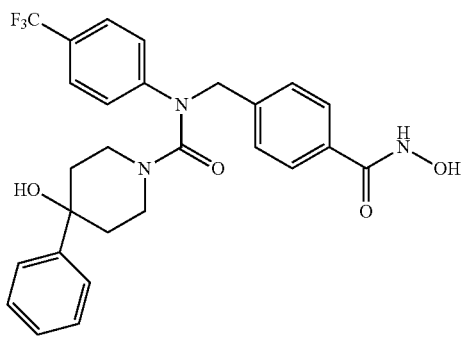 [SMILES: O=C(NO)c1ccc(CN(C(=O)N2CCC(O)(c3ccccc3)CC2)c2ccc(C(F)(F)F)cc2)cc1]

Compound of Formula 1-4 (methyl 4-((4-hydroxy-4-phenyl-N-(4-(trifluoromethyl)phenyl)piperidine-1-carboxamido)methyl)benzoate; 0.17 g, 0.32 mmol) was dissolved in methanol (10 ml), and hydroxylamine (50 wt % aqueous solution; 0.20 mL) and potassium hydroxide (0.09 g, 1.61 mmol) were then added and stirred overnight. After completion of the reaction, the methanol was removed by distillation under reduced pressure, and the organic layer was extracted with ethyl acetate and water, dehydrated with anhydrous magnesium sulfate, filtered, and then concentrated under reduced pressure. The residue was purified by column chromatography (silica; methanol/dichloromethane=10%) to give the desired Compound 486 (0.09 g, 55%) in the form of a white solid.

$^1$H NMR (400 MHz, DMSO-d$_6$) δ 11.13 (brs, 1H), 8.98 (brs, 1H), 7.84-7.82 (m, 2H), 7.55-7.53 (m, 2H), 7.43-7.30 (m, 9H), 4.42 (s, 2H), 3.39-3.29 (m, 4H), 2.10-2.05 (m, 2H), 1.84-1.81 (m, 2H). MS (ESI) m/z 496 (M$^+$+H).

Example 111: Synthesis of Compound 487

Formula 6-2: 4-((3-bromophenylamino)methyl)-3-fluorobenzonitrile

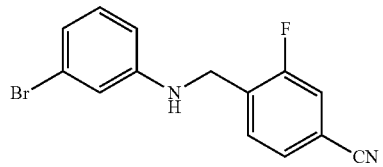 [SMILES: N#Cc1ccc(CNc2cccc(Br)c2)c(F)c1]

Compound of Formula 6-1 (4-(bromomethyl)-3-fluorobenzonitrile; 1.93 g, 9.02 mmol) was dissolved in acetonitrile (20 mL), and then 3-bromoaniline (1.18 mL, 10.8 mmol) and N,N-diisopropylethylamine (2.40 mL, 13.5 mmol) were added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 6-2 (2.57 g, 93%) in the form of a light yellow liquid.

Formula 6-3: 4-((3-bromophenylamino)methyl)-3-fluorobenzoic acid

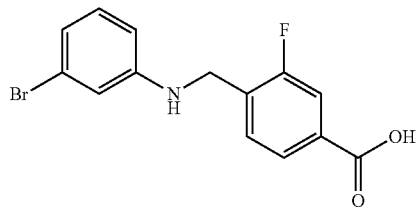 [SMILES: O=C(O)c1ccc(CNc2cccc(Br)c2)c(F)c1]

Compound of Formula 6-2 (4-((3-bromophenylamino)methyl)-3-fluorobenzonitrile; 2.57 g, 8.42 mmol) and lithium hydroxide monohydrate (3.53 g, 84.2 mmol) were dissolved in methanol (20 mL)/water (10 mL) and stirred under reflux for 16 hours. Then, the concentrate was obtained by removing the solvent from the reaction mixture under reduced pressure. 1 N hydrochloric acid aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure to give the desired compound of Formula 6-3 (2.57 g, 94%) in the form of a light yellow solid.

Formula 6-4; methyl 4-((3-bromophenylamino)methyl)-3-fluorobenzoate

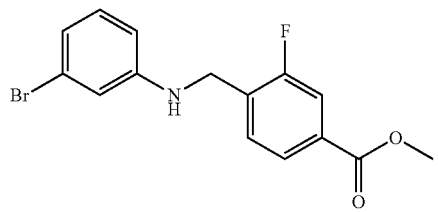 [SMILES: COC(=O)c1ccc(CNc2cccc(Br)c2)c(F)c1]

Compound of Formula 6-3 (4-((3-bromophenylamino)methyl)-3-fluorobenzoic acid; 2.57 g, 7.93 mmol), methanol (6.43 mL, 159 mmol), and N,N-diisopropylethylamine (4.21 mL, 23.8 mmol) were dissolved in THF (50 mL), and then 1-ethyl-3-[3-dimethylaminopropyl]carbodiimide hydrochloride (EDC, 3.04 g, 15.9 mmol) and 1-hydroxybenzotriazole hydrate (HOBt, 2.14 g, 15.9 mmol) were added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20%) to give the desired compound of Formula 6-4 (2.48 g, 93%) in the form of a yellow liquid.

Formula 6-5: methyl 4-(((3-bromophenyl)((4-nitrophenoxy)carbonyl)amino)methyl)-3-fluorobenzoate

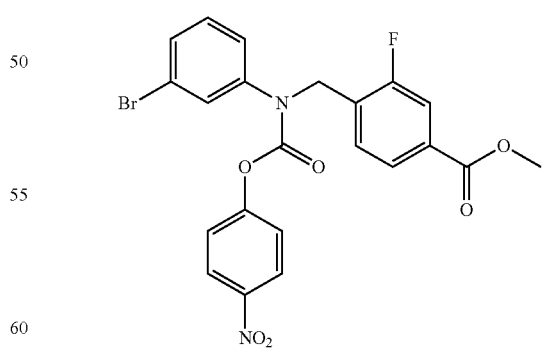

Compound of Formula 6-4 (methyl 4-((3-bromophenylamino)methyl)-3-fluorobenzoate; 2.48 g, 7.33 mmol), 4-nitrophenyl chloroformate (1.63 g, 8.07 mmol), and potassium carbonate (1.52 g, 11.0 mmol) were dissolved in acetonitrile (30 mL) at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure to give the desired compound of Formula 6-5 (3.40 g, 92%) in the form of a yellow liquid.

Formula 6-6: methyl 4-((N-(3-bromophenyl)morpholine-4-carboxamido)methyl)-3-fluorobenzoate

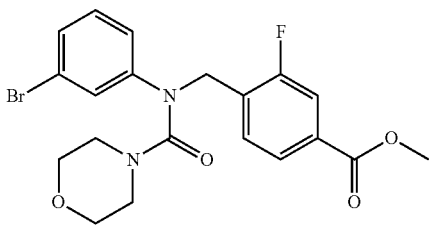 [SMILES: COC(=O)c1ccc(CN(C(=O)N2CCOCC2)c2cccc(Br)c2)c(F)c1]

Compound of Formula 6-5 (methyl 4-(((3-bromophenyl)((4-nitrophenoxy)carbonyl)amino)methyl)-3-fluorobenzoate; 1.80 g, 3.58 mmol), morpholine (0.944 mL, 10.7 mmol), and potassium carbonate (2.47 g, 17.9 mmol) were dissolved in dimethylformamide (15 mL) at 50° C. and stirred at the same temperature for 16 hours. Then, saturated ammonium chloride aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30-60%) to give the desired compound of Formula 6-6 (1.58 g, 98%) in the form of a yellow liquid.

Compound 487: N-(3-bromophenyl)-N-(2-fluoro-4-(hydroxycarbamoyl)benzyl)morpholine-4-carboxamide

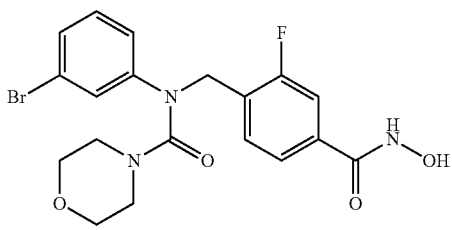 [SMILES: O=C(NO)c1ccc(CN(C(=O)N2CCOCC2)c2cccc(Br)c2)c(F)c1]

Compound of Formula 6-6 (methyl 4-((N-(3-bromophenyl)morpholine-4-carboxamido)methyl)-3-fluorobenzoate; 0.200 g, 0.443 mmol) was dissolved in methanol (10 mL), hydroxylamine (50.0 wt % aqueous solution; 1.90 mL, 31.0 mmol) was added at room temperature, and then potassium hydroxide (0.249 g, 4.43 mmol) was added and stirred at the same temperature for 30 minutes. Then, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (2 mL) and diethylether (20 mL) were added to the concentrate and stirred. Then, the precipitated solid was filtered and dried to give the desired Compound 487 (0.162 g, 81%) in the form of a light brown solid.
$^1$H NMR (400 MHz, DMSO-$d_6$) δ 11.23 (brs, 1H), 9.14 (brs, 1H), 7.54-7.45 (m, 3H), 7.40 (s, 1H), 7.31-7.27 (m, 2H), 7.15 (m, 1H), 4.88 (s, 2H), 3.41-3.38 (m, 4H), 3.14-3.12 (m, 4H). MS (ESI) m/z 452, 454 (M$^+$+H).

Example 112: Synthesis of Compound 488

Formula 6-6: methyl 4-((N-(3-bromophenyl)-4-hydroxypiperidine-1-carboxamido)methyl)-3-fluorobenzoate

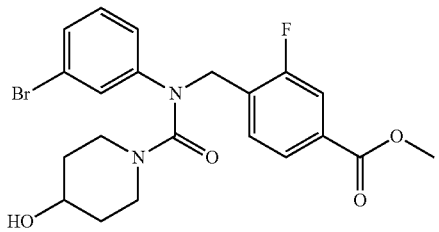 [SMILES: COC(=O)c1ccc(CN(C(=O)N2CCC(O)CC2)c2cccc(Br)c2)c(F)c1]

Compound of Formula 6-5 (methyl 4-(((3-bromophenyl)((4-nitrophenoxy)carbonyl)amino)methyl)-3-fluorobenzoate; 1.60 g, 3.18 mmol), 4-hydroxypiperidine (0.965 g, 9.54 mmol), and potassium carbonate (2.20 g, 15.9 mmol) were dissolved in dimethylformamide (15 mL) at 50° C. and stirred at the same temperature for 16 hours. Then, saturated ammonium chloride aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50-80%) to give the desired compound of Formula 6-6 (1.16 g, 78%) in the form of a yellow liquid.

Compound 488: N-(3-bromophenyl)-N-(2-fluoro-4-(hydroxycarbamoyl)benzyl)-4-hydroxypiperidine-1-carboxamide

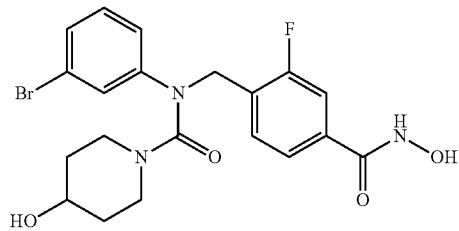 [SMILES: O=C(NO)c1ccc(CN(C(=O)N2CCC(O)CC2)c2cccc(Br)c2)c(F)c1]

Compound of Formula 6-6 (methyl 4-((N-(3-bromophenyl)-4-hydroxypiperidine-1-carboxamido)methyl)-3-fluorobenzoate; 0.200 g, 0.430 mmol) was dissolved in methanol (10 mL), hydroxylamine (50.0 wt % aqueous solution; 1.84 mL, 30.1 mmol) was added at room temperature, and then potassium hydroxide (0.241 g, 4.30 mmol) was added and stirred at the same temperature for 30 minutes. Then, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (2 mL) and diethylether (20 mL) were added to the concentrate and stirred. Then, the precipitated solid was filtered and dried to give the desired Compound 488 (0.101 g, 50%) in the form of a light yellow solid.

$^1$H NMR (400 MHz, DMSO-d$_6$) δ 11.23 (brs, 1H), 9.14 (brs, 1H), 7.63-7.46 (m, 3H), 7.32 (s, 1H), 7.27-7.24 (m, 2H), 6.90 (m, 1H), 4.85 (s, 2H), 4.68 (s, 1H), 3.55-3.45 (m, 3H), 2.87-2.82 (m, 2H), 1.56-1.53 (m, 2H), 1.15-1.12 (m, 2H). MS (ESI) m/z 466, 468 (M$^+$+H).

Example 113: Synthesis of Compound 489

Compound 489: tert-butyl 4-(3-(N-(4-(hydroxycarbamoyl)benzyl)morpholine-4-carboxamido)phenyl)piperidine-1-carboxylate

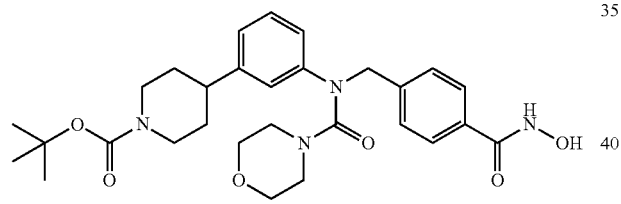

Compound of Formula 4-4 (tert-butyl 4-(3-(N-(4-(methoxycarbonyl)benzyl)morpholine-4-carboxamido)phenyl)piperydine-1-carboxylate; 0.100 g, 0.186 mmol) was dissolved in methanol (10 mL), hydroxylamine (50.0 wt % aqueous solution; 1.14 mL, 18.6 mmol) was added at room temperature, and then potassium hydroxide (0.104 g, 1.86 mmol) was added and stirred at the same temperature for 30 minutes. Then, the reaction mixture was concentrated under reduced pressure until its volume became about 1 mL, and saturated sodium hydrogen carbonate aqueous solution (1 mL) was added and stirred. Then, the precipitated solid was filtered and dried to give the desired Compound 489 (0.086 g, 86%) in the form of a white solid.

$^1$H NMR (400 MHz, DMSO-d$_6$) δ 7.63 (d, 2H, J=8.4 Hz), 7.34 (d, 2H, J=8.3 Hz), 7.22 (t, 1H, J=7.6 Hz), 6.99-6.93 (m, 3H), 4.84 (s, 2H), 4.06-4.02 (m, 2H), 3.40-3.37 (m, 4H), 3.12-3.10 (m, 4H), 2.66-2.63 (m, 2H), 1.71-1.68 (m, 2H), 1.44 (m, 3H), 1.40 (s, 9H). MS (ESI) m/z 539 (M$^+$+H).

Example 114: Synthesis of Compound 490

Formula 4-4: tert-butyl 4-(3-(N-(4-(methoxycarbonyl)benzyl)morpholine-4-carboxamido)phenyl)piperidine-1-carboxylate

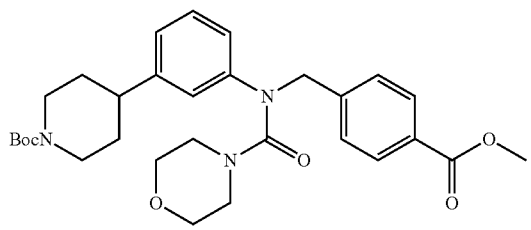 [SMILES: COC(=O)c1ccc(CN(C(=O)N2CCOCC2)c2cccc(C3CCN(C(=O)OC(C)(C)C)CC3)c2)cc1]

Compound of Formula 4-1 (tert-butyl 4-(3-(N-(4-(methoxycarbonyl)benzyl)morpholine-4-carboxamido)phenyl)-5,6-dihydro pyridine-1(2H)-carboxylate; 3.28 g, 6.12 mmol) was dissolved in THF (30 mL) at room temperature, Pd/C (130 mg) was slowly added, a hydrogen balloon was attached, and then the mixture was stirred at the same temperature for 16 hours. The reaction mixture was filtered through celite pad, and the filtrate was concentrated under reduced pressure to give the desired compound of Formula 4-4 (3.28 g, 99%) in the form of a white solid.

Formula 4-5: methyl 4-((N-(3-(piperidine-4-yl)phenyl)morpholine-4-carboxamido)methyl)benzoate hydrochloride

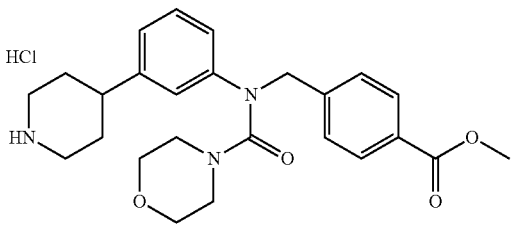 [SMILES: Cl ; COC(=O)c1ccc(CN(C(=O)N2CCOCC2)c2cccc(C3CCNCC3)c2)cc1]

Compound of Formula 4-4 (tert-butyl 4-(3-(N-(4-(methoxycarbonyl)benzyl)morpholine-4-carboxamido)phenyl)piperidin-1-carboxylate; 3.10 g, 5.77 mmol) was dissolved in 1,4-dioxane (10 mL), and then hydrogen chloride (4.0 M 1,4-dioxane solution; 14.4 mL, 57.7 mmol) was added at room temperature and stirred at the same temperature for 3 hours. The reaction mixture was concentrated under reduced pressure to give the desired compound of Formula 4-5 (2.65 g, 99%) in the form of a white solid.

Formula 4-6: methyl 4-((N-(3-(1-acetylpiperidin-4-yl)phenyl)morpholine-4-carboxamido)methyl)benzoate

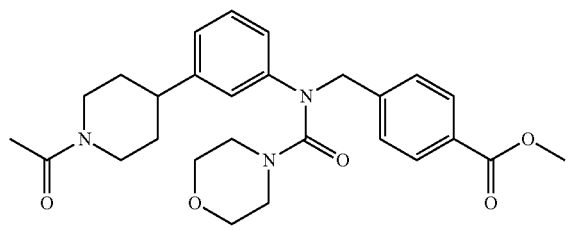 [SMILES: COC(=O)c1ccc(CN(C(=O)N2CCOCC2)c2cccc(C3CCN(C(C)=O)CC3)c2)cc1]

Compound of Formula 4-5 (methyl 4-((N-(3-(piperidine-4-yl)phenyl)morpholine-4-carboxamido)methyl)benzoate hydrochloride; 0.150 g, 0.316 mmol) and N,N-diisopropylethylamine (0.168 mL, 0.949 mmol) were dissolved in dichloromethane (3 mL), and then acetic acid anhydride (0.065 g, 0.633 mmol) was added at room temperature and stirred at the same temperature for 1 hour. Saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=80-100%) to give the desired compound of Formula 4-6 (0.148 g, 98%) in the form of a colorless liquid.

Compound 490: N-(3-(1-acetylpiperidin-4-yl)phenyl)-N-(4-(hydroxycarbamoyl)benzyl)morpholine-4-carboxamide

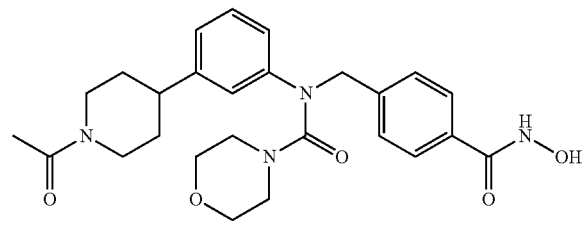 [SMILES: CC(=O)N1CCC(c2cccc(N(Cc3ccc(C(=O)NO)cc3)C(=O)N3CCOCC3)c2)CC1]

Compound of Formula 4-6 (methyl 4-((N-(3-(1-acetylpiperidin-4-yl)phenyl)morpholine-4-carboxamido)methyl)benzoate; 0.148 g, 0.309 mmol) was dissolved in methanol (10 mL), hydroxylamine (50.0 wt % aqueous solution; 1.32 mL, 21.6 mmol) was added at room temperature, and then potassium hydroxide (0.173 g, 3.09 mmol) was added and stirred at the same time for 30 minutes. The concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (5 mL) and hexane (20 mL) were added to the concentrate and stirred. Then, the precipitated solid was filtered and dried to give the desired Compound 490 (0.036 g, 24%) in the form of a white solid.

$^1$H NMR (400 MHz, DMSO-d$_6$) δ 11.12 (brs, 1H), 9.03 (brs, 1H), 7.63 (d, 2H, J=8.4 Hz), 7.33 (d, 2H, J=8.4 Hz), 7.22 (t, 1H, J=7.9 Hz), 6.99-6.93 (m, 3H), 4.84 (s, 2H), 4.50 (m, 1H), 3.89 (m, 1H), 3.39-3.36 (m, 4H), 3.12-3.10 (m, 4H), 2.68 (m, 1H), 2.57-2.53 (m, 2H), 2.01 (s, 3H), 1.74-1.70 (m, 2H), 1.54 (m, 1H), 1.38 (m, 1H). MS (ESI) m/z 481 (M$^+$+H).

Example 115: Synthesis of Compound 491

Formula 4-6: methyl 4-((N-(3-(1-(methylsulfonyl)piperidin-4-yl)phenyl)morpholine-4-carboxamido)methyl)benzoate

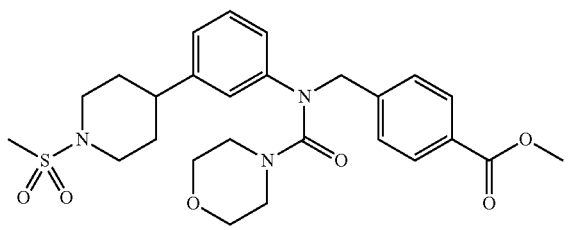

Compound of Formula 4-5 (methyl 4-((N-(3-(piperidine-4-yl)phenyl)morpholine-4-carboxamido)methyl)benzoate hydrochloride; 0.150 g, 0.316 mmol) and N,N-diisopropylethylamine (0.168 mL, 0.949 mmol) were dissolved in dichloromethane (3 mL), and then methanesulfonyl chloride (0.049 ml, 0.633 mmol) was added at room temperature and stirred at the same temperature for 1 hour. Saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50-100%) to give the desired compound of Formula 4-6 (0.119 g, 73%) in the form of a colorless liquid.

Compound 491: N-(4-(hydroxycarbamoyl)benzyl)-N-(3-(1-(methylsulfonyl)piperidin-4-yl)phenyl)morpholine-4-carboxamide

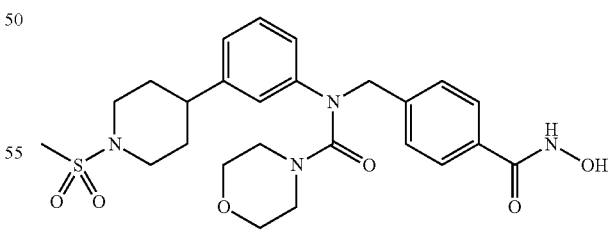

Compound of Formula 4-6 (methyl 4-((N-(3-(1-(methylsulfonyl)piperidin-4-yl)phenyl)morpholine-4-carboxamido)methyl)benzoate; 0.119 g, 0.231 mmol) was dissolved in methanol (10 mL), hydroxylamine (50.0 wt % aqueous solution; 0.988 mL, 16.2 mmol) was added at room temperature, and then potassium hydroxide (0.129 g, 2.31 mmol) was added and stirred at the same time for 30 minutes. The concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (5 mL) and hexane (20 mL) were added to the concentrate and stirred. Then, the precipitated solid was filtered and dried to give the desired Compound 491 (0.043 g, 36%) in the form of a white solid.

$^1$H NMR (400 MHz, DMSO-$d_6$) δ 11.13 (brs, 1H), 8.98 (brs, 1H), 7.64 (d, 2H, J=8.2 Hz), 7.34 (d, 2H, J=8.3 Hz), 7.23 (t, 1H, J=7.8 Hz), 7.02 (s, 1H), 6.97 (d, 2H, J=7.9 Hz), 4.85 (s, 2H), 3.66-3.63 (m, 2H), 3.38-3.36 (m, 4H), 3.28-3.26 (m, 2H), 3.12-3.10 (m, 4H), 2.79-2.76 (m, 2H), 2.66-2.61 (m, 2H), 1.82-1.79 (m, 2H), 1.64-1.60 (m, 2H). MS (ESI) m/z 517 (M$^+$+H).

Example 116: Synthesis of Compound 492

Formula 4-6: methyl 4-((N-(3-(1-(isopropylcarbamoyl)piperidin-4-yl)phenyl)morpholine-4-carboxamido)methyl)benzoate

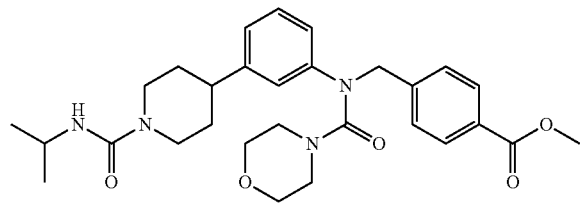 [SMILES: COC(=O)c1ccc(CN(C(=O)N2CCOCC2)c2cccc(C3CCN(C(=O)NC(C)C)CC3)c2)cc1]

Compound of Formula 4-5 (methyl 4-((N-(3-(piperidine-4-yl)phenyl)morpholine-4-carboxamido)methyl)benzoate hydrochloride; 0.150 g, 0.316 mmol) and N,N-diisopropylethylamine (0.168 mL, 0.949 mmol) were dissolved in dichloromethane (3 mL), and then isopropyl isocyanate (0.054 ml, 0.633 mmol) was added at room temperature and stirred at the same temperature for 1 hour. Saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50-100%) to give the desired compound of Formula 4-6 (0.101 g, 61%) in the form of a white solid.

Compound 492: N-(4-(hydroxycarbamoyl)benzyl)-N-(3-(1-(isopropylcarbamoyl)piperidin-4-yl)phenyl)morpholine-4-carboxamide

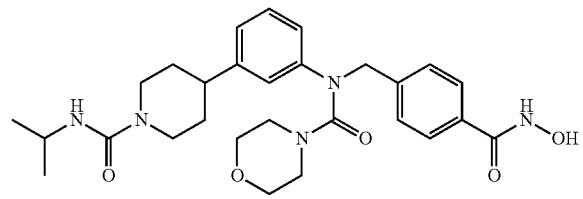 [SMILES: CC(C)NC(=O)N1CCC(c2cccc(N(Cc3ccc(C(=O)NO)cc3)C(=O)N3CCOCC3)c2)CC1]

Compound of Formula 4-6 (methyl 4-((N-(3-(1-(isopropylcarbamoyl)piperidin-4-yl)phenyl)morpholine-4-carboxamido)methyl)benzoate; 0.101 g, 0.193 mmol) was dissolved in methanol (10 mL), hydroxylamine (50.0 wt % aqueous solution; 0.827 mL, 13.5 mmol) was added at room temperature, and then potassium hydroxide (0.108 g, 1.93 mmol) was added and stirred at the same time for 30 minutes. The concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (5 mL) and hexane (20 mL) were added to the concentrate and stirred. Then, the precipitated solid was filtered and dried to give the desired Compound 492 (0.047 g, 46%) in the form of a light brown solid.

$^1$H NMR (400 MHz, DMSO-$d_6$) δ 7.63 (d, 2H, J=8.2 Hz), 7.34 (d, 2H, J=8.2 Hz), 7.22 (t, 1H, J=8.2 Hz), 6.97-6.92 (m, 3H), 6.13 (d, 1H, J=7.5 Hz), 4.84 (s, 2H), 4.08-4.05 (m, 2H), 3.76 (m, 1H), 3.34 (m, 4H), 3.11 (m, 4H), 2.69-2.63 (m, 3H), 1.67-1.64 (m, 2H), 1.47-1.42 (m, 2H), 1.04 (d, 6H, J=6.6 Hz). MS (ESI) m/z 524 (M$^+$+H).

Example 117: Synthesis of Compound 493

Compound 493: N-(4-(hydroxycarbamoyl)benzyl)-N-(3-(piperidin-4-yl)phenyl)morpholine-4-carboxamide hydrochloride

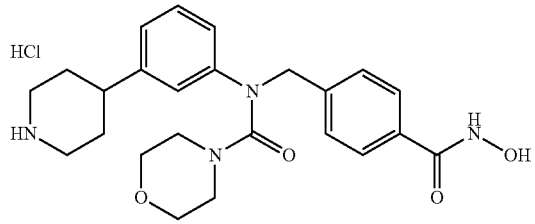 [SMILES: Cl ; O=C(NO)c1ccc(CN(C(=O)N2CCOCC2)c2cccc(C3CCNCC3)c2)cc1]

Compound 489 (tert-butyl 4-(3-(N-(4-(hydroxycarbamoyl)benzyl)morpholine-4-carboxamido)phenyl)piperidine-1-carboxylate; 0.050 g, 0.093 mmol) was dissolved in 1,4-dioxane (3 mL), hydrogen chloride (4.0 M 1,4-dioxane solution; 0.696 mL, 2.79 mmol) was then added at room temperature and stirred at the same temperature, and the reaction mixture was concentrated under reduced pressure. Diethylether (10 mL) was added to the concentrate and stirred. Then, the precipitated solid was filtered and dried to give the desired Compound 493 (0.027 g, 61%) in the form of a brown solid.

$^1$H NMR (400 MHz, DMSO-$d_6$) δ 11.16 (brs, 1H), 9.04 (brs, 1H), 8.88 (brs, 1H), 7.64 (d, 2H, J=7.8 Hz), 7.37-7.24 (m, 3H), 7.12-6.98 (m, 2H), 4.87 (s, 2H), 3.26 (m, 3H), 3.11 (m, 4H), 2.94 (m, 2H), 2.82 (m, 2H), 1.83-1.78 (m, 3H), 1.39 (m, 4H). MS (ESI) m/z 439 (M$^+$+H).

Example 118: Synthesis of Compound 494

Formula 1-4: methyl 4-((4-acetyl-N-(3-(trifluoromethyl)phenyl)piperazine-1-carboxamido)methyl)benzoate

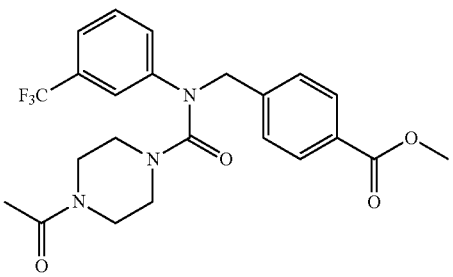

Compound of Formula 1-3 (methyl 4-((((4-nitrophenoxy)carbonyl)(3-(trifluoromethyl)phenyl)amino)methyl)benzoate; 0.21 g, 0.45 mmol) was dissolved in dimethylformamide (3 mL), and potassium carbonate (0.19 g, 1.34 mmol) and 1-(piperazin-1-yl)ethanone (0.06 g, 0.45 mmol) were then added. The mixture was reacted at 60° C. for 1 day and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=60%) to give the desired compound of Formula 1-4 (0.16 g, 75%).

Compound 494: 4-acetyl-N-(4-(hydroxycarbamoyl)benzyl)-N-(3-(trifluoromethyl)phenyl)piperazine-1-carboxamide

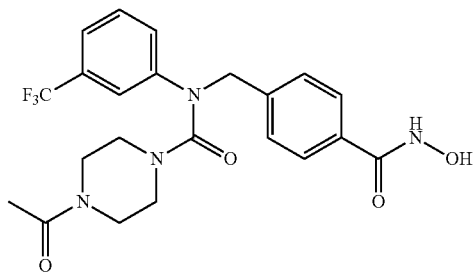

Compound of Formula 1-4 (methyl 4-((4-acetyl-N-(3-(trifluoromethyl)phenyl)piperazine-1-carboxamido)methyl)benzoate; 0.16 g, 0.33 mmol) was dissolved in methanol (5 mL), and hydroxylamine (50 wt % aqueous solution; 0.21 mL) and potassium hydroxide (0.09 g, 1.67 mmol) were then added and stirred overnight. After completion of the reaction, the methanol was removed by distillation under reduced pressure, and the organic layer was extracted with ethyl acetate and water, dehydrated with anhydrous sodium sulfate, filtered, and then concentrated under reduced pressure. The residue was purified by column chromatography (silica; methanol/dichloromethane=10%) to give the desired Compound 494 (0.02 g, 10%) in the form of a yellow solid.

$^1$H NMR (400 MHz, DMSO-$d_6$) δ 11.16 (brs, 1H), 9.17 (brs, 1H), 7.65 (d, 2H, J=8.2 Hz), 7.53-7.36 (m, 6H), 4.95 (s, 2H), 3.29 (m, 4H), 3.15 (m, 4H), 1.94 (s, 3H). MS (ESI) m/z 465 (M$^+$+H).

Example 119: Synthesis of Compound 495

Formula 1-4: (R)-methyl 4-((3-fluoro-N-(3-(trifluoromethyl)phenyl)pyrrolidine-1-carboxamido)methyl)benzoate

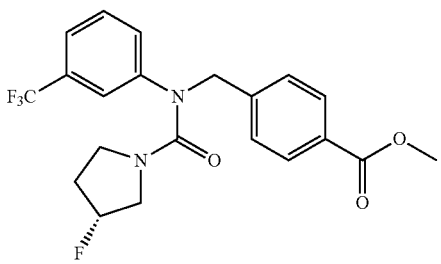 [SMILES: COC(=O)c1ccc(CN(C(=O)N2CC[C@@H](F)C2)c2cccc(C(F)(F)F)c2)cc1]

Compound of Formula 1-3 (methyl 4-((((4-nitrophenoxy)carbonyl)(3-(trifluoromethyl)phenyl)amino)methyl)benzoate; 0.23 g, 0.49 mmol) was dissolved in dimethylformamide (5 mL), and potassium carbonate (0.20 g, 1.48 mmol) and (R)-3-fluoropyrrolidine hydrochloride (0.12 g, 0.99 mmol) were then added. The mixture was reacted at 60° C. for 1 day and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=40%) to give the desired compound of Formula 1-4 (0.18 g, 87%).

Compound 495: (R)-3-fluoro-N-(4-(hydroxycarbamoyl)benzyl)-N-(3-(trifluoromethyl)phenyl)pyrrolidine-1-carboxamide

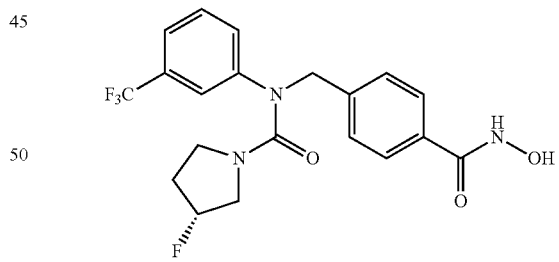

Compound of Formula 1-4 ((R)-methyl 4-((3-fluoro-N-(3-(trifluoromethyl)phenyl)pyrrolidine-1-carboxamido)methyl)benzoate; 0.18 g, 0.43 mmol) was dissolved in methanol (5 mL), and hydroxylamine (50 wt % aqueous solution; 0.26 mL) and potassium hydroxide (0.12 g, 2.16 mmol) were then added and stirred overnight. After completion of the reaction, the methanol was removed by distillation under reduced pressure, and the organic layer was extracted with ethyl acetate and saturated potassium carbonate aqueous solution, dehydrated with anhydrous sodium sulfate, filtered, and then concentrated under reduced pressure. The residue was purified by column chromatography (silica; methanol/dichloromethane=10%) to give the desired Compound 495 (0.10 g, 54%) in the form of a white solid.

$^1$H NMR (400 MHz, DMSO-$d_6$) δ 11.14 (brs, 1H), 9.00 (brs, 1H), 7.64 (d, 2H, J=7.7 Hz), 7.52 (t, 1H, J=7.9 Hz), 7.45-7.35 (m, 5H), 5.19 (d, 1H, J=53.1 Hz), 4.99-4.89 (m, 2H), 3.32-3.18 (m, 3H), 3.09-3.02 (m, 1H), 1.99-1.83 (m, 2H). MS (ESI) m/z 426 (M$^+$+H).

Example 120: Synthesis of Compound 496

Formula 1-4: (S)-methyl 4-((3-fluoro-N-(3-(trifluoromethyl)phenyl)pyrrolidine-1-carboxamido)methyl)benzoate

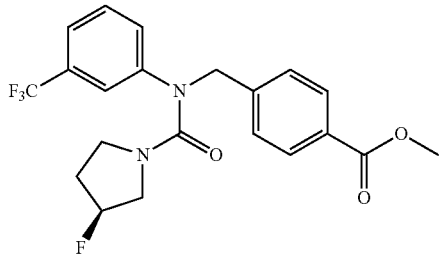

Compound of Formula 1-3 (methyl 4-((((4-nitrophenoxy)carbonyl)(3-(trifluoromethyl)phenyl)amino)methyl)benzoate; 0.29 g, 0.62 mmol) was dissolved in dimethylformamide (5 mL), and potassium carbonate (0.26 g, 1.86 mmol) and (S)-3-fluoropyrrolidine hydrochloride (0.16 g, 1.24 mmol) were then added. The mixture was reacted at 60° C. for 1 day and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=40%) to give the desired compound of Formula 1-4 (0.20 g, 75%).

Compound 496: (S)-3-fluoro-N-(4-(hydroxycarbamoyl)benzyl)-N-(3-(trifluoromethyl)phenyl)pyrrolidine-1-carboxamide

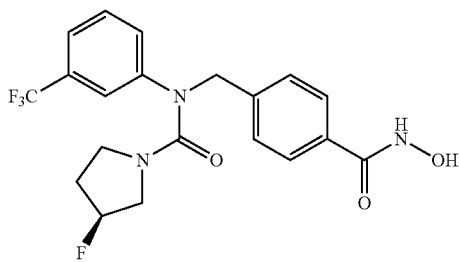

Compound of Formula 1-4 ((S)-methyl 4-((3-fluoro-N-(3-(trifluoromethyl)phenyl)pyrrolidine-1-carboxamido)methyl)benzoate; 0.20 g, 0.47 mmol) was dissolved in methanol (5 mL), and hydroxylamine (50 wt % aqueous solution; 0.29 mL) and potassium hydroxide (0.13 g, 2.33 mmol) were then added and stirred overnight. After completion of the reaction, the methanol was removed by distillation under reduced pressure, and the organic layer was extracted with ethyl acetate and saturated potassium carbonate aqueous solution, dehydrated with anhydrous sodium sulfate, filtered, and then concentrated under reduced pressure. The residue was purified by column chromatography (silica; methanol/dichloromethane=10%) to give the desired Compound 496 (0.14 g, 72%) in the form of a white solid.

$^1$H NMR (400 MHz, DMSO-$d_6$) δ 11.15 (brs, 1H), 10.18 (brs, 1H), 9.00 (brs, 1H), 7.65 (d, 2H, J=8.2 Hz), 7.53-7.49 (m, 1H), 7.45-7.33 (m, 5H), 5.19 (d, 1H, J=53.2 Hz), 4.99-4.89 (m, 2H), 3.36-3.19 (m, 3H), 3.09-3.02 (m, 1H), 1.99-1.83 (m, 2H). MS (ESI) m/z 426 (M$^+$+H).

Example 121: Synthesis of Compound 497

Formula 1-4: (R)-methyl 4-((2-(hydroxymethyl)-N-(3-(trifluoromethyl)phenyl)pyrrolidine-1-carboxamido)methyl)benzoate

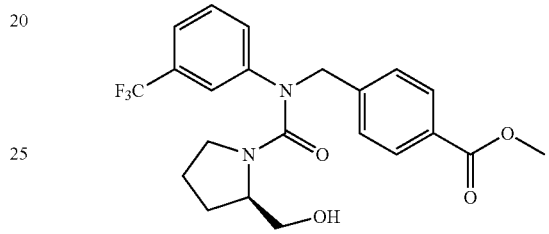

Compound of Formula 1-3 (methyl 4-((((4-nitrophenoxy)carbonyl)(3-(trifluoromethyl)phenyl)amino)methyl)benzoate; 0.23 g, 0.48 mmol) was dissolved in dimethylformamide (5 mL), and potassium carbonate (0.20 g, 1.44 mmol) and (R)-pyrrolidin-2-ylmethanol (0.10 g, 0.96 mmol) were then added. The mixture was reacted at 60° C. for 1 day and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=40%) to give the desired compound of Formula 1-4 (0.15 g, 73%).

Compound 497: (R)—N-(4-(hydroxycarbamoyl)benzyl)-2-(hydroxymethyl)-N-(3-(trifluoromethyl)phenyl)pyrrolidine-1-carboxamide

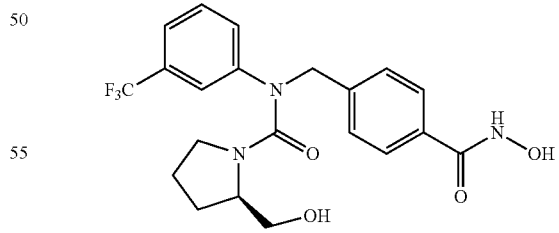

Compound of Formula 1-4 ((R)-methyl 4-((2-(hydroxymethyl)-N-(3-(trifluoromethyl)phenyl)pyrrolidine-1-carboxamido)methyl)benzoate; 0.15 g, 0.39 mmol) was dissolved in methanol (5 mL), and hydroxylamine (50 wt % aqueous solution; 0.21 mL) and potassium hydroxide (0.10 g, 1.74 mmol) were then added and stirred overnight. After completion of the reaction, the methanol was removed by distillation under reduced pressure, and the organic layer was extracted with ethyl acetate and saturated potassium carbonate aqueous solution, dehydrated with anhydrous sodium sulfate, filtered, and then concentrated under reduced pressure. The residue was purified by column chromatography (silica; methanol/dichloromethane=10%) to give the desired Compound 497 (0.04 g, 28%) in the form of a white solid.

$^1$H NMR (400 MHz, DMSO-d$_6$) δ 11.13 (brs, 1H), 8.98 (brs, 1H), 7.84-7.82 (m, 3H), 7.65-7.63 (m, 1H), 7.41-7.17 (m, 4H), 4.42 (s, 2H), 3.88-3.63 (m, 2H), 3.43-3.30 (m, 3H), 1.67-1.42 (m, 4H). MS (ESI) m/z 438 (M$^+$+H).

Example 122: Synthesis of Compound 498

Formula 1-4: (S)-methyl 4-((2-(trifluoromethyl)-N-(3-(trifluoromethyl)phenyl)pyrrolidine-1-carboxamido)methyl)benzoate

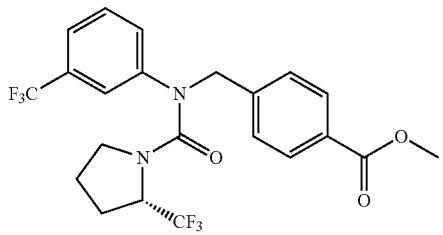 [SMILES: COC(=O)c1ccc(CN(C(=O)N2CCC[C@H]2C(F)(F)F)c2cccc(C(F)(F)F)c2)cc1]

Compound of Formula 1-3 (methyl 4-((((4-nitrophenoxy) carbonyl)(3-(trifluoromethyl)phenyl)amino)methyl)benzoate; 0.22 g, 0.47 mmol) was dissolved in dimethylformamide (5 mL), and potassium carbonate (0.20 g, 1.42 mmol) and (S)-2-(trifluoromethyl)pyrrolidine (0.13 g, 0.95 mmol) were then added. The mixture was reacted at 60° C. for 1 day and then diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=30%) to give the desired compound of Formula 1-4 (0.17 g, 74%).

Compound 498: (S)—N-(4-(hydroxycarbamoyl) benzyl)-2-(trifluoromethyl)-N-(3-(trifluoromethyl) phenyl)pyrrolidine-1-carboxamide

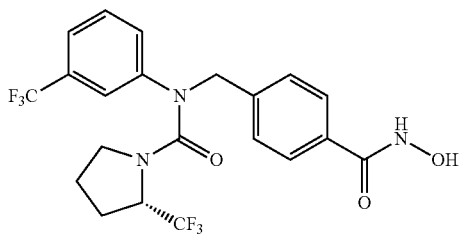 [SMILES: O=C(NO)c1ccc(CN(C(=O)N2CCC[C@H]2C(F)(F)F)c2cccc(C(F)(F)F)c2)cc1]

Compound of Formula 1-4 ((S)-methyl 4-((2-(trifluoromethyl)-N-(3-(trifluoromethyl)phenyl)pyrrolidine-1-carboxamido)methyl)benzoate; 0.17 g, 0.35 mmol) was dissolved in methanol (5 mL), and hydroxylamine (50 wt % aqueous solution; 0.21 mL) and potassium hydroxide (0.10 g, 1.74 mmol) were then added and stirred overnight. After completion of the reaction, the methanol was removed by distillation under reduced pressure, and the organic layer was extracted with ethyl acetate and saturated potassium carbonate aqueous solution, dehydrated with anhydrous sodium sulfate, filtered, and then concentrated under reduced pressure. The residue was purified by column chromatography (silica; methanol/dichloromethane=10%) to give the desired Compound 498 (0.07 g, 44%) in the form of a white solid.

$^1$H NMR (400 MHz, DMSO-d$_6$) δ 11.13 (brs, 1H), 8.98 (brs, 1H), 7.84-7.82 (m, 3H), 7.65-7.63 (m, 1H), 7.41-7.17 (m, 4H), 4.42 (s, 2H), 4.17-4.15 (m, 1H), 3.40-3.30 (m, 2H), 1.67-1.42 (m, 4H). MS (ESI) m/z 438 (M$^+$+H).

Example 123: Synthesis of Compound 499

Formula 10-2: methyl 4-((3-(hydroxymethyl)phenylamino)methyl)benzoate

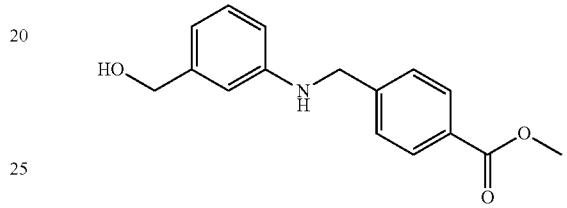

Compound of Formula 10-1 (3-hydroxymethylaniline; 5.00 g, 40.6 mmol), methyl 4-formylbenzoate (8.00 g, 48.7 mmol) and acetic acid (4.64 mL, 81.2 mmol) were dissolved in methanol (100 mL) and stirred at room temperature for 30 minutes, and then sodium cyanoborohydride (3.83 g, 60.9 mmol) was added and stirred at the same temperature for 16 hours. Then, the concentrate was obtained by removing the solvent from the reaction mixture under reduced pressure. Saturated sodium hydrogen carbonate aqueous solution was poured into the obtained concentrate, and then the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20-50%) to give the desired compound of Formula 10-2 (10.9 g, 99%) in the form of a light yellow solid.

Formula 10-3: methyl 4-(((3-(hydroxymethyl)phenyl)((4-nitrophenoxy)carbonyl)amino)methyl)benzoate

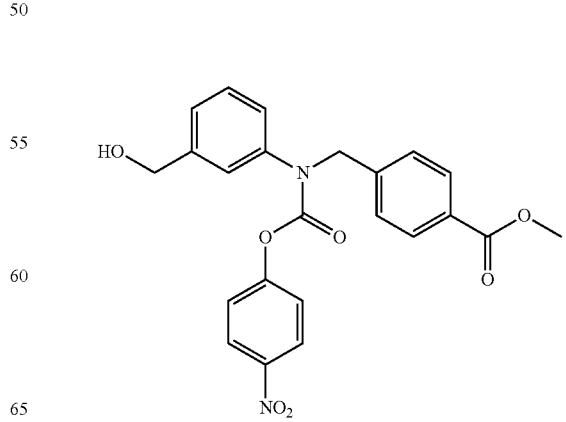

Compound of Formula 10-2 (methyl 4-((3-(hydroxymethyl)phenylamino)methyl)benzoate; 1.60 g, 5.90 mmol) and potassium carbonate (1.63 g, 11.8 mmol) were dissolved in acetonitrile (100 mL), and then 4-nitrophenyl chloroformate (1.31 g, 6.49 mmol) was added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure to give the desired compound of Formula 10-3 (2.43 g, 94%) in the form of a yellow liquid.

Formula 10-4: methyl 4-((N-(3-(hydroxymethyl)phenyl)morpholine-4-carboxamido)methyl)benzoate

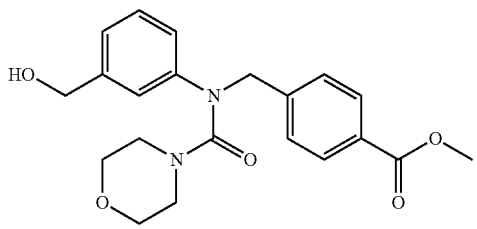 [SMILES: COC(=O)c1ccc(CN(C(=O)N2CCOCC2)c2cccc(CO)c2)cc1]

Compound of Formula 10-3 (methyl 4-(((3-(hydroxymethyl)phenyl)((4-nitrophenoxy)carbonyl)amino)methyl)benzoate; 2.43 g, 5.57 mmol), morpholine (2.45 mL, 27.8 mmol) and potassium carbonate (3.85 g, 27.8 mmol) were dissolved in dimethylformamide (20 mL) at room temperature and stirred at the same temperature for 60 hours. Then, saturated ammonium chloride aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50-100%) to give the desired compound of Formula 10-4 (1.96 g, 92%) in the form of a yellow liquid.

Formula 10-5: 4-((N-(3-(hydroxymethyl)phenyl)morpholine-4-carboxamido)methyl)benzoic acid

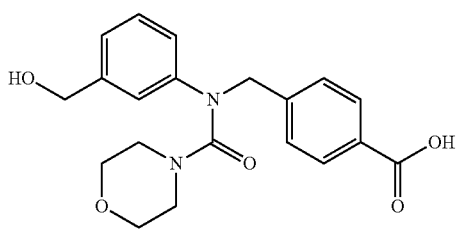 [SMILES: O=C(O)c1ccc(CN(C(=O)N2CCOCC2)c2cccc(CO)c2)cc1]

Compound of Formula 10-4 (methyl 4-((N-(3-(hydroxymethyl)phenyl)morpholine-4-carboxamido)methyl)benzoate; 1.96 g, 5.10 mmol) and lithium hydroxide monohydrate (2.14 g, 51.0 mmol) were dissolved in methanol (10 mL)/water (5 mL) and stirred at 50° C. for 16 hours. Then, the concentrate was obtained by removing the solvent from the reaction mixture under reduced pressure. 0.5 N hydrochloric acid aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure to give the desired compound of Formula 10-5 (1.82 g, 96%) in the form of a light yellow solid.

Formula 10-6: N-(3-(hydroxymethyl)phenyl)-N-(4-(tetrahydro-2H-pyran-2-yloxycarbamoyl)benzyl)morpholine-4-carboxamide

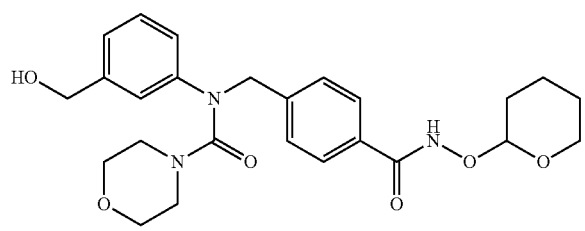 [SMILES: O=C(NOC1CCCCO1)c1ccc(CN(C(=O)N2CCOCC2)c2cccc(CO)c2)cc1]

Compound of Formula 10-5 (4-((N-(3-(hydroxymethyl)phenyl)morpholine-4-carboxamido)methyl)benzoic acid; 1.82 g, 4.91 mmol) and N,N-diisopropylethylamine (2.61 mL, 14.7 mmol) were dissolved in dichloromethane (30 mL), and then O-(tetrahydropyran-2-yl)hydroxylamine (0.748 g, 6.39 mmol) was added at room temperature. Then, 1-ethyl-3-[3-dimethylaminopropyl]carbodiimide hydrochloride (EDC, 1.88 g, 9.83 mmol) and 1-hydroxybenzotriazole hydrate (HOBt, 1.34 g, 9.83 mmol) were added and then stirred at the same temperature for 16 hours. Then, saturated sodium hydrogen carbonate aqueous solution was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=70-100%) to give the desired compound of Formula 10-6 (1.35 g, 58%) in the form of a white solid.

Compound 499: N-(4-(hydroxycarbamoyl)benzyl)-N-(3-(hydroxymethyl)phenyl)morpholine-4-carboxamide

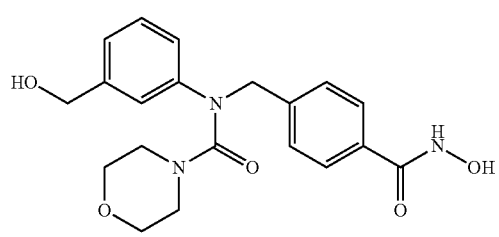 [SMILES: O=C(NO)c1ccc(CN(C(=O)N2CCOCC2)c2cccc(CO)c2)cc1]

Compound of Formula 10-6 (N-(3-(hydroxymethyl)phenyl)-N-(4-(tetrahydro-2H-pyran-2-yloxycarbamoyl)benzyl)morpholine-4-carboxamide; 0.050 g, 0.106 mmol) was dissolved in methanol (3 mL), and then hydrogen chloride (4.0 M 1,4-dioxane solution; 0.799 mL, 3.20 mmol) was added at room temperature and stirred at the same temperature for 1 hour. Then, the concentrate was obtained by removing the solvent from the reaction mixture under reduced pressure. Saturated sodium hydrogen carbonate aqueous solution was poured into the obtained concentrate, and then the organic layer was extracted with ethyl acetate. The organic layer was washed with saturated sodium chloride aqueous solution, dehydrated with anhydrous magnesium sulfate, and then concentrated under reduced pressure to give the desired Compound 499 (0.016 g, 39%) in the form of a light yellow solid.

$^1$H NMR (400 MHz, DMSO-$d_6$) δ 11.12 (brs, 1H), 8.97 (brs, 1H), 7.64 (d, 2H, J=8.2 Hz), 7.35 (d, 2H, J=8.2 Hz), 7.27 (m, 1H), 7.10 (s, 1H), 6.99-6.97 (m, 2H), 4.88 (s, 2H), 4.43 (s, 2H), 3.38 (m, 4H), 3.16 (m, 4H). MS (ESI) m/z 386 (M$^+$+H).

Example 124: Synthesis of Compound 500

Formula 10-7: methyl 4-((N-(3-(fluoromethyl)phenyl)morpholine-4-carboxamido)methyl)benzoate

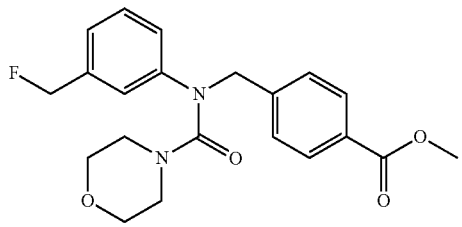 [SMILES: COC(=O)c1ccc(CN(C(=O)N2CCOCC2)c2cccc(CF)c2)cc1]

Compound of Formula 10-5 (4-((N-(3-(hydroxymethyl)phenyl)morpholine-4-carboxamido)methyl)benzoic acid; 1.25 g, 3.25 mmol) was dissolved in dichloromethane (20 mL), and then diethylaminosulfur trifluoride (DAST, 0.424 mL, 3.58 mmol) was added 0° C. and stirred at the same temperature for 1 hour. Then, saturated sodium hydrogen carbonate aqueous solution was poured into the reaction mixture, and the organic layer was extracted with dichloromethane. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30-50%) to give the desired compound of Formula 10-7 (0.617 g, 49%) in the form of a colorless liquid.

Compound 500: N-(3-(fluoromethyl)phenyl)-N-(4-(hydroxycarbamoyl)benzyl)morpholine-4-carboxamide

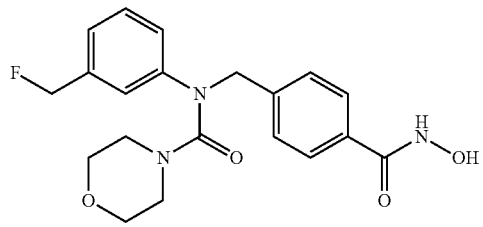

Compound of Formula 10-7 (methyl 4-((N-(3-(fluoromethyl)phenyl)morpholine-4-carboxamido)methyl)benzoate; 0.100 g, 0.259 mmol) was dissolved in methanol (10 mL), hydroxylamine (50.0 wt % aqueous solution; 1.11 mL, 18.1 mmol) was added room temperature, and then potassium hydroxide (0.145 g, 2.59 mmol) was added and stirred at the same temperature for 30 minutes. Then, the concentrate was obtained by removing the solvent from the reaction mixture under reduced pressure. saturated sodium hydrogen carbonate aqueous solution was poured into the obtained concentrate, and then the organic layer was extracted with ethyl acetate. The organic layer was washed with saturated sodium chloride aqueous solution, dehydrated with anhydrous magnesium sulfate, and then concentrated under reduced pressure. Dichloromethane (5 mL) and hexane (30 mL) were added to the concentrate and stirred. Then, the precipitated solid was filtered and dried to give the desired Compound 500 (0.089 g, 89%) in the form of a white solid.

$^1$H NMR (400 MHz, DMSO-$d_6$) δ 11.12 (brs, 1H), 8.98 (brs, 1H), 7.64 (d, 2H, J=8.3 Hz), 7.36-7.32 (m, 3H), 7.20 (s, 1H), 7.15 (d, 1H, J=7.5 Hz), 7.09 (d, 1H, J=7.4 Hz), 5.36 (d, 2H, J=47.5 Hz), 4.87 (s, 2H), 3.39 (t, 4H, J=4.6 Hz), 3.13 (t, 4H, J=4.6 Hz). MS (ESI) m/z 388 (M$^+$+H).

Example 125: Synthesis of Compound 511

Formula 6-7: methyl 4-((N-(3-(benzo[d][1,3]dioxol-5-yl)phenyl)morpholine-4-carboxamido)methyl)-3-fluorobenzoate

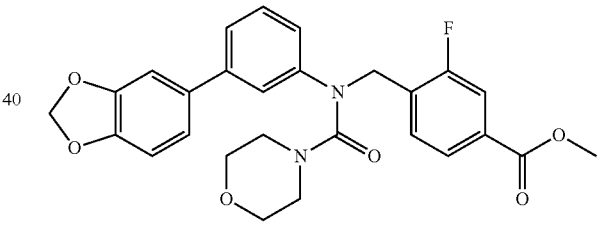

Compound of Formula 6-6 (methyl 4-((N-(3-bromophenyl)morpholine-4-carboxamido)methyl)-3-fluorobenzoate; 0.200 g, 0.443 mmol), benzo[d][1,3]dioxol-5-ylboronic acid (0.096 g, 0.576 mmol), Pd(dppf)Cl$_2$ (0.018 g, 0.022 mmol) and sodium carbonate (2.0 M aqueous solution; 0.665 mL, 1.33 mmol) were dissolved in 1,4-dioxane (2 mL) and stirred at 110° C. for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=30-60%) to give the desired compound of Formula 6-7 (0.077 g, 35%) in the form of a white solid.

Compound 511: N-(3-(benzo[d][1,3]dioxol-5-yl)phenyl)-N-(2-fluoro-4-(hydroxycarbamoyl)benzyl)morpholine-4-carboxamide

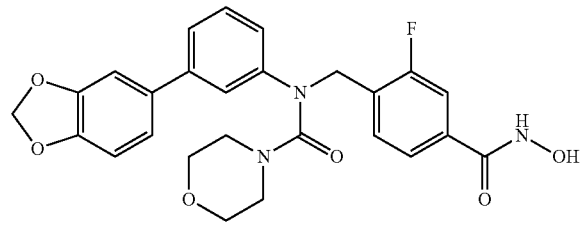 [SMILES: O=C(NO)c1ccc(CN(C(=O)N2CCOCC2)c2cccc(-c3ccc4c(c3)OCO4)c2)c(F)c1]

Compound of Formula 6-7 (methyl 4-((N-(3-(benzo[d][1,3]dioxol-5-yl)phenyl)morpholine-4-carboxamido)methyl)-3-fluorobenzoate; 0.077 g, 0.156 mmol) was dissolved in methanol (10 mL), hydroxylamine (50.0 wt % aqueous solution; 0.956 mL, 15.6 mmol) was added at room temperature, and then potassium hydroxide (0.088 g, 1.56 mmol) was added and stirred at the same temperature for 30 minutes. Then, the concentrate was obtained by removing the solvent from the reaction mixture under reduced pressure. saturated sodium hydrogen carbonate aqueous solution was poured into the obtained concentrate and stirred. Then, the precipitated solid was filtered and dried to give the desired Compound 511 (0.056 g, 73%) in the form of a white solid.

MS (ESI) m/z 494 (M$^+$+H).

Example 126: Synthesis of Compound 512

Formula 6-7: methyl 4-((N-(3-(3,6-dihydro-2H-pyran-4-yl)phenyl)morpholine-4-carboxamido)methyl)-3-fluorobenzoate

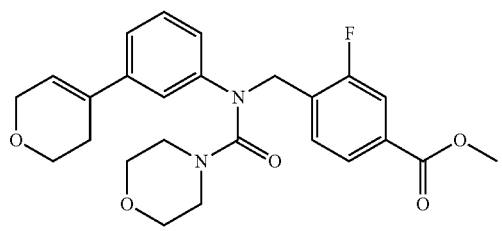 [SMILES: COC(=O)c1ccc(CN(C(=O)N2CCOCC2)c2cccc(C3=CCOCC3)c2)c(F)c1]

Compound of Formula 6-6 (methyl 4-((N-(3-bromophenyl)morpholine-4-carboxamido)methyl)-3-fluorobenzoate; 0.300 g, 0.665 mmol), 3,6-dihydro-2H-pyran-4-boronic acid pinacol ester (0.182 g, 0.864 mmol), Pd(dppf)Cl$_2$ (0.027 g, 0.033 mmol) and sodium carbonate (2.0 M aqueous solution; 0.997 mL, 1.99 mmol) were dissolved in 1,4-dioxane (3 mL) and stirred at 110° C. for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20-50%) to give the desired compound of Formula 6-7 (0.068 g, 23%) in the form of a light brown solid.

Compound 512: N-(3-(3,6-dihydro-2H-pyran-4-yl)phenyl)-N-(2-fluoro-4-(hydroxycarbamoyl)benzyl)morpholine-4-carboxamide

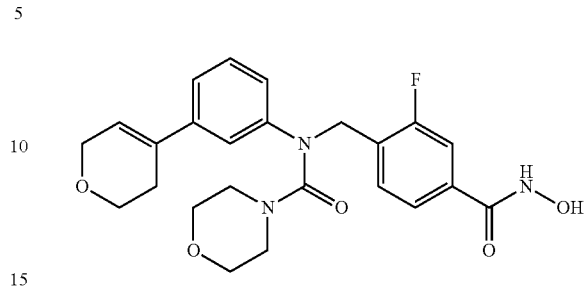

Compound of Formula 6-7 (methyl 4-((N-(3-(3,6-dihydro-2H-pyran-4-yl)phenyl)morpholine-4-carboxamido)methyl)-3-fluorobenzoate; 0.068 g, 0.150 mmol) was dissolved in methanol (10 mL), hydroxylamine (50.0 wt % aqueous solution; 0.915 mL, 15.0 mmol) was added at room temperature, and then potassium hydroxide (0.084 g, 1.50 mmol) was added and stirred at the same temperature for 30 minutes. Then, the concentrate was obtained by removing the solvent from the reaction mixture under reduced pressure. saturated sodium hydrogen carbonate aqueous solution was poured into the obtained concentrate and was extracted with ethyl acetate. The organic layer was washed with saturated sodium chloride aqueous solution, dehydrated with anhydrous magnesium sulfate, and then concentrated under reduced pressure. Dichloromethane (3 mL) and hexane (20 mL) were added to the concentrate and stirred. Then, the precipitated solid was filtered and dried to give the desired Compound 512 (0.028 g, 41%) in the form of a white solid.

$^1$H NMR (400 MHz, DMSO-d$_6$) δ 11.25 (brs, 1H), 9.11 (brs, 1H), 7.53-7.43 (m, 3H), 7.29 (m, 1H), 7.21-7.17 (m, 2H), 7.04 (m, 1H), 6.25 (s, 1H), 4.88 (s, 2H), 4.20 (m, 2H), 3.79 (m, 2H), 3.36 (m, 4H), 3.12 (m, 4H), 2.38 (m, 2H). MS (ESI) m/z 456 (M$^+$+H).

Example 127: Synthesis of Compound 513

Formula 6-7: methyl 4-((N-(3-(benzo[d][1,3]dioxol-5-yl)phenyl)-4-hydroxypiperidine-1-carboxamido)methyl)-3-fluorobenzoate

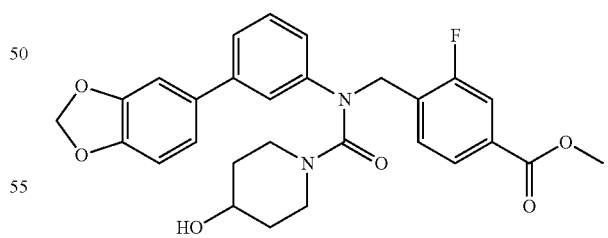

Compound of Formula 6-6 (methyl 4-((N-(3-bromophenyl)-4-hydroxypiperidine-1-carboxamido)methyl)-3-fluorobenzoate; 0.200 g, 0.430 mmol), benzo[d][1,3]dioxol-5-ylboronic acid (0.093 g, 0.559 mmol), Pd(dppf)Cl$_2$ (0.018 g, 0.021 mmol) and sodium carbonate (2.0 M aqueous solution; 0.645 mL, 1.29 mmol) were dissolved in 1,4-dioxane (2 mL) and stirred at 110° C. for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=40-70%) to give the desired compound of Formula 6-7 (0.037 g, 17%) in the form of a light yellow solid.

Compound 513: N-(3-(benzo[d][1,3]dioxol-5-yl)phenyl)-N-(2-fluoro-4-(hydroxycarbamoyl)benzyl)-4-hydroxypiperidine-1-carboxamide

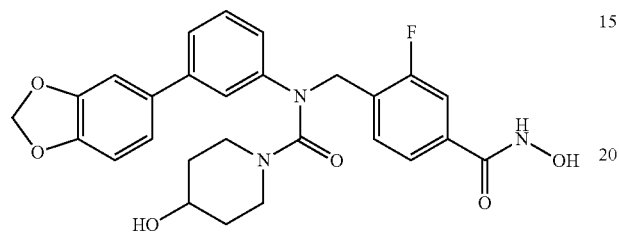

Compound of Formula 6-7 (methyl 4-((N-(3-(benzo[d][1,3]dioxol-5-yl)phenyl)-4-hydroxypiperidine-1-carboxamido)methyl)-3-fluorobenzoate; 0.037 g, 0.073 mmol) was dissolved in methanol (10 mL), hydroxylamine (50.0 wt % aqueous solution; 0.447 mL, 7.31 mmol) was added at room temperature, and then potassium hydroxide (0.041 g, 0.730 mmol) was added and stirred at the same temperature for 30 minutes. Then, the concentrate was obtained by removing the solvent from the reaction mixture under reduced pressure. Saturated sodium hydrogen carbonate aqueous solution was poured into the obtained concentrate and stirred. Then, the precipitated solid was filtered and dried to give the desired Compound 513 (0.032 g, 86%) in the form of a light brown solid.

$^1$H NMR (400 MHz, DMSO-$d_6$) δ 7.63-7.59 (m, 2H), 7.54 (m, 1H), 7.36-7.32 (m, 3H), 7.21 (m, 1H), 7.09 (m, 1H), 7.02 (m, 1H), 6.96 (m, 1H), 6.65 (s, 2H), 4.89 (s, 2H), 4.63 (d, 1H, J=4.0 Hz), 3.52-3.49 (m, 3H), 2.85-2.82 (m, 2H), 1.53-1.50 (m, 2H), 1.13-1.09 (m, 2H). MS (ESI) m/z 508 (M$^+$+H).

Example 128: Synthesis of Compound 514

Formula 6-7: methyl 4-((N-(3-(3,6-dihydro-2H-pyran-4-yl)phenyl)-4-hydroxypiperidine-1-carboxamido)methyl)-3-fluorobenzoate

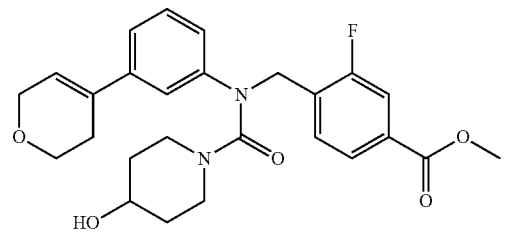 [SMILES: COC(=O)c1ccc(CN(C(=O)N2CCC(O)CC2)c2cccc(C3=CCOCC3)c2)c(F)c1]

Compound of Formula 6-6 (methyl 4-((N-(3-bromophenyl)-4-hydroxypiperidine-1-carboxamido)methyl)-3-fluorobenzoate; 0.300 g, 0.645 mmol), 3,6-dihydro-2H-pyran-4-boronic acid pinacol ester (0.176 g, 0.838 mmol), Pd(dppf)Cl$_2$ (0.026 g, 0.032 mmol) and sodium carbonate (2.0 M aqueous solution; 0.967 mL, 1.93 mmol) were dissolved in 1,4-dioxane (3 mL) and stirred at 110° C. for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=50-80%) to give the desired compound of Formula 6-7 (0.078 g, 26%) in the form of a light yellow solid.

Compound 514: N-(3-(3,6-dihydro-2H-pyran-4-yl)phenyl)-N-(2-fluoro-4-(hydroxycarbamoyl)benzyl)-4-hydroxypiperidine-1-carboxamide

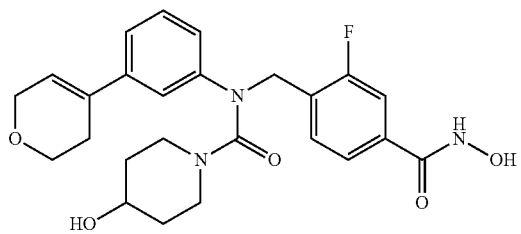 [SMILES: O=C(NO)c1ccc(CN(C(=O)N2CCC(O)CC2)c2cccc(C3=CCOCC3)c2)c(F)c1]

Compound of Formula 6-7 (methyl 4-((N-(3-(3,6-dihydro-2H-pyran-4-yl)phenyl)-4-hydroxypiperidine-1-carboxamido)methyl)-3-fluorobenzoate; 0.078 g, 0.166 mmol) was dissolved in methanol (10 mL), hydroxylamine (50.0 wt % aqueous solution; 1.02 mL, 16.6 mmol) was added at room temperature, and then potassium hydroxide (0.093 g, 1.67 mmol) was added and stirred at the same temperature for 30 minutes. Then, the concentrate was obtained by removing the solvent from the reaction mixture under reduced pressure. saturated sodium hydrogen carbonate aqueous solution was poured into the obtained concentrate and was extracted with ethyl acetate. The organic layer was washed with saturated sodium chloride aqueous solution, dehydrated with anhydrous magnesium sulfate, and then concentrated under reduced pressure. Dichloromethane (3 mL) and hexane (20 mL) were added to the concentrate and stirred. Then, the precipitated solid was filtered and dried to give the desired Compound 514 (0.036 g, 46%) in the form of a light green solid.

$^1$H NMR (400 MHz, DMSO-$d_6$) δ 11.25 (brs, 1H), 9.11 (brs, 1H), 7.54-7.44 (m, 3H), 7.28 (t, 1H, J=7.8 Hz), 7.18-7.15 (m, 2H), 7.00 (d, 1H, J=8.6 Hz), 6.23 (s, 1H), 4.84 (s, 2H), 4.63 (d, 1H, J=4.0 Hz), 4.19 (m, 2H), 3.79 (t, 2H, J=5.4 Hz), 3.52-3.46 (m, 3H), 2.83-2.76 (m, 2H), 2.37 (m, 2H), 1.52-1.49 (m, 2H), 1.16-1.13 (m, 2H). MS (ESI) m/z 470 (M$^+$+H).

Example 129: Synthesis of Compound 517

Formula 4-7: ethyl 4-((N-(3-(1-(2-hydroxy-2-methylpropyl)piperidine-4-yl)phenyl)morpholine-4-carboxamido)methyl)benzoate

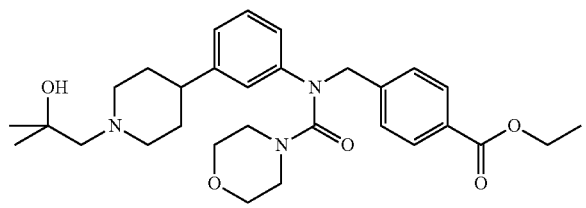 [SMILES: CCOC(=O)c1ccc(CN(C(=O)N2CCOCC2)c2cccc(C3CCN(CC(C)(C)O)CC3)c2)cc1]

Compound of Formula 4-5 (methyl 4-((N-(3-(piperidin-4-yl)phenyl)morpholine-4-carboxyamido)methyl)benzoate hydrochloride; 0.540 g, 1.139 mmol), 2,2-dimethyloxirane (0.411 g, 5.696 mmol) and potassium carbonate (0.472 g, 3.42 mmol) were mixed with water (1 mL)/ethanol (3 mL). Then, the mixture was heated at 120° C. for 20 minutes under microwave irradiation, and then the temperature was lowered to room temperature. Then, the concentrate was obtained by removing the solvent from the reaction mixture under reduced pressure. water was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=2-10%) to give the desired compound of Formula 4-7 (0.325 g, 55%) in the form of a colorless liquid.

Compound 517: N-(3-(1-(2-hydroxy-2-methylpropyl)piperidine-4-yl)phenyl)-N-(4-(hydroxycarbamoyl)benzyl)morpholine-4-carboxamide

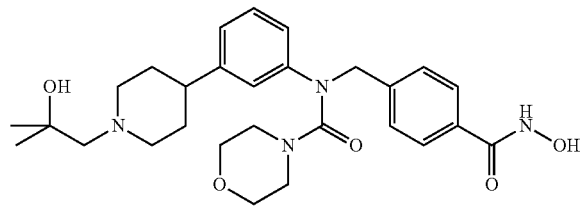 [SMILES: CC(C)(O)CN1CCC(c2cccc(N(Cc3ccc(C(=O)NO)cc3)C(=O)N3CCOCC3)c2)CC1]

Compound of Formula 4-7 (ethyl 4-((N-(3-(1-(2-hydroxy-2-methylpropyl)piperidine-4-yl)phenyl)morpholine-4-carboxamido)methyl)benzoate; 0.050 g, 0.095 mmol) was dissolved in methanol (10 mL), hydroxylamine (50.0 wt % aqueous solution; 0.584 mL, 9.55 mmol) was added at room temperature, and then potassium hydroxide (0.054 g, 0.955 mmol) was added and stirred at the same temperature for 30 minutes. Then, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (2 mL) and hexane (20 mL) were added to the concentrate and stirred. Then, the precipitated solid was filtered and dried to give the desired Compound 517 (0.032 g, 66%) in the form of a white solid.

$^1$H NMR (400 MHz, DMSO-$d_6$) δ 11.12 (brs, 1H), 8.98 (brs, 1H), 7.63 (d, 2H, J=8.2 Hz), 7.34 (d, 2H, J=8.1 Hz), 7.21 (m, 1H), 6.97-6.93 (m, 3H), 4.83 (s, 2H), 3.37-3.34 (m, 6H), 3.12-3.10 (m, 4H), 3.00 (m, 1H), 2.32 (m, 1H), 2.19-2.14 (m, 3H), 1.68-1.62 (m, 4H), 1.22 (s, 3H), 1.10 (m, 4H). MS (ESI) m/z 511 (M$^+$+H).

Example 130: Synthesis of Compound 518

Formula 4-8: ethyl 4-((N-(3-(1-(2-fluoro-2-methylpropyl)piperidine-4-yl)phenyl)morpholine-4-carboxamido)methyl)benzoate

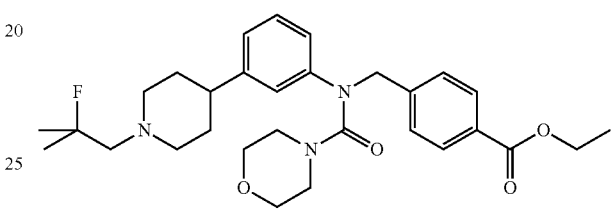

Compound of Formula 4-7 (ethyl 4-((N-(3-(1-(2-hydroxy-2-methylpropyl)piperidine-4-yl)phenyl)morpholine-4-carboxamido)methyl)benzoate; 0.275 g, 0.525 mmol) was dissolved in dichloromethane (20 mL), and then diethylaminosulfur trifluoride (DAST, 0.068 mL, 0.578 mmol) was added at 0° C. and stirred at the same temperature for 1 hour. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; methanol/dichloromethane=2-10%) to give the desired compound of Formula 4-8 (0.146 g, 53%) in the form of a colorless liquid.

Compound 518: N-(3-(1-(2-fluoro-2-methylpropyl)piperidine-4-yl)phenyl)-N-(4-(hydroxycarbamoyl)benzyl)morpholine-4-carboxamide

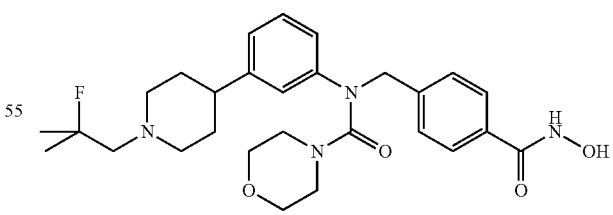

Compound of Formula 4-8 (ethyl 4-((N-(3-(1-(2-fluoro-2-methylpropyl)piperidine-4-yl)phenyl)morpholine-4-carboxamido)methyl)benzoate; 0.146 g, 0.278 mmol) was dissolved in methanol (10 mL), hydroxylamine (50.0 wt % aqueous solution; 1.19 mL, 19.4 mmol) was added at room temperature, and then potassium hydroxide (0.156 g, 2.78 mmol) was added and stirred at the same temperature. Then, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. Dichloromethane (2 mL) and hexane (20 mL) were added to the concentrate and stirred. Then, the precipitated solid was filtered and dried to give the desired Compound 518 (0.092 g, 65%) in the form of a white solid.

$^1$H NMR (400 MHz, DMSO-$d_6$) δ 11.12 (brs, 1H), 8.99 (brs, 1H), 7.64 (d, 2H, J=8.3 Hz), 7.34 (d, 2H, J=8.2 Hz), 7.21 (t, 1H, J=7.7 Hz), 6.98-6.94 (m, 3H), 4.84 (s, 2H), 3.37-3.35 (m, 4H), 3.14-3.10 (m, 4H), 2.97-2.95 (m, 2H), 2.46-2.38 (m, 3H), 2.17-2.14 (m, 2H), 1.67-1.60 (m, 4H), 1.33 (s, 3H), 1.28 (s, 3H). MS (ESI) m/z 513 (M$^+$+H).

Example 131: Synthesis of Compound 520

Formula 1-4: (R)-methyl 4-((3-fluoro-N-(4-(trifluoromethyl)phenyl)pyrrolidine-1-carboxamido)methyl)benzoate

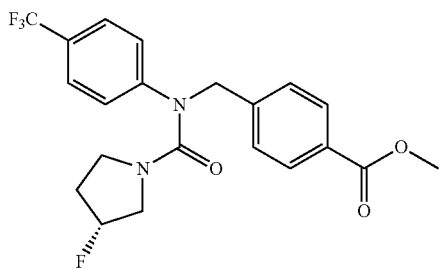 [SMILES: COC(=O)c1ccc(CN(C(=O)N2CC[C@@H](F)C2)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.239 g, 0.504 mmol), (R)-3-fluoropyrrolidine hydrochloride (0.127 g, 1.008 mmol) and potassium carbonate (0.209 g, 1.513 mmol) were dissolved in N,N-dimethylformamide (5 ml) and it was stirred at 60° C. for 24 hours, and then the reaction was completed with lowering the temperature to room temperature. Saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; ethyl acetate/hexane=40%) to give the desired compound of Formula 1-4 (0.081 g, 37.8%) in the form of white solid.

Compound 520, (R)-3-fluoro-N-(4-(hydroxycarbamoyl)benzyl)-N-(4-(trifluoromethyl)phenyl)pyrrolidine-1-carboxamide

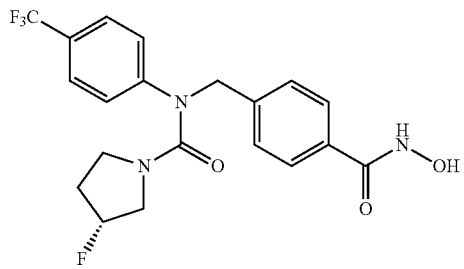 [SMILES: O=C(NO)c1ccc(CN(C(=O)N2CC[C@@H](F)C2)c2ccc(C(F)(F)F)cc2)cc1]

Compound of Formula 1-4 ((R)-methyl 4-((3-fluoro-N-(4-(trifluoromethyl)phenyl)pyrrolidine-1-carboxamido)methyl)benzoate; 0.081 g, 0.191 mmol) and hydroxylamine (50 wt % aqueous solution; 0.063 g, 1.909 mmol) were dissolved in methanol (5 ml) and stirred at room temperature for 24 hours. the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 520 (0.067 g, 83.0%) in the form of a white solid.

$^1$H NMR (400 MHz, DMSO-$d_6$) δ 11.1 (s, 1H), 8.99 (s, 1H), 7.66-7.63 (m, 4H), 7.37 (d, 2H, J=8.1 Hz), 7.30 (d, 2H, J=8.4 Hz), 5.27 (s, 0.5H), 5.14 (s, 0.5H), 4.98-4.88 (m, 2H), 3.34-3.30 (m, 2H), 3.18-3.11 (m, 2H), 2.02-1.92 (m, 2H); MS (ESI) m/z 426.1 (M$^+$+H).

Example 132: Synthesis of Compound 521

Formula 1-4: (S)-methyl 4-((3-fluoro-N-(4-(trifluoromethyl)phenyl)pyrrolidine-1-carboxamido)methyl)benzoate

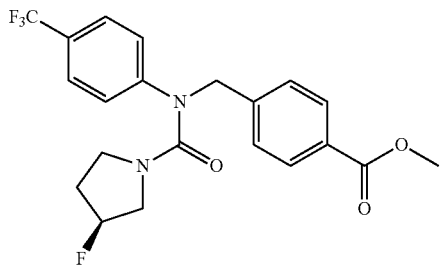 [SMILES: COC(=O)c1ccc(CN(C(=O)N2CC[C@H](F)C2)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.312 g, 0.659 mmol), (S)-3-fluoropyrrolidine hydrochloride (0.165 g, 1.317 mmol) and potassium carbonate (0.273 g, 1.976 mmol) were dissolved in N,N-dimethylformamide (5 ml) and it was stirred at 60° C. for 24 hours, and then the reaction was completed with lowering the temperature to room temperature. Saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; ethyl acetate/hexane=40%) to give the desired compound of Formula 1-4 (0.115 g, 41.0%) in the form of white solid.

Compound 521, (S)-3-fluoro-N-(4-(hydroxycarbamoyl)benzyl)-N-(4-(trifluoromethyl)phenyl)pyrrolidine-1-carboxamide

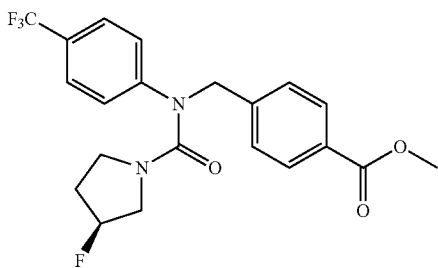 [SMILES: COC(=O)c1ccc(CN(C(=O)N2CC[C@H](F)C2)c2ccc(C(F)(F)F)cc2)cc1]

Compound of Formula 1-4 ((S)-methyl 4-((3-fluoro-N-(4-(trifluoromethyl)phenyl)pyrrolidine-1-carboxamido)methyl)benzoate; 0.115 g, 0.271 mmol) and hydroxylamine (50 wt % aqueous solution; 0.090 g, 2.710 mmol) were dissolved in methanol (5 ml) and stirred at room temperature for 24 hours. the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 521 (0.075 g, 65.2%) in the form of a white solid.

$^1$H NMR (400 MHz, DMSO-$d_6$) δ 11.1 (s, 1H), 9.00 (s, 1H), 7.66-7.63 (m, 4H), 7.37 (d, 2H, J=8.1 Hz), 7.30 (d, 2H, J=8.4 Hz), 5.27 (s, 0.5H), 5.14 (s, 0.5H), 5.02-4.88 (m, 2H), 3.34-3.30 (m, 2H), 3.24-3.11 (m, 2H), 2.07-1.86 (m, 2H); MS (ESI) m/z 426.1 (M$^+$+H).

Example 133: Synthesis of Compound 522

Formula 1-4: (R)-methyl 4-((2-(hydroxymethyl)-N-(4-(trifluoromethyl)phenyl)pyrrolidine-1-carboxamido)methyl)benzoate

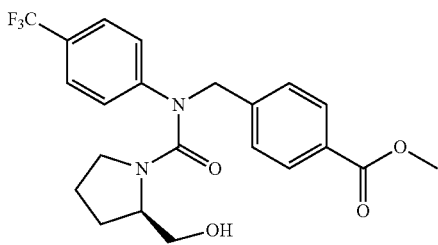 [SMILES: COC(=O)c1ccc(CN(C(=O)N2CCC[C@@H]2CO)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.312 g, 0.659 mmol), (R)-pyrrolidin-2-ylmethanol (0.133 g, 1.317 mmol) and potassium carbonate (0.273 g, 1.976 mmol) were dissolved in N,N-dimethylformamide (5 ml) and it was stirred at 60° C. for 24 hours, and then the reaction was completed with lowering the temperature to room temperature. Saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; ethyl acetate/hexane=50%) to give the desired compound of Formula 1-4 (0.116 g, 40.4%) in the form of yellow liquid.

Compound 522, (R)—N-(4-(hydroxycarbamoyl)benzyl)-2-(hydroxymethyl)-N-(4-(trifluoromethyl)phenyl)pyrrolidine-1-carboxamide

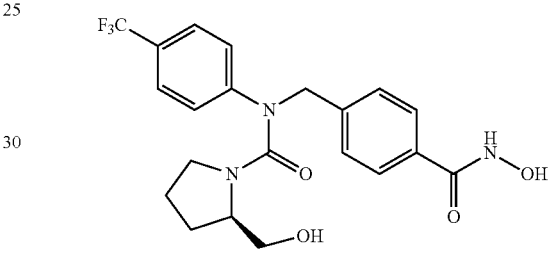

Compound of Formula 1-4 (((R)-methyl 4-((2-(hydroxymethyl)-N-(4-(trifluoromethyl)phenyl)pyrrolidine-1-carboxamido)methyl)benzoate; 0.116 g, 0.273 mmol) and hydroxylamine (50 wt % aqueous solution; 0.088 g, 2.658 mmol) were dissolved in methanol (5 ml) and stirred at room temperature for 24 hours. the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 522 (0.025 g, 20.7%) in the form of a white solid.

$^1$H NMR (400 MHz, DMSO-$d_6$) δ 11.1 (s, 1H), 8.99 (s, 1H), 7.65 (d, 2H, J=8.3 Hz), 7.59 (d, 2H, J=8.6 Hz), 7.38 (d, 2H, J=8.2 Hz), 7.32 (d, 2H, J=8.5 Hz), 5.07 (s, 0.5H), 5.03 (s, 0.5H), 4.85-4.79 (m, 2H), 3.99-3.94 (m, 1H), 3.60-3.50 (m, 2H), 3.12-3.07 (m, 1H), 2.67-2.59 (m, 1H), 1.89-1.83 (m, 1H), 1.75-1.66 (m, 2H), 1.62-1.60 (m, 1H); MS (ESI) m/z 438.2 (M$^+$+H).

Example 134: Synthesis of Compound 529

Formula 1-2: methyl 4-(((3-fluorophenyl)amino)methyl)benzoate

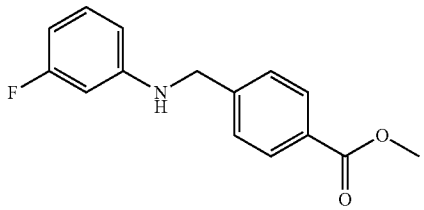 [SMILES: COC(=O)c1ccc(CNc2cccc(F)c2)cc1]

Compound of Formula 1-1 (3-fluoroaniline; 0.865 mL, 8.999 mmol) and methyl 4-formylbenzoate (1.477 g, 8.999 mmol) were dissolved in methanol (50 mL) and stirred at room temperature for 3 hours. Then, acetic acid (1.029 mL, 17.999 mmol) and sodium cyanoborohydride (95.0%, 0.595 g, 8.999 mmol) were added and further stirred at the same temperature for 24 hours. Saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=0-20%) to give the desired compound of Formula 1-2 (1.840 g, 78.9%) in the form of a colorless liquid.

Formula 1-3: methyl 4-(((3-fluorophenyl)((4-nitrophenoxy)carbonyl)amino)methyl)benzoate

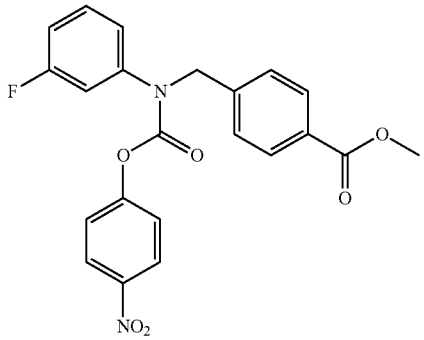 [SMILES: COC(=O)c1ccc(CN(C(=O)Oc2ccc([N+](=O)[O-])cc2)c2cccc(F)c2)cc1]

Compound of Formula 1-2 (methyl 4-(((3-fluorophenyl)amino)methyl)benzoate; 2.700 g, 10.413 mmol), 4-nitrophenyl carbonochloridate (4.198 g, 20.827 mmol), and then potassium carbonate (4.318 g, 31.240 mmol) were dissolved in acetonitrile (100 mL) at room temperature and stirred at the same temperature for 24 hours. Saturated sodium chloride aqueous solution was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=0-20%) to give the desired compound of Formula 1-3 (2.650 g, 60.0%) in the form of a colorless liquid.

Formula 1-4: methyl 4-((4-acetyl-N-(3-fluorophenyl)piperazine-1-carboxamido)methyl)benzoate

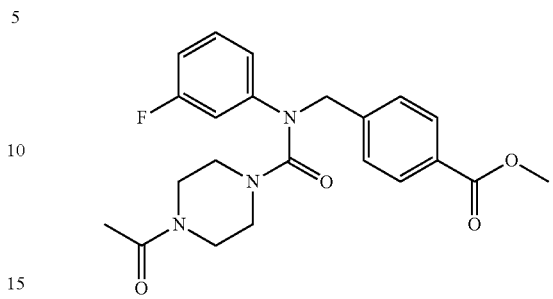

Compound of Formula 1-3 (methyl 4-(((3-fluorophenyl)((4-nitrophenoxy)carbonyl)amino)methyl)benzoate; 0.247 g, 0.582 mmol), 1-(piperazine-1-yl)ethanone (0.145 mL, 1.164 mmol) and potassium carbonate (0.241 g, 1.746 mmol) were dissolved in N,N-dimethylformamide (5 mL) at 60° C. and stirred at the same temperature for 16 hours. Saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=40-100%) to give the desired compound of Formula 1-4 (0.112 g, 46.7%) in the form of a light yellow liquid.

Compound 529: 4-acetyl-N-(3-fluorophenyl)-N-(4-(hydroxycarbamoyl)benzyl)piperazine-1-carboxamide

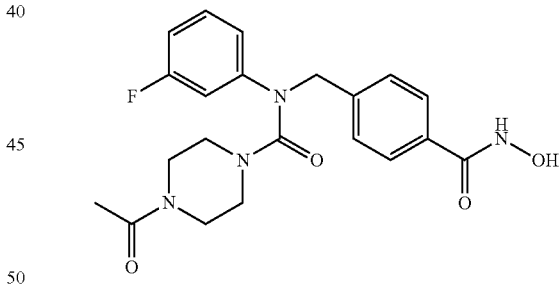

Compound of Formula 1-4 (methyl 4-((4-acetyl-N-(3-fluorophenyl)piperazine-1-carboxamido)methyl)benzoate; 0.112 g, 0.271 mmol) and hydroxylamine (50.0 wt % aqueous solution, 0.166 mL, 2.709 mmol) were dissolved in methanol (10 mL), and then potassium hydroxide (0.076 g, 1.354 mmol) was added at room temperature and stirred at the same temperature for 16 hours. Then, the concentrate was obtained by removing the solvent from the reaction mixture under reduced pressure. saturated sodium hydrogen carbonate aqueous solution was poured into the obtained concentrate, and the organic layer was extracted with ethyl acetate. The organic layer was dehydrated with anhydrous magnesium sulfate, and then concentrated under reduced pressure. The precipitated solid was filtered and dried to give the desired Compound 529 (0.048 g, 42.8%) in the form of a yellow solid.

¹H NMR (400 MHz, DMSO-d₆) δ 11.1 (s, 1H), 8.99 (s, 1H), 7.64 (d, 2H, J=8.2 Hz), 7.37 (d, 2H, J=8.2 Hz), 7.33-7.28 (m, 1H), 7.07-7.02 (m, 1H), 6.99-6.94 (m, 1H), 6.89-6.84 (m, 1H), 4.89 (s, 2H), 3.30-3.29 (m, 2H), 3.20-3.15 (m, 4H), 2.55-2.54 (m, 1H), 2.45-2.44 (m, 1H), 1.94 (s, 3H); MS (ESI) m/z 415.1 (M⁺+H).

Example 135: Synthesis of Compound 530

Formula 1-2: methyl 4-((3-fluorophenylamino)methyl)benzoate

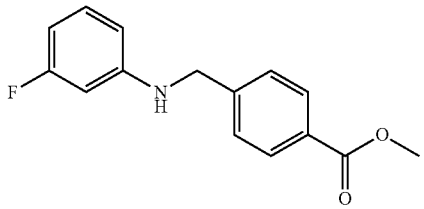 [SMILES: COC(=O)c1ccc(CNc2cccc(F)c2)cc1]

Compound of Formula 1-1 (methyl 4-formylbenzoate; 1.47 g, 8.99 mmol) was dissolved in methanol (50 mL), and 3-fluorobenzenamine (1.0 g, 8.99 mmol) was then added. The mixture was reacted at room temperature for 3 hours, and sodium cyanoborohydride (NaCNBH3; 0.56 g, 8.99 mmol) and acetic acid (1.03 mL, 17.99 mmol) were then added. After the mixture was reacted at room temperature for 1 day, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was dehydrated with anhydrous magnesium sulfate and then concentrated under reduced pressure. The residue was purified by column chromatography (silica; ethyl acetate/hexane=20%) to give the desired compound of Formula 1-2 (1.84 g, 79%).

Formula 1-3: methyl 4-(((3-fluorophenyl)((4-nitrophenoxy)carbonyl)amino)methyl)benzoate

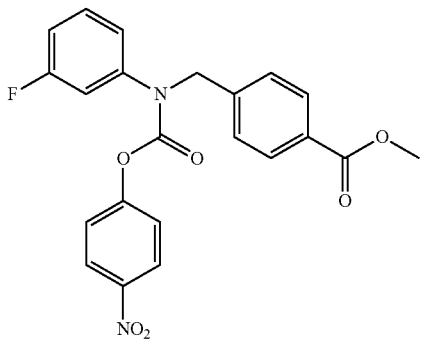 [SMILES: COC(=O)c1ccc(CN(C(=O)Oc2ccc([N+](=O)[O-])cc2)c2cccc(F)c2)cc1]

Compound of Formula 1-2 (methyl 4-((3-fluorophenylamino)methyl)benzoate; 2.7 g, 10.4 mmol) and 4-nitrophenyl chloroformate (4.20 g, 20.8 mmol) were dissolved in acetonitrile (100 mL), and potassium carbonate (4.32 g, 31.2 mmol) was then added. The mixture was reacted at room temperature for 1 day and then diluted with ethyl acetate. The reaction mixture was washed with saturated sodium chloride aqueous solution, dehydrated with anhydrous sodium sulfate, filtered, and then concentrated under reduced pressure. The residue was purified by column chromatography (silica; ethyl acetate/hexane=20%) to give the desired compound of Formula 1-3 (2.65 g, 60%) in the form of a colorless oil.

Formula 1-4: methyl 4-((N-(3-fluorophenyl)morpholine-4-carboxamido)methyl)benzoate

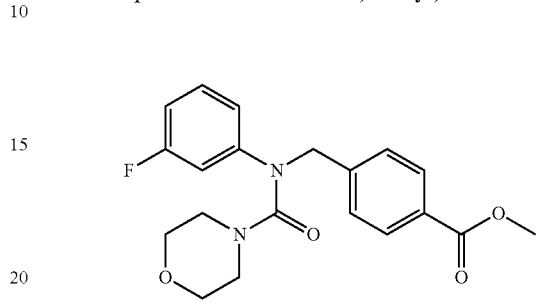

Compound of Formula 1-3 (methyl 4-(((3-fluorophenyl)((4-nitrophenoxy)carbonyl)amino)methyl)benzoate; 0.32 g, 0.75 mmol) was dissolved in dimethylformamide (5 mL), and potassium carbonate (0.31 g, 2.24 mmol) and morpholine (0.13 mL, 1.49 mmol) were then added. The mixture was reacted at 60° C. for 1 day and diluted with saturated ammonium chloride solution. The organic layer was extracted with ethyl acetate, dehydrated with anhydrous sodium sulfate, filtered, and then concentrated under reduced pressure. The residue was purified by column chromatography (silica; ethyl acetate/hexane=30%) to give the desired compound of Formula 1-4 (0.13 g, 45%).

Compound 530: N-(3-fluorophenyl)-N-(4-(hydroxycarbamoyl)benzyl)morpholine-4-carboxamide

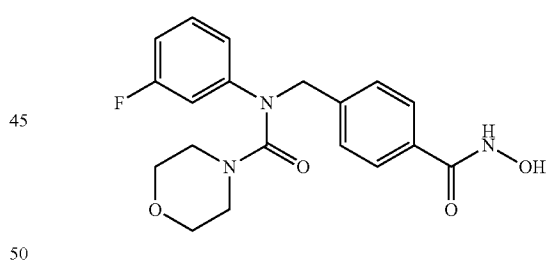

Compound of Formula 1-4 (methyl 4-((N-(3-fluorophenyl)morpholine-4-carboxamido)methyl)benzoate; 0.108 g, 0.290 mmol) was dissolved in methanol (10 mL), hydroxylamine (50.0 wt % aqueous solution; 1.19 mL, 19.4 mmol) was added at room temperature, and then potassium hydroxide (0.156 g, 2.78 mmol) was added and stirred at the same temperature for 16 hours. The concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The precipitated solid was filtered and dried to give the desired Compound 530 (0.062 g, 57%) in the form of a white solid.

¹H NMR (400 MHz, DMSO-d₆) δ 11.14 (brs, 1H), 8.99 (brs, 1H), 7.65 (d, 2H, J=7.0 Hz), 7.38-7.30 (m, 3H), 7.05-6.85 (m, 3H), 4.89 (s, 1H), 3.44-3.42 (m, 4H), 3.18-3.15 (m, 4H), 2.08 (s, 3H). MS (ESI) m/z 374 (M⁺+H).

Example 136: Synthesis of Compound 531

Formula 12-1: tert-butyl 4-((4-(methoxycarbonyl) benzyl)(3-(trifluoromethyl)phenyl)carbamoyl)piperazine-1-carboxylate

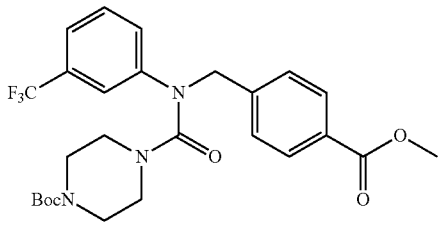 [SMILES: COC(=O)c1ccc(CN(C(=O)N2CCN(C(=O)OC(C)(C)C)CC2)c2cccc(C(F)(F)F)c2)cc1]

Compound of Formula 1-3 (methyl 4-((((4-nitrophenoxy) carbonyl)(3-(trifluoromethyl)phenyl)amino)methyl)benzoate; 1.040 g, 2.192 mmol), tert-butyl piperazine-1-carboxylate (0.817 g, 4.385 mmol) and potassium carbonate (0.909 g, 6.577 mmol) were dissolved in N,N-dimethylformamide (10 mL) at 60° C. and stirred at the same temperature for 1 day. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=20-60%) to give the desired compound of Formula 12-1 (0.679 g, 59.4%) in the form of a white solid.

Formula 12-2; methyl 4-((N-(3-(trifluoromethyl) phenyl)piperazine-1-carboxamido)methyl)benzoate hydrochloride

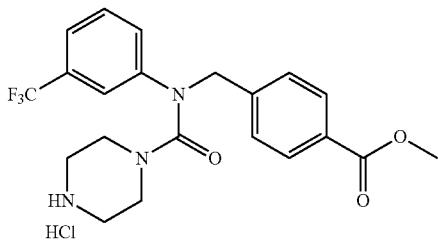 [SMILES: COC(=O)c1ccc(CN(C(=O)N2CCNCC2)c2cccc(C(F)(F)F)c2)cc1 ; Cl]

Compound of Formula 12-1 (tert-butyl 4-((4-(methoxycarbonyl)benzyl)(3-(trifluoromethyl)phenyl)carbamoyl)piperazine-1-carboxylate; 0.360 g, 0.690 mmol) was dissolved in 1,4-dioxane (5 mL) at room temperature, and then hydrochloric acid (4.0 M 1,4-dioxane solution; 0.863 mL, 3.451 mmol) was added to the solution and stirred at the same temperature for 2 hours. Then, the reaction mixture was concentrated under reduced pressure. The obtained product was used without any purification process and compound of Formula 12-2 (0.370 g, 117.1%) was obtained in the form of a light yellow liquid.

Formula 12-3: ethyl 4-((4-(2-hydroxy-2-methylpropyl)-N-(3-(trifluoromethyl)phenyl)piperazine-1-carboxamido)methyl)benzoate

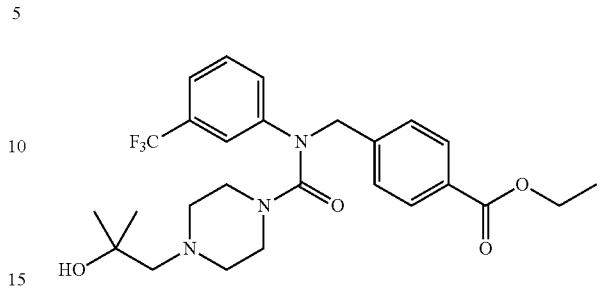

Compound of Formula 12-2 (methyl 4-((N-(3-(trifluoromethyl)phenyl)piperazine-1-carboxamido)methyl)benzoate hydrochloride; 0.310 g, 0.677 mmol), 2,2-dimethyloxirane (0.610 mL, 6.770 mmol) and potassium carbonate (0.936 g, 6.770 mmol) were mixed with ethanol (4 mL)/water (1 mL) and heated at 110° C. for 1 hour under microwave irradiation, and then the temperature was lowered to room temperature. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=30-70%) to give the desired compound of Formula 12-3 (0.121 g, 35.2%) in the form of a colorless liquid.

Formula 12-4: ethyl 4-((4-(2-fluoro-2-methylpropyl)-N-(3-(trifluoromethyl)phenyl)piperazine-1-carboxamido)methyl)benzoate

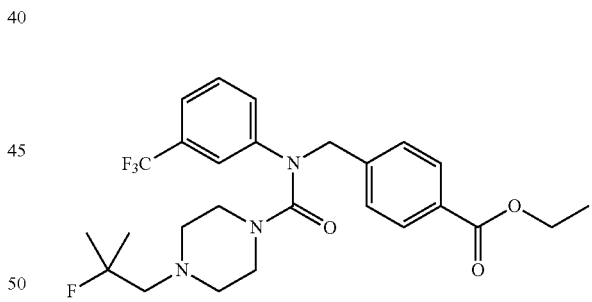

Compound of Formula 12-3 (ethyl 4-((4-(2-hydroxy-2-methylpropyl)-N-(3-(trifluoromethyl)phenyl)piperazine-1-carboxamido)methyl)benzoate; 0.121 g, 0.238 mmol) was dissolved in methylene chloride (10 mL), and then DAST (0.034 mL, 0.262 mmol) was added at 0° C. and stirred at the same temperature for 2 hours. Then, saturated sodium hydrogen carbonate aqueous solution was poured into the reaction mixture, and the organic layer was extracted with methylene chloride. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=30-60%) to give the desired compound of Formula 12-4 (0.056 g, 46.0%) in the form of a colorless liquid.

Compound 531: 4-(2-fluoro-2-methylpropyl)-N-(4-(hydroxycarbamoyl)benzyl)-N-(3-(trifluoromethyl)phenyl)piperazine-1-carboxamide

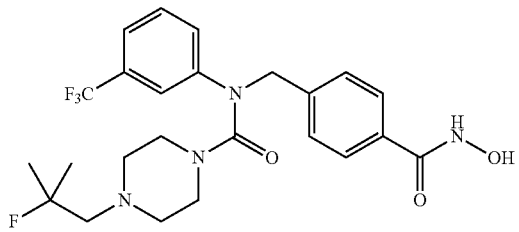 [SMILES: CC(C)(F)CN1CCN(C(=O)N(Cc2ccc(C(=O)NO)cc2)c2cccc(C(F)(F)F)c2)CC1]

Compound of Formula 12-4 (ethyl 4-((4-(2-fluoro-2-methylpropyl)-N-(3-(trifluoromethyl)phenyl)piperazine-1-carboxamido)methyl)benzoate; 0.056 g, 0.110 mmol), hydroxylamine (50.0 wt % aqueous solution; 0.067 mL, 1.099 mmol) and potassium hydroxide (0.031 g, 0.550 mmol) were dissolved in methanol (5 mL) at room temperature and stirred and the same temperature for 16 hours. Then, the concentrate was obtained by removing the solvent from the reaction mixture under reduced pressure. saturated sodium hydrogen carbonate aqueous solution was poured into the obtained concentrate, and then the organic layer was extracted with ethyl acetate. The organic layer was dehydrated with anhydrous magnesium sulfate and then concentrated under reduced pressure. The precipitated solid was filtered and dried to give the desired Compound 531 (0.045 g, 82.5%) in the form of a light yellow solid.

$^1$H NMR (400 MHz, DMSO-$d_6$) δ 11.1 (brs, 1H), 9.20 (brs, 1H), 7.65 (d, 2H, J=8.1 Hz), 7.53-7.49 (m, 1H), 7.39-7.36 (m, 5H), 4.92 (s, 2H), 3.61-3.56 (m, 1H), 3.42-3.37 (m, 2H), 2.55-2.45 (m, 2H), 2.44-2.38 (m, 1H), 2.32-2.29 (m, 4H), 1.28 (s, 3H), 1.23 (s, 3H); MS (ESI) m/z 497.2 (M$^+$+H).

Example 137: Synthesis of Compound 532

Formula 6-2: 3-fluoro-4-(((3-(trifluoromethyl)phenyl)amino)methyl)benzonitrile

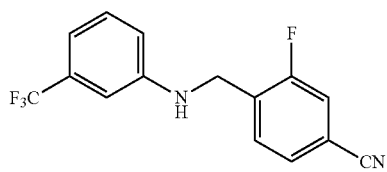 [SMILES: N#Cc1ccc(CNc2cccc(C(F)(F)F)c2)c(F)c1]

Compound of Formula 1-1 (3-(trifluoromethyl)aniline; 0.998 mL, 8.068 mmol) was dissolved in acetonitrile (60 mL), and then 4-(bromomethyl)-3-fluorobenzonitrile (2.072 g, 9.682 mmol) and DIPEA (2.143 mL, 12.102 mmol) were added at room temperature and stirred at the same temperature for 1 day. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=5-20%) to give the desired compound of Formula 6-2 (2.380 g, 64.4%) in the form of a yellow liquid.

Formula 6-3: 3-fluoro-4-(((3-(trifluoromethyl)phenyl)amino)methyl)benzoic acid

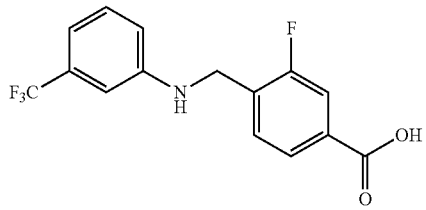 [SMILES: O=C(O)c1ccc(CNc2cccc(C(F)(F)F)c2)c(F)c1]

Compound of Formula 6-2 (3-fluoro-4-(((3-(trifluoromethyl)phenyl)amino)methyl)benzonitrile; 2.310 g, 7.850 mmol) and lithium hydroxide (3.294 g, 78.505 mmol) were mixed with methanol (40 mL)/H$_2$O (20 mL) and then stirred under reflux for 16 hours. Then, the temperature was lowered to room temperature, and the reaction mixture was concentrated under reduced pressure. 2 M hydrochloric acid aqueous solution was added to adjust the pH to 1, and then the precipitated solid was filtered and dried to give the desired compound of Formula 6-3 (1.700 g, 69.1%) in the form of a white solid.

Formula 6-4: methyl 3-fluoro-4-(((3-(trifluoromethyl)phenyl)amino)methyl)benzoate

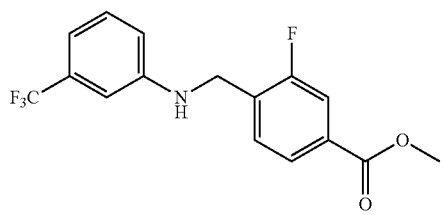 [SMILES: COC(=O)c1ccc(CNc2cccc(C(F)(F)F)c2)c(F)c1]

Compound of Formula 6-3 (3-fluoro-4-(((3-(trifluoromethyl)phenyl)amino)methyl)benzoic acid; 1.700 g, 5.427 mmol), methanol (4.402 mL, 108.540 mmol), EDC (2.081 g, 10.854 mmol), HOBt (1.467 g, 10.854 mmol) and DIPEA (2.883 mL, 16.281 mmol) were dissolved in tetrahydrofuran (50 mL) at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=10-40%) to give the desired compound of Formula 6-4 (1.500 g, 84.5%) in the form of a colorless liquid.

Formula 6-5: methyl 3-fluoro-4-((((4-nitrophenoxy)carbonyl)(3-(trifluoromethyl)phenyl)amino)methyl)benzoate

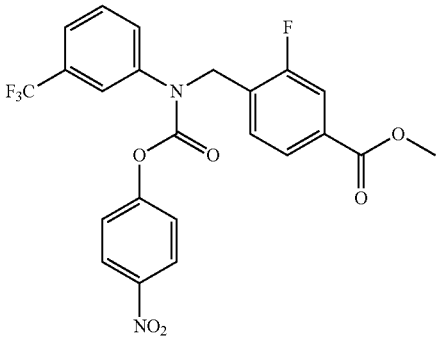 [SMILES: COC(=O)c1ccc(CN(C(=O)Oc2ccc([N+](=O)[O-])cc2)c2cccc(C(F)(F)F)c2)c(F)c1]

Compound of Formula 6-4 (methyl 3-fluoro-4-(((3-(trifluoromethyl)phenyl)amino)methyl)benzoate; 1.500 g, 4.583 mmol), 4-nitrophenyl carbonochloridate (1.848 g, 9.167 mmol) and potassium carbonate (1.900 g, 13.750 mmol) were dissolved in acetonitrile (80 mL) at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=10-40%) to give the desired compound of Formula 6-5 (0.927 g, 41.1%) in the form of a colorless liquid.

Formula 6-6: methyl 3-fluoro-4-((N-(3-(trifluoromethyl)phenyl)morpholine-4-carboxamido)methyl)benzoate

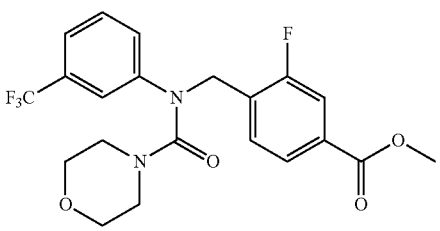 [SMILES: COC(=O)c1ccc(CN(C(=O)N2CCOCC2)c2cccc(C(F)(F)F)c2)c(F)c1]

Compound of Formula 6-5 (methyl 3-fluoro-4-((((4-nitrophenoxy)carbonyl)(3-(trifluoromethyl)phenyl)amino)methyl)benzoate; 0.129 g, 0.262 mmol), morpholine (0.046 mL, 0.524 mmol) and potassium carbonate (0.109 g, 0.786 mmol) were dissolved in N,N-dimethylformamide (5 mL) at 60° C. and stirred at the same temperature for 2 days. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=30-60%) to give the desired compound of Formula 6-6 (0.094 g, 81.5%) in the form of a colorless liquid.

Compound 532: N-(2-fluoro-4-(hydroxycarbamoyl)benzyl)-N-(3-(trifluoromethyl)phenyl)morpholine-4-carboxamide

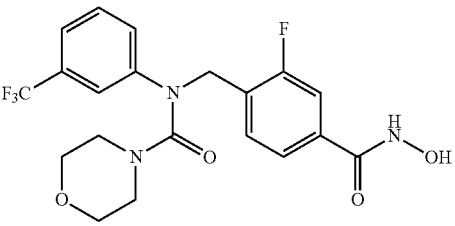 [SMILES: O=C(NO)c1ccc(CN(C(=O)N2CCOCC2)c2cccc(C(F)(F)F)c2)c(F)c1]

Compound of Formula 6-6 (methyl 3-fluoro-4-((N-(3-(trifluoromethyl)phenyl)morpholine-4-carboxamido)methyl)benzoate; 0.094 g, 0.213 mmol) and hydroxylamine (50.0 wt % aqueous solution; 0.071 g, 2.134 mmol) were dissolved in methanol (5 mL), and then potassium hydroxide (0.060 g, 1.067 mmol) was added at room temperature and stirred at the same temperature for 2 hours, and the reaction mixture was concentrated under reduced pressure. Diethylether (10 mL) was added to the concentrate and stirred. Then, the precipitated solid was filtered and dried to give the desired Compound 532 (0.068 g, 72.2%) in the form of a light yellow solid.

$^1$H NMR (400 MHz, DMSO-$d_6$) δ 11.2 (brs, 1H), 9.13 (brs, 1H), 7.57-7.42 (m, 7H), 4.94 (s, 2H), 3.44-3.34 (m, 4H), 3.18-3.12 (m, 4H); MS (ESI) m/z 442.1 (M$^+$+H).

Example 138: Synthesis of Compound 533

Formula 7-4: methyl 4-(((5-chloropyridin-2-yl)amino)methyl)benzoate

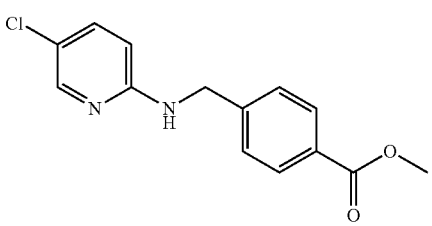 [SMILES: COC(=O)c1ccc(CNc2ccc(Cl)cn2)cc1]

Compound of Formula 7-3 (5-chloropyridin-2-amine, 2.000 g, 15.557 mmol) and methyl 4-formylbenzoate (2.554 g, 15.557 mmol) were dissolved in methanol (50 mL), and then acetic acid (0.890 mL, 15.557 mmol) was added to the reaction solution and stirred at room temperature for 2 hours. Then, sodium cyanoborohydride (0.978 g, 15.557 mmol) was added and stirred for 1 day. Then, the methanol was removed by air-drying to precipitate a solid, and the resulting solid was filtered and dried to give the desired compound of Formula 7-4 (2.700 g, 62.7%) in the form of a white solid.

Formula 7-5: methyl 4-(((5-chloropyridin-2-yl)((4-nitrophenoxy)carbonyl)amino)methyl)benzoate

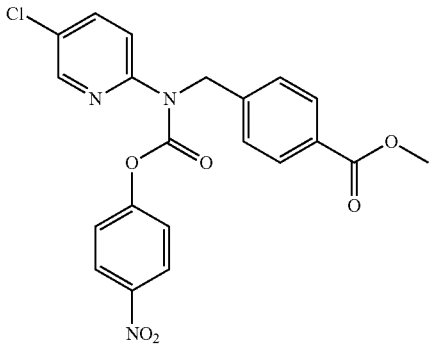 [SMILES: COC(=O)c1ccc(CN(C(=O)Oc2ccc([N+](=O)[O-])cc2)c2ccc(Cl)cn2)cc1]

Compound of Formula 7-4 (methyl 4-(((5-chloropyridin-2-yl)amino)methyl)benzoate; 1.000 g, 3.614 mmol) and 4-nitrophenyl chloroformate (0.801 g, 3.975 mmol) were dissolved in dichloromethane (30 mL) at room temperature and stirred at the same temperature for 3 days, and the solid was filtered out. Then, water was poured into the reaction mixture, and the organic layer was extracted with dichloromethane. Then, the organic layer was washed with saturated sodium chloride aqueous solution, dehydrated with anhydrous magnesium sulfate, and then concentrated under reduced pressure. The concentrate was purified and concentrated by column chromatography (silica; ethyl acetate: hexane=20-30%) to give the desired compound of Formula 7-5 (0.160 g, 10.0%) in the form of a white solid.

Formula 7-6: methyl 4-((N-(5-chloropyridin-2-yl)morpholine-4-carboxamido)methyl)benzoate

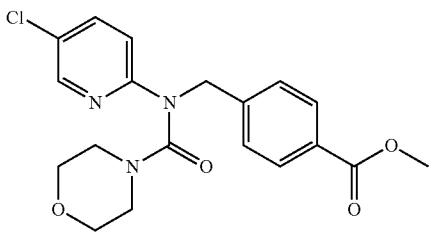 [SMILES: COC(=O)c1ccc(CN(C(=O)N2CCOCC2)c2ccc(Cl)cn2)cc1]

Compound of Formula 7-5 (methyl 4-(((5-chloropyridin-2-yl)((4-nitrophenoxy)carbonyl)amino)methyl)benzoate; 0.100 g, 0.226 mmol) and morpholine (0.024 mL, 0.272 mmol) were dissolved in dimethylformamide (10 mL) at 60° C. and stirred at the same temperature for 12 hours. Then, the dimethylformamide was removed under reduced pressure, water was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=20-30%) to give the desired compound of Formula 7-6 (0.032 g, 36.3%) in the form of a colorless oil.

Compound 533: N-(5-chloropyridin-2-yl)-N-(4-(hydroxycarbamoyl)benzyl)morpholine-4-carboxamide

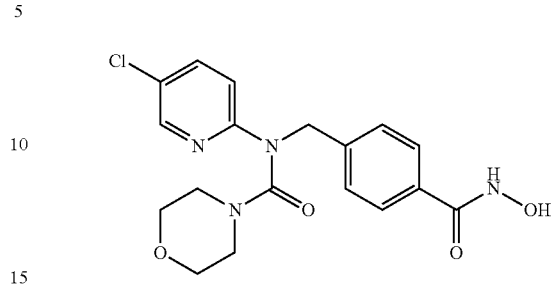

Compound of Formula 7-6 (methyl 4-((N-(5-chloropyridin-2-yl)morpholine-4-carboxamido)methyl)benzoate; 0.032 g, 0.082 mmol) was dissolved in methanol (10 mL) at room temperature, and then hydroxylamine hydrochloride (0.028 g, 0.410 mmol), potassium hydroxide (0.046 g, 0.821 mmol) and hydroxylamine (50 wt % aqueous solution; 0.211 mL, 1.642 mmol) were added to the reaction solution and stirred at the same temperature for 6 hours. Then, water was poured into the reaction mixture, and the organic layer was extracted with ethyl acetate. Then, the organic layer was washed with saturated sodium chloride aqueous solution, dehydrated with anhydrous magnesium sulfate, and then concentrated under reduced pressure. Dichloromethane and hexane were added to the concentrate and stirred. Then, the precipitated solid was filtered and dried to give the desired Compound 533 (0.011 g, 34.3%) in the form of a white solid.
$^1$H NMR (400 MHz, DMSO-$d_6$) δ 8.31 (d, 1H, J=1.5 Hz), 7.79-7.76 (m, 1H), 7.64 (d, 2H, J=7.3 Hz), 7.29 (d, 2H, J=7.8 Hz), 7.08 (d, 1H, J=8.9 Hz), 4.95 (s, 2H), 3.46-3.45 (m, 4H), 3.24-3.23 (m, 4H); MS (ESI) m/z 391.1 (M$^+$+H).

Example 139: Synthesis of Compound 543

Formula 1-4: methyl 4-((4-(2-morpholinoethyl)-N-(4-(trifluoromethyl)phenyl)piperazine-1-carboxamido)methyl)benzoate

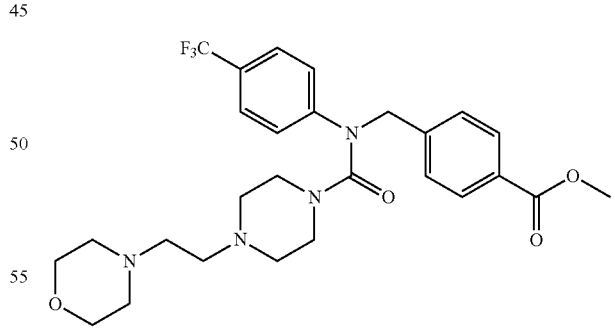

Compound of Formula 1-3 (methyl 4-((((4-nitrophenoxy)carbonyl)(4-(trifluoromethyl)phenyl)amino)methyl)benzoate; 0.253 g, 0.534 mmol), 4-(2-(piperazin-1-yl)ethyl)morpholine (0.213 g, 1.068 mmol) and potassium carbonate (0.221 g, 1.602 mmol) were dissolved in N,N-dimethylformamide (5 ml) and it was stirred at 60° C. for 2 days. saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; methanol/dichloromethane=10%) to give the desired compound of Formula 1-4 (0.139 g, 48.5%) in the form of colorless liquid.

Compound 543, N-(4-(hydroxycarbamoyl)benzyl)-4-(2-morpholinoethyl)-N-(4-(trifluoromethyl)phenyl)piperazine-1-carboxamide

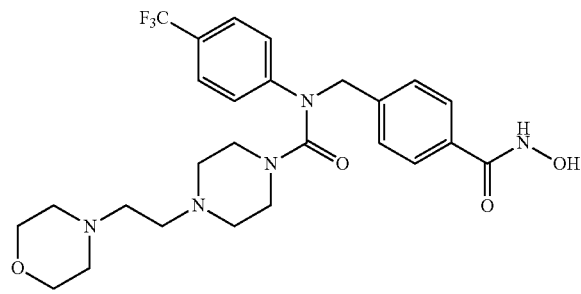 [SMILES: O=C(NO)c1ccc(CN(C(=O)N2CCN(CCN3CCOCC3)CC2)c2ccc(C(F)(F)F)cc2)cc1]

Compound of Formula 1-4 (methyl 4-((4-(2-morpholinoethyl)-N-(4-(trifluoromethyl)phenyl)piperazine-1-carboxamido)methyl)benzoate; 0.139 g, 0.260 mmol) and hydroxylamine (50 wt % aqueous solution; 0.159 ml, 2.600 mmol) were dissolved in methanol (5 ml) and potassium hydroxide (0.073 g, 1.300 mmol) was added. It was stirred at room temperature for 16 hours. the concentrate was obtained by removing the solvent from the reaction mixture under reduced pressure. saturated sodium hydrogen carbonate aqueous solution was poured into the obtained concentrate, and the organic layer was extracted with ethyl acetate. The organic layer was dehydrated with anhydrous magnesium sulfate, and then concentrated under reduced pressure. The precipitated solid was filtered and dried to give the desired Compound 543 (0.055 g, 39.5%) in the form of a white solid.

$^1$H NMR (400 MHz, DMSO-$d_6$) δ 11.2 (brs, 1H), 9.10 (brs, 1H), 7.64-7.56 (m, 4H), 7.34 (d, 2H, J=8.0 Hz), 7.20 (d, 2H, J=8.8 Hz), 4.89 (s, 2H), 3.49-3.47 (m, 4H), 3.16-3.14 (m, 4H), 2.31-2.24 (m, 12H); MS (ESI) m/z 536.2 (M$^+$+H).

Example 140: Synthesis of Compound 544

Formula 1-4: methyl 4-((4-(pyridin-4-yl)-N-(4-(trifluoromethyl)phenyl)piperazine-1-carboxamido)methyl)benzoate

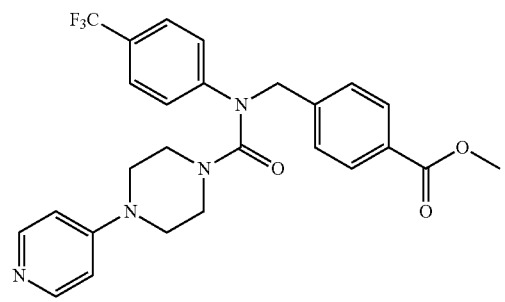 [SMILES: COC(=O)c1ccc(CN(C(=O)N2CCN(c3ccncc3)CC2)c2ccc(C(F)(F)F)cc2)cc1]

Compound of Formula 1-3 (methyl 4-((((4-nitrophenoxy)carbonyl)(4-(trifluoromethyl)phenyl)amino)methyl)benzoate; 0.230 g, 0.484 mmol), 1-(pyridin-4-yl)piperazine (0.159 g, 0.968 mmol) and potassium carbonate (0.201 g, 1.451 mmol) were dissolved in N,N-dimethylformamide (5 ml) and it was stirred at 60° C. for 2 days. Saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; methanol/dichloromethane=10%) to give the desired compound of Formula 1-4 (0.104 g, 43.0%) in the form of colorless liquid.

Compound 544, N-(4-(hydroxycarbamoyl)benzyl)-4-(pyridin-4-yl)-N-(4-(trifluoromethyl)phenyl)piperazine-1-carboxamide

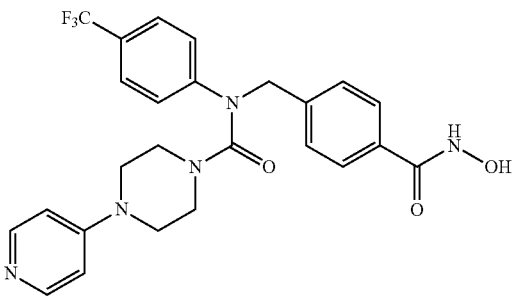 [SMILES: O=C(NO)c1ccc(CN(C(=O)N2CCN(c3ccncc3)CC2)c2ccc(C(F)(F)F)cc2)cc1]

Compound of Formula 1-4 (methyl 4-((4-(pyridin-4-yl)-N-(4-(trifluoromethyl)phenyl)piperazine-1-carboxamido)methyl)benzoate; 0.104 g, 0.209 mmol) and hydroxylamine (50 wt % aqueous solution; 0.128 ml, 2.086 mmol) were dissolved in methanol (5 ml) and potassium hydroxide (0.059 g, 1.043 mmol) was added. It was stirred at room temperature for 16 hours. the reaction mixture was concentrated under reduced pressure. Saturated sodium hydrogen carbonate aqueous solution (30 ml) was poured into the concentrate and stirred. The precipitated solid was filtered and dried to give the desired Compound 544 (0.086 g, 82.7%) in the form of a white solid.

$^1$H NMR (400 MHz, DMSO-$d_6$) δ 11.1 (brs, 1H), 8.99 (brs, 1H), 8.10 (d, 2H, J=6.4 Hz), 7.63-7.58 (m, 4H), 7.35 (d, 2H, J=8.4 Hz), 7.29 (d, 2H, J=8.0 Hz), 6.72 (d, 2H, J=6.4 Hz), 4.93 (s, 2H), 3.28 (s, 4H); MS (ESI) m/z 500.2 (M$^+$+H).

Example 141: Synthesis of Compound 545

Formula 1-4: methyl 4-((4-(2-morpholino-2-oxo-ethyl)-N-(4-(trifluoromethyl)phenyl)piperazine-1-carboxamido)methyl)benzoate

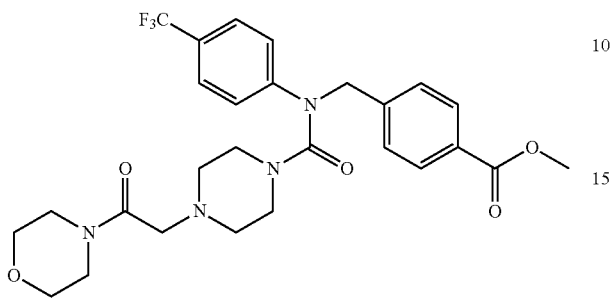

Compound of Formula 1-3 (methyl 4-((((4-nitrophenoxy)carbonyl)(4-(trifluoromethyl)phenyl)amino)methyl)benzoate; 0.213 g, 0.450 mmol), 1-morpholino-2-(piperazin-1-yl)ethanone (0.192 g, 0.900 mmol) and potassium carbonate (0.187 g, 1.350 mmol) were dissolved in N,N-dimethylformamide (5 ml) and it was stirred at 60° C. for 2 days. Saturated sodium hydrogen carbonate aqueous solution was poured into the reaction mixture and the organic layer was extracted with ethyl acetate. The organic layer was washed with saturated sodium chloride aqueous solution, dehydrated with anhydrous sodium sulfate, filtered, and then concentrated under reduced pressure. The concentrate was purified and concentrated by column chromatography (silica; methanol/dichloromethane=10%) to give the desired compound of Formula 1-4 (0.109 g, 44.1%) in the form of colorless liquid.

Compound 545, N-(4-(hydroxycarbamoyl)benzyl)-4-(2-morpholino-2-oxoethyl)-N-(4-(trifluoromethyl)phenyl)piperazine-1-carboxamide

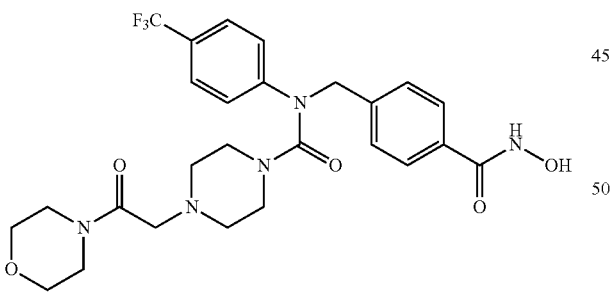

Compound of Formula 1-4 (methyl 4-((4-(2-morpholino-2-oxoethyl)-N-(4-(trifluoromethyl)phenyl)piperazine-1-carboxamido)methyl)benzoate; 0.109 g, 0.199 mmol) and hydroxylamine (50 wt % aqueous solution; 0.122 ml, 1.987 mmol) were dissolved in methanol (5 ml) and potassium hydroxide (0.056 g, 0.994 mmol) was added. It was stirred at room temperature for 16 hours. the reaction mixture was concentrated under reduced pressure. Saturated sodium hydrogen carbonate aqueous solution (30 ml) was poured into the concentrate and stirred. The precipitated solid was filtered and dried to give the desired Compound 545 (0.057 g, 52.0%) in the form of a white solid.

$^1$H NMR (400 MHz, DMSO-$d_6$) δ 11.1 (brs, 1H), 8.99 (brs, 1H), 7.64-7.57 (m, 4H), 7.32-7.30 (m, 2H), 7.20 (d, 2H, J=8.4 Hz), 4.88 (s, 2H), 3.48-3.46 (m, 6H), 3.36-3.35 (m, 2H), 3.17 (brs, 4H), 3.08 (s, 2H), 2.26 (brs, 4H); MS (ESI) m/z 550.2 (M$^+$+H).

Example 142: Synthesis of Compound 577

Formula 6-2: 3-fluoro-4-((4-(trifluoromethyl)phenylamino)methyl)benzonitrile

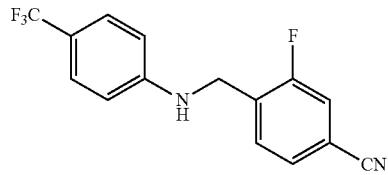 [SMILES: N#Cc1ccc(CNc2ccc(C(F)(F)F)cc2)c(F)c1]

Compound of Formula 6-1 (4-(bromomethyl)-3-fluorobenzonitrile; 1.10 g, 5.06 mmol) was dissolved in acetonitrile (60 mL), and then 4-(trifluoromethyl)benzenamine (0.39 mL, 4.30 mmol) and N,N-diisopropylethylamine (1.14 mL, 6.45 mmol) were added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10-30%) to give the desired compound of Formula 6-2 (0.11 g, 28%) in the form of a colorless oil.

Formula 6-3

3-fluoro-4-((4-(trifluoromethyl)phenylamino)methyl)benzoic acid

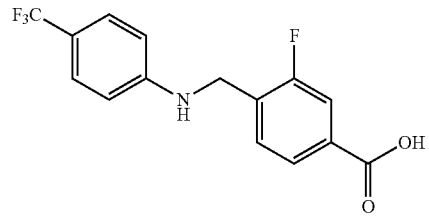 [SMILES: O=C(O)c1ccc(CNc2ccc(C(F)(F)F)cc2)c(F)c1]

Compound of Formula 6-2 (3-fluoro-4-((4-(trifluoromethyl)phenylamino)methyl)benzonitrile; 0.93 g, 3.17 mmol) and lithium hydroxide monohydrate (1.33 g, 31.73 mmol) were dissolved in methanol (30 mL)/water (15 mL) and stirred under reflux for 16 hours. Then, the concentrate was obtained by removing the solvent from the reaction mixture under reduced pressure. 2 N hydrochloric acid aqueous solution was poured into the obtained concentrate, and the precipitated solid was filtered to give the desired compound of Formula 6-3 (0.36 g, 37%) in the form of a light white solid.

Formula 6-4: methyl 3-fluoro-4-((4-(trifluoromethyl)phenylamino)methyl)benzoate

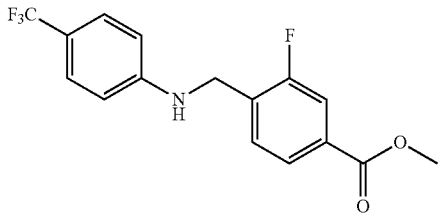 [SMILES: COC(=O)c1ccc(CNc2ccc(C(F)(F)F)cc2)c(F)c1]

Compound of Formula 6-3 (3-fluoro-4-((4-(trifluoromethyl)phenylamino)methyl)benzoic acid; 0.36 g, 1.17 mmol), methanol (0.95 mL, 23.49 mmol) and N,N-diisopropylethylamine (0.62 mL, 3.52 mmol) were dissolved in THF (30 mL), and then 1-ethyl-3-[3-dimethylaminopropyl] carbodiimide hydrochloride (EDC, 0.45 g, 2.35 mmol) and 1-hydroxybenzotriazole hydrate (HOBt, 0.31 g, 2.35 mmol) were added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10-40%) to give the desired compound of Formula 6-4 (0.11 g, 28%) in the form of a white solid.

Formula 6-5: methyl 3-fluoro-4-((((4-nitrophenoxy)carbonyl)(4-(trifluoromethyl)phenyl)amino)methyl)benzoate

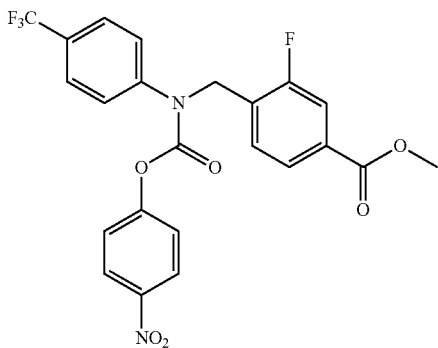 [SMILES: COC(=O)c1ccc(CN(C(=O)Oc2ccc([N+](=O)[O-])cc2)c2ccc(C(F)(F)F)cc2)c(F)c1]

Compound of Formula 6-4 (methyl 3-fluoro-4-((4-(trifluoromethyl)phenylamino)methyl)benzoate; 0.61 g, 1.86 mmol), 4-nitrophenyl chloroformate (0.75 g, 3.72 mmol) and potassium carbonate (0.77 g, 5.59 mmol) were dissolved in acetonitrile (50 mL) at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10-30%) to give the desired compound of Formula 6-5 (0.62 g, 67%) in the form of a colorless oil.

Formula 6-6: methyl 3-fluoro-4-((N-(4-(trifluoromethyl)phenyl)morpholine-4-carboxamido)methyl)benzoate

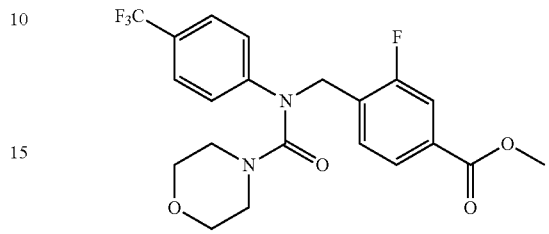

Compound of Formula 6-5 (methyl 3-fluoro-4-((((4-nitrophenoxy)carbonyl)(4-(trifluoromethyl)phenyl)amino)methyl)benzoate; 0.31 g, 0.63 mmol), morpholine (0.11 mL, 1.25 mmol) and potassium carbonate (0.26 g, 1.88 mmol) were dissolved in dimethylformamide (5 mL) at 60° C. and stirred at the same temperature for 16 hours. Then, saturated ammonium chloride aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=20-60%) to give the desired compound of Formula 6-6 (1.58 g, 98%) in the form of a colorless liquid.

Compound 577: N-(2-fluoro-4-(hydroxycarbamoyl)benzyl)-N-(4-(trifluoromethyl)phenyl)morpholine-4-carboxamide

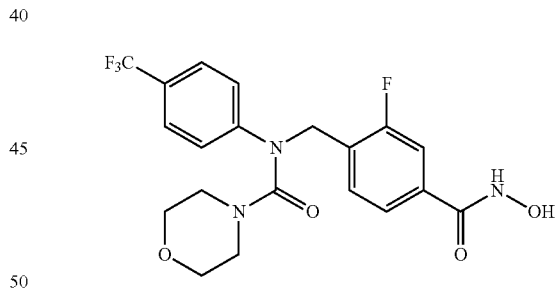

Compound of Formula 6-6 (methyl 3-fluoro-4-((N-(4-(trifluoromethyl)phenyl)morpholine-4-carboxamido)methyl)benzoate; 0.15 g, 0.35 mmol) was dissolved in MeOH (10 mL), and the hydroxylamine (50.0 wt % aqueous solution; 0.21 mL, 3.49 mmol) and potassium hydroxide (0.078 g, 1.40 mmol) were added at room temperature and stirred at the same temperature overnight. Then, the concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 577 (0.084 g, 54%) in the form of a white solid.

¹H NMR (400 MHz, DMSO-d₆) δ 11.2 (brs, 1H), 9.11 (brs, 1H), 7.63 (d, 2H, J=8.8 Hz), 7.52-7.43 (m, 3H), 7.28 (d, 2H, J=8.4 Hz), 4.92 (s, 2H), 3.41-3.39 (m, 4H), 3.16-3.15 (m, 4H).

Example 143: Synthesis of Compound 578

Formula 6-6: methyl 4-((3,3-difluoro-N-(4-(trifluoromethyl)phenyl)azetidine-1-carboxamido)methyl)3-fluorobenzoate

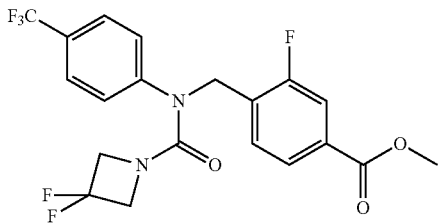 [SMILES: COC(=O)c1ccc(CN(C(=O)N2CC(F)(F)C2)c2ccc(C(F)(F)F)cc2)c(F)c1]

Compound of Formula 6-5 (methyl 3-fluoro-4-((((4-nitrophenoxy)carbonyl)(4-(trifluoromethyl)phenyl)amino)methyl)benzoate; 0.31 g, 0.63 mmol), 3,3-difluoroazetidine hydrochloride (0.16 g, 1.25 mmol) and potassium carbonate (0.26 g, 1.88 mmol) were dissolved in dimethylformamide (5 mL) at 60° C. and stirred at the same temperature for 16 hours. Then, saturated ammonium chloride aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The residue was purified and concentrated by column chromatography (silica; ethyl acetate/hexane=10-40%) to give the desired compound of Formula 6-6 (0.19 g, 68%) in the form of a colorless liquid.

Compound 578: 3,3-difluoro-N-(2-fluoro-4-(hydroxycarbamoyl)benzyl)-N-(4-(trifluoromethyl)phenyl) azetidine-1-carboxamide

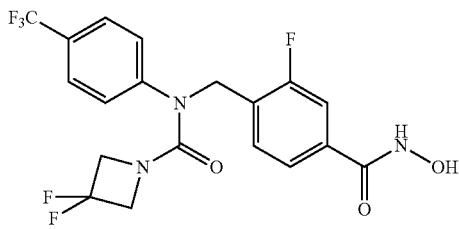 [SMILES: O=C(NO)c1ccc(CN(C(=O)N2CC(F)(F)C2)c2ccc(C(F)(F)F)cc2)c(F)c1]

Compound of Formula 6-6 (methyl 4-((3,3-difluoro-N-(4-(trifluoromethyl)phenyl)azetidine-1-carboxamido) methyl)3-fluorobenzoate; 0.19 g, 0.42 mmol) was dissolved in MeOH (10 mL), and the hydroxylamine (50.0 wt % aqueous solution; 0.26 mL, 4.27 mmol) and potassium hydroxide (0.12 g, 2.14 mmol) were added at room temperature and stirred at the same temperature overnight. Then, the reaction mixture was concentrated under reduced pressure. Saturated sodium hydrogen carbonate aqueous solution (50 ml) was poured into the concentrate and stirred. The precipitated solid was filtered and dried to give the desired Compound 578 (0.15 g, 82%) in the form of a white solid.

¹H NMR (400 MHz, DMSO-d₆) δ 11.2 (brs, 1H), 9.10 (brs, 1H), 7.70 (d, 2H, J=8.4 Hz), 7.52-7.44 (m, 4H), 7.42-7.39 (m, 1H), 4.95 (s, 2H), 3.94-3.88 (m, 4H).

Example 144: Synthesis of Compound 580

Formula 1-4: methyl 4-((N-(4-(trifluoromethyl)phenyl)-1,4-oxazepane-4-carboxamido)methyl)benzoate

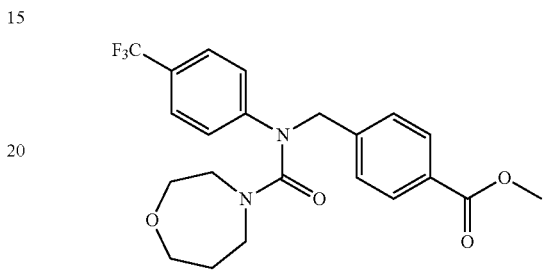

Compound of Formula 1-3 (methyl 4-((((4-nitrophenoxy)carbonyl)(4-(trifluoromethyl)phenyl)amino)methyl)benzoate; 0.29 g, 0.62 mmol was dissolved in dimethylformamide. 1,4-oxazepane (0.17 g, 1.24 mmol) and potassium carbonate (0.25 g, 1.86 mmol) were added. It was reacted at 60° C. for one day, and then diluted with saturated ammonium chloride solution. The organic layer was extracted with ethyl acetate, dehydrated with anhydrous sodium sulfate, filtered, and then concentrated under reduced pressure. The residue was purified and concentrated by column chromatography (silica; ethyl acetate/hexane=10-40%) to give the desired compound of Formula 1-4 (0.08 g, 30%) in the form of colorless liquid.

Compound 580, N-(4-(hydroxycarbamoyl)benzyl)-N-(4-(trifluoromethyl)phenyl)-1,4-oxazepane-4-carboxamide

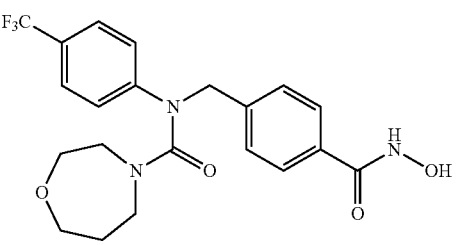 [SMILES: O=C(NO)c1ccc(CN(C(=O)N2CCCOCC2)c2ccc(C(F)(F)F)cc2)cc1]

Compound of Formula 1-4 (methyl 4-((N-(4-(trifluoromethyl)phenyl)-1,4-oxazepane-4-carboxamido)methyl)benzoate; 0.082 g, 0.18 mmol) was dissolved in MeOH (10 ml). Hydroxylamine (50 wt % aqueous solution; 0.057 ml, 0.939 mmol) and potassium hydroxide (0.10 g, 1.87 mmol) were added and reacted at room temperature for overnight. The concentrate was obtained by removing the solvent from the reaction mixture under reduced pressure. Saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 580 (0.03 g, 40%) in the form of a white solid.

$^1$H NMR (400 MHz, DMSO-d$_6$) δ 11.2 (brs, 1H), 9.19 (brs, 1H), 7.63-7.59 (m, 4H), 7.39 (d, 2H, J=8.0 Hz), 7.22 (d, 2H, J=8.4 Hz), 4.88 (s, 2H), 3.54-3.49 (m, 4H), 3.40-3.28 (m, 4H), 1.75-1.66 (m, 2H).

Example 145: Synthesis of Compound 651

Formula 12-5: methyl 4-((4-((4-hydroxy-tetrahydro-2H-pyran-4-yl)methyl)-N-(3-(trifluoromethyl)phenyl)piperazine-1-carboxamido)methyl)benzoate

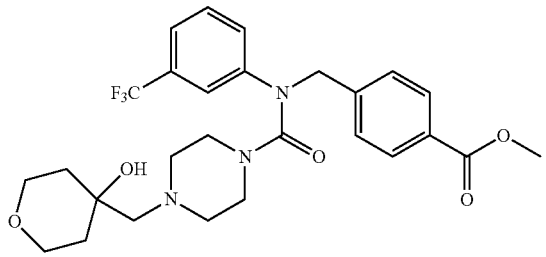 [SMILES: COC(=O)c1ccc(CN(C(=O)N2CCN(CC3(O)CCOCC3)CC2)c2cccc(C(F)(F)F)c2)cc1]

Compound of Formula 12-2 (methyl 4-((N-(3-(trifluoromethyl)phenyl)piperazine-1-carboxamido)methyl)benzoate hydrochloride; 0.15 g, 0.35 mmol), 1,6-dioxaspiro[2,5]octane (0.12 mL, 1.06 mmol) and N,N-diisopropylethylamine (0.30 mL, 1.78 mmol) were mixed with ethanol (10 mL) and heated at 110° C. for 40 minutes under microwave irradiation, and then the temperature was lowered to room temperature. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/methylene chloride=10%) to give the desired compound of Formula 12-5 (0.11 g, 58%) in the form of a colorless liquid.

Compound 651: 4-((4-hydroxy-tetrahydro-2H-pyran-4-yl)methyl)-N-(4-(hydroxycarbamoyl)benzyl)-N-(3-(trifluoromethyl)phenyl)piperazine-1-carboxamide

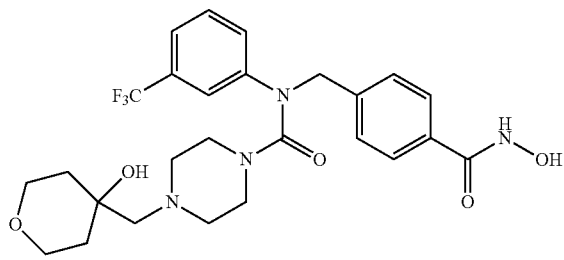 [SMILES: O=C(NO)c1ccc(CN(C(=O)N2CCN(CC3(O)CCOCC3)CC2)c2cccc(C(F)(F)F)c2)cc1]

Compound of Formula 12-5 (methyl 4-((4-((4-hydroxy-tetrahydro-2H-pyran-4-yl)methyl)-N-(3-(trifluoromethyl) phenyl)piperazine-1-carboxamido)methyl)benzoate; 0.11 g, 0.20 mmol) and hydroxylamine (50.0 wt % aqueous solution; 0.06 mL, 1.04 mmol) were dissolved in methanol (10 mL), and then potassium hydroxide (0.11 g, 2.09 mmol) was added at room temperature and stirred at the same temperature for 16 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/methylene chloride=10%) to give the desired Compound 651 (0.07 g, 70%) in the form of a white solid.

$^1$H NMR (400 MHz, DMSO-d$_6$) δ 11.1 (brs, 1H), 9.02 (brs, 1H), 7.66 (d, 2H, J=7.7 Hz), 7.53-7.49 (m, 1H), 7.39-7.37 (m, 5H), 4.92 (s, 2H), 4.15 (s, 1H), 3.60-3.54 (m, 4H), 3.16 (s, 4H), 2.35 (s, 4H), 2.18 (s, 2H), 1.52-1.47 (m, 2H), 1.35-1.31 (m, 2H).

Example 146: Synthesis of Compound 683

Formula 1-4: methyl 4-((4-benzyl-N-(3-(trifluromethyl)phenyl)piperazine-1-carboxamido)methyl)benzoate

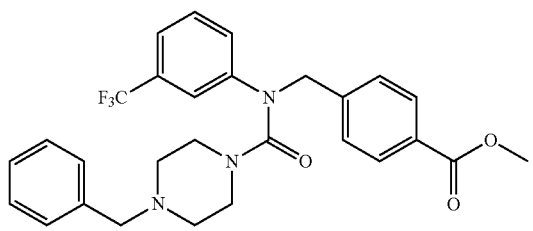 [SMILES: COC(=O)c1ccc(CN(C(=O)N2CCN(Cc3ccccc3)CC2)c2cccc(C(F)(F)F)c2)cc1]

Compound of Formula 1-3 (methyl 4-(((((4-nitrophenoxy)carbonyl)(3-(trifluoromethyl)phenylamino)methyl)benzoate; 0.13 g, 0.27 mmol) was dissolved in dimethylformamide (2 mL), and potassium carbonate (0.11 g, 0.83 mmol) and 1-benzylpiperazine (0.10 mL, 0.55 mmol) were then added. The mixture was reacted at 40° C. for 16 hours. The dimethylformamide was removed under reduced pressure, water was poured into the reaction mixture and the organic layer was extract with ethyl acetate. The organic layer was washed with saturated sodium chloride aqueous solution, dehydrated with anhydrous sodium sulfate, and then concentrated under reduced pressure. The residue was purified and concentrated by column chromatography (silica; ethyl acetate/hexane=20-60%) to give the desired compound of Formula 1-4 (0.07 g, 53%) in the form of a colorless oil.

Compound 683: 4-benzyl-N-(4-(hydroxycarbamoyl)benzyl)-N-(3-(trifluoromethyl)phenyl)piperazine-1-carboxamide

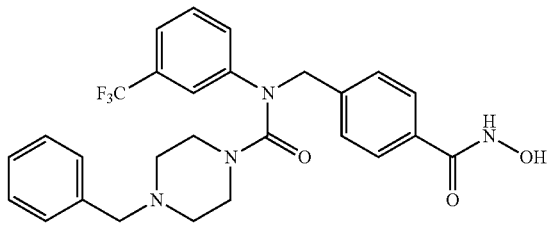 [SMILES: O=C(NO)c1ccc(CN(C(=O)N2CCN(Cc3ccccc3)CC2)c2cccc(C(F)(F)F)c2)cc1]

Compound of Formula 1-4 (methyl 4-((4-benzyl-N-(3-(trifluromethyl)phenyl)piperazine-1-carboxamido)methyl)benzoate; 0.07 g, 0.14 mmol) and hydroxylamine (50.0 wt % aqueous solution; 0.045 mL, 0.743 mmol) were dissolved in methanol (10 mL) at room temperature, and then potassium hydroxide (0.08 g, 1.48 mmol) was added and stirred at the same temperature for 16 hours. The reaction mixture was concentrated under reduced pressure. Saturated sodium hydrogen carbonate (50 ml) was poured into the concentrate and stirred. The precipitated solid was filtered and dried to give the desired Compound 683 (0.06 g, 89%) in the form of a white solid.

$^1$H NMR (400 MHz, DMSO-$d_6$) δ 11.1 (brs, 1H), 9.03 (brs, 1H), 7.64 (d, 2H, J=8.2 Hz), 7.52-7.48 (m, 1H), 7.39-7.35 (m, 5H), 7.31-7.17 (m, 5H), 4.87 (s, 2H), 3.39 (s, 2H), 3.17 (s, 4H), 2.33 (s, 4H).

Example 147: Synthesis of Compound 684

Formula 1-4: methyl 4-((4-(3-methoxyphenyl)-N-(3-(trifluromethyl)phenyl)piperazine-1-carboxamido)methyl)benzoate

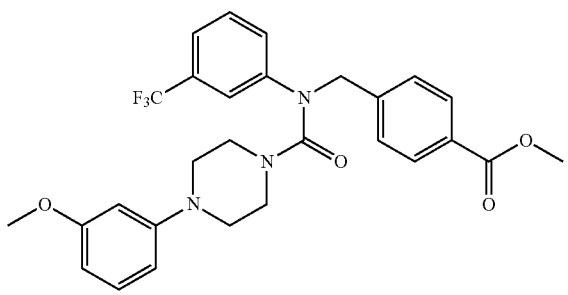

Compound of Formula 1-3 (methyl 4-(((((4-nitrophenoxy)carbonyl)(3-(trifluoromethyl)phenyl amino)methyl)benzoate; 0.13 g, 0.28 mmol) was dissolved in dimethylformamide (2 mL), and potassium carbonate (0.11 g, 0.85 mmol) and 1-(3-methoxyphenyl)piperazine (0.10 mL, 0.56 mmol) were then added. The mixture was reacted at 40° C. for 16 hours. The dimethylformamide was removed under reduced pressure, water was poured into the reaction mixture and the organic layer was extract with ethyl acetate. The organic layer was washed with saturated sodium chloride aqueous solution, dehydrated with anhydrous sodium sulfate, and then concentrated under reduced pressure. The residue was purified and concentrated by column chromatography (silica; ethyl acetate/hexane=10-40%) to give the desired compound of Formula 1-4 (0.07 g, 47%) in the form of a colorless oil.

Compound 684: N-(4-(hydroxycarbamoyl)benzyl)-4-(3-methoxyphenyl)-N-(3-(trifluoromethyl)phenyl)piperazine-1-carboxamide

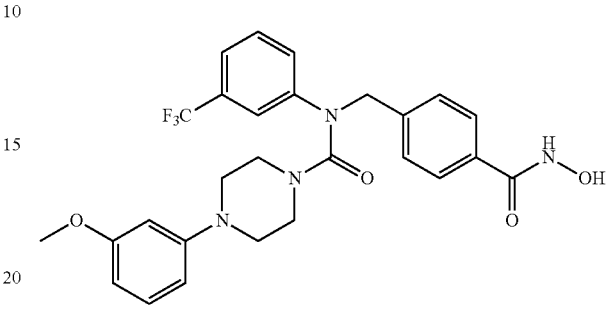

Compound of Formula 1-4 (methyl 4-((4-(3-methoxyphenyl)-N-(3-(trifluromethyl)phenyl)piperazine-1-carboxamido)methyl)benzoate; 0.07 g, 0.13 mmol) and hydroxylamine (50.0 wt % aqueous solution; 0.04 mL, 0.67 mmol) were dissolved in methanol (10 mL) at room temperature, and then potassium hydroxide (0.07 g, 1.34 mmol) was added and stirred at the same temperature for 16 hours. The reaction mixture was concentrated under reduced pressure. Saturated sodium hydrogen carbonate (50 ml) was poured into the concentrate and stirred. The precipitated solid was filtered and dried to give the desired Compound 684 (0.05 g, 77%) in the form of a white solid.

$^1$H NMR (400 MHz, DMSO-$d_6$) δ 7.65 (d, 2H, J=8.1 Hz), 7.54-7.44 (m, 3H), 7.39-7.34 (m, 3H), 7.08 (t, 1H, J=8.2 Hz), 6.46-6.35 (m, 3H), 4.92 (s, 2H), 3.68 (s, 3H), 3.30 (s, 4H), 2.97 (s, 4H).

Example 148: Synthesis of Compound 716

Formula 12-6: methyl 4-((4-fluoro-tetrahydro-2H-pyran-4-yl)methyl)-N-(3-(trifluoromethyl)phenyl)piperazine-1-carboxamido)methyl)benzoate

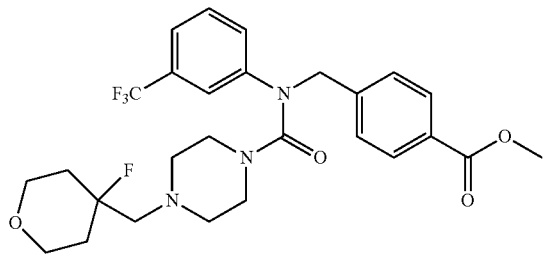 [SMILES: COC(=O)c1ccc(CN(C(=O)N2CCN(CC3(F)CCOCC3)CC2)c2cccc(C(F)(F)F)c2)cc1]

Compound of Formula 12-5 (methyl 4-((4-((4-hydroxy-tetrahydro-2H-pyran-4-yl)methyl)-N-(3-(trifluoromethyl)phenyl)piperazine-1-carboxamido)methyl)benzoate; 0.28 g, 0.52 mmol) was dissolved in methylene chloride (15 mL), and then DAST (0.08 mL, 0.58 mmol) was added at 0° C. and stirred at the same temperature for 3 hours. Then, saturated sodium hydrogen carbonate aqueous solution was poured into the reaction mixture, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; ethyl acetate/hexane=30-90%) to give the desired compound of Formula 12-6 (0.15 g, 54%) in the form of a colorless liquid.

Compound 716: 4-((4-fluorotetrahydro-2H-pyran-4-yl)methyl)-N-(4-(hydroxycarbamoyl)benzyl)-N-(3-(trifluoromethyl)phenyl)piperazine-1-carboxamide

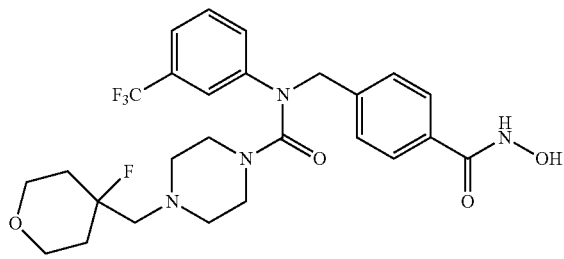 [SMILES: O=C(NO)c1ccc(CN(C(=O)N2CCN(CC3(F)CCOCC3)CC2)c2cccc(C(F)(F)F)c2)cc1]

Compound of Formula 12-6 (methyl 4-((4-fluoro-tetrahydro-2H-pyran-4-yl)methyl)-N-(3-(trifluoromethyl)phenyl)piperazine-1-carboxamido)methyl)benzoate; 0.15 g, 0.28 mmol) and hydroxylamine (50.0 wt % aqueous solution; 0.08 mL, 1.44 mmol) were dissolved in MeOH (10 mL), and potassium hydroxide (0.16 g, 2.88 mmol) was to the mixture and stirred at room temperature and stirred at the same temperature for 16 hours. Then, the concentrate was obtained by removing the solvent from the reaction mixture under reduced pressure. saturated sodium hydrogen carbonate aqueous solution was poured into the obtained concentrate, and the organic layer was extracted with ethyl acetate. The organic layer was washed with saturated sodium chloride aqueous solution, dehydrated with anhydrous magnesium sulfate, and then concentrated under reduced pressure. The concentrate was purified and concentrated by column chromatography (silica; methanol/dichloromethane=10%) to give the desired Compound 716 (0.06 g, 41%) in the form of a white solid.

$^1$H NMR (400 MHz, DMSO-$d_6$) δ 11.1 (brs, 1H), 9.00 (brs, 1H), 7.65 (d, 2H, J=7.7 Hz), 7.53-7.49 (m, 1H), 7.39-7.35 (m, 5H), 4.92 (s, 2H), 3.64-3.61 (m, 2H), 3.52-3.49 (m, 2H), 3.22-3.16 (m, 4H), 2.46 (s, 2H), 2.33-2.29 (m, 4H), 1.69-1.67 (m, 4H).

Example 149: Synthesis of Compound 717

Formula 1-4: methyl 4-((4-phenyl-N-(3-(triflurom-ethyl)phenyl)piperazine-1-carboxamido)methyl) benzoate

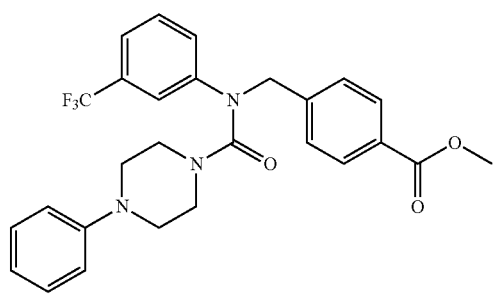 [SMILES: COC(=O)c1ccc(CN(C(=O)N2CCN(c3ccccc3)CC2)c2cccc(C(F)(F)F)c2)cc1]

Compound of Formula 1-3 (methyl 4-((((4-nitrophenoxy)carbonyl)(3-(trifluoro-methyl)phenyl amino)methyl)benzoate; 0.12 g, 0.26 mmol) was dissolved in dimethylformamide (5 mL), and potassium carbonate (0.10 g, 0.79 mmol) and 1-phenylpiperazine (0.08 mL, 0.56 mmol) were then added. The mixture was reacted at 40° C. for 16 hours. The dimethylformamide was removed under reduced pressure, water was poured into the reaction mixture and the organic layer was extract with ethyl acetate. The organic layer was washed with saturated sodium chloride aqueous solution, dehydrated with anhydrous sodium sulfate, and then concentrated under reduced pressure. The residue was purified and concentrated by column chromatography (silica; ethyl acetate/hexane=5-70%) to give the desired compound of Formula 1-4 (0.07 g, 57%) in the form of a colorless oil.

Compound 717: N-(4-(hydroxycarbamoyl)benzyl)-4-phenyl-N-(3-(trifluoromethyl)phenyl)piperazine-1-carboxamide

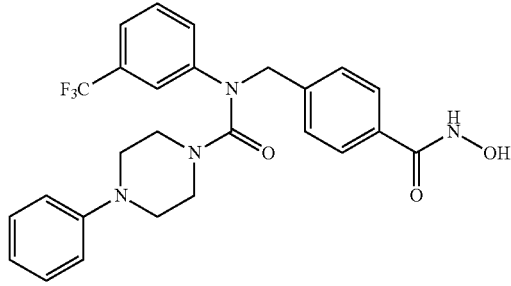 [SMILES: O=C(NO)c1ccc(CN(C(=O)N2CCN(c3ccccc3)CC2)c2cccc(C(F)(F)F)c2)cc1]

Compound of Formula 1-4 (methyl 4-((4-phenyl-N-(3-(trifluromethyl)phenyl)piperazine-1-carboxamido)methyl) benzoate; 0.07 g, 0.15 mmol) was dissolved in methanol (10 mL) at room temperature, and then hydroxylamine (50.0 wt % aqueous solution; 0.04 mL, 0.76 mmol) and potassium hydroxide (0.08 g, 1.52 mmol) was added and stirred at the same temperature for 16 hours. The reaction mixture was concentrated under reduced pressure. Saturated sodium hydrogen carbonate (30 ml) was poured into the concentrate and stirred. The precipitated solid was filtered and dried to give the desired Compound 717 (0.05 g, 70%) in the form of a white solid.

$^1$H NMR (400 MHz, DMSO-$d_6$) δ 7.65 (d, 2H, J=8.2 Hz), 7.58-7.46 (m, 3H), 7.39-7.31 (m, 3H), 7.20-7.16 (m, 2H), 6.87 (d, 2H, J=8.0 Hz), 6.80-6.76 (m, 1H), 4.95 (s, 2H), 3.32-3.30 (m, 4H), 2.98-2.95 (m, 4H).

Example 150: Synthesis of Compound 718

Formula 1-4: methyl 4-((4-benzhydryl-N-(3-(trifluromethyl)phenyl)piperazine-1-carboxamido)methyl)benzoate

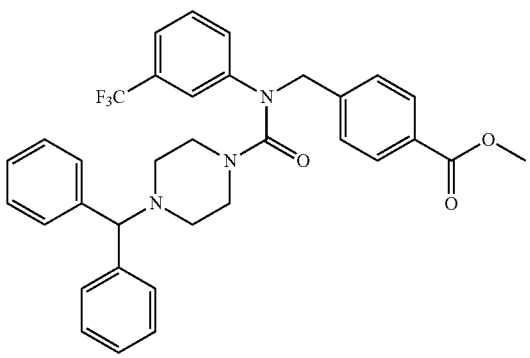 [SMILES: COC(=O)c1ccc(CN(C(=O)N2CCN(C(c3ccccc3)c3ccccc3)CC2)c2cccc(C(F)(F)F)c2)cc1]

Compound of Formula 1-3 (methyl 4-((((4-nitrophenoxy)carbonyl)(3-(trifluoromethyl)phenyl amino)methyl)benzoate; 0.14 g, 0.29 mmol) was dissolved in dimethylformamide (5 mL), and potassium carbonate (0.12 g, 0.88 mmol) and 1-benzhydrylpiperazine (0.15 g, 0.59 mmol) were then added. The mixture was reacted at 40° C. for 16 hours. The dimethylformamide was removed under reduced pressure, water was poured into the reaction mixture and the organic layer was extract with ethyl acetate. The organic layer was washed with saturated sodium chloride aqueous solution, dehydrated with anhydrous sodium sulfate, and then concentrated under reduced pressure. The residue was purified and concentrated by column chromatography (silica; ethyl acetate/hexane=5-70%) to give the desired compound of Formula 1-4 (0.13 g, 77%) in the form of a colorless oil.

Compound 718: 4-benzhydryl-N-(4-(hydroxycarbamoyl)benzyl)-N-(3-(trifluoromethyl)phenyl)piperazine-1-carboxamide

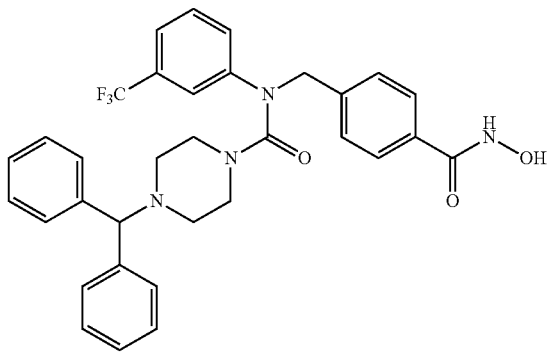 [SMILES: O=C(NO)c1ccc(CN(C(=O)N2CCN(C(c3ccccc3)c3ccccc3)CC2)c2cccc(C(F)(F)F)c2)cc1]

Compound of Formula 1-4 (methyl 4-((4-benzhydryl-N-(3-(trifluromethyl)phenyl)piperazine-1-carboxamido)methyl)benzoate; 0.13 g, 0.22 mmol) was dissolved in methanol (10 mL) at room temperature, and then hydroxylamine (50.0 wt % aqueous solution; 0.07 mL, 1.14 mmol) and potassium hydroxide (0.12 g, 2.28 mmol) was added and stirred at the same temperature for 16 hours. The reaction mixture was concentrated under reduced pressure. The precipitated solid was filtered and dried to give the desired Compound 718 (0.06 g, 46%) in the form of a pale yellow solid.

$^1$H NMR (400 MHz, DMSO-d$_6$) δ 7.62-7.59 (m, 2H), 7.49-7.43 (m, 1H), 7.38-7.32 (m, 7H), 7.27-7.22 (m, 6H), 7.17-7.13 (m, 2H), 4.85 (s, 2H), 4.20 (s, 1H), 3.19 (brs, 4H), 2.13 (brs, 4H).

Example 151: Synthesis of Compound 765

Formula 10-8: methyl 4-((4-ethyl-N-(3-(hydroxymethyl)phenyl)piperazine-1-carboxamido)methyl)benzoate

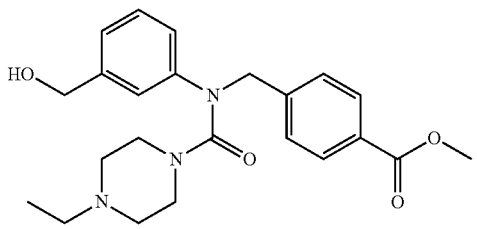 [SMILES: CCN1CCN(C(=O)N(Cc2ccc(C(=O)OC)cc2)c2cccc(CO)c2)CC1]

Compound of Formula 10-3 (methyl 4-(((3-(hydroxymethyl)phenyl)((4-nitrophenoxy)carbonyl)amino)methyl) benzoate; 0.500 g, 1.15 mmol), 1-ethyl-piperazine (0.392 g, 3.44 mmol) and potassium carbonate (0.792 g, 5.73 mmol) were mixed with N,N-dimethylformaldehyde (5 mL) at room temperature and stirred at the same temperature for 60 hours. Then, saturated ammonium chloride aqueous solution was poured into the reaction mixture, and the organic layer was extracted with ethyl acetate. The organic layer was washed with saturated sodium hydrogen carbonate aqueous solution, dehydrated with anhydrous magnesium sulfate, and then concentrated under reduced pressure. The concentrate was purified and concentrated by column chromatography (silica; methanol/methylene chloride=10%) to give the desired compound of Formula 10-8 (0.252 g, 54%) in the form of a light yellow liquid.

Formula 10-9: methyl 4-((4-ethyl-N-(3-(fluoromethyl)phenyl)piperazine-1-carboxamido)methyl)benzoate

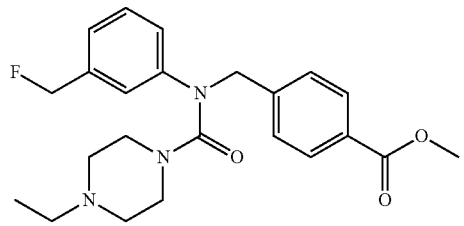 [SMILES: CCN1CCN(C(=O)N(Cc2ccc(C(=O)OC)cc2)c2cccc(CF)c2)CC1]

Compound of Formula 10-8 (methyl 4-((4-ethyl-N-(3-(hydroxymethyl)phenyl)piperazine-1-carboxamido)methyl) benzoate; 0.252 g, 0.61 mmol) was dissolved in methylene chloride (10 mL) at room temperature, and then diethylaminosulfur trifluoride (0.089 mL, 0.67 mmol) was added to the solution and stirred at the same temperature for 2 hours. Then, saturated sodium hydrogen carbonate aqueous solution was poured into the reaction mixture, and the organic layer was extracted with methylene chloride. The organic layer was washed with saturated sodium chloride aqueous solution, dehydrated with anhydrous magnesium sulfate, filtered, and then concentrated under reduced pressure. The concentrate was purified and concentrated by column chromatography (silica; methanol/methylene chloride=10%) to give the desired compound of Formula 10-9 (0.210 g, 83%) in the form of a yellow liquid.

Compound 765: 4-ethyl-N-(3-(fluoromethyl)phenyl)-N-(4-(hydroxycarbamoyl)benzyl)piperazine-1-carboxamide

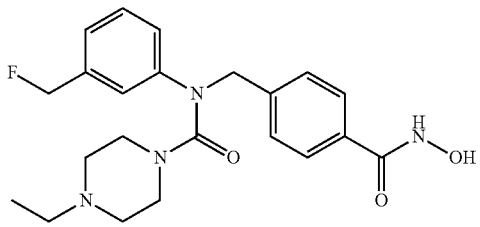 [SMILES: CCN1CCN(C(=O)N(Cc2ccc(C(=O)NO)cc2)c2cccc(CF)c2)CC1]

Compound of Formula 10-9 (methyl 4-((4-ethyl-N-(3-(fluoromethyl)phenyl)piperazine-1-carboxamido)methyl)benzoate; 0.210 g, 0.508 mmol) was dissolved in methanol (10 mL) at room temperature, and then hydroxylamine (50 wt % aqueous solution; 3.11 mL, 50.79 mmol) and potassium hydroxide (0.285 g, 5.08 mmol) were added to the solution and stirred at the same temperature for 3 hours. Then, the concentrate was obtained by removing the solvent from the reaction mixture under reduced pressure. Saturated sodium hydrogen carbonate aqueous solution was poured into the obtained concentrate, and then the organic layer was extracted with ethyl acetate. The organic layer was washed with saturated sodium chloride aqueous solution, dehydrated with anhydrous magnesium sulfate, filtered, and then concentrated under reduced pressure. The obtained product was used without any purification process to give the desired Compound 765 (0.137 g, 65.1%) in the form of a white solid.

$^1$H NMR (400 MHz, DMSO-$d_6$) δ 11.16 (brs, 1H), 9.10 (brs, 1H), 7.66 (d, 2H, J=8.1 Hz), 7.38-7.29 (m, 3H), 7.17 (s, 1H), 7.13-7.08 (m, 2H), 5.37 (d, 2H, J=47.5 Hz), 4.88 (s, 2H), 3.16 (m, 4H), 2.23 (q, 2H, J=7.1 Hz), 2.17 (m, 4H), 0.93 (t, 3H, J=7.1 Hz). MS (ESI) m/z 415 (M$^+$+H).

Example 152: Synthesis of Compound 766

Formula 10-10: tert-butyl 4-((3-(hydroxymethyl)phenyl)(4-(methoxycarbonyl)benzyl)carbamoyl)piperazine-1-carboxylate

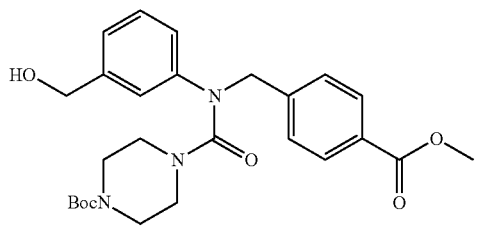 [SMILES: COC(=O)c1ccc(CN(C(=O)N2CCN(C(=O)OC(C)(C)C)CC2)c2cccc(CO)c2)cc1]

Compound of Formula 10-3 (methyl 4-(((3-(hydroxymethyl)phenyl)((4-nitrophenoxy)carbonyl)amino)methyl)benzoate; 1.000 g, 2.29 mmol), 1-Boc-piperazine (1.280 g, 6.87 mmol) and potassium carbonate (1.583 g, 11.46 mmol) were mixed with N,N-dimethylformamide (7 mL) at room temperature and stirred at the same temperature for 60 hours. Then, saturated ammonium chloride aqueous solution was poured into the reaction mixture, and the organic layer was extracted with ethyl acetate. The organic layer was washed with saturated sodium hydrogen carbonate aqueous solution, dehydrated with anhydrous magnesium sulfate, and then concentrated under reduced pressure. The concentrate was purified and concentrated by column chromatography (silica; ethyl acetate/hexane=30-60%) to give the desired compound of Formula 10-10 (0.263 g, 24%) in the form of a white solid.

Formula 10-11: tert-butyl 4-((3-(fluoromethyl)phenyl)(4-(methoxycarbonyl)benzyl)carbamoyl)piperazine-1-carboxylate

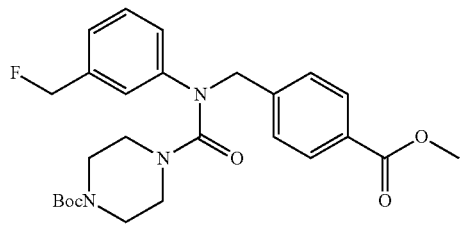 [SMILES: COC(=O)c1ccc(CN(C(=O)N2CCN(C(=O)OC(C)(C)C)CC2)c2cccc(CF)c2)cc1]

Compound of Formula 10-10 (tert-butyl 4-((3-(hydroxymethyl)phenyl)(4-(methoxycarbonyl)benzyl)carbamoyl)piperazine-1-carboxylate; 0.263 g, 0.54 mmol) was dissolved in methylene chloride (10 mL) at room temperature, and then diethylaminosulfur trifluoride (0.079 mL, 0.60 mmol) was added to the solution and stirred at the same temperature for 2 hours. Then, saturated sodium hydrogen carbonate aqueous solution was poured into the reaction mixture, and the organic layer was extracted with methylene chloride. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20-50%) to give the desired compound of Formula 10-11 (0.221 g, 84%) in the form of a colorless liquid.

Formula 10-12: methyl 4-((N-(3-(fluoromethyl)phenyl)piperazine-1-carboxamido)methyl)benzoate hydrochloride

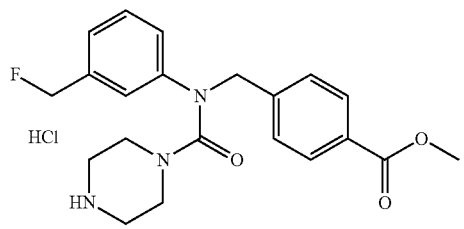 [SMILES: COC(=O)c1ccc(CN(C(=O)N2CCNCC2)c2cccc(CF)c2)cc1 ; Cl]

Compound of Formula 10-11 (tert-butyl 4-((3-(fluoromethyl)phenyl)(4-(methoxycarbonyl)benzyl)carbamoyl)piperazine-1-carboxylate; 0.221 g, 0.46 mmol) was dissolved in 1,4-dioxane (5 mL) at room temperature, and then hydrochloric acid (4 M 1,4-dioxane solution; 5.689 mL, 22.76 mmol) was added to the solution and stirred at the same temperature for 1 hour. Then, the solvent was removed from the reaction mixture under reduced pressure, and ethyl acetate (10 mL) and hexane (30 mL) were added to the concentrate and stirred. Then, the precipitated solid was filtered, washed with hexane, and dried to give the desired compound of Formula 10-12 (0.160 g, 83%) in the form of a white solid.

Formula 10-13: methyl 4-((N-(3-(fluoromethyl)phenyl)-4-(2-hydroxy-2-methylpropyl)piperazine-1-carboxamido)methyl)benzoate

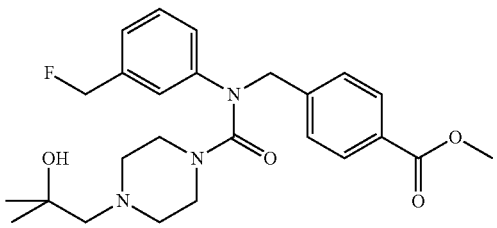 [SMILES: COC(=O)c1ccc(CN(C(=O)N2CCN(CC(C)(C)O)CC2)c2cccc(CF)c2)cc1]

Compound of Formula 10-12 (methyl 4-((N-(3-(fluoromethyl)phenyl)piperazine-1-carboxamido)methyl)benzoate hydrochloride; 0.137 g, 0.33 mmol), 2,2-dimethyloxirane (0.289 mL, 3.25 mmol) and potassium carbonate (0.224 g, 1.62 mmol) were mixed with ethanol (10 mL) and heated at 110° C. for 20 minutes under microwave irradiation. Then, the temperature was lowered to room temperature, and the reaction was completed. Then, the concentrate was obtained by removing the solvent from the reaction mixture under reduced pressure. water was poured into the obtained concentrate, and the organic layer was extracted with ethyl acetate. The organic layer was washed with saturated sodium chloride aqueous solution, dehydrated with anhydrous magnesium sulfate, filtered, and then concentrated under reduced pressure. The obtained product was used without any purification process to give the desired compound of Formula 10-13 (0.129 g, 87%) in the form of a blight yellow liquid.

Formula 10-14: methyl 4-((4-(2-fluoro-2-methylpropyl)-N-(3-(fluoromethyl)phenyl)piperazine-1-carboxamido)methyl)benzoate

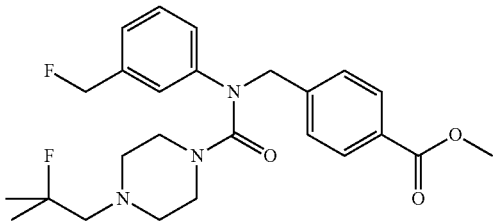 [SMILES: COC(=O)c1ccc(CN(C(=O)N2CCN(CC(C)(C)F)CC2)c2cccc(CF)c2)cc1]

Compound of Formula 10-13 (methyl 4-((N-(3-(fluoromethyl)phenyl)-4-(2-hydroxy-2-methylpropyl)piperazine-1-carboxamido)methyl)benzoate; 0.129 g, 0.28 mmol) was dissolved in methylene chloride (10 mL) at room temperature, and then diethylaminosulfurtrifluoride (0.041 mL, 0.31 mmol) was added to the solution and stirred at the same temperature for 2 hours. Then, saturated sodium hydrogen carbonate aqueous solution was poured into the reaction mixture, and the organic layer was extracted with methylene chloride. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=10-40%) to give the desired compound of Formula 10-14 (0.111 g, 86%) in the form of a colorless liquid.

Compound 766: 4-(2-fluoro-2-methylpropyl)-N-(3-(fluoromethyl)phenyl)-N-(4-(hydroxycarbamoyl)benzyl)piperazine-1-carboxamide

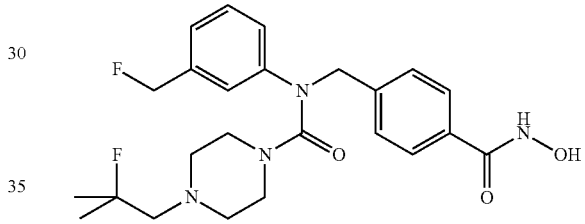

Compound of Formula 10-14 (methyl 4-((4-(2-fluoro-2-methylpropyl)-N-(3-(fluoromethyl)phenyl)piperazine-1-carboxamido)methyl)benzoate; 0.111 g, 0.24 mmol) was dissolved in methanol (10 mL) at room temperature, and then hydroxylamine (50 wt % aqueous solution; 1.477 mL, 24.16 mmol) and potassium hydroxide (0.136 g, 2.42 mmol) were added to the solution and stirred at the same temperature for 3 hours. Then, the concentrate was obtained by removing the solvent from the reaction mixture under reduced pressure. saturated sodium hydrogen carbonate aqueous solution was poured into the obtained concentrate, and then the organic layer was extracted with ethyl acetate. The organic layer was washed with saturated sodium chloride aqueous solution, dehydrated with anhydrous magnesium sulfate, filtered, and then concentrated under reduced pressure. The obtained product was used without any purification process to give the desired Compound 766 (0.087 g, 78%) in the form of a white solid.

$^1$H NMR (400 MHz, DMSO-$d_6$) δ 11.15 (brs, 1H), 9.04 (brs, 1H), 7.65 (d, 2H, J=8.2 Hz), 7.37-7.32 (m, 3H), 7.16 (s, 1H), 7.12-7.08 (m, 2H), 5.37 (d, 2H, J=47.5 Hz), 4.87 (s, 2H), 3.16 (m, 4H), 2.36 (s, 2H, J=23.0 Hz), 2.33 (m, 4H), 1.29 (s, 3H), 1.23 (s, 3H). MS (ESI) m/z 461 (M$^+$+H).

Example 153: Synthesis of Compound 771

Formula 1-2: methyl 4-(((2-(trifluoromethoxy)phenyl)amino)methyl)benzoate

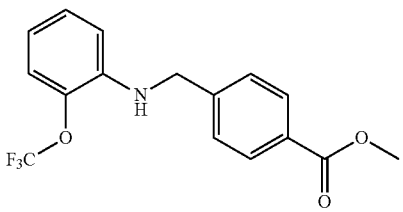 [SMILES: COC(=O)c1ccc(CNc2ccccc2OC(F)(F)F)cc1]

Compound of Formula 1-1 (2-(trifluoromethoxy)aniline; 0.385 mL, 4.625 mmol), methyl 4-(bromomethyl)benzoate (1.271 g, 5.550 mmol) and DIPEA (1.228 mL, 6.937 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-2 (0.806 g, 53.6%) in the form of a colorless liquid.

Formula 1-3: methyl 4-((((4-nitrophenoxy)carbonyl)(2-(trifluoromethoxy)phenyl)amino)methyl)benzoate

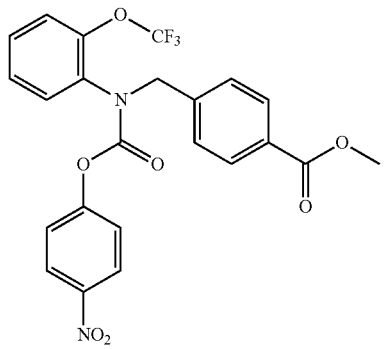 [SMILES: COC(=O)c1ccc(CN(C(=O)Oc2ccc([N+](=O)[O-])cc2)c2ccccc2OC(F)(F)F)cc1]

Compound of Formula 1-2 (methyl 4-(((2-(trifluoromethoxy)phenyl)amino)methyl)benzoate; 0.806 g, 2.477 mmol), 4-nitrophenyl chloroformate (0.549 g, 2.725 mmol) and potassium carbonate (0.685 g, 4.955 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (1.172 g, 96.5%) in the form of a yellow liquid.

Formula 1-4: methyl 4-((N-(2-(trifluoromethoxy)phenyl)morpholine-4-carboxamido)methyl)benzoate

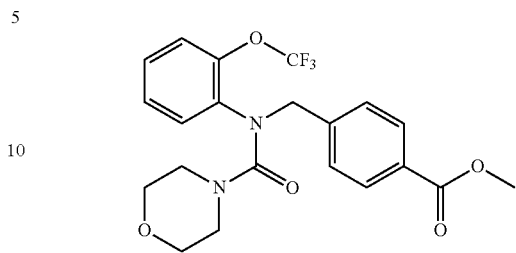

Compound of Formula 1-3 (methyl 4-((((4-nitrophenoxy)carbonyl)(2-(trifluoromethoxy)phenyl)amino)methyl)benzoate; 1.172 g, 2.390 mmol), morpholine (2.082 g, 23.899 mmol) and potassium carbonate (1.652 g, 11.950 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30%) to give the desired compound of Formula 1-4 (0.948 g, 90.4%) in the form of a colorless liquid.

Compound 771: N-(4-(hydroxycarbamoyl)benzyl)-N-(2-(trifluoromethoxy)phenyl)morpholine-4-carboxamide

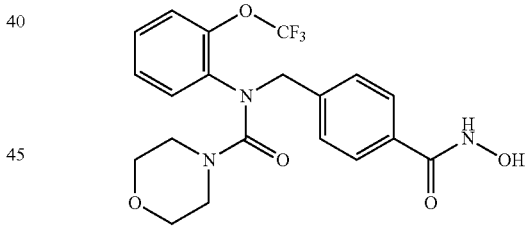

Compound of Formula 1-4 (methyl 4-((N-(2-(trifluoromethoxy)phenyl)morpholine-4-carboxamido)methyl)benzoate; 0.948 g, 2.162 mmol), hydroxylamine (50.0 wt % aqueous solution; 1.323 mL, 21.624 mmol) and potassium hydroxide (1.213 g, 21.624 mmol) were dissolved in methanol (3 mL) at room temperature and stirred at the same temperature for 3 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 771 (0.656 g, 69.0%) in the form of a white solid.

$^1$H NMR (400 MHz, DMSO-$d_6$) d 7.68 (d, 2H, J=8.0 Hz), 7.39~7.32 (m, 6H), 4.76 (s, 2H), 3.36~3.35 (m, 4H), 3.10 (m, 4H); MS (ESI) m/z 440.1 (M$^+$+H).

Example 154: Synthesis of Compound 772

Formula 1-2: methyl 4-(((4-(trifluoromethoxy)phenyl)amino)methyl)benzoate

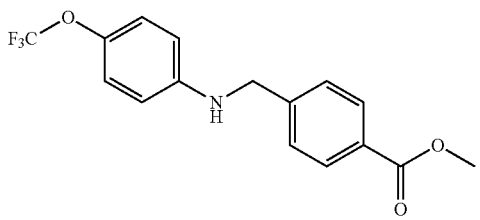 [SMILES: COC(=O)c1ccc(CNc2ccc(OC(F)(F)F)cc2)cc1]

Compound of Formula 1-1 (4-(trifluoromethoxy)aniline; 0.385 mL, 4.625 mmol), methyl 4-(bromomethyl)benzoate (1.271 g, 5.550 mmol) and DIPEA (1.228 mL, 6.937 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-2 (0.645 g, 42.8%) in the form of a colorless liquid.

Formula 1-3: methyl 4-((((4-nitrophenoxy)carbonyl)(4-(trifluoromethoxy)phenyl)amino)methyl)benzoate

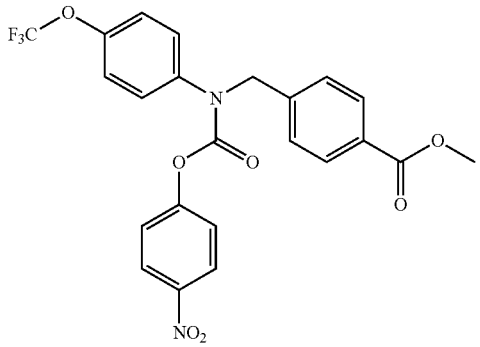 [SMILES: COC(=O)c1ccc(CN(C(=O)Oc2ccc([N+](=O)[O-])cc2)c2ccc(OC(F)(F)F)cc2)cc1]

Compound of Formula 1-2 (methyl 4-(((4-(trifluoromethoxy)phenyl)amino)methyl)benzoate; 0.645 g, 1.981 mmol), 4-nitrophenyl chloroformate (0.439 g, 2.180 mmol) and potassium carbonate (0.548 g, 3.963 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (0.633 g, 65.1%) in the form of a white solid.

Formula 1-4: methyl 4-((N-(4-(trifluoromethoxy)phenyl)morpholine-4-carboxamido)methyl)benzoate

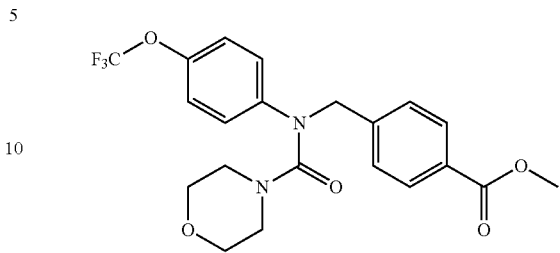

Compound of Formula 1-3 (methyl 4-((((4-nitrophenoxy)carbonyl)(4-(trifluoromethoxy)phenyl)amino)methyl)benzoate; 0.633 g, 1.291 mmol), morpholine (1.125 g, 12.909 mmol) and potassium carbonate (0.892 g, 6.454 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30%) to give the desired compound of Formula 1-4 (0.555 g, 98.1%) in the form of a colorless liquid.

Compound 772: N-(4-(hydroxycarbamoyl)benzyl)-N-(4-(trifluoromethoxy)phenyl)morpholine-4-carboxamide

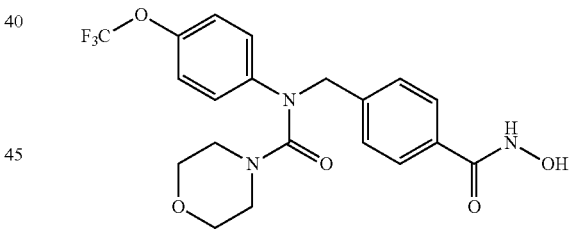

Compound of Formula 1-4 (methyl 4-((N-(4-(trifluoromethoxy)phenyl)morpholine-4-carboxamido)methyl)benzoate; 0.555 g, 1.266 mmol), hydroxylamine (50.0 wt % aqueous solution; 0.774 mL, 12.660 mmol) and potassium hydroxide (0.710 g, 12.660 mmol) were dissolved in methanol (3 mL) at room temperature and stirred at the same temperature for 3 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 772 (0.544 g, 97.8%) in the form of a white solid.

$^1$H NMR (400 MHz, DMSO-$d_6$) d 10.33 (brs, 1H), 9.78 (brs, 1H), 7.65 (d, 2H, J=7.8 Hz), 7.42 (t, 1H, J=8.2 Hz), 7.37 (d, 2H, J=7.8 Hz), 7.18 (d, 1H, J=7.6 Hz), 7.12 (s, 1H), 7.03 (d, 1H, J=8.3 Hz), 4.91 (s, 2H), 3.43 (m, 4H), 3.17 (m, 4H); MS (ESI) m/z 440.1 (M⁺+H).

Example 155: Synthesis of Compound 773

Formula 1-2: methyl 4-(((3-(trifluoromethoxy)phenyl)amino)methyl)benzoate

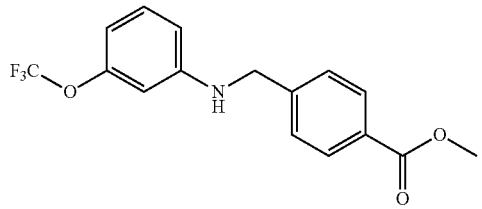 [SMILES: COC(=O)c1ccc(CNc2cccc(OC(F)(F)F)c2)cc1]

Compound of Formula 1-1 (3-(trifluoromethoxy)aniline; 0.385 mL, 4.625 mmol), methyl 4-(bromomethyl)benzoate (1.271 g, 5.550 mmol) and DIPEA (1.228 mL, 6.937 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-2 (0.607 g, 40.3%) in the form of a white solid.

Formula 1-3: methyl 4-((((4-nitrophenoxy)carbonyl)(3-(trifluoromethoxy)phenyl)amino)methyl)benzoate

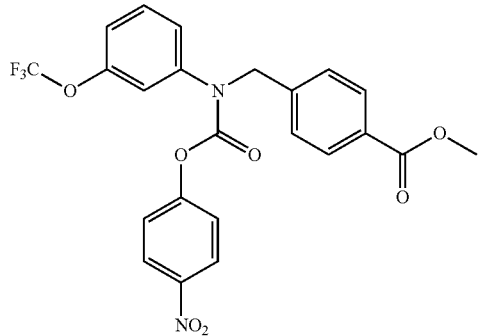 [SMILES: COC(=O)c1ccc(CN(C(=O)Oc2ccc([N+](=O)[O-])cc2)c2cccc(OC(F)(F)F)c2)cc1]

Compound of Formula 1-2 (methyl 4-(((3-(trifluoromethoxy)phenyl)amino)methyl)benzoate; 0.607 g, 1.865 mmol), 4-nitrophenyl chloroformate (0.413 g, 2.051 mmol) and potassium carbonate (0.515 g, 3.730 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (0.649 g, 71.0%) in the form of a white solid.

Formula 1-4: methyl 4-((N-(3-(trifluoromethoxy)phenyl)morpholine-4-carboxamido)methyl)benzoate

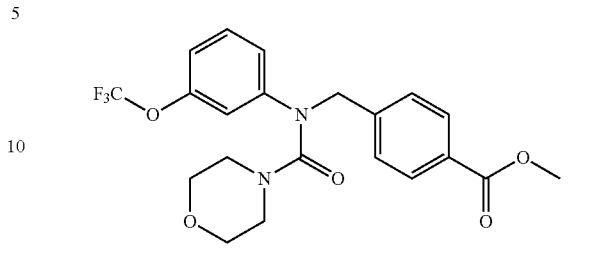

Compound of Formula 1-3 (methyl 4-((((4-nitrophenoxy)carbonyl)(3-(trifluoromethoxy)phenyl)amino)methyl)benzoate; 0.649 g, 1.324 mmol), morpholine (1.154 g, 13.243 mmol) and potassium carbonate (0.915 g, 6.621 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30%) to give the desired compound of Formula 1-4 (0.512 g, 88.2%) in the form of a colorless liquid.

Compound 773: N-(4-(hydroxycarbamoyl)benzyl)-N-(3-(trifluoromethoxy)phenyl)morpholine-4-carboxamide

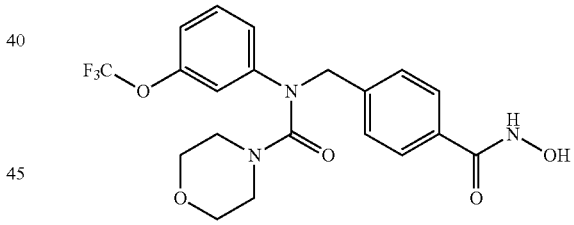

Compound of Formula 1-4 (methyl 4-((N-(3-(trifluoromethoxy)phenyl)morpholine-4-carboxamido)methyl)benzoate; 0.512 g, 1.168 mmol), hydroxylamine (50.0 wt % aqueous solution; 0.714 mL, 11.679 mmol) and potassium hydroxide (0.655 g, 11.679 mmol) were dissolved in methanol (3 mL) at room temperature and stirred at the same temperature for 3 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 773 (0.417 g, 81.3%) in the form of a white solid.
¹H NMR (400 MHz, DMSO-d₆) d 10.35 (brs, 1H), 8.68 (brs, 1H), 7.67 (d, 2H, J=8.0 Hz), 7.37 (d, 2H, J=8.0 Hz), 7.31~7.24 (m, 4H), 4.88 (s, 2H), 3.42 (m, 4H), 3.15 (m, 4H); MS (ESI) m/z 440.1 (M⁺+H).

Example 156: Synthesis of Compound 774

Formula 1-2: methyl 4-(((2-methoxy-5-(trifluoromethyl)phenyl)amino)methyl)benzoate

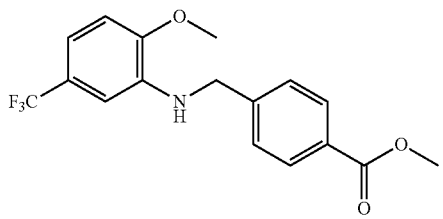 [SMILES: COC(=O)c1ccc(CNc2cc(C(F)(F)F)ccc2OC)cc1]

Compound of Formula 1-1 (2-methoxy-5-(trifluoromethyl)aniline; 0.385 mL, 4.625 mmol), methyl 4-(bromomethyl)benzoate (1.271 g, 5.550 mmol) and DIPEA (1.228 mL, 6.937 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-2 (0.607 g, 40.3%) in the form of a white solid.

Formula 1-3: methyl 4-(((2-methoxy-5-(trifluoromethyl)phenyl)((4-nitrophenoxy)carbonyl)amino)methyl)benzoate

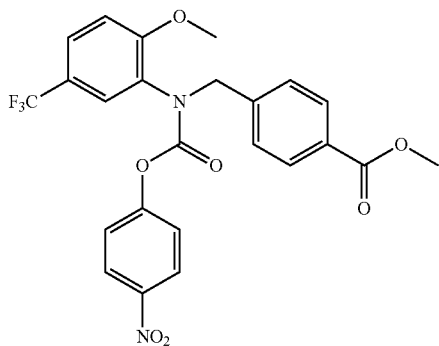 [SMILES: COC(=O)c1ccc(CN(C(=O)Oc2ccc([N+](=O)[O-])cc2)c2cc(C(F)(F)F)ccc2OC)cc1]

Compound of Formula 1-2 (methyl 4-(((2-methoxy-5-(trifluoromethyl)phenyl)amino)methyl)benzoate; 0.607 g, 1.865 mmol), 4-nitrophenyl chloroformate (0.413 g, 2.051 mmol) and potassium carbonate (0.515 g, 3.730 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (0.649 g, 71.0%) in the form of a white solid.

Formula 1-4: methyl 4-((N-(2-methoxy-5-(trifluoromethyl)phenyl)morpholine-4-carboxamido)methyl)benzoate

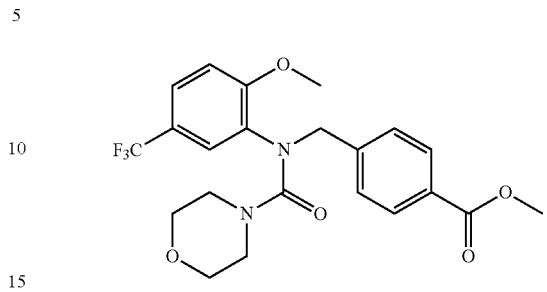

Compound of Formula 1-3 (methyl 4-(((2-methoxy-5-(trifluoromethyl)phenyl)((4-nitrophenoxy)carbonyl)amino)methyl)benzoate; 0.649 g, 1.324 mmol), morpholine (1.154 g, 13.243 mmol) and potassium carbonate (0.915 g, 6.621 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30%) to give the desired compound of Formula 1-4 (0.512 g, 88.2%) in the form of a colorless liquid.

Compound 774: N-(4-(hydroxycarbamoyl)benzyl)-N-(2-methoxy-5-(trifluoromethyl)phenyl)morpholine-4-carboxamide

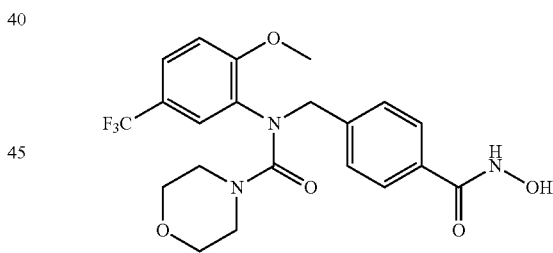

Compound of Formula 1-4 (methyl 4-((N-(2-methoxy-5-(trifluoromethyl)phenyl)morpholine-4-carboxamido)methyl)benzoate; 0.512 g, 1.168 mmol), hydroxylamine (50.0 wt % aqueous solution; 0.714 mL, 11.679 mmol) and potassium hydroxide (0.655 g, 11.679 mmol) were dissolved in methanol (3 mL) at room temperature and stirred at the same temperature for 3 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 774 (0.417 g, 81.3%) in the form of a white solid.

$^1$H NMR (400 MHz, DMSO-$d_6$) d 10.35 (brs, 1H), 8.68 (brs, 1H), 7.67 (d, 2H, J=8.0 Hz), 7.37 (d, 2H, J=8.0 Hz), 7.31~7.24 (m, 4H), 4.88 (s, 2H), 3.42 (m, 4H), 3.15 (m, 4H); MS (ESI) m/z 454.1 (M⁺+H).

Example 157: Synthesis of Compound 776

Formula 1-2: methyl 4-(((2-chloro-5-(trifluoromethyl)phenyl)amino)methyl)benzoate

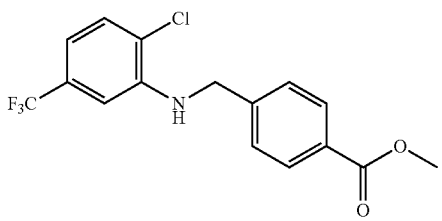

Compound of Formula 1-1 (2-chloro-5-(trifluoromethyl) aniline; 0.352 mL, 2.557 mmol), methyl 4-(bromomethyl)benzoate (0.703 g, 3.068 mmol) and DIPEA (0.679 mL, 3.835 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-2 (0.752 g, 85.6%) in the form of a white solid.

Formula 1-3: methyl 4-(((2-chloro-5-(trifluoromethyl)phenyl)((4-nitrophenoxy)carbonyl)amino)methyl)benzoate

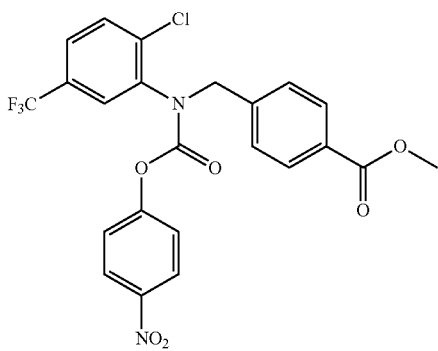 [SMILES: COC(=O)c1ccc(CN(C(=O)Oc2ccc([N+](=O)[O-])cc2)c2cc(C(F)(F)F)ccc2Cl)cc1]

Compound of Formula 1-2 (methyl 4-(((2-chloro-5-(trifluoromethyl)phenyl)amino)methyl)benzoate; 0.752 g, 2.188 mmol), 4-nitrophenyl chloroformate (0.485 g, 2.407 mmol) and potassium carbonate (0.605 g, 4.376 mmol) were dissolved in acetonitrile (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (0.903 g, 81.1%) in the form of a white solid.

Formula 1-4: methyl 4-((N-(2-chloro-5-(trifluoromethyl)phenyl)morpholine-4-carboxamido)methyl)benzoate

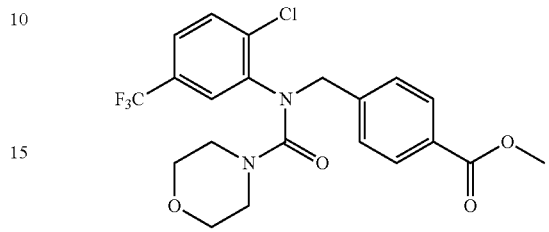

Compound of Formula 1-3 (methyl 4-(((2-chloro-5-(trifluoromethyl)phenyl)((4-nitrophenoxy)carbonyl)amino)methyl)benzoate; 0.903 g, 1.775 mmol), morpholine (1.546 g, 17.747 mmol) and potassium carbonate (1.226 g, 8.873 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30%) to give the desired compound of Formula 1-4 (0.582 g, 71.8%) in the form of a colorless liquid.

Compound 776: N-(2-chloro-5-(trifluoromethyl)phenyl)-N-(4-(hydroxycarbamoyl)benzyl)morpholine-4-carboxamide

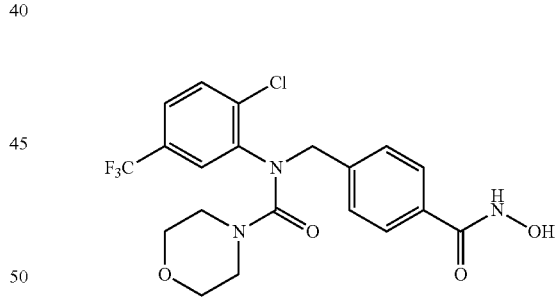

Compound of Formula 1-4 (methyl 4-((N-(2-chloro-5-(trifluoromethyl)phenyl)morpholine-4-carboxamido)methyl)benzoate; 0.582 g, 1.274 mmol), hydroxylamine (50.0 wt % aqueous solution; 0.779 mL, 12.740 mmol) and potassium hydroxide (0.715 g, 12.740 mmol) were dissolved in methanol (3 mL) at room temperature and stirred at the same temperature for 3 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 776 (0.521 g, 89.3%) in the form of a ivory solid.

$^1$H NMR (400 MHz, DMSO-d$_6$) d 10.33 (brs, 1H), 8.67 (brs, 1H), 7.76 (d, 1H, J=8.1 Hz), 7.65 (s, 1H), 7.64 (s, 2H), 7.60 (d, 1H, J=8.3 Hz), 7.36 (d, 2H, J=8.1 Hz), 4.82 (s, 2H), 3.33 (m, 4H), 3.13~3.12 (m, 4H); MS (ESI) m/z 458.0 (M$^+$+H).

Example 158: Synthesis of Compound 778

Formula 7-4: methyl 4-((((6-(trifluoromethyl)pyridin-2-yl)amino)methyl)benzoate

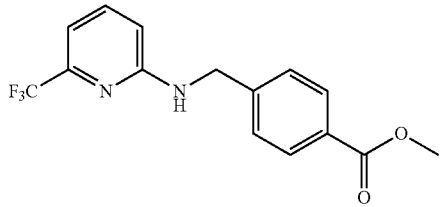 [SMILES: COC(=O)c1ccc(CNc2cccc(C(F)(F)F)n2)cc1]

Compound of Formula 7-3 (6-(trifluoromethyl)pyridin-2-amine (0.500 g, 3.084 mmol), methyl 4-(bromomethyl)benzoate (1.413 g, 6.169 mmol) and DIPEA (1.092 mL, 6.169 mmol) were dissolved in acetonitrile (10 mL) at room temperature and stirred at the same temperature for 16 hours. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 7-4 (0.588 g, 61.4%) in the form of a white solid.

Formula 7-5: methyl 4-((((4-nitrophenoxy)carbonyl)(6-(trifluoromethyl)pyridin-2-yl)amino)methyl)benzoate

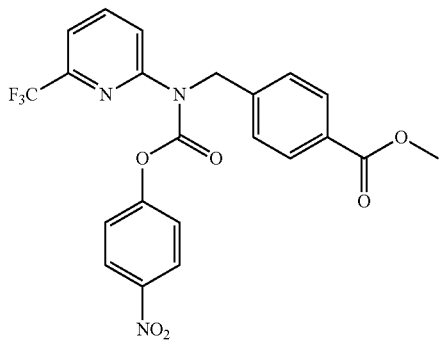 [SMILES: COC(=O)c1ccc(CN(C(=O)Oc2ccc([N+](=O)[O-])cc2)c2cccc(C(F)(F)F)n2)cc1]

Compound of Formula 7-4 (methyl 4-(((6-(trifluoromethyl)pyridin-2-yl)amino)methyl)benzoate; 0.588 g, 1.895 mmol), 4-nitrophenyl chloroformate (0.420 g, 2.085 mmol) and potassium carbonate (0.524 g, 3.790 mmol) were dissolved in acetonitrile (10 mL) at room temperature and stirred at the same temperature for 16 hours. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 7-5 (0.295 g, 32.7%) in the form of a yellow liquid.

Formula 7-6: methyl 4-((N-(6-(trifluoromethyl)pyridin-2-yl)morpholine-4-carboxamido)methyl)benzoate

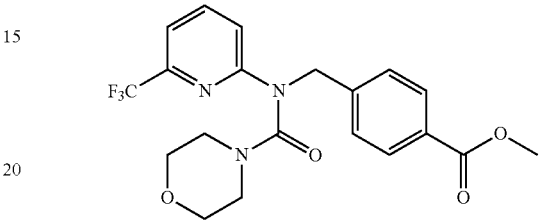

Compound of Formula 7-5 (methyl 4-((((4-nitrophenoxy)carbonyl)(6-(trifluoromethyl)pyridin-2-yl)amino)methyl)benzoate; 0.295 g, 0.621 mmol), morpholine (0.541 mL, 6.206 mmol) and potassium carbonate (0.429 g, 3.103 mmol) were dissolved in N,N-dimethylformamide (5 mL) at room temperature and stirred at the same temperature for 1 hour. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 7-6 (0.112 g, 42.6%) in the form of a colorless liquid.

Compound 778: N-(4-(hydroxycarbamoyl)benzyl)-N-(6-(trifluoromethyl)pyridin-2-yl)morpholine-4-carboxamide

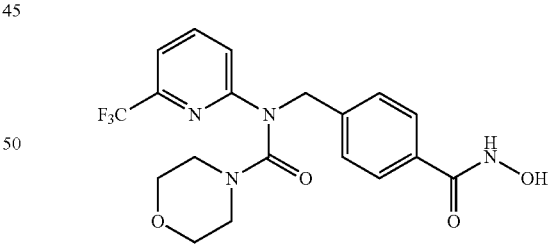

Compound of Formula 7-6 (methyl 4-((N-(6-(trifluoromethyl)pyridin-2-yl)morpholine-4-carboxamido)methyl)benzoate; 0.112 g, 0.265 mmol), hydroxylamine (50.0 wt % aqueous solution; 0.162 mL, 2.645 mmol) and potassium hydroxide (0.148 g, 2.645 mmol) were dissolved in methanol (5 mL) at room temperature and stirred at the same temperature for 1 hour. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50-80%) to give the desired Compound 778 (0.072 g, 64.1%) in the form of a white solid.

$^1$H NMR (400 MHz, CD$_3$OD) d 7.88 (t, 1H, J=7.9 Hz), 7.70 (d, 2H, J=8.1 Hz), 7.53 (d, 2H, J=8.1 Hz), 7.35 (d, 1H, J=7.4 Hz), 7.24 (d, 1H, J=8.4 Hz), 5.11 (s, 2H), 3.55 (t, 4H, J=4.7 Hz), 3.36 (t, 4H, J=4.6 Hz); MS (ESI) m/z 425.1 (M$^+$+H).

Example 159: Synthesis of Compound 791

Formula 1-2: methyl 4-(((2,3-difluorophenyl)amino)methyl)benzoate

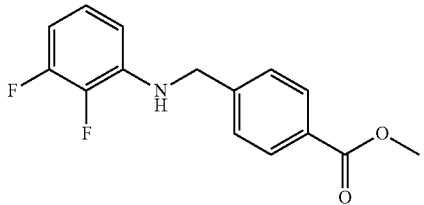 [SMILES: COC(=O)c1ccc(CNc2cccc(F)c2F)cc1]

Compound of Formula 1-1 (2,3-difluoroaniline (0.300 g, 2.324 mmol), methyl 4-(bromomethyl)benzoate (0.639 g, 2.788 mmol) and DIPEA (0.809 mL, 4.647 mmol) were dissolved in acetonitrile (3 mL) at room temperature and stirred at the same temperature for 17 hours. Water was poured into the reaction mixture, and the organic layer was extracted with dichloromethane. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=10%) to give the desired compound of Formula 1-2 (0.284 g, 44.1%) in the form of a white solid.

Formula 1-3: methyl 4-(((2,3-difluorophenyl)((4-nitrophenoxy)carbonyl)amino)methyl)benzoate

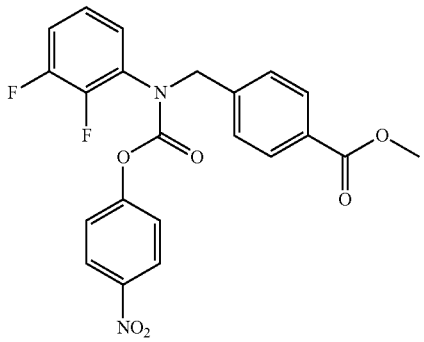

Compound of Formula 1-2 (methyl 4-(((2,3-difluorophenyl)amino)methyl)benzoate; 0.275 g, 0.992 mmol), 4-nitrophenyl chloroformate (0.240 g, 1.190 mmol) and potassium carbonate (0.274 g, 1.948 mmol) were dissolved in dichloromethane (3 mL) at room temperature and stirred at the same temperature for 20 hours. Water was poured into the reaction mixture, and the organic layer was extracted with dichloromethane. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-3 (0.177 g, 40.3%) in the form of a colorless oil.

Formula 1-4: methyl 4-((N-(2,3-difluorophenyl) morpholine-4-carboxamido)methyl)benzoate

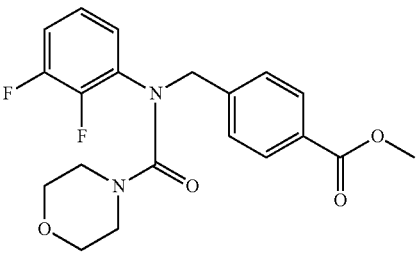 [SMILES: COC(=O)c1ccc(CN(C(=O)N2CCOCC2)c2cccc(F)c2F)cc1]

Compound of Formula 1-3 (methyl 4-(((2,3-difluorophenyl)((4-nitrophenoxy)carbonyl)amino)methyl)benzoate; 0.170 g, 0.384 mmol), morpholine (0.338 ml, 3.843 mmol) and potassium carbonate (0.265 g, 1.921 mmol) were dissolved in N,N-dimethylformamide (2 mL) at 50° C. and stirred at the same temperature for 18 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 1-4 (0.113 g, 75.3%) in the form of a colorless liquid.

Compound 791: N-(2,3-difluorophenyl)-N-(4-(hydroxycarbamoyl)benzyl)morpholine-4-carboxamide

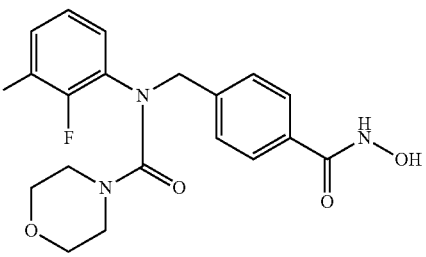

Compound of Formula 1-4 (methyl 4-((N-(2,3-difluorophenyl)morpholine-4-carboxamido)methyl)benzoate; 0.105 g, 0.269 mmol), hydroxylamine (50.0 wt % aqueous solution; 0.329 mL, 5.379 mmol) and potassium hydroxide (0.151 g, 2.690 mmol) were mixed and stirred at room temperature for 1 hour. Saturated sodium hydrogen carbonate aqueous solution was poured into the reaction solution, and the organic layer was extracted with dichloromethane. The organic layer was dehydrated with anhydrous magnesium sulfate, filtered, and then concentrated under reduced pressure to give the desired Compound 791 (0.074 g, 70.3%) in the form of a light brown solid.
MS (ESI) m/z 392.13 (M⁺+H).

Example 160: Synthesis of Compound 797

Formula 12-7: methyl 4-(((3S,5R)-3,5-dimethyl-N-(3-(trifluoromethyl)phenyl)piperazine-1-carboxamido)methyl)benzoate

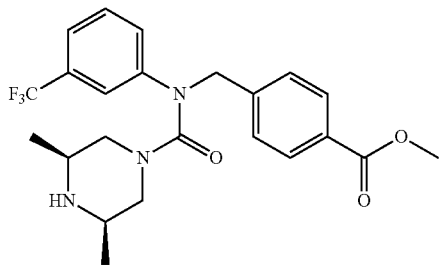

Compound of Formula 1-3 (methyl 4-((((4-nitrophenoxy)carbonyl)(3-(trifluoromethyl)phenyl)amino)methyl)benzoate; 1.263 g, 2.662 mmol), (2S,6R)-2,6-dimethylpiperazine (1.520 g, 13.309 mmol) and potassium carbonate (0.736 g, 5.323 mmol) were dissolved in N,N-dimethylformamide (5 mL) at 40° C. and stirred at the same temperature for 16 hours. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20-50%) to give the desired compound of Formula 12-7 (0.726 g, 60.7%) in the form of a yellow liquid.

Formula 12-8: methyl 4-(((3S,5R)-4-ethyl-3,5-dimethyl-N-(3-(trifluoromethyl)phenyl)piperazine-1-carboxamido)methyl)benzoate

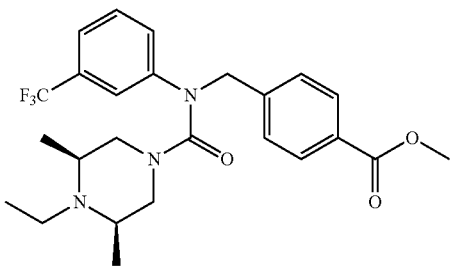 [SMILES: CCN1[C@H](C)CN(C(=O)N(Cc2ccc(C(=O)OC)cc2)c2cccc(C(F)(F)F)c2)C[C@@H]1C]

Compound of Formula 12-7 (methyl 4-(((3S,5R)-3,5-dimethyl-N-(3-(trifluoromethyl)phenyl)piperazine-1-carboxamido)methyl)benzoate; 0.200 g, 0.445 mmol), iodoethane (0.107 mL, 1.335 mmol) and potassium carbonate (0.184 g, 1.335 mmol) were mixed with acetonitrile (10 mL) and heated at 120° C. for 20 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=30-80%) to give the desired compound of Formula 12-8 (0.109 g, 51.3%) in the form of a colorless liquid.

Compound 797: (3S,5R)-4-ethyl-N-(4-(hydroxycarbamoyl)benzyl)-3,5-dimethyl-N-(3-(trifluoromethyl)phenyl)piperazine-1-carboxamide

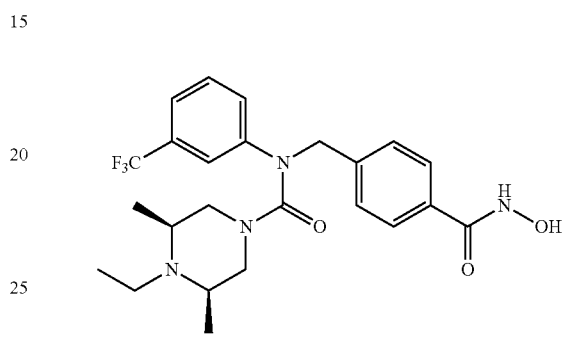

Compound of Formula 12-8 (methyl 4-(((3S,5R)-4-ethyl-3,5-dimethyl-N-(3-(trifluoromethyl)phenyl)piperazine-1-carboxamido)methyl)benzoate; 0.109 g, 0.228 mmol), hydroxylamine (50.0 wt % aqueous solution; 0.140 mL, 2.283 mmol) and potassium hydroxide (0.128 g, 2.283 mmol) were dissolved in methanol (2 mL) at room temperature and stirred at the same temperature for 1 hour. Then, the solvent was removed from the reaction mixture under reduced pressure, and saturated sodium hydrogen carbonate aqueous solution (20 mL) was added to the concentrate and stirred. Then, the precipitated solid was filtered, washed with diethylether, and dried to give the desired Compound 797 (0.071 g, 65.0%) in the form of a white solid.
¹H NMR (400 MHz, CD₃OD) d 7.68 (d, 2H, J=8.3 Hz), 7.55 (t, 1H, J=8.2 Hz), 7.45~7.42 (m, 5H), 4.98 (s, 2H), 3.65 (d, 2H, J=11.6 Hz), 2.89 (q, 2H, J=7.1 Hz), 2.52~2.42 (m, 4H), 0.96 (d, 6H, J=5.8 Hz), 0.97 (s, 3H), 0.95 (s, 3H), 0.86 (t, 3H, J=7.2 Hz); MS (ESI) m/z 479.1 (M⁺+H).

Example 161: Synthesis of Compound 800

Formula 1-4: methyl 4-((2,6-dimethyl-N-(3-(trifluoromethoxy)phenyl)morpholine-4-carboxamido)methyl)benzoate

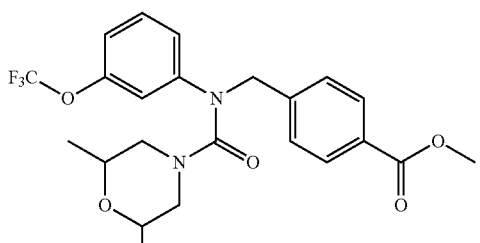

Compound of Formula 1-3 (methyl 4-((((4-nitrophenoxy)carbonyl)(3-(trifluoro-methoxy)phenyl)amino)methyl)benzoate; 0.200 g, 0.408 mmol), 2,6-dimethylmorpholine (0.235 g, 2.039 mmol) and potassium carbonate (0.169 g, 1.224 mmol) were dissolved in N,N-dimethylformamide (5 mL) at 40° C. and stirred at the same temperature for 16 hours. Then, the temperature was lowered to room temperature, and the reaction was completed. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 1-4 (0.166 g, 87.3%) in the form of a yellow liquid.

Compound 800: N-(4-(hydroxycarbamoyl)benzyl)-2,6-dimethyl-N-(3-(trifluoromethoxy)phenyl)morpholine-4-carboxamide

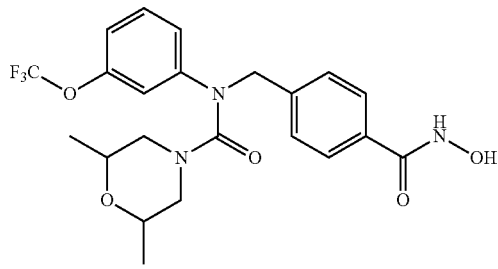 [SMILES: CC1CN(C(=O)N(Cc2ccc(C(=O)NO)cc2)c2cccc(OC(F)(F)F)c2)CC(C)O1]

Compound of Formula 1-4 (methyl 4-((2,6-dimethyl-N-(3-(trifluoromethoxy)phenyl)morpholine-4-carboxamido)methyl)benzoate; 0.166 g, 0.356 mmol), hydroxylamine (50.0 wt % aqueous solution; 0.218 mL, 3.559 mmol) and potassium hydroxide (0.200 g, 3.559 mmol) were dissolved in methanol (2 mL) at room temperature and stirred at the same temperature for 3 hours. Then, the solvent was removed from the reaction mixture under reduced pressure, and saturated sodium hydrogen carbonate aqueous solution (20 mL) was added to the concentrate and stirred. Then, the precipitated solid was filtered, washed with hexane, and dried to give the desired Compound 800 (0.098 g, 59.0%) in the form of a light ivory solid.

$^1$H NMR (400 MHz, CD$_3$OD) d 7.68 (d, 2H, J=8.4 Hz), 7.43 (d, 2H, J=8.4 Hz), 7.43 (t, 1H, J=8.1 Hz), 7.16 (ddd, 1H, J=8.2, 2.0, 0.8 Hz), 7.06 (d, 1H, J=0.9 Hz), 7.04 (d, 1H, J=1.0 Hz), 4.96 (s, 2H), 3.66 (d, 2H, J=12.4 Hz), 3.44~3.40 (m, 2H), 2.38 (dd, 2H, J=13.2, 10.6 Hz), 1.04 (s, 3H), 1.02 (s, 3H); MS (ESI) m/z 468.1 (M$^+$+H).

Example 162: Synthesis of Compound 801

Formula 1-4: methyl 4-((2,6-dimethyl-N-(2-(trifluoromethoxy)phenyl)morpholine-4-carboxamido)methyl)benzoate

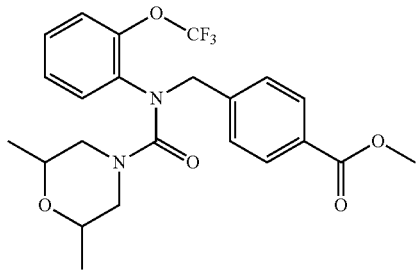

Compound of Formula 1-3 (methyl 4-((((4-nitrophenoxy)carbonyl)(2-(trifluoromethoxy)phenyl)amino)methyl)benzoate; 0.300 g, 0.612 mmol), 2,6-dimethylmorpholine (0.352 g, 3.059 mmol) and potassium carbonate (0.254 g, 1.835 mmol) were dissolved in N,N-dimethylformamide (5 mL) at room temperature and stirred at the same temperature for 16 hours. Water was poured into the reaction mixture, and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 1-4 (0.116 g, 40.7%) in the form of a yellow liquid.

Compound 801: N-(4-(hydroxycarbamoyl)benzyl)-2,6-dimethyl-N-(2-(trifluoromethoxy)phenyl)morpholine-4-carboxamide

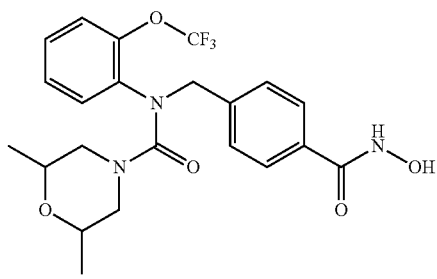 [SMILES: CC1CN(C(=O)N(Cc2ccc(C(=O)NO)cc2)c2ccccc2OC(F)(F)F)CC(C)O1]

Compound of Formula 1-4 (methyl 4-((2,6-dimethyl-N-(2-(trifluoromethoxy)phenyl)morpholine-4-carboxamido)methyl)benzoate; 0.116 g, 0.249 mmol), hydroxylamine (50.0 wt % aqueous solution; 0.152 mL, 2.487 mmol) and potassium hydroxide (0.140 g, 2.487 mmol) were dissolved in methanol (2 mL) at room temperature and stirred at the same temperature for 3 hours. Then, water was poured into the reaction mixture and the organic layer was extracted with ethyl acetate. The organic layer was washed with saturated sodium chloride aqueous solution, dehydrated with anhydrous magnesium sulfate, filtered, and then concentrated under reduced pressure. The concentrate was purified by column chromatography (Waters, C18; acetonitrile/0.1% trifluoro acetic acid aqueous solution=5-70%) and concentrated with SPE cartridge to give the desired compound of Compound 801 (0.020 g, 17.5%) in the form of a white solid.

$^1$H NMR (400 MHz, DMSO-d$_6$) d 7.66 (d, 2H, J=8.4 Hz), 7.40~7.32 (m, 6H), 4.73 (s, 2H), 3.52 (s, 2H), 3.25~3.18 (m, 2H), 2.25 (dd, 2H, J=13.0, 10.7 Hz), 0.92 (s, 3H), 0.91 (s, 3H); MS (ESI) m/z 468.1 (M$^+$+H).

Example 163: Synthesis of Compound 802

Formula 12-8: methyl 4-(((3S,5R)-4-benzyl-3,5-dimethyl-N-(3-(trifluoromethyl)phenyl)piperazine-1-carboxamido)methyl)benzoate

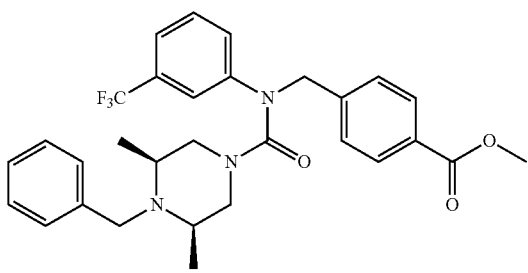 [SMILES: COC(=O)c1ccc(CN(C(=O)N2C[C@@H](C)N(Cc3ccccc3)[C@@H](C)C2)c2cccc(C(F)(F)F)c2)cc1]

Compound of Formula 12-7 (methyl 4-(((3S,5R)-3,5-dimethyl-N-(3-(trifluoromethyl)phenyl)piperazine-1-carboxamido)methyl)benzoate; 0.200 g, 0.445 mmol), (bromomethyl)benzene (2.324 g, 1.335 mmol) and potassium carbonate (0.184 g, 1.335 mmol) were mixed with acetonitrile (3 mL) and heated at 120° C. for 40 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 12-8 (0.113 g, 47.1%) in the form of a colorless liquid.

Compound 802: (3S,5R)-4-benzyl-N-(4-(hydroxycarbamoyl)benzyl)-3,5-dimethyl-N-(3-(trifluoromethyl)phenyl)piperazine-1-carboxamide

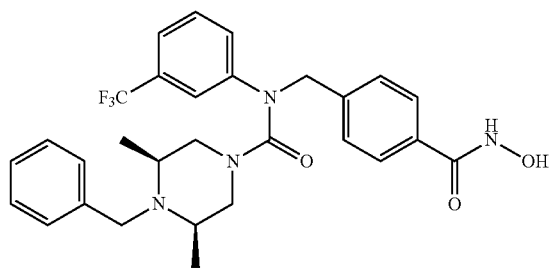 [SMILES: C[C@@H]1CN(C(=O)N(Cc2ccc(C(=O)NO)cc2)c2cccc(C(F)(F)F)c2)C[C@H](C)N1Cc1ccccc1]

Compound of Formula 12-8 (methyl 4-(((3S,5R)-4-benzyl-3,5-dimethyl-N-(3-(trifluoromethyl)phenyl)piperazine-1-carboxamido)methyl)benzoate; 0.113 g, 0.209 mmol), hydroxylamine (50.0 wt % aqueous solution; 0.128 mL, 2.094 mmol) and potassium hydroxide (0.118 g, 2.094 mmol) were dissolved in methanol (2 mL) at room temperature and stirred at the same temperature for 3 hour. Then, the solvent was removed from the reaction mixture under reduced pressure, and saturated sodium hydrogen carbonate aqueous solution (10 mL) was added to the concentrate and stirred. Then, the precipitated solid was filtered, washed with hexane, and dried to give the desired Compound 802 (0.010 g, 8.8%) in the form of a ivory solid.

$^1$H NMR (400 MHz, DMSO-d$_6$) d 7.63 (d, 2H, J=8.3 Hz), 7.50 (t, 1H, J=8.0 Hz), 7.39~7.38 (m, 3H), 7.31~7.25 (m, 6H), 7.18~7.15 (m, 1H), 4.88 (s, 2H), 3.65 (s, 2H), 3.57 (s, 2H), 3.52 (s, 2H), 2.38~2.29 (m, 2H), 0.81 (s, 3H), 0.79 (s, 3H); MS (ESI) m/z 541.1 (M$^+$+H).

Example 164: Synthesis of Compound 803

Formula 12-8: methyl 4-(((3S,5R)-3,5-dimethyl-4-(2,2,3,3,3-pentafluoropropyl)-N-(3-(trifluoromethyl)phenyl)piperazine-1-carboxamido)methyl)benzoate

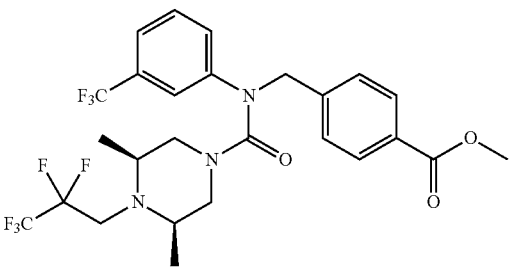 [SMILES: COC(=O)c1ccc(CN(C(=O)N2C[C@@H](C)N(CC(F)(F)C(F)(F)F)[C@@H](C)C2)c2cccc(C(F)(F)F)c2)cc1]

Compound of Formula 12-7 (methyl 4-(((3S,5R)-3,5-dimethyl-N-(3-(trifluoromethyl)phenyl)piperazine-1-carboxamido)methyl)benzoate; 0.200 g, 0.445 mmol), 2,2,3,3,3-pentafluoropropyltrifluoromethansulfonate (0.221 ml, 1.335 mmol) and potassium carbonate (0.184 g, 1.335 mmol) were mixed with acetonitrile (3 mL) and heated at 120° C. for 30 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=20%) to give the desired compound of Formula 12-8 (0.042 g, 16.2%) in the form of a colorless liquid.

Compound 803: (3S,5R)—N-(4-(hydroxycarbamoyl)benzyl)-3,5-dimethyl-4-(2,2,3,3,3-pentafluoropropyl)-N-(3-(trifluoromethyl)phenyl)piperazine-1-carboxamide

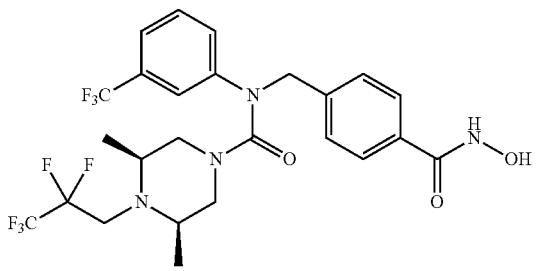 [SMILES: C[C@@H]1CN(C(=O)N(Cc2ccc(C(=O)NO)cc2)c2cccc(C(F)(F)F)c2)C[C@H](C)N1CC(F)(F)C(F)(F)F]

Compound of Formula 12-8 (methyl 4-(((3S,5R)-3,5-dimethyl-4-(2,2,3,3,3-pentafluoropropyl)-N-(3-(trifluoromethyl)phenyl)piperazine-1-carboxamido)methyl)benzoate; 0.042 g, 0.072 mmol), hydroxylamine (50.0 wt % aqueous solution; 0.044 mL, 0.722 mmol) and potassium hydroxide (0.041 g, 0.722 mmol) were dissolved in methanol (2 mL) at room temperature and stirred at the same temperature for 1 hour. Then, the solvent was removed from the reaction mixture under reduced pressure, and saturated sodium hydrogen carbonate aqueous solution (10 mL) was added to the concentrate and stirred. Then, the precipitated solid was filtered, washed with hexane, and dried to give the desired Compound 803 (0.016 g, 38.0%) in the form of a white solid.

$^1$H NMR (400 MHz, CD$_3$OD) d 7.69 (d, 2H, J=8.3 Hz), 7.53 (t, 1H, J=7.8 Hz), 7.43~7.38 (m, 5H), 4.96 (s, 2H), 3.59 (d, 2H, J=12.5 Hz), 2.63~2.53 (m, 4H), 1.36~1.31 (m, 2H), 0.97 (s, 3H), 0.96 (s, 3H); MS (ESI) m/z 583.2 (M$^+$+H).

Example 165: Synthesis of Compound 826

Formula 7-6: methyl 4-((4-ethyl-N-(6-(trifluoromethyl)pyridin-2-yl)piperazine-1-carboxamido)methyl)benzoate

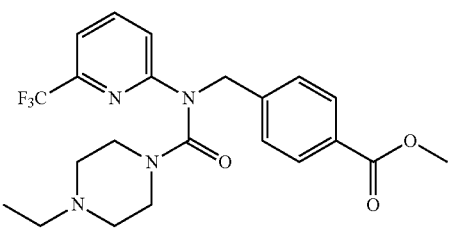 [SMILES: CCN1CCN(C(=O)N(Cc2ccc(C(=O)OC)cc2)c2cccc(C(F)(F)F)n2)CC1]

Compound of Formula 7-5 (methyl 4-((((4-nitrophenoxy)carbonyl)(6-(trifluoromethyl)pyridin-2-yl)amino)methyl)benzoate; 0.500 g, 1.052 mmol), 1-ethylpiperazine (0.240 g, 2.104 mmol) and potassium carbonate (0.291 g, 2.104 mmol) were mixed with N,N-dimethylformamide (3 mL) and heated at 150° C. for 30 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 7-6 (0.276 g, 58.2%) in the form of a yellow liquid.

Compound 826: 4-ethyl-N-(4-(hydroxycarbamoyl)benzyl)-N-(6-(trifluoromethyl)pyridin-2-yl)piperazine-1-carboxamide

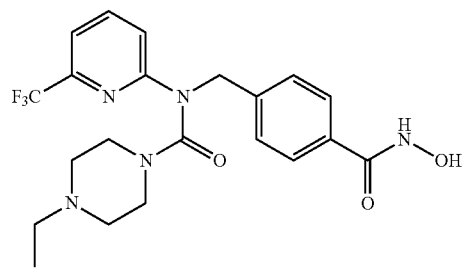 [SMILES: CCN1CCN(C(=O)N(Cc2ccc(C(=O)NO)cc2)c2cccc(C(F)(F)F)n2)CC1]

Compound of Formula 7-6 (methyl 4-((4-ethyl-N-(6-(trifluoromethyl)pyridin-2-yl)piperazine-1-carboxamido)methyl)benzoate; 0.276 g, 0.613 mmol), hydroxylamine (50.0 wt % aqueous solution; 0.375 mL, 6.127 mmol) and potassium hydroxide (0.344 g, 6.127 mmol) were dissolved in methanol (1 mL) at room temperature and stirred at the same temperature for 1 hours. The solvent was removed from the reaction mixture, and the saturated sodium hydrogen carbonate aqueous solution (20 mL) was added to the concentrate and stirred. Then, the precipitated solid was filtered and dried to give the desired Compound 826 (0.089 g, 32.2%) in the form of a yellow solid.

$^1$H NMR (400 MHz, CD$_3$OD) d 7.88 (t, 1H, J=7.9 Hz), 7.71 (d, 2H, J=8.3 Hz), 7.49 (d, 2H, J=8.3 Hz), 7.35 (d, 1H, J=7.5 Hz), 7.20 (d, 1H, J=8.5 Hz), 5.10 (s, 2H), 3.40 (t, 4H, J=4.9 Hz), 2.40 (q, 2H, J=7.3 Hz), 2.35 (t, 4H, J=5.0 Hz), 1.07 (t, 3H, J=7.2 Hz); MS (ESI) m/z 452.1 (M$^+$+H).

Example 166: Synthesis of Compound 827

Formula 7-6: methyl 4-((2,6-dimethyl-N-(6-(trifluoromethyl)pyridin-2-yl)morpholine-4-carboxamido)methyl)benzoate

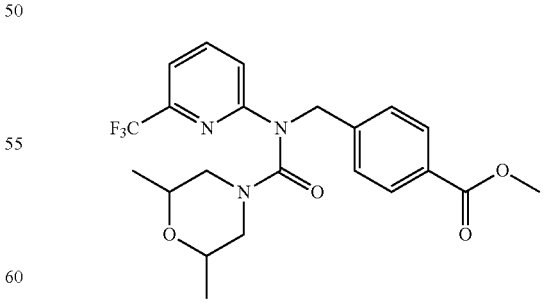

Compound of Formula 7-5 (methyl 4-((((4-nitrophenoxy)carbonyl)(6-(trifluoromethyl)pyridin-2-yl)amino)methyl)benzoate; 0.100 g, 0.210 mmol), 2,6-dimethylmorpholine (0.048 g, 0.421 mmol) and potassium carbonate (0.058 g, 0.421 mmol) were mixed with N,N-dimethylformamide (3 mL) and heated at 150° C. for 30 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 7-6 (0.076 g, 79.7%) in the form of a yellow liquid.

Compound 827: N-(4-(hydroxycarbamoyl)benzyl)-2,6-dimethyl-N-(6-(trifluoromethyl)pyridin-2-yl)morpholine-4-carboxamide

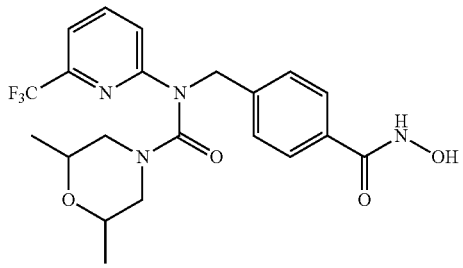 [SMILES: CC1CN(C(=O)N(Cc2ccc(C(=O)NO)cc2)c2cccc(C(F)(F)F)n2)CC(C)O1]

Compound of Formula 7-6 (methyl 4-((2,6-dimethyl-N-(6-(trifluoromethyl)pyridin-2-yl)morpholine-4-carboxamido)methyl)benzoate; 0.076 g, 0.168 mmol), hydroxylamine (50.0 wt % aqueous solution; 0.103 mL, 1.684 mmol) and potassium hydroxide (0.094 g, 1.684 mmol) were dissolved in methanol (1 mL) at room temperature and stirred at the same temperature for 1 hours. The solvent was removed from the reaction mixture, and the saturated sodium hydrogen carbonate aqueous solution (20 mL) was added to the concentrate and stirred. Then, the precipitated solid was filtered and dried to give the desired Compound 827 (0.042 g, 55.5%) in the form of a white solid.

$^1$H NMR (400 MHz, CD$_3$OD) d 7.88 (t, 1H, J=7.7 Hz), 7.70 (d, 2H, J=8.4 Hz), 7.53 (d, 2H, J=8.4 Hz), 7.36 (d, 1H, J=7.4 Hz), 7.21 (d, 1H, J=8.5 Hz), 5.12 (s, 2H), 3.71 (d, 2H, J=12.5 Hz), 3.45~3.38 (m, 2H), 2.53 (dd, 2H, J=10.7, 13.1 Hz), 1.07 (s, 3H), 1.05 (s, 3H); MS (ESI) m/z 453.1 (M$^+$+H)

Example 167: Synthesis of Compound 828

Formula 7-6: methyl 4-((N-(6-(trifluoromethyl)pyridin-2-yl)piperidine-1-carboxamido)methyl)benzoate

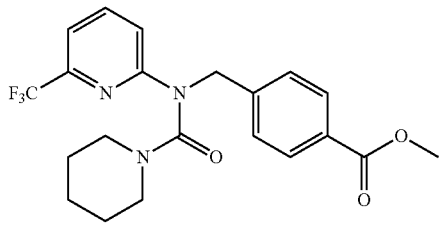 [SMILES: COC(=O)c1ccc(CN(C(=O)N2CCCCC2)c2cccc(C(F)(F)F)n2)cc1]

Compound of Formula 7-5 (methyl 4-((((4-nitrophenoxy)carbonyl)(6-(trifluoromethyl)pyridin-2-yl)amino)methyl)

benzoate; 0.100 g, 0.210 mmol), piperidine (0.036 g, 0.421 mmol) and potassium carbonate (0.058 g, 0.421 mmol) were mixed with N,N-dimethylformamide (3 mL) and heated at 150° C. for 30 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 7-6 (0.063 g, 71.1%) in the form of a yellow liquid.

Compound 828: N-(4-(hydroxycarbamoyl)benzyl)-N-(6-(trifluoromethyl)pyridin-2-yl)piperidine-1-carboxamide

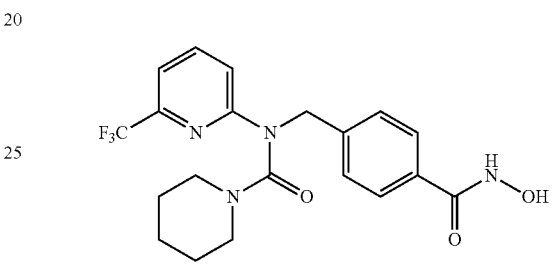

Compound of Formula 7-6 (methyl 4-((N-(6-(trifluoromethyl)pyridin-2-yl)piperidine-1-carboxamido)methyl)benzoate; 0.063 g, 0.149 mmol), hydroxylamine (50.0 wt % aqueous solution; 0.091 mL, 1.495 mmol) and potassium hydroxide (0.084 g, 1.495 mmol) were dissolved in methanol (1 mL) at room temperature and stirred at the same temperature for 1 hours. The solvent was removed from the reaction mixture, and the saturated sodium hydrogen carbonate aqueous solution (20 mL) was added to the concentrate and stirred. Then, the precipitated solid was filtered, washed with hexane and dried to give the desired Compound 828 (0.017 g, 26.6%) in the form of a white solid.

$^1$H NMR (400 MHz, CD$_3$OD) d 7.86 (t, 1H, J=8.0 Hz), 7.70 (d, 2H, J=8.3 Hz), 7.54 (d, 2H, J=8.4 Hz), 7.33 (d, 1H, J=7.4 Hz), 7.16 (d, 1H, J=8.6 Hz), 5.11 (s, 2H), 3.50~3.39 (m, 4H), 1.65~1.53 (m, 6H); MS (ESI) m/z 423.1 (M$^+$+H).

Example 168: Synthesis of Compound 829

Formula 7-6: (S)-methyl 4-((3-fluoro-N-(6-(trifluoromethyl)pyridin-2-yl)pyrrolidine-1-carboxamido)methyl)benzoate

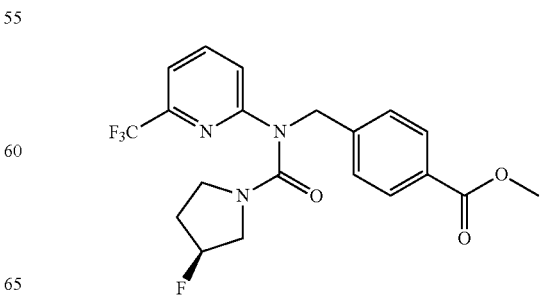

Compound of Formula 7-5 (methyl 4-((((4-nitrophenoxy) carbonyl)(6-(trifluoromethyl)pyridin-2-yl)amino)methyl) benzoate; 0.100 g, 0.210 mmol), (S)-3-fluoropyrrolidine (0.037 g, 0.421 mmol) and potassium carbonate (0.058 g, 0.421 mmol) were mixed with N,N-dimethylformamide (3 mL) and heated at 150° C. for 30 minutes under microwave irradiation. Then, the temperature was lowered to room temperature, and the reaction was completed. Then, water was poured into the reaction mixture, and the organic layer was extracted with ethyl acetate. Then, the organic layer was washed with saturated sodium chloride aqueous solution, dehydrated with anhydrous magnesium sulfate, filtered, and then concentrated under reduced pressure. The concentrate was purified and concentrated by column chromatography (silica; ethyl acetate/hexane=50%) to give the desired compound of Formula 7-6 (0.077 g, 85.4%) in the form of a yellow liquid.

Compound 829: (S)-3-fluoro-N-(4-(hydroxycarbamoyl)benzyl)-N-(6-(trifluoromethyl)pyridin-2-yl)pyrrolidine-1-carboxamide

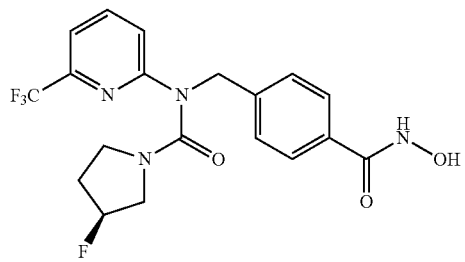

Compound of Formula 7-6 ((S)-methyl 4-((3-fluoro-N-(6-(trifluoromethyl)pyridin-2-yl)pyrrolidine-1-carboxamido)methyl)benzoate; 0.100 g, 0.235 mmol), hydroxylamine (50.0 wt % aqueous solution; 0.144 mL, 2.351 mmol) and potassium hydroxide (0.132 g, 2.351 mmol) were dissolved in methanol (1 mL) at room temperature and stirred at the same temperature for 1 hours. The solvent was removed from the reaction mixture, and the saturated sodium hydrogen carbonate aqueous solution (20 mL) was added to the concentrate and stirred. Then, the precipitated solid was filtered, washed with hexane and dried to give the desired Compound 829 (0.051 g, 51.1%) in the form of a white solid.

$^1$H NMR (400 MHz, CD$_3$OD) d 7.94 (d, 1H, J=8.4 Hz), 7.89 (t, 1H, J=7.7 Hz), 7.68 (d, 1H, J=8.3 Hz), 7.53 (d, 2H, J=8.4 Hz), 7.37 (d, 1H, J=7.4 Hz), 7.24 (d, 1H, J=8.4 Hz), 5.14 (s, 2H), 3.56~3.38 (m, 5H), 2.21~1.92 (m, 2H); MS (ESI) m/z 427.1 (M$^+$+H).

A structural formula of compound is shown in table 1 to table 13.

TABLE 1

| Compound | Structural formula |
|---|---|
| 252 | |
| 253 | |
| 254 | |
| 255 | |
| 256 | |
| 260 | |
| 261 | |
| 262 | |

TABLE 1-continued
| Compound | Structural formula |
|---|---|
| 263 | 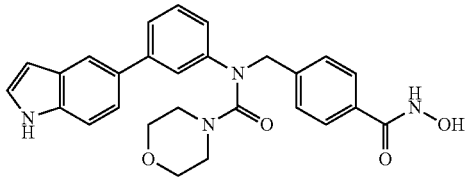 [SMILES: O=C(NO)c1ccc(CN(C(=O)N2CCOCC2)c2cccc(-c3ccc4[nH]ccc4c3)c2)cc1] |
| 279 | 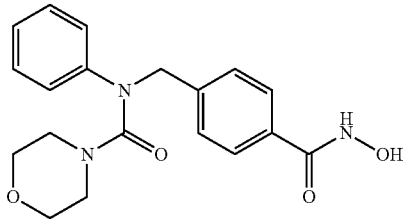 [SMILES: O=C(NO)c1ccc(CN(C(=O)N2CCOCC2)c2ccccc2)cc1] |
| 280 | 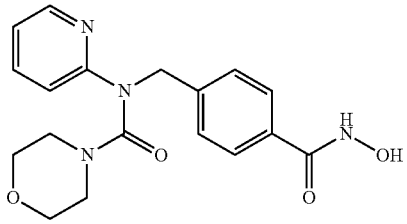 [SMILES: O=C(NO)c1ccc(CN(C(=O)N2CCOCC2)c2ccccn2)cc1] |
TABLE 1-continued
| Compound | Structural formula |
|---|---|
| 281 | 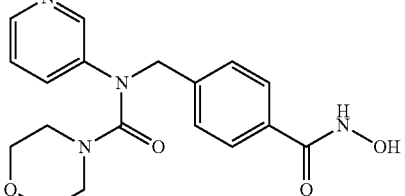 |
| 309 | 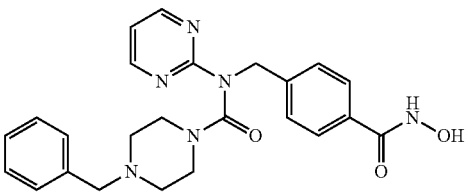 [SMILES: O=C(NO)c1ccc(CN(C(=O)N2CCN(Cc3ccccc3)CC2)c2ncccn2)cc1] |
| 311 | 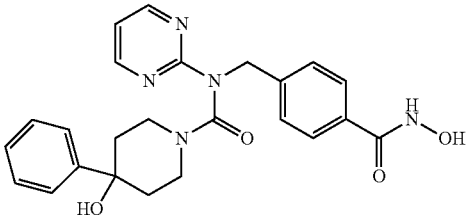 [SMILES: O=C(NO)c1ccc(CN(C(=O)N2CCC(O)(c3ccccc3)CC2)c2ncccn2)cc1] |
TABLE 2
| Compound | Structural formula |
|---|---|
| 312 | 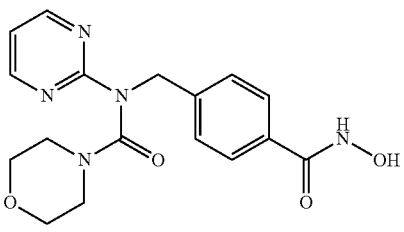 [SMILES: O=C(NO)c1ccc(CN(C(=O)N2CCOCC2)c2ncccn2)cc1] |
| 313 | 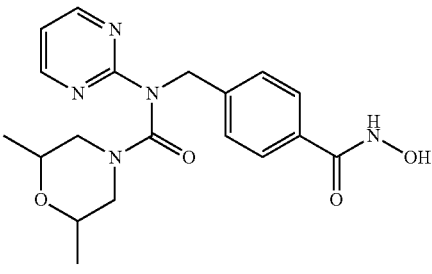 |

TABLE 2-continued
| Compound | Structural formula |
|---|---|
| 329 | 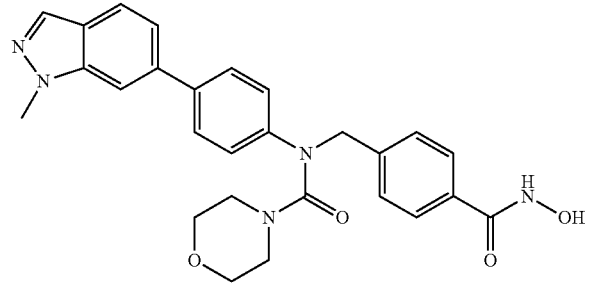 [SMILES: Cn1ncc2ccc(-c3ccc(N(Cc4ccc(C(=O)NO)cc4)C(=O)N4CCOCC4)cc3)cc21] |
| 330 | 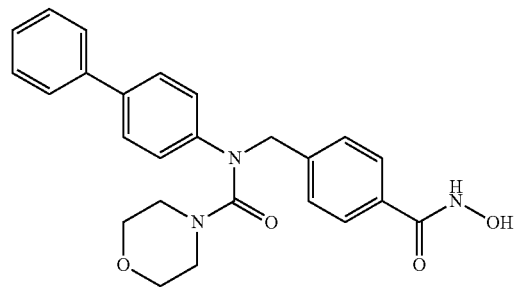 [SMILES: O=C(NO)c1ccc(CN(C(=O)N2CCOCC2)c2ccc(-c3ccccc3)cc2)cc1] |
| 331 | 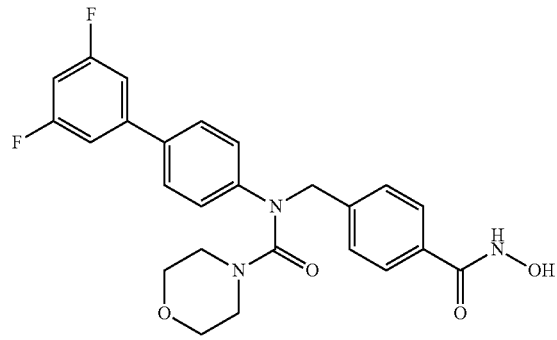 [SMILES: O=C(NO)c1ccc(CN(C(=O)N2CCOCC2)c2ccc(-c3cc(F)cc(F)c3)cc2)cc1] |
| 332 | 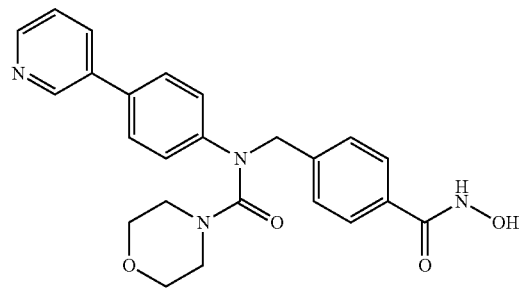 [SMILES: O=C(NO)c1ccc(CN(C(=O)N2CCOCC2)c2ccc(-c3cccnc3)cc2)cc1] |
| 333 | 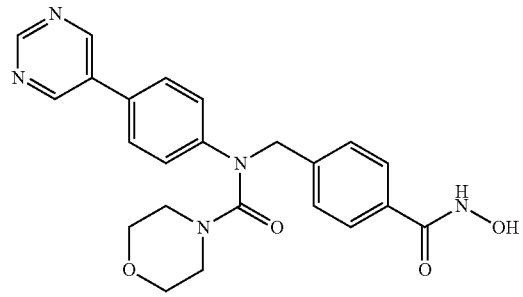 [SMILES: O=C(NO)c1ccc(CN(C(=O)N2CCOCC2)c2ccc(-c3cncnc3)cc2)cc1] |

TABLE 2-continued
| Compound | Structural formula |
|---|---|
| 334 | 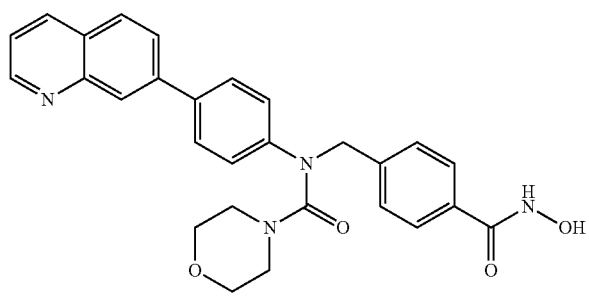 [SMILES: O=C(NO)c1ccc(CN(C(=O)N2CCOCC2)c2ccc(-c3ccc4cccnc4c3)cc2)cc1] |
| 335 | 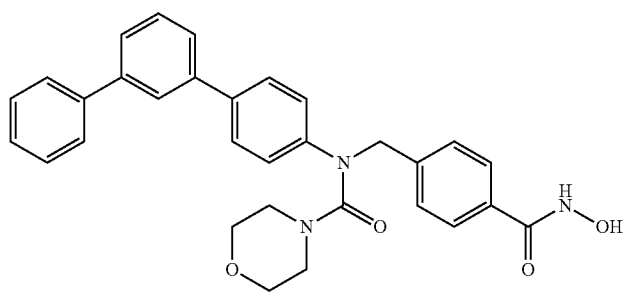 [SMILES: O=C(NO)c1ccc(CN(C(=O)N2CCOCC2)c2ccc(-c3cccc(-c4ccccc4)c3)cc2)cc1] |
| 336 | 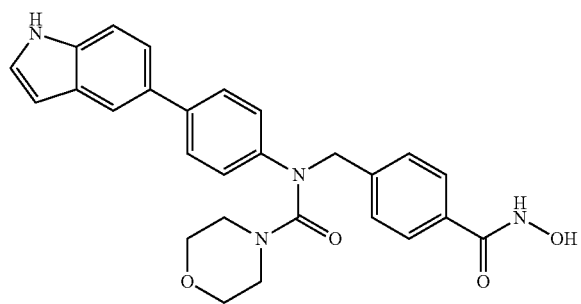 [SMILES: O=C(NO)c1ccc(CN(C(=O)N2CCOCC2)c2ccc(-c3ccc4[nH]ccc4c3)cc2)cc1] |
| 337 | 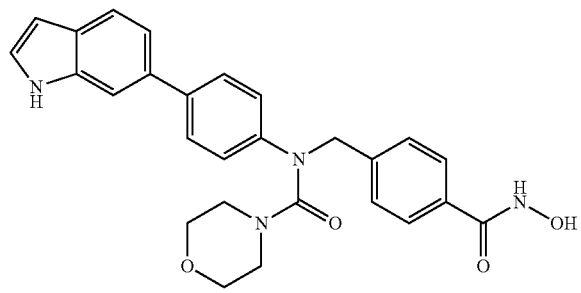 [SMILES: O=C(NO)c1ccc(CN(C(=O)N2CCOCC2)c2ccc(-c3ccc4cc[nH]c4c3)cc2)cc1] |
| 338 | 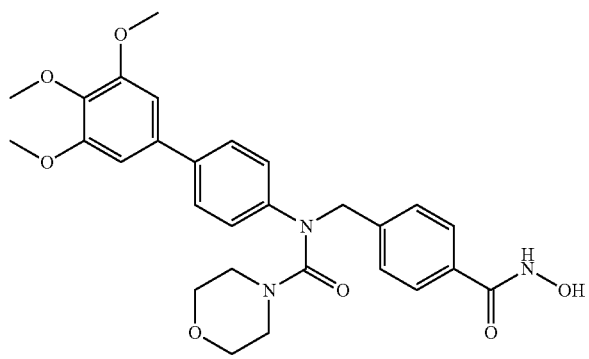 [SMILES: COc1cc(-c2ccc(N(Cc3ccc(C(=O)NO)cc3)C(=O)N3CCOCC3)cc2)cc(OC)c1OC] |

TABLE 2-continued
| Compound | Structural formula |
|---|---|
| 339 | 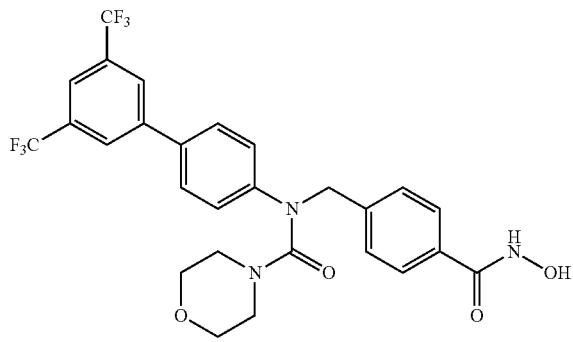 [SMILES: O=C(NO)c1ccc(CN(C(=O)N2CCOCC2)c2ccc(-c3cc(C(F)(F)F)cc(C(F)(F)F)c3)cc2)cc1] |
| 340 | 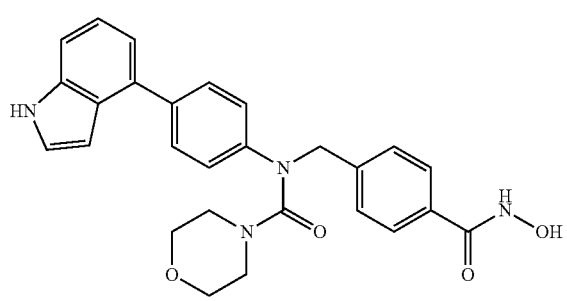 [SMILES: O=C(NO)c1ccc(CN(C(=O)N2CCOCC2)c2ccc(-c3cccc4[nH]ccc34)cc2)cc1] |
TABLE 3
| Compound | Structural formula |
|---|---|
| 341 | |
| 342 | |
| 343 | |
| 352 | |
| 353 | |
| 354 | |

TABLE 3-continued
| Compound | Structural formula |
|---|---|
| 355 | 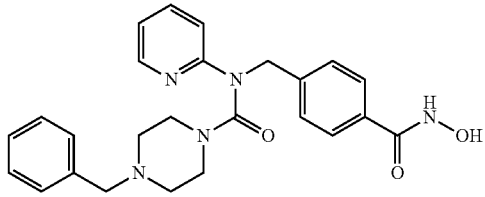 [SMILES: O=C(NO)c1ccc(CN(C(=O)N2CCN(Cc3ccccc3)CC2)c2ccccn2)cc1] |
| 356 | 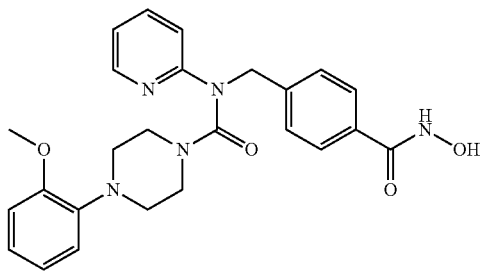 [SMILES: COc1ccccc1N1CCN(C(=O)N(Cc2ccc(C(=O)NO)cc2)c2ccccn2)CC1] |
| 357 | 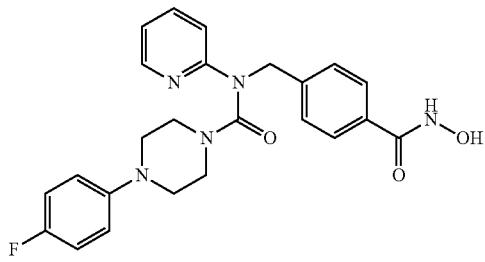 [SMILES: O=C(NO)c1ccc(CN(C(=O)N2CCN(c3ccc(F)cc3)CC2)c2ccccn2)cc1] |
| 358 | 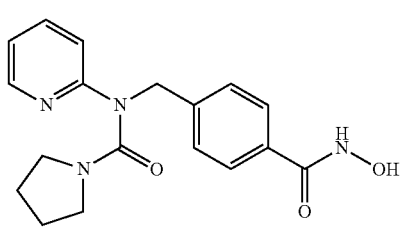 [SMILES: O=C(NO)c1ccc(CN(C(=O)N2CCCC2)c2ccccn2)cc1] |
| 370 | 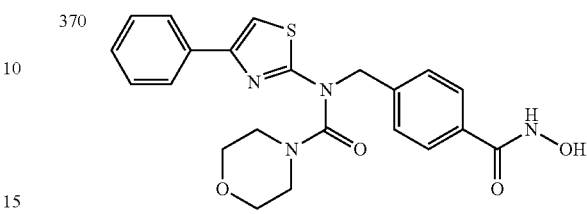 |
| 371 | 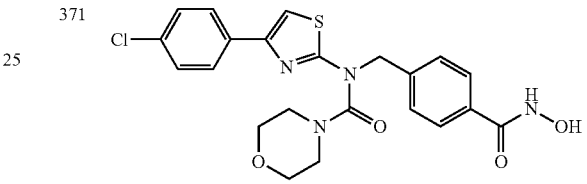 |
| 372 | 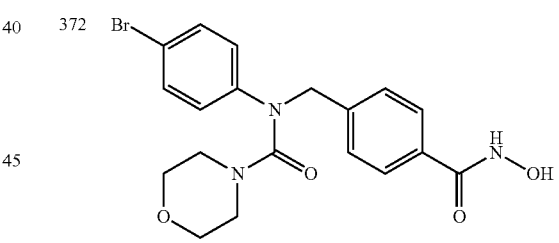 |
| 374 | 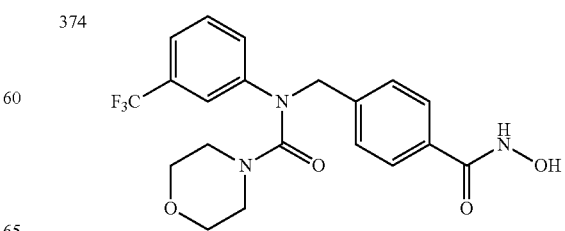 |

TABLE 4
| Compound | Structural formula |
|---|---|
| 376 | 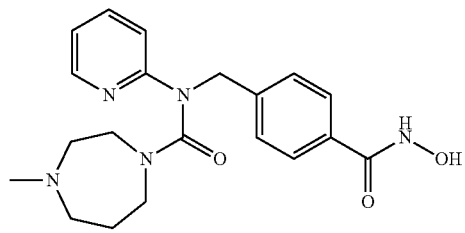 [SMILES: CN1CCCN(C(=O)N(Cc2ccc(C(=O)NO)cc2)c2ccccn2)CC1] |
| 377 | 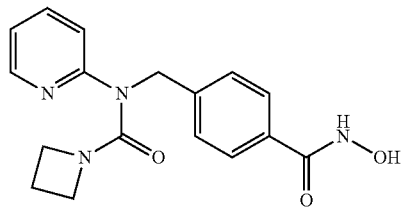 [SMILES: O=C(NO)c1ccc(CN(C(=O)N2CCC2)c2ccccn2)cc1] |
| 379 | 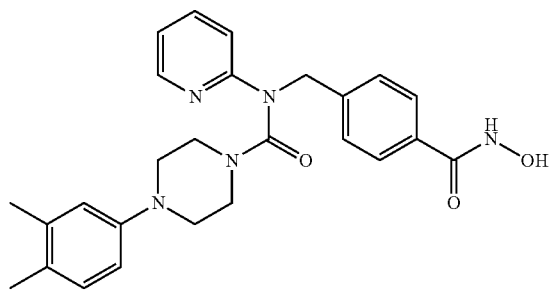 [SMILES: Cc1ccc(N2CCN(C(=O)N(Cc3ccc(C(=O)NO)cc3)c3ccccn3)CC2)cc1C] |
| 380 | 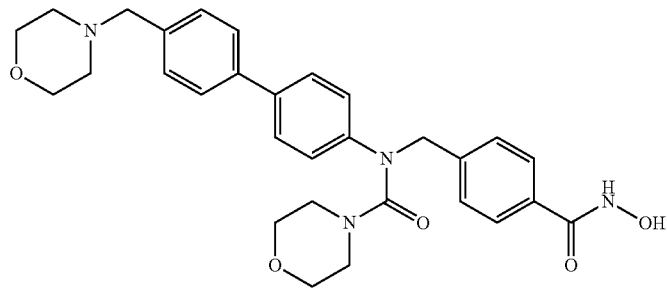 [SMILES: O=C(NO)c1ccc(CN(C(=O)N2CCOCC2)c2ccc(-c3ccc(CN4CCOCC4)cc3)cc2)cc1] |
| 381 | 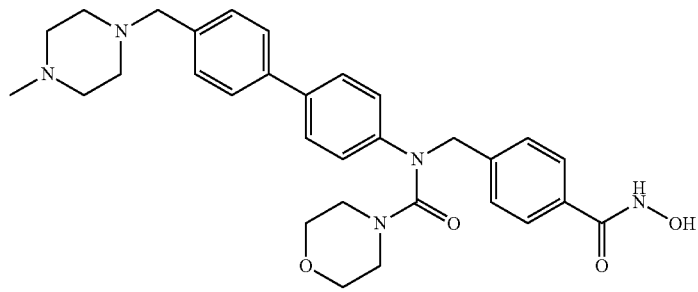 [SMILES: CN1CCN(Cc2ccc(-c3ccc(N(Cc4ccc(C(=O)NO)cc4)C(=O)N4CCOCC4)cc3)cc2)CC1] |

TABLE 4-continued
| Compound | Structural formula |
|---|---|
| 382 | 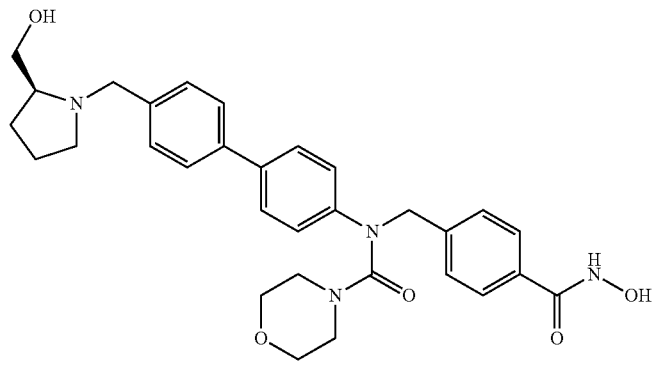 [SMILES: O=C(NO)c1ccc(CN(C(=O)N2CCOCC2)c2ccc(-c3ccc(CN4CCC[C@H]4CO)cc3)cc2)cc1] |
| 383 | 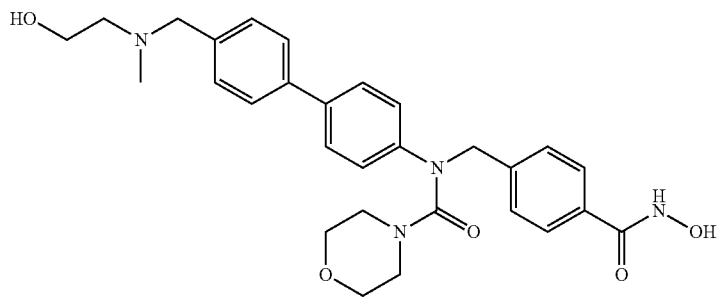 [SMILES: CN(CCO)Cc1ccc(-c2ccc(N(Cc3ccc(C(=O)NO)cc3)C(=O)N3CCOCC3)cc2)cc1] |
| 385 | 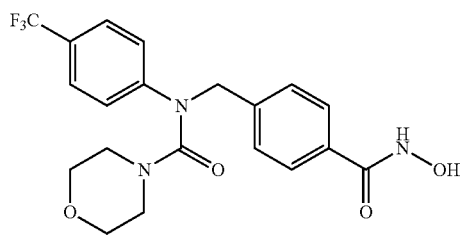 [SMILES: O=C(NO)c1ccc(CN(C(=O)N2CCOCC2)c2ccc(C(F)(F)F)cc2)cc1] |
| 386 | 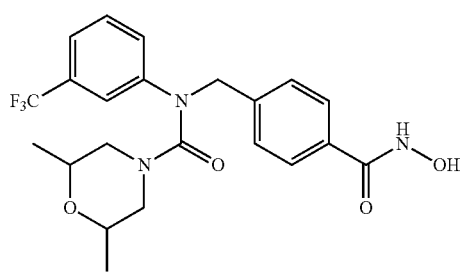 [SMILES: CC1CN(C(=O)N(Cc2ccc(C(=O)NO)cc2)c2cccc(C(F)(F)F)c2)CC(C)O1] |
| 389 | 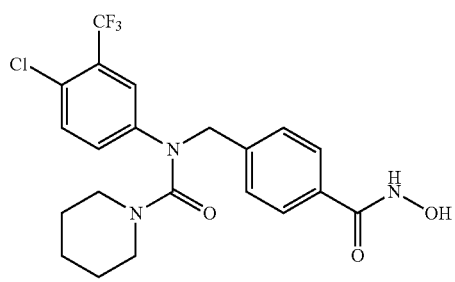 |

TABLE 4-continued
| Compound | Structural formula |
|---|---|
| 390 | 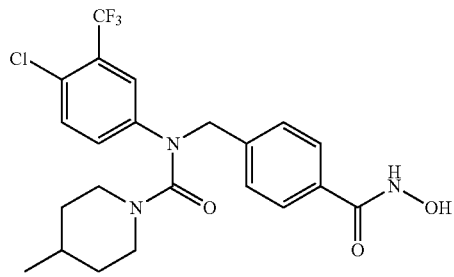 [SMILES: CC1CCN(C(=O)N(Cc2ccc(C(=O)NO)cc2)c2ccc(Cl)c(C(F)(F)F)c2)CC1] |
| 391 | 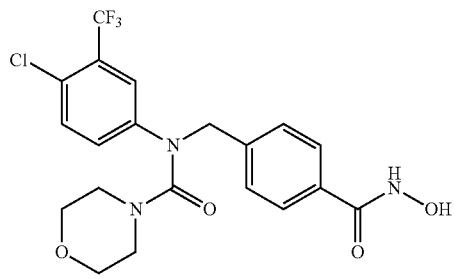 [SMILES: O=C(NO)c1ccc(CN(C(=O)N2CCOCC2)c2ccc(Cl)c(C(F)(F)F)c2)cc1] |
| 392 | 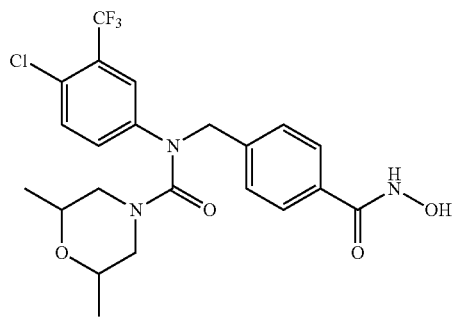 [SMILES: CC1CN(C(=O)N(Cc2ccc(C(=O)NO)cc2)c2ccc(Cl)c(C(F)(F)F)c2)CC(C)O1] |
| 393 | 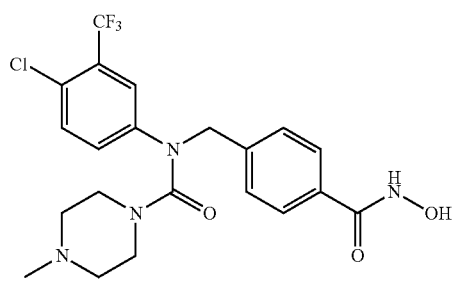 |

TABLE 5
| Compound | Structural formula |
|---|---|
| 394 | 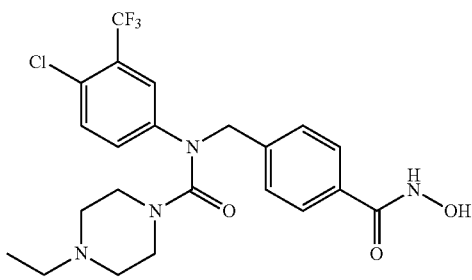 [SMILES: CCN1CCN(C(=O)N(Cc2ccc(C(=O)NO)cc2)c2ccc(Cl)c(C(F)(F)F)c2)CC1] |
| 395 | 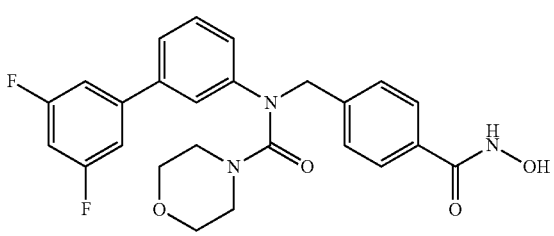 [SMILES: O=C(NO)c1ccc(CN(C(=O)N2CCOCC2)c2cccc(-c3cc(F)cc(F)c3)c2)cc1] |
| 396 | 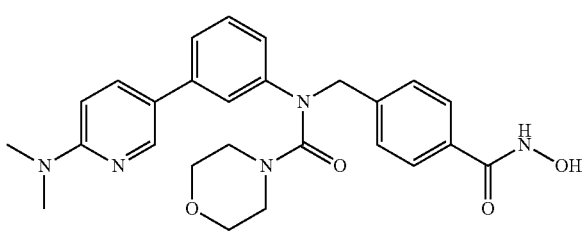 [SMILES: CN(C)c1ccc(-c2cccc(N(Cc3ccc(C(=O)NO)cc3)C(=O)N3CCOCC3)c2)cn1] |
| 397 | 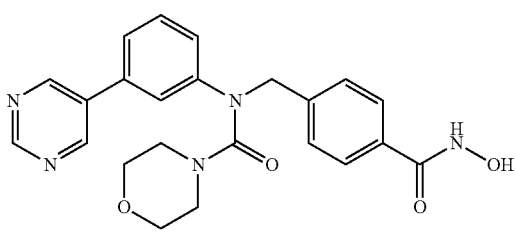 [SMILES: O=C(NO)c1ccc(CN(C(=O)N2CCOCC2)c2cccc(-c3cncnc3)c2)cc1] |
| 398 | 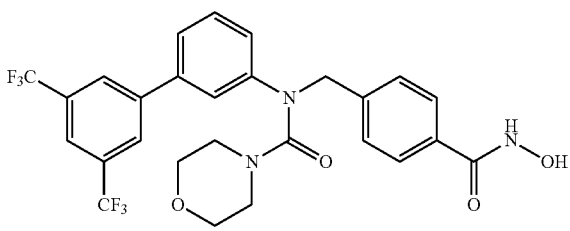 [SMILES: O=C(NO)c1ccc(CN(C(=O)N2CCOCC2)c2cccc(-c3cc(C(F)(F)F)cc(C(F)(F)F)c3)c2)cc1] |
| 399 | 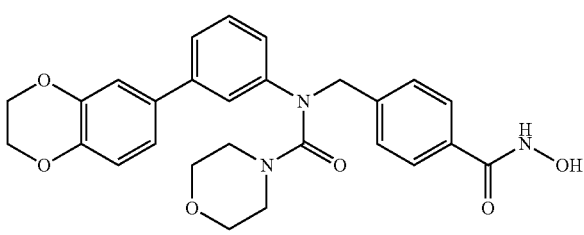 [SMILES: O=C(NO)c1ccc(CN(C(=O)N2CCOCC2)c2cccc(-c3ccc4c(c3)OCCO4)c2)cc1] |

TABLE 5-continued
| Compound | Structural formula |
|---|---|
| 400 | 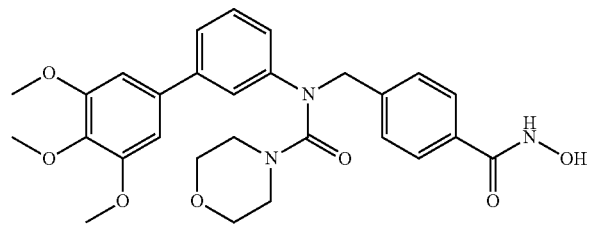 [SMILES: COc1cc(-c2cccc(N(Cc3ccc(C(=O)NO)cc3)C(=O)N3CCOCC3)c2)cc(OC)c1OC] |
| 401 | 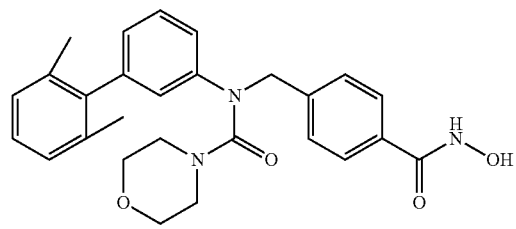 [SMILES: Cc1cccc(C)c1-c1cccc(N(Cc2ccc(C(=O)NO)cc2)C(=O)N2CCOCC2)c1] |
| 402 | 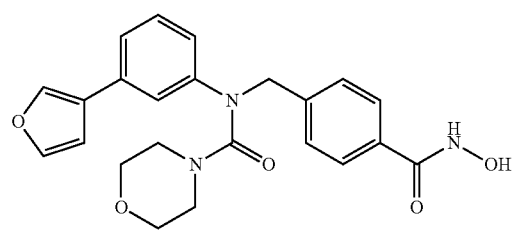 [SMILES: O=C(NO)c1ccc(CN(C(=O)N2CCOCC2)c2cccc(-c3ccoc3)c2)cc1] |
| 403 | 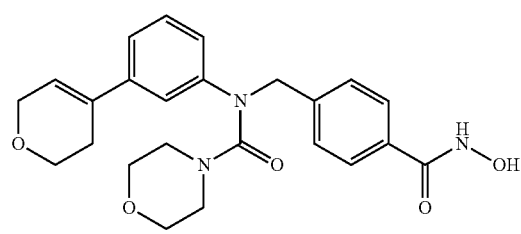 [SMILES: O=C(NO)c1ccc(CN(C(=O)N2CCOCC2)c2cccc(C3=CCOCC3)c2)cc1] |
| 404 | 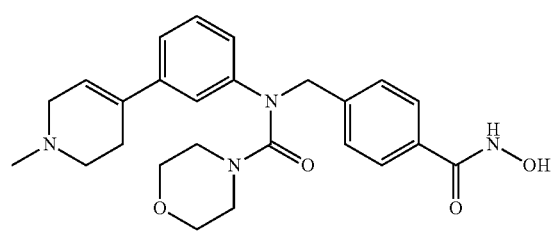 [SMILES: CN1CC=C(c2cccc(N(Cc3ccc(C(=O)NO)cc3)C(=O)N3CCOCC3)c2)CC1] |
| 405 | 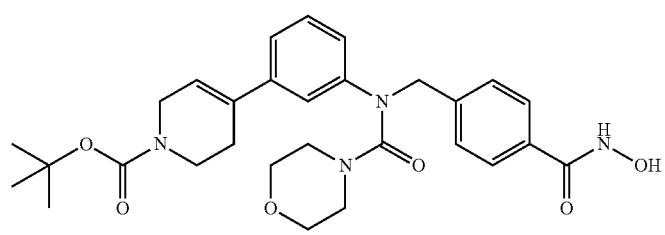 [SMILES: CC(C)(C)OC(=O)N1CC=C(c2cccc(N(Cc3ccc(C(=O)NO)cc3)C(=O)N3CCOCC3)c2)CC1] |

TABLE 5-continued

| Compound | Structural formula |
|---|---|
| 413 | (2,4-difluorophenyl)-N-benzyl morpholine-4-carboxamide with hydroxamic acid |
| 414 | (2,4-difluorophenyl)-N-benzyl piperidine-1-carboxamide with hydroxamic acid |

TABLE 6

| Compound | Structural formula |
|---|---|
| 415 | 2,6-dimethylmorpholine carboxamide derivative with 2,4-difluorophenyl and benzohydroxamic acid |
| 416 | 4-methylpiperazine carboxamide derivative with 2,4-difluorophenyl and benzohydroxamic acid |
| 418 | morpholine carboxamide derivative with 3-(benzo[d][1,3]dioxol-5-yl)phenyl and benzohydroxamic acid |
| 419 | morpholine carboxamide derivative with 3-(1-acetyl-1,2,3,6-tetrahydropyridin-4-yl)phenyl and benzohydroxamic acid |
| 420 | morpholine carboxamide derivative with 3-(1-(methylsulfonyl)-1,2,3,6-tetrahydropyridin-4-yl)phenyl and benzohydroxamic acid |
| 438 | piperidine carboxamide derivative with 2-fluoro-4-methylphenyl and benzohydroxamic acid |
| 439 | morpholine carboxamide derivative with 2-fluoro-4-methylphenyl and benzohydroxamic acid |
| 440 | 2,6-dimethylmorpholine carboxamide derivative with 2-fluoro-4-methylphenyl and benzohydroxamic acid |

TABLE 6-continued
| Compound | Structural formula |
|---|---|
| 441 | 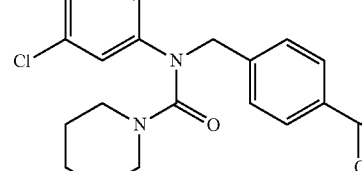 |
| 450 | 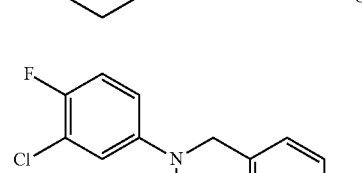 |
| 451 | 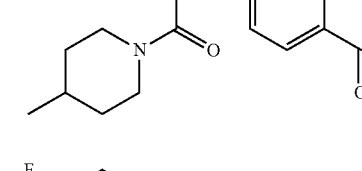 |
| 453 | 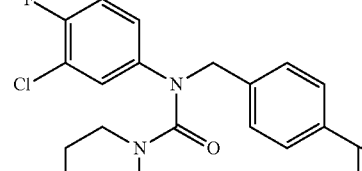 |
| 454 | 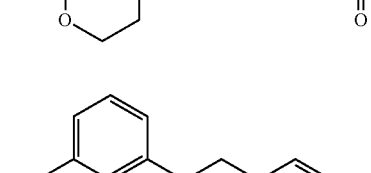 |
| 455 | 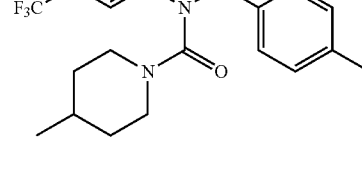 |
TABLE 7
| Compound | Structural formula |
|---|---|
| 456 | |
| 457 | |
| 458 | |
| 459 | |
| 460 | |
| 461 | |

TABLE 7-continued

| Compound | Structural formula |
|---|---|
| 462 | (benzodioxole-phenyl)-N(CH2-C6H4-C(O)NHOH)-C(O)-piperidine |
| 463 | (benzodioxole-phenyl)-N(CH2-C6H4-C(O)NHOH)-C(O)-(4-hydroxypiperidine) |
| 464 | (benzodioxole-phenyl)-N(CH2-C6H4-C(O)NHOH)-C(O)-(2-methylmorpholine) |
| 465 | (benzodioxole-phenyl)-N(CH2-C6H4-C(O)NHOH)-C(O)-(4-hydroxy-4-phenylpiperidine) |
| 466 | (benzodioxole-phenyl)-N(CH2-C6H4-C(O)NHOH)-C(O)-(4-methylpiperazine) |
| 467 | (benzodioxole-phenyl)-N(CH2-C6H4-C(O)NHOH)-C(O)-(4-(2-hydroxyethyl)piperazine) |
| 468 | (benzodioxole-phenyl)-N(CH2-C6H4-C(O)NHOH)-C(O)-pyrrolidine |
| 469 | (benzodioxole-phenyl)-N(CH2-C6H4-C(O)NHOH)-C(O)-(2-(hydroxymethyl)pyrrolidine) |

TABLE 8

| Compound | Structural formula |
|---|---|
| 470 | (benzodioxole-phenyl)-N(CH2-C6H4-C(O)NHOH)-C(O)-(4-(cyclopropanecarbonyl)piperazine) |
| 471 | (benzodioxole-phenyl)-N(CH2-C6H4-C(O)NHOH)-C(O)-azetidine |
| 477 | (3-chloro-4-fluorophenyl)-N(CH2-C6H4-C(O)NHOH)-C(O)-(2,6-dimethylmorpholine) |
| 478 | (3-chloro-4-fluorophenyl)-N(CH2-C6H4-C(O)NHOH)-C(O)-(4-methylpiperazine) |

TABLE 8-continued

| Compound | Structural formula |
|---|---|
| 479 | |
| 480 | |
| 481 | |
| 482 | |
| 483 | |
| 484 | |
| 485 | |
| 486 | |
| 487 | |
| 488 | |

313 314
TABLE 9
| Compound | Structural formula |
|---|---|
| 489 | 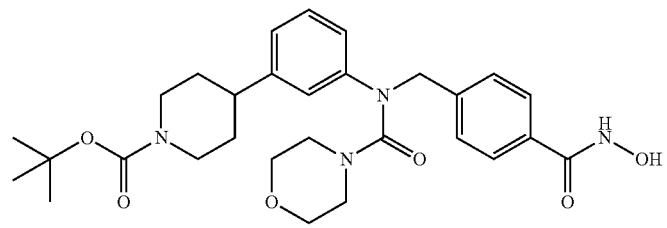 [SMILES: CC(C)(C)OC(=O)N1CCC(c2cccc(N(Cc3ccc(C(=O)NO)cc3)C(=O)N3CCOCC3)c2)CC1] |
| 490 | 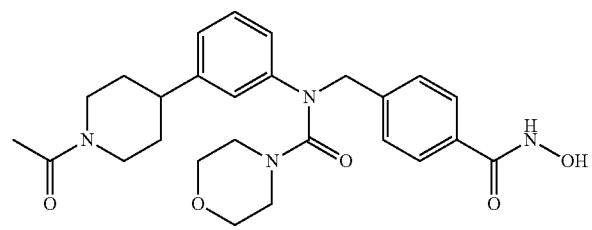 [SMILES: CC(=O)N1CCC(c2cccc(N(Cc3ccc(C(=O)NO)cc3)C(=O)N3CCOCC3)c2)CC1] |
| 491 | 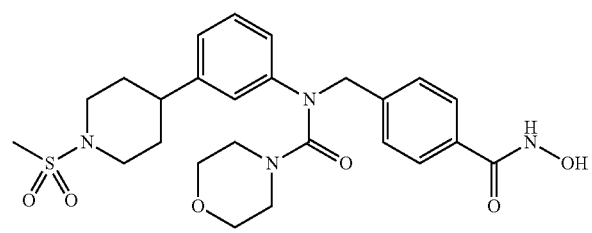 [SMILES: CS(=O)(=O)N1CCC(c2cccc(N(Cc3ccc(C(=O)NO)cc3)C(=O)N3CCOCC3)c2)CC1] |
| 492 | 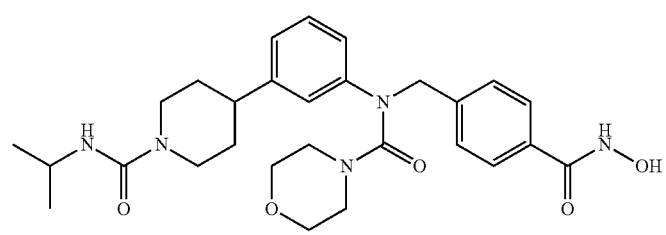 [SMILES: CC(C)NC(=O)N1CCC(c2cccc(N(Cc3ccc(C(=O)NO)cc3)C(=O)N3CCOCC3)c2)CC1] |
| 493 | 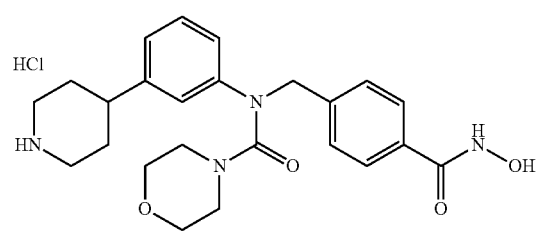 [SMILES: Cl ; O=C(NO)c1ccc(CN(C(=O)N2CCOCC2)c2cccc(C3CCNCC3)c2)cc1] |
| 494 | 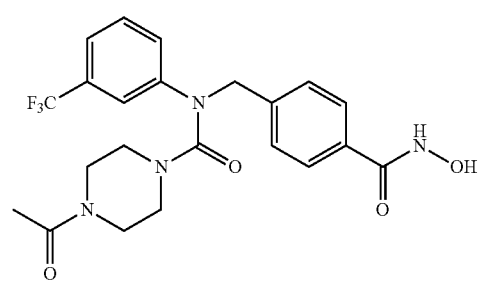 [SMILES: CC(=O)N1CCN(C(=O)N(Cc2ccc(C(=O)NO)cc2)c2cccc(C(F)(F)F)c2)CC1] |

TABLE 9-continued
| Compound | Structural formula |
|---|---|
| 495 | 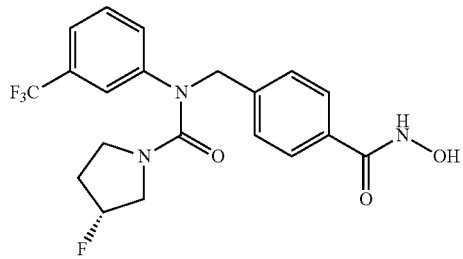 [SMILES: O=C(NO)c1ccc(CN(C(=O)N2CC[C@@H](F)C2)c2cccc(C(F)(F)F)c2)cc1] |
| 496 | 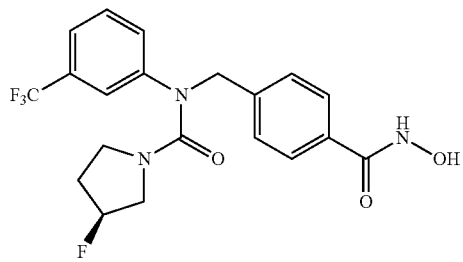 [SMILES: O=C(NO)c1ccc(CN(C(=O)N2CC[C@H](F)C2)c2cccc(C(F)(F)F)c2)cc1] |
| 497 | 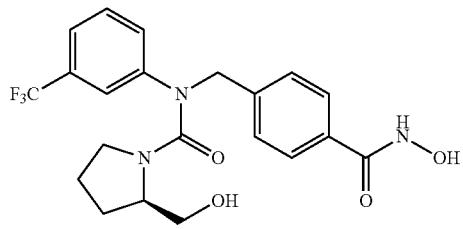 [SMILES: O=C(NO)c1ccc(CN(C(=O)N2CCC[C@@H]2CO)c2cccc(C(F)(F)F)c2)cc1] |
| 498 | 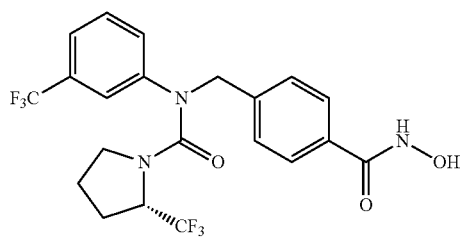 [SMILES: O=C(NO)c1ccc(CN(C(=O)N2CCC[C@H]2C(F)(F)F)c2cccc(C(F)(F)F)c2)cc1] |
| 499 | 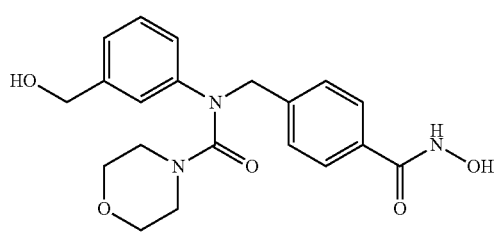 [SMILES: O=C(NO)c1ccc(CN(C(=O)N2CCOCC2)c2cccc(CO)c2)cc1] |
| 500 | 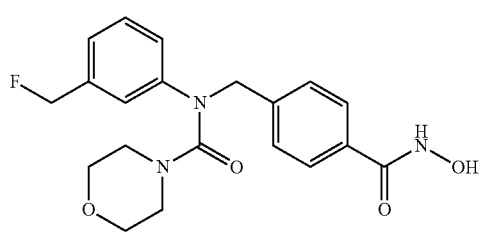 [SMILES: O=C(NO)c1ccc(CN(C(=O)N2CCOCC2)c2cccc(CF)c2)cc1] |

TABLE 9-continued
| Compound | Structural formula |
|---|---|
| 511 | 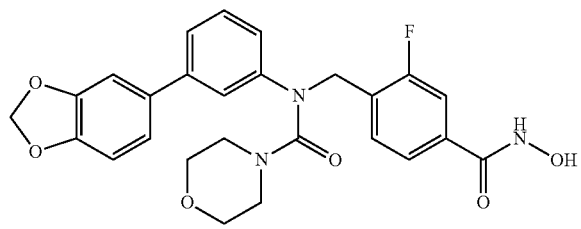 [SMILES: O=C(NO)c1ccc(CN(C(=O)N2CCOCC2)c2cccc(-c3ccc4c(c3)OCO4)c2)c(F)c1] |
| 512 | 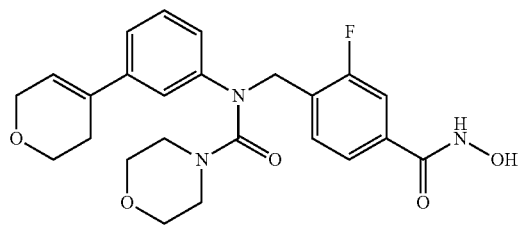 [SMILES: O=C(NO)c1ccc(CN(C(=O)N2CCOCC2)c2cccc(C3=CCOCC3)c2)c(F)c1] |
TABLE 10
| Compound | Structural formula |
|---|---|
| 513 | 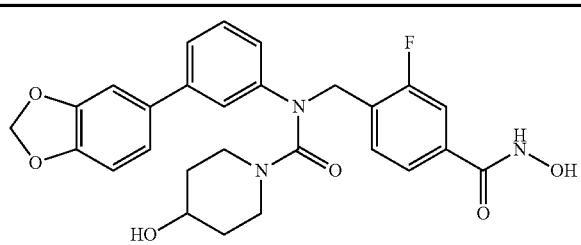 |
| 514 | 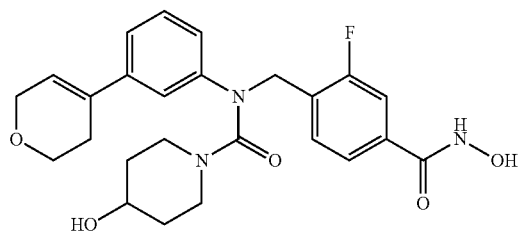 [SMILES: O=C(NO)c1ccc(CN(C(=O)N2CCC(O)CC2)c2cccc(C3=CCOCC3)c2)c(F)c1] |
| 517 | 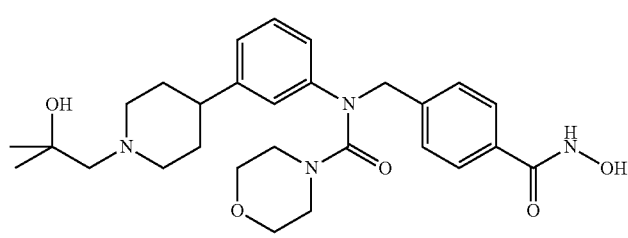 [SMILES: CC(C)(O)CN1CCC(c2cccc(N(Cc3ccc(C(=O)NO)cc3)C(=O)N3CCOCC3)c2)CC1] |
| 518 | 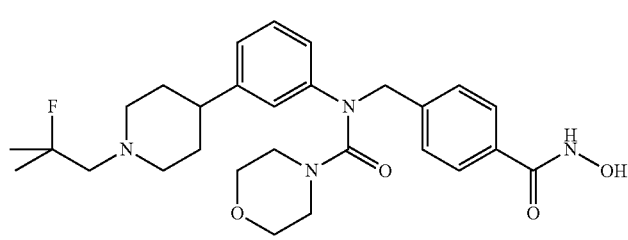 [SMILES: CC(C)(F)CN1CCC(c2cccc(N(Cc3ccc(C(=O)NO)cc3)C(=O)N3CCOCC3)c2)CC1] |

TABLE 10-continued
| Compound | Structural formula |
|---|---|
| 520 | 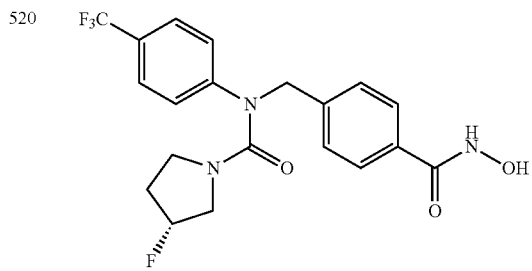 |
| 521 | 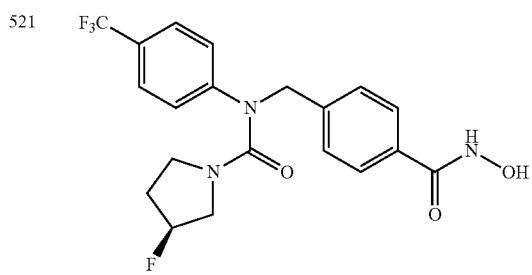 |
| 522 | 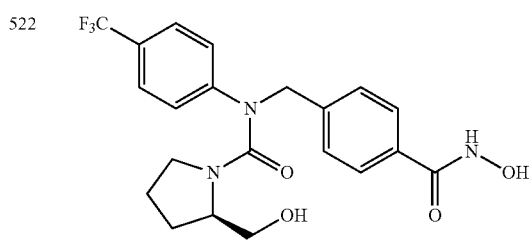 |
| 529 | 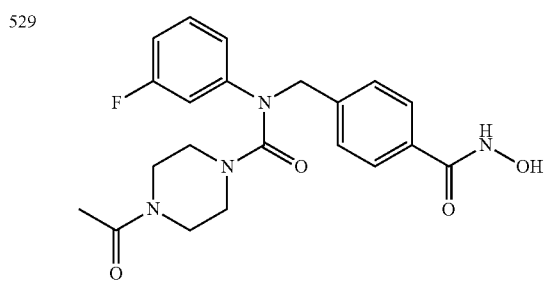 |
| 530 | 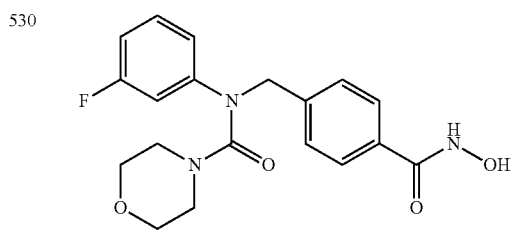 |
| 531 | 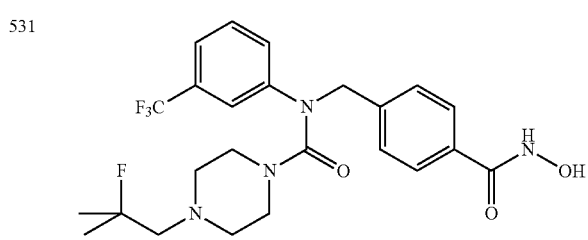 |

TABLE 10-continued
| Compound | Structural formula |
|---|---|
| 532 | 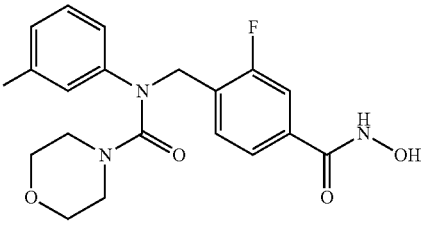 |
| 533 | 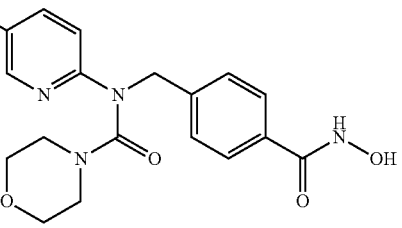 |
| 543 | 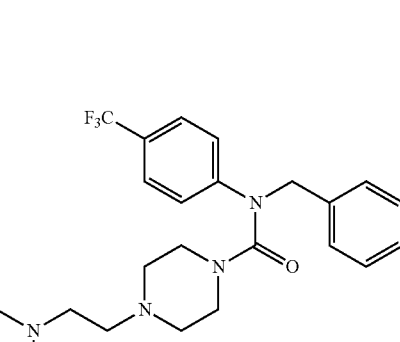 |
| 544 | 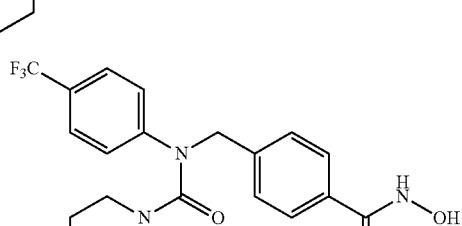 |
TABLE 11
| Compound | Structural formula |
|---|---|
| 545 | |
| 577 | |

TABLE 11-continued
| Compound | Structural formula |
|---|---|
| 578 | 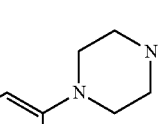 |
| 580 | 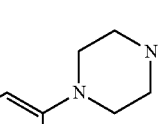 |
| 651 | 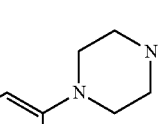 |
| 683 | 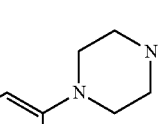 |
| 684 | 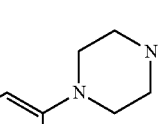 |
| 716 | 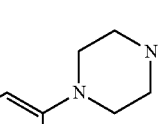 |
| 717 | 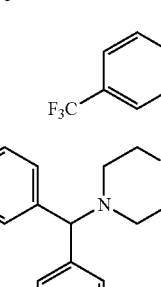 |
| 718 | 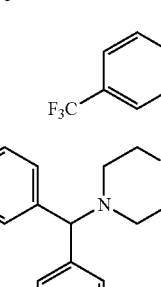 |
| 765 | 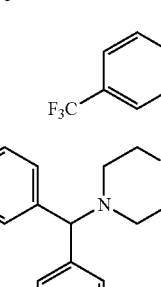 |
| 766 | 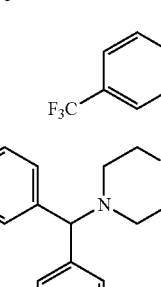 |
| 771 | 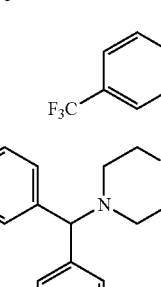 |
| 772 | 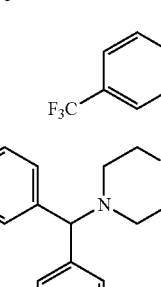 |

TABLE 12
| Compound | Structural formula |
|---|---|
| 773 | 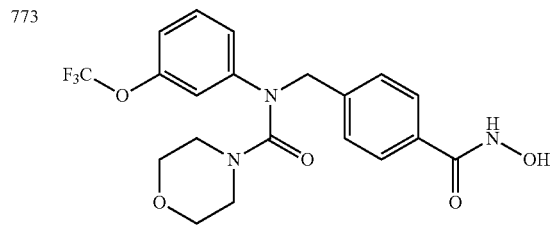 |
| 774 | 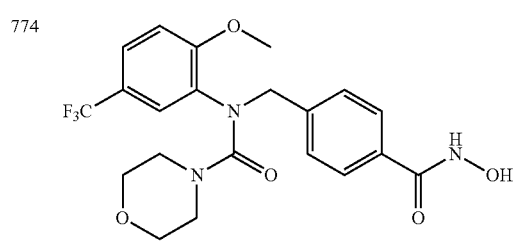 |
| 776 | 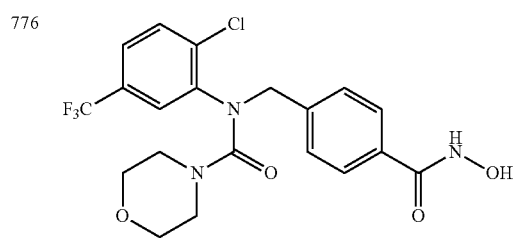 |
| 778 | 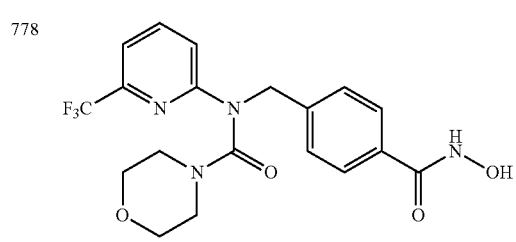 |
| 791 | 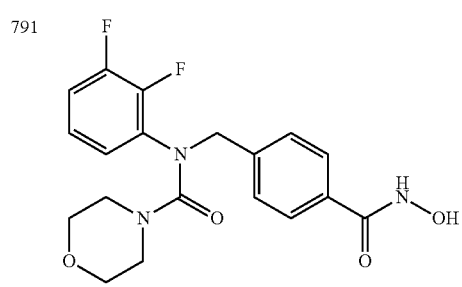 |
| 797 | 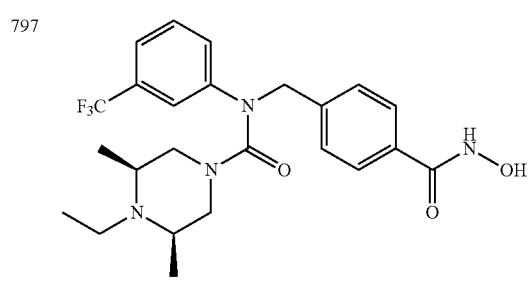 |
TABLE 12-continued
| Compound | Structural formula |
|---|---|
| 800 | 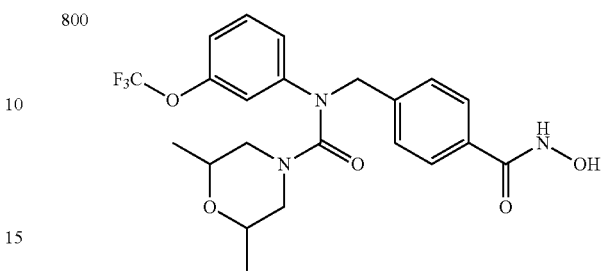 |
| 801 | 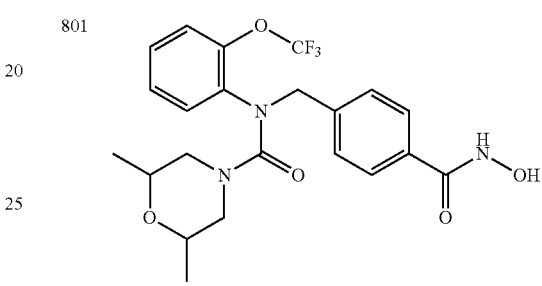 |
| 802 | 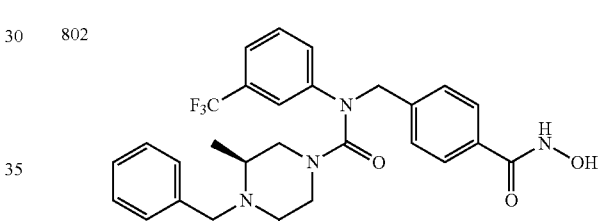 |
| 803 | 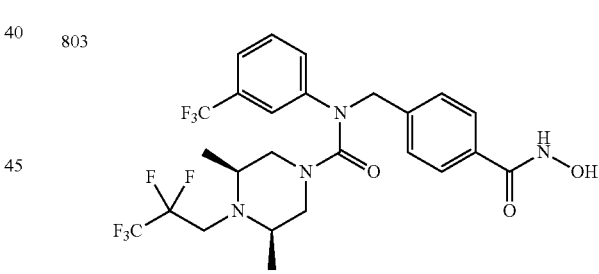 |
| 826 | 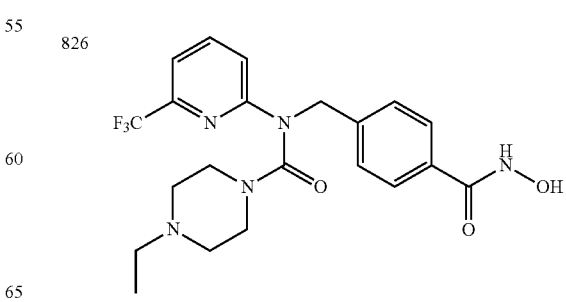 |

TABLE 12-continued

| Compound | Structural formula |
|---|---|
| 827 | 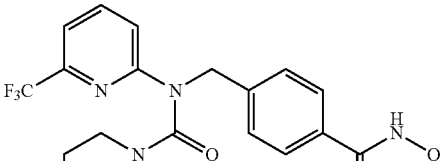 |

TABLE 13

| Compound | Structural formula |
|---|---|
| 828 | 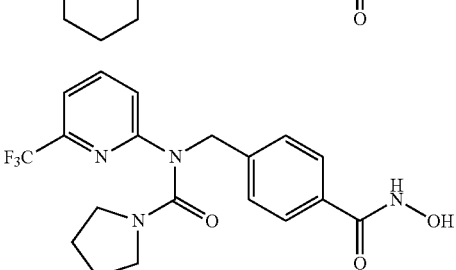 |
| 829 | |

Protocols for Measurement and Analysis of Activities of Inventive Compounds

Example 170: Determination of Inhibition of HDAC Activities (In Vitro)

Selective HDAC6 inhibitors are critical for the selectivity of HDAC1 inhibition, which causes side effects, and thus the selectivity of HDAC1/6 enzymes and the cell selectivity (HDAC1: Histone acetylation/HDAC6: Tubulin acetylation) were determined.

1. Test of HDAC Activities (HDAC1 and HDAC6)

The HDAC inhibitory activities of test materials were measured using the HDAC1 Fluorimetric Drug Discovery Assay Kit (Enzolifesciences: BML-AK511) and HDAC6 human recombinant (Calbiochem: 382180). In the HDAC1 assay, the samples were treated with concentrations of 100, 1000, and 10000 nM, and in the HDAC6 assay, the samples were treated with concentrations of 0.1, 1, 10, 100, and 1000 nM. After the treatment of the samples, the samples were reacted at 37° C. for 60 minutes, treated with a developer, and then reacted at 37° C. for 30 minutes. Then, the fluorescence intensity (Ex 390, Em 460) was measured using the FlexStation 3 (Molecular device).

The results are shown in Table 14.

As shown in Table 14, the novel urea derivatives of the present invention exhibit excellent HDAC1/6 enzyme selectivity.

TABLE 14

| HDAC inhibitory activities (HDAC 1, 6) | | |
|---|---|---|
| Compound | HDAC6 (uM) | HDAC1 (uM) |
| 252 | 0.006 | 0.151 |
| 254 | 0.002 | 0.173 |
| 256 | 0.001 | 0.148 |
| 260 | 0.007 | 0.551 |
| 261 | 0.002 | 0.072 |
| 262 | 0.001 | 0.164 |
| 263 | 0.002 | 0.075 |
| 279 | 0.001 | 0.292 |
| 280 | 0.005 | 1.26 |
| 281 | 0.027 | 3.91 |
| 309 | 0.003 | ND |
| 311 | 0.013 | 22.9 |
| 312 | 0.007 | 22.7 |
| 313 | 0.007 | 35.9 |
| 352 | 0.007 | 4.62 |
| 353 | 0.010 | 4.53 |
| 354 | 0.009 | 3.91 |
| 355 | 0.005 | 2.34 |
| 356 | 0.004 | 3.82 |
| 357 | 0.003 | 3.28 |
| 358 | 0.009 | 4.17 |
| 370 | 0.001 | 0.710 |
| 371 | 0.020 | 1.33 |
| 372 | 0.001 | 0.212 |
| 376 | 0.004 | ND |
| 377 | 0.005 | ND |
| 379 | 0.004 | ND |
| 385 | 0.005 | 0.976 |
| 386 | 0.006 | 4.04 |
| 389 | 0.037 | 7.83 |
| 390 | 0.020 | 6.22 |
| 391 | 0.003 | 2.12 |
| 392 | 0.005 | 2.87 |
| 393 | 0.005 | 1.11 |
| 394 | 0.011 | 2.59 |
| 395 | 0.005 | 0.489 |
| 396 | 0.005 | 0.257 |
| 397 | 0.014 | 1.0 |
| 398 | 0.032 | 4.45 |
| 399 | 0.007 | 0.302 |
| 400 | 0.008 | 0.770 |
| 401 | 0.008 | 1.79 |
| 402 | 0.003 | 0.170 |
| 403 | 0.001 | 0.453 |
| 404 | 0.016 | 3.50 |
| 405 | 0.003 | 1.45 |
| 413 | 0.0004 | 0.860 |
| 414 | 0.001 | 1.17 |
| 415 | 0.005 | 1.22 |
| 416 | 0.002 | 0.930 |
| 418 | 0.002 | 0.190 |
| 419 | 0.005 | 0.460 |
| 420 | 0.004 | 0.310 |
| 438 | 0.004 | 1.74 |
| 439 | 0.002 | 0.632 |
| 440 | 0.002 | 0.988 |
| 441 | 0.002 | 0.447 |
| 450 | 0.005 | 6.40 |
| 451 | 0.005 | 4.81 |
| 453 | 0.003 | 0.604 |
| 454 | 0.005 | 1.32 |
| 455 | 0.006 | 1.98 |
| 456 | 0.003 | 1.27 |
| 457 | 0.005 | 3.36 |
| 458 | 0.001 | 0.474 |
| 459 | 0.014 | 7.35 |
| 460 | 0.003 | 2.37 |
| 461 | 0.001 | 2.72 |
| 462 | 0.014 | 1.93 |
| 463 | 0.003 | 0.284 |
| 464 | 0.010 | 1.17 |
| 465 | 0.009 | 2.28 |
| 466 | 0.003 | 0.408 |
| 467 | 0.001 | 0.240 |
| 468 | 0.010 | 12.3 |
| 469 | 0.012 | 5.34 |

TABLE 14-continued

HDAC inhibitory activities (HDAC 1, 6)

| Compound | HDAC6 (uM) | HDAC1 (uM) |
|---|---|---|
| 470 | 0.001 | 0.635 |
| 471 | 0.014 | 1.15 |
| 478 | 0.009 | 0.190 |
| 479 | 0.007 | 0.280 |
| 480 | 0.018 | 1.07 |
| 481 | 0.015 | 2.08 |
| 482 | 0.001 | 0.680 |
| 483 | 0.007 | 0.840 |
| 484 | 0.002 | 0.680 |
| 485 | 0.008 | 0.860 |
| 486 | 0.006 | 1.45 |
| 487 | 0.007 | 0.178 |
| 488 | 0.0005 | 1.17 |
| 489 | 0.0005 | 1.22 |
| 490 | 0.019 | 0.703 |
| 491 | 0.009 | 3.22 |
| 492 | 0.002 | 1.26 |
| 493 | 0.011 | 0.883 |
| 494 | 0.001 | 0.692 |
| 495 | 0.011 | 3.33 |
| 496 | 0.001 | 1.12 |
| 497 | 0.002 | 0.936 |
| 498 | 0.027 | 4.71 |
| 499 | 0.005 | 3.63 |
| 500 | 0.003 | 1.00 |
| 511 | 0.012 | 0.636 |
| 512 | 0.014 | 1.45 |
| 513 | 0.015 | 0.654 |
| 514 | 0.015 | 1.24 |
| 517 | 0.028 | 0.427 |
| 518 | 0.014 | 0.495 |
| 520 | 0.036 | 1.172 |
| 521 | 0.010 | 0.261 |
| 522 | 0.011 | 0.177 |
| 529 | 0.002 | 0.574 |
| 530 | 0.0014 | 0.161 |
| 531 | 0.0051 | 1.820 |
| 532 | 0.0019 | 0.577 |
| 533 | 0.0045 | 1.888 |
| 543 | 0.009 | 0.447 |
| 544 | 0.021 | 0.503 |
| 545 | 0.017 | 0.545 |
| 577 | 0.0012 | 1.004 |
| 578 | 0.0093 | 1.254 |
| 580 | 0.021 | 0.667 |
| 651 | 0.0046 | 0.765 |
| 683 | 0.0014 | 0.545 |
| 684 | 0.019 | 4.981 |
| 716 | 0.0064 | 0.727 |
| 717 | 0.024 | 2.372 |
| 718 | 0.405 | 8.541 |
| 765 | 0.0018 | 0.433 |
| 766 | 0.003 | 0.838 |
| 771 | 0.0645 | >10 |
| 772 | 0.0025 | 0.349 |
| 773 | 0.0028 | 0.312 |
| 774 | 0.119 | 12.294 |
| 776 | 0.0315 | 1.983 |
| 778 | 0.011 | 6.435 |
| 791 | 0.0011 | 0.585 |
| 797 | 0.002 | 1.601 |
| 800 | 0.078 | 0.633 |
| 801 | 0.0597 | 14.925 |
| 802 | 0.0094 | 1.596 |
| 803 | 0.213 | 5.323 |
| 826 | 0.0118 | 1.853 |
| 827 | 0.0247 | 1.743 |
| 828 | 0.0367 | 4.142 |
| 829 | 0.0082 | 1.603 |

The inhibitory activities of Compounds 255 and 374 on all HDACs were confirmed (by Reaction Biology Corp.). The results are shown in Table 15:

TABLE 15

HDAC inhibitory activities of Compounds 255 and 374

| uM | 255 | 374 |
|---|---|---|
| HDAC 1 | 0.16 | 2.12 |
| HDAC 2 | 0.69 | 4.88 |
| HDAC 3 | 1.63 | 10.3 |
| HDAC 4 | 6.86 | 16.4 |
| HDAC 5 | 8.27 | ND |
| HDAC 6 | 0.001 | 0.005 |
| HDAC 7 | 1.5 | 5.25 |
| HDAC 8 | 0.65 | 2.07 |
| HDAC 9 | 3.52 | 10.3 |
| HDAC 10 | 1.47 | 16.2 |
| HDAC 11 | 0.78 | 8.42 |
| Selectivity (HDAC6/1) | 160 | 424 |

As shown in Table 15, it was found that Compound 255 had a selectivity of 160 times for HDAC6: 0.001 µM and HDAC1: 0.16 µM and Compound 374 had a selectivity of 424 times for HDAC6: 0.005 µM and HDAC1: 2.12 µM.

2. Determination of Acetylation of Tubulin, Histone H3 and Histone H4 in Cells

To determine the selectivity for HDAC6 in cells, the acetylation levels of Tubulin, Histone H3 and Histone H4 depending on the concentration of compounds were measured by Western blot.

RPMI8226 ($1.0 \times 10^6$ cells/well) cells were seeded on six-well plates and treated with drugs (Compounds 255 and 374) at each concentration. After 24 hours, the proteins were extracted with RIPA buffer and quantified by the Bradford method. 25 µg of protein was lysed in sample buffer, electrophoresed on a 4-12% gradient gel, and then transferred to nitrocellulose membranes for 50 minutes. Then transferred protein was blocked with 5% skim milk for 1 hour. Anti-acetyl H3 (1:2,000), anti-acetyl H4 (1:5,000), anti-acetyl tubulin (1:5,000), and anti-β-actin antibody (1:10,000) were added into 5% skim milk, and the membranes were immersed in the skim milk, reacted at 4° C. for 16 hours, and then washed three times for 10 minutes each with 1×TBS-T. Then, IgG-HRP antibody (1:5,000) was added into 5% skim milk, and then the membranes were immersed in the skim milk, reacted at room temperature for 40 minutes, and then washed three times for −10 minutes each with 1×TBS-T. Then, the acetylation levels were determined with a LAS 3000 using ECL solution.

The results are shown in FIGS. 1 and 2.

As shown in FIGS. 1 and 2, it was found that both Compound 255 (FIG. 1) and Compound 374 (FIG. 2) had excellent activities at low concentrations as tubulin acetylation (HDAC6) was expressed at a low concentration of about 10 nM. On the contrary, it was found that Compound 255 and Compound 374 had little or no activity at low concentrations as histone acetylation (HDAC1) was expressed at a concentration of 1 µM of Compound 255 and 10 µM of Compound 374. Therefore, it was found from the difference in the expressed concentration of tubulin and histone that the novel urea compounds of the present invention have excellent cell selectivity.

Example 170: Efficacy of Compounds 254, 255 and 374 in Collagen-Induced Arthritis Models The efficacy of the novel urea derivatives of the present invention on the treatment of arthritis in collagen-induced arthritis models was determined.

An emulsion was prepared by mixing bovine collagen type II (Chondrex) and complete Freund's adjuvant (Chondrex) at a ratio of 1:1 until the viscosity was measured using a 1 ml pipette. Each 100 μL of emulsion was intradermally injected into the tail of DBA/1J mice for the first immunization. After 21 days, an emulsion was prepared by mixing bovine collagen type II and incomplete Freund's adjuvant (Chondrex) at a ratio of 1:1 by the same method as above. Each of 100 μL of emulsion was intradermally injected into the upper part of the tail of DBA/1J mice for the second boosting immunization. After the second boosting immunization, the mice were grouped according to body weight, the test drug was administered to each group, and the effects of the test drugs were measured by measuring the clinical score and the body weight. The clinical scores were assigned from 0 to 4, and the total clinical score was determined by evaluating the feet of each mouse and summing up the scores (normal: 0, most severe edema: 16). That is, the efficacy in the arthritis models was evaluated with the severity of edema of the joint, and a higher score was assigned to more severe edema.

The above experimental results are shown in FIGS. 3 and 4.

As shown in FIG. 3, the clinical score of the vehicle group was 11.6, and that of the group treated with Compound 254 in an amount of 30 mg/kg twice a day was 6.4, from which it can be seen that the arthritis symptoms were improved by more than 40%. Moreover, the clinical scores of the groups treated with Compound 255 in an amount of 10 and 30 mg/kg twice a day were 5.2 and 6.5, from which it can be seen that the arthritis symptoms were improved by more than 50%. Moreover, as shown in FIG. 4, the clinical score of the vehicle (v) group was 6.7, and those of the group treated with Compound 374 at different concentrations were 2.8 and 2.5, from which it can be seen that the arthritis symptoms were improved by more than 60%. That is, severe edema was observed in the vehicle group untreated with no drugs, while the edema was significantly reduced in the group treated with the novel urea compounds of the present invention, from which it can be seen that the arthritis symptoms were significantly reduced.

Example 171: Efficacy of Compounds 255, 374 and 461 in Adjuvant-Induced Arthritis Models The efficacy of the novel urea derivatives of the present invention on the treatment of arthritis in adjuvant-induced arthritis models was determined.

Complete Freund's Adjuvant (Chondrex) containing 10 mg/mL Heat killed mycobacteria toxin was sufficiently mixed, and then 100 μL was taken and intradermally injected into the upper part of the tail of Lewis rat to induce arthritis. After 10 days, the length of the ankle circumference of rats was measured, and then the rats were grouped and used in the experiment. Each compound was intraperitoneally injected twice a day. The clinical score, the length of the ankle circumference, and the weight were measured twice a week after the administration of the compounds. The clinical scores were assigned from 0 to 4 based on the thesis of Woods, etc. (J. Immunology, 1214-1222, 2001), and the total clinical score was determined by evaluating the feet of each rat and summing up the scores (normal: 0, most severe edema: 16). The length of the ankle circumference was calculated based on the formula of $2 \times 3.14(\sqrt{(a^2+b^2)/2})$ after measuring top-bottom sides (a) of the foot and lateral sides (b) of the foot. The final value was determined by averaging the calculated values of each foot.

Figure 5B:
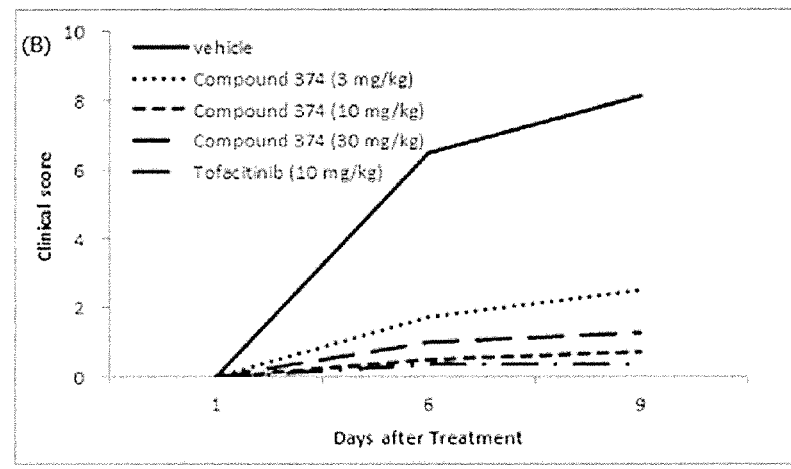
Figure 5C:
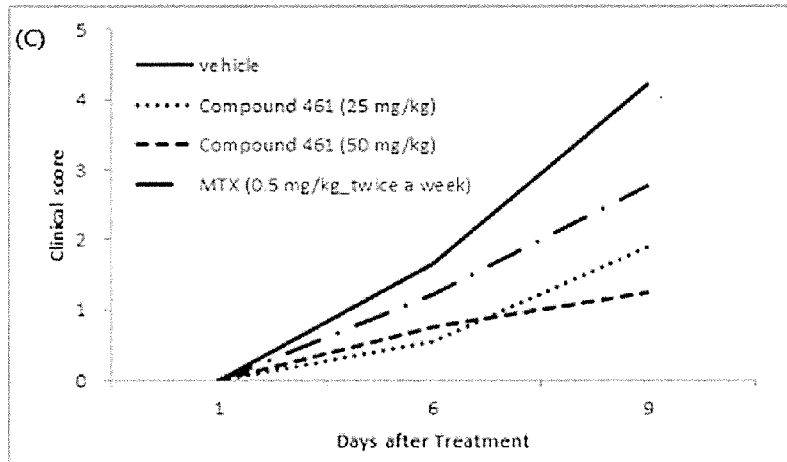

The results are shown in FIG. 5. In FIG. 5, (A) shows the experimental results of Compound 255, (B) shows the experimental results of Compound 374, and (C) shows the experimental results of Compound 461. In (A) of FIG. 5, the clinical store of the vehicle group was 4.9, and those of the experimental groups treated with Compound 255 in an amount of 3, 10, and 30 mg/kg twice a day were 3.0, 2.6, and 0.7, from which it can be seen that the arthritis symptoms were improved by 40 to 90%. In (B) of FIG. 5, the clinical store of the vehicle group was 8.1, and those of the experimental groups treated with Compound 374 in an amount of 3, 10, and 30 mg/kg twice a day were 2.5, 0.8, and 1.3, from which it can be seen that the arthritis symptoms were improved by 70 to 90%. In each experiment, the comparison of Compounds 255 and 374 with the control compound Tofacitinib reveals that they have an equivalent efficacy. In (C) of FIG. 5, the clinical store of the vehicle group was 4.2, and those of the experimental groups treated with Compound 461 in an amount of 25 and 50 mg/kg twice a day were 1.9 and 1.3, from which it can be seen that the arthritis symptoms were improved by more than 50 to 70%, which were higher than that of MTX used as the control group.

Example 172: Efficacy of Compound 254 and 255 in Colitis Models

The efficacy of the novel urea derivatives of the present invention on the treatment of colitis in colitis models was determined.

3.0% dextran sulfate sodium (DSS: MP biomedicals) was dissolved in deionized water and supplied to 9-week-old C57BL/6J mice for 5 to 7 days and then water was normally supplied to the mice to induce colitis in animal models. The experimental animals were classified into a solvent control group and each group treated with Compound 254 and Compound 255 as test materials based on the body weight of the experimental animals. The test material was intraperitoneally injected twice a day after 8 days from the supply of DSS. The evaluation of the efficacy in colitis models was made by determining the degree to which the weight, lost due to the disease, was recovered to normal level, and the results are shown in FIG. 6.

As shown in FIG. 6, the weights of the disease-induced models were lost as 17.5 to 18 g and then recovered to 18.5 to 19.0 g by the administration of Compound 254 and 19 to 19.5 g by the administration of Compound 255, indicating that the efficacy was excellent. As a result, the efficacy of the novel urea derivatives on treatment of colitis was confirmed.

Example 173: Anticancer Activities in Multiple Myeloma

The efficacy of the novel urea derivatives of the present invention on the treatment of multiple myeloma was determined by western blot, MTT assay and combination index.

1. Determination of Acetylation of Tubulin, Histone H3 and Histone H4

The acetylation of tubulin, histone H3 and Histone H4 on RPMI8226 cells ($1.0 \times 10^6$ cells/well) derived from myeloma was determined in the same manner as the cell determination in Example 1.

The results are shown in FIGS. 1 and 2.

As shown in FIGS. 1 and 2, it was found that Compounds 255 and 374 have the efficacy on the treatment of multiple myeloma with excellent cell selectivity.

2. Determination of Cell Viability

RPMI 8226 cells were seeded in 96-well U-bottom plate at $3\times10^5$ cells/ml in 180 μl per well, and 20 μl of test material was added to the plate. The cells were incubated in a 37° C. humidified 5% $CO_2$ incubator for 48 hours, and each 20 μl of 5 mg/ml 2-(4,5-dimethylthiazol-2-yl)-2,5-diphenyltetrazolium bromide (MTT) solution dissolved in PBS was added and incubated again for 4 hours. After the formation of formazan, the medium was completely removed, 200 μl of DMSO was added, and then the absorbance was measured using a microplate reader at 570 nm.

3. Determination of Combination Index (CI) for Combination Treatment

For the quantitative analysis of drug interaction between the novel urea compounds of the present invention and Velcade (BOZ) well known as a therapeutic agent for multiple myeloma, the combination index (CI) of cell fractions on cytotoxicity caused by the drugs was calculated based on the dose-response curve of single and combination treatments. For the analysis of the interaction between two drugs, the CI was measured using Compusyn software (Combosyn Inc.) according to the method of Chou and Talalay (CompuSyn by Ting-Chao Chou and Nick Martin, 2005). The CI is the dose ratio of two anticancer agents treated with the dose of two anticancers at the point representing the equivalent cytotoxic effects. CI<1, CI=1, and CI>1 are interpreted as synergism, additivity, and antagonism, respectively.

The results are shown in Table 16 and FIG. 7.

TABLE 16

Analysis of Combination Index for Combination Treatment

| Compound 255 (μM) | BOZ (nM) | CI (1) | CI (2) | CI (3) |
|---|---|---|---|---|
| 1.0 | 10.0 | 0.416 | 0.518 | 0.417 |
| 1.0 | 5.0 | 0.469 | 0.679 | 0.475 |
| 1.0 | 2.5 | 0.940 | 1.146 | 0.998 |
| 0.5 | 10.0 | 0.491 | 0.529 | 0.428 |
| 0.5 | 5.0 | 0.751 | 0.789 | 0.727 |
| 0.5 | 2.5 | 1.120 | 1.115 | 1.087 |
| 0.25 | 10.0 | 0.482 | 0.309 | 0.417 |
| 0.25 | 5.0 | 0.560 | 0.710 | 0.737 |
| 0.25 | 2.5 | 1.182 | 1.034 | 1.068 |

As shown in Table 16 and FIG. 7, the efficacy of the combination of two drugs can be determined by the combination index (CI), and the combination effect is excellent when this index is not less than 1. In the case of Compound 255, the CI is not less than 1 in most doses, from which it can be seen that the combination effect is excellent.

The invention claimed is:

1. A compound of Formula I:

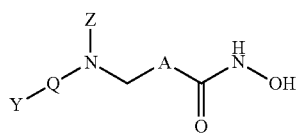

[Formula I]

or an optical isomer thereof or pharmaceutically acceptable salt thereof, wherein:

A is

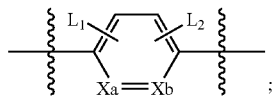

$X_a$ and $X_b$ are each independently C or N;

$L_1$ and $L_2$ are each independently hydrogen, —F, —Cl, —Br, —I, —$CF_3$, or —$C_{1-3}$ straight or branched chain alkyl;

Q is C(=O), S(=O)$_2$, S(=O), or C(=NH);

Y is selected from the group consisting of:

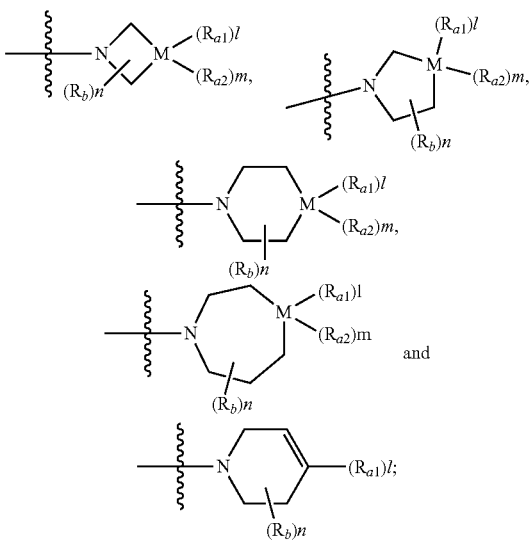

M is C, O, N, S(=O)$_2$, or S;

l and m are each independently an integer of 0 or 1;

$R_{a1}$ and $R_{a2}$ are each independently hydrogen, hydroxy,
—$C_{1-4}$ straight or branched chain alkyl, substituted with one or more F, Cl, Br or I or unsubstituted, a —$C_{1-4}$ straight or branched chain alcohol, benzhydryl,
a —$C_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, $OCH_3$, $CH_3$, $CH_2CH_3$, F, Cl, Br, or I), a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, $OCH_3$, $CH_3$, $CH_2CH_3$, F, Cl, Br, or I), phenyl, substituted with one or more F, Cl, Br, I, $C_{1-4}$ alkoxy, $C_{1-2}$ alkyl, or hydroxy or unsubstituted, benzyl, substituted with one or more F, Cl, Br, I, $C_{1-4}$ alkoxy, $C_{1-2}$ alkyl, or hydroxy or unsubstituted, —S(=O)$_2$$CH_3$, —F, —Cl, —Br, —I, a —$C_{1-6}$ straight or branched chain alkoxy, —$C_{2-6}$ alkyl alkoxy, —C(=O) $R_x$, wherein $R_x$ is a straight or branched $C_{1-3}$ alkyl or $C_{3-10}$ cycloalkyl,

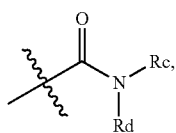

wherein $R_c$ and $R_d$ are each independently hydrogen, a $C_{1-3}$ straight or branched chain alkyl,

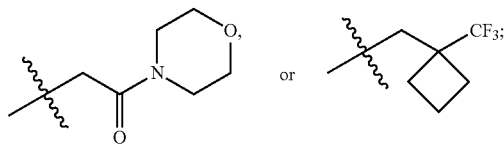 [SMILES: *CC(=O)N1CCOCC1 ; *CC1(C(F)(F)F)CCC1]

n is an integer of 0, 1, or 2;

$R_b$ is hydrogen, hydroxy, a $—C_{1-6}$ straight or branched chain alkyl, substituted with one or more F, Cl, Br, or I or unsubstituted, $—C(═O)CH_3$, a $—C_{1-4}$ straight or branched chain alcohol, a $—C_{1-6}$ straight or branched chain alkoxy, a $—C_{2-6}$ straight or branched chain alkyl alkoxy, $—CF_3$, $—F$, $—Cl$, $—Br$, $—I$, or

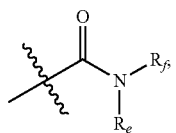

wherein $R_e$ and $R_f$ are each independently hydrogen or a $—C_{1-3}$ straight or branched chain alkyl; and Z is selected from the group consisting of the following substituents:

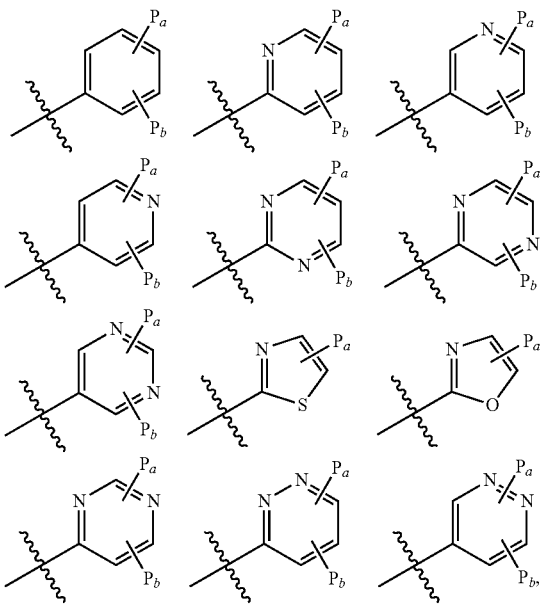

wherein $P_a$ and $P_b$ are each independently

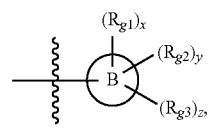

hydrogen, hydroxy,
a $—C_{1-4}$ straight or branched chain alkyl, substituted with one or more F, Cl, Br or I or unsubstituted,
$—F$, $—Cl$, $—Br$, $—I$, $—CF_3$, $—OCF_3$, $—CN$, a $—C_{1-6}$ straight or branched alkoxy, a $—C_{2-6}$ straight or branched alkyl alkoxy, $—CH_2F$, or a $—C_{1-3}$ alcohol,
wherein

is selected from among phenyl, pyridine, pyrimidine, thiazole, indole, indazole, piperazine, quinoline, furan, tetrahydropyridine, piperidine,

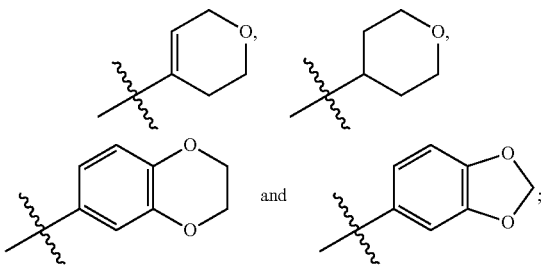

x, y and z are each independently an integer of 0 or 1; and
$R_{g1}$, $R_{g2}$ and $R_{g3}$ are each independently selected from among hydrogen, hydroxy, a $—C_{1-3}$ alkyl, $—CF_3$, a $—C_{1-6}$ straight or branched chain alkoxy, a $—C_{2-6}$ straight or branched chain alkyl alkoxy, $—C(═O)CH_3$, a $—C_{1-4}$ straight or branched chain alcohol, $—N(CH_3)_2$, $—F$, $—Cl$, $—Br$, $—I$, phenyl, $—S(═O)_2CH_3$,

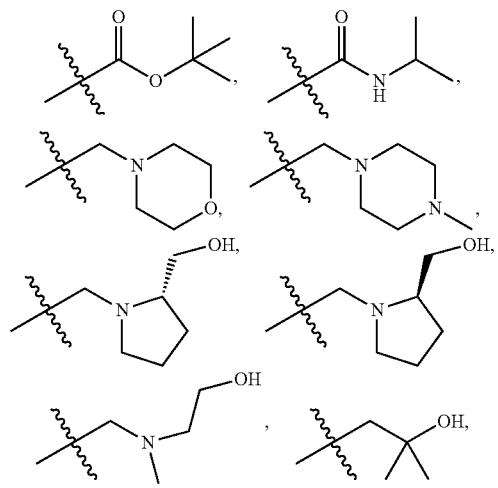

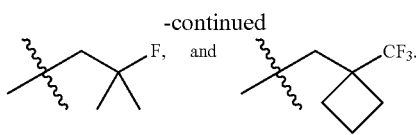

2. The compound of claim 1 of Formula II:

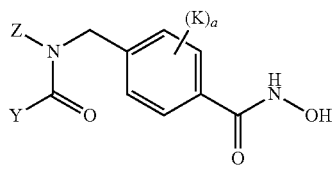

Formula II wherein:
a is an integer of 0, 1 or 2;
K is independently hydrogen, —F, —Cl, —Br or —I;
Y is selected from the group consisting of:

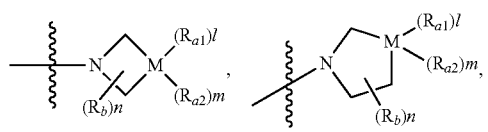

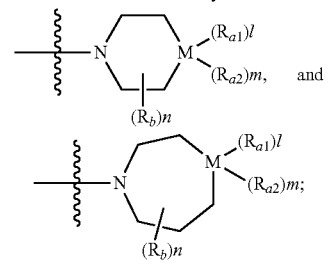

M is C, O or N;
l and m are each independently an integer of 0 or 1;
$R_{a1}$ and $R_{a2}$ are each independently hydrogen, hydroxy, a —$C_{1-4}$ straight or branched chain alkyl, substituted with one or more F, Cl, Br or I or unsubstituted, a —$C_{1-4}$ straight or branched chain alcohol, benzhydryl, a —$C_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I),
a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, OCH$_3$, CH$_3$, CH$_2$CH$_3$, F, Cl, Br, or I),
phenyl, unsubstituted or substituted with one or more F, Cl, Br, I, C$_{1-4}$ alkoxy, C$_{1-2}$ alkyl, or hydroxy,
benzyl, substituted with one or more F, Cl, Br, I, C$_{1-4}$ alkoxy, C$_{1-2}$ alkyl, or hydroxy, or unsubstituted,
—S(=O)$_2$CH$_3$, —F, —Cl, —Br, —I, a —C$_{1-6}$ straight or branched chain alkoxy, —C$_{2-6}$ alkyl alkoxy, —C(=O) R$_x$, wherein R$_x$ is straight or branched C$_{1-3}$ alkyl or C$_{3-10}$ cycloalkyl,

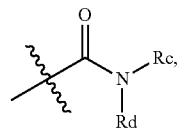

wherein R$_c$ and R$_d$ are each independently hydrogen, C$_{1-3}$ straight or branched chain alkyl,

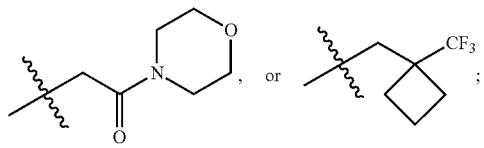 [SMILES: *CC(=O)N1CCOCC1 ; *CC1(C(F)(F)F)CCC1]

n is an integer of 0, 1, or 2;
R$_b$ is hydrogen, hydroxy, a —C$_{1-6}$ straight or branched chain alkyl, substituted with one or more F, Cl, Br, or I or unsubstituted,
—C(=O)CH$_3$, a —C$_{1-4}$ straight or branched chain alcohol, a —C$_{1-6}$ straight or branched chain alkoxy, a —C$_{2-6}$ straight or branched chain alkyl alkoxy, —CF$_3$, —F, —Cl, —Br, —I, or

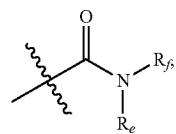

wherein R$_e$ and R$_f$ are each independently hydrogen or a —C$_{1-3}$ straight or branched chain alkyl; and
Z is selected from the group consisting of the following substituents:

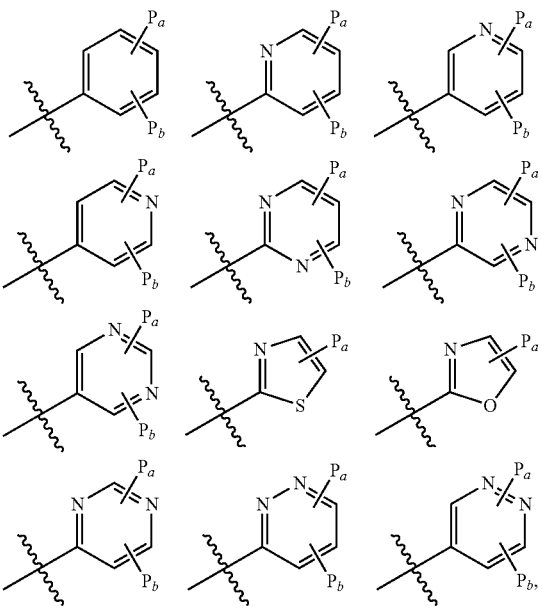

wherein $P_a$ and $P_b$ are each independently

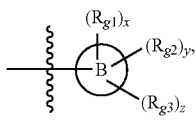

hydrogen, hydroxy,
a —$C_{1-4}$ straight or branched chain alkyl, substituted with one or more F, Cl, Br or I or unsubstituted,
—F, —Cl, —Br, —I, —$CF_3$, —$OCF_3$, —CN, a —$C_{1-6}$ straight or branched alkoxy, a —$C_{2-6}$ straight or branched alkyl alkoxy, —$CH_2F$, or a —$C_{1-3}$ alcohol, wherein

is selected from among phenyl, pyridine, pyrimidine, thiazole, indole, indazole, piperazine, quinoline, furan, tetrahydropyridine, piperidine,

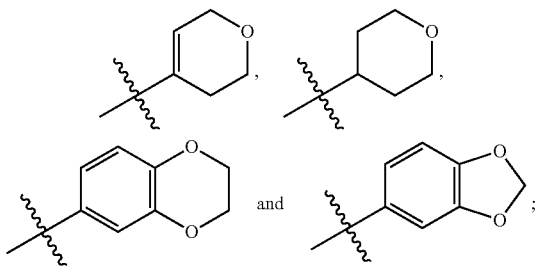

x, y and z are each independently an integer of 0 or 1; and $R_{g1}$, $R_{g2}$ and $R_{g3}$ are each independently selected from among hydrogen, hydroxy, a —$C_{1-3}$ alkyl, —$CF_3$, a —$C_{1-6}$ straight or branched chain alkoxy, a —$C_{2-6}$ straight or branched chain alkyl alkoxy, —C(=O)$CH_3$, a —$C_{1-4}$ straight or branched chain alcohol, —N($CH_3$)$_2$, —F, —Cl, —Br, —I, phenyl, —S(=O)$_2CH_3$,

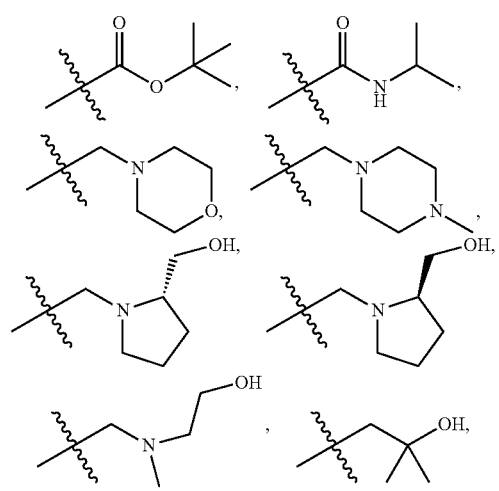

-continued

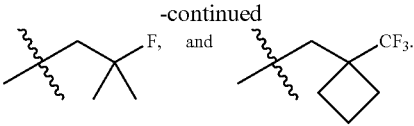

3. The compound of claim 2, wherein:
a is an integer of 0, 1 or 2;
K is independently hydrogen, —F, —Cl, —Br or —I;
Y is

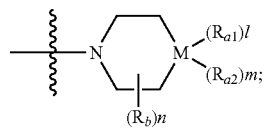

M is C, O or N;
l and m are each independently an integer of 0 or 1;
$R_{a1}$ and $R_{a2}$ are each independently hydrogen, hydroxy,
a —$C_{1-4}$ straight or branched chain alkyl, substituted with one or more F, Cl, Br or I or unsubstituted,
a —$C_{1-4}$ straight or branched chain alcohol, benzhydryl,
a —$C_{1-4}$ straight or branched chain alkyl substituted with a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, $OCH_3$, $CH_3$, $CH_2CH_3$, F, Cl, Br, or I),
a saturated or unsaturated 5- to 7-membered heterocyclic compound comprising 1 to 3 heteroatoms selected from N, O, and S as a ring member (wherein the heterocyclic compound may be unsubstituted or at least one hydrogen may be optionally substituted with OH, $OCH_3$, $CH_3$, $CH_2CH_3$, F, Cl, Br, or I),
phenyl, substituted with one or more F, Cl, Br, I, $C_{1-4}$ alkoxy, $C_{1-2}$ alkyl, or hydroxy or unsubstituted,
benzyl, substituted with one or more F, Cl, Br, I, $C_{1-4}$ alkoxy, $C_{1-2}$ alkyl, or hydroxy or unsubstituted,
—S(=O)$_2CH_3$, —F, —Cl, —Br, —I, a —$C_{1-6}$ straight or branched chain alkoxy, a —$C_{2-6}$ alkyl alkoxy, —C(=O)$R_x$, wherein $R_x$ is a straight or branched $C_{1-3}$ alkyl or a $C_{3-10}$ cycloalkyl, or

n is an integer of 0, 1, or 2;
$R_b$ is hydrogen, —$C_{1-6}$ straight or branched chain alkyl, unsubstituted or substituted with one or more F, Cl, Br, or I; and
Z is selected from the group consisting of the following substituents:

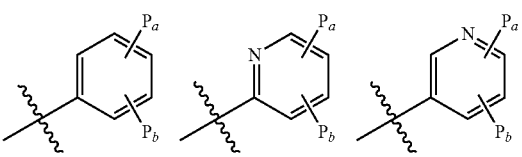

-continued

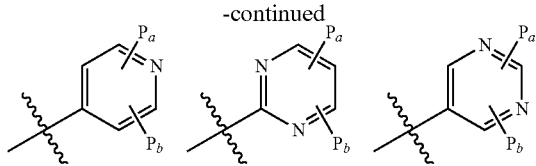

wherein $P_a$ and $P_b$ are each independently hydrogen, hydroxy, a —$C_{1-4}$ straight or branched chain alkyl, substituted with one or more F, Cl, Br or I or unsubstituted, —F, —Cl, —Br, —I, —$CF_3$, —$OCF_3$, —CN, a —$C_{1-6}$ straight or branched alkoxy, a —$C_{2-6}$ straight or branched alkyl alkoxy, —$CH_2F$, a —$C_{1-3}$ alcohol,

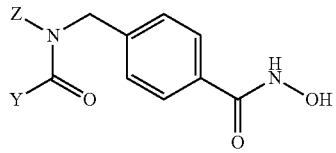 or 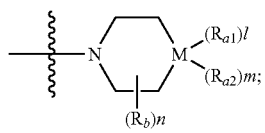.

4. The compound of claim 2 of Formula III:

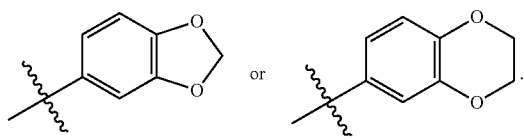 [SMILES: *c1ccc2c(c1)OCO2 ; *c1ccc2c(c1)OCCO2]

Formula III wherein:
Y is

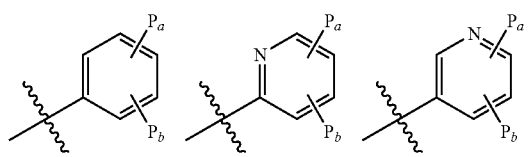

M is C, O or N;
l and m are each independently an integer of 0 or 1;
$R_{a1}$ and $R_{a2}$ are each independently hydrogen, a —$C_{1-4}$ straight or branched chain alkyl, substituted with one or more F, Cl, Br or I or unsubstituted, or a —$C_{1-4}$ straight or branched chain alkyl substituted with a phenyl, pyridine or pyrimidine (wherein the phenyl, pyridine or pyrimidine may be unsubstituted or at least one hydrogen may be optionally substituted with OH, $OCH_3$, $CH_3$, $CH_2CH_3$, F, Cl, Br, or I);
n is an integer of 0, 1, or 2;
$R_b$ is hydrogen, or a —$C_{1-6}$ straight or branched chain alkyl, unsubstituted or substituted with one or more F, Cl, Br, or I; and
Z is selected from the group consisting of the following substituents:

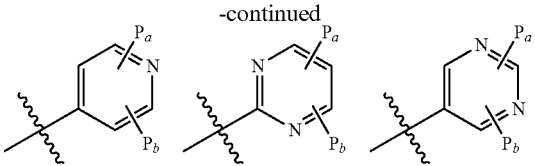

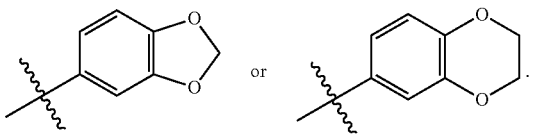

wherein $P_a$ and $P_b$ are each independently hydrogen, —F, —Cl, —Br, —$CF_3$, —$OCF_3$, —$CH_2F$, or

.

5. The compound of claim 1 selected from the group consisting of the following compounds:
N-(4-(hydroxycarbamoyl)benzyl)-N-(3-(1-methyl-1H-indazol-5-yl)phenyl)-morpholine-4-carboxamide,
N-(4-(hydroxycarbamoyl)benzyl)-4-methyl-N-(3-(1-methyl-1H-indazol-5-yl)-phenyl)piperazine-1-carboxamide,
N-(4-(hydroxycarbamoyl)benzyl)-N-(3-(1-methyl-1H-indazol-6-yl)phenyl)-morpholine-4-carboxamide,
N-(3-bromophenyl)-N-(4-(hydroxycarbamoyl)benzyl) morpholine-4-carboxamide,
N-(3-bromophenyl)-N-(4-(hydroxycarbamoyl)benzyl)-4-methylpiperazine-1-carboxamide,
N-(4-(hydroxycarbamoyl)benzyl)-N-(3-(1-methyl-1H-indazol-5-yl)phenyl)-piperidine-1-carboxamide,
N-(3-(1H-indol-6-yl)phenyl)-N-(4-(hydroxycarbamoyl) benzyl)morpholine-4-carboxamide,
N-(4-(hydroxycarbamoyl)benzyl)-N-(3-(pyridin-3-yl) phenyl)morpholine-4-carboxamide,
N-(3-(1H-indol-5-yl)phenyl)-N-(4-(hydroxycarbamoyl) benzyl)morpholine-4-carboxamide,
N-(4-(hydroxycarbamoyl)benzyl)-N-phenylmorpholine-4-carboxamide,
N-(4-(hydroxycarbamoyl)benzyl)-N-(pyridin-2-yl)morpholine-4-carboxamide,
N-(4-(hydroxycarbamoyl)benzyl)-N-(pyridin-3-yl)morpholine-4-carboxamide,
4-benzyl-N-(4-(hydroxycarbamoyl)benzyl)-N-(pyrimidin-2-yl)piperazine-1-carboxamide,
4-hydroxy-N-(4-(hydroxycarbamoyl)benzyl)-4-phenyl-N-(pyrimidin-2-yl)-piperidine-1-carboxamide,
N-(4-(hydroxycarbamoyl)benzyl)-N-(pyrimidin-2-yl) morpholine-4-carboxamide,
N-(4-(hydroxycarbamoyl)benzyl)-2,6-dimethyl-N-(pyrimidin-2-yl)morpholine-4-carboxamide,
N-(4-(hydroxycarbamoyl)benzyl)-N-(4-(1-methyl-1H-indazol-6-yl)phenyl)-morpholine-4-carboxamide,
N-(biphenyl-4-yl)-N-(4-(hydroxycarbamoyl)benzyl)morpholine-4-carboxamide,
N-(3',5'-difluorobiphenyl-4-yl)-N-(4-(hydroxycarbamoyl)benzyl)morpholine-4-carboxamide,
N-(4-(hydroxycarbamoyl)benzyl)-N-(4-(pyridin-3-yl) phenyl)morpholine-4-carboxamide,
N-(4-(hydroxycarbamoyl)benzyl)-N-(4-(pyrimidin-5-yl) phenyl)morpholine-4-carboxamide,
N-(4-(hydroxycarbamoyl)benzyl)-N-(4-(quinolin-7-yl) phenyl)morpholine-4-carboxamide, N-(4-(hydroxycarbamoyl)benzyl)-N-(4-(biphenyl-3-yl)phenyl)morpholine-4-carboxamide,
N-(4-(1H-indol-5-yl)phenyl)-N-(4-(hydroxycarbamoyl)benzyl)morpholine-4-carboxamide,
N-(4-(1H-indol-6-yl)phenyl)-N-(4-(hydroxycarbamoyl)benzyl)morpholine-4-carboxamide,
N-(4-(hydroxycarbamoyl)benzyl)-N-(3',4',5'-trimethoxybiphenyl-4-yl)morpholine-4-carboxamide,
N-(3',5'-bis(trifluoromethyl)biphenyl-4-yl)-N-(4-(hydroxycarbamoyl)benzyl)-morpholine-4-carboxamide,
N-(4-(1H-indol-4-yl)phenyl)-N-(4-(hydroxycarbamoyl)benzyl)morpholine-4-carboxamide,
N-(4-(hydroxycarbamoyl)benzyl)-N-(pyridin-2-yl)piperidine-1-carboxamide,
N-(4-(hydroxycarbamoyl)benzyl)-4-methyl-N-(pyridin-2-yl)piperidine-1-carboxamide,
N-(4-(hydroxycarbamoyl)benzyl)-2,6-dimethyl-N-(pyridin-2-yl)morpholine-4-carboxamide,
N-(4-(hydroxycarbamoyl)benzyl)-4-phenyl-N-(pyridin-2-yl)-5,6-dihydropyridine-1-(2H)-carboxamide,
N-(4-(hydroxycarbamoyl)benzyl)-4-methyl-N-(pyridin-2-yl)piperazine-1-carboxamide,
4-ethyl-N-(4-(hydroxycarbamoyl)benzyl)-N-(pyridin-2-yl)piperazine-1-carboxamide,
4-benzyl-N-(4-(hydroxycarbamoyl)benzyl)-N-(pyridin-2-yl)piperazine-1-carboxamide,
N-(4-(hydroxycarbamoyl)benzyl)-4-(2-methoxyphenyl)-N-(pyridin-2-yl)piperazine-1-carboxamide,
4-(4-fluorophenyl)-N-(4-(hydroxycarbamoyl)benzyl)-N-(pyridin-2-yl)piperazine-1-carboxamide,
N-(4-(hydroxycarbamoyl)benzyl)-N-(pyridin-2-yl)pyrrolidine-1-carboxamide,
N-(4-(hydroxycarbamoyl)benzyl)-N-(4-phenylthiazol-2-yl)morpholine-4-carboxamide,
N-(4-(4-chlorophenyl)thiazol-2-yl)-N-(4-(hydroxycarbamoyl)benzyl)morpholine-4-carboxamide,
N-(4-bromophenyl)-N-(4-(hydroxycarbamoyl)benzyl)morpholine-4-carboxamide,
N-(4-(hydroxycarbamoyl)benzyl)-N-(3-(trifluoromethyl)phenyl)morpholine-4-carboxamide,
N-(4-(hydroxycarbamoyl)benzyl)-4-methyl-N-(pyridin-2-yl)-1,4-diazepane-1-carboxamide,
N-(4-(hydroxycarbamoyl)benzyl)-N-(pyridin-2-yl)azetidine-1-carboxamide,
4-(3,4-dimethylphenyl)-N-(4-(hydroxycarbamoyl)benzyl)-N-(pyridin-2-yl)-piperazine-1-carboxamide,
N-(4-(hydroxycarbamoyl)benzyl)-N-(4'-(morpholinomethyl)biphenyl-4-yl)-morpholine-4-carboxamide,
N-(4-(hydroxycarbamoyl)benzyl)-N-(4'-((4-methylpiperazin-1-yl)methyl)biphenyl-4-yl)morpholine-4-carboxamide,
(S)—N-(4-(hydroxycarbamoyl)benzyl)-N-(4'-((2-(hydroxymethyl)pyrrolidin-1-yl)-methyl)biphenyl-4-yl)morpholine-4-carboxamide,
N-(4-(hydroxycarbamoyl)benzyl)-N-(4'-(((2-hydroxyethyl)(methyl)amino)methyl)-biphenyl-4-yl)morpholine-4-carboxamide,
N-(4-(hydroxycarbamoyl)benzyl)-N-(4-(trifluoromethyl)phenyl)morpholine-4-carboxamide,
N-(4-(hydroxycarbamoyl)benzyl)-2,6-dimethyl-N-(3-(trifluoromethyl)phenyl)-morpholine-4-carboxamide,
N-(4-chloro-3-(trifluoromethyl)phenyl)-N-(4-(hydroxycarbamoyl)benzyl)-piperidine-1-carboxamide,
N-(4-chloro-3-(trifluoromethyl)phenyl)-N-(4-(hydroxycarbamoyl)benzyl)-4-methylpiperidine-1-carboxamide,
N-(4-chloro-3-(trifluoromethyl)phenyl)-N-(4-(hydroxycarbamoyl)benzyl)-morpholine-4-carboxamide,
N-(4-chloro-3-(trifluoromethyl)phenyl)-N-(4-(hydroxycarbamoyl)benzyl)-2,6-dimethylmorpholine-4-carboxamide,
N-(4-chloro-3-(trifluoromethyl)phenyl)-N-(4-(hydroxycarbamoyl)benzyl)-4-methylpiperazine-1-carboxamide,
N-(4-chloro-3-(trifluoromethyl)phenyl)-4-ethyl-N-(4-(hydroxycarbamoyl)benzyl)-piperazine-1-carboxamide,
N-(3',5'-difluorobiphenyl-3-yl)-N-(4-(hydroxycarbamoyl)benzyl)morpholine-4-carboxamide,
N-(3-(6-(dimethylamino)pyridin-3-yl)phenyl)-N-(4-(hydroxycarbamoyl)benzyl)-morpholine-4-carboxamide,
N-(4-(hydroxycarbamoyl)benzyl)-N-(3-(pyrimidin-5-yl)phenyl)morpholine-4-carboxamide,
N-(3',5'-bis(trifluoromethyl)biphenyl-3-yl)-N-(4-(hydroxycarbamoyl)benzyl)-morpholine-4-carboxamide,
N-(3-(2,3-dihydrobenzo[b][1,4]dioxin-6-yl)phenyl)-N-(4-(hydroxycarbamoyl)-benzyl)morpholine-4-carboxamide,
N-(4-(hydroxycarbamoyl)benzyl)-N-(3',4',5'-trimethoxybiphenyl-3-yl)morpholine-4-carboxamide,
N-(2',6'-dimethylbiphenyl-3-yl)-N-(4-(hydroxycarbamoyl)benzyl)morpholine-4-carboxamide,
N-(3-(furan-3-yl)phenyl)-N-(4-(hydroxycarbamoyl)benzyl)morpholine-4-carboxamide,
N-(3-(3,6-dihydro-2H-pyran-4-yl)phenyl)-N-(4-(hydroxycarbamoyl)benzyl)-morpholine-4-carboxamide,
N-(4-(hydroxycarbamoyl)benzyl)-N-(3-(1-methyl-1,2,3,6-tetrahydropyridin-4-yl)phenyl)morpholine-4-carboxamide,
tert-butyl 4-(3-(N-(4-(hydroxycarbamoyl)benzyl)morpholine-4-carboxamido)-phenyl)-5,6-dihydropyridine-1(2H)-carboxylate,
N-(2,4-difluorophenyl)-N-(4-(hydroxycarbamoyl)benzyl)morpholine-4-carboxamide,
N-(2,4-difluorophenyl)-N-(4-(hydroxycarbamoyl)benzyl)piperidine-1-carboxamide,
N-(2,4-difluorophenyl)-N-(4-(hydroxycarbamoyl)benzyl)-2,6-dimethylmorpholine-4-carboxamide,
N-(2,4-difluorophenyl)-N-(4-(hydroxycarbamoyl)benzyl)-4-methylpiperazine-1-carboxamide,
N-(3-(benzo[d][1,3]dioxol-5-yl)phenyl)-N-(4-(hydroxycarbamoyl)benzyl)morpholine-4-carboxamide,
N-(3-(1-acetyl-1,2,3,6-tetrahydropyridin-4-yl)phenyl)-N-(4-(hydroxycarbamoyl)-benzyl)morpholine-4-carboxamide,
N-(4-(hydroxycarbamoyl)benzyl)-N-(3-(1-(methylsulfonyl)-1,2,3,6-tetrahydropyridin-4-yl)phenyl)morpholine-4-carboxamide,
N-(2-fluoro-4-methylphenyl)-N-(4-(hydroxycarbamoyl)benzyl)piperidine-1-carboxamide,
N-(2-fluoro-4-methylphenyl)-N-(4-(hydroxycarbamoyl)benzyl)morpholine-4-carboxamide,
N-(2-fluoro-4-methylphenyl)-N-(4-(hydroxycarbamoyl)benzyl)-2,6-dimethylmorpholine-4-carboxamide,
N-(2-fluoro-4-methylphenyl)-N-(4-(hydroxycarbamoyl)benzyl)-4-methyl-piperazine-1-carboxamide,
4-acetyl-N-(4-(hydroxycarbamoyl)benzyl)-N-(pyridin-2-yl)-1,4-diazepane-1-carboxamide,
4-(cyclopropanecarbonyl)-N-(4-(hydroxycarbamoyl)benzyl)-N-(pyridin-2-yl)-piperazine-1-carboxamide,
4-ethyl-N-(2-fluoro-4-methylphenyl)-N-(4-(hydroxycarbamoyl)benzyl)piperazine-1-carboxamide, N-(2-fluoro-4-methylphenyl)-N-(4-(hydroxycarbamoyl)benzyl)-4-(2-methoxy-phenyl)piperazine-1-carboxamide,
N-(2-fluoro-4-methylphenyl)-4-(4-fluorophenyl)-N-(4-(hydroxycarbamoyl)-benzyl)piperazine-1-carboxamide,
N-(3-chloro-4-fluorophenyl)-N-(4-(hydroxycarbamoyl)benzyl)piperidine-1-carboxamide,
N-(3-chloro-4-fluorophenyl)-N-(4-(hydroxycarbamoyl)benzyl)-4-methylpiperidine-1-carboxamide,
N-(3-chloro-4-fluorophenyl)-N-(4-(hydroxycarbamoyl)benzyl)morpholine-4-carboxamide,
N-(4-(hydroxycarbamoyl)benzyl)-4-methyl-N-(3-(trifluoromethyl)phenyl)-piperidine-1-carboxamide,
N-(4-(hydroxycarbamoyl)benzyl)-N-(3-(trifluoromethyl)phenyl)piperidine-1-carboxamide,
4-ethyl-N-(4-(hydroxycarbamoyl)benzyl)-N-(3-(trifluoromethyl)phenyl)piperazine-1-carboxamide,
N-(3-(benzo[d][1,3]dioxol-5-yl)phenyl)-N-(4-(hydroxycarbamoyl)benzyl)-piperidine-1-carboxamide,
N-(3-(benzo[d][1,3]dioxol-5-yl)phenyl)-4-hydroxy-N-(4-(hydroxycarbamoyl)-benzyl)piperidine-1-carboxamide,
N-(3-(benzo[d][1,3]dioxol-5-yl)phenyl)-N-(4-(hydroxycarbamoyl)benzyl)-2,6-dimethylmorpholine-4-carboxamide,
N-(3-(benzo[d][1,3]dioxol-5-yl)phenyl)-4-hydroxy-N-(4-(hydroxycarbamoyl)-benzyl)-4-phenylpiperidine-1-carboxamide,
N-(3-(benzo[d][1,3]dioxol-5-yl)phenyl)-N-(4-(hydroxycarbamoyl)benzyl)-4-methylpiperazine-1-carboxamide,
N-(3-(benzo[d][1,3]dioxol-5-yl)phenyl)-N-(4-(hydroxycarbamoyl)benzyl)-4-(2-hydroxyethyl)piperazine-1-carboxamide,
N-(3-(benzo[d][1,3]dioxol-5-yl)phenyl)-N-(4-(hydroxycarbamoyl)benzyl)-pyrrolidine-1-carboxamide,
(S)—N-(3-(benzo[d][1,3]dioxol-5-yl)phenyl)-N-(4-(hydroxycarbamoyl)benzyl)-2-(hydroxymethyl)pyrrolidine-1-carboxamide,
N-(3-(benzo[d][1,3]dioxol-5-yl)phenyl)-4-(cyclopropanecarbonyl)-N-(4-(hydroxy-carbamoyl)benzyl)piperazine-1-carboxamide,
N-(3-(benzo[d][1,3]dioxol-5-yl)phenyl)-N-(4-(hydroxycarbamoyl)benzyl)azetidine-1-carboxamide,
N-(3-chloro-4-fluorophenyl)-N-(4-(hydroxycarbamoyl)benzyl)-2,6-dimethylmorpholine-4-carboxamide,
N-(3-chloro-4-fluorophenyl)-N-(4-(hydroxycarbamoyl)benzyl)-4-methylpiperazine-1-carboxamide,
N-(3-chloro-4-fluorophenyl)-4-ethyl-N-(4-(hydroxycarbamoyl)benzyl)piperazine-1-carboxamide,
4-benzyl-N-(3-chloro-4-fluorophenyl)-N-(4-(hydroxycarbamoyl)benzyl)piperazine-1-carboxamide,
N-(3-chloro-4-fluorophenyl)-N-(4-(hydroxycarbamoyl)benzyl)-4-(2-methoxy-phenyl)piperazine-1-carboxamide,
N-(3-chloro-4-fluorophenyl)-4-(4-fluorophenyl)-N-(4-(hydroxycarbamoyl)-benzyl)piperazine-1-carboxamide,
N-(4-(hydroxycarbamoyl)benzyl)-N-(3-(tetrahydro-2H-pyran-4-yl)phenyl)-morpholine-4-carboxamide,
N-(4-(hydroxycarbamoyl)benzyl)-N-(3-methoxyphenyl)morpholine-4-carboxamide,
3,3-difluoro-N-(4-(hydroxycarbamoyl)benzyl)-N-(4-(trifluoromethyl)phenyl)-azetidine-1-carboxamide,
4-hydroxy-N-(4-(hydroxycarbamoyl)benzyl)-4-phenyl-N-(4-(trifluoromethyl)-phenyl)piperidine-1-carboxamide,
N-(3-bromophenyl)-N-(2-fluoro-4-(hydroxycarbamoyl)benzyl)morpholine-4-carboxamide,
N-(3-bromophenyl)-N-(2-fluoro-4-(hydroxycarbamoyl)benzyl)-4-hydroxy-piperidine-1-carboxamide,
tert-butyl 4-(3-(N-(4-(hydroxycarbamoyl)benzyl)morpholine-4-carboxamido)-phenyl)piperidine-1-carboxylate,
N-(3-(1-acetylpiperidin-4-yl)phenyl)-N-(4-(hydroxycarbamoyl)benzyl)morpholine-4-carboxamide,
N-(4-(hydroxycarbamoyl)benzyl)-N-(3-(1-(methylsulfonyl)piperidin-4-yl)phenyl)-morpholine-4-carboxamide,
N-(4-(hydroxycarbamoyl)benzyl)-N-(3-(1-(isopropylcarbamoyl)piperidin-4-yl)-phenyl)morpholine-4-carboxamide,
N-(4-(hydroxycarbamoyl)benzyl)-N-(3-(piperidin-4-yl)phenyl)morpholine-4-carboxamide hydrochloride,
4-acetyl-N-(4-(hydroxycarbamoyl)benzyl)-N-(3-(trifluoromethyl)phenyl)-piperazine-1-carboxamide,
(R)-3-fluoro-N-(4-(hydroxycarbamoyl)benzyl)-N-(3-(trifluoromethyl)phenyl)-pyrrolidine-1-carboxamide,
(S)-3-fluoro-N-(4-(hydroxycarbamoyl)benzyl)-N-(3-(trifluoromethyl)phenyl)-pyrrolidine-1-carboxamide,
(R)—N-(4-(hydroxycarbamoyl)benzyl)-2-(hydroxymethyl)-N-(3-(trifluoromethyl)-phenyl)pyrrolidine-1-carboxamide,
(S)—N-(4-(hydroxycarbamoyl)benzyl)-2-(trifluoromethyl)-N-(3-(trifluoromethyl)-phenyl)pyrrolidine-1-carboxamide,
N-(4-(hydroxycarbamoyl)benzyl)-N-(3-(hydroxymethyl)phenyl)morpholine-4-carboxamide,
N-(3-(fluoromethyl)phenyl)-N-(4-(hydroxycarbamoyl)benzyl)morpholine-4-carboxamide,
N-(3-(benzo[d][1,3]dioxol-5-yl)phenyl)-N-(2-fluoro-4-(hydroxycarbamoyl)benzyl)-morpholine-4-carboxamide,
N-(3-(3,6-dihydro-2H-pyran-4-yl)phenyl)-N-(2-fluoro-4-(hydroxycarbamoyl)-benzyl)morpholine-4-carboxamide,
N-(3-(benzo[d][1,3]dioxol-5-yl)phenyl)-N-(2-fluoro-4-(hydroxycarbamoyl)benzyl)-4-hydroxypiperidine-1-carboxamide,
N-(3-(3,6-dihydro-2H-pyran-4-yl)phenyl)-N-(2-fluoro-4-(hydroxycarbamoyl)-benzyl)-4-hydroxypiperidine-1-carboxamide,
N-(3-(1-(2-hydroxy-2-methylpropyl)piperidin-4-yl)phenyl)-N-(4-(hydroxy-carbamoyl)benzyl)morpholine-4-carboxamide,
N-(3-(1-(2-fluoro-2-methylpropyl)piperidin-4-yl)phenyl)-N-(4-(hydroxy-carbamoyl)benzyl)morpholine-4-carboxamide,
(R)-3-fluoro-N-(4-(hydroxycarbamoyl)benzyl)-N-(4-(trifluoromethyl)phenyl)-pyrrolidine-1-carboxamide,
(S)-3-fluoro-N-(4-(hydroxycarbamoyl)benzyl)-N-(4-(trifluoromethyl)phenyl)-pyrrolidine-1-carboxamide,
(R)—N-(4-(hydroxycarbamoyl)benzyl)-2-(hydroxymethyl)-N-(4-(trifluoromethyl)-phenyl)pyrrolidine-1-carboxamide,
4-acetyl-N-(3-fluorophenyl)-N-(4-(hydroxycarbamoyl)benzyl)piperazine-1-carboxamide,
N-(3-fluorophenyl)-N-(4-(hydroxycarbamoyl)benzyl)morpholine-4-carboxamide, 4-(2-fluoro-2-methylpropyl)-N-(4-(hydroxycarbamoyl) benzyl)-N-(3-(trifluoro-methyl)phenyl)piperazine-1-carboxamide, N-(2-fluoro-4-(hydroxycarbamoyl)benzyl)-N-(3-(trifluoromethyl)phenyl)-morpholine-4-carboxamide, N-(5-chloropyridin-2-yl)-N-(4-(hydroxycarbamoyl)benzyl)morpholine-4-carboxamide, N-(4-(hydroxycarbamoyl)benzyl)-4-(2-morpholinoethyl)-N-(4-(trifluoromethyl)-phenyl)piperazine-1-carboxamide, N-(4-(hydroxycarbamoyl)benzyl)-4-(pyridin-4-yl)-N-(4-(trifluoromethyl)phenyl)-piperazine-1-carboxamide, N-(4-(hydroxycarbamoyl)benzyl)-4-(2-morpholino-2-oxoethyl)-N-(4-(trifluoro-methyl)phenyl)piperazine-1-carboxamide, N-(2-fluoro-4-(hydroxycarbamoyl)benzyl)-N-(4-(trifluoromethyl)phenyl)-morpholine-4-carboxamide, 3,3-difluoro-N-(2-fluoro-4-(hydroxycarbamoyl)benzyl)-N-(4-(trifluoromethyl)-phenyl)azetidine-1-carboxamide, N-(4-(hydroxycarbamoyl)benzyl)-N-(4-(trifluoromethyl)phenyl)-1,4-oxazepane-4-carboxamide, N-(4-(hydroxycarbamoyl)benzyl)-4-(4-hydroxytetrahydro-2H-pyran-4-yl)methyl)-N-(3-(trifluoromethyl) phenyl)piperazine-1-carboxamide, 4-benzyl-N-(4-(hydroxycarbamoyl)benzyl)-N-(3-(trifluoromethyl)phenyl)-piperazine-1-carboxamide, N-(4-(hydroxycarbamoyl)benzyl)-4-(3-methoxyphenyl)-N-(3-(trifluoromethyl)-phenyl)piperazine-1-carboxamide, 4-((4-fluorotetrahydro-2H-pyran-4-yl)methyl)-N-(4-(hydroxycarbamoyl)benzyl)-N-(3-(trifluoromethyl)phenyl)piperazine-1-carboxamide, N-(4-(hydroxycarbamoyl)benzyl)-4-phenyl-N-(3-(trifluoromethyl)phenyl)-piperazine-1-carboxamide, 4-benzhydryl-N-(4-(hydroxycarbamoyl)benzyl)-N-(3-(trifluoromethyl)phenyl)-piperazine-1-carboxamide, 4-ethyl-N-(3-(fluoromethyl)phenyl)-N-(4-(hydroxycarbamoyl)benzyl)piperazine-1-carboxamide, 4-(2-fluoro-2-methylpropyl)-N-(3-(fluoromethyl)phenyl)-N-(4-(hydroxy-carbamoyl)benzyl)piperazine-1-carboxamide, N-(4-(hydroxycarbamoyl)benzyl)-N-(2-(trifluoromethoxy)phenyl)morpholine-4-carboxamide, N-(4-(hydroxycarbamoyl)benzyl)-N-(4-(trifluoromethoxy)phenyl)morpholine-4-carboxamide, N-(4-(hydroxycarbamoyl)benzyl)-N-(3-(trifluoromethoxy)phenyl)morpholine-4-carboxamide, N-(4-(hydroxycarbamoyl)benzyl)-N-(2-methoxy-5-(trifluoromethyl)phenyl)-morpholine-4-carboxamide, N-(2-chloro-5-(trifluoromethyl)phenyl)-N-(4-(hydroxycarbamoyl)benzyl)-morpholine-4-carboxamide, N-(4-(hydroxycarbamoyl)benzyl)-N-(6-(trifluoromethyl) pyridin-2-yl)morpholine-4-carboxamide, N-(2,3-difluorophenyl)-N-(4-(hydroxycarbamoyl)benzyl)morpholine-4-carboxamide, (3S,5R)-4-ethyl-N-(4-(hydroxycarbamoyl)benzyl)-3,5-dimethyl-N-(3-(trifluoromethyl)phenyl)piperazine-1-carboxamide, N-(4-(hydroxycarbamoyl)benzyl)-2,6-dimethyl-N-(3-(trifluoromethoxy)-phenyl)morpholine-4-carboxamide, N-(4-(hydroxycarbamoyl)benzyl)-2,6-dimethyl-N-(2-(trifluoromethoxy)-phenyl)morpholine-4-carboxamide, (3S,5R)-4-benzyl-N-(4-(hydroxycarbamoyl)benzyl)-3,5-dimethyl-N-(3-(trifluoromethyl)phenyl)piperazine-1-carboxamide, (3S,5R)—N-(4-(hydroxycarbamoyl)benzyl)-3,5-dimethyl-4-(2,2,3,3,3-pentafluoropropyl)-N-(3-(trifluoromethyl)phenyl)piperazine-1-carboxamide, 4-ethyl-N-(4-(hydroxycarbamoyl)benzyl)-N-(6-(trifluoromethyl)pyridin-2-yl)-piperazine-1-carboxamide, N-(4-(hydroxycarbamoyl)benzyl)-2,6-dimethyl-N-(6-(trifluoromethyl)pyridin-2-yl)morpholine-4-carboxamide, N-(4-(hydroxycarbamoyl)benzyl)-N-(6-(trifluoromethyl)pyridin-2-yl)piperidine-1-carboxamide, and (S)-3-fluoro-N-(4-(hydroxycarbamoyl)benzyl)-N-(6-(trifluoromethyl)pyridin-2-yl)-pyrrolidine-1-carboxamide.

6. The compound of claim 5 selected from the group consisting of the following compounds:

N-(3-bromophenyl)-N-(4-(hydroxycarbamoyl)benzyl) morpholine-4-carboxamide,

N-(4-(hydroxycarbamoyl)benzyl)-N-phenylmorpholine-4-carboxamide,

N-(4-(hydroxycarbamoyl)benzyl)-N-(pyridin-2-yl)morpholine-4-carboxamide,

N-(4-(hydroxycarbamoyl)benzyl)-N-(pyrimidin-2-yl) morpholine-4-carboxamide,

N-(4-(hydroxycarbamoyl)benzyl)-N-(3-(trifluoromethyl) phenyl)morpholine-4-carboxamide, N-(3-(benzo[d][1,3]dioxol-5-yl)phenyl)-N-(4-(hydroxycarbamoyl)benzyl)-morpholine-4-carboxamide, N-(3-chloro-4-fluorophenyl)-N-(4-(hydroxycarbamoyl) benzyl)morpholine-4-carboxamide, 4-ethyl-N-(4-(hydroxycarbamoyl)benzyl)-N-(3-(trifluoromethyl)phenyl)piperazine-1-carboxamide, N-(3-(fluoromethyl)phenyl)-N-(4-(hydroxycarbamoyl) benzyl)morpholine-4-carboxamide, N-(3-fluorophenyl)-N-(4-(hydroxycarbamoyl)benzyl) morpholine-4-carboxamide, and (3 S,5R)-4-ethyl-N-(4-(hydroxycarbamoyl)benzyl)-3,5-dimethyl-N-(3-(trifluoromethyl)phenyl)piperazine-1-carboxamide.

7. A pharmaceutical composition, comprising a compound of claim 1 as an active ingredient in a therapeutically effective amount for the prevention or treatment of a histone deacetylase-mediated disease.

* * * * *